(12) United States Patent
Saccomano et al.

(10) Patent No.: US 12,338,436 B2
(45) Date of Patent: Jun. 24, 2025

(54) SYNTHETIC GUIDE MOLECULES, COMPOSITIONS AND METHODS RELATING THERETO

(71) Applicant: Editas Medicine, Inc., Cambridge, MA (US)

(72) Inventors: Sam Saccomano, Boulder, CO (US); Stacy Capehart, Boulder, CO (US); Bruce Eaton, Boulder, CO (US); Karin Zemski Berry, Boulder, CO (US)

(73) Assignee: Editas Medicine, Inc., Cambridge, MA (US)

( * ) Notice: Subject to any disclaimer, the term of this patent is extended or adjusted under 35 U.S.C. 154(b) by 1082 days.

(21) Appl. No.: 17/255,140

(22) PCT Filed: Jun. 28, 2019

(86) PCT No.: PCT/US2019/039848
§ 371 (c)(1),
(2) Date: Dec. 22, 2020

(87) PCT Pub. No.: WO2020/006423
PCT Pub. Date: Jan. 2, 2020

(65) Prior Publication Data
US 2021/0269799 A1    Sep. 2, 2021

Related U.S. Application Data

(60) Provisional application No. 62/692,492, filed on Jun. 29, 2018.

(51) Int. Cl.
*C12N 15/113* (2010.01)
*C12N 15/11* (2006.01)

(52) U.S. Cl.
CPC .......... *C12N 15/113* (2013.01); *C12N 15/111* (2013.01); *C12N 2310/20* (2017.05); *C12N 2330/30* (2013.01)

(58) Field of Classification Search
CPC .... C12N 15/11–113; C12N 15/87–907; C12N 2330/30; C12N 2310/20
See application file for complete search history.

(56) References Cited

U.S. PATENT DOCUMENTS

| | | | |
|---|---|---|---|
| 8,546,553 B2 | 10/2013 | Terns et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,023,649 B2 | 5/2015 | Mali et al. |
| 9,074,199 B1 | 7/2015 | Chavez et al. |
| 9,228,207 B2 | 1/2016 | Liu et al. |
| 9,234,213 B2 | 1/2016 | Wu |
| 9,260,723 B2 | 2/2016 | Mali et al. |
| 9,260,752 B1 | 2/2016 | May et al. |
| 9,267,135 B2 | 2/2016 | Church et al. |
| 9,322,037 B2 | 4/2016 | Liu et al. |
| 9,340,799 B2 | 5/2016 | Liu et al. |
| 9,340,800 B2 | 5/2016 | Liu et al. |
| 9,388,430 B2 | 7/2016 | Liu et al. |
| 9,404,098 B2 | 8/2016 | Terns et al. |
| 9,410,198 B2 | 8/2016 | May et al. |
| 9,422,553 B2 | 8/2016 | Terns et al. |
| 9,512,446 B1 | 12/2016 | Joung et al. |
| 9,567,603 B2 | 2/2017 | Joung et al. |
| 9,567,604 B2 | 2/2017 | Joung et al. |
| 9,580,701 B2 | 2/2017 | May et al. |
| 9,580,727 B1 | 2/2017 | Donohoue et al. |
| 9,587,252 B2 | 3/2017 | Church et al. |
| 9,637,739 B2 | 5/2017 | Siksnys et al. |
| 9,650,617 B2 | 5/2017 | May et al. |
| 9,663,782 B2 | 5/2017 | Yu et al. |
| 9,677,090 B2 | 6/2017 | Donohoue et al. |

(Continued)

FOREIGN PATENT DOCUMENTS

EP           3409776 A1   12/2018
WO    WO-2007/025097 A2    3/2007
(Continued)

OTHER PUBLICATIONS

US 10,077,445 B2, 09/2018, Dounda et al. (withdrawn)
(Continued)

*Primary Examiner* — Layla D Berry
(74) *Attorney, Agent, or Firm* — Choate, Hall & Stewart LLP; Charles E. Lyon; Dustin K. Goncharoff

(57) ABSTRACT

Chemical syntheses of guide molecules are disclosed, along with compositions and methods relating thereto. A cost-effective and straightforward chemical synthesis of high-purity unimolecular guide molecules with minimal n−1 and/or n+1 species, truncation species, and other contaminants by providing, among other things, methods for synthesizing unimolecular guide molecules that involve cross-linking two or more pre-annealed guide fragments.

15 Claims, 54 Drawing Sheets

Specification includes a Sequence Listing.

(56) References Cited

U.S. PATENT DOCUMENTS

| | | |
|---|---|---|
| 9,688,971 B2 | 6/2017 | Doudna et al. |
| 9,688,972 B2 | 6/2017 | May et al. |
| 9,725,714 B2 | 8/2017 | May et al. |
| 9,738,908 B2 | 8/2017 | Wu |
| 9,745,562 B2 | 8/2017 | Donohoue et al. |
| 9,745,600 B2 | 8/2017 | Donohoue et al. |
| 9,752,132 B2 | 9/2017 | Joung et al. |
| 9,771,600 B2 | 9/2017 | Donohoue et al. |
| 9,771,601 B2 | 9/2017 | May et al. |
| 9,790,490 B2 | 10/2017 | Zhang et al. |
| 9,803,194 B2 | 10/2017 | May et al. |
| 9,809,814 B1 | 11/2017 | May et al. |
| 9,816,081 B1 | 11/2017 | Donohoue et al. |
| 9,816,093 B1 | 11/2017 | Donohoue et al. |
| 9,822,370 B2 | 11/2017 | Musunuru et al. |
| 9,822,372 B2 | 11/2017 | Zhang et al. |
| 9,840,702 B2 | 12/2017 | Collingwood et al. |
| 9,840,713 B2 | 12/2017 | Zhang |
| 9,868,962 B2 | 1/2018 | May et al. |
| 9,873,894 B2 | 1/2018 | Conway et al. |
| 9,879,269 B2 | 1/2018 | Barrangou et al. |
| 9,879,283 B2 | 1/2018 | Ravinder et al. |
| 9,885,026 B2 | 2/2018 | Brouns et al. |
| 9,885,033 B2 | 2/2018 | Joung et al. |
| 9,902,974 B2 | 2/2018 | Conway et al. |
| 9,909,122 B2 | 3/2018 | May et al. |
| 9,926,545 B2 | 3/2018 | Joung et al. |
| 9,926,546 B2 | 3/2018 | Joung et al. |
| 9,932,566 B2 | 4/2018 | Kennedy et al. |
| 9,944,912 B2 | 4/2018 | Joung et al. |
| 9,957,490 B1 | 5/2018 | Donohoue et al. |
| 9,963,689 B2 | 5/2018 | Doudna et al. |
| 9,963,719 B1 | 5/2018 | Friedland et al. |
| 9,970,001 B2 | 5/2018 | Miller |
| 9,970,024 B2 | 5/2018 | Church et al. |
| 9,970,026 B2 | 5/2018 | Donohoue et al. |
| 9,970,027 B2 | 5/2018 | Donohoue et al. |
| 9,970,029 B1 | 5/2018 | Donohoue et al. |
| 10,023,853 B1 | 7/2018 | Donohoue et al. |
| 10,059,940 B2 | 8/2018 | Zhong |
| 10,066,233 B2 | 9/2018 | Barrangou et al. |
| 10,077,453 B2 | 9/2018 | Liu et al. |
| 10,093,910 B2 | 10/2018 | Joung et al. |
| 10,100,291 B2 | 10/2018 | Chavez et al. |
| 10,100,333 B2 | 10/2018 | Donohoue et al. |
| 10,113,167 B2 | 10/2018 | Doudna et al. |
| 10,113,179 B2 | 10/2018 | Begemann et al. |
| 10,113,207 B2 | 10/2018 | Wang |
| 10,119,133 B2 | 11/2018 | Joung et al. |
| 10,125,354 B1 | 11/2018 | Donohoue et al. |
| 10,125,361 B2 | 11/2018 | May et al. |
| 10,138,472 B2 | 11/2018 | Donohoue et al. |
| 10,190,137 B2 | 1/2019 | Zhang et al. |
| 10,196,619 B1 | 2/2019 | Donohoue et al. |
| 10,202,589 B2 | 2/2019 | Joung et al. |
| 10,202,619 B2 | 2/2019 | Wu |
| 10,227,611 B2 | 3/2019 | Doudna et al. |
| 10,266,850 B2 | 4/2019 | Doudna et al. |
| 10,301,651 B2 | 5/2019 | Doudna et al. |
| 10,308,961 B2 | 6/2019 | Doudna et al. |
| 10,329,587 B2 | 6/2019 | Church et al. |
| 10,337,001 B2 | 7/2019 | Ryan et al. |
| 10,351,878 B2 | 7/2019 | Doudna et al. |
| 10,358,658 B2 | 7/2019 | Doudna et al. |
| 10,358,659 B2 | 7/2019 | Doudna et al. |
| 10,369,232 B2 | 8/2019 | Chivukula et al. |
| 10,377,998 B2 | 8/2019 | Zhang et al. |
| 10,378,027 B2 | 8/2019 | Joung et al. |
| 10,385,360 B2 | 8/2019 | Doudna et al. |
| 10,392,607 B2 | 8/2019 | Sternberg et al. |
| 10,400,253 B2 | 9/2019 | Doudna et al. |
| 10,407,697 B2 | 9/2019 | Doudna et al. |
| 10,415,059 B2 | 9/2019 | Joung et al. |
| 10,415,061 B2 | 9/2019 | Doudna et al. |
| 10,421,980 B2 | 9/2019 | Doudna et al. |
| 10,428,319 B2 | 10/2019 | Steinberg et al. |
| 10,428,352 B2 | 10/2019 | Doudna et al. |
| 10,435,679 B2 | 10/2019 | Chavez et al. |
| 10,435,708 B2 | 10/2019 | Mali et al. |
| 10,443,076 B2 | 10/2019 | Doudna et al. |
| 10,479,982 B2 | 11/2019 | Joung et al. |
| 10,487,341 B2 | 11/2019 | Doudna et al. |
| 10,494,621 B2 | 12/2019 | Zhang et al. |
| 10,513,712 B2 | 12/2019 | Doudna et al. |
| 10,519,467 B2 | 12/2019 | Jinek et al. |
| 10,526,591 B2 | 1/2020 | Joung et al. |
| 10,526,619 B2 | 1/2020 | Doudna et al. |
| 10,544,405 B2 | 1/2020 | Weiss et al. |
| 10,550,372 B2 | 2/2020 | Konermann et al. |
| 10,550,407 B2 | 2/2020 | Doudna et al. |
| 10,563,225 B2 | 2/2020 | Church et al. |
| 10,563,227 B2 | 2/2020 | Doudna et al. |
| 10,570,415 B2 | 2/2020 | Doudna et al. |
| 10,577,631 B2 | 3/2020 | Doudna et al. |
| 10,597,679 B2 | 3/2020 | Liu et al. |
| 10,597,680 B2 | 3/2020 | Doudna et al. |
| 10,604,752 B2 | 3/2020 | Chen et al. |
| 10,612,045 B2 | 4/2020 | Doudna et al. |
| 10,626,419 B2 | 4/2020 | Doudna et al. |
| 10,633,642 B2 | 4/2020 | Joung et al. |
| 10,640,778 B2 | 5/2020 | Barrangou et al. |
| 10,640,788 B2 | 5/2020 | Zhang et al. |
| 10,640,789 B2 | 5/2020 | Church et al. |
| 10,640,791 B2 | 5/2020 | Doudna et al. |
| 10,669,540 B2 | 6/2020 | Zhang et al. |
| 10,669,560 B2 | 6/2020 | Doudna et al. |
| 10,676,759 B2 | 6/2020 | Doudna et al. |
| 10,683,490 B2 | 6/2020 | Chavez et al. |
| 10,696,986 B2 | 6/2020 | Zhang et al. |
| 10,704,033 B1 | 7/2020 | Kim et al. |
| 10,704,062 B2 | 7/2020 | Liu et al. |
| 10,711,285 B2 | 7/2020 | Zhang et al. |
| 10,717,990 B2 | 7/2020 | Mali et al. |
| 10,724,021 B1 | 7/2020 | Kim et al. |
| 10,724,050 B1 | 7/2020 | Doering et al. |
| 10,731,181 B2 | 8/2020 | Chen et al. |
| 10,745,678 B1 | 8/2020 | Kim et al. |
| 10,745,714 B2 | 8/2020 | Gersbach et al. |
| 10,745,716 B2 | 8/2020 | Chen et al. |
| 10,752,920 B2 | 8/2020 | Doudna et al. |
| 10,760,064 B2 | 9/2020 | Joung et al. |
| 10,767,168 B2 | 9/2020 | Joung et al. |
| 10,767,169 B1 | 9/2020 | Kim et al. |
| 10,767,174 B2 | 9/2020 | Kim et al. |
| 10,767,175 B2 | 9/2020 | Dellinger et al. |
| 10,767,176 B2 | 9/2020 | Collingwood et al. |
| 10,767,193 B2 | 9/2020 | Seebeck et al. |
| 10,774,344 B1 | 9/2020 | Doudna et al. |
| 10,787,654 B2 | 9/2020 | Barrangou et al. |
| 10,793,842 B2 | 10/2020 | Sternberg et al. |
| 10,793,878 B1 | 10/2020 | Doudna et al. |
| 10,808,233 B2 | 10/2020 | Joung et al. |
| 10,844,378 B2 | 11/2020 | Siksnys et al. |
| 10,844,403 B2 | 11/2020 | Joung et al. |
| 10,851,357 B2 | 12/2020 | Davidson et al. |
| 10,851,380 B2 | 12/2020 | Kim et al. |
| 10,876,100 B2 | 12/2020 | Zhang et al. |
| 2010/0076057 A1 | 3/2010 | Sontheimer et al. |
| 2010/0093617 A1 | 4/2010 | Barrangou et al. |
| 2013/0011828 A1 | 1/2013 | Barrangou et al. |
| 2014/0068797 A1 | 3/2014 | Doudna et al. |
| 2014/0093941 A1 | 4/2014 | Terns et al. |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0199767 A1 | 7/2014 | Barrangou et al. |
| 2014/0242664 A1 | 8/2014 | Zhang et al. |
| 2014/0242699 A1 | 8/2014 | Zhang |
| 2014/0256046 A1 | 9/2014 | Zhang et al. |
| 2014/0273037 A1 | 9/2014 | Wu |
| 2014/0273226 A1 | 9/2014 | Wu |
| 2014/0273230 A1 | 9/2014 | Chen et al. |

(56) References Cited

U.S. PATENT DOCUMENTS

| | | |
|---|---|---|
| 2014/0273233 A1 | 9/2014 | Chen et al. |
| 2014/0287938 A1 | 9/2014 | Zhang et al. |
| 2014/0294773 A1 | 10/2014 | Brouns et al. |
| 2014/0302563 A1 | 10/2014 | Doudna et al. |
| 2014/0310830 A1 | 10/2014 | Zhang et al. |
| 2014/0315985 A1 | 10/2014 | May et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0356956 A1 | 12/2014 | Church et al. |
| 2014/0357523 A1 | 12/2014 | Zeiner et al. |
| 2014/0357530 A1 | 12/2014 | Zhang et al. |
| 2014/0377868 A1 | 12/2014 | Joung et al. |
| 2015/0020223 A1 | 1/2015 | Zhang et al. |
| 2015/0024499 A1 | 1/2015 | Brouns et al. |
| 2015/0024500 A1 | 1/2015 | Yu et al. |
| 2015/0031132 A1 | 1/2015 | Church et al. |
| 2015/0031133 A1 | 1/2015 | Church et al. |
| 2015/0031134 A1 | 1/2015 | Zhang et al. |
| 2015/0044772 A1 | 2/2015 | Zhao |
| 2015/0045546 A1 | 2/2015 | Siksnys et al. |
| 2015/0050699 A1 | 2/2015 | Siksnys et al. |
| 2015/0056705 A1 | 2/2015 | Conway et al. |
| 2015/0059010 A1 | 2/2015 | Cigan et al. |
| 2015/0071889 A1 | 3/2015 | Musunuru et al. |
| 2015/0071898 A1 | 3/2015 | Liu et al. |
| 2015/0071899 A1 | 3/2015 | Liu et al. |
| 2015/0071901 A1 | 3/2015 | Liu et al. |
| 2015/0071902 A1 | 3/2015 | Liu et al. |
| 2015/0079681 A1 | 3/2015 | Zhang |
| 2015/0082478 A1 | 3/2015 | Cigan et al. |
| 2015/0176013 A1 | 6/2015 | Musunuru et al. |
| 2015/0184139 A1 | 7/2015 | Zhang et al. |
| 2015/0203872 A1 | 7/2015 | Zhang |
| 2015/0232833 A1 | 8/2015 | Mali et al. |
| 2015/0232882 A1 | 8/2015 | Zhang et al. |
| 2015/0240261 A1 | 8/2015 | Siksnys et al. |
| 2015/0247150 A1 | 9/2015 | Zhang et al. |
| 2015/0252358 A1 | 9/2015 | Maeder et al. |
| 2015/0259684 A1 | 9/2015 | Church et al. |
| 2015/0259704 A1 | 9/2015 | Church et al. |
| 2015/0284727 A1 | 10/2015 | Kim et al. |
| 2015/0291961 A1 | 10/2015 | Siksnys et al. |
| 2015/0291965 A1 | 10/2015 | Zhang et al. |
| 2015/0291966 A1 | 10/2015 | Zhang et al. |
| 2015/0322457 A1 | 11/2015 | Kim et al. |
| 2015/0344912 A1 | 12/2015 | Kim et al. |
| 2015/0353905 A1 | 12/2015 | Weiss et al. |
| 2015/0353917 A1 | 12/2015 | Miller |
| 2015/0356239 A1 | 12/2015 | Zhang et al. |
| 2015/0376586 A1 | 12/2015 | May et al. |
| 2015/0376587 A1 | 12/2015 | May et al. |
| 2016/0002670 A1 | 1/2016 | Church et al. |
| 2016/0010076 A1 | 1/2016 | Joung et al. |
| 2016/0010154 A1 | 1/2016 | Laganiere et al. |
| 2016/0017366 A1 | 1/2016 | Chen et al. |
| 2016/0024523 A1 | 1/2016 | Joung et al. |
| 2016/0024524 A1 | 1/2016 | Joung et al. |
| 2016/0032274 A1 | 2/2016 | Church et al. |
| 2016/0040189 A1 | 2/2016 | Kennedy et al. |
| 2016/0046949 A1 | 2/2016 | May et al. |
| 2016/0046961 A1 | 2/2016 | Jinek et al. |
| 2016/0046962 A1 | 2/2016 | May et al. |
| 2016/0046963 A1 | 2/2016 | May et al. |
| 2016/0046978 A1 | 2/2016 | May et al. |
| 2016/0060653 A1 | 3/2016 | Doudna et al. |
| 2016/0060654 A1 | 3/2016 | Doudna et al. |
| 2016/0068864 A1 | 3/2016 | Doudna et al. |
| 2016/0068887 A1 | 3/2016 | May et al. |
| 2016/0076020 A1 | 3/2016 | May et al. |
| 2016/0090607 A1 | 3/2016 | Conway et al. |
| 2016/0102322 A1 | 4/2016 | Ravinder et al. |
| 2016/0102324 A1 | 4/2016 | Duchateau et al. |
| 2016/0108470 A1 | 4/2016 | May et al. |
| 2016/0115488 A1 | 4/2016 | Zhang et al. |
| 2016/0115489 A1 | 4/2016 | Zhang et al. |
| 2016/0122774 A1 | 5/2016 | Duchateau et al. |
| 2016/0130608 A1 | 5/2016 | Doudna et al. |
| 2016/0130609 A1 | 5/2016 | Doudna et al. |
| 2016/0138008 A1 | 5/2016 | Doudna et al. |
| 2016/0138046 A1 | 5/2016 | Wu |
| 2016/0145646 A1 | 5/2016 | Frendewey et al. |
| 2016/0153003 A1 | 6/2016 | Joung et al. |
| 2016/0153004 A1 | 6/2016 | Zhang et al. |
| 2016/0153006 A1 | 6/2016 | Zhang et al. |
| 2016/0160210 A1 | 6/2016 | Mali et al. |
| 2016/0168592 A1 | 6/2016 | Church et al. |
| 2016/0175462 A1 | 6/2016 | Zhang et al. |
| 2016/0177304 A1 | 6/2016 | Collingwood et al. |
| 2016/0184362 A1 | 6/2016 | Duchateau et al. |
| 2016/0186152 A1 | 6/2016 | Brouns et al. |
| 2016/0186213 A1 | 6/2016 | Zhang et al. |
| 2016/0186214 A1 | 6/2016 | Brouns et al. |
| 2016/0201072 A1 | 7/2016 | Cigan et al. |
| 2016/0201089 A1 | 7/2016 | Gersbach et al. |
| 2016/0208243 A1 | 7/2016 | Zhang et al. |
| 2016/0208288 A1 | 7/2016 | Liu et al. |
| 2016/0215275 A1 | 7/2016 | Zhong |
| 2016/0215276 A1 | 7/2016 | Liu et al. |
| 2016/0215300 A1 | 7/2016 | May et al. |
| 2016/0222416 A1 | 8/2016 | Church et al. |
| 2016/0237437 A1 | 8/2016 | Agrawal et al. |
| 2016/0237455 A1 | 8/2016 | Glucksmann et al. |
| 2016/0237456 A1 | 8/2016 | Church et al. |
| 2016/0251640 A1 | 9/2016 | May et al. |
| 2016/0272965 A1 | 9/2016 | Zhang et al. |
| 2016/0281072 A1 | 9/2016 | Zhang |
| 2016/0289673 A1 | 10/2016 | Huang et al. |
| 2016/0289675 A1 | 10/2016 | Ryan et al. |
| 2016/0298097 A1 | 10/2016 | Chavez et al. |
| 2016/0298125 A1 | 10/2016 | Chen et al. |
| 2016/0298132 A1 | 10/2016 | Chen et al. |
| 2016/0298133 A1 | 10/2016 | Chen et al. |
| 2016/0298134 A1 | 10/2016 | Chen et al. |
| 2016/0298135 A1 | 10/2016 | Chen et al. |
| 2016/0298136 A1 | 10/2016 | Chen et al. |
| 2016/0298137 A1 | 10/2016 | Chen et al. |
| 2016/0298138 A1 | 10/2016 | Chen et al. |
| 2016/0304907 A1 | 10/2016 | Mali et al. |
| 2016/0312198 A1 | 10/2016 | Joung et al. |
| 2016/0312199 A1 | 10/2016 | Joung et al. |
| 2016/0312280 A1 | 10/2016 | May et al. |
| 2016/0319260 A1 | 11/2016 | Joung et al. |
| 2016/0319261 A1 | 11/2016 | Joung et al. |
| 2016/0319281 A1 | 11/2016 | Tsai et al. |
| 2016/0319349 A1 | 11/2016 | May et al. |
| 2016/0340662 A1 | 11/2016 | Zhang et al. |
| 2016/0354487 A1 | 12/2016 | Zhang et al. |
| 2016/0355795 A1 | 12/2016 | Ran et al. |
| 2016/0355796 A1 | 12/2016 | Davidson et al. |
| 2016/0355797 A1 | 12/2016 | Konermann et al. |
| 2016/0355816 A1 | 12/2016 | Terns et al. |
| 2016/0362667 A1 | 12/2016 | Donohoue et al. |
| 2016/0362668 A1 | 12/2016 | May et al. |
| 2017/0002339 A1 | 1/2017 | Barrangou et al. |
| 2017/0037416 A1 | 2/2017 | Barrangou et al. |
| 2017/0037432 A1 | 2/2017 | Donohoue et al. |
| 2017/0044508 A1 | 2/2017 | Donohoue et al. |
| 2017/0044535 A1 | 2/2017 | Collingwood et al. |
| 2017/0044536 A1 | 2/2017 | Collingwood et al. |
| 2017/0044537 A1 | 2/2017 | Collingwood et al. |
| 2017/0044569 A9 | 2/2017 | Church et al. |
| 2017/0051276 A1 | 2/2017 | May et al. |
| 2017/0051310 A1 | 2/2017 | Doudna et al. |
| 2017/0051312 A1 | 2/2017 | Jinek et al. |
| 2017/0058271 A1 | 3/2017 | Joung et al. |
| 2017/0073705 A1 | 3/2017 | Chen et al. |
| 2017/0080107 A1 | 3/2017 | Chivukula et al. |
| 2017/0081650 A1 | 3/2017 | Joung et al. |
| 2017/0107536 A1 | 4/2017 | Zhang et al. |
| 2017/0114334 A1 | 4/2017 | May et al. |
| 2017/0114369 A1 | 4/2017 | Donohoue et al. |
| 2017/0121694 A1 | 5/2017 | May et al. |
| 2017/0152508 A1 | 6/2017 | Joung et al. |

(56) References Cited

U.S. PATENT DOCUMENTS

| | | |
|---|---|---|
| 2017/0152528 A1 | 6/2017 | Zhang |
| 2017/0159073 A1 | 6/2017 | Donohoue et al. |
| 2017/0166893 A1 | 6/2017 | Doudna et al. |
| 2017/0166903 A1 | 6/2017 | Zhang et al. |
| 2017/0175142 A1 | 6/2017 | Zhang et al. |
| 2017/0175144 A1 | 6/2017 | Zhang et al. |
| 2017/0191078 A1 | 7/2017 | Zhang et al. |
| 2017/0191082 A1 | 7/2017 | Chen et al. |
| 2017/0198269 A1 | 7/2017 | Zhang et al. |
| 2017/0204388 A1 | 7/2017 | Donohoue et al. |
| 2017/0211142 A1 | 7/2017 | Smargon et al. |
| 2017/0226534 A1 | 8/2017 | May et al. |
| 2017/0233703 A1 | 8/2017 | Xie et al. |
| 2017/0233762 A1 | 8/2017 | Zalatan et al. |
| 2017/0268022 A1 | 9/2017 | Liu et al. |
| 2017/0283831 A1 | 10/2017 | Zhang et al. |
| 2017/0298330 A1 | 10/2017 | Sato et al. |
| 2017/0306307 A1 | 10/2017 | Zhang et al. |
| 2017/0306335 A1 | 10/2017 | Zhang et al. |
| 2017/0314002 A1 | 11/2017 | Gong |
| 2017/0314016 A1 | 11/2017 | Kim et al. |
| 2017/0321214 A1 | 11/2017 | Zhang et al. |
| 2017/0327805 A1 | 11/2017 | Joung et al. |
| 2017/0327806 A1 | 11/2017 | Joung et al. |
| 2017/0327820 A1 | 11/2017 | May et al. |
| 2017/0335346 A1 | 11/2017 | Donohoue et al. |
| 2017/0335347 A1 | 11/2017 | Donohoue et al. |
| 2017/0349894 A1 | 12/2017 | Dahlman et al. |
| 2017/0349915 A1 | 12/2017 | May et al. |
| 2017/0355985 A1 | 12/2017 | Dellinger et al. |
| 2018/0002682 A1 | 1/2018 | Sternberg et al. |
| 2018/0030425 A1 | 2/2018 | Joung et al. |
| 2018/0051281 A1 | 2/2018 | Ryan et al. |
| 2018/0057810 A1 | 3/2018 | Zhang et al. |
| 2018/0066242 A1 | 3/2018 | Zhang et al. |
| 2018/0066258 A1 | 3/2018 | Powell |
| 2018/0073002 A1 | 3/2018 | Deiters et al. |
| 2018/0080051 A1 | 3/2018 | Sheikh et al. |
| 2018/0094257 A1 | 4/2018 | Wang et al. |
| 2018/0100148 A1 | 4/2018 | Vakulskas et al. |
| 2018/0112213 A1 | 4/2018 | Welstead et al. |
| 2018/0119121 A1 | 5/2018 | Brouns et al. |
| 2018/0119140 A1 | 5/2018 | Porteus et al. |
| 2018/0119173 A1 | 5/2018 | Donohoue et al. |
| 2018/0119175 A1 | 5/2018 | Conway et al. |
| 2018/0127780 A1 | 5/2018 | Liu et al. |
| 2018/0127783 A1 | 5/2018 | Zhang et al. |
| 2018/0135073 A1 | 5/2018 | Chen et al. |
| 2018/0142236 A1 | 5/2018 | He et al. |
| 2018/0142263 A1 | 5/2018 | May et al. |
| 2018/0148735 A1 | 5/2018 | Begemann et al. |
| 2018/0155708 A1 | 6/2018 | Church et al. |
| 2018/0155716 A1 | 6/2018 | Zhang et al. |
| 2018/0155720 A1 | 6/2018 | Donohoue et al. |
| 2018/0163188 A1 | 6/2018 | Xie et al. |
| 2018/0163213 A1 | 6/2018 | Aneja et al. |
| 2018/0179521 A1 | 6/2018 | Rahdar et al. |
| 2018/0179523 A1 | 6/2018 | Collingwood et al. |
| 2018/0187176 A1 | 7/2018 | Behlke et al. |
| 2018/0187186 A1 | 7/2018 | Yin et al. |
| 2018/0187195 A1 | 7/2018 | Siksnys et al. |
| 2018/0195089 A1 | 7/2018 | Ravinder et al. |
| 2018/0201956 A1 | 7/2018 | Friedland et al. |
| 2018/0208921 A1 | 7/2018 | Joung et al. |
| 2018/0208931 A1 | 7/2018 | Doudna et al. |
| 2018/0216088 A1 | 8/2018 | Joung et al. |
| 2018/0230495 A1 | 8/2018 | Doudna et al. |
| 2018/0230496 A1 | 8/2018 | Doudna et al. |
| 2018/0230497 A1 | 8/2018 | Doudna et al. |
| 2018/0237801 A1 | 8/2018 | Doudna et al. |
| 2018/0245099 A1 | 8/2018 | Donohoue et al. |
| 2018/0245100 A1 | 8/2018 | Doudna et al. |
| 2018/0245101 A1 | 8/2018 | Doudna et al. |
| 2018/0251791 A1 | 9/2018 | Doudna et al. |
| 2018/0251793 A1 | 9/2018 | Doudna et al. |
| 2018/0251794 A1 | 9/2018 | Doudna et al. |
| 2018/0251795 A1 | 9/2018 | Charpentier et al. |
| 2018/0265864 A1 | 9/2018 | Li et al. |
| 2018/0273981 A1 | 9/2018 | Doudna et al. |
| 2018/0282713 A1 | 10/2018 | Van Der Oost |
| 2018/0282714 A1 | 10/2018 | Joung et al. |
| 2018/0282722 A1 | 10/2018 | Jakimo et al. |
| 2018/0282764 A1 | 10/2018 | Jinek et al. |
| 2018/0291383 A1 | 10/2018 | Musunuru et al. |
| 2018/0298360 A1 | 10/2018 | Sternberg et al. |
| 2018/0298406 A1 | 10/2018 | Doudna et al. |
| 2018/0298407 A1 | 10/2018 | Doudna et al. |
| 2018/0312824 A1 | 11/2018 | Zhang et al. |
| 2018/0312827 A1 | 11/2018 | Donohoue et al. |
| 2018/0312874 A1 | 11/2018 | Doudna et al. |
| 2018/0312875 A1 | 11/2018 | Doudna et al. |
| 2018/0312876 A1 | 11/2018 | Doudna et al. |
| 2018/0320163 A1 | 11/2018 | Koonin et al. |
| 2018/0320197 A1 | 11/2018 | Gersbach et al. |
| 2018/0320201 A1 | 11/2018 | Vakulskas et al. |
| 2018/0327761 A1 | 11/2018 | Duchateau et al. |
| 2018/0346927 A1 | 12/2018 | Doudna et al. |
| 2018/0355332 A1 | 12/2018 | Steinberg et al. |
| 2019/0002889 A1 | 1/2019 | Cheng et al. |
| 2019/0002921 A1 | 1/2019 | Doudna et al. |
| 2019/0002922 A1 | 1/2019 | Doudna et al. |
| 2019/0002923 A1 | 1/2019 | Doudna et al. |
| 2019/0010471 A1 | 1/2019 | Zhang et al. |
| 2019/0010481 A1 | 1/2019 | Joung et al. |
| 2019/0010520 A1 | 1/2019 | Doudna et al. |
| 2019/0040416 A1 | 2/2019 | Chavez et al. |
| 2019/0048338 A1 | 2/2019 | Yin et al. |
| 2019/0048340 A1 | 2/2019 | Charpentier et al. |
| 2019/0062790 A1 | 2/2019 | Doudna et al. |
| 2019/0071688 A1 | 3/2019 | Begemann et al. |
| 2019/0083656 A1 | 3/2019 | Khalili et al. |
| 2019/0085329 A1 | 3/2019 | Siksnys et al. |
| 2019/0093129 A1 | 3/2019 | Doudna et al. |
| 2019/0106687 A1 | 4/2019 | Joung et al. |
| 2019/0106693 A1 | 4/2019 | Rinn et al. |
| 2019/0106711 A1 | 4/2019 | Doudna et al. |
| 2019/0106712 A1 | 4/2019 | Doudna et al. |
| 2019/0106713 A1 | 4/2019 | Doudna et al. |
| 2019/0106714 A1 | 4/2019 | Doudna et al. |
| 2019/0106715 A1 | 4/2019 | Doudna et al. |
| 2019/0169639 A1 | 6/2019 | Zhang et al. |
| 2019/0218547 A1 | 7/2019 | Lee et al. |
| 2019/0218602 A1 | 7/2019 | Zhang et al. |
| 2019/0225961 A1 | 7/2019 | Robb et al. |
| 2019/0241911 A1 | 8/2019 | Dong et al. |
| 2019/0264186 A1 | 8/2019 | Yamano et al. |
| 2019/0284583 A1 | 9/2019 | Doudna et al. |
| 2019/0316121 A1 | 10/2019 | Smith et al. |
| 2019/0367949 A1 | 12/2019 | Crawley et al. |
| 2019/0382751 A1 | 12/2019 | Radhar et al. |
| 2019/0382758 A1* | 12/2019 | Aoki .................. C12N 15/907 |
| 2019/0390195 A1 | 12/2019 | Tondera et al. |
| 2019/0390229 A1 | 12/2019 | Potter et al. |
| 2020/0010817 A1 | 1/2020 | Van Der Oost |
| 2020/0056164 A1 | 2/2020 | Steinberg et al. |
| 2020/0056209 A1 | 2/2020 | May et al. |
| 2020/0109382 A1 | 4/2020 | Zhang et al. |
| 2020/0149020 A1 | 5/2020 | Cereseto et al. |
| 2020/0149021 A1 | 5/2020 | Li et al. |
| 2020/0149022 A1 | 5/2020 | Kim et al. |
| 2020/0155606 A1 | 5/2020 | Lamothe-Dreuzy et al. |
| 2020/0172564 A1 | 6/2020 | Dombrowski |
| 2020/0172935 A1 | 6/2020 | Dong et al. |
| 2020/0208141 A1 | 7/2020 | Sanjana |
| 2020/0216825 A1 | 7/2020 | Vakulskas et al. |
| 2020/0239879 A1 | 7/2020 | Choudhary et al. |
| 2020/0255861 A1 | 8/2020 | Doench et al. |
| 2020/0299660 A1 | 9/2020 | Doudna et al. |
| 2020/0299689 A1 | 9/2020 | Lee |
| 2020/0318172 A1 | 10/2020 | Zhang et al. |
| 2020/0318173 A1 | 10/2020 | Zhang et al. |
| 2020/0332273 A1 | 10/2020 | Thomas et al. |

(56) References Cited

U.S. PATENT DOCUMENTS

| | | |
|---|---|---|
| 2020/0332274 A1 | 10/2020 | Thomas et al. |
| 2020/0347387 A1 | 11/2020 | Lee |
| 2023/0111575 A1 | 4/2023 | Heil et al. |

FOREIGN PATENT DOCUMENTS

| | | |
|---|---|---|
| WO | WO-2010/011961 A2 | 1/2010 |
| WO | WO-2013/098244 A1 | 7/2013 |
| WO | WO-2013/141680 A1 | 9/2013 |
| WO | WO-2013/142578 A1 | 9/2013 |
| WO | WO-2013/176772 A1 | 11/2013 |
| WO | WO-2014/018423 A2 | 1/2014 |
| WO | WO-2014/065596 A1 | 5/2014 |
| WO | WO-2014/089290 A1 | 6/2014 |
| WO | WO-2014/093479 A1 | 6/2014 |
| WO | WO-2014/093595 A1 | 6/2014 |
| WO | WO-2014/093622 A2 | 6/2014 |
| WO | WO-2014/093635 A1 | 6/2014 |
| WO | WO-2014/093655 A2 | 6/2014 |
| WO | WO-2014/093661 A2 | 6/2014 |
| WO | WO-2014/093694 A1 | 6/2014 |
| WO | WO-2014/093701 A1 | 6/2014 |
| WO | WO-2014/093709 A1 | 6/2014 |
| WO | WO-2014/093712 A1 | 6/2014 |
| WO | WO-2014/093718 A1 | 6/2014 |
| WO | WO-2014/099744 A1 | 6/2014 |
| WO | WO-2014/099750 A2 | 6/2014 |
| WO | WO-2014/113493 A1 | 7/2014 |
| WO | WO-2014/144288 A1 | 9/2014 |
| WO | WO-2014/144592 A2 | 9/2014 |
| WO | WO-2014/144761 A2 | 9/2014 |
| WO | WO-2014/145599 A2 | 9/2014 |
| WO | WO-2014/150624 A1 | 9/2014 |
| WO | WO-2014/152432 A2 | 9/2014 |
| WO | WO-2014/165825 A2 | 10/2014 |
| WO | WO-2014/186585 A2 | 11/2014 |
| WO | WO-2014/191518 A1 | 12/2014 |
| WO | WO-2014/191521 A2 | 12/2014 |
| WO | WO-2014/197568 A2 | 12/2014 |
| WO | WO-2014/197748 A2 | 12/2014 |
| WO | WO-2014/204578 A1 | 12/2014 |
| WO | WO-2014/204724 A1 | 12/2014 |
| WO | WO-2014/204725 A1 | 12/2014 |
| WO | WO-2014/204727 A1 | 12/2014 |
| WO | WO-2014/204728 A1 | 12/2014 |
| WO | WO-2014/204729 A1 | 12/2014 |
| WO | WO-2015/006290 A1 | 1/2015 |
| WO | WO-2015/006294 A2 | 1/2015 |
| WO | WO-2015/010114 A1 | 1/2015 |
| WO | WO-2015/013583 A2 | 1/2015 |
| WO | WO-2015/021426 A1 | 2/2015 |
| WO | WO-2015/026885 A1 | 2/2015 |
| WO | WO-2015/035139 A2 | 3/2015 |
| WO | WO-2015/035162 A2 | 3/2015 |
| WO | WO-2015/048577 A2 | 4/2015 |
| WO | WO-2015/048690 A1 | 4/2015 |
| WO | WO-2015/070083 A1 | 5/2015 |
| WO | WO-2015/077318 A1 | 5/2015 |
| WO | WO-2015/089351 A1 | 6/2015 |
| WO | WO-2015/089354 A1 | 6/2015 |
| WO | WO-2015/089427 A1 | 6/2015 |
| WO | WO-2015/089473 A1 | 6/2015 |
| WO | WO-2015/089486 A2 | 6/2015 |
| WO | WO-2015/112896 A2 | 7/2015 |
| WO | WO-2015/138510 A1 | 9/2015 |
| WO | WO-2015/148863 A2 | 10/2015 |
| WO | WO-2015/188056 A1 | 12/2015 |
| WO | WO-2015/188065 A1 | 12/2015 |
| WO | WO-2015/200555 A2 | 12/2015 |
| WO | WO-2016/011080 A2 | 1/2016 |
| WO | WO-2016/022363 A2 | 2/2016 |
| WO | WO-2016/022866 A1 | 2/2016 |
| WO | WO-2016/028682 A1 | 2/2016 |
| WO | WO-2016/049258 A2 | 3/2016 |
| WO | WO-2016/054106 A1 | 4/2016 |
| WO | WO-2016/057821 A2 | 4/2016 |
| WO | WO-2016/057951 A2 | 4/2016 |
| WO | WO-2016/065364 A1 | 4/2016 |
| WO | WO-2016/073990 A2 | 5/2016 |
| WO | WO-2016/081923 A2 | 5/2016 |
| WO | WO-2016/089433 A1 | 6/2016 |
| WO | WO-2016/094867 A1 | 6/2016 |
| WO | WO-2016/094872 A1 | 6/2016 |
| WO | WO-2016/094874 A1 | 6/2016 |
| WO | WO-2016/100951 A2 | 6/2016 |
| WO | WO-2016/106236 A1 | 6/2016 |
| WO | WO-2016/106244 A1 | 6/2016 |
| WO | WO-2016/112242 A1 | 7/2016 |
| WO | WO-2016/114972 A1 | 7/2016 |
| WO | WO-2016/123230 A1 | 8/2016 |
| WO | WO-2016/141224 A1 | 9/2016 |
| WO | WO-2016/148994 A1 | 9/2016 |
| WO | WO-2016/154596 A1 | 9/2016 |
| WO | WO-2016/161207 A1 | 10/2016 |
| WO | WO-2016/164356 A1 | 10/2016 |
| WO | WO-2016/164797 A1 | 10/2016 |
| WO | WO-2016/166340 A1 | 10/2016 |
| WO | WO-2016/167300 A1 | 10/2016 |
| WO | WO-2016/172727 A1 | 10/2016 |
| WO | WO-2016/182917 A1 | 11/2016 |
| WO | WO-2016/186745 A1 | 11/2016 |
| WO | WO-2016/196655 A1 | 12/2016 |
| WO | WO-2016/201155 A1 | 12/2016 |
| WO | WO-2016/205613 A1 | 12/2016 |
| WO | WO-2016/205711 A1 | 12/2016 |
| WO | WO-2016/205749 A1 | 12/2016 |
| WO | WO-2016/205759 A1 | 12/2016 |
| WO | WO-2017/004261 A1 | 1/2017 |
| WO | WO-2017/004279 A2 | 1/2017 |
| WO | WO-2017/015015 A1 | 1/2017 |
| WO | WO-2017/027423 A1 | 2/2017 |
| WO | WO-2017/040348 A1 | 3/2017 |
| WO | WO-2017/044776 A1 | 3/2017 |
| WO | WO-2017/048969 A1 | 3/2017 |
| WO | WO-2017/053431 A2 | 3/2017 |
| WO | WO-2017/064546 A1 | 4/2017 |
| WO | WO-2017/066588 A2 | 4/2017 |
| WO | WO-2017/068377 A1 | 4/2017 |
| WO | WO-2017/070598 A1 | 4/2017 |
| WO | WO-2017/070633 A2 | 4/2017 |
| WO | WO-2017/096328 A1 | 6/2017 |
| WO | WO-2017/099494 A1 | 6/2017 |
| WO | WO-2017/106251 A1 | 6/2017 |
| WO | WO-2017/106657 A1 | 6/2017 |
| WO | WO-2017/127807 A1 | 7/2017 |
| WO | WO-2017/131237 A1 | 8/2017 |
| WO | WO-2017/136335 A1 | 8/2017 |
| WO | WO-2017/136794 A1 | 8/2017 |
| WO | WO-2017/161068 A1 | 9/2017 |
| WO | WO-2017/180711 A1 | 10/2017 |
| WO | WO-2017/181107 A2 | 10/2017 |
| WO | WO-2017/184768 A1 | 10/2017 |
| WO | WO-2017/184786 A1 | 10/2017 |
| WO | WO-2017/184799 A1 | 10/2017 |
| WO | WO-2017/189308 A1 | 11/2017 |
| WO | WO-2017/189821 A1 | 11/2017 |
| WO | WO-2017/190664 A1 | 11/2017 |
| WO | WO-2017/197238 A1 | 11/2017 |
| WO | WO-2017/205290 A1 | 11/2017 |
| WO | WO-2017/214460 A1 | 12/2017 |
| WO | WO-2017/219027 A1 | 12/2017 |
| WO | WO-2017/219033 A1 | 12/2017 |
| WO | WO-2017/222773 A1 | 12/2017 |
| WO | WO-2017/222834 A1 | 12/2017 |
| WO | WO-2017/223449 A1 | 12/2017 |
| WO | WO-2018/005691 A1 | 1/2018 |
| WO | WO-2018/009822 A1 | 1/2018 |
| WO | WO-2018/022634 A1 | 2/2018 |
| WO | WO-2018/035387 A1 | 2/2018 |
| WO | WO-2018/035388 A1 | 2/2018 |
| WO | WO-2018/049073 A1 | 3/2018 |
| WO | WO-2018/049077 A1 | 3/2018 |
| WO | WO-2018/049079 A1 | 3/2018 |
| WO | WO-2018/052247 A1 | 3/2018 |

(56) References Cited

FOREIGN PATENT DOCUMENTS

| | | |
|---|---|---|
| WO | WO-2018/053053 A1 | 3/2018 |
| WO | WO-2018/057946 A2 | 3/2018 |
| WO | WO-2018/064352 A1 | 4/2018 |
| WO | WO-2018/064371 A1 | 4/2018 |
| WO | WO-2018/068053 A2 | 4/2018 |
| WO | WO-2018/069474 A1 | 4/2018 |
| WO | WO-2018/071868 A1 | 4/2018 |
| WO | WO-2018/071892 A1 | 4/2018 |
| WO | WO-2018/074979 A1 | 4/2018 |
| WO | WO-2018/085414 A1 | 5/2018 |
| WO | WO-2018/089664 A1 | 5/2018 |
| WO | WO-2018/093954 A1 | 5/2018 |
| WO | WO-2018/094356 A2 | 5/2018 |
| WO | WO-2018/098383 A1 | 5/2018 |
| WO | WO-2018/106693 A1 | 6/2018 |
| WO | WO-2018/106727 A1 | 6/2018 |
| WO | WO-2018/107028 A1 | 6/2018 |
| WO | WO-2018/108272 A1 | 6/2018 |
| WO | WO-2018/108338 A1 | 6/2018 |
| WO | WO-2018/108339 A1 | 6/2018 |
| WO | WO-2018/109101 A1 | 6/2018 |
| WO | WO-2018/112451 A1 | 6/2018 |
| WO | WO-2018/125964 A1 | 7/2018 |
| WO | WO-2018/126176 A1 | 7/2018 |
| WO | WO-2018/130830 A1 | 7/2018 |
| WO | WO-2018/149418 A1 | 8/2018 |
| WO | WO-2018/149888 A1 | 8/2018 |
| WO | WO-2018/170015 A1 | 9/2018 |
| WO | WO-2018/172556 A1 | 9/2018 |
| WO | WO-2018/188571 A1 | 10/2018 |
| WO | WO-2018/191715 A2 | 10/2018 |
| WO | WO-2018/195540 A1 | 10/2018 |
| WO | WO-2018/195545 A2 | 10/2018 |
| WO | WO-2018/197495 A1 | 11/2018 |
| WO | WO-2018/209158 A2 | 11/2018 |
| WO | WO-2018/209320 A1 | 11/2018 |
| WO | WO-2018/209712 A1 | 11/2018 |
| WO | WO-2018/213351 A1 | 11/2018 |
| WO | WO-2018/217981 A1 | 11/2018 |
| WO | WO-2018/221685 A1 | 12/2018 |
| WO | WO-2018/226855 A1 | 12/2018 |
| WO | WO-2018/227114 A1 | 12/2018 |
| WO | WO-2019/006471 A2 | 1/2019 |
| WO | WO-2019/009682 A2 | 1/2019 |
| WO | WO-2019/018041 A1 | 1/2019 |
| WO | WO-2019/036513 A1 | 2/2019 |
| WO | WO-2019/040650 A1 | 2/2019 |
| WO | WO-2019/046540 A1 | 3/2019 |
| WO | WO-2019/048881 A1 | 3/2019 |
| WO | WO-2019/048882 A1 | 3/2019 |
| WO | WO-2019/049913 A1 | 3/2019 |
| WO | WO-2019/051419 A1 | 3/2019 |
| WO | WO-2019/060469 A2 | 3/2019 |
| WO | WO-2019/067322 A1 | 4/2019 |
| WO | WO-2019/070762 A1 | 4/2019 |
| WO | WO-2019/072596 A1 | 4/2019 |
| WO | WO-2019/074542 A1 | 5/2019 |
| WO | WO-2019/084168 A1 | 5/2019 |
| WO | WO-2019/084664 A1 | 5/2019 |
| WO | WO-2019/089796 A1 | 5/2019 |
| WO | WO-2019/089804 A1 | 5/2019 |
| WO | WO-2019/089808 A1 | 5/2019 |
| WO | WO-2019/089820 A1 | 5/2019 |
| WO | WO-2019/090173 A1 | 5/2019 |
| WO | WO-2019/090174 A1 | 5/2019 |
| WO | WO-2019/090175 A1 | 5/2019 |
| WO | WO-2019/092042 A1 | 5/2019 |
| WO | WO-2019/099943 A1 | 5/2019 |
| WO | WO-2019/103442 A2 | 5/2019 |
| WO | WO-2019/126709 A1 | 6/2019 |
| WO | WO-2019/126716 A1 | 6/2019 |
| WO | WO-2019/126762 A2 | 6/2019 |
| WO | WO-2019/126774 A1 | 6/2019 |
| WO | WO-2019/147014 A1 | 8/2019 |
| WO | WO-2019/168953 A1 | 9/2019 |
| WO | WO-2019/178427 A1 | 9/2019 |
| WO | WO-2019/178428 A1 | 9/2019 |
| WO | WO-2019/183000 A1 | 9/2019 |
| WO | WO-2019/183150 A1 | 9/2019 |
| WO | WO-2019/233990 A1 | 12/2019 |
| WO | WO-2019/237069 A1 | 12/2019 |
| WO | WO-2020/005980 A1 | 1/2020 |
| WO | WO-2020/006423 A1 | 1/2020 |
| WO | WO-2020/014577 A1 | 1/2020 |
| WO | WO-2020/030984 A2 | 2/2020 |
| WO | WO-2020/032711 A1 | 2/2020 |
| WO | WO-2020/033601 A1 | 2/2020 |
| WO | WO-2020/033774 A1 | 2/2020 |
| WO | WO-2020/041751 A1 | 2/2020 |
| WO | WO-2020/065062 A1 | 4/2020 |
| WO | WO-2020/069029 A1 | 4/2020 |
| WO | WO-2020/085441 A1 | 4/2020 |
| WO | WO-2020/091069 A1 | 5/2020 |
| WO | WO-2020/111983 A2 | 6/2020 |
| WO | WO-2020/111984 A2 | 6/2020 |
| WO | WO-2020/142754 A2 | 7/2020 |
| WO | WO-2020/146290 A1 | 7/2020 |
| WO | WO-2020/150373 A1 | 7/2020 |
| WO | WO-2020/154714 A2 | 7/2020 |
| WO | WO-2020/163307 A1 | 8/2020 |
| WO | WO-2020/168234 A1 | 8/2020 |
| WO | WO-2020/168291 A1 | 8/2020 |
| WO | WO-2020/172502 A1 | 8/2020 |
| WO | WO-2020/180699 A1 | 9/2020 |
| WO | WO-2020/181101 A1 | 9/2020 |
| WO | WO-2020/181102 A1 | 9/2020 |
| WO | WO-2020/182941 A1 | 9/2020 |
| WO | WO-2020/186059 A2 | 9/2020 |
| WO | WO-2020/191102 A1 | 9/2020 |
| WO | WO-2020/198641 A2 | 10/2020 |
| WO | WO-2020/209959 A1 | 10/2020 |
| WO | WO-2020/218657 A1 | 10/2020 |
| WO | WO-2020/219908 A1 | 10/2020 |
| WO | WO-2020/223514 A2 | 11/2020 |
| WO | WO-2020/223553 A2 | 11/2020 |
| WO | WO-2020/225719 A1 | 11/2020 |
| WO | WO-2020/264254 A1 | 12/2020 |

OTHER PUBLICATIONS

Supporting Information for He, K. et al"Conjugation and evaluation of triazole-linked single guide RNA . . . " ChemBioChem, vol. 17, pp. 1809-1812. (Year: 2016).*
Karvelis, T. et al"crRNA and tracrRNA guide Cas9-mediated DNA . . . " RNA Biol., vol. 10, No. 5, pp. 841-851. (Year: 2013).*
Chen, Z. et al"Tetrazine-ligated CRISPR sgRNAs for efficient genome editing" ACS Chem. Biol., vol. 17, pp. 1045-1050. (Year: 2022).*
Bae, S. et al., Cas-OFFinder: a fast and versatile algorithm that searches for potential off-target sites of Cas9 RNA-guided endonucleases, Bioinformatics, 30(10): 1473-5 (2014).
Briner, A. E. et al. Guide RNA functional modules direct Cas9 activity and orthogonality Molecular Cell, 56(2), 333-339 (2014).
Davis, L. and Maizels, N., Homology-directed repair of DNA nicks via pathways distinct from canonical double-strand break repair, PNAS, 111(10):E924-932 (2014).
Fine, E. J. et al., Trans-spliced Cas9 allows cleavage of HBB and CCR5 genes in human cells using compact expression cassettes, Sci. Rep., 5:10777 (2015).
Frit, P. et al., Alternative end-joining pathway(s): bricolage at DNA breaks, DNA Repair, 17:81-97 (2014).
Fu, Y. et al., Improving CRISPR-Cas nuclease specificity using truncated guide RNAs, Nat biotechnol., 32(3): 279-84 (2014).
Guilinger, J. P. et al., Fusion of catalytically inactive Cas9 to FokI nuclease improves the specificity of genome modification, Nature Biotechnology, 32: 577-582 (2014).
He, K. et al, Conjugation and Evaluation of Triazole-Linked Single Guide RNA for CRISPR-Cas9 Gene Editing, Chembiochem., 17(19): 1809-1812 (2016).
Heigwer, F. et al., E-CRISP: fast CRISPR target site identification, Nat. methods, 11(2): 122-3 (2014).

(56) References Cited

OTHER PUBLICATIONS

Hendel, A. et al., Chemically modified guide RNAs enhance CRISPR-Cas genome editing in human primary cells, Nature Biotechnology, 33(9): 985-989 (2015).
Hsu, P. et al, DNA targeting specificity of RNA-guided Cas9 nuclease, Nature Biotechnology, 31(9): 827-832 (2013).
International Search Report for PCT/US2017/069019 (Synthetic Guide Molecules, Compositions and Methods Relating Thereto, filed Dec. 29, 2017), issued ISA/EPO, 8 pages (Jun. 18, 2018).
International Search Report for PCT/US2019/039848 (Synthetic Guide Molecules, Compositions and Methods Relating Thereto, filed Jun. 28, 2019), issued by ISA/US, 6 pages ( Nov. 29, 2019).
Iyama, T. and Wilson, D. M., DNA repair mechanisms in dividing and non-dividing cells, DNA Repair (Amst.), 12(8): 620-636 (2013).
Jiang, W. et al., RNA-guided editing of bacterial genomes using CRISPR-Cas systems [Manuscript title: CRISPR-assisted editing of bacterial genomes], Nat Biotechnol., 31(3): 233-9 (2013).
Jinek, M. et al., A programmable dual-RNA-guided DNA endonuclease in adaptive, bacterial immunity, Science, 337(6096): 816-821 (2012).
Kelley, M. L. et al., Versatility of chemically synthesized guide RNAs for CRISPR-Cas9 genome editing, Journal of Biotechnology, 233: 74-83 (2016).
Kim, J. S. et al., An evolutionary Monte Carlo algorithm for predicting DNA hybridization, Biosystems, 7(5): 69-75 (2008).
Kleinstiver, B. P. et al, High-fidelity CRISPR-Cas9 nucleases with no detectable genome-wide off-target effects, Nature, 28; 529, 490-495 (2016).
Kleinstiver, B. P. et al., Broadening the targeting range of *Staphylococcus aureus* CRISPR-Cas9 by modifying PAM recognition, Nat Biotechnol., 33(12): 1293-1298 (2015).
Kleinstiver, B. P. et al., Engineered CRISPR-Cas9 nucleases with altered PAM specificities, Nature, 523(7561):481-5 (2015).
Komor, A. C. et al. Programmable editing of a target base in genomic DNA without double-stranded DNA cleavage, Nature, 533:420-424 (2016).
Makarova, K. S. et al. Evolution and classification of the CRISPR-Cas systems, Nat. Rev. Microbiol., 9(6): 467-477 (2011).
Mali, P. et al., RNA-guided human genome engineering via Cas9, Science, 339(6121): 823-826 (2013).
Nishimasu, H. et al., Crystal structure of Cas9 in complex with guide RNA and target DNA. Cell, 156: 935-949 (2014).
Nishimasu, H. et al., Crystal Structure of *Staphylococcus aureus* Cas9, Cell, 162:1113-1126 (2015).
Ran, F. A. et al., Double nicking by RNA-guided CRISPR Cas9 for enhanced genome editing specificity, Cell 154(6), 1380-1389 (2013).
Richardson, C. D. et al., Enhancing homology-directed genome editing by catalytically active and inactive CRISPR-Cas9 using asymmetric donor DNA, Nature Biotechnology, 34:339-344 (2016).
Shmakov et al., Discovery and Functional Characterization of Diverse Class 2 CRISPR-Cas Systems, Molecular Cell, 60(3):385-397 (2015).
Tsai, S.Q. et al. Open-source guideseq software for analysis of GUIDE-seq data, Nat. Biotechnol., 34(5): 483 (2016).
Tulpan, D. et al, Free energy estimation of short DNA duplex hybridizations, BMC Bioinformatics, 11(105) (2010).
Written Opinion for PCT/US2017/069019 (Synthetic Guide Molecules, Compositions and Methods Relating Thereto, filed Dec. 29, 2017), issued ISA/EPO, 13 pages (Jun. 18, 2018).
Written Opinion for PCT/US2019/039848 (Synthetic Guide Molecules, Compositions and Methods Relating Thereto, filed Jun. 28, 2019), issued by ISA/US, 6 pages ( Nov. 29, 2019).
Xiao, A. et al., CasOT: a genome-wide Cas9/gRNA off-target searching tool, Bioinformatics, 30(8): 1180-1182 (2014).
Yamano, T. et al. Crystal Structure of Cpf1 in Complex with Guide RNA and Target DNA, Cell, 165(4): 949-962 (2016).
You, Y. et al., Measuring Thermodynamic Details of DNA Hybridization Using Fluorescence, Biopolymers, 95(7):472-486 (2011).
Zetsche, B. et al., A split-Cas9 architecture for inducible genome editing and transcription modulation, Nat. Biotechnol., 33(2):139-42 (2015).
Zetsche, B. et al., Cpf1 is a single RNA-guided endonuclease of a class 2 CRISPR-Cas system, Cell, 163:759-771 (2015).
Arn, E and Abelson, J., The 2'-5' RNA Ligase of *Escherichia coli*, J. Biol. Chem., 271(49):31145-31153 (1996).
Sontakke, V. et al., 4-(Acetylthio)-2,2-dimethyl-3-oxobutyl and 4-(tert-Butyldisulfanyl)-2,2-dimethyl-3-oxobutyl as Protecting Groups for Nucleoside 5-Phosphoramidates Derived from L-Alanine Methyl Ester, 2015, Eur. J. Org. Chem., 5004-5012 (2015).
U.S. Appl. No. 16/474,198, Heil et al.
Arar, K. et al., Synthesis and antiviral activity of peptide-oligonucleotide conjugates prepared by using N alpha-(bromoacetyl)peptides, Bioconjug. Chem., 6: 573-577 (1995).
Lu, K. et al., Chemical strategies for the synthesis of peptide-oligonucleotide conjugates, Bioconjug. Chem., 21: 187-202 (2010).
NEB.com; In vitro digestion of DNA with Cas9 nuclease, S> pyogenes (M0386), accessed Sep. 27, 2023 (2023).

\* cited by examiner

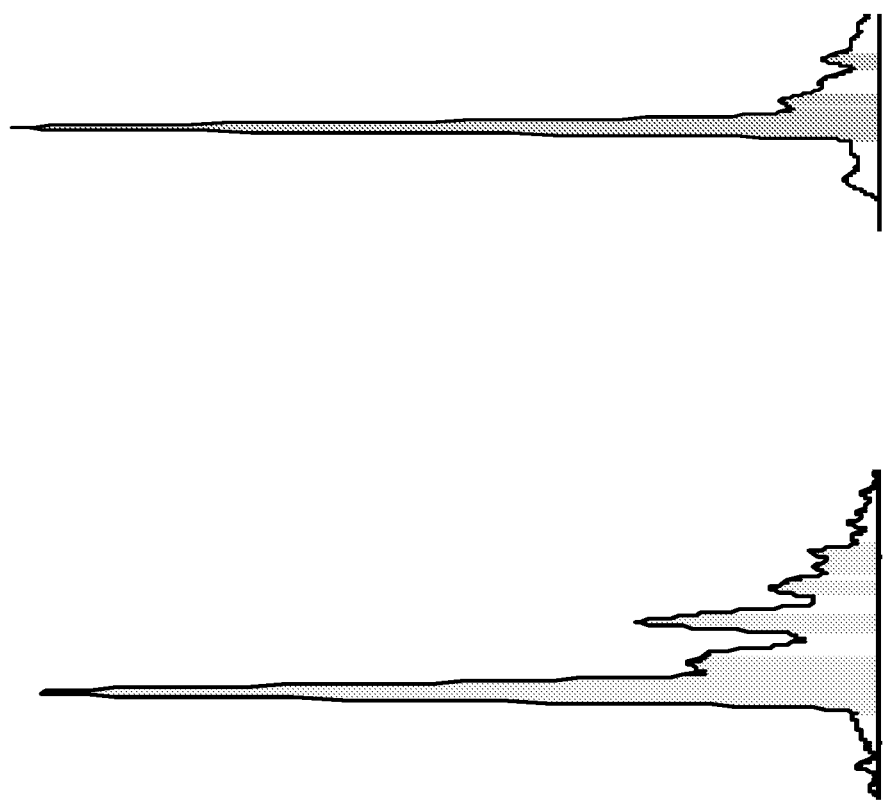

SEQUENCE LISTING

```
<160> NUMBER OF SEQ ID NOS: 123

<210> SEQ ID NO 1
<211> LENGTH: 13
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 1
guuuuagagc uag                                                          13

<210> SEQ ID NO 2
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
auagcaaguu aaaau                                                        15

<210> SEQ ID NO 3
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
guuuuagagc u                                                            11

<210> SEQ ID NO 4
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
agcaaguuaa aau                                                          13

<210> SEQ ID NO 5
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
guuuuagagc uag                                                          13

<210> SEQ ID NO 6
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
cuagcaaguu aaaau                                                        15

<210> SEQ ID NO 7
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 7
guuuuagagc uaug                                                              14

<210> SEQ ID NO 8
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
cauagcaagu uaaaau                                                            16

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
guauuagagc uaugcuguuu u                                                      21

<210> SEQ ID NO 10
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
aaaacagcau agcaaguuaa uau                                                    23

<210> SEQ ID NO 11
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
guauuagagc uaugcu                                                            16

<210> SEQ ID NO 12
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
agcauagcaa guuaauau                                                          18

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 13
guuuuagagc uaugcuguuu u                                              21

<210> SEQ ID NO 14
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
aaaacagcau agcaaguuaa aau                                            23

<210> SEQ ID NO 15
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
guuuuagagc uaugcu                                                    16

<210> SEQ ID NO 16
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
agcauagcaa guuaaaaa                                                  18

<210> SEQ ID NO 17
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
guuuuagagc uaaag                                                     15

<210> SEQ ID NO 18
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
auuuagcaag uuaaaau                                                   17

<210> SEQ ID NO 19
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
```
guuuuagagc uaa                                                        13

<210> SEQ ID NO 20
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
uuagcaaguu aaaau                                                      15

<210> SEQ ID NO 21
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
guuuuagagc uaaaggg                                                    17

<210> SEQ ID NO 22
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
accuuuagca aguuaaaau                                                  19

<210> SEQ ID NO 23
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
guuuuagagc uag                                                        13

<210> SEQ ID NO 24
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
guuuuaguac ucu                                                        13

<210> SEQ ID NO 25
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
agaaucuacu aaaac        15

<210> SEQ ID NO 26
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26 guuuaguac ucugua        16

<210> SEQ ID NO 27
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
uacagaaucu acuaaaac        18

<210> SEQ ID NO 28
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28 guuuaguac ucuguaauuu uagg        24

<210> SEQ ID NO 29
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ccuaaaauua cagaaucuac uaaaac        26

<210> SEQ ID NO 30
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30 guuuaguac ucuguaauuu uagguauga        29

<210> SEQ ID NO 31
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
ucauaccuaa aauuacagaa ucuacuaaaa c        31

```
<210> SEQ ID NO 32
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 32
nnnnnnnnnn nnnnnnnnnn guuuuagagc uagaaauagc aaguuaaaau aaggcuaguc      60
cguuaucaac uugaaaaagu ggcaccgagu cggugcuuuu                           100

<210> SEQ ID NO 33
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 33
nnnnnnnnnn nnnnnnnnnn guuuuagagc uaga                                 34

<210> SEQ ID NO 34
<211> LENGTH: 66
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
aauagcaagu uaaaauaagg cuaguccguu aucaacuuga aaaguggca ccgagucggu       60 gcuuuu                                                                66

<210> SEQ ID NO 35
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 35
nnnnnnnnnn nnnnnnnnnn guuuuagagc uaga                                 34

<210> SEQ ID NO 36
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
```
guaacggcag acuucuccuc guuuuagagc uaga                                    34

```
<210> SEQ ID NO 37
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
```
guaacggcag acuucuccuc guuuuagagc ua                                      32

```
<210> SEQ ID NO 38
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
```
guaacggcag acuucuccuc guuuuagagc uagg                                    34

```
<210> SEQ ID NO 39
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
```
guaacggcag acuucuccuc guuuuagagc uaugc                                   35

```
<210> SEQ ID NO 40
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
```
guaacggcag acuucuccuc guauuagagc uaugcuguuu ug                           42

```
<210> SEQ ID NO 41
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
```
guaacggcag acuucuccuc guauuagagc uaugcug                                 37

```
<210> SEQ ID NO 42
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
```
guaacggcag acuucuccuc guuuuagagc uaugcuguuu ug                42

<210> SEQ ID NO 43
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
guaacggcag acuucuccuc guuuuagagc uaugcug                    37

<210> SEQ ID NO 44
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
guaacggcag acuucuccuc guuuuagagc uaaaga                     36

<210> SEQ ID NO 45
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
guaacggcag acuucuccuc guuuuagagc uaaa                       34

<210> SEQ ID NO 46
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
guaacggcag acuucuccuc guuuuagagc uaaaggga                   38

<210> SEQ ID NO 47
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
guaacggcag acuucuccuc guuuuagagc uagda                      35

<210> SEQ ID NO 48
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
cuaacaguug cuuuuaucac guuuuagagc uaugc                      35

<210> SEQ ID NO 49
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
cuaacaguug cuuuuaucac guuuuagagc uaugcug                              37

<210> SEQ ID NO 50
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
cuaacaguug cuuuuaucac guuuuagagc uaugcuguuu ug                        42

<210> SEQ ID NO 51
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
cuaacaguug cuuuuaucac guauuagagc uaugcuguuu ug                        42

<210> SEQ ID NO 52
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
cuaacaguug cuuuuaucac guuuuagagc uaga                                 34

<210> SEQ ID NO 53
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
guaacggcag acuucuccuc guuuuaguac ucug                                 34

<210> SEQ ID NO 54
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
guaacggcag acuucuccuc guuuuaguac ucuguaa                              37

<210> SEQ ID NO 55
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
guaacggcag acuucuccuc guuuuaguac ucuguaauuu aggu                    45

<210> SEQ ID NO 56
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
guaacggcag acuucuccuc guuuuaguac ucuguaauuu agguaugag               50

<210> SEQ ID NO 57
<211> LENGTH: 66
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
aauagcaagu uaaaauaagg cuaguccguu aucaacuuga aaaaguggca ccgagucggu   60
gcuuuu                                                              66

<210> SEQ ID NO 58
<211> LENGTH: 66
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
aauagcaagu uaaaauaagg cuaguccguu aucaacuuga aaaaguggca ccgagucggu   60
gcuuuu                                                              66

<210> SEQ ID NO 59
<211> LENGTH: 64
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
uagcaaguua aaauaaggcu aguccguuau caacuugaaa aaguggcacc gagucggugc   60
uuuu                                                                64

<210> SEQ ID NO 60
<211> LENGTH: 66
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 60
ccuagcaagu uaaaauaagg cuaguccguu aucaacuuga aaaaguggca ccgagucggu    60
gcuuuu                                                              66

<210> SEQ ID NO 61
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
gcauagcaag uuaaaauaag gcuaguccgu uaucaacuug aaaaaguggc accgagucgg    60
ugcuuuu                                                             67

<210> SEQ ID NO 62
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
caaaacagca uagcaaguua auauaaggcu aguccguuau caacugaaa aaguggcacc     60 gagucggugc uuuu                                                     74

<210> SEQ ID NO 63
<211> LENGTH: 69
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
cagcauagca aguuaauaua aggcuagucc guuaucaacu ugaaaaagug gcaccgaguc    60
ggugcuuuu                                                           69

<210> SEQ ID NO 64
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
caaaacagca uagcaaguua aaauaaggcu aguccguuau caacugaaa aaguggcacc     60 gagucggugc uuuu                                                     74

<210> SEQ ID NO 65
<211> LENGTH: 69
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
cagcauagca aguuaaaaaa aggcuagucc guuaucaacu ugaaaaagug gcaccgaguc    60
```

```
ggugcuuuu                                                             69

<210> SEQ ID NO 66
<211> LENGTH: 68
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
aauuuagcaa guuaaaauaa ggcuaguccg uuaucaacuu gaaaaagugg caccgagucg     60
gugcuuuu                                                             68

<210> SEQ ID NO 67
<211> LENGTH: 66
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
uuuagcaagu uaaauaagg cuaguccguu aucaacuuga aaaguggca ccgagucggu       60 gcuuuu                                                               66

<210> SEQ ID NO 68
<211> LENGTH: 70
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
aaccuuuagc aaguuaaaau aaggcuaguc cguuaucaac uugaaaaagu ggcaccgagu     60
cggugcuuuu                                                           70

<210> SEQ ID NO 69
<211> LENGTH: 66
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
aauagcaagu uaaauaagg cuaguccguu aucaacuuga aaaguggca ccgagucggu       60 gcuuuu                                                               66

<210> SEQ ID NO 70
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
gcauagcaag uuaaauaag gcuaguccgu uaucaacuug aaaaaguggc accgagucgg      60
ugcuuuu                                                              67
```

<210> SEQ ID NO 71
<211> LENGTH: 69
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 71
cagcauagca aguuaaaaua aggcuagucc guuaucaacu ugaaaaagug gcaccgaguc    60
ggugcuuuu                                                           69

<210> SEQ ID NO 72
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 72
caaaacagca uagcaaguua aaauaaggcu aguccguuau caacugaaa aaguggcacc    60 gagucggugc uuuu                                                     74

<210> SEQ ID NO 73
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 73
caaaacagca uagcaaguua auauaaggcu aguccguuau caacugaaa aaguggcacc    60 gagucggugc uuuu                                                     74

<210> SEQ ID NO 74
<211> LENGTH: 66
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 74
aauagcaagu uaaauaaagg cuaguccguu aucaacuuga aaaguggca ccgagucggu    60 gcuuuu                                                              66

<210> SEQ ID NO 75
<211> LENGTH: 62
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 75
cagaaucuac uaaaacaagg caaaaugccg uguuuaucuc gucaacuugu uggcgagauu    60
uu                                                                  62

<210> SEQ ID NO 76
<211> LENGTH: 65
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 76
uuacagaauc uacuaaaaca aggcaaaaug ccguguuuau cucgucaacu uguuggcgag     60
auuuu                                                                65

<210> SEQ ID NO 77
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
accuaaaauu acagaaucua cuaaaacaag gcaaaaugcc guguuuaucu cgucaacuug     60
uuggcgagau uuu                                                       73

<210> SEQ ID NO 78
<211> LENGTH: 78
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
cucauaccua aaauuacaga aucuacuaaa acaaggcaaa augccguguu uaucucguca     60
acuuguuggc gagauuuu                                                  78

<210> SEQ ID NO 79
<211> LENGTH: 54
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: a, c, u, g, unknown or other
<220> FEATURE:
<221> NAME/KEY: modified_base
<222> LOCATION: (27)..(48)
<223> OTHER INFORMATION: a, c, u, g, unknown or other
<220> FEATURE:
<221> NAME/KEY: misc_feature
<222> LOCATION: (27)..(48)
<223> OTHER INFORMATION: This region may encompass 2-22 nucleotides
<220> FEATURE:
<221> NAME/KEY: modified_base
<222> LOCATION: (49)..(54)
<223> OTHER INFORMATION: a, c, u, g, unknown or other
<220> FEATURE:
<221> NAME/KEY: misc_feature
<222> LOCATION: (49)..(54)
<223> OTHER INFORMATION: This region may encompass 0-6 nucleotides
<220> FEATURE:
<223> OTHER INFORMATION: See specification as filed for detailed
      description of substitutions and preferred embodiments

<400> SEQUENCE: 79
nnnnnnnnnn nnnnnuuuua gagcuannnn nnnnnnnnnn nnnnnnnnnn nnnn           54

<210> SEQ ID NO 80
<211> LENGTH: 71
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, u, g, unknown or other
<220> FEATURE:
<221> NAME/KEY: misc_feature
<222> LOCATION: (1)..(6)
<223> OTHER INFORMATION: This region may encompass 0-6 nucleotides
<220> FEATURE:
<221> NAME/KEY: modified_base
<222> LOCATION: (7)..(28)
<223> OTHER INFORMATION: a, c, u, g, unknown or other
<220> FEATURE:
<221> NAME/KEY: misc_feature
<222> LOCATION: (7)..(28)
<223> OTHER INFORMATION: This region may encompass 2-22 nucleotides
<220> FEATURE:
<221> NAME/KEY: modified_base
<222> LOCATION: (42)..(71)
<223> OTHER INFORMATION: a, c, u, g, unknown or other
<220> FEATURE:
<223> OTHER INFORMATION: See specification as filed for detailed
      description of substitutions and preferred embodiments

<400> SEQUENCE: 80
nnnnnnnnnn nnnnnnnnnn nnnnnnnnua gcaaguuaaa annnnnnnnn nnnnnnnnnn    60
nnnnnnnnnn n                                                         71

<210> SEQ ID NO 81
<211> LENGTH: 54
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: a, c, u, g, unknown or other
<220> FEATURE:
<221> NAME/KEY: modified_base
<222> LOCATION: (27)..(48)
<223> OTHER INFORMATION: a, c, u, g, unknown or other
<220> FEATURE:
<221> NAME/KEY: misc_feature
<222> LOCATION: (27)..(48)
<223> OTHER INFORMATION: This region may encompass 2-22 nucleotides
<220> FEATURE:
<221> NAME/KEY: modified_base
<222> LOCATION: (49)..(54)
<223> OTHER INFORMATION: a, c, u, g, unknown or other
<220> FEATURE:
<221> NAME/KEY: misc_feature
<222> LOCATION: (49)..(54)
<223> OTHER INFORMATION: This region may encompass 0-6 nucleotides
<220> FEATURE:
<223> OTHER INFORMATION: See specification as filed for detailed
      description of substitutions and preferred embodiments

<400> SEQUENCE: 81
nnnnnnnnnn nnnnnuauua gagcuannnn nnnnnnnnnn nnnnnnnnnn nnnn           54

<210> SEQ ID NO 82
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (1)..(6)
<223> OTHER INFORMATION: a, c, u, g, unknown or other
<220> FEATURE:
<221> NAME/KEY: misc_feature
<222> LOCATION: (1)..(6)
<223> OTHER INFORMATION: This region may encompass 0-6 nucleotides
<220> FEATURE:
<221> NAME/KEY: modified_base
<222> LOCATION: (7)..(28)
<223> OTHER INFORMATION: a, c, u, g, unknown or other
<220> FEATURE:
<221> NAME/KEY: misc_feature
<222> LOCATION: (7)..(28)
<223> OTHER INFORMATION: This region may encompass 2-22 nucleotides
<220> FEATURE:
<221> NAME/KEY: modified_base
<222> LOCATION: (42)..(71)
<223> OTHER INFORMATION: a, c, u, g, unknown or other
<220> FEATURE:
<223> OTHER INFORMATION: See specification as filed for detailed
      description of substitutions and preferred embodiments

<400> SEQUENCE: 82
nnnnnnnnnn nnnnnnnnnn nnnnnnnnua gcaaguuaau annnnnnnnn nnnnnnnnnn    60
nnnnnnnnnn n                                                          71

<210> SEQ ID NO 83
<211> LENGTH: 57
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: a, c, u, g, unknown or other
<220> FEATURE:
<221> NAME/KEY: modified_base
<222> LOCATION: (30)..(51)
<223> OTHER INFORMATION: a, c, u, g, unknown or other
<220> FEATURE:
<221> NAME/KEY: misc_feature
<222> LOCATION: (30)..(51)
<223> OTHER INFORMATION: This region may encompass 2-22 nucleotides
<220> FEATURE:
<221> NAME/KEY: modified_base
<222> LOCATION: (52)..(57)
<223> OTHER INFORMATION: a, c, u, g, unknown or other
<220> FEATURE:
<221> NAME/KEY: misc_feature
<222> LOCATION: (52)..(57)
<223> OTHER INFORMATION: This region may encompass 0-6 nucleotides
<220> FEATURE:
<223> OTHER INFORMATION: See specification as filed for detailed
      description of substitutions and preferred embodiments

<400> SEQUENCE: 83
nnnnnnnnnn nnnnnguuuu aguacucugn nnnnnnnnnn nnnnnnnnnn nnnnnnn    57

<210> SEQ ID NO 84
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, u, g, unknown or other
<220> FEATURE:
```

-continued

```
<221> NAME/KEY: misc_feature
<222> LOCATION: (1)..(6)
<223> OTHER INFORMATION: This region may encompass 0-6 nucleotides
<220> FEATURE:
<221> NAME/KEY: modified_base
<222> LOCATION: (7)..(28)
<223> OTHER INFORMATION: a, c, u, g, unknown or other
<220> FEATURE:
<221> NAME/KEY: misc_feature
<222> LOCATION: (7)..(28)
<223> OTHER INFORMATION: This region may encompass 2-22 nucleotides
<220> FEATURE:
<221> NAME/KEY: modified_base
<222> LOCATION: (45)..(74)
<223> OTHER INFORMATION: a, c, u, g, unknown or other
<220> FEATURE:
<223> OTHER INFORMATION: See specification as filed for detailed
      description of substitutions and preferred embodiments

<400> SEQUENCE: 84
nnnnnnnnnn nnnnnnnnnn nnnnnnnnca gaaucuacua aaacnnnnnn nnnnnnnnnn      60
nnnnnnnnnn nnnn                                                       74

<210> SEQ ID NO 85
<211> LENGTH: 57
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: a, c, u, g, unknown or other
<220> FEATURE:
<221> NAME/KEY: modified_base
<222> LOCATION: (30)..(51)
<223> OTHER INFORMATION: a, c, u, g, unknown or other
<220> FEATURE:
<221> NAME/KEY: misc_feature
<222> LOCATION: (30)..(51)
<223> OTHER INFORMATION: This region may encompass 2-22 nucleotides
<220> FEATURE:
<221> NAME/KEY: modified_base
<222> LOCATION: (52)..(57)
<223> OTHER INFORMATION: a, c, u, g, unknown or other
<220> FEATURE:
<221> NAME/KEY: misc_feature
<222> LOCATION: (52)..(57)
<223> OTHER INFORMATION: This region may encompass 0-6 nucleotides
<220> FEATURE:
<223> OTHER INFORMATION: See specification as filed for detailed
      description of substitutions and preferred embodiments

<400> SEQUENCE: 85
nnnnnnnnnn nnnnnguauu aguacucugn nnnnnnnnnn nnnnnnnnnn nnnnnnn         57

<210> SEQ ID NO 86
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, u, g, unknown or other
<220> FEATURE:
<221> NAME/KEY: misc_feature
<222> LOCATION: (1)..(6)
<223> OTHER INFORMATION: This region may encompass 0-6 nucleotides
<220> FEATURE:
<221> NAME/KEY: modified_base
```

```
<222> LOCATION: (7)..(28)
<223> OTHER INFORMATION: a, c, u, g, unknown or other
<220> FEATURE:
<221> NAME/KEY: misc_feature
<222> LOCATION: (7)..(28)
<223> OTHER INFORMATION: This region may encompass 2-22 nucleotides
<220> FEATURE:
<221> NAME/KEY: modified_base
<222> LOCATION: (45)..(74)
<223> OTHER INFORMATION: a, c, u, g, unknown or other
<220> FEATURE:
<223> OTHER INFORMATION: See specification as filed for detailed
      description of substitutions and preferred embodiments

<400> SEQUENCE: 86
nnnnnnnnnn nnnnnnnnnn nnnnnnnnca gaaucuacua auacnnnnnn nnnnnnnnnn        60
nnnnnnnnnn nnnn                                                          74

<210> SEQ ID NO 87
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
uaauuuuagg                                                               10

<210> SEQ ID NO 88
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
uaauuuuagg u                                                             11

<210> SEQ ID NO 89
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
uaauuuuagg ua                                                            12

<210> SEQ ID NO 90
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
uaauuuuagg uau                                                           13

<210> SEQ ID NO 91
<211> LENGTH: 14
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 91
uaauuuuagg uaug                                                          14

<210> SEQ ID NO 92
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
uaauuuuagg uauga                                                         15

<210> SEQ ID NO 93
<211> LENGTH: 101
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(21)
<223> OTHER INFORMATION: a, c, u, g, unknown or other

<400> SEQUENCE: 93
nnnnnnnnnn nnnnnnnnnn nguuuuagag cuagaaauag caaguuaaaa uaaggcuagu        60
ccguuaucaa cuugaaaaag uggcaccgag ucggugcuuu u                           101

<210> SEQ ID NO 94
<211> LENGTH: 104
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(21)
<223> OTHER INFORMATION: a, c, u, g, unknown or other

<400> SEQUENCE: 94
nnnnnnnnnn nnnnnnnnnn nguuuuagua cucuggaaac agaaucuacu aaacaaggc         60 aaaaugccgu guuuaucucg ucaacuuguu ggcgagauuu uuuu                        104

<210> SEQ ID NO 95
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 95
nnnnnnnnnn nnnnnnnnnn guuuuagagc uaga                                    34

<210> SEQ ID NO 96
<211> LENGTH: 66
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 96
aauagcaagu uaaaauaagg cuaguccguu aucaacuuga aaaaguggca ccgagucggu    60
gcuuuu                                                               66

<210> SEQ ID NO 97
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 97
nnnnnnnnnn nnnnnnnnnn guuuuagagc ua                                  32

<210> SEQ ID NO 98
<211> LENGTH: 64
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
uagcaaguua aaauaaggcu aguccguuau caacuugaaa aguggcacc gagucggugc    60 uuuu                                                                 64

<210> SEQ ID NO 99
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 99
nnnnnnnnnn nnnnnnnnnn guuuuagagc uagg                                34

<210> SEQ ID NO 100
<211> LENGTH: 66
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
ccuagcaagu uaaaauaagg cuaguccguu aucaacuuga aaaaguggca ccgagucggu    60
gcuuuu                                                               66

<210> SEQ ID NO 101
<211> LENGTH: 35
<212> TYPE: RNA
<213> ORGANISM: Artificial Sequence
```

-continued

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 101
nnnnnnnnnn nnnnnnnnnn guuuuagagc uaugc                                35

<210> SEQ ID NO 102
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
gcauagcaag uuaaaauaag gcuaguccgu uaucaacuug aaaaaguggc accgagucgg     60
ugcuuuu                                                              67

<210> SEQ ID NO 103
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 103
nnnnnnnnnn nnnnnnnnnn guauuagagc uaugcuguuu ug                       42

<210> SEQ ID NO 104
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
caaaacagca uagcaaguua auauaaggcu aguccguuau caacugaaa aaguggcacc     60 gagucggugc uuuu                                                      74

<210> SEQ ID NO 105
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 105
nnnnnnnnnn nnnnnnnnnn guauuagagc uaugcug                             37

<210> SEQ ID NO 106
<211> LENGTH: 69
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
cagcauagca aguuaauaua aggcuagucc guuaucaacu ugaaaagug gcaccgaguc    60 ggugcuuuu                                                          69

<210> SEQ ID NO 107
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 107
nnnnnnnnnn nnnnnnnnnn guuuuagagc uaugcuguuu ug                     42

<210> SEQ ID NO 108
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
caaaacagca uagcaaguua aaauaaggcu aguccguuau caacuugaaa aaguggcacc   60
gagucggugc uuuu                                                    74

<210> SEQ ID NO 109
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 109
nnnnnnnnnn nnnnnnnnnn guuuuagagc uaugcug                           37

<210> SEQ ID NO 110
<211> LENGTH: 69
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
cagcauagca aguuaaaaaa aggcuagucc guuaucaacu ugaaaagug gcaccgaguc    60 ggugcuuuu                                                          69

<210> SEQ ID NO 111
<211> LENGTH: 37
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 111
nnnnnnnnnn nnnnnnnnnn guuuuagagc uaugcug                              37

<210> SEQ ID NO 112
<211> LENGTH: 69
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
cagcauagca aguuaaaaua aggcuagucc guuaucaacu ugaaaaagug gcaccgaguc      60
ggugcuuuu                                                             69

<210> SEQ ID NO 113
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 113
nnnnnnnnnn nnnnnnnnnn guuuuaguac ucug                                 34

<210> SEQ ID NO 114
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
cagaaucuac uaaacaagg caaaaugccg uguuuaucuc gucaacuugu uggcgagauu       60
uu                                                                    62

<210> SEQ ID NO 115
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 115
nnnnnnnnnn nnnnnnnnnn guuuuaguac ucguaa                               37
```

```
<210> SEQ ID NO 116
<211> LENGTH: 65
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
uuacagaauc uacuaaaaca aggcaaaaug ccguguuuau cucgucaacu uguuggcgag    60
auuuu                                                               65

<210> SEQ ID NO 117
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 117
nnnnnnnnnn nnnnnnnnnn guuuuaguac ucuguaauuu uaggu                   45

<210> SEQ ID NO 118
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
accuaaaauu acagaaucua cuaaaacaag gcaaaaugcc guguuuaucu cgucaacuug    60
uuggcgagau uuu                                                      73

<210> SEQ ID NO 119
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 119
nnnnnnnnnn nnnnnnnnnn guuuuaguac ucuguaauuu uagguaugag               50

<210> SEQ ID NO 120
<211> LENGTH: 78
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
cucauaccua aaauuacaga aucuacuaaa acaaggcaaa augccguguu uaucucguca    60
acuuguuggc gagauuuu                                                 78
```

```
<210> SEQ ID NO 121
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: This sequence may encompass 1-10 nucleotides

<400> SEQUENCE: 121
aaaaaaaaaa                                                              10

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: This sequence may encompass 10-20 nucleotides

<400> SEQUENCE: 122
aaaaaaaaaa aaaaaaaaaa                                                   20

<210> SEQ ID NO 123
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(200)
<223> OTHER INFORMATION: This sequence may encompass 25-200 nucleotides

<400> SEQUENCE: 123
aaaaaaaaaa aaaaaaaaaa aaaaaaaaaa aaaaaaaaaa aaaaaaaaaa aaaaaaaaaa       60
aaaaaaaaaa aaaaaaaaaa aaaaaaaaaa aaaaaaaaaa aaaaaaaaaa aaaaaaaaaa      120
aaaaaaaaaa aaaaaaaaaa aaaaaaaaaa aaaaaaaaaa aaaaaaaaaa aaaaaaaaaa      180
aaaaaaaaaa aaaaaaaaaa                                                  200
```

SYNTHETIC GUIDE MOLECULES, COMPOSITIONS AND METHODS RELATING THERETO

CROSS REFERENCE TO RELATED APPLICATIONS

This application is a U.S. National Stage Application of PCT/US19/39848, filed Jun. 28, 2019, which claims the benefit of U.S. Application No. 62/692,492, filed on Jun. 29, 2018, the contents of each of which are hereby incorporated by reference in their entirety.

FIELD

The present disclosure relates to CRISPR/Cas-related methods and components for editing a target nucleic acid sequence, or modulating expression of a target nucleic acid sequence. More particularly, this disclosure relates to synthetic guide molecules and related systems, methods and compositions.

BACKGROUND

CRISPRs (Clustered Regularly Interspaced Short Palindromic Repeats) evolved in bacteria and archaea as an adaptive immune system to defend against viral attack. Upon exposure to a virus, short segments of viral DNA are integrated into the CRISPR locus. RNA is transcribed from a portion of the CRISPR locus that includes the viral sequence. That RNA, which contains sequence complementary to the viral genome, mediates targeting of an RNA-guided nuclease protein such as Cas9 or Cpf1 to a target sequence in the viral genome. The RNA-guided nuclease, in turn, cleaves and thereby silences the viral target.

Recently, CRISPR systems have been adapted for genome editing in eukaryotic cells. These systems generally include a protein component (the RNA-guided nuclease) and a nucleic acid component (generally referred to as a guide molecule, guide RNA or gRNA). These two components form a complex that interacts with specific target DNA sequences recognized by, or complementary to, the two components of the system and optionally edits or alters the target sequence, for example by means of site-specific DNA cleavage. The editing or alteration of the target sequence may also involve the recruitment of cellular DNA repair mechanisms such as non-homologous end-joining (NHEJ) or homology-directed repair (HDR).

The value of CRISPR systems as a means of treating genetic diseases has been widely appreciated, but certain technical challenges must be addressed for therapeutics based on these systems to achieve broad clinical application. Among other things, a need exists for cost-effective and straightforward commercial-scale synthesis of high-quality CRISPR system components.

For instance, most guide molecules are currently synthesized by one of two methods: in-vitro transcription (IVT) and chemical synthesis. IVT typically involves the transcription of RNA from a DNA template by means of a bacterial RNA polymerase such as T7 polymerase. At present, IVT manufacturing of guide molecules in accordance with good manufacturing practice (GMP) standards required by regulators in the US and abroad may be costly and limited in scale. In addition, IVT synthesis may not be suitable for all guide RNA sequences: the T7 polymerase tends to transcribe sequences which initiate with a 5' guanine more efficiently than those initiated with another 5' base, and may recognize stem-loop structures followed by poly-uracil tracts, which structures are present in certain guide molecules, as a signal to terminate transcription, resulting in truncated guide molecule transcripts.

Chemical synthesis, on the other hand, is inexpensive and GMP-production for shorter oligonucleotides (e.g., less than 100 nucleotides in length) is readily available. Chemical synthesis methods are described throughout the literature, for instance by Beaucage and Carruthers, Curr Protoc Nucleic Acid Chem. 2001 May; Chapter 3: Unit 3.3 (Beaucage & Carruthers), which is incorporated by reference in its entirety and for all purposes herein. These methods typically involve the stepwise addition of reactive nucleotide monomers until an oligonucleotide sequence of a desired length is reached. In the most commonly used synthesis regimes (such as the phosphoramidite method) monomers are added to the 5' end of the oligonucleotide. These monomers are often 3' functionalized (e.g. with a phosphoramidite) and include a 5' protective group (such as a 4,4' dimethoxytrityl), for example according to Formula I, below:

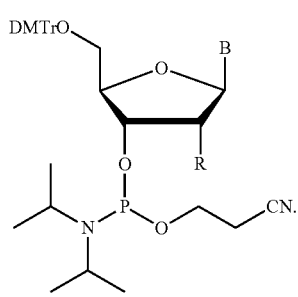

I

In Formula I, DMTr is 4,4'-dimethoxytrityl, R is a group which is compatible with the oligonucleotide synthesis conditions, non-limiting examples of which include H, F, O-alkyl, or a protected hydroxyl group, and B is any suitable nucleobase. (Beaucage & Carruthers). The use of 5' protected monomers necessitates a deprotection step following each round of addition in which the 5' protective group is removed to leave a hydroxyl group.

Whatever chemistry is utilized, the stepwise addition of 5' residues does not occur quantitatively; some oligonucleotides will "miss" the addition of some residues. This results in a synthesis product that includes the desired oligonucleotide, but is contaminated with shorter oligonucleotides missing various residues (referred to as "n−1 species," though they may include n−2, n−3, etc. as well as other truncation or deletion species). To minimize contamination by n−1 species, many chemical synthesis schemes include a "capping" reaction between the stepwise addition step and the deprotection step. In the capping reaction, a non-reactive moiety is added to the 5' terminus of those oligonucleotides that are not terminated by a 5' protective group; this non-reactive moiety prevents the further addition of monomers to the oligonucleotide, and is effective in reducing n−1 contamination to acceptably low levels during the synthesis of oligonucleotides of around 60 or 70 bases in length. However, the capping reaction is not quantitative either, and may be ineffective in preventing n−1 contamination in longer oligonucleotides such as unimolecular guide RNAs. On the other hand, there are occasions where DMT protection is lost during the coupling reaction, which result in longer oligonucleotides (referred to as "n+1 species," though they may include n+2, n+3, etc.). Unimolecular guide RNAs contaminated with n−1 species and/or n+1 species may not behave in the same ways as full-length guide RNAs prepared by other means, potentially complicating the use of synthesized guide RNAs in therapeutics.

SUMMARY

This disclosure addresses the need for a cost-effective and straightforward chemical synthesis of high-purity unimolecular guide molecules with minimal n−1 and/or n+1 species, truncation species, and other contaminants by providing, among other things, methods for synthesizing unimolecular guide molecules that involve cross-linking two or more pre-annealed guide fragments. In some embodiments, a unimolecular guide molecule provided herein has improved sequence fidelity at the 5' end, reducing undesired off-target editing. Also provided herein are compositions comprising, or consisting essentially of, the full length unimolecular guide molecules, which are substantially free of n−1 and/or n+1 contamination.

Certain aspects of this disclosure encompass the realization that pre-annealing of guide fragments may be particularly useful when the guide fragments are homomultifunctional (e.g., homobifunctional), such as the amine-functionalized fragments used in urea-based cross-linking methods described herein. Indeed, pre-annealing homomultifunctional guide fragments into heterodimers can reduce the formation of undesirable homodimers. This disclosure therefore also provides compositions comprising, or consisting essentially of, the full length unimolecular guide molecules, which are substantially free of side products (for example, homodimers). In some aspects, the present disclosure relates to a method of synthesizing a unimolecular guide molecule for a CRISPR system, the method comprising steps of:
  annealing a first oligonucleotide and a second oligonucleotide to form a duplex between a 3' region of the first oligonucleotide and a 5' region of the second oligonucleotide, wherein the first oligonucleotide comprises a first reactive group which is at least one of a 2' reactive group and a 3' reactive group, and wherein the second oligonucleotide comprises a second reactive group which is a 5' reactive group; and
  conjugating the annealed first and second oligonucleotides via the first and second reactive groups to form a unimolecular guide RNA molecule that includes a covalent bond linking the first and second oligonucleotides.

In some aspects, the present disclosure relates to unimolecular guide molecules for a CRISPR system. In some embodiments, a unimolecular guide molecule provided herein is for a Type II CRISPR system.

In some embodiments, a 5' region of the first oligonucleotide comprises a targeting domain that is fully or partially complementary to a target domain within a target sequence (e.g., a target sequence within a eukaryotic gene).

In some embodiments, a 3' region of the second oligonucleotide comprises one or more stem-loop structures.

In some embodiments, a unimolecular guide molecule provided herein is capable of interacting with a Cas9 molecule and mediating the formation of a Cas9/guide molecule complex.

In some embodiments, a unimolecular guide molecule provided herein is in a complex with a Cas9 or an RNA-guided nuclease.

In some embodiments, a unimolecular guide molecule provided herein comprises, from 5' to 3°:
  a first guide molecule fragment, comprising:
    a targeting domain sequence;
    a first lower stem sequence;
    a first bulge sequence; and
    a first upper stem sequence;
  a non-nucleotide chemical linkage; and
  a second guide molecule fragment, comprising
    a second upper stem sequence;
    a second bulge sequence; and
    a second lower stem sequence,
  wherein (a) at least one nucleotide in the first lower stem sequence is base paired with a nucleotide in the second lower stem sequence, and (b) at least one nucleotide in the first upper stem sequence is base paired with a nucleotide in the second upper stem sequence.

In some embodiments, the unimolecular guide molecule does not include a tetraloop sequence between the first and second upper stem sequences. In some embodiments, the first and/or second upper stem sequences comprise nucleotides that number from 4 to 22, inclusive.

In some embodiments, the unimolecular guide molecule is of formula $A_{3'}\text{-}i$ or $A_{2'}\text{-}i$:

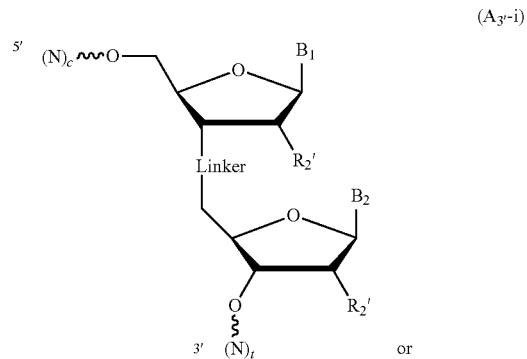

(A$_{3'}$-i)

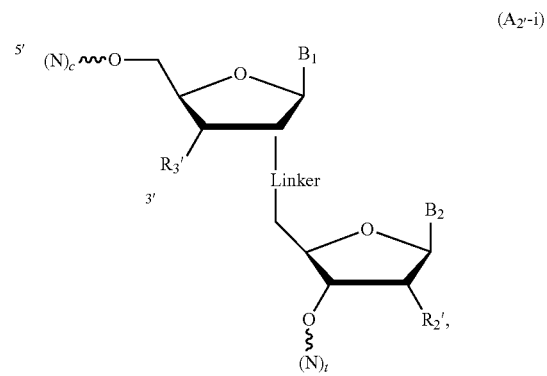

(A$_{2'}$-i)

wherein each N in (N)$_c$ and (N)$_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;

(N)$_c$ includes a 3' region that is complementary or partially complementary to, and forms a duplex with, a 5' region of (N)$_t$;

c is an integer 20 or greater;

t is an integer 20 or greater;

Linker is a non-nucleotide chemical linkage;

B$_1$ and B$_2$ are each independently a nucleobase;

each of R$_2$' and R$_3$' is independently H, OH, fluoro, chloro, bromo, NH$_2$, SH, S—R', or O—R' wherein each R' is independently a protection group or an alkyl group, wherein the alkyl group may be optionally substituted; and each ∿∿∿ represents independently a phosphodiester linkage, a phosphorothioate linkage, a phosphonoacetate linkage, a thiophosphonoacetate linkage, or a phosphoroamidate linkage.

In some embodiments, (N)$_c$ comprises a 3' region that comprises at least a portion of a repeat from a Type II CRISPR system. In some embodiments, (N)$_c$ comprises a 3' region that comprises a targeting domain that is fully or partially complementary to a target domain within a target sequence. In some embodiments, (N)$_t$ comprises a 3' region that comprises one or more stem-loop structures.

In some embodiments, the unimolecular guide molecule is of formula B$_3$'-i or B$_2$'-i:

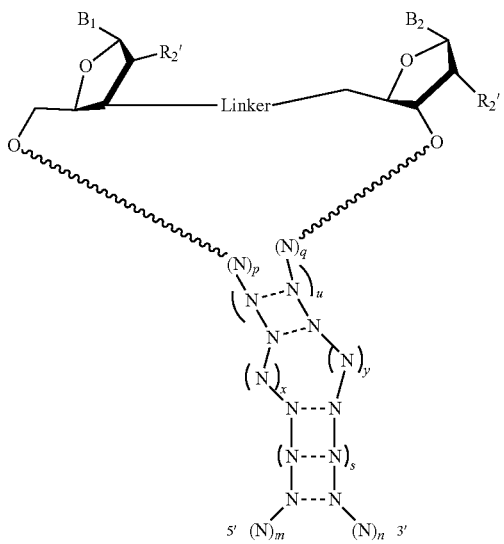

(B$_3$'-i)

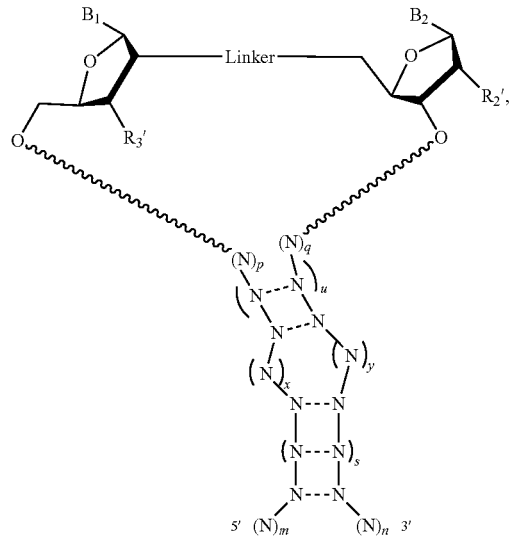

(B$_2$'-i)

wherein:
each N is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage; and each N—N independently represents two complementary nucleotides, optionally two complementary nucleotides that are hydrogen bonding base-paired;

p and q are each an integer between 0 and 6, inclusive, and p+q is an integer between 0 and 6, inclusive;

u is an integer between 2 and 22, inclusive;

s is an integer between 1 and 10, inclusive;

x is an integer between 1 and 3, inclusive;

y is >x and an integer between 3 and 5, inclusive;

m is an integer 15 or greater; and n is an integer 30 or greater.

In some embodiments, the guide molecule does not comprise a tetraloop (i.e., p and q are each 0). In some embodiments, the lower stem sequence and the upper stem sequence do not comprise an identical sequence of more than 3 nucleotides. In some embodiments, u is an integer between 3 and 22, inclusive.

In some embodiments, a guide molecule of formula A$_3$'-i, A$_2$'-i, B$_3$'-i, or B$_2$'-i is provided, wherein:

Linker is a non-nucleotide chemical linkage selected from a covalent bond and an optionally substituted, bivalent, straight or branched, saturated or unsaturated C$_1$-C$_{50}$ hydrocarbon chain, wherein one or more methylene units are optionally replaced by —O—, —S—, —N(R)—, —C(O)—, —C(S)—, —C(NR)—, —C(NOR)—, —C(NNR$_2$)—, —OC(O)—, —C(O)O—, —C(O)N(R)—, —N(R)C(O)—, —C(NR)O—, —OC(NR)—, —C(NR)NR—, —N(R)C(NR)—, —N(R)C(O)N(R)—, —N(R)C(O)O—, —OC(O)N(R)—, —N(R)C(O)S—, —SC(O)N(R)—, —N(R)C(NR)N(R)—, —SO$_2$—, —SO$_2$N(R)—, —N(R)SO$_2$—, —OP(O)(OH)O—, —OP(S)(OH)O—, —OP(S)(SH)O—, —OP(S)(COOH)O—, —OP(O)(COOH)O—, —OP(O)(NR$_2$)O—, —NP(O)(OH)O—, —OP(O)(OH)N—, or -Cy-;

each R is independently hydrogen or an optionally substituted group selected from $C_{1-6}$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur; and Cy is an optionally substituted, mono- or multicyclic, 3- to 20-membered, bivalent ring system, wherein the ring system is fully saturated, fully or partially unsaturated, or aromatic, and wherein the ring system contains 0-6 heteroatoms selected from the group consisting of O, N, and S.

In some embodiments, Linker comprises a urea, carbamate, amidine, amide, phosphoramidate, phosphodiester, disulfide, thioether or maleimide, as described herein.

In some embodiments, the unimolecular guide molecule comprises a group of formula $J_{3'}$-i or $J_{2'}$-i:

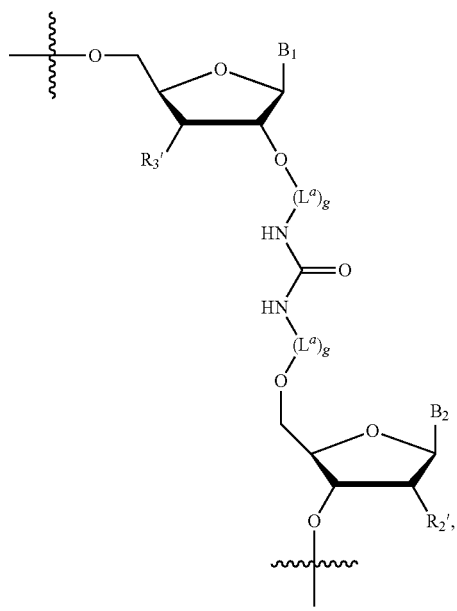

(J$_{2'}$-i)

wherein $B_1$, $B_2$, $R_2'$, and $R_3'$ are as defined in formulas $A_{3'}$-i and $A_{2'}$-i above; each g is independently 0, 1, 2, 3, 4, or 5; and $L^a$ is as described below and defined herein.

In some embodiments, the unimolecular guide molecule comprises a group of formula $J_{3'}$-ii, $J_{2'}$-ii, $J_{3'}$-iii, or $J_{2'}$-iii:

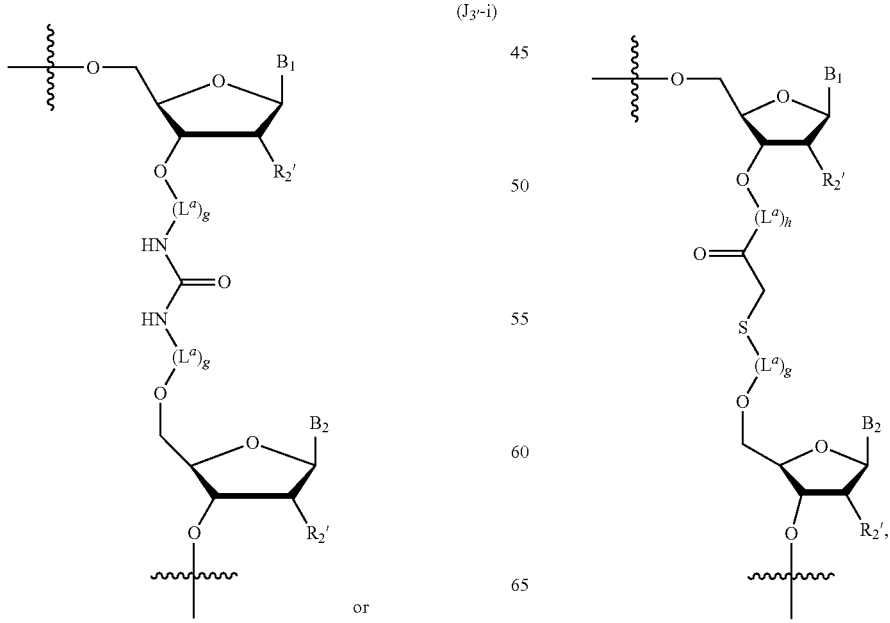

(J$_{3'}$-i)

or (J$_{3'}$-ii)

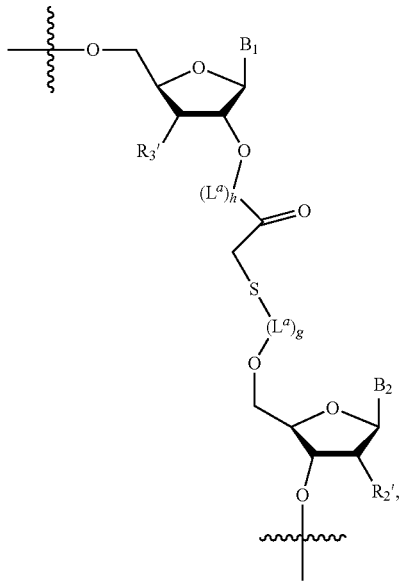

(J₂'-ii)

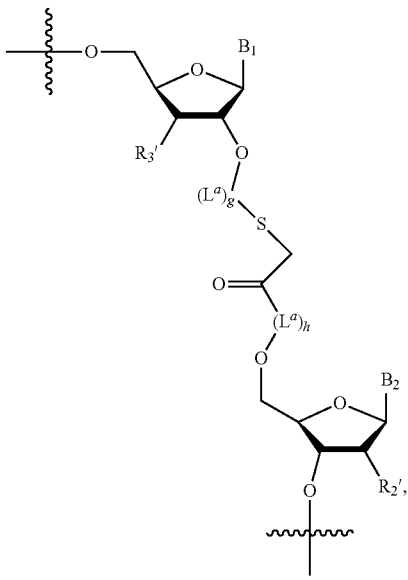

(J₂'-iii)

wherein $B_1$, $B_2$, $R_2'$, and $R_3'$ are as defined in formulas $J_3'$-i and $J_2'$-i above; each g is independently 0, 1, 2, 3, 4, or 5; each h is independently 0, 1, 2, 3, or 4; and $L^a$ is as described below and defined herein.

In some aspects, the present disclosure relates to a composition of guide molecules for a CRISPR system, comprising, or consisting essentially of, unimolecular guide molecules provided herein. In some embodiments, less than about 10% of the guide molecules comprise a truncation at a 5' end, relative to a reference guide molecule sequence. In some embodiments, at least about 99% of the guide molecules comprise a 5' sequence comprising nucleotides 1-20 of the guide molecule that is 100% identical to a corresponding 5' sequence of the reference guide molecule sequence.

In some embodiments, a composition of guide molecules provided herein is substantially free of homodimers. In some embodiments, the composition of guide molecules is substantially free of n+1 species. In some embodiments, the composition of guide molecules is substantially free of n−1 species. In some embodiments, the composition of guide molecules is substantially free of byproducts. In some embodiments, the composition of guide molecules is not substantially free of byproducts.

In some embodiments, a composition provided herein has not been subjected to any purification steps.

In some embodiments, a composition provided herein comprises a unimolecular guide molecule suspended in solution or in a pharmaceutically acceptable carrier.

In some aspects, the present disclosure relates to oligonucleotides useful for synthesizing a unimolecular guide molecule provided herein and/or for synthesizing a unimolecular guide molecule by a method provided herein. In some embodiments, the oligonucleotide intermediate is an annealed duplex. The present disclosure also provides methods of synthesizing unimolecular guide molecules provided herein.

In some aspects, the present disclosure relates to a method of altering a nucleic acid in a cell or subject comprising administering to the subject a guide molecule or a composition provided herein.

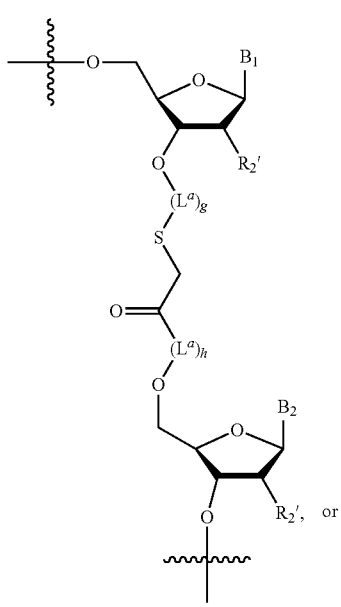

(J₃'-iii)

or

In some aspects, the present disclosure relates to a genome editing system comprising a guide molecule provided herein. In some embodiments, the genome editing system and/or the guide molecule is for use in therapy. In some embodiments, the genome editing system and/or the guide molecule is for use in the production of a medicament.

BRIEF DESCRIPTION OF THE DRAWINGS

The accompanying drawings are intended to provide illustrative, and schematic rather than comprehensive, examples of certain aspects and embodiments of the present disclosure. The drawings are not intended to be limiting or binding to any particular theory or model, and are not necessarily to scale. Without limiting the foregoing, nucleic acids and polypeptides may be depicted as linear sequences, or as schematic two- or three-dimensional structures; these depictions are intended to be illustrative rather than limiting or binding to any particular model or theory regarding their structure.

FIG. 5E shows expanded versions of the mass spectra. The mass spectrum for the commercially prepared synthetic unimolecular guide molecule is on the left side (34% purity by total mass) while the mass spectrum for the guide molecule conjugated with a urea linker according to the process of Example 1 is on the right side (72% purity by total mass).

In FIG. 15D, the typical a-d and x-z ions were observed, and MS/MS fragment ions on either side of the UR linkage from the 5'-end (m/z=487.1 and 461.1) and the 3'-end (m/z=603.1 and 577.1) were observed. In FIG. 15E, only two product ions were observed, including a MS/MS fragment ion from the 5'-end of the carbamate linkage (m/z=595.2) and the 3'-end of the CA linkage (m/z=603.1).

DETAILED DESCRIPTION

Definitions and Abbreviations

Figure 1A:
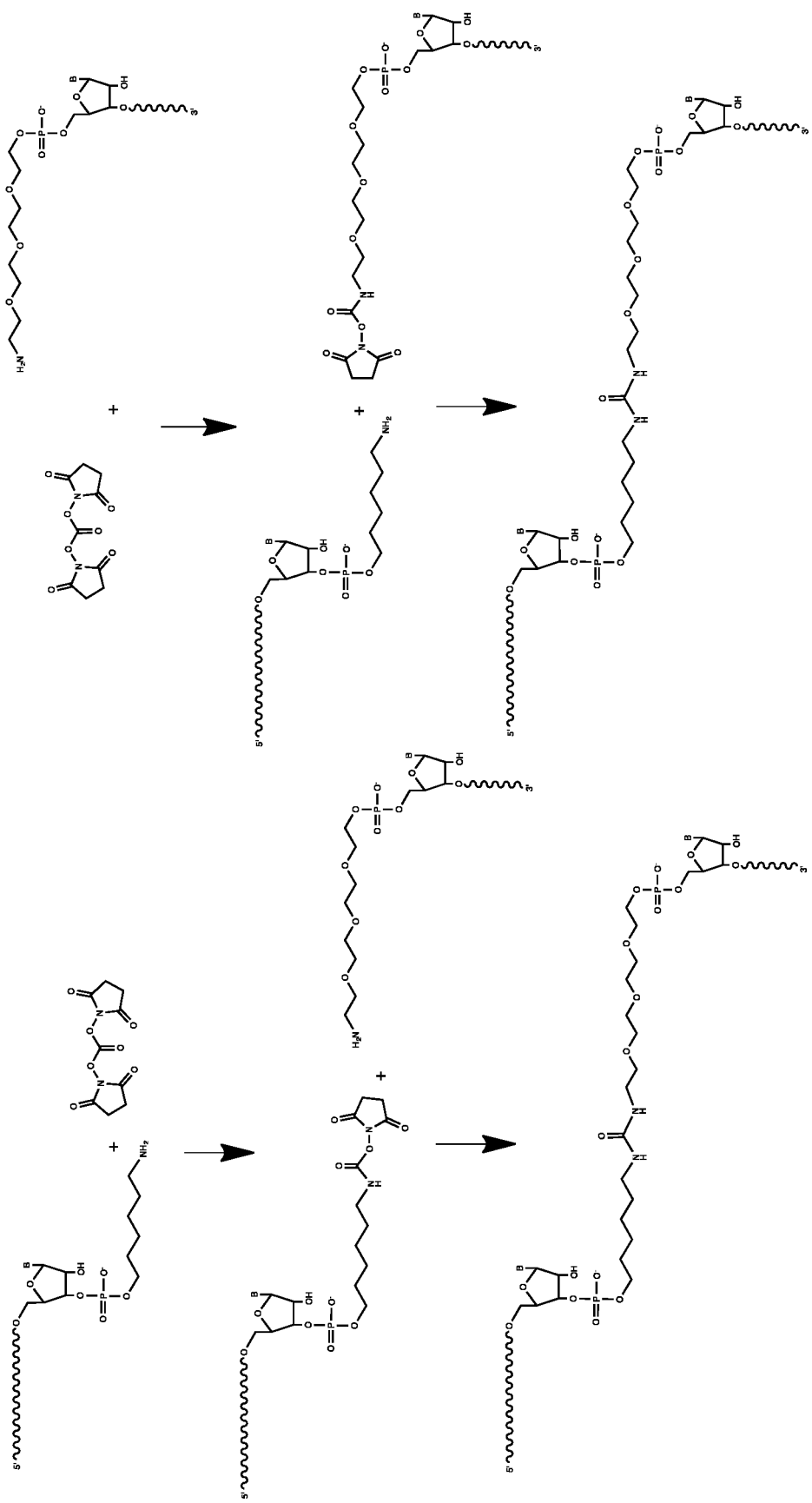
FIG. 1A depicts an exemplary cross-linking reaction process according to certain embodiments of this disclosure.

Unless otherwise specified, each of the following terms has the meaning associated with it in this section.

The indefinite articles "a" and "an" refer to at least one of the associated noun, and are used interchangeably with the terms "at least one" and "one or more." For example, "a module" means at least one module, or one or more modules.

The conjunctions "or" and "and/or" are used interchangeably as non-exclusive disjunctions.

The phrase "consisting essentially of" means that the species recited are the predominant species, but that other species may be present in trace amounts or amounts that do not affect structure, function or behavior of the subject composition. For instance, a composition that consists essentially of a particular species will generally comprise 90%, 95%, 96%, or more (by mass or molarity) of that species.

The phrase "substantially free of molecules" means that the molecules are not major components in the recited composition. For example, a composition substantially free of a molecule means that the molecule is less than 5%, 4%, 3%, 2%, 1%, 0.5%, or 0.1% (by mass or molarity) in the composition. The amount of a molecule can be determined by various analytical techniques, e.g., as described in the Examples. In some embodiments, compositions provided herein are substantially free of certain molecules, wherein the molecules are less than 5%, 4%, 3%, 2%, 1%, 0.5%, or 0.1% (by mass or molarity) as determined by gel electrophoresis. In some embodiments, compositions provided herein are substantially free of certain molecules, wherein the molecules are less than 5%, 4%, 3%, 2%, 1%, 0.5%, or 0.1% (by mass or molarity) as determined by mass spectrometry.

"Domain" is used to describe a segment of a protein or nucleic acid. Unless otherwise indicated, a domain is not required to have any specific functional property.

The term "complementary" refers to pairs of nucleotides that are capable of forming a stable base pair through hydrogen bonding. For example, U is complementary to A and G is complementary to C. It will be appreciated by those skilled in the art that whether a particular pair of complementary nucleotides are associated through hydrogen bond base pairing (e.g., within a guide molecule duplex) may depend on the context (e.g., surrounding nucleotides and chemical linkage) and external conditions (e.g., temperature and pH). It is therefore to be understood that complementary nucleotides are not necessarily associated through hydrogen bond base pairing.

A "covariant" sequence differs from a reference sequence by substitution of one or more nucleotides in the reference sequence with a complementary nucleotide (e.g., one or more Us are replaced with As, one or more Gs are replaced with Cs, etc.). When used with reference to a region that includes two complementary sequences that form a duplex (e.g., the upper stem of a guide molecule), the term "covariant" encompasses duplexes with one or more nucleotide swaps between the two complementary sequences of the reference duplex (i.e., one or more A-U swaps and/or one or more G-C swaps) as illustrated in Table 1 below:

TABLE 1

Covariant sequences of a sequence of three nucleotides.

| | |
|---|---|
| A----U | U----A |
| G----C | G----C |
| C----G | C----G |
| A----U | A----U |
| C----G | G----C |
| C----G | G----C |
| U----A | U----A |
| C----G | G----C |
| C----G | G----C |
| A----U | U----A |
| C----G | C----G |
| G----C | G----C |

In some embodiments, a covariant sequence may exhibit substantially the same energetic favorability of a particular annealing reaction as the reference sequence (e.g., formation of a duplex in the context of a guide molecule of the present disclosure). As described elsewhere in the present disclosure, the energetic favorability of a particular annealing reaction may be measured empirically or predicted using computational models.

An "indel" is an insertion and/or deletion in a nucleic acid sequence. An indel may be the product of the repair of a DNA double strand break, such as a double strand break formed by a genome editing system of the present disclosure. An indel is most commonly formed when a break is repaired by an "error prone" repair pathway such as the NHEJ pathway described below.

"Gene conversion" refers to the alteration of a DNA sequence by incorporation of an endogenous homologous sequence (e.g., a homologous sequence within a gene array). "Gene correction" refers to the alteration of a DNA sequence by incorporation of an exogenous homologous sequence, such as an exogenous single or double stranded donor template DNA. Gene conversion and gene correction are products of the repair of DNA double-strand breaks by HDR pathways such as those described below.

Indels, gene conversion, gene correction, and other genome editing outcomes are typically assessed by sequencing (most commonly by "next-gen" or "sequencing-by-synthesis" methods, though Sanger sequencing may still be used) and are quantified by the relative frequency of numerical changes (e.g., +1, +2 or more bases) at a site of interest among all sequencing reads. DNA samples for sequencing may be prepared by a variety of methods known in the art, and may involve the amplification of sites of interest by polymerase chain reaction (PCR), the capture of DNA ends generated by double strand breaks, as in the GUIDEseq process described in Tsai et al. (Nat. Biotechnol. 34 (5): 483 (2016), incorporated by reference herein) or by other means well known in the art. Genome editing outcomes may also be assessed by in situ hybridization methods such as the FiberComb™ system commercialized by Genomic Vision (Bagneux, France), and by any other suitable methods known in the art.

"Alt-HDR," "alternative homology-directed repair," or "alternative HDR" are used interchangeably to refer to the process of repairing DNA damage using a homologous nucleic acid (e.g., an endogenous homologous sequence, e.g., a sister chromatid, or an exogenous nucleic acid, e.g., a template nucleic acid). Alt-HDR is distinct from canonical HDR in that the process utilizes different pathways from canonical HDR, and can be inhibited by the canonical HDR mediators, RAD51 and BRCA2. Alt-HDR is also distinguished by the involvement of a single-stranded or nicked homologous nucleic acid template, whereas canonical HDR generally involves a double-stranded homologous template.

"Canonical HDR," "canonical homology-directed repair" or "cHDR" refer to the process of repairing DNA damage using a homologous nucleic acid (e.g., an endogenous homologous sequence, e.g., a sister chromatid, or an exogenous nucleic acid, e.g., a template nucleic acid). Canonical HDR typically acts when there has been significant resection at the double strand break, forming at least one single stranded portion of DNA. In a normal cell, cHDR typically involves a series of steps such as recognition of the break, stabilization of the break, resection, stabilization of single stranded DNA, formation of a DNA crossover intermediate, resolution of the crossover intermediate, and ligation. The process requires RAD51 and BRCA2, and the homologous nucleic acid is typically double-stranded.

Unless indicated otherwise, the term "HDR" as used herein encompasses both canonical HDR and alt-HDR.

"Non-homologous end joining" or "NHEJ" refers to ligation-mediated repair and/or non-template-mediated repair including canonical NHEJ (cNHEJ) and alternative NHEJ (altNHEJ), which in turn includes microhomology-mediated end joining (MMEJ), single-strand annealing (SSA), and synthesis-dependent microhomology-mediated end joining (SD-MMEJ).

"Replacement" or "replaced," when used with reference to a modification of a molecule (e.g., a nucleic acid or protein), does not require a process limitation but merely indicates that the replacement entity is present.

"Subject" means a human or non-human animal. A human subject can be any age (e.g., an infant, child, young adult, or adult), and may suffer from a disease, or may be in need of alteration of a gene. Alternatively, the subject may be an animal, which term includes, but is not limited to, mammals, birds, fish, reptiles, amphibians, and more particularly non-human primates, rodents (such as mice, rats, hamsters, etc.), rabbits, guinea pigs, dogs, cats, and so on. In certain embodiments of this disclosure, the subject is livestock, e.g., a cow, a horse, a sheep, or a goat. In certain embodiments, the subject is poultry.

"Treat," "treating," and "treatment" mean the treatment of a disease in a subject (e.g., a human subject), including one or more of inhibiting the disease, i.e., arresting or preventing its development or progression; relieving the disease, i.e., causing regression of the disease state; relieving one or more symptoms of the disease; and curing the disease.

"Prevent," "preventing," and "prevention" refer to the prevention of a disease in a subject, e.g., in a human, including (a) avoiding or precluding the disease; (b) affecting the predisposition toward the disease; or (c) preventing or delaying the onset of at least one symptom of the disease.

A "kit" refers to any collection of two or more components that together constitute a functional unit that can be employed for a specific purpose. By way of illustration (and not limitation), one kit according to this disclosure can include a guide molecule complexed or able to complex with an RNA-guided nuclease, and accompanied by (e.g., suspended in, or suspendable in) a pharmaceutically acceptable carrier. The kit can be used to introduce the complex into, for example, a cell or a subject, for the purpose of causing a desired genomic alteration in such cell or subject. The components of a kit can be packaged together, or they may be separately packaged. Kits according to this disclosure also optionally include directions for use (DFU) that describe the use of the kit, e.g., according to a method of this disclosure. The DFU can be physically packaged with the kit, or it can be made available to a user of the kit, for instance by electronic means.

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. The polynucleotides, nucleotide sequences, nucleic acids, etc. can be chimeric mixtures or derivatives or modified versions thereof, single-stranded or double-stranded. They can be modified at the base moiety, sugar moiety, or phosphate backbone, for example, to improve stability of the molecule, its hybridization parameters, etc. A nucleotide sequence typically carries genetic information, including, but not limited to, the information used by cellular machinery to make proteins and enzymes. These terms include double- or single-stranded genomic DNA, RNA, any synthetic and genetically manipulated polynucleotide, and both sense and antisense polynucleotides. These terms also include nucleic acids containing modified bases.

Conventional IUPAC notation is used in nucleotide sequences presented herein, as shown in Table 2, below (see also Cornish-Bowden A, Nucleic Acids Res. 1985 May 10; 13 (9): 3021-30, incorporated by reference herein). It should be noted, however, that "T" denotes "Thymine or Uracil" in those instances where a sequence may be encoded by either DNA or RNA, for example in guide molecule targeting domains.

TABLE 2

IUPAC nucleic acid notation

| Character | Base |
|---|---|
| A | Adenine |
| T | Thymine or Uracil |
| G | Guanine |
| C | Cytosine |
| U | Uracil |
| K | G or T/U |
| M | A or C |
| R | A or G |
| Y | C or T/U |
| S | C or G |
| W | A or T/U |
| B | C, G or T/U |
| V | A, C or G |
| H | A, C or T/U |
| D | A, G or T/U |
| N | A, C, G or T/U |

The terms "protein," "peptide" and "polypeptide" are used interchangeably to refer to a sequential chain of amino acids linked together via peptide bonds. The terms include individual proteins, groups or complexes of proteins that associate together, as well as fragments or portions, variants, derivatives and analogs of such proteins. Peptide sequences are presented herein using conventional notation, beginning with the amino or N-terminus on the left, and proceeding to the carboxyl or C-terminus on the right. Standard one-letter or three-letter abbreviations can be used.

The term "variant" refers to an entity such as a polypeptide, polynucleotide or small molecule that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity.

Overview

Certain embodiments of this disclosure relate, in general, to methods for synthesizing guide molecules in which two or more guide fragments are (a) annealed to one another, and then (b) cross-linked using an appropriate cross-linking chemistry. The inventors have found that methods comprising a step of pre-annealing guide fragments prior to cross-linking them improves the efficiency of cross-linking and tends to favor the formation of a desired heterodimeric product, even when a homomultifunctional cross-linker is used. While not wishing to be bound by any theory, the improvements in cross-linking efficiency and, consequently, in the yield of the desired reaction product, are thought to be due to the increased stability of an annealed heterodimer as a cross-linking substrate as compared with non-annealed homodimers, and/or the reduction in the fraction of free RNA fragments available to form homodimers, etc. achieved by pre-annealing.

The methods of this disclosure, which include pre-annealing of guide fragments, have a number of advantages, including without limitation: they allow for high yields to be achieved even when the fragments are homomultifunctional (e.g., homobifunctional), such as the amine-functionalized fragments used in the urea-based cross-linking methods described herein; the reduction or absence of undesirable homodimers and other reaction products may in turn simplify downstream purification; and because the fragments used for cross-linking tend to be shorter than full-length guide molecules, they may exhibit a lower level of contamination by n−1 species, truncation species, n+1 species, and other contaminants than observed in full-length synthetic guide molecules.

With respect to pre-annealing, those of skill in the art will appreciate that longer tracts of annealed bases may be more stable than shorter tracts, and that between two tracts of similar length, a greater degree of annealing will generally be associated with greater stability. Accordingly, in certain embodiments of this disclosure, fragments are designed so as to maximize the degree of annealing between fragments, and/or to position functionalized 3' or 5' ends in close proximity to annealed bases and/or to each other.

Figure 1B:
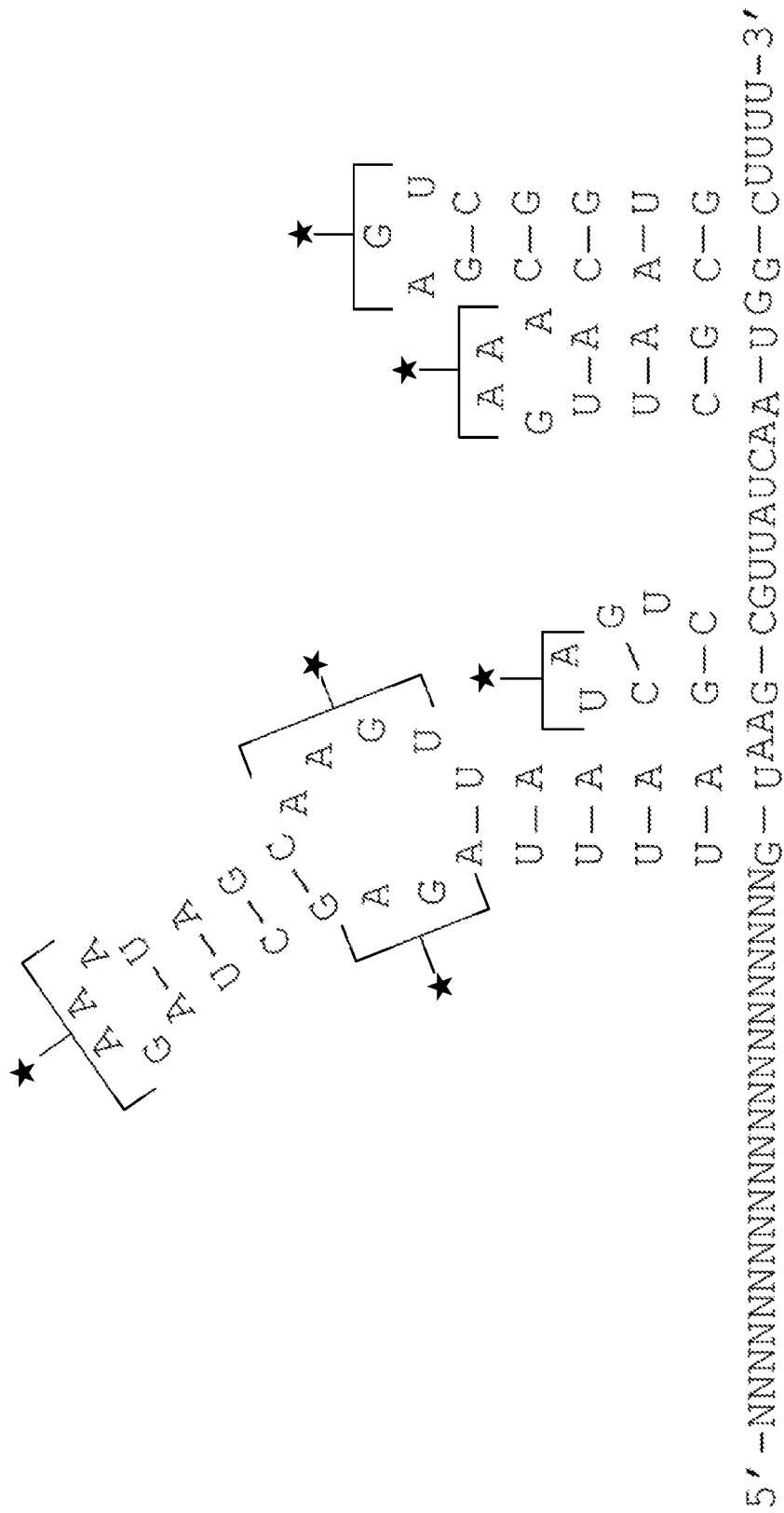
FIG. 1B depicts, in two-dimensional schematic form, an exemplary S. pyogenes guide molecule highlighting positions (with a star) at which first and second guide molecule fragments are cross-linked together according to various embodiments of this disclosure.
Figure 1C:
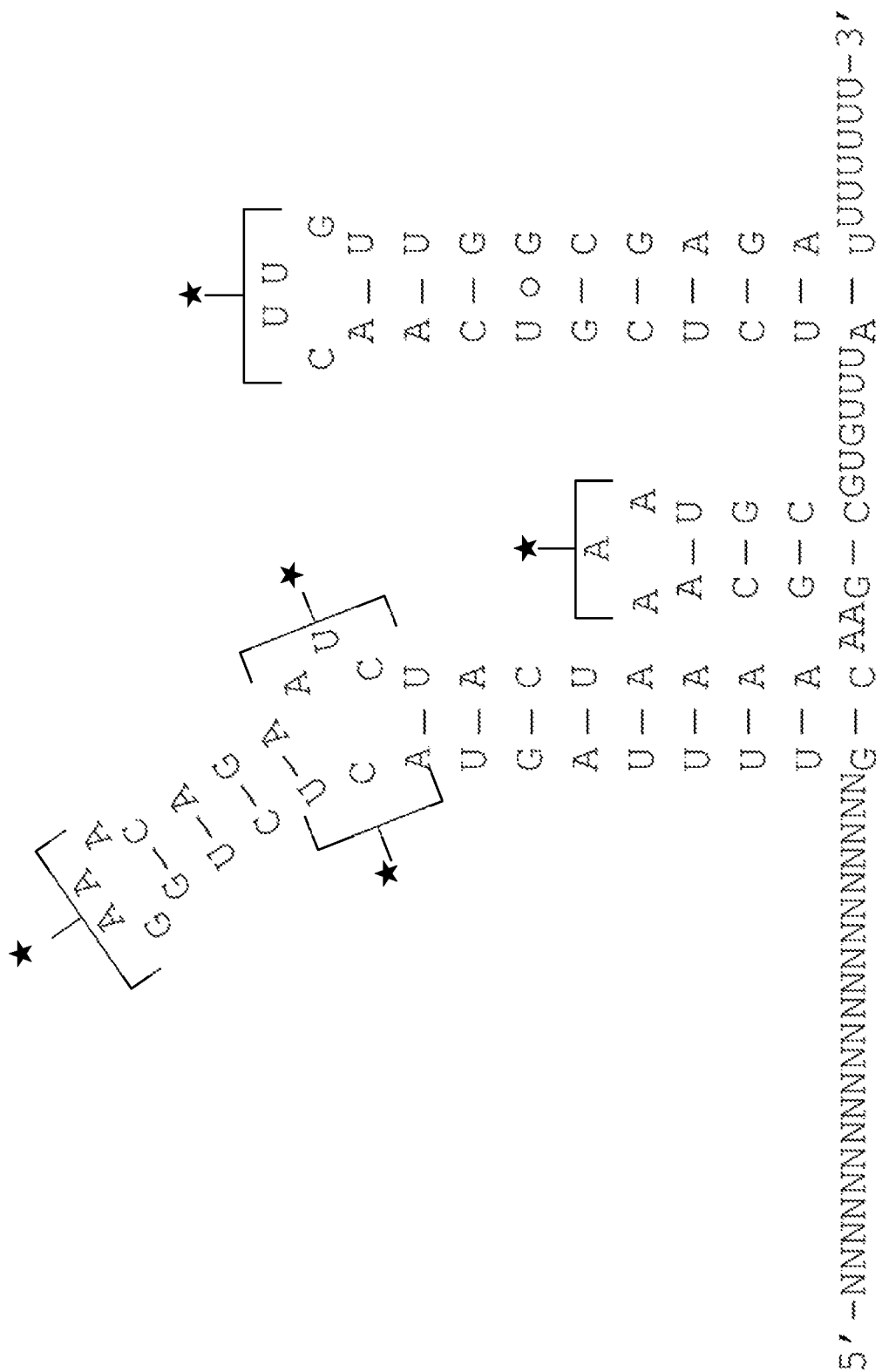
FIG. 1C depicts, in two-dimensional schematic form, an exemplary S. aureus guide molecule highlighting positions (with a star) at which first and second guide molecule fragments are cross-linked together according to various embodiments of this disclosure.

As is discussed in greater detail below, certain unimolecular guide molecules, particularly unimolecular Cas9 guide molecules, are characterized by comparatively large stem-loop structures. For example, FIGS. 1B and 1C depict the two-dimensional structures of unimolecular S. pyogenes and S. aureus gRNAs, and it will be evident from the figures that both gRNAs generally include a relatively long stem-loop structure with a "bulge." In certain embodiments, synthetic guide molecules include a cross-link between fragments within this stem loop structure. This is achieved, in some cases, by cross-linking first and second fragments having complementary regions at or near their 3' and 5' ends, respectively; the 3' and 5' ends of these fragments are functionalized to facilitate the cross-linking reaction, as shown for example in Formulas II and III, below:

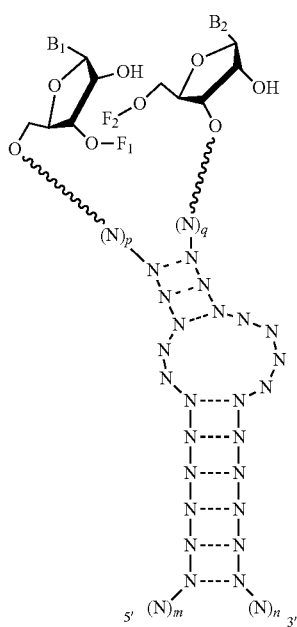

II

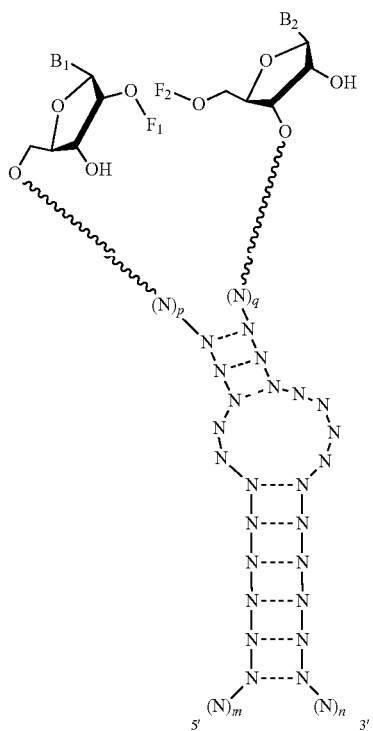

III

In these formulas, p and q are each independently an integer between 0 and 6, inclusive and p+q is an integer between 0 and 6, inclusive;

m is an integer between 20 and 40, inclusive;

n is an integer between 30 and 70, inclusive;

each ∿∿∿ represents a phosphodiester linkage, a phosphorothioate linkage, a phosphonoacetate linkage, a thiophosphonoacetate linkage, or a phosphoroamidate linkage;

N—N independently represents two complementary nucleotides, optionally two complementary nucleotides that are hydrogen bonding base-paired; and $F_1$ and $F_2$ each comprise a functional group such that they can undergo a cross-linking reaction to cross-link the two guide fragments.

Exemplary cross-linking chemistries are set forth in Table 3 below.

TABLE 3

Exemplary cross-linking chemistries

| Reaction Type | Reaction Summary |
|---|---|
| Thiol-yne | $R_1$———≡ + HS—$R_2$ → [vinyl sulfide product with S—$R_2$ and $R_1$] |
| NHS esters | [NHS ester of $R_1$] + $H_2N$—$R_2$ → [amide $R_1$-C(O)-NH-$R_2$] |

TABLE 3-continued

Exemplary cross-linking chemistries

| Reaction Type | Reaction Summary |
|---|---|
| Thiol-ene | $R_1{-}CH{=}CH_2 + HS{-}R_2 \xrightarrow{h\nu,\ cat.} R_1{-}CH_2CH_2{-}S{-}R_2$ |
| Isocyanates | $R_1{-}NCO + HX{-}R_2 \longrightarrow R_1{-}NH{-}C(O){-}X{-}R_2$    X = S or NH |
| Epoxide or aziridine | Epoxide or aziridine + $HS{-}R_2 \longrightarrow$ HO-CH(R_1)-CH_2-S-R_2 or H_2N-CH(R_1)-CH_2-S-R_2 |
| Aldehyde-aminoxy | $R_1{-}CHO + H_2N{-}O{-}R_2 \longrightarrow R_1{-}CH{=}N{-}O{-}R_2$ |
| Cu-catalyzed-azide-alkyne cycloaddition | $R_1{-}N_3 + HC{\equiv}C{-}R_2 \xrightarrow{Cu^{+}}$ 1,4-triazole |
| Strain-promoted cycloaddition | Cyclooctyne cycloaddition (with azide or nitrile oxide or nitrone); Norbornene cycloaddition (with azide or nitrile oxide or nitrone); Oxanorbornadiene cycloaddition |

TABLE 3-continued
Exemplary cross-linking chemistries
| Reaction Type | Reaction Summary |
|---|---|
| | 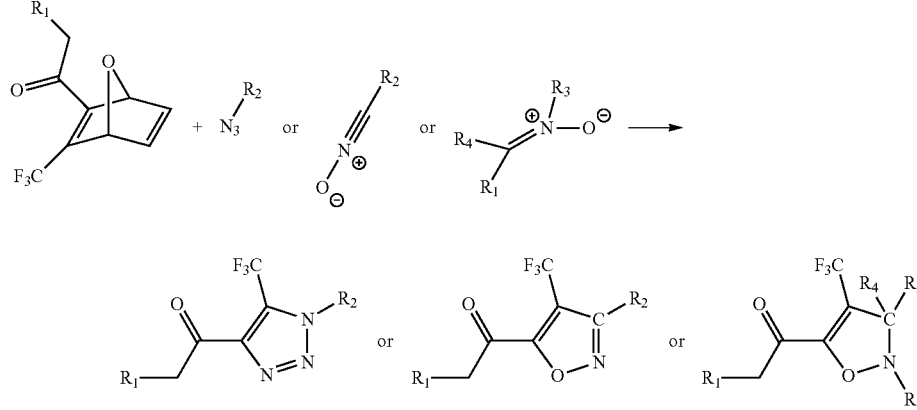 |
| Staudinger ligation | 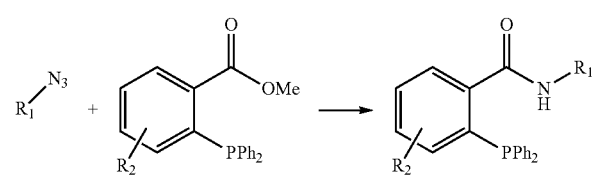 |
| Tetrazine ligation | 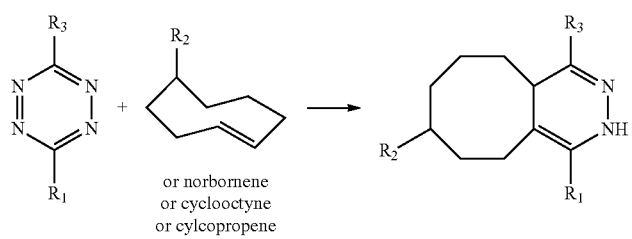 |
| Photo-induced tetrazole-alkene cycloaddition | 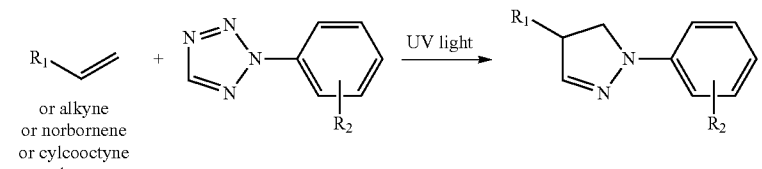 |

TABLE 3-continued

Exemplary cross-linking chemistries

| Reaction Type | Reaction Summary |
|---|---|
| [4 + 1] cycloaddition | 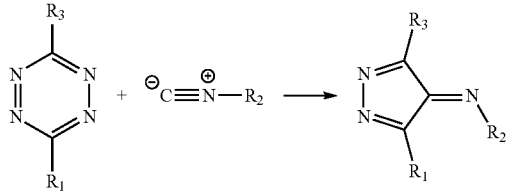 |
| Quadricyclane ligation | 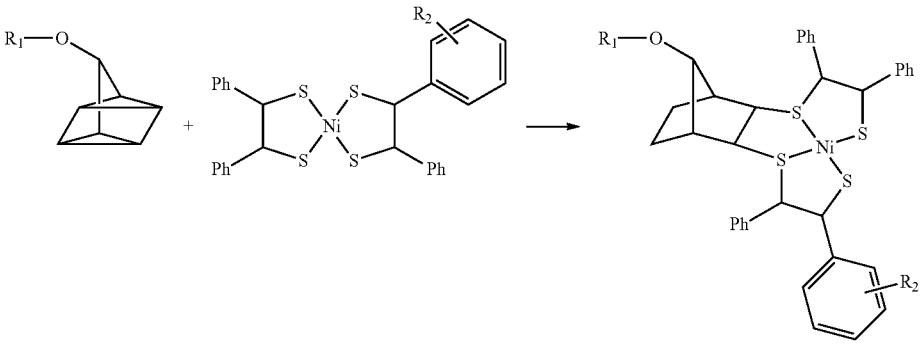 |

While Formulas II and III depict a cross-linker positioned within a "tetraloop" structure (or a cross-linker replacing the "tetraloop" structure) in the guide molecule repeat-antirepeat duplex, it will be appreciated that cross-linkers may be positioned anywhere in the molecules, for example, in any stem loop structure occurring within a guide molecule, including naturally-occurring stem loops and engineered stem loops. In particular, certain embodiments of this disclosure relate to guide molecules lacking a tetraloop structure and comprising a cross-linker positioned at the terminus of first and second complementary regions (for instance, at the 3' terminus of a first upper stem region and the 5' terminus of a second upper stem region).

Formulas II and III depict guide molecules that may ($p>0$ and $q>0$) or may not ($p=0$ and $q=0$) contain a "tetraloop" structure in the repeat-antirepeat duplex. One aspect of this invention is the recognition that guide molecules lacking a "tetraloop" may exhibit enhanced ligation efficiency as a result of having the functionalized 3' and 5' ends in close proximity and in a suitable orientation.

Alternatively, or additionally, a cross-linking reaction according to this disclosure can include a "splint" or a single stranded oligonucleotide that hybridizes to a sequence at or near the functionalized 3' and 5' ends in order to stably bring those functionalized ends into proximity with one-another.

The present disclosure also encompasses the recognition that guide molecules with longer duplexes (e.g., with extended upper stems) may exhibit enhanced ligation efficiency as compared to guide molecules with shorter duplexes. These longer duplex structures are referred to in this disclosure as "extended duplexes," and are generally (but not necessarily) positioned in proximity to a functionalized nucleotide in a guide fragment. Thus, in some embodiments, the present disclosure provides guide molecules of Formulas VIII and IX, below:

VIII

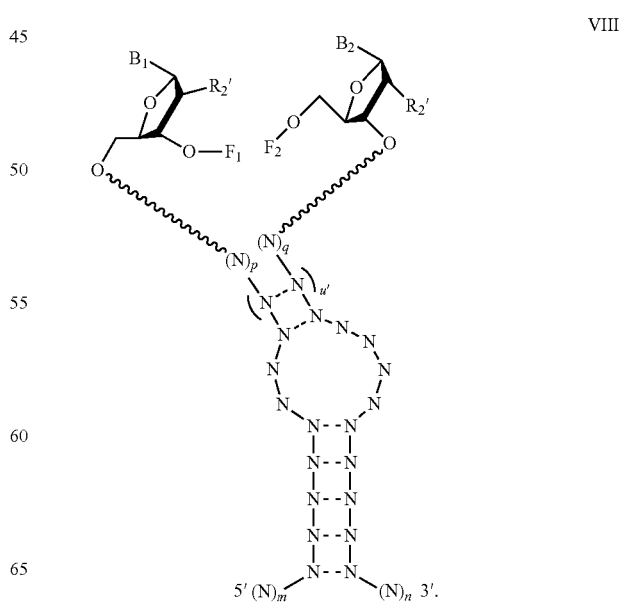

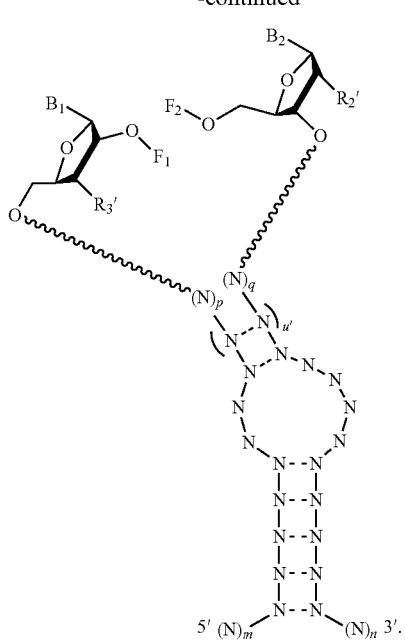

In Formulas VIII and IX, p and q are each independently an integer between 0 and 4, inclusive;

p+q is an integer between 0 and 4, inclusive;

u' is an integer between 2 and 22, inclusive; and other variables are defined as in Formulas II and III.

Formulas VIII and IX depict a duplex with an optionally extended upper stem, as well as an optional tetraloop (i.e., no tetraloop when p and q are 0). Guide molecules of Formula VIII and IX may be advantageous due to increased ligation efficiency resulting from a longer upper stem. Furthermore, the combination of a longer upper stem and the absence of a tetraloop may be beneficial for achieving an appropriate orientation of reactive groups $F_1$ and $F_2$ for the ligation reaction.

Another aspect of this invention relates to the recognition that guide fragments may include multiple regions of complementarity within a single guide fragment and/or between different guide fragments. For example, in certain embodiments of this disclosure, first and second guide fragments are designed with complementary upper and lower stem regions that, when fully annealed, result in a heterodimer in which (a) first and second functional groups are positioned at the terminus of a duplexed upper stem region in suitable proximity for a cross-linking reaction and/or (b) a duplexed structure is formed between the first and second guide fragments that is capable of supporting the formation of a complex between the guide molecule and the RNA-guided nuclease. However, it may be possible for the first and second guide fragments to anneal incompletely with one another, or to form internal duplexes or homodimers, whereby (a) and/or (b) does not occur. As one example, in S. pyogenes guide molecules based on the wild-type crRNA and tracrRNA sequences, there may be multiple highly complementary sequences such as poly-U or poly-A tracts in the lower and upper stem that may lead to improper "staggered" heterodimers involving annealing between upper and lower stem regions, rather than the desired annealing of upper stem regions with one another. Similarly, undesirable duplexes may form between the targeting domain sequence of a guide fragment and another region of the same guide fragment or a different fragment, and mispairing may occur between otherwise complementary regions of first and second guide fragments, potentially resulting in incomplete duplexation, bulges and/or unpaired segments.

While it is not practical to predict all possible undesirable internal or intermolecular duplex structures that may form between guide fragments, the inventors have found that, in some cases, modifications made to reduce or prevent the formation of a specific mis-pairing or undesirable duplex may have a significant effect on the yield of a desired guide molecule product in a cross-linking reaction, and/or result in a reduction of one or more contaminant species from the same reaction. Thus, in some embodiments, the present disclosure provides guide molecules and methods where the primary sequence of the guide fragments has been designed to avoid a particular mispairing or undesirable duplex (e.g., by swapping two complementary nucleotides between the first and second guide fragments). For example, an A-U swap in the upper stem of the wild-type S. pyogenes guide fragments mentioned above would produce a first guide fragment that includes non-identical UUUU and UAUU sequences and a second guide fragment that includes sequences complementary to the modified sequences of the first fragment, namely AAAA and AUAA sequences. More broadly, guides may incorporate sequence changes, such as a nucleotide swap between two duplexed portions of an upper or lower stem, an insertion, deletion or replacement of a sequence in an upper or lower stem, or structural changes such as the incorporation of locked nucleic acids (LNAs) in positions selected to reduce or eliminate the formation of a secondary structure.

While not wishing to be bound by any theory, it is believed that the duplex extensions, sequence modifications and structural modifications described herein promote the formation of desirable duplexes and reduce mis-pairing and the formation of undesirable duplexes by increasing the energetic favorability of the formation of a desirable duplex relative to the formation of a mis-paired or undesirable duplex. The energetic favorability of a particular annealing reaction may be represented by the Gibbs free energy ($\Delta G$); negative $\Delta G$ values are associated with spontaneous reactions, and a first annealing reaction is more energetically favorable than a second reaction if the $\Delta G$ of the first reaction is less than (i.e., more negative than) the $\Delta G$ of the second reaction. $\Delta G$ may be assessed empirically, based on the thermal stability (melting behavior) of particular duplexes, for example using NMR, fluorescence quenching, UV absorbance, calorimetry, etc. as described by You, Tatourov and Owczarzy, "Measuring Thermodynamic Details of DNA Hybridization Using Fluorescence" Biopolymers Vol. 95, No. 7, pp. 472-486 (2011), which is incorporated by reference herein for all purposes. (See, e.g., "Introduction" at pp. 472-73 and "Materials and Methods" at pp. 473-475.) However, it may be more practical when designing guide fragments and annealing reactions to employ computational models to evaluate the free energy of correct duplexation and of selected mis-pairing or undesirable duplexation reactions, and a number of tools are available to perform such modeling, including the biophysics.idtdna.com tool hosted by Integrated DNA Technologies (Coralville, Iowa). Alternatively or additionally, a number of algorithms utilizing thermodynamic nearest neighbor models (TNN) are described in the literature. See, e.g., Tulpan, Andronescu and Leger, "*Free energy estimation of short DNA duplex hybridizations*," BMC Bioinformatics, Vol. 11, No. 105 (2010). (See "Background" on pp. 1-2 describing TNN models and the MultiRNAFold package, the Vienna package and the UNAFold package). Other algorithms have also been described in the literature, e.g., by Kim et al. "*An evolutionary Monte Carlo algorithm for predicting DNA hybridization*," J. Biosystems Vol. 7, No. 5 (2007). (See section 2 on pp. 71-2 describing the model.) Each of the foregoing references is incorporated by reference in its entirety and for all purposes.

Figure 3A:
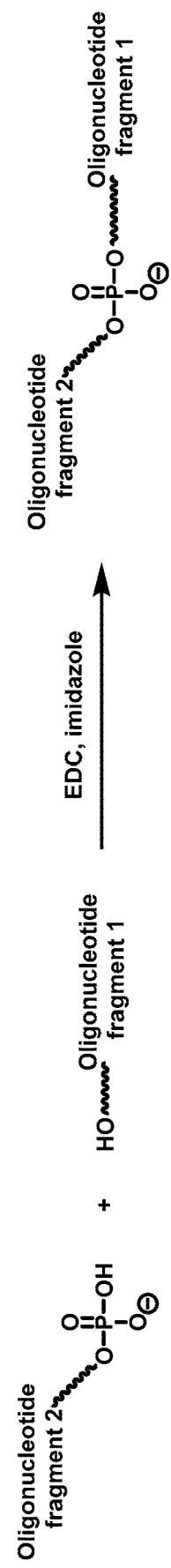
FIG. 3A depicts an exemplary cross-linking reaction process according to certain embodiments of this disclosure.
Figure 3B:
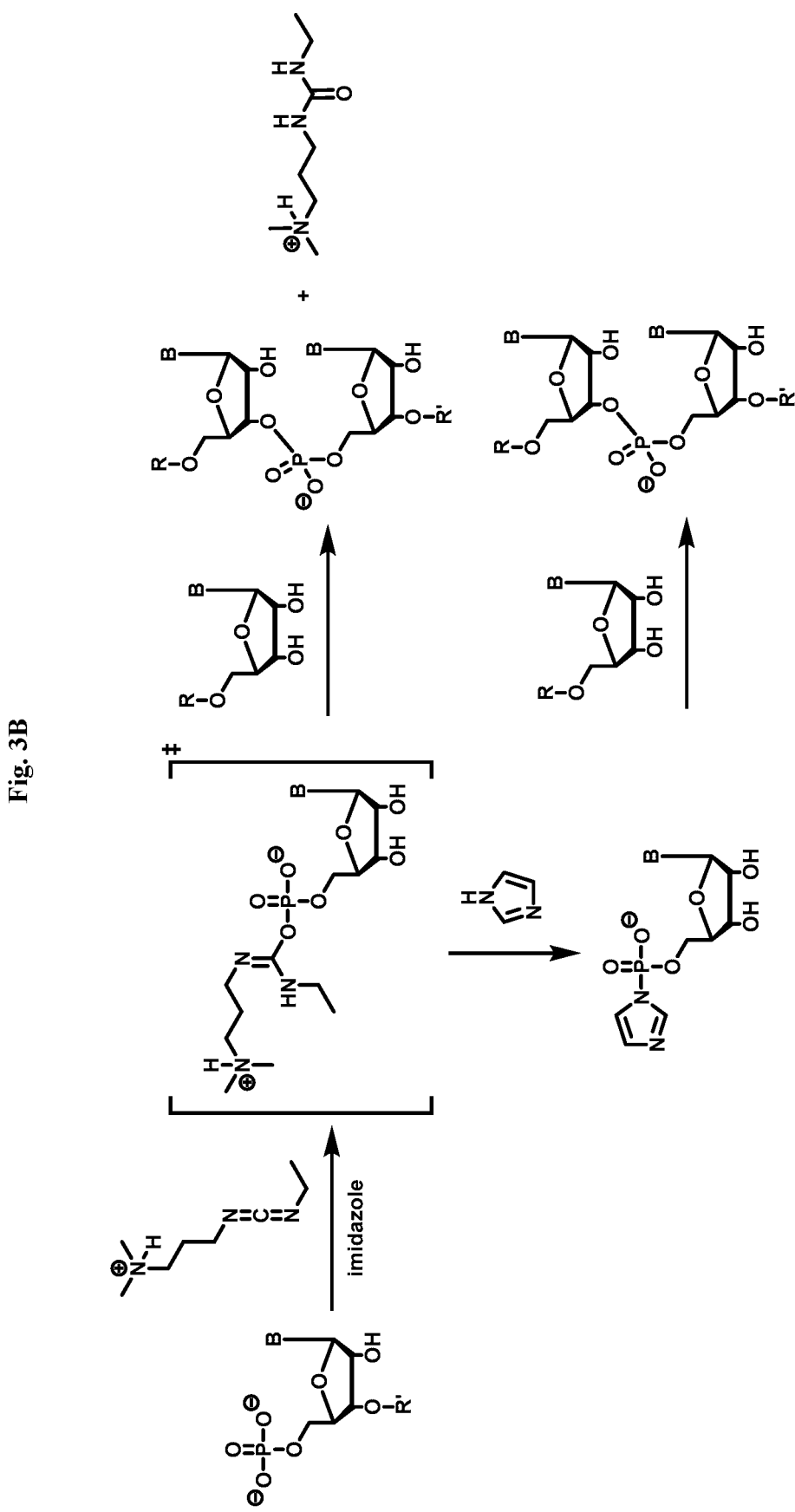
FIG. 3B depicts steps in an exemplary cross-linking reaction process according to certain embodiments of this disclosure.
Figure 3C:
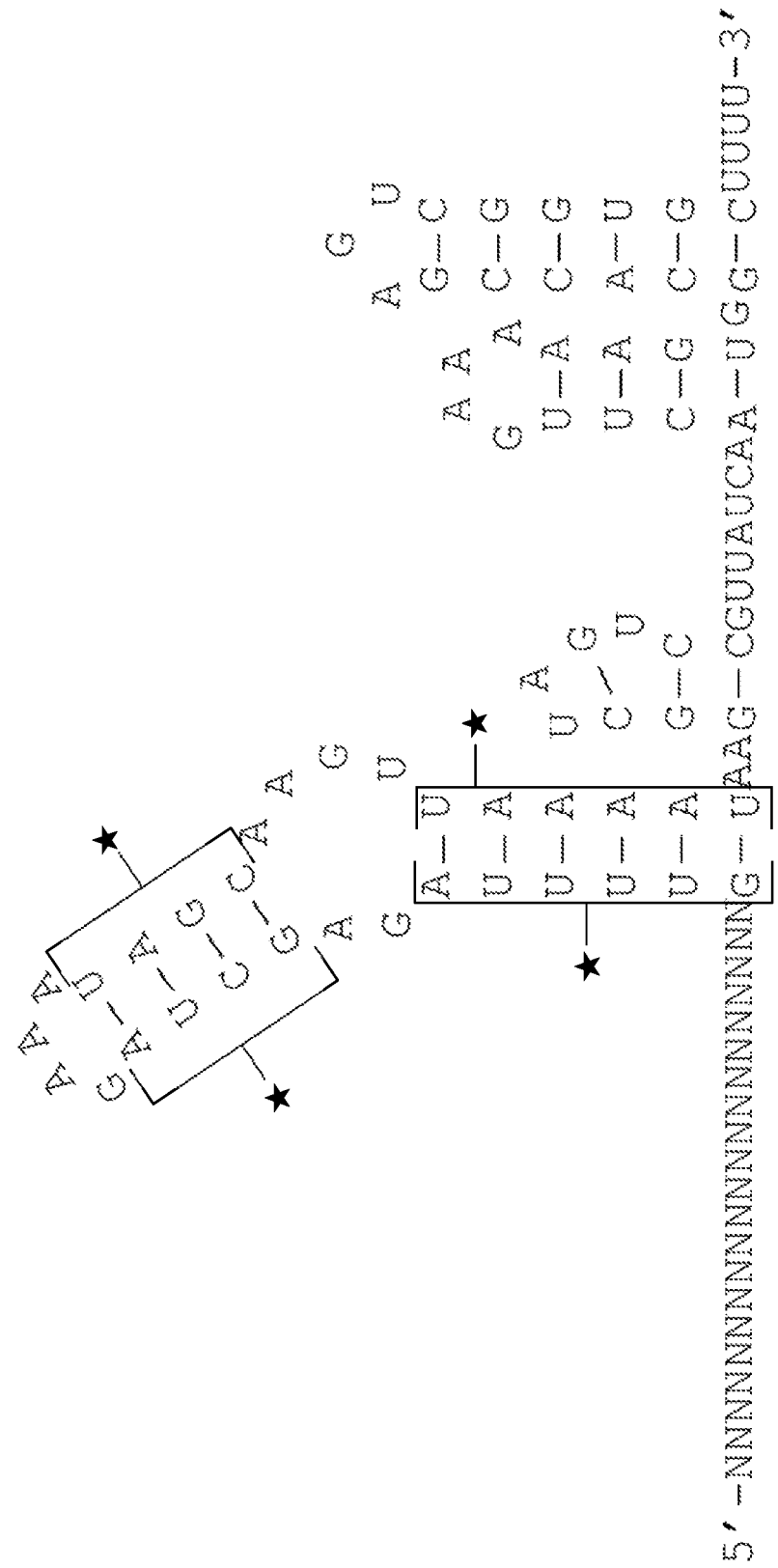
FIG. 3C depicts, in two-dimensional schematic form, an exemplary S. pyogenes guide molecule highlighting positions at which first and second guide molecule fragments are cross-linked together according to various embodiments of this disclosure.
Figure 3D:
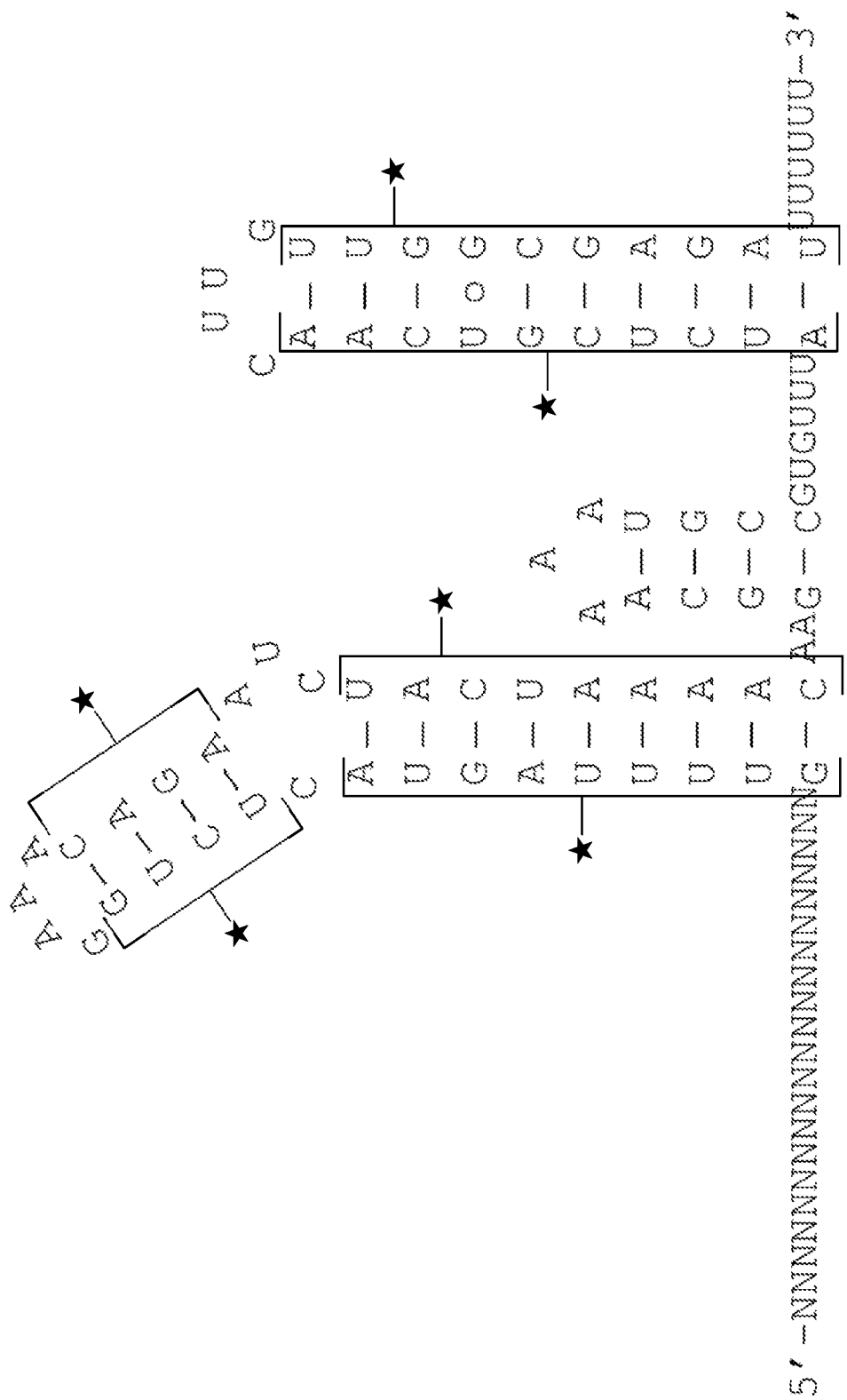
FIG. 3D depicts, in two-dimensional schematic form, an exemplary S. aureus guide molecule highlighting positions at which first and second guide molecule fragments are cross-linked together according to various embodiments of this disclosure.

The arrangement depicted in Formulas II and III may be particularly advantageous where the functional groups are positioned on linking groups comprising multiple carbons. For less bulky cross-linkers, it may be desirable to achieve close apposition between functionalized 3' and 5' ends. FIGS. 3C and 3D identify duplexed portions of *S. pyogenes* and *S. aureus* gRNAs suitable for the use of shorter linkers, including without limitation phosphodiester bonds. These positions are generally selected to permit annealing between fragments, and to position functionalized 3' and 5' ends such that they are immediately adjacent to one another prior to cross-linking. Exemplary 3' and 5' positions located within (rather than adjacent to) a tract of annealed residues are shown in Formulas IV, V, VI and VII below:

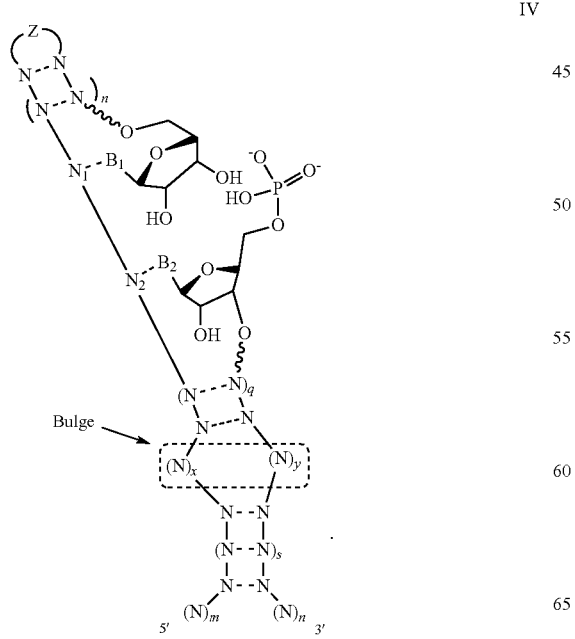

IV

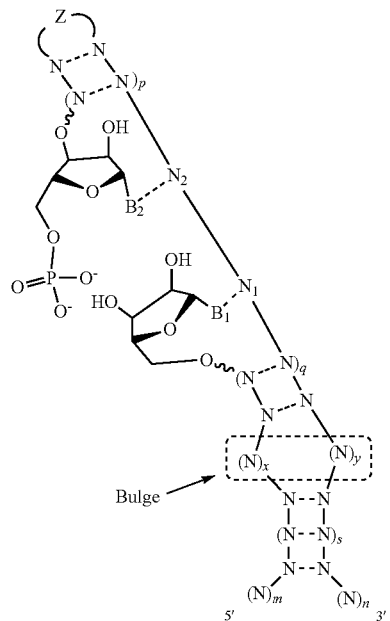

V

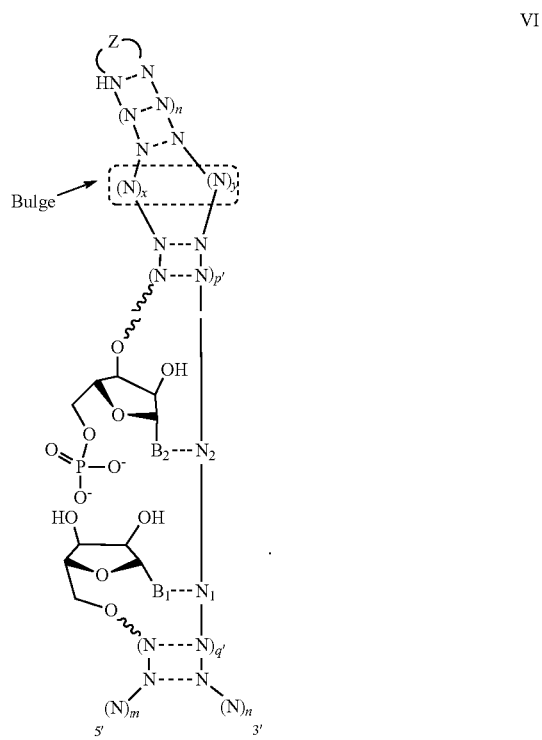

VI

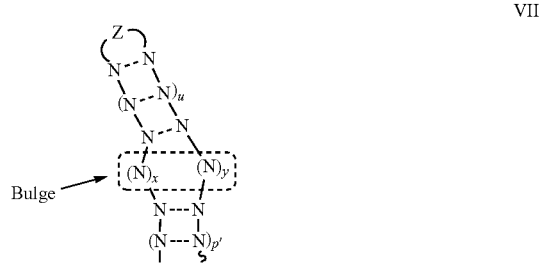

VII

-continued

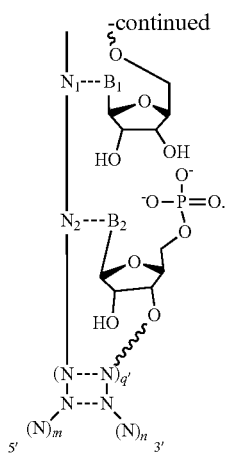

wherein:
Z represents a nucleotide loop which is 4-6 nucleotides long, optionally 4 or 6 nucleotides long;
p and q are each independently an integer between 0-2, inclusive, optionally 0;
p' is an integer between 0-4, inclusive, optionally 0;
q' is an integer between 2-4, inclusive, optionally 2;
x is an integer between 0-6, inclusive optionally 2;
y is an integer between 0-6, inclusive, optionally 4;
u is an integer between 0-4, inclusive, optionally 2;
s is an integer between 2-6, inclusive, optionally 4;
m is an integer between 20-40, inclusive;
n is an integer between 30-70, inclusive;
$B_1$ and $B_2$ are each independently a nucleobase;
each N in $(N)_m$ m and $(N)_n$ is independently a nucleotide residue;
$N_1$ and $N_2$ are each independently a nucleotide residue; and
N—N independently represents two complementary nucleotides, optionally two complementary nucleotides that are hydrogen bonding base-paired; and each ∿∿ represents a phosphodiester linkage, a phosphorothioate linkage, a phosphonoacetate linkage, a thiophosphonoacetate linkage, or a phosphoroamidate linkage.

The present disclosure also encompasses the recognition that the arrangement depicted in any of Formulas II, III, IV, V, VI, or VII may be advantageous for avoiding side products in cross-linking reactions, as well as allowing for homobifunctional reactions to occur without homodimerization. Pre-annealing of the two heterodimeric strands orients the reactive groups toward the desired coupling and disfavors reaction with other potential reactive groups in the guide molecule.

The present disclosure also encompasses the recognition that an overhang in a stem structure of the guide molecule (e.g., when p>q or q>p in Formula II or III), may be particularly advantageous for orienting two oligonucleotides in a cross-linking reaction. Improved efficiency of the reaction may be observed in some such cases.

The present disclosure also encompasses the recognition that cross-linking strategies that do not require the use of specialty phosphoramidite precursors may be particularly advantageous due to lower costs and increased overall yields and/or efficiencies. Accordingly, in some embodiments, the present disclosure provides methods of preparing unimolecular guide molecules, wherein one oligonucleotide intermediate terminates in a natural and/or unmodified ribonucleotide.

The present disclosure also encompasses the recognition that hydroxyl groups in proximity to the reactive groups (e.g., the 2'-OH on the 3' end of the first fragment) are preferably modified to avoid the formation of certain side products. In particular, as illustrated below, the inventors discovered that a carbamate side product may form when amine-functionalized fragments are used in the urea-based cross-linking methods described herein:

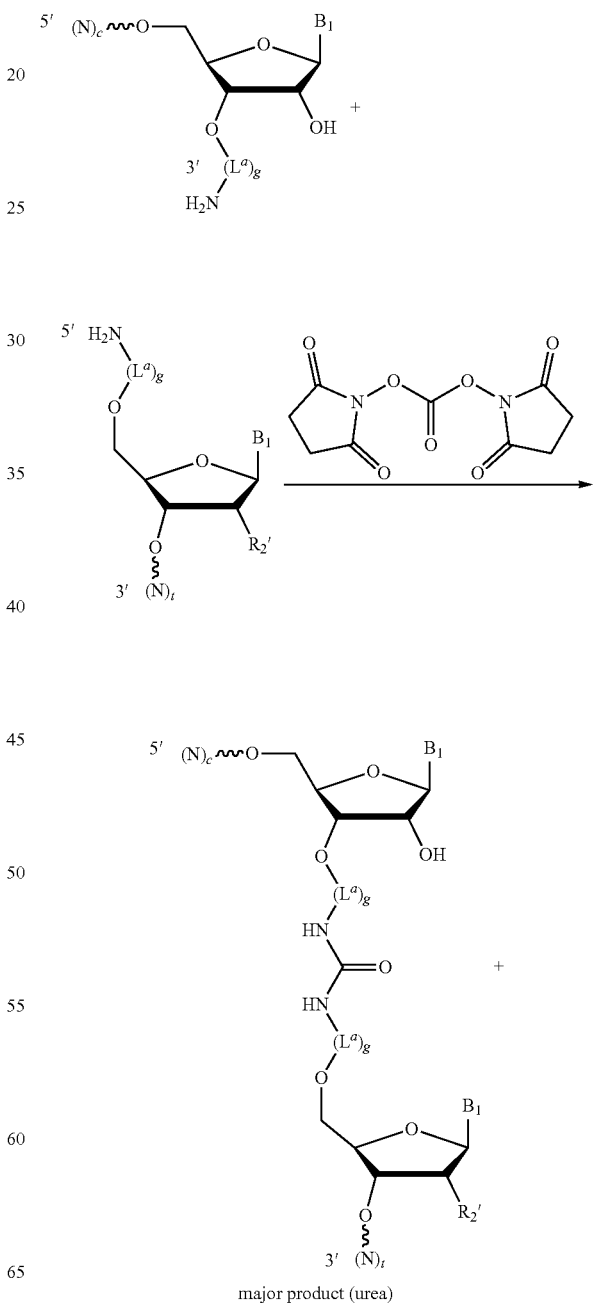

major product (urea)

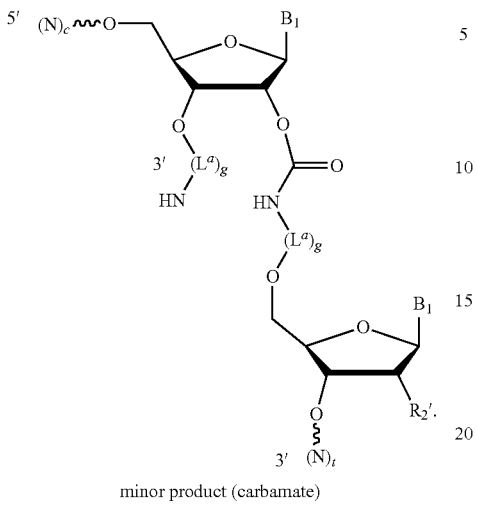

minor product (carbamate)

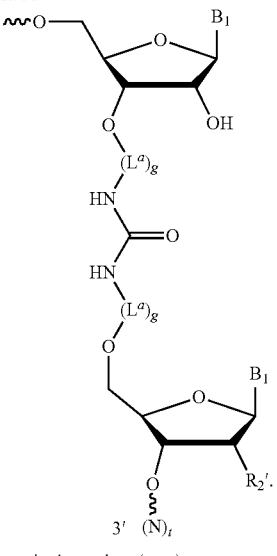

single product (urea)

Thus, in certain embodiments, the 2'-OH on the 3' end of the first fragment is modified (e.g., to H, halogen, —OMe, etc.) in order to prevent formation of the carbamate side product. For example, the 2'-OH is modified to a 2'-H:

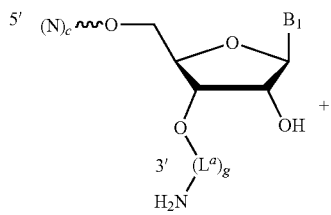

+

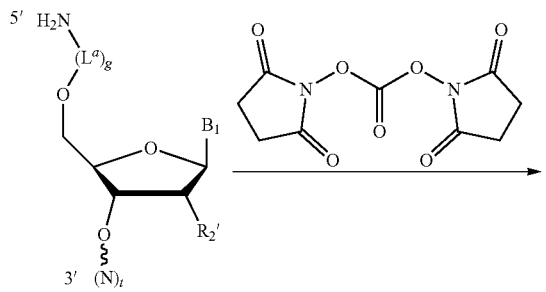

It will be appreciated that the above strategy of modifying the $B_1$ and/or $B_2$ nucleotide (e.g., modifying the 2' or 3' position of the sugar) in order to avoid side products may be applicable when using a variety of linker chemistries, of which urea chemistry is one non-limiting example.

Turning next to cross-linking, several considerations are relevant in selection of cross-linker linking moieties, functional groups and reactive groups. Among these are linker size, solubility in aqueous solution and biocompatibility, as well as the functional group reactivity, optimal reaction conditions for cross-linking, and any necessary reagents, catalyst, etc. required for cross-linking.

In general, linker size and solubility are selected to preserve or achieve a desired RNA secondary structure, and to avoid disruption or destabilization of the complex between guide molecule and RNA-guided nuclease. These two factors are somewhat related, insofar as organic linkers above a certain length may be poorly soluble in aqueous solution and may interfere sterically with surrounding nucleotides within the guide molecule and/or with amino acids in an RNA-guided nuclease complexed with the guide molecule.

A variety of linkers are suitable for use in the various embodiments of this disclosure. Certain embodiments make use of common linking moieties including, without limitation, polyvinylether, polyethylene, polypropylene, polyethylene glycol (PEG), polypropylene glycol (PEG), polyvinyl alcohol (PVA), polyglycolide (PGA), polylactide (PLA), polycaprolactone (PCL), and copolymers thereof. In some embodiments, no linker is used.

As to functional groups, in embodiments in which a bifunctional cross-linker is used to link 5' and 3' ends of guide fragments, the 3' or 5' ends of the guide fragments to be linked are modified with functional groups that react with the reactive groups of the cross-linker. In general, these modifications comprise one or more of amine, sulfhydryl, carboxyl, hydroxyl, alkene (e.g., a terminal alkene), azide and/or another suitable functional group. Multifunctional (e.g., bifunctional) cross-linkers are also generally known in the art, and may be either heterofunctional or homofunctional, and may include any suitable functional group, including without limitation isothiocyanate, isocyanate, acyl azide, an NHS ester, sulfonyl chloride, tosyl ester, tresyl ester, aldehyde, amine, epoxide, carbonate (e.g., bis(p-nitrophenyl) carbonate), aryl halide, alkyl halide, imido ester, carboxylate, alkyl phosphate, anhydride, fluorophenyl ester, HOBt ester, hydroxymethyl phosphine, O-methylisourea, DSC, NHS carbamate, glutaraldehyde, activated double bond, cyclic hemiacetal, NHS carbonate, imidazole carbamate, acyl imidazole, methylpyridinium ether, azlactone, cyanate ester, cyclic imidocarbonate, chlorotriazine, dehydroazepine, 6-sulfo-cytosine derivatives, maleimide, aziridine, TNB thiol, Ellman's reagent, peroxide, vinylsulfone, phenylthioester, diazoalkanes, diazoacetyl, epoxide, diazonium, benzophenone, anthraquinone, diazo derivatives, diazirine derivatives, psoralen derivatives, alkene, phenyl boronic acid, etc.

These and other cross-linking chemistries are known in the art, and are summarized in the literature, including by Greg T. Hermanson, Bioconjugate Techniques, $3^{rd}$ Ed. 2013, published by Academic Press, which is incorporated by reference herein in its entirety and for all purposes.

Compositions comprising guide molecules synthesized by the methods provided by this disclosure are, in certain embodiments, characterized by high purity of the desired guide molecule reaction product, with low levels of contamination with undesirable species, including n−1 species, truncations, n+1 species, guide fragment homodimers, unreacted functionalized guide fragments, etc. In certain embodiments of this disclosure, a purified composition comprising synthetic guide molecules can comprise a plurality of species within the composition (i.e., the guide molecule is the most common species within the composition, by mass or molarity). Alternatively, or additionally, compositions according to the embodiments of this disclosure can comprise ≥70%, ≥75%, ≥80%, ≥85%, ≥90%, ≥95%, ≥96%, ≥97%, ≥98%, and/or ≥99%, of a guide molecule having a desired length (e.g., lacking a truncation at a 5' end, relative to a reference guide molecule sequence) and a desired sequence (e.g., comprising a 5' sequence of a reference guide molecule sequence).

For example, in some embodiments, a composition comprising guide molecules according to the disclosure (e.g., guide molecules comprising fragments cross-linked using an appropriate cross-linking chemistry described herein) includes less than about 20%, 15%, 10%, 9%, 8%, 7%, 6%, 5%, 4%, 3%, 2%, 1%, or less, of guide molecules that comprise a truncation at a 5' end, relative to a reference guide molecule sequence.

Additionally or alternatively, a composition comprising guide molecules according to the disclosure (e.g., guide molecules comprising fragments cross-linked using an appropriate cross-linking chemistry described herein) includes at least about 90%, 95%, 96%, 97%, 98%, 99%, or 100% of guide molecules with a 5' sequence (e.g., a 5' sequence comprising or consisting of nucleotides 1-30, 1-25, or 1-20 of the guide molecule) that is 100% identical to a corresponding 5' sequence of a reference guide molecule sequence. In some embodiments, if the composition comprises guide molecules with a 5' sequence that is less than 100% identical to a corresponding 5' sequence of the reference guide molecule sequence, and such guide molecules are present at a level greater than or equal to 0.1%, such guide molecule does not comprise a targeting domain for a potential off-target site. In some embodiments, a composition comprising guide molecules according to the disclosure includes at least about 80%, 85%, 90%, 91%, 92%, 93%, 94%, 95%, 96%, 97%, 98%, 99% or more guide molecules that do not comprise a truncation at a 5' end (relative to a reference guide molecule sequence), and at least about 90%, 95%, 96%, 97%, 98%, 99%, or 100% of such guide molecules (i.e., such guide molecule not comprising a truncation at a 5' end) have a 5' sequence (e.g., a 5' sequence comprising or consisting of nucleotides 1-30, 1-25, or 1-20 of the guide molecule) that is 100% identical to the corresponding 5' sequence of the reference guide molecule sequence, and if the composition comprises guide molecules with a 5' sequence that is less than 100% identical to a corresponding 5' sequence of the reference guide molecule sequence, and such guide molecules are present at a level greater than or equal to 0.1%, such guide molecule does not comprise a targeting domain for a potential off-target site.

In some embodiments, compositions comprising guide molecules according to the disclosure include less than about 10% of guide molecules that comprise a truncation at a 5' end, relative to a reference guide molecule sequence and exhibit an acceptable level of activity/efficacy. In some embodiments, compositions comprising guide molecules according to the disclosure include (i) at least about 99% of guide molecules having a 5' sequence (e.g., a 5' sequence comprising or consisting of nucleotides 1-30, 1-25, or 1-20 of the guide molecule) that is 100% identical to the corresponding 5' sequence of the reference guide molecule sequence, and (ii) if the composition comprises guide molecules with a 5' sequence that is less than 100% identical to a corresponding 5' sequence of the reference guide molecule sequence, and such guide molecules are present at a level greater than or equal to 0.1%, such guide molecule does not comprise a targeting domain for a potential off-target site, and compositions exhibit an acceptable level of specificity and/or safety.

The purity of a composition provided herein may be expressed as a fraction of total guide molecule (by mass or molarity) within the composition, as a fraction of all RNA or all nucleic acid (by mass or molarity) within the composition, as a fraction of all solutes within the composition (by mass), and/or as a fraction of the total mass of the composition.

The purity of a composition comprising a guide molecule according to this disclosure is assessed by any suitable means known in the art. For example, the relative abundance of the desired guide molecule species can be assessed qualitatively or semi-quantitatively by means of gel electrophoresis. Alternatively or additionally, the purity of a desired guide molecule species is assessed by chromatography (e.g., liquid chromatography, HPLC, FPLC, gas chromatography), spectrometry (e.g., mass spectrometry, whether based on time-of-flight, sector field, quadrupole mass, ion trap, orbitrap, Fourier transform ion cyclotron resonance, or other technology), nuclear magnetic resonance (NMR) spectroscopy (e.g., visible, infrared or ultraviolet), thermal stability methods (e.g., differential scanning calorimetry, etc.), sequencing methods (e.g., using a template switching oligonucleotide) and combinations thereof (e.g., chromatography-spectrometry, etc.).

The synthetic guide molecules provided herein operate in substantially the same manner as any other guide molecules (e.g., gRNA), and generally operate by (a) forming a complex with an RNA-guided nuclease such as Cas9, (b) interacting with a target sequence including a region complementary to a targeting sequence of the guide molecule and a protospacer adjacent motif (PAM) recognized by the RNA-guided nuclease, and optionally (c) modifying DNA within or adjacent to the target sequence, for instance by forming a DNA double strand break, single strand break, etc.

that may be repaired by DNA repair pathways operating within a cell containing the guide molecule and RNA-guided nuclease.

In some embodiments, a guide molecule described herein, e.g., a guide molecule produced using a method described herein, can act as a substrate for an enzyme (e.g., a reverse transcriptase) that acts on RNA. Without wishing to be bound by theory, cross-linkers present within guide molecules described herein may be compatible with such processive enzymes due to close apposition of reactive ends promoted by pre-annealing according to methods of the disclosure.

The exemplary embodiments described herein focus on the application of the synthesis and cross-linking methods described herein to the assembly of guide molecules from two guide fragments. However, the methods described herein have a variety of applications, many of which will be evident to skilled artisans. These applications are within the scope of the present disclosure. As one example, the methods of this disclosure may be employed in the linking of heterologous sequences to guide molecules. Heterologous sequences may include, without limitation, DNA donor templates as described in WO 2017/180711 by Cotta-Ramusino, et al., which is incorporated by reference herein for all purposes. (See, e.g., Section I, "gRNA Fusion Molecules" at p. 23, describing covalently linked template nucleic acids, and the use of splint oligos to facilitate ligation of the template to the 3' end of the guide molecule.) Heterologous sequences can also include nucleic acid sequences that are recognized by peptide DNA or RNA binding domains, such as MS2 loops, also described in Section I of WO 2017/180711 above.

This overview has focused on a handful of exemplary embodiments that illustrate certain principles relating to the synthesis of guide molecules, and compositions comprising such guide molecules. For clarity, however, this disclosure encompasses modifications and variations that have not been described but that will be evident to those of skill in the art. With that in mind, the following disclosure is intended to illustrate the operating principles of genome editing systems more generally. What follows should not be understood as limiting, but rather illustrative of certain principles of genome editing systems, which, in combination with the instant disclosure, will inform those of skill in the art about additional implementations of and modifications that are within the scope of this disclosure.

Genome Editing Systems

The term "genome editing system" refers to any system having RNA-guided DNA editing activity. Genome editing systems of the present disclosure include at least two components adapted from naturally occurring CRISPR systems: a guide molecule (e.g., guide RNA or gRNA) and an RNA-guided nuclease. These two components form a complex that is capable of associating with a specific nucleic acid sequence and editing the DNA in or around that nucleic acid sequence, for instance by making one or more of a single-strand break (an SSB or nick), a double-strand break (a DSB) and/or a point mutation.

Naturally occurring CRISPR systems are organized evolutionarily into two classes and five types (Makarova et al. Nat Rev Microbiol. 2011 June; 9 (6): 467-477 (Makarova), incorporated by reference herein), and while genome editing systems of the present disclosure may adapt components of any type or class of naturally occurring CRISPR system, the embodiments presented herein are generally adapted from Class 2, and type II or V CRISPR systems. Class 2 systems, which encompass types II and V, are characterized by relatively large, multidomain RNA-guided nuclease proteins (e.g., Cas9 or Cpf1) and one or more guide RNAs (e.g., a crRNA and, optionally, a tracrRNA) that form ribonucleoprotein (RNP) complexes that associate with (i.e. target) and cleave specific loci complementary to a targeting (or spacer) sequence of the crRNA. Genome editing systems according to the present disclosure similarly target and edit cellular DNA sequences, but differ significantly from CRISPR systems occurring in nature. For example, the unimolecular guide molecules described herein do not occur in nature, and both guide molecules and RNA-guided nucleases according to this disclosure may incorporate any number of non-naturally occurring modifications.

Genome editing systems can be implemented (e.g., administered or delivered to a cell or a subject) in a variety of ways, and different implementations may be suitable for distinct applications. For instance, a genome editing system is implemented, in certain embodiments, as a protein/RNA complex (a ribonucleoprotein, or RNP), which can be included in a pharmaceutical composition that optionally includes a pharmaceutically acceptable carrier and/or an encapsulating agent, such as a lipid or polymer micro- or nano-particle, micelle, liposome, etc. In certain embodiments, a genome editing system is implemented as one or more nucleic acids encoding the RNA-guided nuclease and guide molecule components described above (optionally with one or more additional components); in certain embodiments, the genome editing system is implemented as one or more vectors comprising such nucleic acids, for instance a viral vector such as an adeno-associated virus; and in certain embodiments, the genome editing system is implemented as a combination of any of the foregoing. Additional or modified implementations that operate according to the principles set forth herein will be apparent to the skilled artisan and are within the scope of this disclosure.

It should be noted that the genome editing systems of the present disclosure can be targeted to a single specific nucleotide sequence, or may be targeted to—and capable of editing in parallel—two or more specific nucleotide sequences through the use of two or more guide molecules. The use of multiple guide molecules is referred to as "multiplexing" throughout this disclosure, and can be employed to target multiple, unrelated target sequences of interest, or to form multiple SSBs or DSBs within a single target domain and, in some cases, to generate specific edits within such target domain. For example, International Patent Publication No. WO 2015/138510 by Maeder et al. (Maeder), which is incorporated by reference herein, describes a genome editing system for correcting a point mutation (C.2991+1655A to G) in the human CEP290 gene that results in the creation of a cryptic splice site, which in turn reduces or eliminates the function of the gene. The genome editing system of Maeder utilizes two guide RNAs targeted to sequences on either side of (i.e., flanking) the point mutation, and forms DSBs that flank the mutation. This, in turn, promotes deletion of the intervening sequence, including the mutation, thereby eliminating the cryptic splice site and restoring normal gene function.

As another example, WO 2016/073990 by Cotta-Ramusino, et al. ("Cotta-Ramusino"), incorporated by reference herein, describes a genome editing system that utilizes two gRNAs in combination with a Cas9 nickase (a Cas9 that makes a single strand nick such as *S. pyogenes* D10A), an arrangement termed a "dual-nickase system." The dual-nickase system of Cotta-Ramusino is configured to make two nicks on opposite strands of a sequence of interest that are offset by one or more nucleotides, which nicks combine to create a double strand break having an overhang (5' in the case of Cotta-Ramusino, though 3' overhangs are also possible). The overhang, in turn, can facilitate homology directed repair events in some circumstances. And, as another example, WO 2015/070083 by Palestrant et al. ("Palestrant", incorporated by reference herein) describes a gRNA targeted to a nucleotide sequence encoding Cas9 (referred to as a "governing RNA"), which can be included in a genome editing system comprising one or more additional gRNAs to permit transient expression of a Cas9 that might otherwise be constitutively expressed, for example in some virally transduced cells. These multiplexing applications are intended to be exemplary, rather than limiting, and the skilled artisan will appreciate that other applications of multiplexing are generally compatible with the genome editing systems described here.

Genome editing systems can, in some instances, form double strand breaks that are repaired by cellular DNA double-strand break mechanisms such as NHEJ or HDR. These mechanisms are described throughout the literature, for example by Davis & Maizels, PNAS, 111 (10): E924-932, Mar. 11, 2014 (Davis) (describing Alt-HDR); Frit et al. DNA Repair 17 (2014) 81-97 (Frit) (describing Alt-NHEJ); and Iyama and Wilson III, DNA Repair (Amst.) 2013-August; 12 (8): 620-636 (Iyama) (describing canonical HDR and NHEJ pathways generally).

Where genome editing systems operate by forming DSBs, such systems optionally include one or more components that promote or facilitate a particular mode of double-strand break repair or a particular repair outcome. For instance, Cotta-Ramusino also describes genome editing systems in which a single stranded oligonucleotide "donor template" is added; the donor template is incorporated into a target region of cellular DNA that is cleaved by the genome editing system, and can result in a change in the target sequence.

In certain embodiments, genome editing systems modify a target sequence, or modify expression of a gene in or near the target sequence, without causing single- or double-strand breaks. For example, a genome editing system may include an RNA-guided nuclease fused to a functional domain that acts on DNA, thereby modifying the target sequence or its expression. As one example, an RNA-guided nuclease can be connected to (e.g., fused to) a cytidine deaminase functional domain, and may operate by generating targeted C-to-A substitutions. Exemplary nuclease/deaminase fusions are described in Komor et al. Nature 533, 420-424 (19 May 2016) ("Komor"), which is incorporated by reference. Alternatively, a genome editing system may utilize a cleavage-inactivated (i.e., a "dead") nuclease, such as a dead Cas9 (dCas9), and may operate by forming stable complexes on one or more targeted regions of cellular DNA, thereby interfering with functions involving the targeted region(s) including, without limitation, mRNA transcription, chromatin remodeling, etc.

Guide Molecules

The term "guide molecule" is used herein to refer to any nucleic acid that promotes the specific association (or "targeting") of an RNA-guided nuclease, such as a Cas9 or a Cpf1, to a target sequence, such as a genomic or episomal sequence, in a cell. A guide molecule may be an RNA molecule or a hybrid RNA/DNA molecule. A guide molecule may comprise non-nucleotide segments (e.g., a non-nucleotide linker). Guide molecules can be unimolecular (comprising a single molecule, and referred to alternatively as chimeric), or modular (comprising more than one, and typically two, separate molecules, such as a crRNA and a tracrRNA, which are usually associated with one another, for instance by duplexing). Guide molecules and their component parts are described throughout the literature, for instance in Briner et al. (Molecular Cell 56 (2), 333-339, Oct. 23, 2014 (Briner), which is incorporated by reference), and in Cotta-Ramusino.

In bacteria and archaea, type II CRISPR systems generally comprise an RNA-guided nuclease protein such as Cas9, a CRISPR RNA (crRNA) that includes a 5' region that is complementary to a foreign sequence, and a trans-activating crRNA (tracrRNA) that includes a 5' region that is complementary to, and forms a duplex with, a 3' region of the crRNA. While not intending to be bound by any theory, it is thought that this duplex facilitates the formation of—and is necessary for the activity of—the Cas9/guide molecule complex. As type II CRISPR systems were adapted for use in gene editing, it was discovered that the crRNA and tracrRNA could be joined into a single unimolecular or chimeric guide RNA, in one non-limiting example, by means of a four nucleotide (e.g., GAAA) "tetraloop" or "linker" sequence bridging complementary regions of the crRNA (at its 3' end) and the tracrRNA (at its 5' end). (Mali et al., Science. 2013 Feb. 15; 339 (6121): 823-826 ("Mali"); Jiang et al., Nat Biotechnol. 2013 March; 31 (3): 233-239 ("Jiang"); and Jinek et al., 2012 Science August 17; 337 (6096): 816-821 ("Jinek"), all of which are incorporated by reference herein.)

Guide molecules, whether unimolecular or modular, include a "targeting domain" that is fully or partially complementary to a target domain within a target sequence, such as a DNA sequence in the genome of a cell where editing is desired. Targeting domains are referred to by various names in the literature, including without limitation "guide sequences" (Hsu et al., Nat Biotechnol. 2013 September; 31 (9): 827-832, ("Hsu"), incorporated by reference herein), "complementarity regions" (Cotta-Ramusino), "spacers" (Briner) and generically as "crRNAs" (Jiang). Irrespective of the names they are given, targeting domains are typically 10-30 nucleotides in length, and in certain embodiments are 16-24 nucleotides in length (for instance, 16, 17, 18, 19, 20, 21, 22, 23 or 24 nucleotides in length), and are at or near the 5' terminus in the case of a Cas9 guide molecule, and at or near the 3' terminus in the case of a Cpf1 guide molecule.

In addition to the targeting domains, guide molecules typically (but not necessarily, as discussed below) include a plurality of domains that may influence the formation or activity of guide molecule/Cas9 complexes. For instance, as mentioned above, the duplexed structure formed by first and secondary complementarity domains of a guide molecule (also referred to as a repeat:anti-repeat duplex) interacts with the recognition (REC) lobe of Cas9 and can mediate the formation of Cas9/guide molecule complexes. (Nishimasu et al., Cell 156, 935-949, Feb. 27, 2014 (Nishimasu 2014) and Nishimasu et al., Cell 162, 1113-1126 Aug. 27, 2015 (Nishimasu 2015), both incorporated by reference herein).

Along with the first and second complementarity domains, Cas9 guide molecules typically include two or more additional duplexed regions that are involved in nuclease activity in vivo but not necessarily in vitro. (Nishimasu 2015). A first stem-loop near the 3' portion of the second complementarity domain is referred to variously as the "proximal domain," (Cotta-Ramusino) "stem loop 1" (Nishimasu 2014 and 2015) and the "nexus" (Briner). One or more additional stem loop structures are generally present near the 3' end of the guide molecule, with the number varying by species: *S. pyogenes* gRNAs typically include two 3' stem loops (for a total of four stem loop structures including the repeat:anti-repeat duplex), while *S. aureus* and other species have only one (for a total of three stem loop structures). A description of conserved stem loop structures (and guide molecule structures more generally) organized by species is provided in Briner.

While the foregoing description has focused on guide molecules for use with Cas9, it should be appreciated that other RNA-guided nucleases have been (or may in the future be) discovered or invented which utilize guide molecules that differ in some ways from those described to this point. For instance, Cpf1 ("CRISPR from Prevotella and Franciscella 1") is a recently discovered RNA-guided nuclease that does not require a tracrRNA to function. (Zetsche et al., 2015, Cell 163, 759-771 Oct. 22, 2015 (Zetsche I), incorporated by reference herein). A guide molecule for use in a Cpf1 genome editing system generally includes a targeting domain and a complementarity domain (alternately referred to as a "handle"). It should also be noted that, in guide molecules for use with Cpf1, the targeting domain is usually present at or near the 3' end, rather than the 5' end as described above in connection with Cas9 guide molecules (the handle is at or near the 5' end of a Cpf1 guide molecule).

Those of skill in the art will appreciate, however, that although structural differences may exist between guide molecules from different prokaryotic species, or between Cpf1 and Cas9 guide molecules, the principles by which guide molecules operate are generally consistent. Because of this consistency of operation, guide molecules can be defined, in broad terms, by their targeting domain sequences, and skilled artisans will appreciate that a given targeting domain sequence can be incorporated in any suitable guide molecule, including unimolecular or chimeric guide molecules, or a guide molecule that includes one or more chemical modifications and/or sequential modifications (substitutions, additional nucleotides, truncations, etc.). Thus, for economy of presentation in this disclosure, guide molecules may be described solely in terms of their targeting domain sequences.

More generally, skilled artisans will appreciate that some aspects of the present disclosure relate to systems, methods and compositions that can be implemented using multiple RNA-guided nucleases. For this reason, unless otherwise specified, the term guide molecule should be understood to encompass any suitable guide molecule (e.g., gRNA) that can be used with any RNA-guided nuclease, and not only those guide molecules that are compatible with a particular species of Cas9 or Cpf1. By way of illustration, the term guide molecule can, in certain embodiments, include a guide molecule for use with any RNA-guided nuclease occurring in a Class 2 CRISPR system, such as a type II or type V or CRISPR system, or an RNA-guided nuclease derived or adapted therefrom.

Cross-Linked Guide Molecules

Certain embodiments of this disclosure are related to guide molecules that are cross linked through, for example, a non-nucleotide chemical linkage. As described above, the position of the linkage may be in the stem loop structure of a guide molecule.

In some embodiments, the unimolecular guide molecule comprises, from 5' to 3':
a first guide molecule fragment, comprising:
a targeting domain sequence;
a first lower stem sequence;
a first bulge sequence; and
a first upper stem sequence;
a non-nucleotide chemical linkage; and
a second guide molecule fragment, comprising
a second upper stem sequence;
a second bulge sequence; and
a second lower stem sequence,
wherein (a) at least one nucleotide in the first lower stem sequence is base paired with a nucleotide in the second lower stem sequence, and (b) at least one nucleotide in the first upper stem sequence is base paired with a nucleotide in the second upper stem sequence.

In some embodiments, the guide molecule does not include a tetraloop sequence between the first and second upper stem sequences. In some embodiments, the first and/or second upper stem sequences comprise nucleotides that independently number from 4 to 22 inclusive. In some embodiments, the first and/or second upper stem sequences comprise nucleotides that independently number from 1 to 22, inclusive. In some embodiments, the first and second upper stem sequences comprise nucleotides that independently number from 8 to 22, inclusive. In some embodiments, the first and second upper stem sequences comprise nucleotides that independently number from 12 to 22, inclusive.

In some embodiments, the guide molecule is characterized in that a Gibbs free energy ($\Delta G$) for the formation of a duplex between the first and second guide molecule fragments is less than a $\Delta G$ for the formation of a duplex between two first guide molecule fragments. In some embodiments, a $\Delta G$ for the formation of a duplex between the first and second guide molecule fragments is characterized by greater than 50%, 60%, 70%, 80%, 90%, or 95% base pairing between each of (i) the first and second upper stem sequences and (ii) the first and second lower stem sequences and/or is less than a $\Delta G$ for the formation of a duplex characterized by less than 50%, 60%, 70%, 80%, 90% or 95% base pairing between (i) and (ii).

In some embodiments, the synthetic guide molecule is of formula $A_{3'}$-i or $A_{2'}$-i:

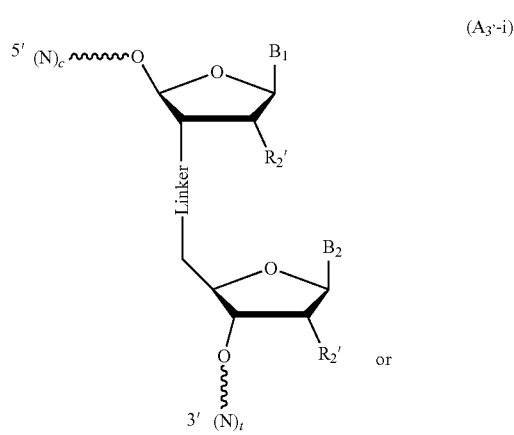

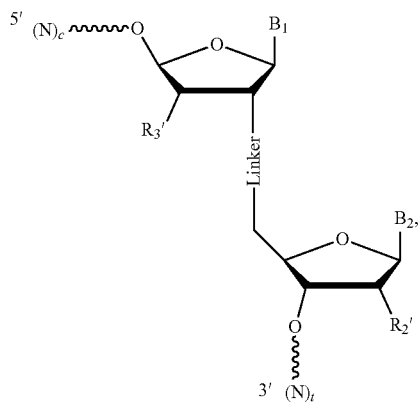

(A₂'-i)

wherein each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;

$(N)_c$ includes a 3' region that is complementary or partially complementary to, and forms a duplex with, a 5' region of $(N)_t$;

c is an integer 20 or greater;

t is an integer 20 or greater;

Linker is a non-nucleotide chemical linkage;

$B_1$ and $B_2$ are each independently a nucleobase;

each of $R_2'$ and $R_3'$ is independently H, OH, fluoro, chloro, bromo, NH₂, SH, S—R', or O—R' wherein each R' is independently a protection group or an alkyl group, wherein the alkyl group may be optionally substituted; and each ∿∿ represents independently a phosphodiester linkage, a phosphorothioate linkage, a phosphonoacetate linkage, a thiophosphonoacetate linkage, or a phosphoroamidate linkage.

In some embodiments, the duplex regions of $(N)_c$ and $(N)_t$ comprise a sequence listed in Table 4.

TABLE 4

Exemplary sequences of duplex regions of $(N)_t$ and $(N)_c$.

| SEQ ID NO. | Sequence |
|---|---|
| 1 | GUUUUAGAGCUAG |
| 2 | AUAGCAAGUUAAAAU |
| 3 | GUUUUAGAGCU |
| 4 | AGCAAGUUAAAAU |
| 5 | GUUUUAGAGCUAG |
| 6 | CUAGCAAGUUAAAU |
| 7 | GUUUUAGAGCUAUG |
| 8 | CAUAGCAAGUUAAAAU |

TABLE 4-continued

Exemplary sequences of duplex regions of $(N)_t$ and $(N)_c$.

| SEQ ID NO. | Sequence |
|---|---|
| 9 | GUAUUAGAGCUAUGCUGUUUU |
| 10 | AAAACAGCAUAGCAAGUUAAUAU |
| 11 | GUAUUAGAGCUAUGCU |
| 12 | AGCAUAGCAAGUUAAUAU |
| 13 | GUUUUAGAGCUAUGCUGUUUU |
| 14 | AAAACAGCAUAGCAAGUUAAAAU |
| 15 | GUUUUAGAGCUAUGCU |
| 16 | AGCAUAGCAAGUUAAAAA |
| 17 | GUUUUAGAGCUAAAG |
| 18 | AUUUAGCAAGUUAAAAU |
| 19 | GUUUUAGAGCUAA |
| 20 | UUAGCAAGUUAAAAU |
| 21 | GUUUUAGAGCUAAAGGG |
| 22 | ACCUUUAGCAAGUUAAAAU |
| 23 | GUUUUAGAGCUAG |
| 24 | GUUUUAGUACUCU |
| 25 | AGAAUCUACUAAAAC |
| 26 | GUUUUAGUACUCUGUA |
| 27 | UACAGAAUCUACUAAAAC |
| 28 | GUUUUAGUACUCUGUAAUUUUAGG |
| 29 | CCUAAAAUUACAGAAUCUACUAAAAC |
| 30 | GUUUUAGUACUCUGUAAUUUUAGGUAUGA |
| 31 | UCAUACCUAAAAUUACAGAAUCUACUAAAAC |

In some embodiments, the guide molecule is of formula $B_{3'}$-i or $B_{2'}$-i:

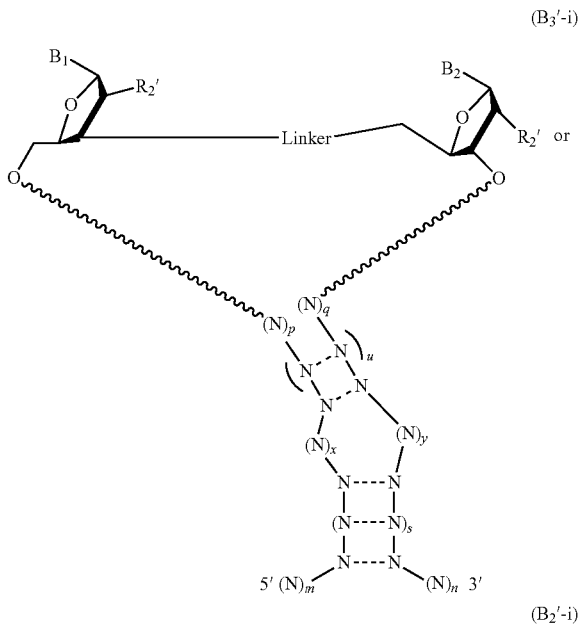

(B$_{3'}$-i)

(B$_{2'}$-i)

wherein:
  each N is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage; and
  each N—N independently represents two complementary nucleotides, optionally two complementary nucleotides that are hydrogen bonding base-paired;
  p and q are each an integer between 0 and 6, inclusive, and p+q is an integer between 0 and 6, inclusive;
  u is an integer between 2 and 22, inclusive;
  s is an integer between 1 and 10, inclusive;
  x is an integer between 1 and 3, inclusive;
  y is >x and an integer between 3 and 5, inclusive;
  m is an integer 15 or greater; and
  n is an integer 30 or greater.

In some embodiments, a guide molecule of formula $B_{3'}$-i or $B_{2'}$-i is provided wherein:
  u is an integer between 2 and 22, inclusive;
  s is an integer between 1 and 8, inclusive;
  x is an integer between 1 and 3, inclusive;
  y is >x and an integer between 3 and 5, inclusive;
  m is an integer between 15 and 50, inclusive; and
  n is an integer between 30 and 70, inclusive.

In some embodiments of formula $B_{3'}$-i or $B_{2'}$-i, (N—N)$_u$ and (N—N)$_s$ do not comprise an identical sequence of 3 or more nucleotides. In some embodiments, (N—N)$_u$ and (N—N)$_s$ do not comprise an identical sequence of 4 or more nucleotides. In some embodiments, (N—N)$_s$ comprises a N'UUU, UN'UU, UUN'U or UUUN' sequence and (N—N)$_y$ comprises a UUUU sequence, wherein N' is A, G or C. In some embodiments, (N—N)$_s$ comprises a UUUU sequence and (N—N)$_u$ comprises a N'UUU, UN'UU, UUN'U or UUUN' sequence, wherein N' is A, G or C. In some embodiments, N' is A. In some embodiments, N' is G. In some embodiments, N' is C.

In some embodiments, the guide molecule is based on gRNAs used in S. pyogenes or S. aureus Cas9 systems. In some embodiments, the guide molecule is of formula $C_{3'}$-i, $C_{2'}$-i, $D_{3'}$-i, or $D_{2'}$-i:

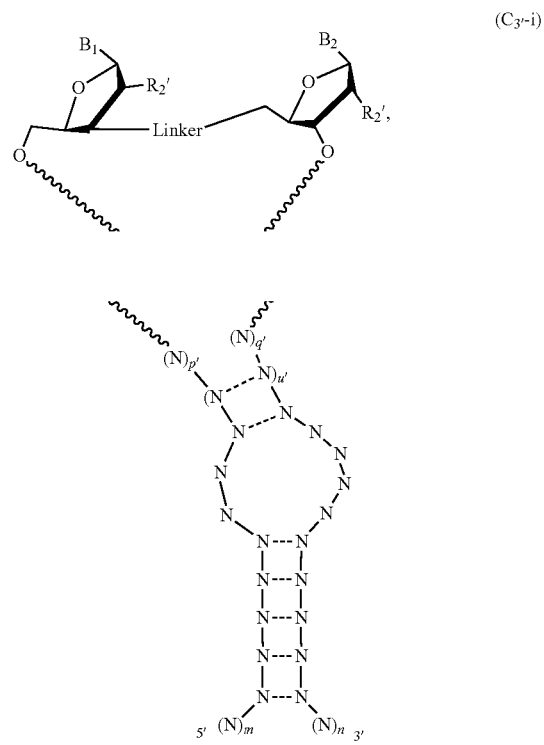

(C$_{3'}$-i)

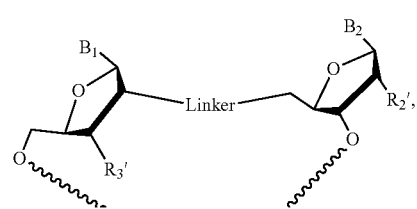

(C$_{2'}$-i)

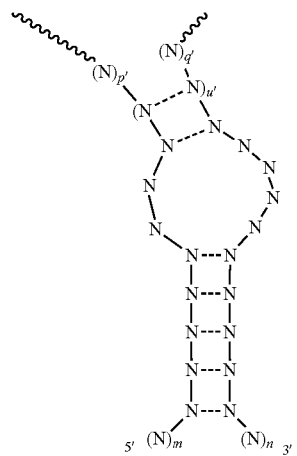
(D3'-i)
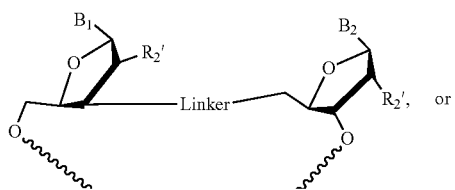  or
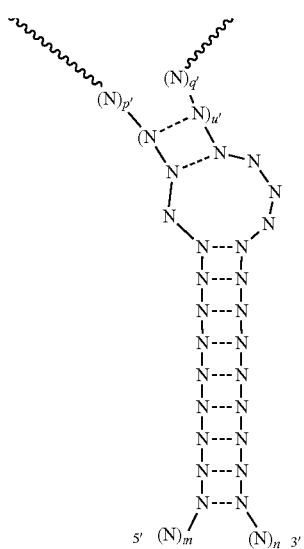
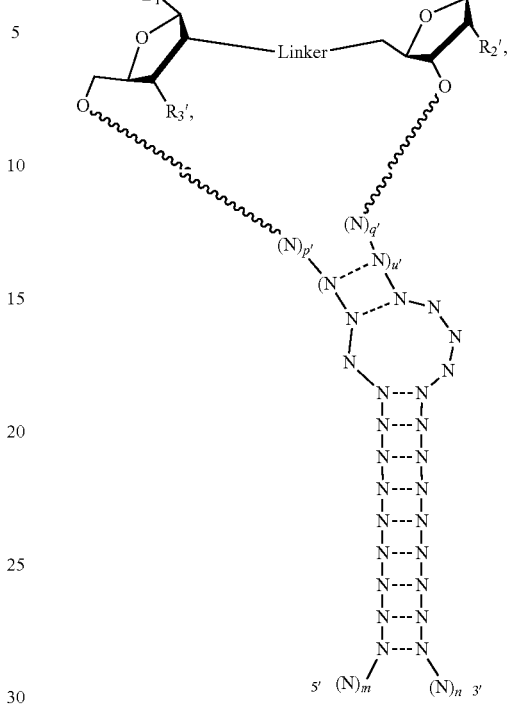
wherein:
u' is an integer between 2 and 22, inclusive; and
p' and q' are each independently an integer between 0 and 6, inclusive, and
p'+q' is an integer between 0 and 6, inclusive.
In some embodiments, the guide molecule is of formula $E_{3'}\text{-i}_U$, $E_{2'}\text{-i}_U$, $E_{3'}\text{-i}_A$, or $E_{2'}\text{-i}_A$:
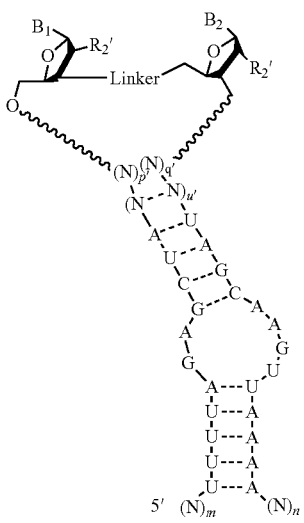

-continued
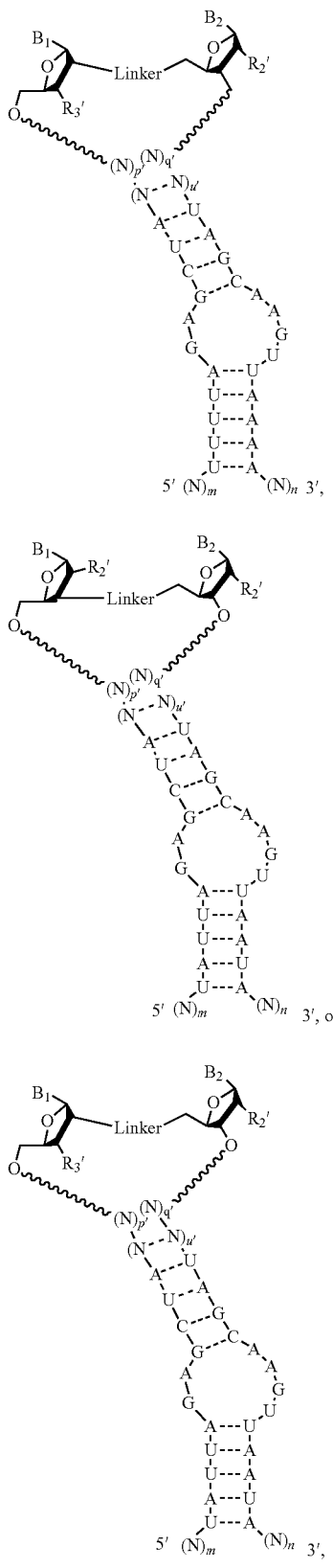
or covariants thereof.
In some embodiments, $(N-N)_u'$ is of formula:
(E$_{2'}$-i$_U$)
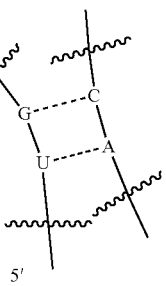
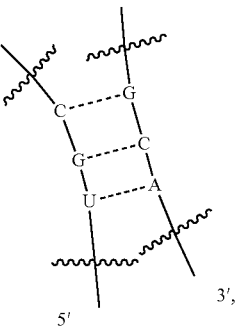
(E$_{3'}$-i$_A$)
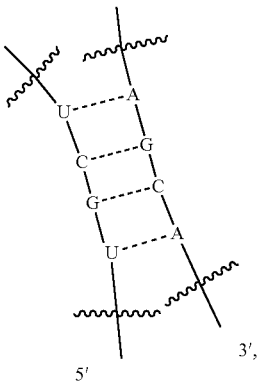
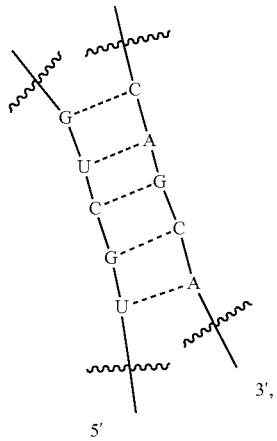
(E$_{2'}$-i$_A$)
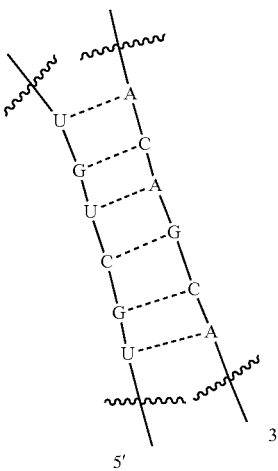

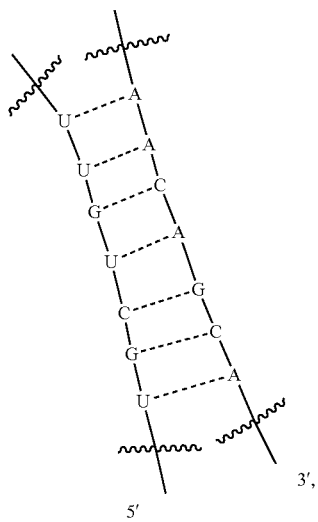
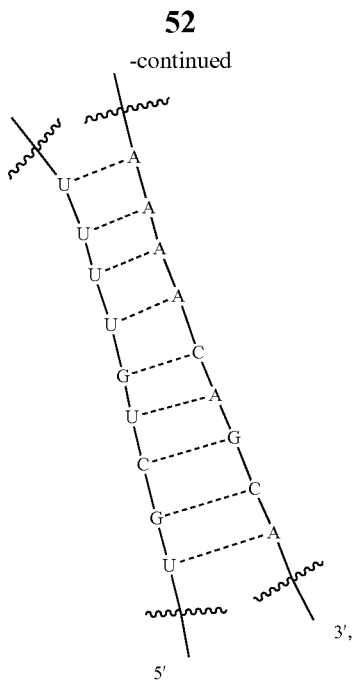
or covariants thereof. In some embodiments, $(N{-}N)_{u'}$ is of formula:
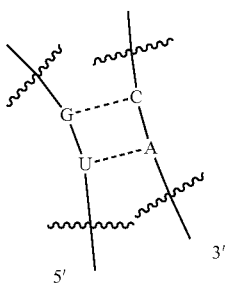
and $B_1$ is a cytosine residue and $B_2$ is a guanine residue, or a covariant thereof. In some embodiments, $(N{-}N)_{u'}$ is of formula:
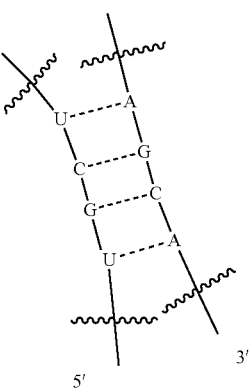
and $B_1$ is a guanine residue and $B_2$ is a cytosine residue, or a covariant thereof. In some embodiments, $(N{-}N)_{u'}$ is of formula:

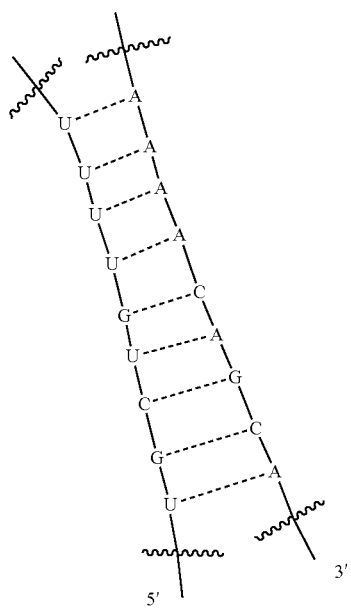
and $B_1$ is a guanine residue and $B_2$ is a cytosine residue, or a covariant thereof.
In some embodiments, the guide molecule is of formula $F_{3'}\text{-}i_U$, $F_{2'}\text{-}i_U$, $F_{3'}\text{-}i_A$, or $F_{2'}\text{-}i_A$:
($F_{3'}\text{-}i_U$)
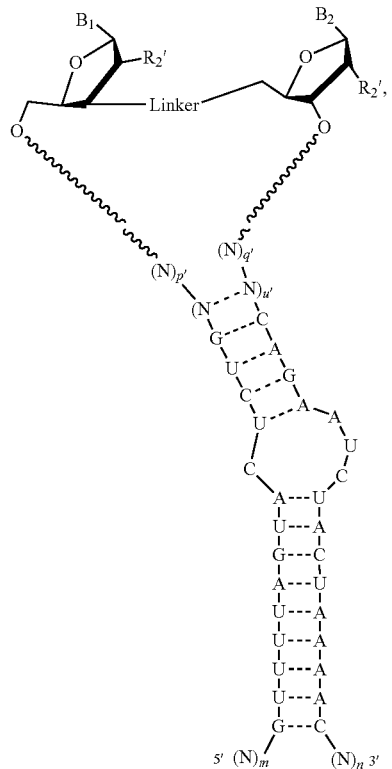
($F_{2'}\text{-}i_U$)
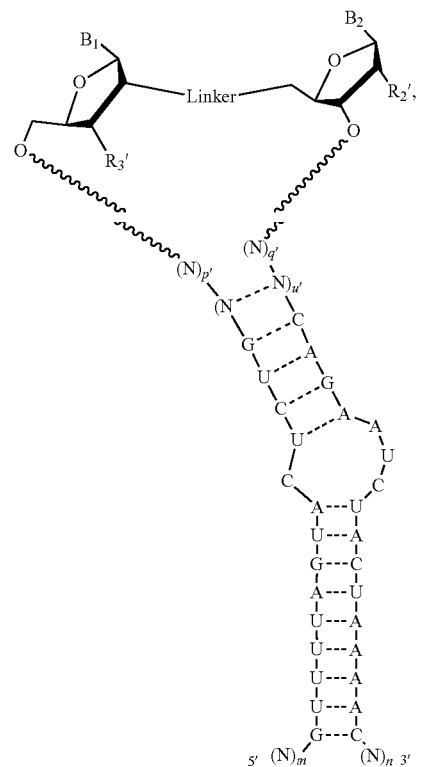
($F_{3'}\text{-}i_A$)
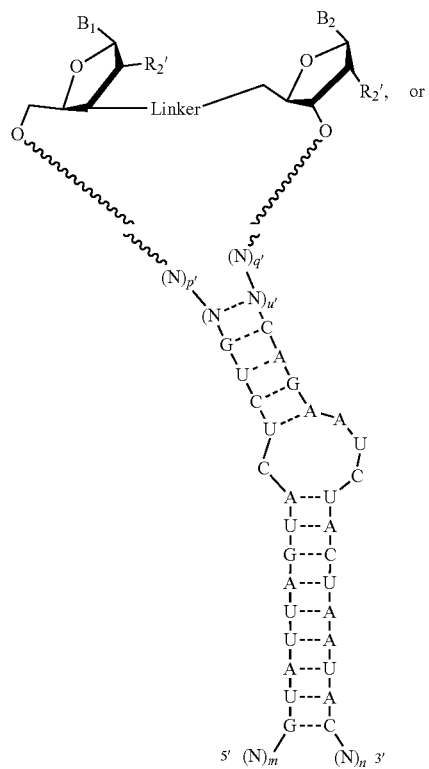
or

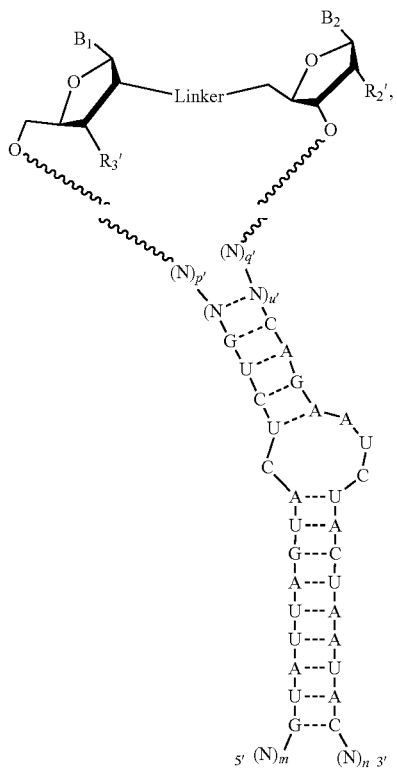
or covariants thereof.
In some embodiments, $(N-N)_{u'}$ is of formula:
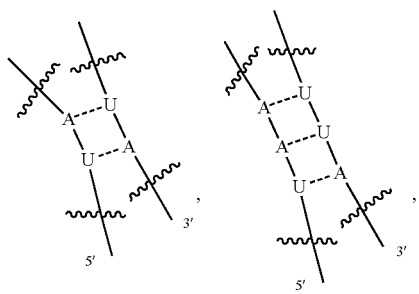
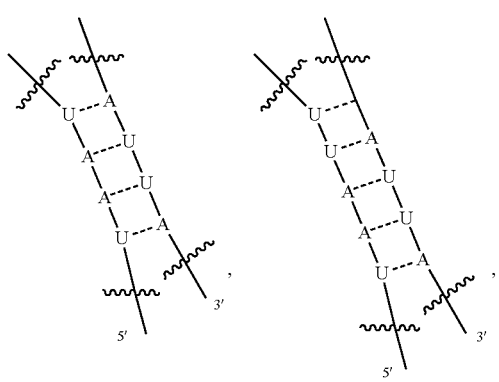
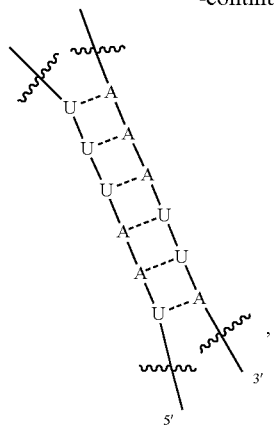
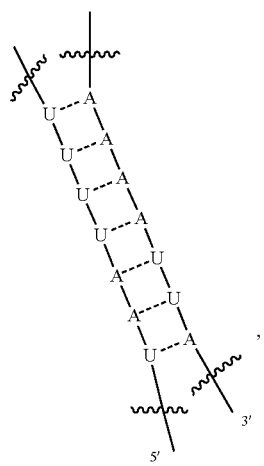
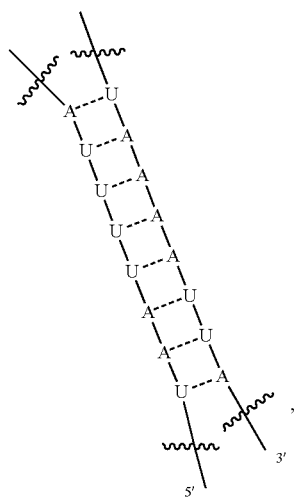

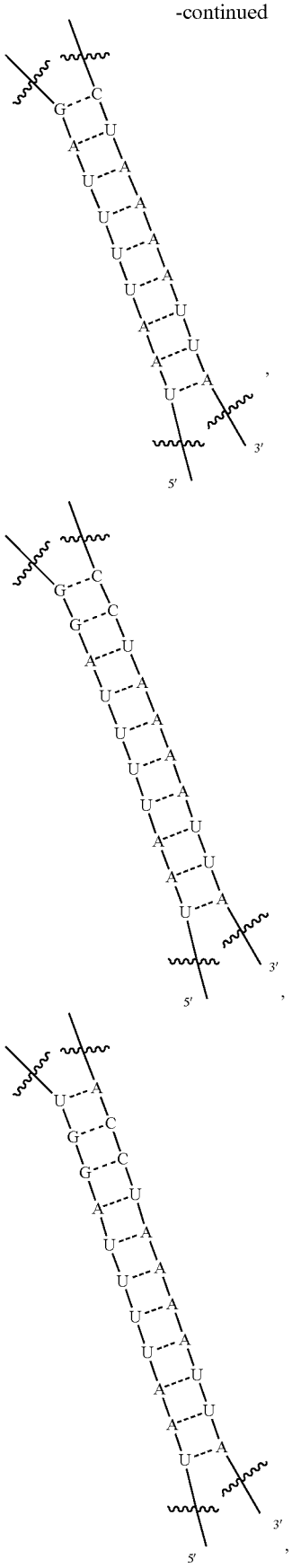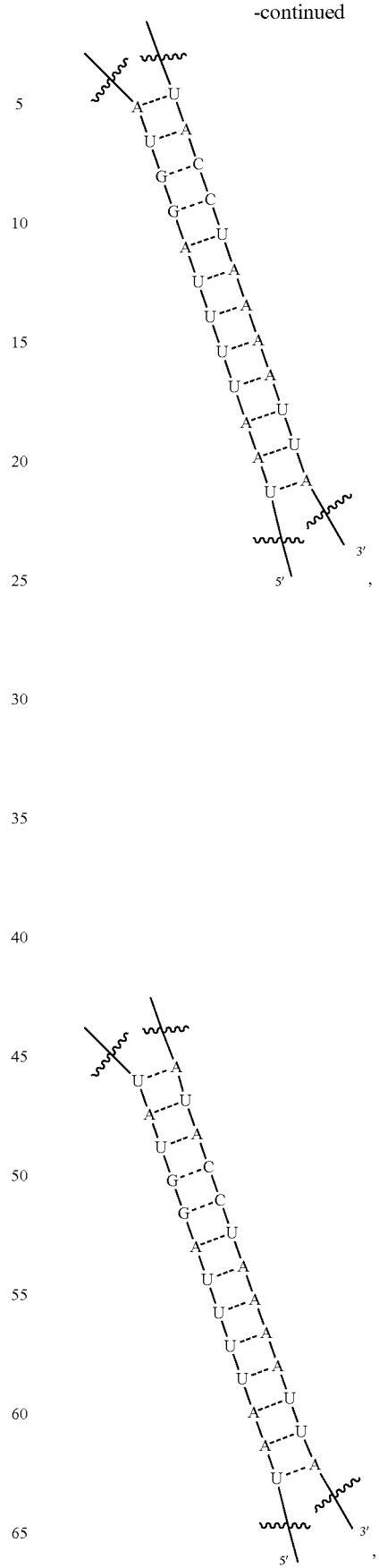

-continued

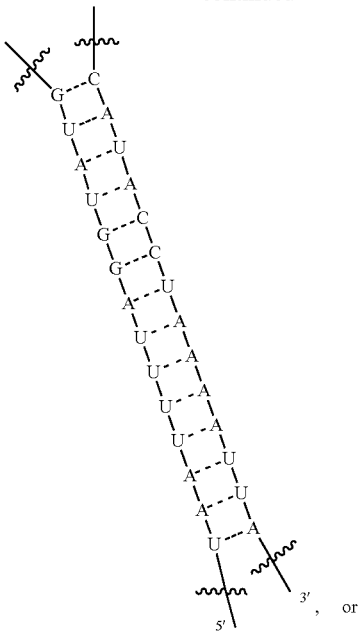

, or or covariants thereof. In some embodiments, $(N-N)_{u'}$ is of formula:

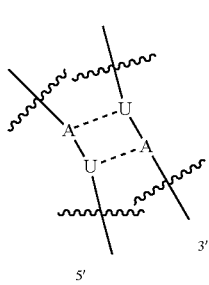

and $B_1$ is a adenine residue and $B_2$ is a uracil residue, or a covariant thereof. In some embodiments, $(N-N)_{u'}$ is of formula and $B_1$ is a uracil residue and $B_2$ is a adenine residue, or a covariant thereof. In some embodiments, $(N-N)_{u'}$ is of formula:

and $B_1$ is a guanine residue and $B_2$ is a cytosine residue, or a covariant thereof.

In some embodiments of any of formulas $A_{3'}\text{-i}$, $A_{2'}\text{-i}$, $B_{3'}\text{-i}$, $B_{2'}\text{-i}$, $C_{3'}\text{-i}$, $C_{2'}\text{-i}$, $D_{3'}\text{-i}$, $D_{2'}\text{-i}$, $E_{3'}\text{-i}_U$, $E_{2'}\text{-i}_U$, $E_{3'}\text{-i}_A$, $E_{2'}\text{-i}_A$, $F_{3'}\text{-i}_U$, $F_{2'}\text{-i}_U$, $F_{3'}\text{-i}_A$, or $F_{2'}\text{-i}_A$:

Linker is a non-nucleotide chemical linkage selected from a covalent bond and an optionally substituted, bivalent, straight or branched, saturated or unsaturated $C_1\text{-}C_{50}$ hydrocarbon chain, wherein one or more methylene units are optionally replaced by —O—, —S—, —N(R)—, —C(O)—, —C(S)—, —C(NR)—, —C(NOR)—, —C(NNR$_2$)—, —OC(O)—, —C(O)O—, —C(O)N(R)—, —N(R)C(O)—, —C(NR)O—, —OC(NR)—, —C(NR)NR—, —N(R)C(NR)—, —N(R)C(O)N(R)—, —N(R)C(O)O—, —OC(O)N(R)—, —N(R)C(O)S—, —SC(O)N(R)—, —N(R)C(NR)N(R)—, —SO$_2$—, —SO$_2$N(R)—, —N(R)SO$_2$—, —OP(O)(OH)O—, —OP(S)(OH)O—, —OP(S)(SH)O—, —OP(S)(COOH)O—, —OP(O)(COOH)O—, —OP(O)(NR$_2$)O—, —NP(O)(OH)O—, —OP(O)(OH)N—, or -Cy-;

each R is independently hydrogen or an optionally substituted group selected from $C_1$-$C_6$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur; and Cy is an optionally substituted, mono- or multicyclic, 3- to 20-membered, bivalent ring system, wherein the ring system is fully saturated, fully or partially unsaturated, or aromatic, and wherein the ring system contains 0-6 heteroatoms selected from the group consisting of O, N, and S.

In some embodiments of any of formulas $A_3$-i, $A_2$-i, $B_3$-i, $B_2$-i, $C_3$-i, $C_2$-i, $D_3$-i, $D_2$-i, $E_3$-$i_U$, $E_2$-$i_U$, $E_3$-$i_A$, $E_2$-$i_A$, $F_3$-$i_U$, $F_2$-$i_U$, $F_3$-$i_A$, or $F_2$-$i_A$, Linker is a non-nucleotide chemical linkage that has the formula -($L^a$)$_f$-M-($L^a$)$_f$-, wherein:

each $L^a$ is independently a covalent bond or an optionally substituted, bivalent, straight or branched, saturated or unsaturated $C_1$-$C_{50}$ hydrocarbon chain, wherein one or more methylene units are optionally replaced by —O—, —S—, —N(R)—, —C(O)—, —C(S)—, —C(NR)—, —C(NOR)—, —C(NNR$_2$)—, —OC(O)—, —C(O)O—, —C(O)N(R)—, —N(R)C(O)—, —C(NR)O—, —OC(NR)—, —C(NR)NR—, —N(R)C(NR)—, —N(R)C(O)N(R)—, —N(R)C(O)O—, —OC(O)N(R)—, —N(R)C(O)S—, —SC(O)N(R)—, —N(R)C(NR)N(R)—, —SO$_2$—, —SO$_2$N(R)—, —N(R)SO$_2$—, —OP(O)(OH)O—, —OP(S)(OH)O—, —OP(S)(SH)O—, —OP(S)(COOH)O—, —OP(O)(COOH)O—, —OP(O)(NR$_2$)O—, —NP(O)(OH)O—, —OP(O)(OH)N—, or -Cy-;

M is —O—, —S—, —S—S—, —N(R)—, —C(O)—, —C(S)—, —C(NR)—, —C(NOR)—, —C(NNR$_2$)—, —OC(O)—, —C(O)O—, —C(O)N(R)—, —N(R)C(O)—, —C(NR)O—, —OC(NR)—, —C(NR)NR—, —N(R)C(NR)—, —N(R)C(O)N(R)—, —N(R)C(O)O—, —OC(O)N(R)—, —N(R)C(O)S—, —SC(O)N(R)—, —N(R)C(NR)N(R)—, —SO$_2$—, —SO$_2$N(R)—, —N(R)SO$_2$—, —OP(O)(OH)O—, —OP(S)(OH)O—, —OP(S)(SH)O—, —OP(S)(COOH)O—, —OP(O)(COOH)O—, —OP(O)(NR$_2$)O—, —NP(O)(OH)O—, —OP(O)(OH)N—, or -Cy-;

each R is independently hydrogen or an optionally substituted group selected from $C_{1-6}$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur;

Cy is an optionally substituted, mono- or multicyclic, 3- to 20-membered, bivalent ring system, wherein the ring system is fully saturated, fully or partially unsaturated, or aromatic, and wherein the ring system contains 0-6 heteroatoms selected from the group consisting of O, N, and S; and each f is independently 0, 1, 2, 3, 4, 5, or 6.

In some embodiments, guide molecules of formulas $A_3$-ii and $A_2$-ii are provided:

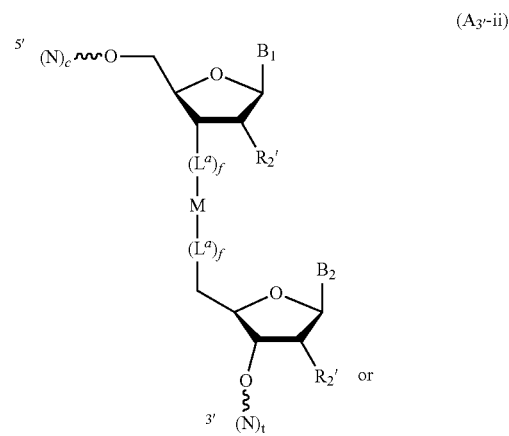

($A_3$-ii)

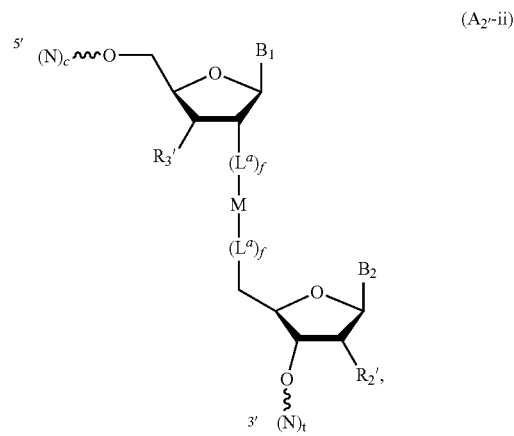

($A_2$-ii)

wherein N, $B_1$, $B_2$, $R_2'$, $R_3'$, c, t, and ⌇ are as defined above in formulas $A_3$-i and $A_2$-i, and $L^a$, M, and f are as described above and defined herein.

In some embodiments, guide molecules of formulas $B_{3'}$-ii and $B_{2'}$-ii are provided:
In some embodiments, guide molecules of formulas $C_{3'}$-ii, $C_{2'}$-ii, $D_{3'}$-ii, and $D_{2'}$-ii are provided:
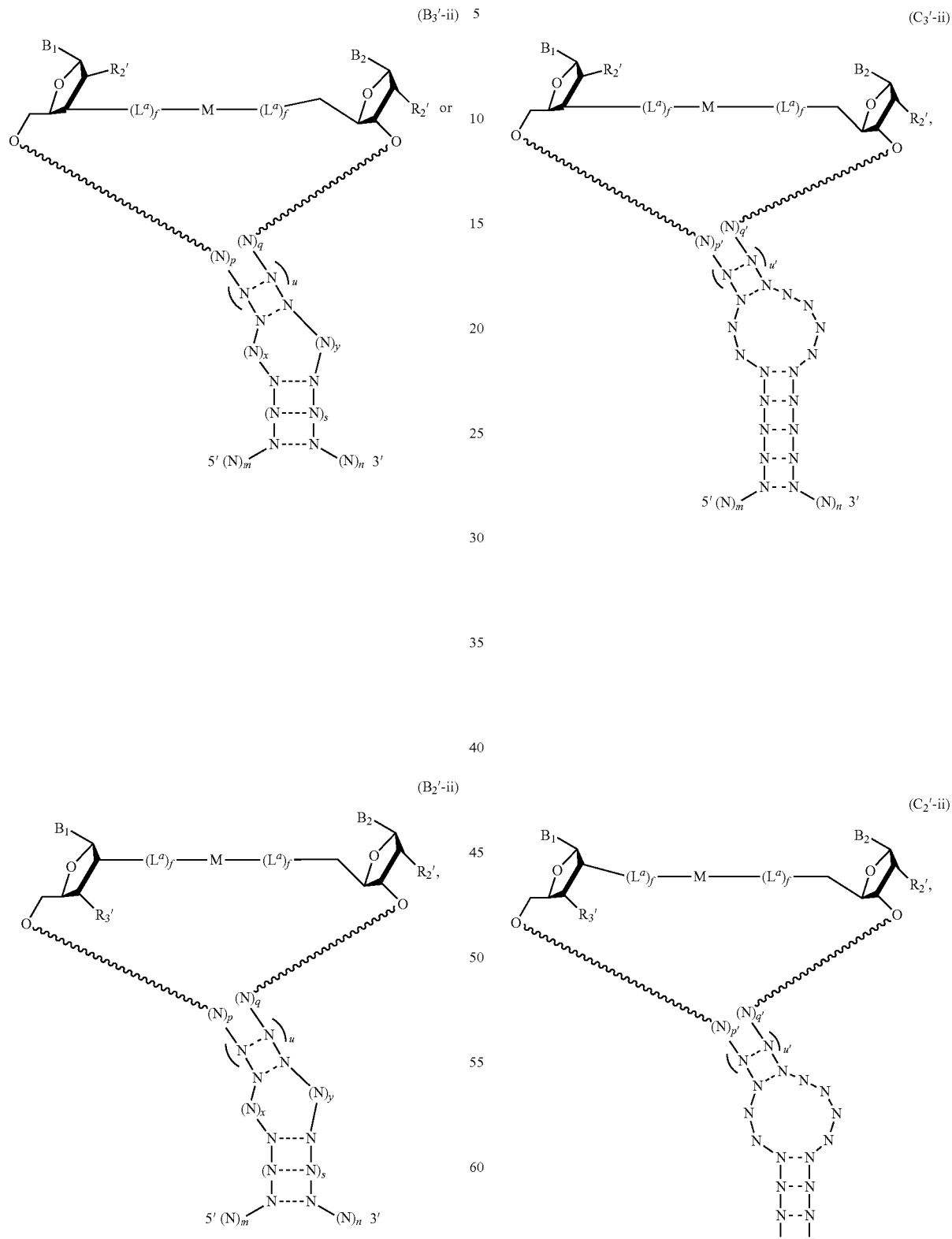
wherein N, $B_1$, $B_2$, $R_2'$, $R_3'$, p, q, u, x, y, s, n, m, and ⁓ are as defined above in formulas $B_{3'}$-i and $B_{2'}$-i, and $L^a$, M, and f are as described above and defined herein.

-continued
(D₃'-ii)
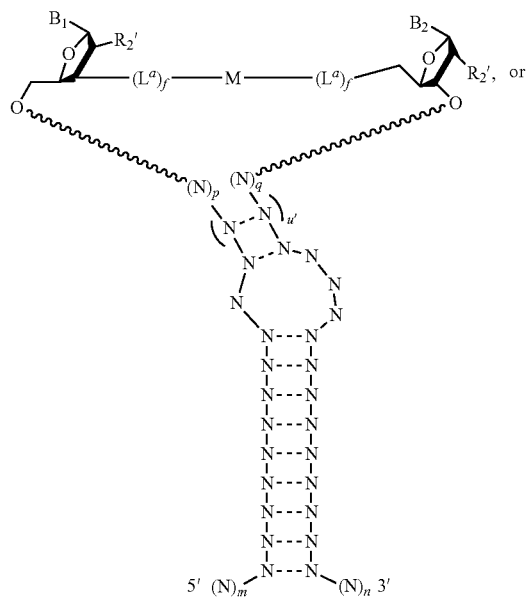
(D₂'-ii)
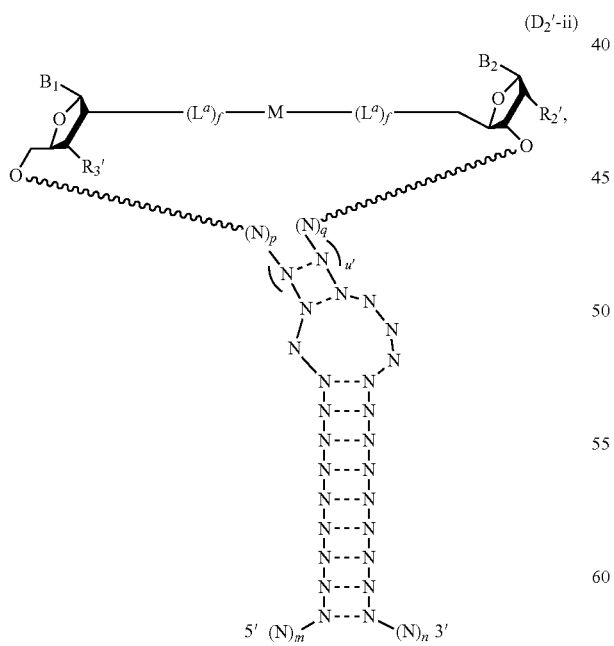
wherein N, B₁, B₂, R₂', R₃', p', q' u', n, m, and ∿∿∿ are as defined above in formulas C₃'-i, C₂'-i, D₃'-i, and D₂'-i, and $L^a$, M, and f are as described above and defined herein.
In some embodiments, guide molecules of formulas $E_{3'}$-ii$_U$, $E_{2'}$-ii$_U$, $E_{3'}$-ii$_A$, and $E_{2'}$-ii$_A$, or covariants thereof, are provided:
(E₃'-ii_U)
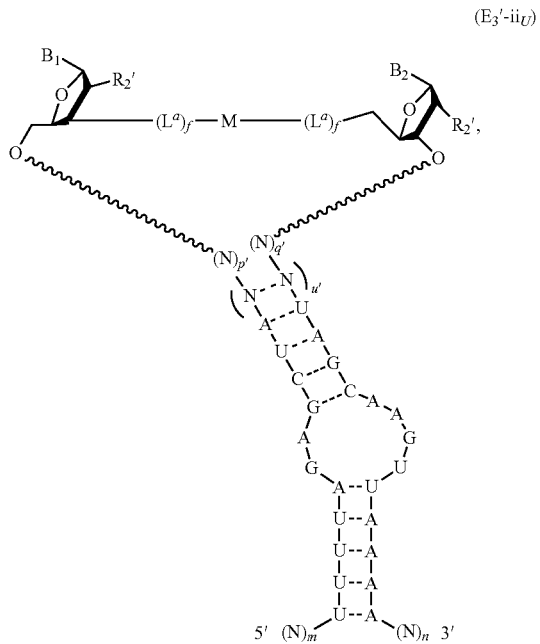
(E₂'-ii_U)
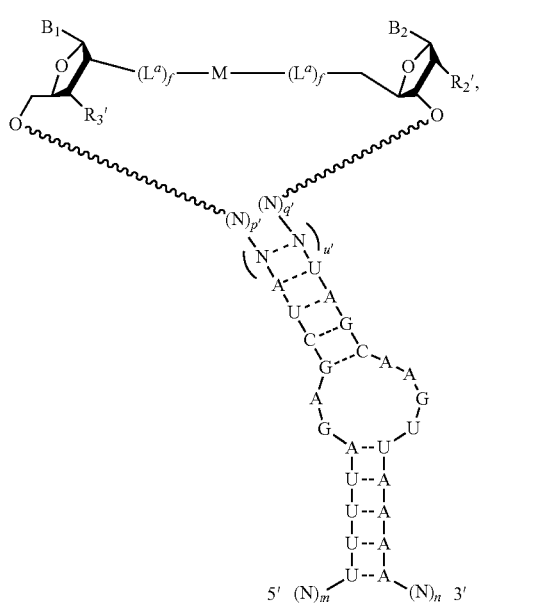

-continued
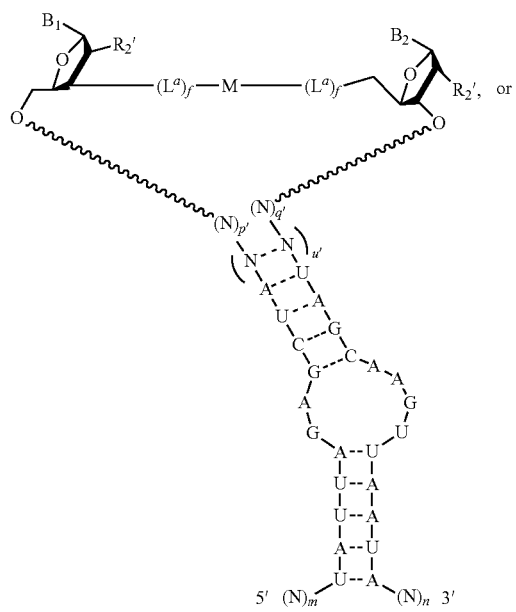
(E3'-ii_A)
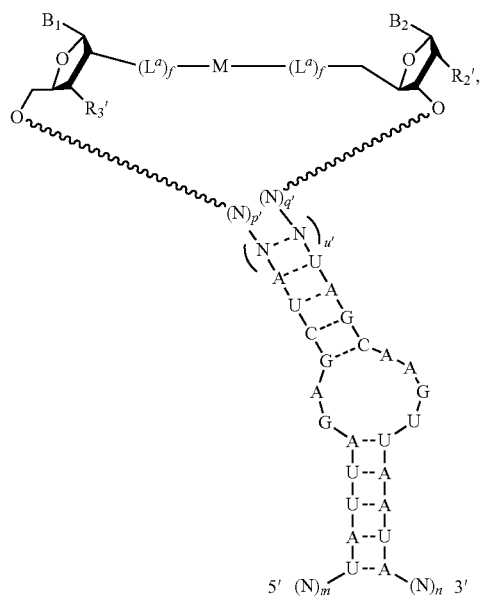
(E2'-ii_A)
wherein N, $B_1$, $B_2$, $R_2'$, $R_3'$ p', q', u', n, m, and ～ are as defined above in formulas $E_3'$-$ii_U$, $E_2'$-$ii_U$, $E_3'$-$ii_A$, and $E_2'$-$ii_A$, and $L^a$, M, and f are as described above and defined herein.
In some embodiments, guide molecules of formulas $F_3'$-$ii_U$, $F_2'$-$ii_U$, $F_3'$-$ii_A$, and $F_2'$-$ii_A$, or covariants thereof, are provided:
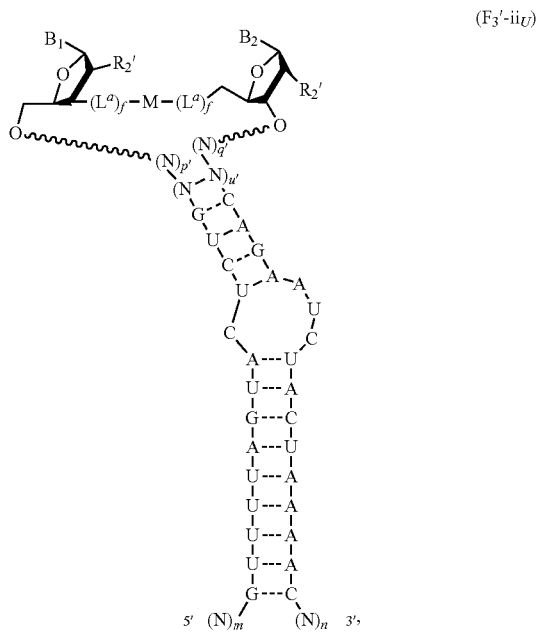
(F3'-ii_U)
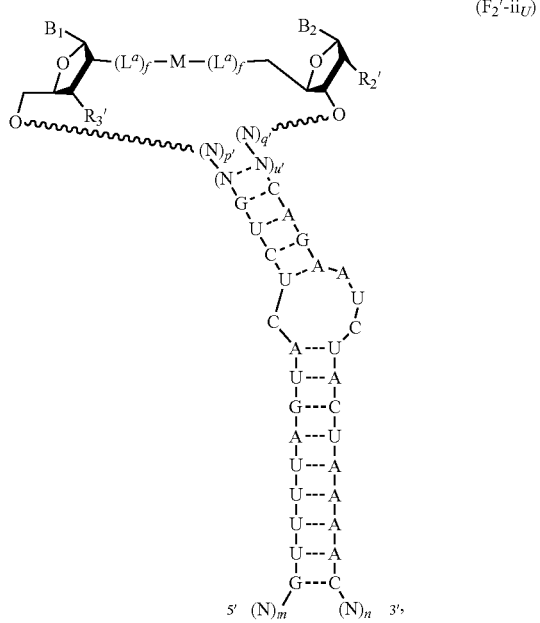
(F2'-ii_U)

-continued

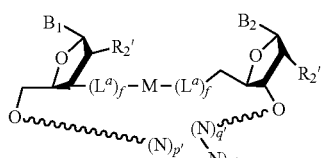

(F3'-ii_A)

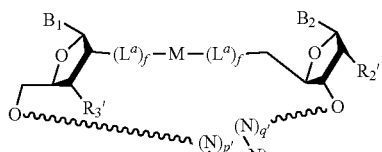

(F2'-ii_A)

wherein N, $B_1$, $B_2$, $R_2'$, $R_3'$, p', q' u', n, m, and ∿∿ are as defined above in formulas $F_{3'}\text{-ii}_U$, $F_{2'}\text{-ii}_U$, $F_{3'}\text{-ii}_A$, and $F_{2'}\text{-ii}_A$, and $L^a$, M, and f are as described above and defined herein.

It will be appreciated that throughout this disclosure, Linkers may be read from both directions, unless otherwise indicated. For example, a Linker of formula -($L^a$)-M-($L^a$)-($L^a$)- includes both 3'-($L^a$)-M-($L^a$)-($L^a$)-5' and 5'-($L^a$)-M-($L^a$)-($L^a$)-3', unless otherwise specified.

In some embodiments of any of Formulas $A_{3'}$-i, $A_{2'}$-i, $B_{3'}$-i, $B_{2'}$-i, $C_{3'}$-i, $C_{2'}$-i, $D_{3'}$-i, $D_{2'}$-i, $E_{3'}\text{-i}_U$, $E_{2'}\text{-i}_U$, $E_{3'}\text{-i}_A$, $E_{2'}\text{-i}_A$, $F_{3'}\text{-i}_U$, $F_{2'}\text{-i}_U$, $F_{3'}\text{-i}_A$, or $F_{2'}\text{-i}_A$, Linker is a non-nucleotide chemical linkage that has the formula -M-$(L^a)_f$- or -$(L^a)_f$-M-. In some embodiments, Linker is 5'-M-$(L^a)_f$-3'. In some embodiments, Linker is 5'-$(L^a)_f$-M-3'.

For example, in some embodiments, in a compound of formula $A_3'$-i, Linker is 5'-M-$(L^a)_f$-3', having the formula $A_{3'}$-xi. In some embodiments, in a compound of formula $A_{2'}$-i, Linker is 5'-M-$(L^a)_f$-3', having the formula $A_{2'}$-xi. In some embodiments, in a compound of formula $A_3'$-i, Linker is 5'-$(L^a)_f$-M-3', having the formula $A_{3'}$-xii. In some embodiments, in a compound of formula $A_{2'}$-i, Linker is 5'-$(L^a)_f$-M-3', having the formula $A_{2'}$-xii.

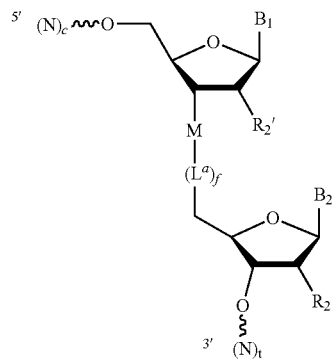

(A3'-xi)

(A2'-xi)

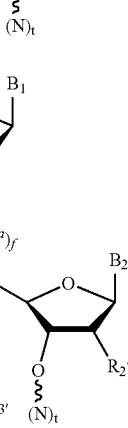

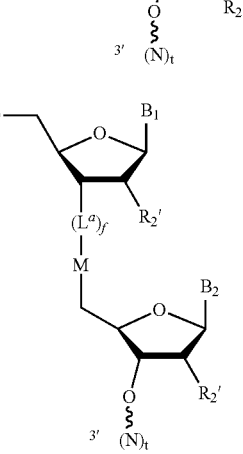

(A3'-xii)

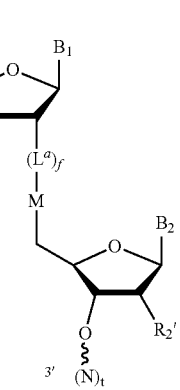

(A2'-xii)

In some embodiments of Formulas $B_3\text{'-i}$ or $B_2\text{'-i}$ or subgenera thereof, p is not equal to q. In some embodiments, p is at least one greater than q. In some embodiments, q is at least one greater than p. In some embodiments, p is one greater than q. In some embodiments, q is one greater than p. In some embodiments, p is two greater than q. In some embodiments, q is two greater than p.

In some embodiments of any of Formulas $C_3\text{'-i}$, $C_2\text{'-i}$, $D_3\text{'-i}$, $D_2\text{'-i}$, $E_3\text{'-i}_U$, $E_2\text{'-i}_U$, $F_3\text{'-i}_A$, $E_2\text{'-i}_A$, $F_3\text{'-i}_U$, $F_2\text{'-i}_U$, $F_3\text{'-i}_A$, or $F_2\text{'-i}_A$ or subgenera thereof, p' is not equal to q'. In some embodiments, p' is at least one greater than q'. In some embodiments, q' is at least one greater than p'. In some embodiments, p' is one greater than q'. In some embodiments, q' is one greater than p'. In some embodiments, p' is two greater than q'. In some embodiments, q' is two greater than p'.

In some embodiments, the guide molecule of any of Formulas $A_3\text{'-ii}$, $A_2\text{'-ii}$, $B_3\text{'-ii}$, $B_2\text{'-ii}$, $C_3\text{'-ii}$, $C_2\text{'-ii}$, $D_3\text{'-ii}$, $D_2\text{'-ii}$, $E_3\text{'-ii}_U$, $E_2\text{'-ii}_U$, $E_3\text{'-ii}_A$, $E_2\text{'-ii}_A$, $F_3\text{'-ii}_U$, $F_2\text{'-ii}_U$, $F_3\text{'-ii}_A$, or $F_2\text{'-ii}_A$ is provided wherein:

M is selected from —N(R)—, —S—, —S—S—, —C(O)N(R)—, —N(R)C(O)—, —C(NR)NR—, —N(R)C(NR)—, —N(R)C(O)N(R)—, —N(R)C(O)O—, —OC(O)N(R)—, —NP(O)(OH)O— or —OP(O)(OH)N—, or

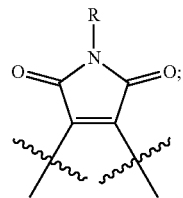

each $L^a$ is independently selected from:

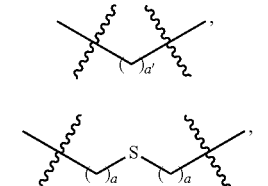
$L^a\text{-}1'$

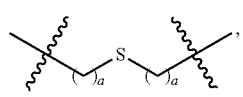
$L^a\text{-}3$

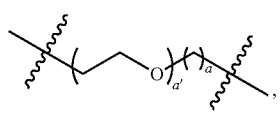
$L^a\text{-}5'$

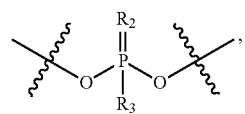
$L^a\text{-}26$

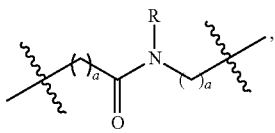
$L^a\text{-}27$

-continued

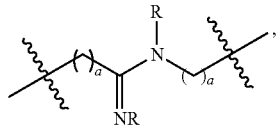
$L^a\text{-}31$

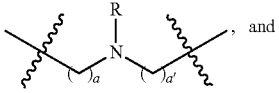
$L^a\text{-}37'$, and

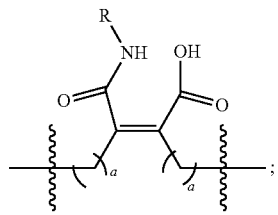
$L^a\text{-}41$ each a is independently an integer between 0 and 16, inclusive;
each a' is independently an integer between 1 and 16, inclusive;
each $R_2$ is independently O or S;
each $R_3$ is independently OH or COOH; and
at least one f is not 0 when M is —NP(O)(OH)O— or —OP(O)(OH)N—.

In some embodiments, the guide molecule of any of Formulas $A_3\text{'-ii}$, $A_2\text{'-ii}$, $B_3\text{'-ii}$, $B_2\text{'-ii}$, $C_3\text{'-ii}$, $C_2\text{'-ii}$, $D_3\text{'-ii}$, $D_2\text{'-ii}$, $E_3\text{'-ii}_U$, $E_2\text{'-ii}_U$, $E_3\text{'-ii}_A$, $E_2\text{'-ii}_A$, $F_3\text{'-ii}_U$, $F_2\text{'-ii}_U$, $F_3\text{'-ii}_A$, or $F_2\text{'-ii}_A$ is provided wherein:

M is selected from —N(R)—, —S—, —S—S—, —C(O)N(R)—, —N(R)C(O)—, —C(NR)NR—, —N(R)C(NR)—, —N(R)C(O)N(R)—, —N(R)C(O)O—, —OC(O)N(R)—, —NP(O)(OH)O— or —OP(O)(OH)N—, or

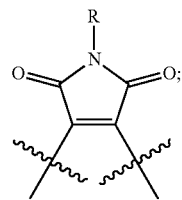

each $L^a$ is independently selected from:

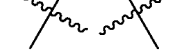
$L^a\text{-}1'$

$L^a\text{-}3$

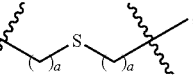
$L^a\text{-}5'$

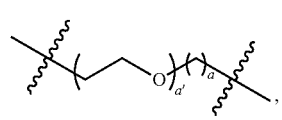

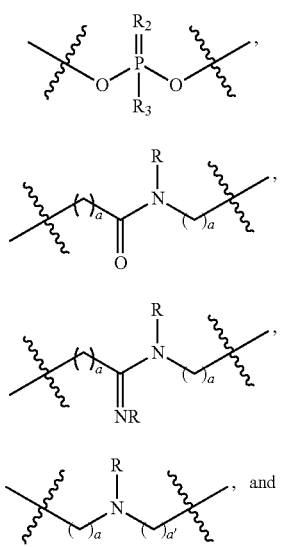
L$^a$-26
L$^a$-27
L$^a$-31
L$^a$-37'
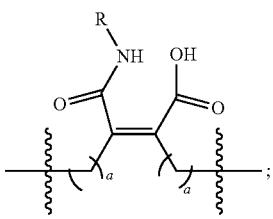
L$^a$-41
each a is independently an integer between 0 and 16, inclusive;
each a' is independently an integer between 1 and 16, inclusive;
each $R_2$ is independently O or S;
each $R_3$ is independently OH or COOH; and
at least one f is not 0 when M is —NP(O)(OH)O— or —OP(O)(OH)N—,
provided that Linker is not:
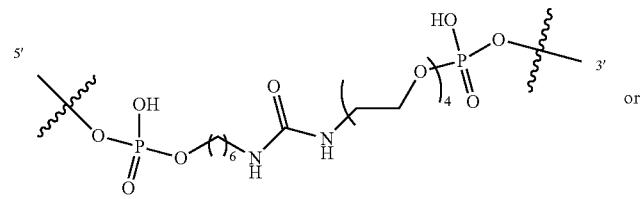
or
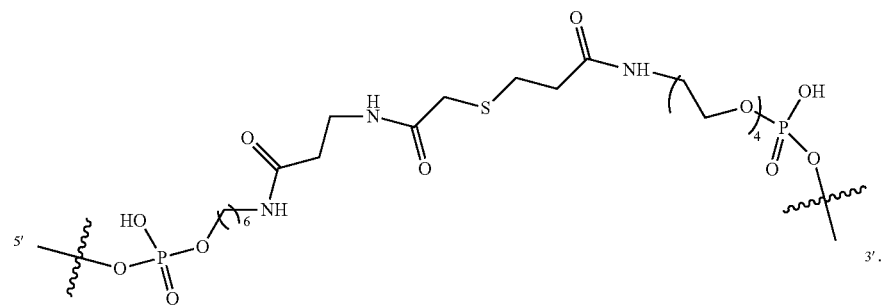

In some embodiments, the guide molecule of any of Formulas $A_{3'}$-ii, $A_{2'}$-ii, $B_{3'}$-ii, $B_{2'}$-ii, $C_{3'}$-ii, $C_{2'}$-ii, $D_{3'}$-ii, $D_{2'}$-ii, $E_{3'}$-ii$_U$, $E_{2'}$-ii$_U$, $E_{3'}$-ii$_A$, $E_{2'}$-ii$_A$, $F_{3'}$-ii$_U$, $F_{2'}$-ii$_U$, $F_{3'}$-ii$_A$, or $F_{2'}$-ii$_A$ is provided wherein:

M is selected from —S—S—, —C(NR)NR—, —N(R)C(NR)—, —N(R)C(O)O—, —OC(O)N(R)—, —NP(O)(OH)O—, —OP(O)(OH)N—, or

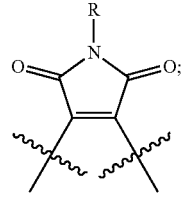

each $L^a$ is independently selected from:

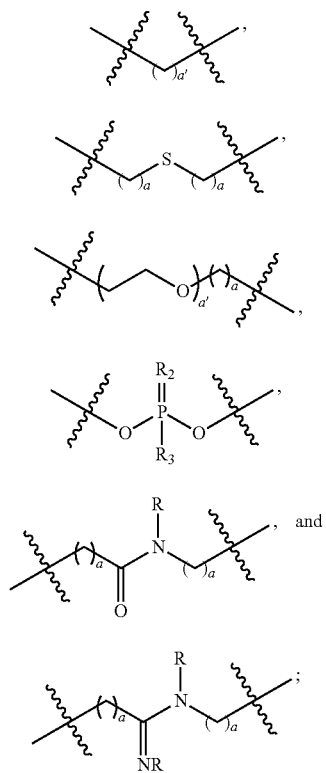

each a is independently an integer between 0 and 16, inclusive;

each a' is independently an integer between 1 and 16, inclusive;

each $R_2$ is independently O or S;

each $R_3$ is independently OH or COOH; and at least one f is not 0, when M is —NP(O)(OH)O— or —OP(O)(OH)N—.

In some embodiments, the guide molecule of any of Formulas $A_{3'}$-ii, $A_{2'}$-ii, $B_{3'}$-ii, $B_{2'}$-ii, $C_{3'}$-ii, $C_{2'}$-ii, $D_{3'}$-ii, $D_{2'}$-ii, $E_{3'}$-ii$_U$, $E_{2'}$-ii$_U$, $E_{3'}$-ii$_A$, $E_{2'}$-ii$_A$, $F_{3'}$-ii$_U$, $F_{2'}$-ii$_U$, $F_{3'}$-ii$_A$, or $F_{2'}$-ii$_A$ is provided wherein:

M is selected from —S—S—, —C(O)N(R)—, —N(R)C(O)—, —C(NR)NR—, —N(R)C(NR)—, —N(R)C(O)O—, —OC(O)N(R)—, —NP(O)(OH)O—, —OP(O)(OH)N—, or

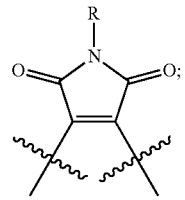

each $L^a$ is independently selected from:

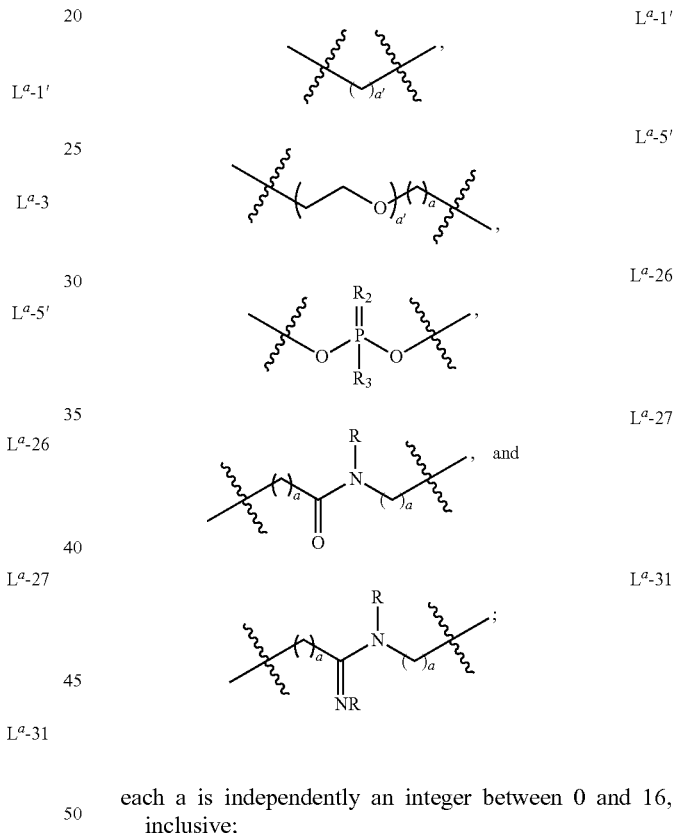

each a is independently an integer between 0 and 16, inclusive;

each a' is independently an integer between 1 and 16, inclusive;

each $R_2$ is independently O or S;

each $R_3$ is independently OH or COOH; and at least one f is not 0, when M is —NP(O)(OH)O— or —OP(O)(OH)N—.

In some embodiments, the guide molecule of any of Formulas $A_{3'}$-ii, $A_{2'}$-ii, $B_{3'}$-ii, $B_{2'}$-ii, $C_{3'}$-ii, $C_{2'}$-ii, $D_{3'}$-ii, $D_{2'}$-ii, $E_{3'}$-ii$_U$, $E_{2'}$-ii$_U$, $E_{3'}$-ii$_A$, $E_{2'}$-ii$_A$, $F_{3'}$-ii$_U$, $F_{2'}$-ii$_U$, $F_{3'}$-ii$_A$, or $F_{2'}$-ii$_A$ is provided wherein:

M is selected from —N(R)—, —S—S—, —C(O)N(R)—, —N(R)C(O)—, —C(NR)NR—, —N(R)C(NR)—, —N(R)C(O)N(R)—, —N(R)C(O)O—, —OC(O)N(R)—, —NP(O)(OH)O—, —OP(O)(OH)N—, or

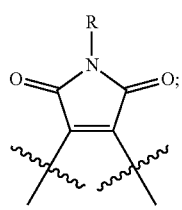

each $L^a$ is independently selected from:

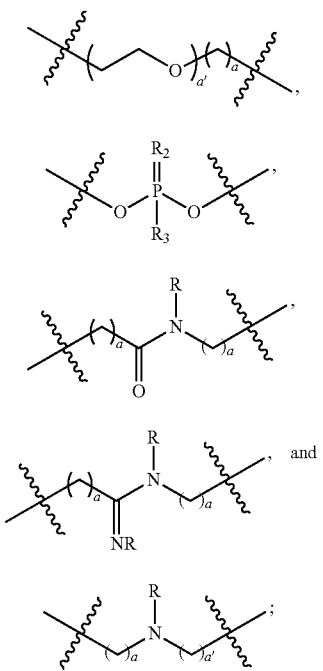

$L^a$-5′

$L^a$-26

$L^a$-27

$L^a$-31

$L^a$-37′ each a is independently an integer between 0 and 16, inclusive;
each a′ is independently an integer between 1 and 16, inclusive;
each $R_2$ is independently O or S;
each $R_3$ is independently OH or COOH; and
at least one f is not 0, when M is —NP(O)(OH)O— or —OP(O)(OH)N—.

In some embodiments of formulas $A_{3'}$-ii, $A_{2'}$-ii, $B_{3'}$-ii, $B_{2'}$-ii, $C_{3'}$-ii, $C_{2'}$-ii, $D_{3'}$-ii, $D_{2'}$-ii, $E_{3'}$-ii$_U$, $E_{2'}$-ii$_U$, $E_{3'}$-ii$_A$, $E_{2'}$-ii$_A$, $F_{3'}$-ii$_U$, $F_{2'}$-ii$_U$, $F_{3'}$-ii$_A$, or $F_{2'}$-ii$_A$ or subgenera thereof, M is —S—, —S—S—, —C(O)N(R)—, —N(R)C(O)—, —C(NR)NR—, —N(R)C(NR)—, —N(R)C(O)N(R)—, —N(R)C(O)O—, —OC(O)N(R)—, —NP(O)(OH)O— or —OP(O)(OH)N—, or

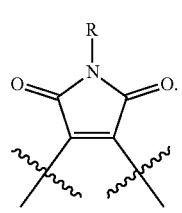

In some embodiments, M is —S—S—, —C(NR)NR—, —N(R)C(NR)—, —N(R)C(O)O—, —OC(O)N(R)—, —NP(O)(OH)O—, —OP(O)(OH)N—, or

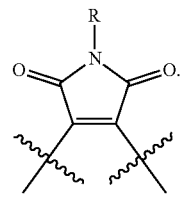

In some embodiments, M is —S—S—, —C(O)N(R)—, —N(R)C(O)—, —C(NR)NR—, —N(R)C(NR)—, —N(R)C(O)O—, —OC(O)N(R)—, —NP(O)(OH)O—, —OP(O)(OH)N—, or

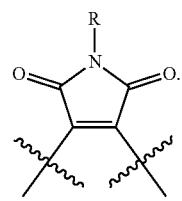

In some embodiments, M is —S—S—, —C(O)N(R)—, —N(R)C(O)—, —C(NR)NR—, —N(R)C(NR)—, —N(R)C(O)N(R)—, —N(R)C(O)O—, —OC(O)N(R)—, —NP(O)(OH)O—, —OP(O)(OH)N—, or

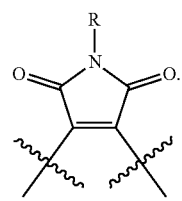

In some embodiments of formulas $A_{3'}$-ii, $A_{2'}$-ii, $B_{3'}$-ii, $B_{2'}$-ii, $C_{3'}$-ii, $C_{2'}$-ii, $D_{3'}$-ii, $D_{2'}$-ii, $E_{3'}$-ii$_U$, $E_{2'}$-ii$_U$, $E_{3'}$-ii$_A$, $E_{2'}$-ii$_A$, $F_{3'}$-ii$_U$, $F_{2'}$-ii$_U$, $F_{3'}$-ii$_A$, or $F_{2'}$-ii$_A$ or subgenera thereof, each $L^a$ is independently selected from:

$L^a$-1′

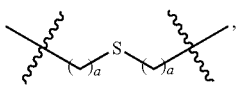

$L^a$-3

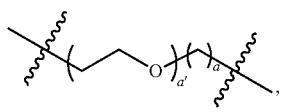

$L^a$-5′

-continued

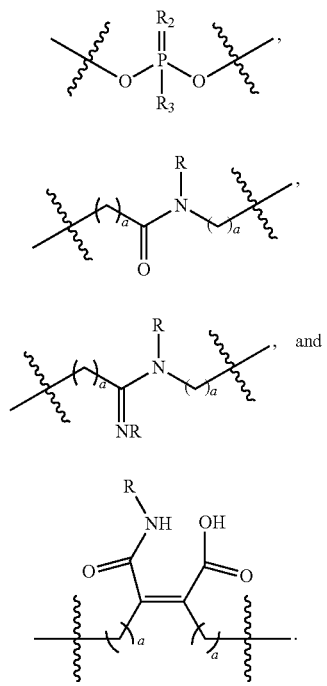

In some embodiments, each $L^a$ is independently selected from:

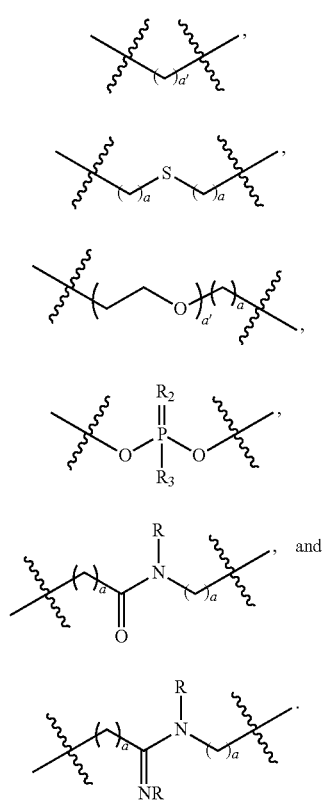

In some embodiments, each $L^a$ is independently selected from:

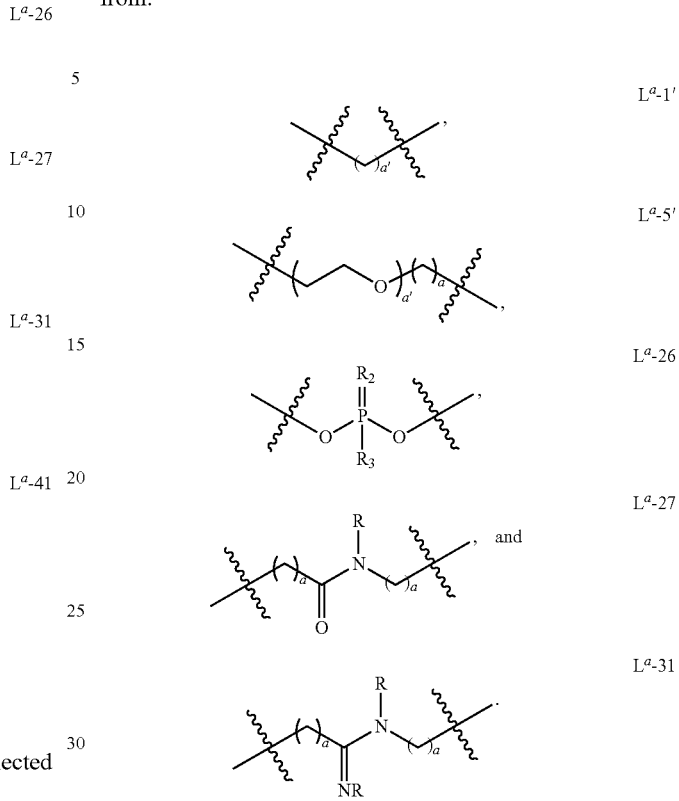

In some embodiments, each $L^a$ is independently selected from:

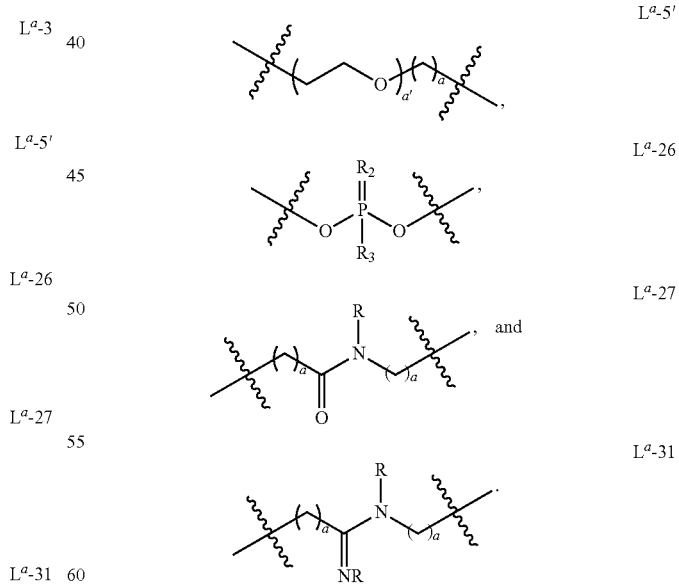

In some embodiments of formulas $A_{3'}$-ii, $A_{2'}$-ii, $B_{3'}$-ii, $B_{2'}$-ii, $C_{3'}$-ii, $C_{2'}$-ii, $D_{3'}$-ii, $D_{2'}$-ii, $E_{3'}$-ii$_U$, $E_{2'}$-ii$_U$, $E_{3'}$-ii$_A$, $E_{2'}$-ii$_A$, $F_{3'}$-ii$_U$, $F_{2'}$-ii$_U$, $F_{3'}$-ii$_A$, or $F_{2'}$-ii$_A$ or subgenera thereof, M is —N(R) C(O)O— or —OC(O)N(R)—. In some embodiments, M is —N(H)C(O)O— or —OC(O)N(H)—.

In some embodiments, -(Lᵃ)$_f$-M-(Lᵃ)$_f$- is:

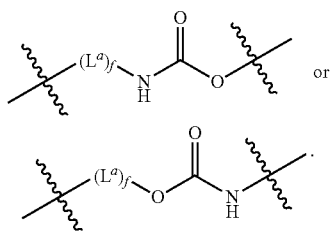 or

In some embodiments, M is —N(R)C(O)O— or —OC(O)N(R)—, and each Lᵃ is independently selected from:

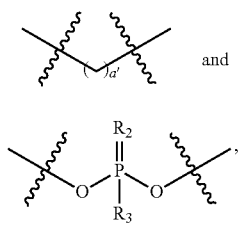

Lᵃ-1′ and

Lᵃ-26 wherein:
each a′ is independently an integer between 1 and 16, inclusive;
each R₂ is independently O or S; and
each R₃ is independently OH or COOH.

In some embodiments, -(Lᵃ)$_f$-M-(Lᵃ)$_f$- is:

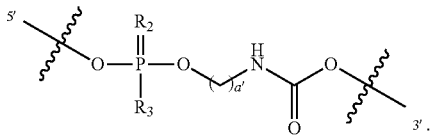

In some embodiments, -(Lᵃ)$_f$-M-(Lᵃ)$_f$- is:

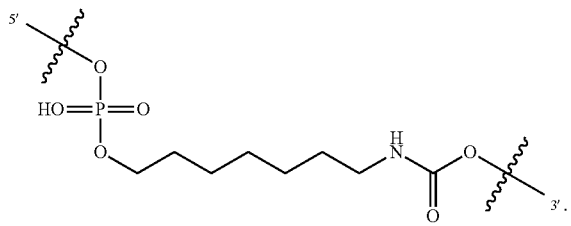

In some embodiments of formulas A$_{3'}$-ii, A$_{2'}$-ii, B$_{3'}$-ii, B$_{2'}$-ii, C$_{3'}$-ii, C$_{2'}$-ii, D$_{3'}$-ii, D$_{2'}$-ii, E$_{3'}$-ii$_U$, E$_{2'}$-ii$_U$, E$_{3'}$-ii$_A$, E$_{2'}$-ii$_A$, F$_{3'}$-ii$_U$, F$_{2'}$-ii$_U$, F$_{3'}$-ii$_A$, or F$_{2'}$-ii$_A$ or subgenera thereof, M is —N(R)C(O)N(R)—. In some embodiments, M is —N(H)C(O)N(H)—.

In some embodiments, -(Lᵃ)$_f$-M-(Lᵃ)$_f$- is:

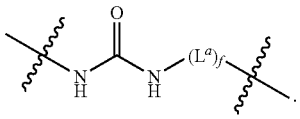

In some embodiments, M is —N(R)C(O)N(R)—, and each Lᵃ is independently selected from:

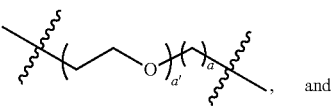

Lᵃ-5′ and

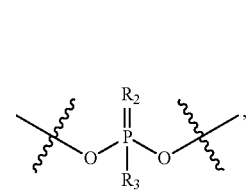

Lᵃ-26 wherein:
each a′ is independently an integer between 1 and 16, inclusive;
each R₂ is independently O or S; and
each R₃ is independently OH or COOH.

In some embodiments, -(Lᵃ)$_f$-M-(Lᵃ)$_f$- is:

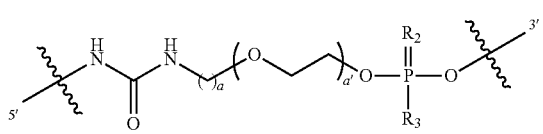

In some embodiments, -(Lᵃ)$_f$-M-(Lᵃ)$_f$- is:

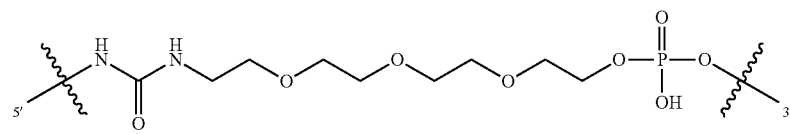

In some embodiments of formulas $A_{3'}$-ii, $A_{2'}$-ii, $B_{3'}$-ii, $B_{2'}$-ii, $C_{3'}$-ii, $C_{2'}$-ii, $D_{3'}$-ii, $D_{2'}$-ii, $E_{3'}$-ii$_U$, $E_{2'}$-ii$_U$, $E_{3'}$-ii$_A$, $E_{2'}$-ii$_A$, $F_{3'}$-ii$_U$, $F_{2'}$-ii$_U$, $F_{3'}$-ii$_A$, or $F_{2'}$-ii$_A$ or subgenera thereof, M is —C(NR)NR— or —N(R)C(NR)—. In some embodiments, M is —C(NH)NH— or —N(H)C(NH)—.

In some embodiments, -(L$^a$)$_f$-M-(L$^a$)$_{f'}$- is of Formula G-viii:

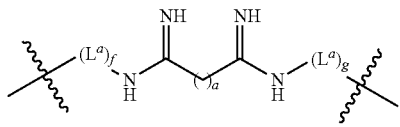

wherein:
  each a is independently an integer between 0 and 16, inclusive; and
  g is 0, 1, 2, 3, 4, or 5.

In some embodiments, -(L$^a$)$_f$-M-(L$^a$)$_{f'}$- is:

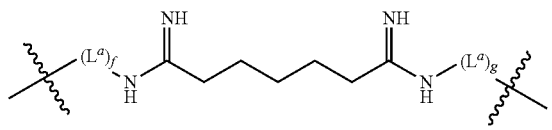

In some embodiments, M is —C(NR)NR— or —N(R)C (NR)—, and each L$^a$ is independently selected from:

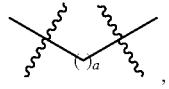
L$^a$-1'

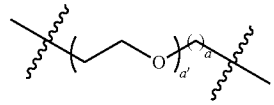
L$^a$-5'

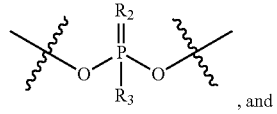
L$^a$-26, and

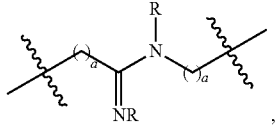
L$^a$-31 wherein:
  each a is independently an integer between 0 and 16, inclusive;
  each a' is independently an integer between 1 and 16, inclusive;
  each R$_2$ is independently O or S; and
  each R$_3$ is independently OH or COOH.

In some embodiments, -(L$^a$)$_f$-M-(L$^a$)$_{f'}$- is:

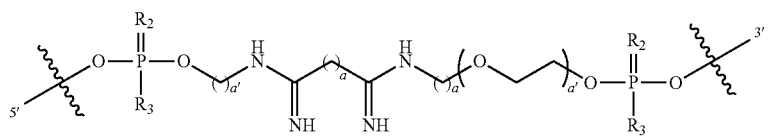

In some embodiments, -(L$^a$)$_f$-M-(L$^a$)$_{f'}$- is:

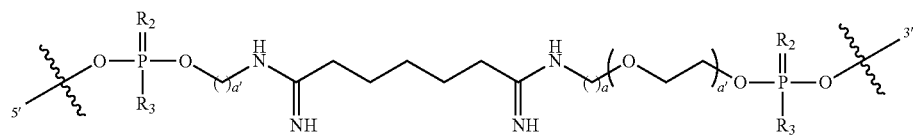

In some embodiments, -(L$^a$)$_f$-M-(L$^a$)$_{f'}$- is:

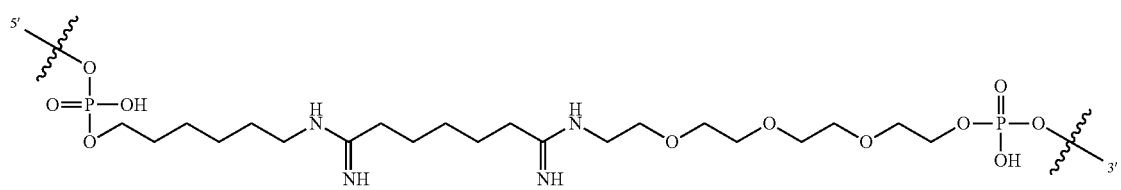 [SMILES: *OP(=O)(O)OCCCCCCNC(=N)CCCCCC(=N)NCCOCCOCCOCCOP(=O)(O)O* ; "."]

In some embodiments of formulas $A_{3'}$-ii, $A_{2'}$-ii, $B_{3'}$-ii, $B_{2'}$-ii, $C_{3'}$-ii, $C_{2'}$-ii, $D_{3'}$-ii, $D_{2'}$-ii, $E_{3'}$-ii$_U$, $E_{2'}$-ii$_U$, $E_{3'}$-ii$_A$, $E_{2'}$-ii$_A$, $F_{3'}$-ii$_U$, $F_{2'}$-ii$_U$, $F_{3'}$-ii$_A$, or $F_{2'}$-ii$_A$ or subgenera thereof, M is —C(O)N(R)— or —N(R)C(O)—. In some embodiments, M is —C(O)N(H)— or —N(H)C(O)—.

In some embodiments, $-(L^a)_f$-M-$(L^a)_{f'}$- is of Formula G-iv:

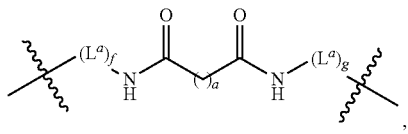

wherein:
each a is independently an integer between 0 and 16, inclusive; and
g is 0, 1, 2, 3, 4, or 5.

In some embodiments, $-(L^a)_f$-M-$(L^a)_{f'}$- is:

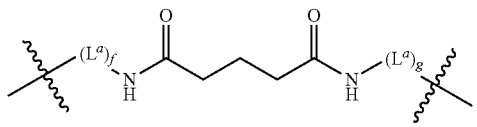

In some embodiments, $-(L^a)_f$-M-$(L^a)_{f'}$- is:

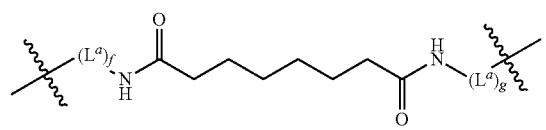

In some embodiments, M is —C(O)N(H)— or —N(H)C(O)—, and each $L^a$ is independently selected from:

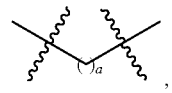
$L^a$-1'

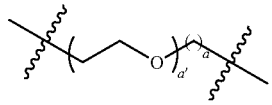
$L^a$-5'

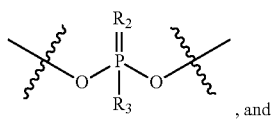
$L^a$-26
, and

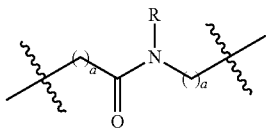
$L^a$-27
, wherein:
each a is independently an integer between 0 and 16, inclusive;
each a' is independently an integer between 1 and 16, inclusive;
each $R_2$ is independently O or S; and
each $R_3$ is independently OH or COOH.

In some embodiments, $-(L^a)_f$-M-$(L^a)_{f'}$- is:

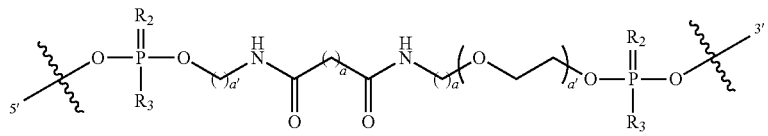

In some embodiments, $-(L^a)_f$-M-$(L^a)_{f'}$- is:

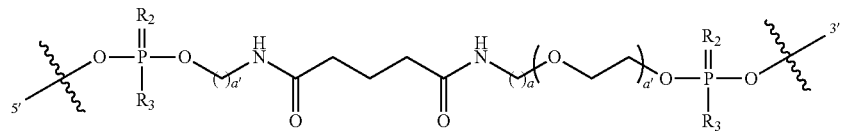

In some embodiments, $-(L^a)_f$-M-$(L^a)_{f'}$- is:

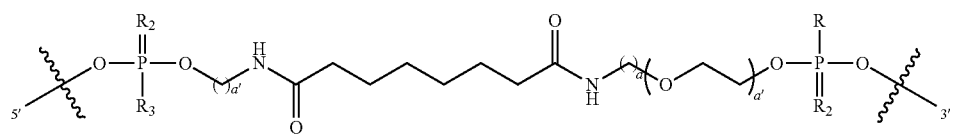

In some embodiments, -(L$^a$)$_f$-M-(L$^a$)$_{f'}$- is:

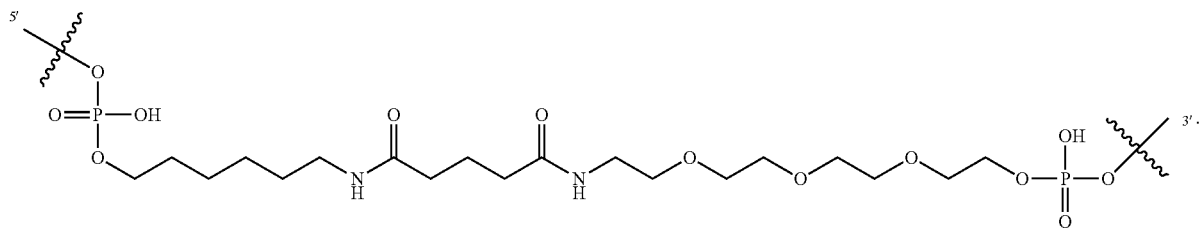 [SMILES: *OP(=O)(O)OCCCCCCNC(=O)CCCC(=O)NCCOCCOCCOCCOP(=O)(O)O*]

In some embodiments, -(L$^a$)$_f$-M-(L$^a$)$_{f'}$- is:

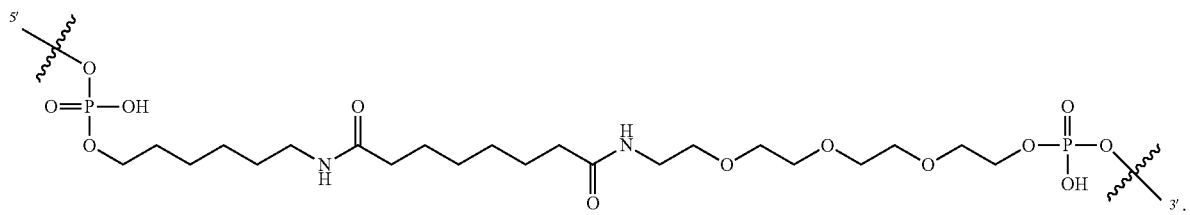 [SMILES: *OP(=O)(O)OCCCCCCNC(=O)CCCCCCC(=O)NCCOCCOCCOCCOP(=O)(O)O*]

In some embodiments of formulas A$_{3'}$-ii, A$_{2'}$-ii, B$_{3'}$-ii, B$_{2'}$-ii, C$_{3'}$-ii, C$_{2'}$-ii, D$_{3'}$-ii, D$_{2'}$-ii, E$_{39}$-ii$_U$, E$_{2'}$-ii$_U$, E$_{3'}$-ii$_A$, E$_{2'}$-ii$_A$, F$_{3'}$-ii$_U$, F$_{2'}$-ii$_U$, F$_{3'}$-ii$_A$, or F$_{2'}$-ii$_A$ or subgenera thereof, M is —NP(O)(OH)O— or —OP(O)(OH)N—.

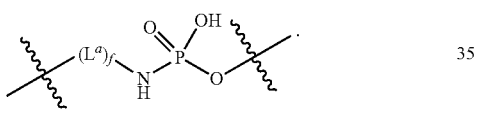

In some embodiments, -(L$^a$)$_f$-M-(L$^a$)$_{f'}$- is:
In some such embodiments, f is 1, 2, 3, 4, 5, or 6.
In some embodiments, -(L$^a$)$_f$-M-(L$^a$)$_{f'}$- is:

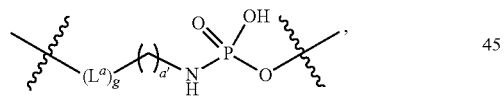

wherein:
each a' is independently an integer between 1 and 16, inclusive; and
g is 0, 1, 2, 3, 4, or 5.

In some embodiments, M is —NP(O)(OH)O— or —OP(O)(OH)N—, and each L$^a$ is independently selected from:

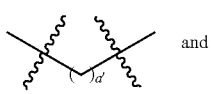

L$^a$-1' and

L$^a$-26

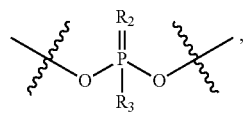

wherein:
each a' is independently an integer between 1 and 16, inclusive;
each R$_2$ is independently O or S; and
each R$_3$ is independently OH or COOH.

In some embodiments, -(L$^a$)$_f$-M-(L$^a$)$_{f'}$- is:

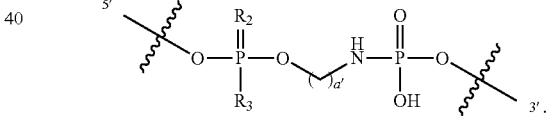

In some embodiments, -(L$^a$)$_f$-M-(L$^a$)$_{f'}$- is:

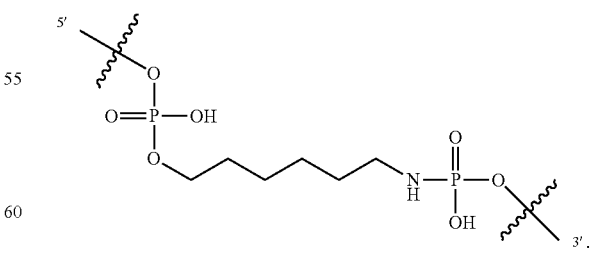

In some embodiments of formulas A$_{3'}$-ii, A$_{2'}$-ii, B$_{3'}$-ii, B$_{2'}$-ii, C$_{3'}$-ii, C$_{2'}$-ii, D$_{3'}$-ii, D$_{2'}$-ii, E$_{3'}$-ii$_U$, E$_{2'}$-ii$_U$, E$_{3'}$-ii$_A$, E$_{2'}$-ii$_A$, F$_{3'}$-ii$_U$, F$_{2'}$-ii$_U$, F$_{3'}$-ii$_A$, or F$_{2'}$-ii$_A$ or subgenera thereof, M is —S—S—.

In some embodiments, -(L$^a$)$_f$-M-(L$^a$)$_f$- is:

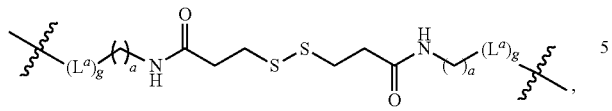

wherein:
each a is independently an integer between 0 and 16, inclusive; and
g is 0, 1, 2, 3, 4, or 5.

In some embodiments, -(L$^a$)$_f$-M-(L$^a$)$_f$- is:

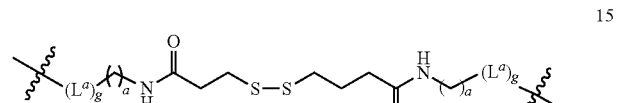

wherein:
each a is independently an integer between 0 and 16, inclusive; and
g is 0, 1, 2, 3, 4, or 5.

In some embodiments, -(L$^a$)$_f$-M-(L$^a$)$_f$- is:

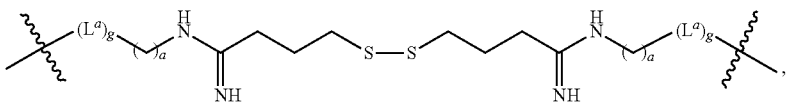

wherein:
each a is independently an integer between 0 and 16, inclusive; and
g is 0, 1, 2, 3, 4, or 5.

In some embodiments, M is —S—S—, and each L$^a$ is independently selected from:

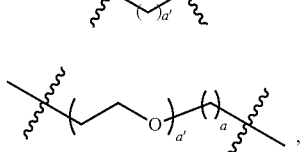
L$^a$-1'

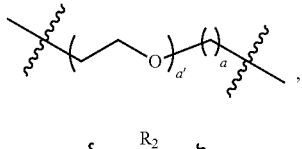
L$^a$-5'

L$^a$-26

-continued

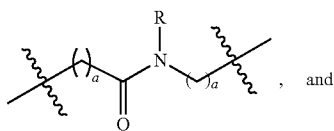
L$^a$-27
, and

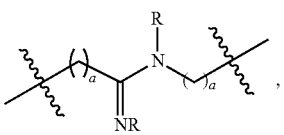
L$^a$-31
, wherein:
each a is independently an integer between 0 and 16, inclusive;
each a' is independently an integer between 1 and 16, inclusive;
each R$_2$ is independently O or S; and
each R$_3$ is independently OH or COOH.

In some embodiments, -(L$^a$)$_f$-M-(L$^a$)$_f$- is:

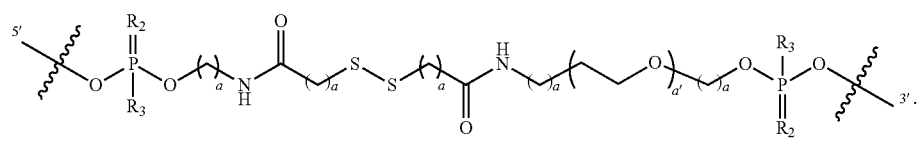

In some embodiments, -(L$^a$)$_f$-M-(L$^a$)$_f$- is:
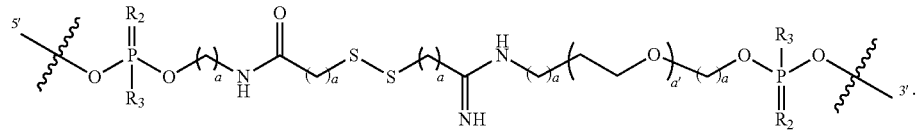
In some embodiments, -(L$^a$)$_f$-M-(L$^a$)$_f$- is:
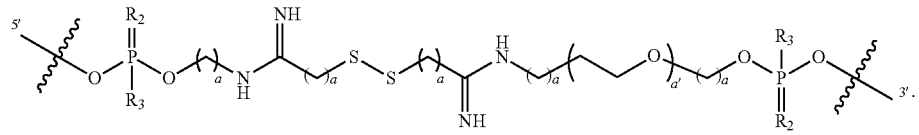
In some embodiments, -(L$^a$)$_f$-M-(L$^a$)$_f$- is:
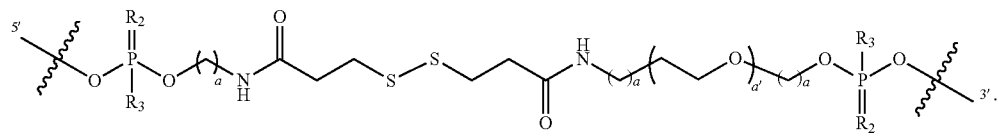
In some embodiments, -(L$^a$)$_f$-M-(L$^a$)$_f$- is:
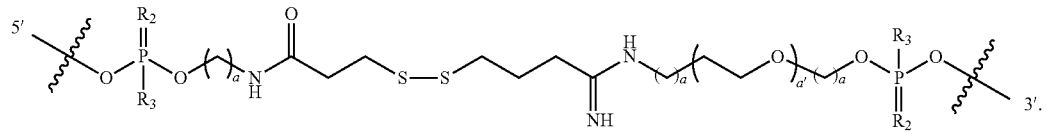
In some embodiments, -(L$^a$)$_f$-M-(L$^a$)$_f$- is:
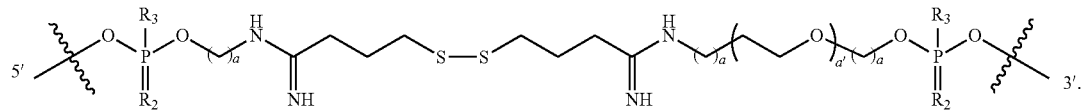
In some embodiments, -(L$^a$)$_f$-M-(L$^a$)$_f$- is:
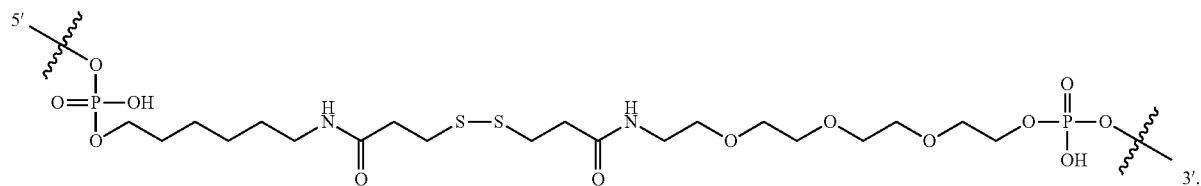 [SMILES: *OP(=O)(O)OCCCCCCNC(=O)CCSSCCC(=O)NCCOCCOCCOCCOP(=O)(O)O*]

In some embodiments, $-(L^a)_{f}\text{-}M\text{-}(L^a)_{f}\text{-}$ is:

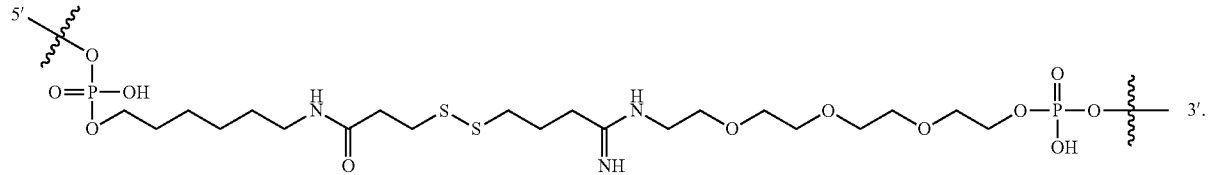 [SMILES: *OP(=O)(O)OCCCCCCNC(=O)CCSSCCCC(=N)NCCOCCOCCOCCOP(=O)(O)O*]

In some embodiments, $-(L^a)_{f}\text{-}M\text{-}(L^a)_{f}\text{-}$ is:

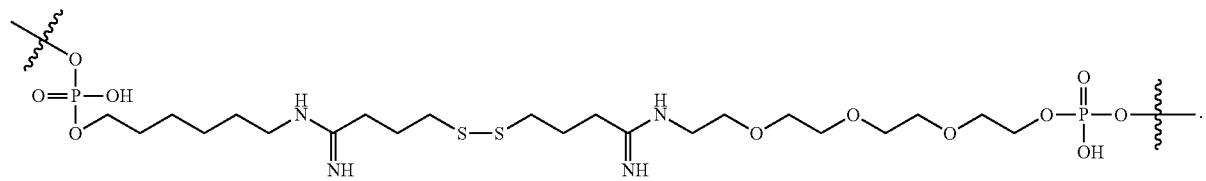 [SMILES: *OP(=O)(O)OCCCCCCNC(=N)CCCSSCCCC(=N)NCCOCCOCCOCCOP(=O)(O)O*]

In some embodiments of formulas $A_{3'}$-ii, $A_{2'}$-ii, $B_{3'}$-ii, $B_{2'}$-ii, $C_{3'}$-ii, $C_{2'}$-ii, $D_{3'}$-ii, $D_{2'}$-ii, $E_{3'}$-ii$_U$, $E_{2'}$-ii$_U$, $E_{3'}$-ii$_A$, $E_{2'}$-ii$_A$, $F_{3'}$-ii$_U$, $F_{2'}$-ii$_U$, $F_{3'}$-ii$_A$, or $F_{2'}$-ii$_A$ or subgenera thereof, M is —S—.

In some embodiments, $-(L^a)_{f}\text{-}M\text{-}(L^a)_{f}\text{-}$ is:

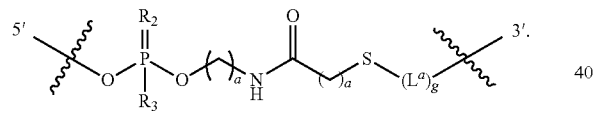

In some embodiments, M is —S—, and each $L^a$ is independently selected from:

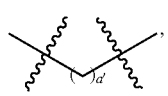
$L^a$-1'

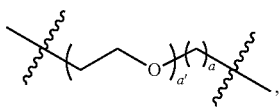
$L^a$-5'

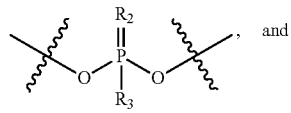
$L^a$-26, and

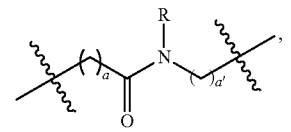
$L^a$-27, wherein:
each a is independently an integer between 0 and 16, inclusive;
each a' is independently an integer between 1 and 16, inclusive;
each $R_2$ is independently O or S; and
each $R_3$ is independently OH or COOH.

In some embodiments, $-(L^a)_{f}\text{-}M\text{-}(L^a)_{f}\text{-}$ is:

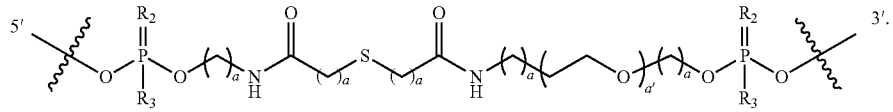

In some embodiments, $-(L^a)_{f}-M-(L^a)_{f'}-$ is:

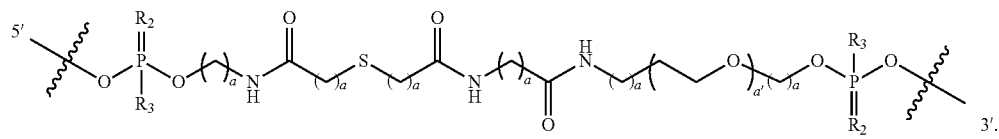

In some embodiments, $-(L^a)_{f}-M-(L^a)_{f'}-$ is:

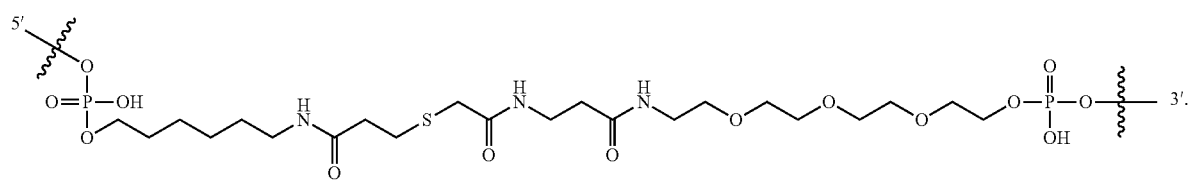 [SMILES: *OP(=O)(O)OCCCCCCNC(=O)CCSCC(=O)NCCC(=O)NCCOCCOCCOCCOP(=O)(O)O*]

In some embodiments, $-(L^a)_{f}-M-(L^a)_{f'}-$ is:

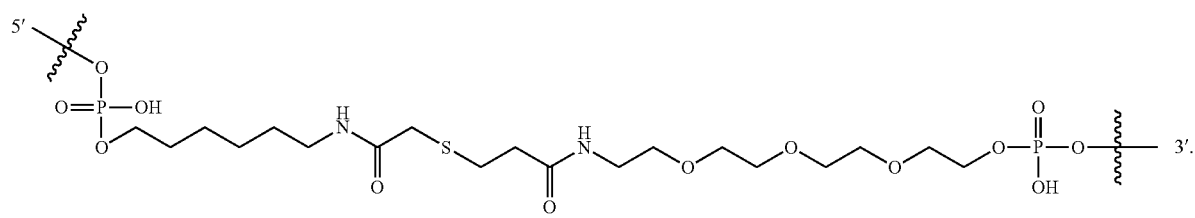 [SMILES: *OP(=O)(O)OCCCCCCNC(=O)CSCCC(=O)NCCOCCOCCOCCOP(=O)(O)O*]

In some embodiments, $-(L^a)_{f}-M-(L^a)_{f'}-$ is:

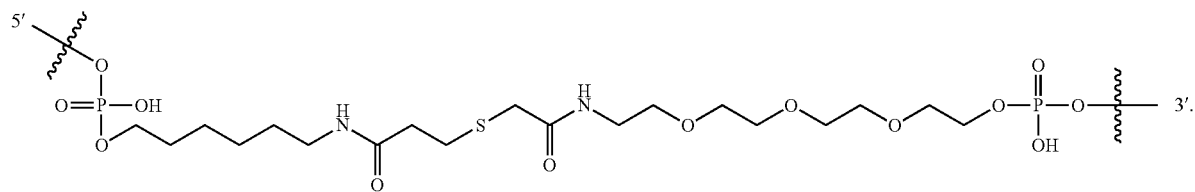 [SMILES: *OP(=O)(O)OCCCCCCNC(=O)CCSCC(=O)NCCOCCOCCOCCOP(=O)(O)O*]

In some embodiments of formulas $A_{3'}$-ii, $A_{2'}$-ii, $B_{3'}$-ii, $B_{2'}$-ii, $C_{3'}$-ii, $C_{2'}$-ii, $D_{3'}$-ii, $D_{2'}$-ii, $E_{3'}$-ii$_U$, $E_{2'}$-ii$_U$, $E_{3'}$-ii$_A$, $E_{2'}$-ii$_A$, $F_{3'}$-ii$_U$, $F_{2'}$-ii$_U$, $F_{3'}$-ii$_A$, or $F_{2'}$-ii$_A$ or subgenera thereof, M is

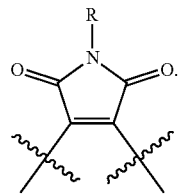

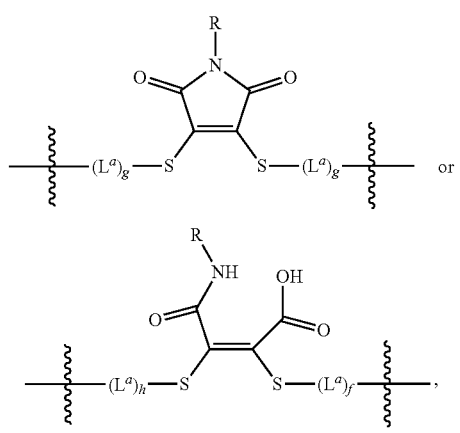

In some such embodiments, R is hydrogen.

In some embodiments of formulas $A_{3'}$-ii, $A_{2'}$-ii, $B_{3'}$-ii, $B_{2'}$-ii, $C_{3'}$-ii, $C_{2'}$-ii, $D_{3'}$-ii, $D_{2'}$-ii, $E_{3'}$-ii$_U$, $E_{2'}$-ii$_U$, $E_{3'}$-ii$_A$, $E_{2'}$-ii$_A$, $F_{3'}$-ii$_U$, $F_{2'}$-ii$_U$, $F_{3'}$-ii$_A$, or $F_{2'}$-ii$_A$ or subgenera thereof, $-(L^a)_{f}-M-(L^a)_{f'}-$ is:

wherein:
  each g is independently selected from 0, 1, 2, 3, 4, or 5; and
  each h is independently selected from 0, 1, 2, 3, or 4.

In some embodiments, $-(L^a)_f\text{-}M\text{-}(L^a)_f\text{-}$ is:

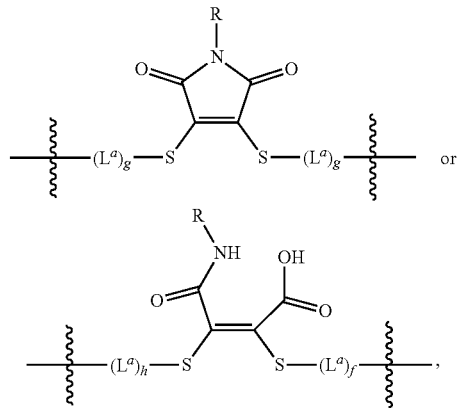

and each $L^a$ is independently selected from:

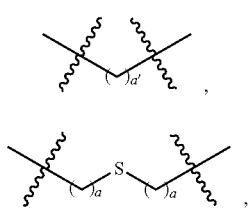

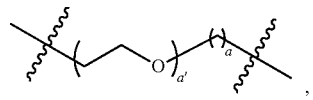

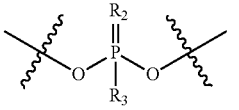

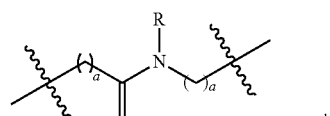

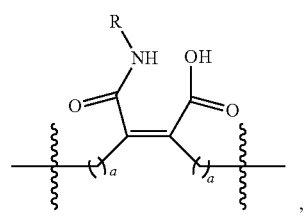

wherein:
  each a is independently an integer between 0 and 16, inclusive;
  each a' is independently an integer between 1 and 16, inclusive;
  each $R_2$ is independently O or S; and
  each $R_3$ is independently OH or COOH.

In some embodiments, $-(L^a)_f\text{-}M\text{-}(L^a)_f\text{-}$ is

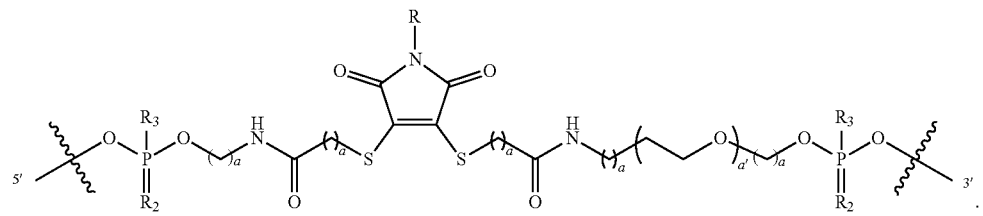

In some embodiments, $-(L^a)_f\text{-}M\text{-}(L^a)_f\text{-}$ is:

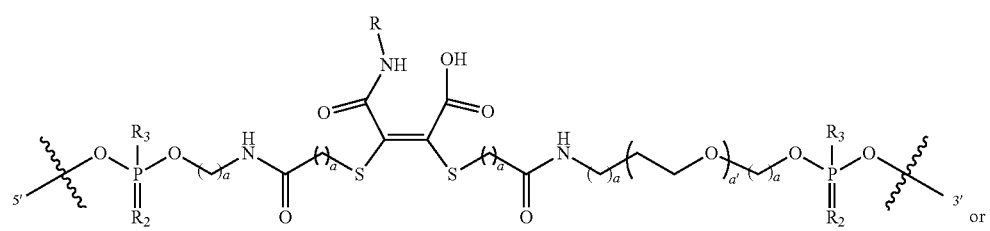

or

-continued

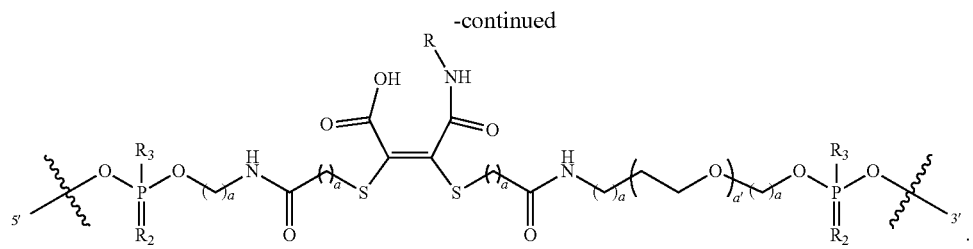

In some embodiments, -(L^a)_f-M-(L^a)_f- is:

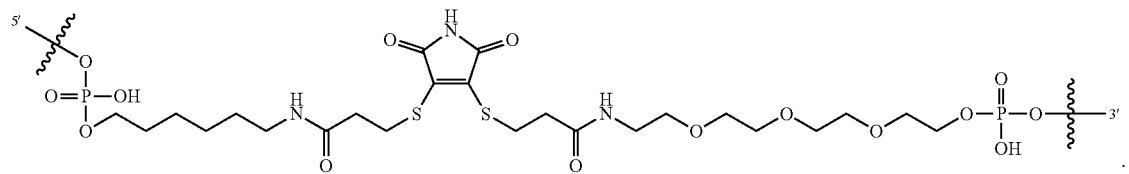 [SMILES: *OP(=O)(O)OCCCCCCNC(=O)CCSC1=C(SCCC(=O)NCCOCCOCCOCCOP(=O)(O)O*)C(=O)NC1=O]

In some embodiments, -(L^a)_f-M-(L^a)_f- is:

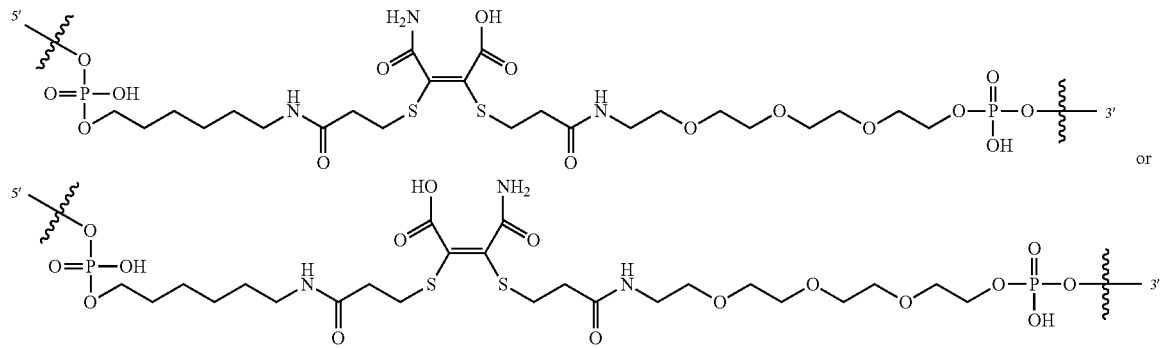

In some embodiments of formulas $A_{3'}$-ii, $A_{2'}$-ii, $B_{3'}$-ii, $B_{2'}$-ii, $C_{3'}$-ii, $C_{2'}$-ii, $D_{3'}$-ii, $D_{2'}$-ii, $E_{3'}$-ii$_U$, $E_{2'}$-ii$_U$, $E_{3'}$-ii$_A$, $E_{2'}$-ii$_A$, $F_{3'}$-ii$_U$, $F_{2'}$-ii$_U$, $F_{3'}$-ii$_A$, or $F_{2'}$-ii$_A$ or subgenera thereof, M is —N(R)—. In some embodiments, M is —N(H)—.

In some embodiments, -(L^a)_f-M-(L^a)_f- is:

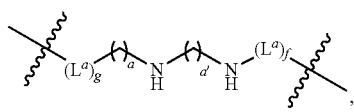

wherein:
each a is independently an integer between 0 and 16;
each a' is independently an integer between 1 and 16; and
g is 0, 1, 2, 3, 4, or 5.

In some embodiments, -(L^a)_f-M-(L^a)_f- is:

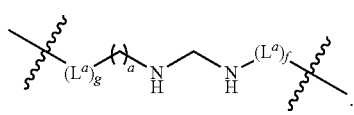

In some embodiments, M is —N(R)—, and each $L^a$ is independently selected from:

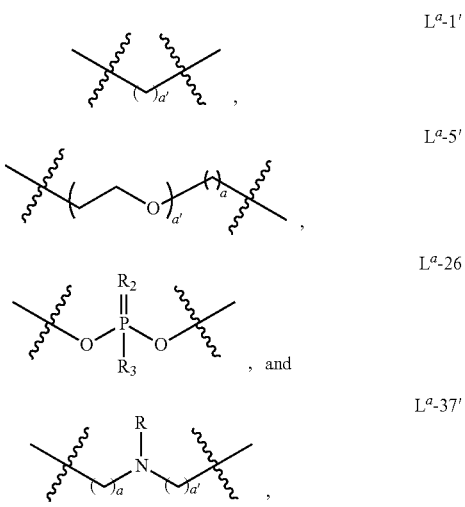

wherein:
each a is independently an integer between 0 and 16, inclusive;
each a' is independently an integer between 1 and 16, inclusive;
each $R_2$ is independently O or S; and
each $R_3$ is independently OH or COOH.

In some embodiments, $-(L^a)_{f}-M-(L^a)_{f'}-$ is:

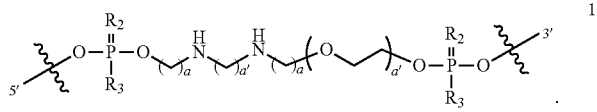

In some embodiments, $-(L^a)_{f}-M-(L^a)_{f'}-$ is:

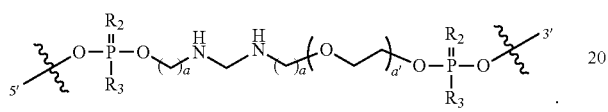

In some embodiments, $-(L^a)_{f}-M-(L^a)_{f'}-$ is:

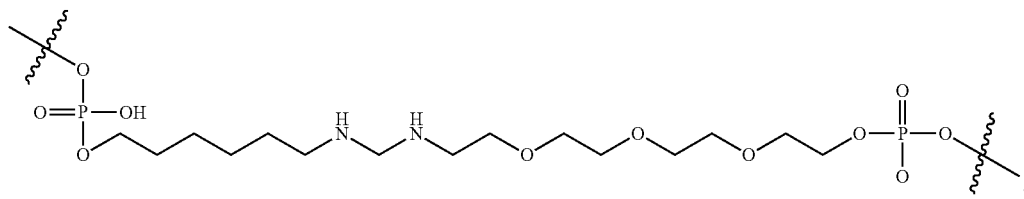 [SMILES: *OP(=O)(O)OCCCCCCNCNCCOCCOCCOCCOP(=O)(O)O*]

In some embodiments, one or more $L^a$ are:

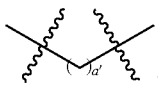

$L^a$-1'

In some such embodiments, a' is an integer between 1 and 16, inclusive. In some such embodiments, a' is an integer between 1 and 8, inclusive. In some such embodiments, a' is 8. In some such embodiments, a' is 7. In some such embodiments, a' is 6. In some such embodiments, a' is 5. In some such embodiments, a' is 4. In some such embodiments, a' is 3. In some such embodiments, a' is 2. In some such embodiments, a' is 1.

In some embodiments, one or more $L^a$ are:

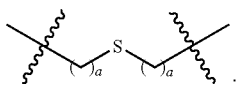

$L^a$-3

In some such embodiments, each a is independently an integer between 0 and 16, inclusive. In some such embodiments, each a is independently an integer between 0 and 8, inclusive. In some such embodiments, each a is independently an integer between 0 and 4, inclusive. In some such embodiments, each a is an integer between 0 and 2, inclusive. In some such embodiments, both a are 0. In some such embodiments, one a is 0 and the other a is 1. In some such embodiments, one a is 0 and the other a is 2. In some such embodiments, both a are 1. In some such embodiments, one a is 1 and the other a is 2. In some such embodiments, both a are 2.

In some embodiments, one or more $L^a$ are:

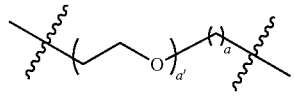

$L^a$-5'

In some such embodiments, each a is independently an integer between 0 and 16, inclusive. In some such embodiments, each a is independently an integer between 0 and 8, inclusive. In some such embodiments, each a independently is an integer between 0 and 4, inclusive. In some such embodiments, each a' is independently an integer between 1 and 16, inclusive. In some such embodiments, each a' is independently an integer between 1 and 8, inclusive. In some such embodiments, each a' independently is an integer between 1 and 4, inclusive. In some such embodiments, $L^a$-5' is:

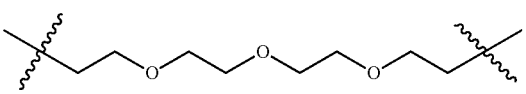

In some embodiments, one or more $L^a$ are:

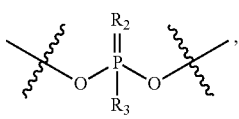

$L^a$-26 wherein $R_2$ is O or S and $R_3$ is OH or COOH. In some such embodiments, $R_2$ is O. In some such embodiments, $R_2$ is S. In some such embodiments, $R_2$ is OH. In some such embodiments, $R_3$ is COOH. In some such embodiments, $R_2$ is O and $R_3$ is OH. In some such embodiments, $R_2$ is O and $R_3$ is COOH. In some such embodiments, $R_2$ is S and $R_3$ is OH. In some such embodiments, $R_2$ is S and $R_3$ is COOH.

In some embodiments, one or more $L^a$ are:

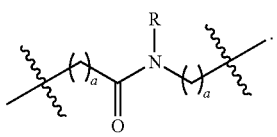

$L^a$-27

In some such embodiments, each a is independently an integer between 0 and 16, inclusive. In some such embodiments, each a is independently an integer between 0 and 8, inclusive. In some such embodiments, each a is independently an integer between 0 and 4, inclusive. In some such embodiments, one or both a is 8. In some such embodiments, one or both a is 7. In some such embodiments, one or both a is 6. In some such embodiments, one or both a is 5. In some such embodiments, one or both a is 4. In some such embodiments, one or both a is 3. In some such embodiments, one or both a is 2. In some such embodiments, one or both a is 1. In some such embodiments, one or both a is 0. In some such embodiments, R is independently hydrogen or an optionally substituted group selected from $C_{1-6}$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur. In some such embodiments, R is hydrogen or an optionally substituted group selected from $C_{1-6}$ aliphatic and phenyl. In some such embodiments, R is hydrogen or $C_{1-6}$ alkyl. In some such embodiments, R is hydrogen.

In some embodiments, one or more $L^a$ are:

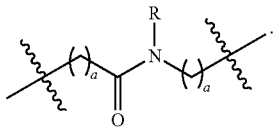

$L^a$-31

In some such embodiments, each a is independently an integer between 0 and 16, inclusive. In some such embodiments, each a is independently an integer between 0 and 8, inclusive. In some such embodiments, each a is independently an integer between 0 and 4, inclusive. In some such embodiments, one or both a is 8. In some such embodiments, one or both a is 7. In some such embodiments, one or both a is 6. In some such embodiments, one or both a is 5. In some such embodiments, one or both a is 4. In some such embodiments, one or both a is 3. In some such embodiments, one or both a is 2. In some such embodiments, one or both a is 1. In some such embodiments, one or both a is 0. In some such embodiments, each R is independently hydrogen or an optionally substituted group selected from $C_{1-6}$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur. In some such embodiments, each R is independently hydrogen or an optionally substituted group selected from $C_{1-6}$ aliphatic and phenyl. In some such embodiments, each R is independently hydrogen or $C_{1-6}$ alkyl. In some such embodiments, each R is hydrogen.

In some embodiments, one or more $L^a$ are:

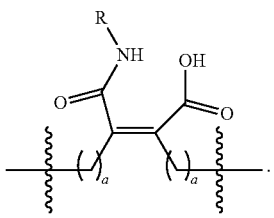

$L^a$-41

In some such embodiments, each a is independently an integer between 0 and 16, inclusive. In some such embodiments, each a is independently an integer between 0 and 8, inclusive. In some such embodiments, each a is independently an integer between 0 and 4, inclusive. In some such embodiments, each a is 0. In some such embodiments, R is independently hydrogen or an optionally substituted group selected from $C_{1-6}$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur. In some such embodiments, R is hydrogen or an optionally substituted group selected from $C_{1-6}$ aliphatic and phenyl. In some such embodiments, R is hydrogen or $C_{1-6}$ alkyl. In some such embodiments, R is hydrogen.

In some embodiments, one or more $L^a$ are:

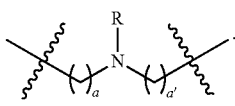

$L^a$-37'

In some such embodiments, each a is independently an integer between 0 and 16, inclusive. In some such embodiments, each a is independently an integer between 0 and 8, inclusive. In some such embodiments, each a is independently an integer between 0 and 4, inclusive. In some such embodiments, each a' is independently an integer between 1 and 16, inclusive. In some such embodiments, each a' is independently an integer between 1 and 8, inclusive. In some such embodiments, each a' independently is an integer between 1 and 4, inclusive. In some such embodiments, a' is 1. In some such embodiments, R is independently hydrogen or an optionally substituted group selected from $C_{1-6}$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur. In some such embodiments, R is hydrogen or an optionally substituted group selected from $C_{1-6}$ aliphatic and phenyl. In some such embodiments, R is hydrogen or $C_{1-6}$ alkyl. In some such embodiments, R is hydrogen.

In some embodiments, -(L$^a$)$_f$- is not:

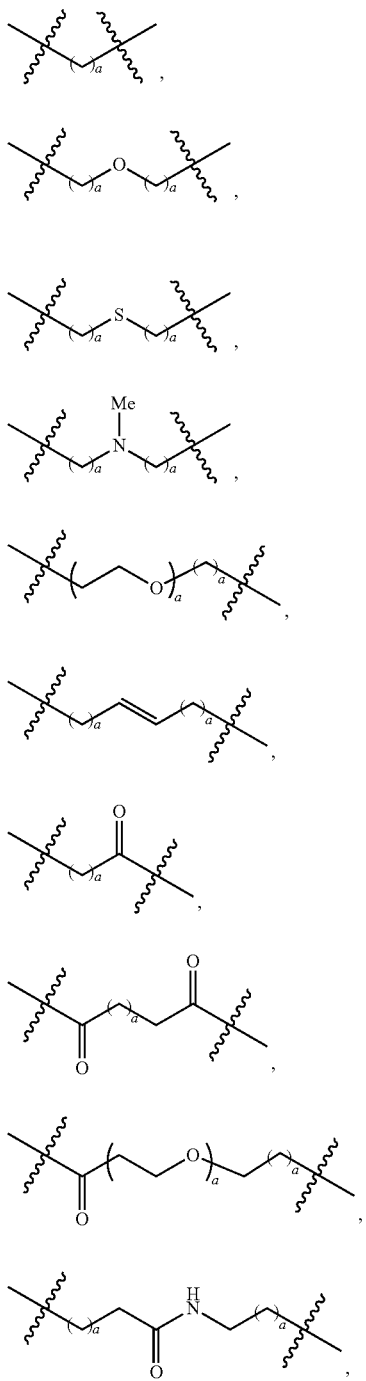
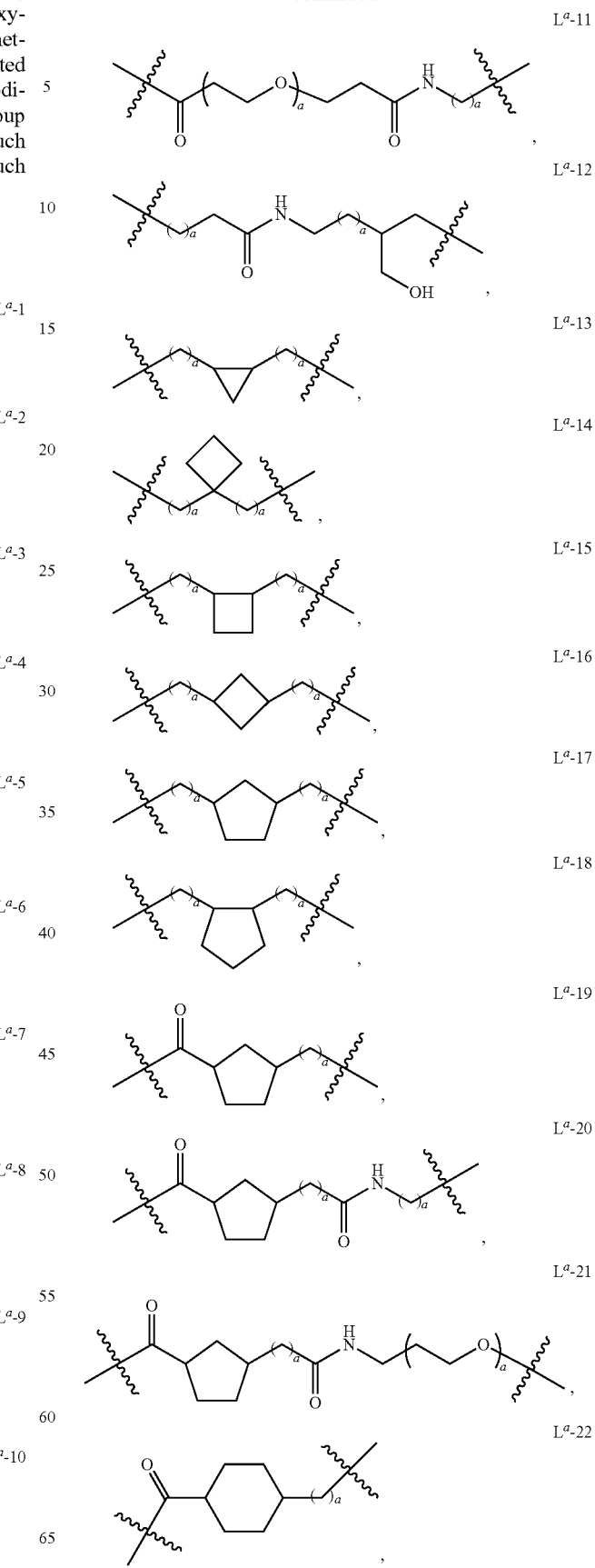

$L^a$-23

[Structure: cyclohexane with C(=O) and CH2-C(=O)-NH-(CH2)a linker]

, and $L^a$-24

[Structure: cyclohexane with C(=O) and CH2-C(=O)-NH-CH2CH2-(O)a linker]

, wherein each a is independently an integer between 0 and 16, inclusive.

In some embodiments, at least one $L^a$ is not any one of $L^a$-1 through $L^a$-24.

In some embodiments, at least one $L^a$ is $L^a$-2

[Structure: -(CH2)a-O-(CH2)a-]

, wherein each a is 0. In some embodiments, at least one $L^a$ is $L^a$-28

[Structure: -C(-)-O-C(-)-]

.

In some embodiments, at least one $-(L^a)_f$- is

[Structure: -O-$(L^a)_g$-]

(i.e., $-(L^a-2)-(L^a)_g-$ or $-(L^a-28)-(L^a)_g-$, wherein each g is 0, 1, 2, 3, 4, or 5.

In some embodiments, Linker is not a structure wherein at least one $-(L^a)_f-$ is $-(L^a-2)-(L^a)_g-$, a is 0, and $-(L^a)_g-$ is selected from $L^a$-1 to $L^a$-24. In some embodiments, $-(L^a)_f-M-(L^a)_f-$ is not a structure wherein at least one $-(L^a)_f-$ is $-(L^a-2)-(L^a)_g-$, a is 0, and $-(L^a)_g-$ is selected from $L^a$-1 to $L^a$-24.

In some embodiments, Linker is not a structure wherein at least one $-(L^a)_f-$ is $-(L^a-28)-(L^a)_g-$, and $-(L^a)_g-$ is selected from $L^a$-1 to $L^a$-24. In some embodiments, $-(L^a)_f-M-(L^a)_f-$ is not a structure wherein at least one $-(L^a)_f-$ is $-(L^a-28)-(L^a)_g-$, and $-(L^a)_g-$ is selected from $L^a$-1 to $L^a$-24.

In some embodiments, at least one $L^a$ is $L^a$-26

[Structure: -O-P(=R2)(R3)-O-]

, wherein $R_2$ is O or S, and $R_3$ is OH or COOH. In some embodiments, at least one $-(L^a)_f-$ is

[Structure: -O-P(=R2)(R3)-O-$(L^a)_g$-]

(i.e., $-(L^a-26)-(L^a)_g-$, wherein each g is independently 0, 1, 2, 3, 4, or 5.

In some embodiments, Linker is not a structure wherein at least one $-(L^a)_f-$ is $-(L^a-26)-(L^a)_g-$, and $-(L^a)_g-$ is selected from $L^a$-1 to $L^a$-24. In some embodiments, $-(L^a)_f-M-(L^a)_f-$ is not a structure wherein at least one $-(L^a)_f-$ is $-(L^a-26)-(L^a)_g-$, and $-(L^a)_g-$ is selected from $L^a$-1 to $L^a$-24.

In some embodiments, each $L^a$ is independently selected from the group consisting of:

$L^a$-1

[Structure: -(CH2)a-]

, $L^a$-3

[Structure: -(CH2)a-S-(CH2)a-]

, $L^a$-5

[Structure: -(CH2)2-O-(CH2)a-(CH2)a-]

, $L^a$-26

[Structure: -O-P(=R2)(R3)-O-]

, and $L^a$-27

[Structure: -(CH2)a-C(=O)-N(R)-(CH2)a-]

wherein:
each a is independently an integer between 0 and 16, inclusive;
each $R_2$ is independently O or S;
each $R_3$ is independently OH or COOH; and
each R is independently hydrogen or an optionally substituted group selected from $C_1$-$C_6$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur.

In some embodiments, each $L^a$ is independently selected from the group consisting of $L^a$-1, $L^a$-3, $L^a$-5, $L^a$-26, and $L^a$-27, wherein $R_2$ is O; $R_3$ is OH; and R is hydrogen.

In some embodiments, each $L^a$ is independently selected from the group consisting of:

$L^a$-1

$L^a$-3

$L^a$-5

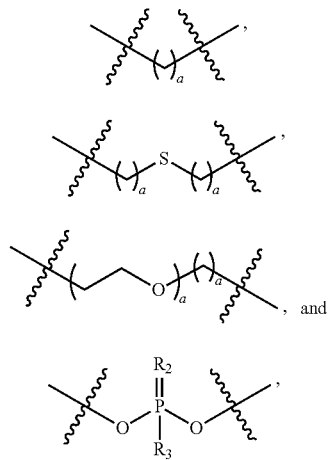
, and $L^a$-26 wherein:
each a is independently an integer between 0 and 16, inclusive;
each $R_2$ is independently O or S;
each $R_3$ is independently OH or COOH; and
each R is independently hydrogen or an optionally substituted group selected from $C_1$-$C_6$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur.

In some embodiments, each $L^a$ is independently selected from the group consisting of $L^a$-1, $L^a$-3, $L^a$-5, and $L^a$-26, wherein $R_2$ is O; $R_3$ is OH; and R is hydrogen.

In some embodiments, each $L^a$ is independently selected from the group consisting of:

$L^a$-1

$L^a$-5

$L^a$-26

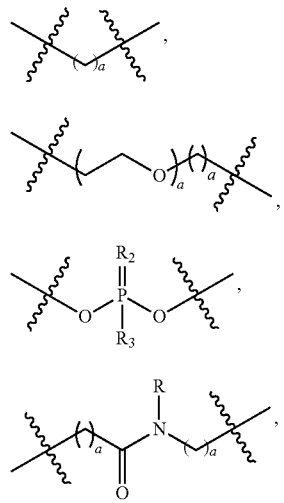

$L^a$-27

-continued

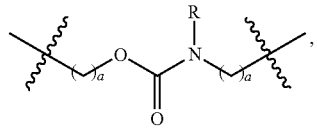
$L^a$-28

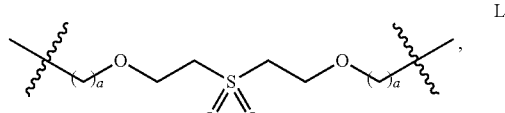
$L^a$-29

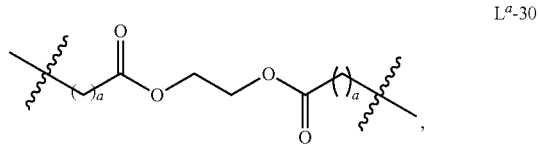
$L^a$-30

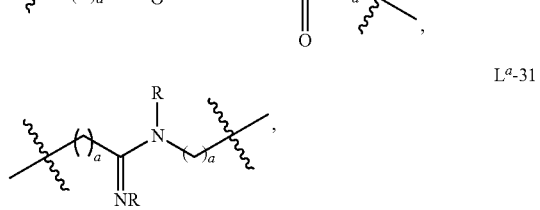
$L^a$-31

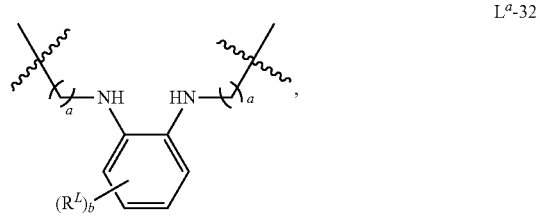
$L^a$-32

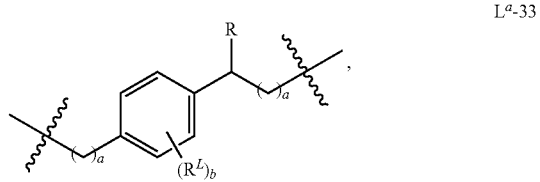
$L^a$-33

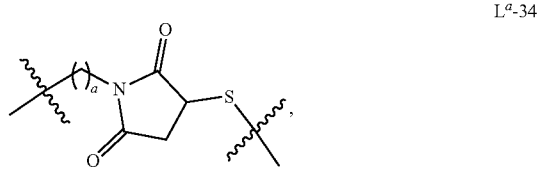
$L^a$-34

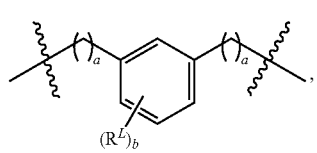
$L^a$-35

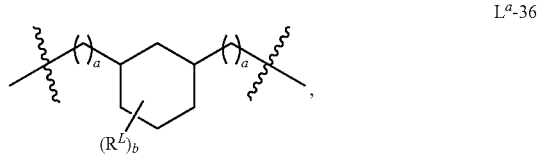
$L^a$-36

$L^a$-37

-continued

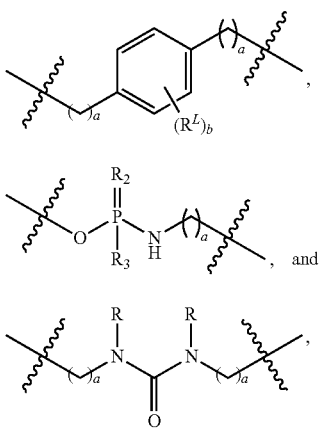

L$^a$-38

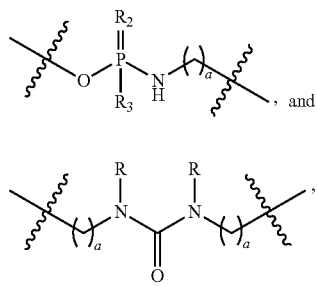

L$^a$-39

L$^a$-39

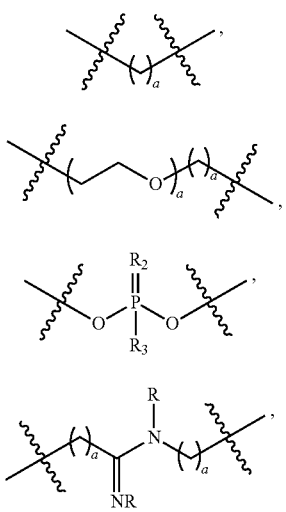

L$^a$-40 wherein:
each a is independently an integer between 0 and 16, inclusive;
each b is independently an integer between 0 and 4, inclusive;
each $R_2$ is independently O or S;
each $R_3$ is independently OH or COOH;
each $R^L$ is independently selected from R, halogen, —OR, —NR$_2$, —SR, —NO$_2$, —CN, —SO$_2$R, —CO$_2$R, and —CONR$_2$; and
each R is independently hydrogen or an optionally substituted group selected from $C_1$-$C_6$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur.

In some embodiments, each $L^a$ is independently selected from the group consisting of $L^a$-1, $L^a$-5, $L^a$-26, $L^a$-27, $L^a$-28, $L^a$-29, $L^a$-30, $L^a$-31, $L^a$-32, $L^a$-33, $L^a$-34, $L^a$-35, $L^a$-36, $L^a$-37, $L^a$-38, $L^a$-39, and $L^a$-40, wherein $R_2$ is O; $R_3$ is OH; and R is hydrogen.

In some embodiments, each $L^a$ is independently selected from the group consisting of:

L$^a$-1

L$^a$-5

L$^a$-26

L$^a$-31

L$^a$-39

, and

L$^a$-40 wherein:
each a is independently an integer between 0 and 16, inclusive;
each $R_2$ is independently O or S;
each $R_3$ is independently OH or COOH; and
each R is independently hydrogen or an optionally substituted group selected from $C_1$-$C_6$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur.

In some embodiments, each $L^a$ is independently selected from the group consisting of $L^a$-1, $L^a$-5, $L^a$-26, $L^a$-31, $L^a$-39, and $L^a$-40 wherein $R_2$ is O; $R_3$ is OH; and R is hydrogen.

In some embodiments, each $L^a$ is independently selected from the group consisting of:

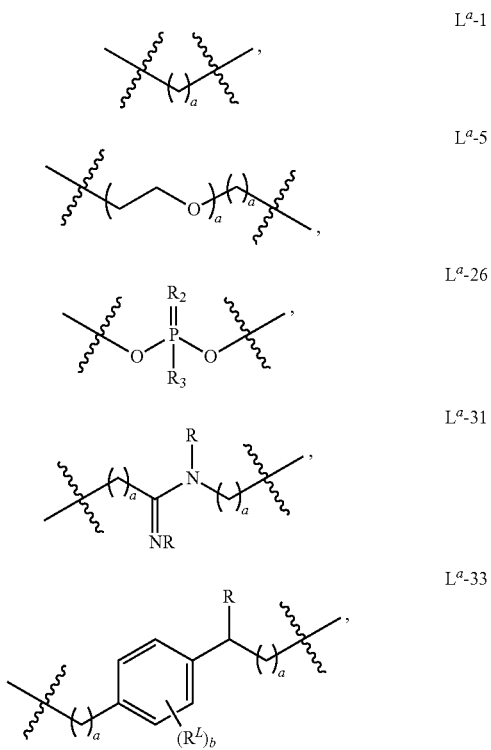

-continued

L$^a$-34
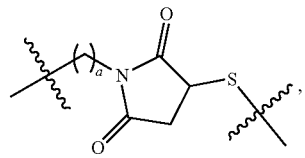

L$^a$-39
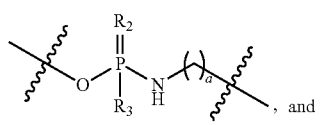
, and

L$^a$-40
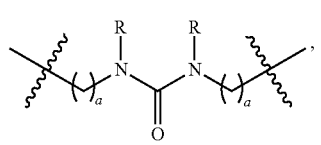

wherein:

each a is independently an integer between 0 and 16, inclusive;

each b is independently an integer between 0 and 4, inclusive;

each $R_2$ is independently O or S;

each $R_3$ is independently OH or COOH;

each R' is independently selected from R, halogen, —OR, —NR$_2$, —SR, —NO$_2$, —CN, —SO$_2$R, —CO$_2$R, and —CONR$_2$; and each R is independently hydrogen or an optionally substituted group selected from $C_1$-$C_6$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur.

In some embodiments, each L$^a$ is independently selected from the group consisting of L$^a$-1, L$^a$-5, L$^a$-26, L$^a$-31, L$^a$-33, L$^a$-34, L$^a$-39, and L$^a$-40, wherein $R_2$ is O; $R_3$ is OH; and R is hydrogen.

In some embodiments, M is not encompassed by a group selected from the group consisting of:

M-1
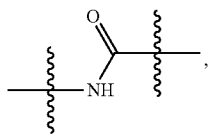

M-2
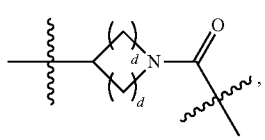

M-3
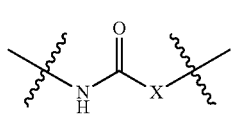

-continued

M-4
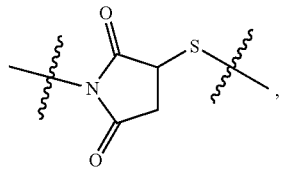

M-5
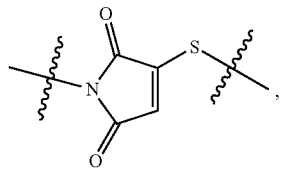

M-6
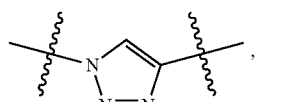

M-7
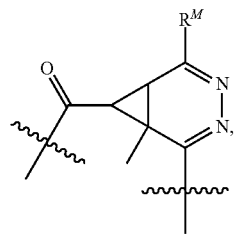

M-8
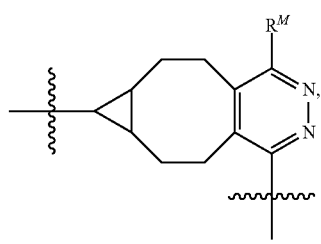

M-9
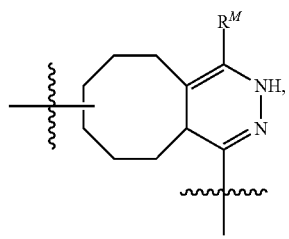

M-10
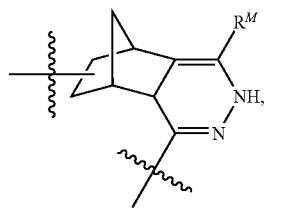

M-11

-continued

M-12
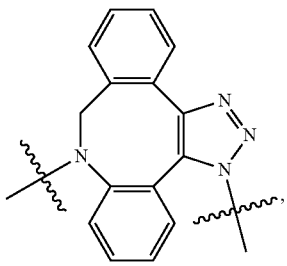

M-13
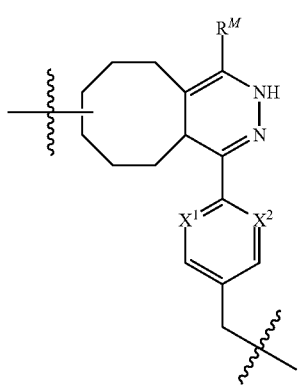

M-14
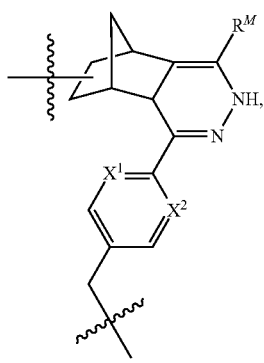

M-15
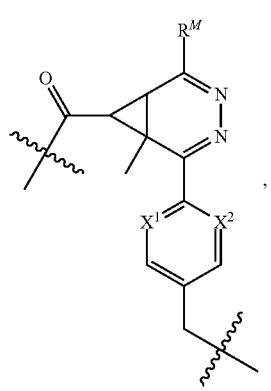

-continued

M-16
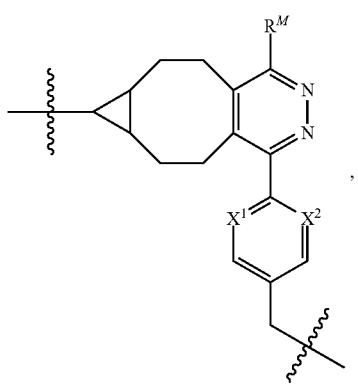

M-17
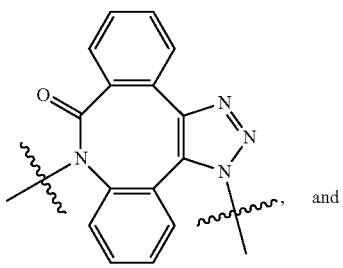

M-18
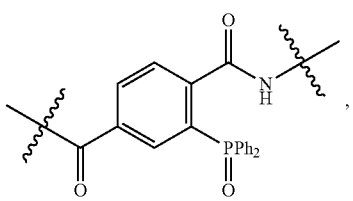

wherein:
each d is independently an integer between 0 and 3, inclusive;
$R^M$ is H, alkyl, aryl, or heteroaryl;
$X^1$ and $X^2$ are each independently N or CH; and
X is NH, O, or S.

In some embodiments, M is or is encompassed by a group selected from the group consisting of:

M-19
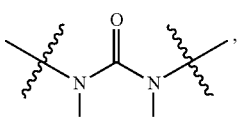

M-20
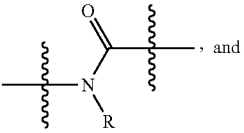, and

M-21
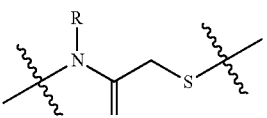

wherein each R is independently hydrogen or an optionally substituted group selected from $C_1$-$C_6$ aliphatic, phenyl, a 4-7 membered heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, M is or is encompassed by a group selected from the group consisting of M-19, M-20, and M-21, wherein R is hydrogen.

In some embodiments, M is or is encompassed by a group selected from the group consisting of:

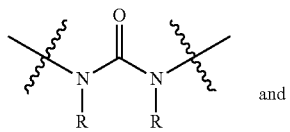
M-19 and

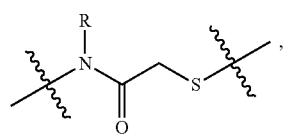
M-21

wherein each R is independently hydrogen or an optionally substituted group selected from $C_1$-$C_6$ aliphatic, phenyl, a 4-7 membered heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, M is or is encompassed by a group selected from the group consisting of M-19 and M-21, wherein R is hydrogen.

In some embodiments, M is or is encompassed by a group selected from the group consisting of:

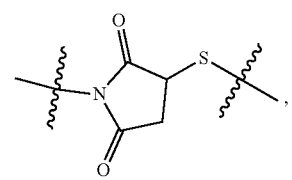
M-4

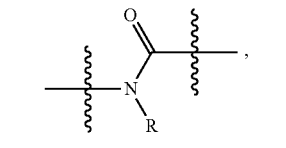
M-20

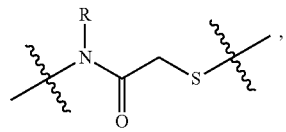
M-21

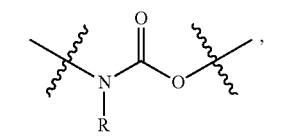
M-22

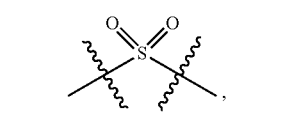
M-23

-continued

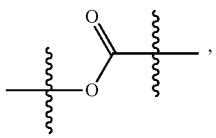
M-24

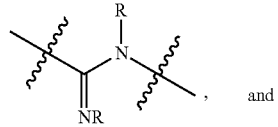
M-25 and

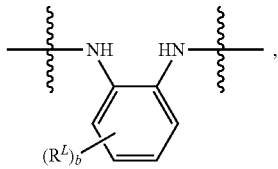
M-26 wherein:
each b is independently an integer between 0 and 4, inclusive;
each $R^L$ is independently selected from R, halogen, —OR, —$NR_2$, —SR, —$NO_2$, —CN, —$SO_2R$, —$CO_2R$, and —$CONR_2$; and
each R is independently hydrogen or an optionally substituted group selected from $C_1$-$C_6$ aliphatic, phenyl, a 4-7 membered heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, M is or is encompassed by a group selected from the group consisting of M-4, M-20, M-21, M-22, M-23, M-24, M-25, and M-26, wherein R is hydrogen.

In some embodiments, M is or is encompassed by a group selected from the group consisting of:

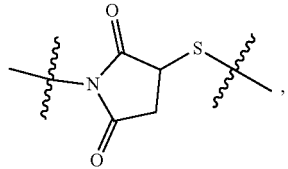
M-4

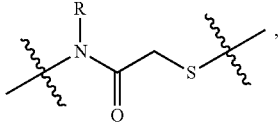
M-21

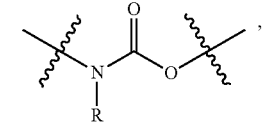
M-22

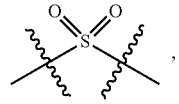
M-23

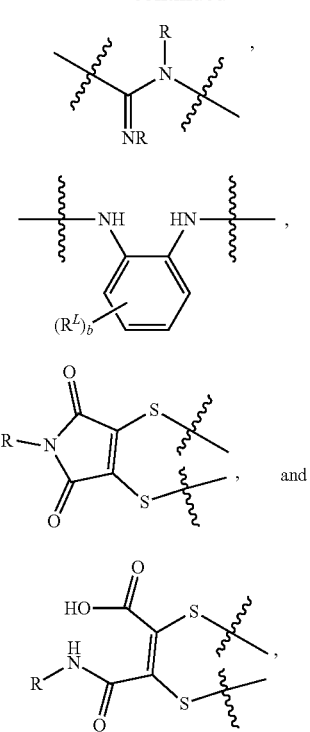

wherein:
each b is independently an integer between 0 and 4, inclusive;
each R' is independently selected from R, halogen, —OR, —NR$_2$, —SR, —NO$_2$, —CN, —SO$_2$R, —CO$_2$R, and —CONR$_2$; and
each R is independently hydrogen or an optionally substituted group selected from C$_1$-C$_6$ aliphatic, phenyl, a 4-7 membered heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

In some embodiments, M is or is encompassed by a group selected from the group consisting of M-4, M-21, M-22, M-23, M-25, M-26, M-29, and M-30, wherein R is hydrogen.

In some embodiments of any formula of this disclosure, each f is independently 0, 1, 2, 3, 4, 5, or 6. In some embodiments, each f is independently 1, 2, 3, 4, 5, or 6. In some embodiments, each f is independently 2, 3, 4, 5, or 6. In some embodiments, each f is independently 0, 1, 2, 3, or 4. In some embodiments, each f is independently 1, 2, or 3. In some embodiments, f is 0. In some embodiments, f is 1. In some embodiments, f is 2. In some embodiments, f is 3. In some embodiments, f is 4. In some embodiments, f is 5. In some embodiments, f is 6. In some embodiments, f is not 0 when M is —NP(O)(OH)O— or —OP(O)(OH)N—.

In some embodiments of any formula of this disclosure, each g is independently 0, 1, 2, 3, 4, or 5. In some embodiments, each g is independently 0, 1, 2, or 3. In some embodiments, each g is independently 0, 1, or 2. In some embodiments, each g is 1, 2, 3, 4, or 5. In some embodiments, each g is 1, 2, or 3. In some embodiments, g is 0. In some embodiments, g is 1. In some embodiments, g is 2. In some embodiments, g is 3. In some embodiments, g is 4. In some embodiments, g is 5.

In some embodiments of any formula of this disclosure, each h is independently 0, 1, 2, 3, or 4. In some embodiments, each h is independently 0, 1, 2, or 3. In some embodiments, each h is independently 1, 2, 3, or 4. In some embodiments, each h is 0, 1, or 2. In some embodiments, each h is 1, 2, or 3. In some embodiments, h is 0. In some embodiments, h is 1. In some embodiments, h is 2. In some embodiments, h is 3. In some embodiments, h is 4.

In some embodiments of any formula of this disclosure, each L$^a$ is different from the others. In some embodiments, each L$^a$ on one side of M is different from every other L$^a$ on the same side of M.

In some embodiments of any formula of this disclosure, Linker is a non-nucleotide chemical linkage that has the formula -(L$^a$)$_f$-M-(L$^a$). In some embodiments, Linker is a non-nucleotide chemical linkage that has the formula -(L$^a$)-(L$^a$)$_g$-M-(L$^a$)-, wherein each g is independently 1, 2, 3, 4, or 5. In some embodiments, Linker is a non-nucleotide chemical linkage that has the formula -(L$^a$)-M-(L$^a$)$_g$-(L$^a$)-, wherein each g is independently 1, 2, 3, 4, or 5.

In some embodiments of any formula of this disclosure, when Linker is a non-nucleotide chemical linkage that has the formula -(L$^a$)$_f$-M-(L$^a$)$_f$, and each -(L$^a$)$_f$- is selected from L$^a$-1 to L$^a$-24, then M is not, or is not encompassed by, a group selected from M-1 to M-18. In some embodiments, Linker is not a structure wherein each -(L$^a$)$_f$- is selected from L$^a$-1 to L$^a$-24, and M is or is encompassed by a group selected from M-1 to M-18. In some embodiments, -(L$^a$)$_f$-M-(L$^a$)$_f$- is not a structure wherein each -(L$^a$)$_f$- is selected from L$^a$-1 to L$^a$-24, and M is or is encompassed by a group selected from M-1 to M-18.

In some embodiments of any formula of this disclosure, Linker is a non-nucleotide chemical linkage that has the formula -(L$^a$-2)-(L$^a$)$_g$-M-(L$^a$)$_g$-(L$^a$-2)-, wherein g is 0, 1, 2, 3, 4, or 5, and a is 0. In some embodiments, Linker is a non-nucleotide chemical linkage that has the formula -(L$^a$-2)-(L$^a$)$_f$-M-(L$^a$)-(L$^a$-2)-. In some embodiments, Linker is a non-nucleotide chemical linkage that has the formula -(L$^a$-2)-(L$^a$)$_g$-M-(L$^a$)-(L$^a$-2)-, wherein g is 0, 1, 2, 3, 4, or 5. In some embodiments, Linker is a non-nucleotide chemical linkage that has the formula -(L$^a$-2)-(L$^a$)-M-(L$^a$)$_g$-(L$^a$-2)-, wherein g is 0, 1, 2, 3, 4, or 5.

In some embodiments, when Linker is a non-nucleotide chemical linkage that has the formula -(L$^a$-2)-(L$^a$)$_g$-M-(L$^a$)$_g$-(L$^a$-2)-, a is 0, and each -(L$^a$)$_g$- is selected from L$^a$-1 to L$^a$-24, then M is not, or is notencompassed by, a group selected from M-1 to M-18. In some embodiments, Linker is not a structure wherein each -(L$^a$)$_f$- is -(L$^a$-2)-(L$^a$)$_g$-, a is 0, each -(L$^a$)$_g$- is selected from L$^a$-1 to L$^a$-24, and M is or is encompassed by a group selected from M-1 to M-18. In some embodiments, -(L$^a$)$_f$-M-(L$^a$)$_f$- is not a structure wherein each -(L$^a$)$_f$- is -(L$^a$-2)-(L$^a$)$_g$-, a is 0, each -(L$^a$)$_g$- is selected from L$^a$-1 to L$^a$-24, and M is or is encompassed by a group selected from M-1 to M-18.

In some embodiments, Linker is a non-nucleotide chemical linkage that has the formula -(L$^a$-28)-(L$^a$)$_g$-M-(L$^a$)$_g$-(L$^a$-28)-, wherein g is 0, 1, 2, 3, 4, or 5. In some embodiments, Linker is a non-nucleotide chemical linkage that has the formula -(L$^a$-28)-(L$^a$)-M-(L$^a$)-(L$^a$-28)-. In some embodiments, Linker is a non-nucleotide chemical linkage that has the formula -(L$^a$-28)-(L$^a$)$_g$-M-(L$^a$)-(L$^a$-28)-, wherein g is 0, 1, 2, 3, 4, or 5. In some embodiments, Linker is a non-nucleotide chemical linkage that has the formula -(L$^a$-28)-(L$^a$)-M-(L$^a$)$_g$-(L$^a$-28)-, wherein g is 0, 1, 2, 3, 4, or 5.

In some embodiments, when Linker is a non-nucleotide chemical linkage that has the formula -(L$^a$-28)-(L$^a$)$_g$-M-(L$^a$)$_g$-(L$^a$-28)-, and each -(L$^a$)$_g$- is selected from L$^a$-1 to $L^a$-24, then M is not, or is not encompassed by, a group selected from M-1 to M-18. In some embodiments, Linker is not a structure wherein each $-(L^a)_f$- is $-(L^a$-28$)-(L^a)_g$-, each $-(L^a)_g$- is selected from $L^a$-1 to $L^a$-24, and M is or is encompassed by a group selected from M-1 to M-18. In some embodiments, $-(L^a)_f$-M-$(L^a)_f$- is not a structure wherein each $-(L^a)_f$- is $-(L^a$-28$)-(L^a)_g$-, each $-(L^a)_g$- is selected from $L^a$-1 to $L^a$-24, and M is or is encompassed by a group selected from M-1 to M-18.

In some embodiments, Linker is a non-nucleotide chemical linkage that has the formula $-(L^a$-26$)-(L^a)_g$-M-$(L^a)_g$-$(L^a$-26$)$-, wherein f is 1, 2, 3, 4, 5, or 6. In some embodiments, Linker is a non-nucleotide chemical linkage that has the formula $-(L^a$-26$)-(L^a)$-M-$(L^a)$-$(L^a$-26$)$-. In some embodiments, Linker is a non-nucleotide chemical linkage that has the formula $-(L^a$-26$)-(L^a)_g$-M-$(L^a)$-$(L^a$-26$)$-, wherein g is 0, 1, 2, 3, 4, or 5. In some embodiments, Linker is a non-nucleotide chemical linkage that has the formula $-(L^a$-26$)$-$(L^a)$-M-$(L^a)_g$-$(L^a$-26$)$-, wherein g is 0, 1, 2, 3, 4, or 5.

In some embodiments, when Linker is a non-nucleotide chemical linkage that has the formula $-(L^a$-26$)-(L^a)_g$-M-$(L^a)_g$-$(L^a$-26$)$-, and each $-(L^a)_g$- is selected from $L^a$-1 to $L^a$-24, then M is not, or is not encompassed by, a group selected from M-1 to M-18. In some embodiments, Linker is not a structure wherein each $-(L^a)_f$- is $-(L^a$-26$)-(L^a)_g$-, each $-(L^a)_g$- is selected from $L^a$-1 to $L^a$-24, and M is or is encompassed by a group selected from M-1 to M-18. In some embodiments, $-(L^a)_f$-M-$(L^a)_f$- is not a structure wherein each $-(L^a)_f$- is $-(L^a$-26$)-(L^a)_g$-, each $-(L^a)_g$- is selected from $L^a$-1 to $L^a$-24, and M is or is encompassed by a group selected from M-1 to M-18.

In some embodiments, a guide molecule is a compound of Formula $A_3$-ii, $A_2$-ii, $B_3$-ii, $B_2$-ii, $C_3$-ii, $C_2$-ii, $D_3$-ii, $D_2$-ii, $E_3$-ii$_U$, $E_2$-ii$_U$, $E_3$-ii$_A$, $E_2$-ii$_A$, $F_3$-ii$_U$, $F_2$-ii$_U$, $F_3$-ii$_A$, or $F_2$-ii$_A$, wherein $-(L^a)_f$-M-$(L^a)_f$- is selected from a group in Table 5, wherein:

each a is an integer between 0 and 16, inclusive, or 24;
each g is 0, 1, 2, 3, 4, or 5;
each h is 0, 1, 2, 3, or 4;
each $R_2$ is independently O or S;
each $R_3$ is independently OH or COOH; and
$L^a$ and f are as described above and defined herein.

TABLE 5

Exemplary Linkers of Formula G

| Formula | $-(L^a)_f$—M—$(L^a)_f$— |
|---|---|
| G-i | $(L^a)_f$-NH-C(=O)-NH-$(L^a)_f$ |
| G-ii | $(L^a)_g$-C(=O)-CH$_2$-S-$(L^a)_f$ |
| G-iii | $(L^a)_f$-NH-C(=O)-O-$(L^a)_f$ |
| G-iv | $(L^a)_f$-NH-C(=O)-(CH$_2$)$_a$-C(=O)-NH-$(L^a)_g$ |
| G-v | $(L^a)_f$-NH-C(=O)-(CH$_2$CH$_2$O)$_a$-CH$_2$CH$_2$-C(=O)-NH-$(L^a)_g$ |
| G-vi | $(L^a)_f$-NH-C(=O)-O-CH$_2$CH$_2$-S(=O)$_2$-CH$_2$CH$_2$-O-C(=O)-NH-$(L^a)_h$ |
| G-vii | $(L^a)_f$-NH-C(=O)-CH$_2$CH$_2$-C(=O)-O-CH$_2$CH$_2$-O-C(=O)-CH$_2$CH$_2$-C(=O)-NH-$(L^a)_h$ |

TABLE 5-continued
Exemplary Linkers of Formula G
| Formula | $-(L^a)_f-M-(L^a)_{f}-$ |
|---|---|
| G-viii | 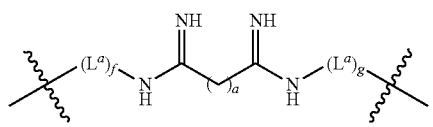 |
| G-ix | |
| | 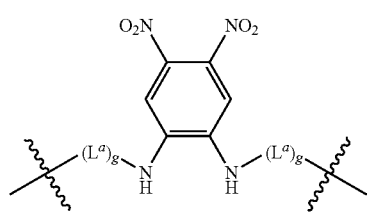 |
| G-x | |
| | 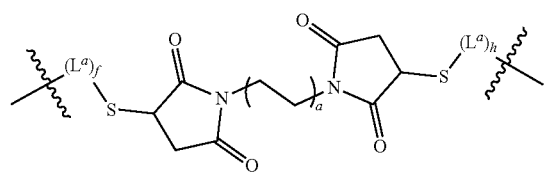 |
| G-xi | |
| | 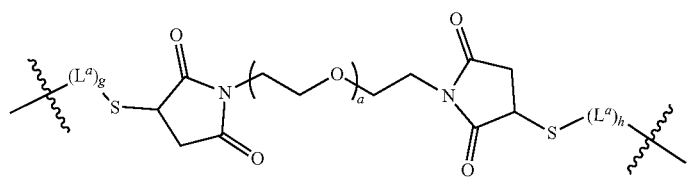 |
| G-xii | |
| | 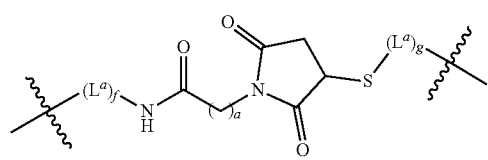 |
| G-xiii | |
| | 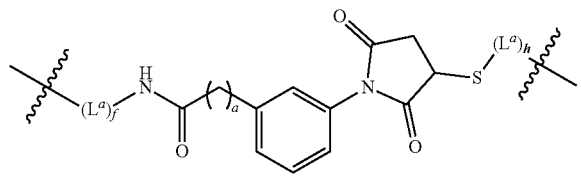 |

TABLE 5-continued
Exemplary Linkers of Formula G
| Formula | —(L$^a$)$_f$—M—(L$^a$)$_{f'}$— |
|---|---|
| G-xiv | 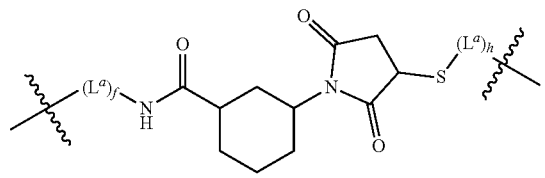 |
| G-xv | 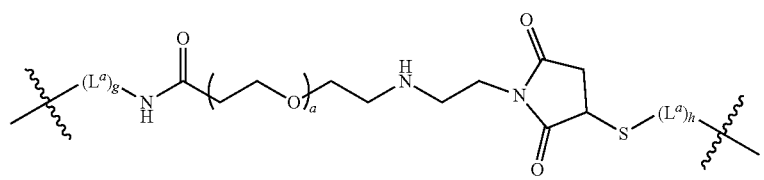 |
| G-xvi | 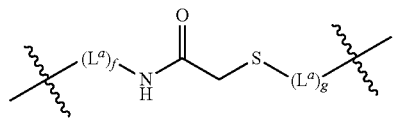 |
| G-xvii | 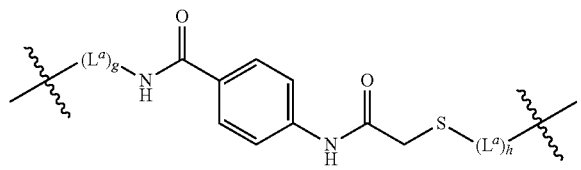 |
| G-xviii | 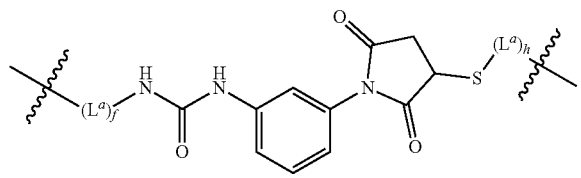 |
| G-xix |  |

In some embodiments, a guide molecule is a compound of Formula $A_3$-ii, $A_2$-ii, $B_3$-ii, $B_2$-ii, $C_3$-ii, $C_2$-ii, $D_3$-ii, $D_2$-ii, $E_3$-ii$_U$, $E_2$-ii$_U$, $E_3$-ii$_A$, $E_2$-ii$_A$, $F_3$-ii$_U$, $F_2$-ii$_U$, $F_3$- ii$_A$, or $F_2$-ii$_A$, wherein -$(L^a)_f$-M-$(L^a)_f$- is selected from a group in Table 6, wherein:

each g is independently 0, 1, 2, 3, 4, or 5; and
$L^a$ is as described above and defined herein.

TABLE 6

Exemplary Linkers of Formula H.

| Formula | —$(L^a)_f$—M—$(L^a)_f$— |
|---|---|
| H-i | 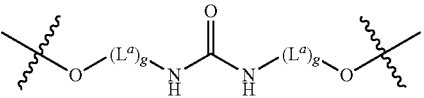 |
| H-ii | 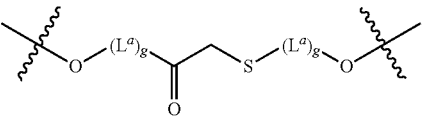 |

In some embodiments, a guide molecule is a compound of Formula $A_3$-ii, $A_2$-ii, $B_3$-ii, $B_2$-ii, $C_3$-ii, $C_2$-ii, $D_3$-ii, $D_2$-ii, $E_3$-ii$_U$, $E_2$-ii$_U$, $E_3$-ii$_A$, $E_2$-ii$_A$, $F_3$-iiy, $F_2$-ii$_U$, $F_3$-ii$_A$, or $F_2$-ii$_A$, wherein -$(L^a)_f$-M-$(L^a)_f$- is not selected from a group in Table 6.

In some embodiments, a guide molecule is a compound of Formula $A_3$-ii, $A_2$-ii, $B_3$-ii, $B_2$-ii, $C_3$-ii, $C_2$-ii, $D_3$-ii, $D_2$-ii, $E_3$-ii$_U$, $E_2$-ii$_U$, $E_3$-ii$_A$, $E_2$-ii$_A$, $F_3$-ii$_U$, $F_2$-ii$_U$, $F_3$-ii$_A$, or $F_2$-ii$_A$, wherein -$(L^a)_f$-M-$(L^a)_f$- is selected from a group in Table 7, wherein:

each g is independently 0, 1, 2, 3, 4, or 5;
each $R_2$ is independently O or S;
each $R_3$ is independently OH or COOH; and
$L^a$ is as described above and defined herein.

TABLE 7

Exemplary Linkers of Formula I.

| Formula | —$(L^a)_f$—M—$(L^a)_f$— |
|---|---|
| I-i | 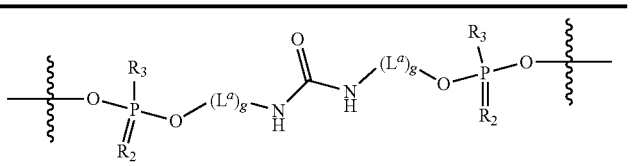 |
| I-ii | 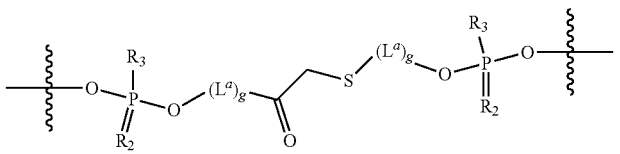 |

In some embodiments, a guide molecule is a compound of Formula $A_3$-ii, $A_2$-ii, $B_3$-ii, $B_2$-ii, $C_3$-ii, $C_2$-ii, $D_3$-ii, $D_2$-ii, $E_3$-ii$_U$, $E_2$-ii$_U$, $E_3$-ii$_A$, $E_2$-ii$_A$, $F_3$-iiy, $F_2$-ii$_U$, $F_3$-ii$_A$, or $F_2$-ii$_A$, wherein -$(L^a)_f$-M-$(L^a)_f$- is not selected from a group in Table 7.

In some embodiments, a guide molecule is a compound of Formula $A_3$-ii, $A_2$-ii, $B_3$-ii, $B_2$-ii, $C_3$-ii, $C_2$-ii, $D_3$-ii, $D_2$-ii, $E_3$-ii$_U$, $E_2$-ii$_U$, $E_3$-ii$_A$, $E_2$-ii$_A$, $F_3$-ii$_U$, $F_2$-ii$_U$, $F_3$- ii$_A$, or $F_2$-ii$_A$, wherein Linker is -$(L^a)_f$-M-$(L^a)_f$-, and wherein:

each -$(L^a)_f$- is independently selected from Table 8;
M is or is encompassed by a group independently selected from Table 9;
each a is independently an integer between 0 and 16, inclusive;
each b is independently an integer between 0 and 4, inclusive;
each $R_2$ is independently O or S;
each $R_3$ is independently OH or COOH;

each $R^L$ is independently selected from R, halogen, —OR, —NR$_2$, —SR, —NO$_2$, —CN, —SO$_2$R, —CO$_2$R, and —CONR$_2$; and each R is independently hydrogen or an optionally substituted group selected from C$_{1-6}$ aliphatic, phenyl, a 4-7 membered heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

TABLE 8

Exemplary —(L$^a$)$_f$— Groups.

—(L$^a$)$_f$—
—(L$^a$-26)—(L$^a$-1)—
—(L$^a$-26)—(L$^a$-5)—
covalent bond
—(L$^a$-26)—(L$^a$-1)—(L$^a$-27)—
—(L$^a$-26)—(L$^a$-5)—(L$^a$-27)—
—(L$^a$-26)—(L$^a$-1)—(L$^a$-27)—(L$^a$-5)—
—(L$^a$-26)—(L$^a$-5)—(L$^a$-27)—(L$^a$-5)—
—(L$^a$-26)—(L$^a$-1)—(L$^a$-27)—(L$^a$-29)—
—(L$^a$-26)—(L$^a$-5)—(L$^a$-27)—(L$^a$-29)—
—(L$^a$-26)—(L$^a$-1)—(L$^a$-27)—(L$^a$-30)—
—(L$^a$-26)—(L$^a$-5)—(L$^a$-27)—(L$^a$-30)—
—(L$^a$-26)—(L$^a$-1)—(L$^a$-31)—
—(L$^a$-26)—(L$^a$-5)—(L$^a$-31)—
—(L$^a$-26)—(L$^a$-1)—(L$^a$-31)—(L$^a$-3)—
—(L$^a$-26)—(L$^a$-5)—(L$^a$-31)—(L$^a$-3)—
—(L$^a$-26)—(L$^a$-1)—(L$^a$-27)—(L$^a$-3)—
—(L$^a$-26)—(L$^a$-5)—(L$^a$-27)—(L$^a$-3)—
—(L$^a$-26)—(L$^a$-1)—(L$^a$-27)—(L$^a$-33)—(L$^a$-3)—
—(L$^a$-26)—(L$^a$-5)—(L$^a$-27)—(L$^a$-33)-(L$^a$-3)—
—(L$^a$-26)—(L$^a$-1)—(L$^a$-27)—(L$^a$-5)—(L$^a$-27)—(L$^a$-3)—
—(L$^a$-26)—(L$^a$-5)—(L$^a$-27)—(L$^a$-5)—(L$^a$-27)—(L$^a$-3)—
—(L$^a$-26)—(L$^a$-1)—(L$^a$-31)—(L$^a$-34)—
—(L$^a$-26)—(L$^a$-5)—(L$^a$-31)—(L$^a$-34)—
—(L$^a$-26)—(L$^a$-1)—(L$^a$-27)—(L$^a$-34)—
—(L$^a$-26)—(L$^a$-5)—(L$^a$-27)—(L$^a$-34)—
—(L$^a$-26)—(L$^a$-1)—(L$^a$-27)—(L$^a$-33)—(L$^a$-34)—
—(L$^a$-26)—(L$^a$-5)—(L$^a$-27)—(L$^a$-33)—(L$^a$-34)—
—(L$^a$-26)—(L$^a$-1)—(L$^a$-27)—(L$^a$-5)—(L$^a$-27)—(L$^a$-34)—
—(L$^a$-26)—(L$^a$-5)—(L$^a$-27)—(L$^a$-5)—(L$^a$-27)—(L$^a$-34)—
—(L$^a$-39)—
—(L$^a$-39)—(L$^a$-37)—
—(L$^a$-39)—(L$^a$-5)—

TABLE 9

Exemplary M Groups.
M

M-19
M-22
M-20
M-25
M-26

In some embodiments, a guide molecule is a compound of Formula A$_3$-ii, A$_2$-ii, B$_3$-ii, B$_2$-ii, C$_3$-ii, C$_2$-ii, D$_3$-ii, D$_2$-ii, E$_3$-ii$_U$, E$_2$-ii$_U$, E$_3$-ii$_A$, E$_2$-ii$_A$, F$_3$-ii$_U$, F$_2$-ii$_U$, F$_3$-ii$_A$, or F$_2$-ii$_A$, wherein Linker is -(L$^a$)$_f$-M-(L$^a$)$_f$-, and wherein:

each -(L$^a$)$_f$- is independently selected from Table 10;
M is or is encompassed by a group independently selected from Table 11;

each a is independently an integer between 0 and 16, inclusive;

each b is independently an integer between 0 and 4, inclusive;

each R$_2$ is independently O or S;

each R$_3$ is independently OH or COOH;

each $R^L$ is independently selected from R, halogen, —OR, —NR$_2$, —SR, —NO$_2$, —CN, —SO$_2$R, —CO$_2$R, and —CONR$_2$; and each R is independently hydrogen or an optionally substituted group selected from C$_{1-6}$ aliphatic, phenyl, a 4-7 membered heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

TABLE 10

Exemplary —(L$^a$)$_f$— Groups.

—(La)$_f$—

—(L$^a$-26)—(L$^a$-1)—
—(L$^a$-26)—(L$^a$-5)—
covalent bond

—(L$^a$-26)—(L$^a$-1)—(L$^a$-31)—
—(L$^a$-26)—(L$^a$-5)—(L$^a$-31)—
—(L$^a$-26)—(L$^a$-1)—(L$^a$-27)—
—(L$^a$-26)—(L$^a$-5)—(L$^a$-27)—
—(L$^a$-26)—(L$^a$-1)—(L$^a$-27)—(L$^a$-33)—
—(L$^a$-26)—(L$^a$-5)—(L$^a$-27)—(L$^a$-33)—
—(L$^a$-26)—(L$^a$-1)—(L$^a$-27)—(L$^a$-5)—(L$^a$-27)—
—(L$^a$-26)—(L$^a$-5)—(L$^a$-27)—(L$^a$-5)—(L$^a$-27)—
—(L$^a$-26)—(L$^a$-1)—(L$^a$-31)—(L$^a$-34)—
—(L$^a$-26)—(L$^a$-5)—(L$^a$-31)—(L$^a$-34)—
—(L$^a$26)—(L$^a$-1)—(L$^a$-27)—(L$^a$-34)—
—(L$^a$-26)—(L$^a$-5)—(L$^a$-27)—(L$^a$-34)—
—(L$^a$-26)—(L$^a$-1)—(L$^a$-27)—(L$^a$-33)—(L$^a$-34)—
—(L$^a$-26)—(L$^a$-5)—(L$^a$-27)—(L$^a$-33)—(L$^a$-34)—
—(L$^a$-26)—(L$^a$-1)—(L$^a$-27)—(L$^a$-5)—(L$^a$-27)—(L$^a$-34)—
—(L$^a$-26)—(L$^a$-5)—(L$^a$-27)—(L$^a$-5)—(L$^a$-27)—(L$^a$-34)—
—(L$^a$-26)—(L$^a$-1)—(L$^a$-27)—(L$^a$-35)—
—(L$^a$-26)—(L$^a$-5)—(L$^a$-27)—(L$^a$-35)—
—(L$^a$-26)—(L$^a$-1)—(L$^a$-27)—(L$^a$-36)—
—(L$^a$-26)—(L$^a$-5)—(L$^a$-27)—(L$^a$-36)—
—(L$^a$-26)—(L$^a$-1)—(L$^a$-27)—(L$^a$-5)—(L$^a$-37)—
—(L$^a$-26)—(L$^a$-5)—(L$^a$-27)—(L$^a$-5)—(L$^a$-37)—
—(L$^a$-26)—(L$^a$-1)—(L$^a$-27)—(L$^a$-38)—
—(L$^a$-26)—(L$^a$-5)—(L$^a$-27)—(L$^a$-38)—
—(L$^a$-26)—(L$^a$-1)—(L$^a$-27)—(L$^a$-38)—(L$^a$-40)—
—(L$^a$-26)—(L$^a$-5)—(L$^a$-27)—(L$^a$-38)—(L$^a$-40)—
—(L$^a$-26)—(L$^a$-1)—(L$^a$-27)—(L$^a$-38)—(L$^a$-28)—
—(L$^a$-26)—(L$^a$-5)—(L$^a$-27)—(L$^a$-38)—(L$^a$-28)—

TABLE 11

Exemplary M Groups.
M

M-4
M-21

In some embodiments, -(L$^a$)-M-(L$^a$)- is not:
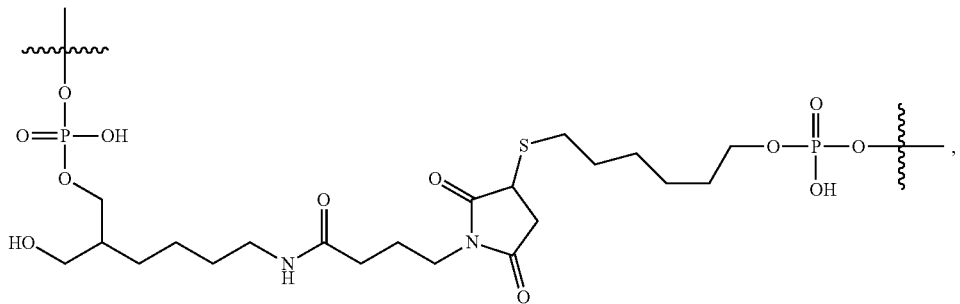
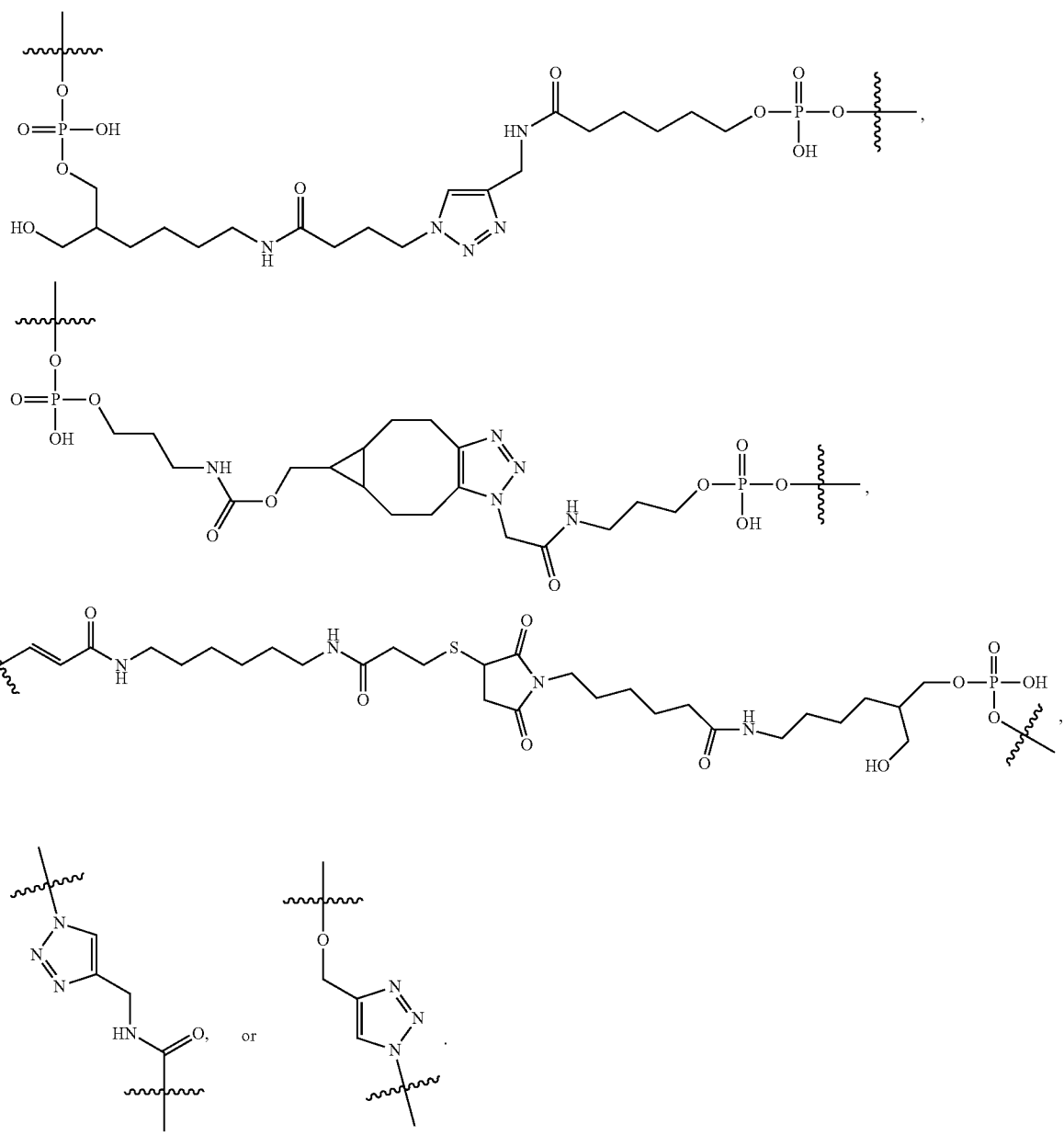

In some embodiments, the chemical linkage of a cross-linked guide molecule comprises a urea. In some embodiments, the guide molecule comprising a urea is of formula $J_{3'}$-i or $J_{2'}$-i:

In some embodiments, the guide molecule comprising a urea is of formula $A_{3'}$-iii or $A_{2'}$-iii:

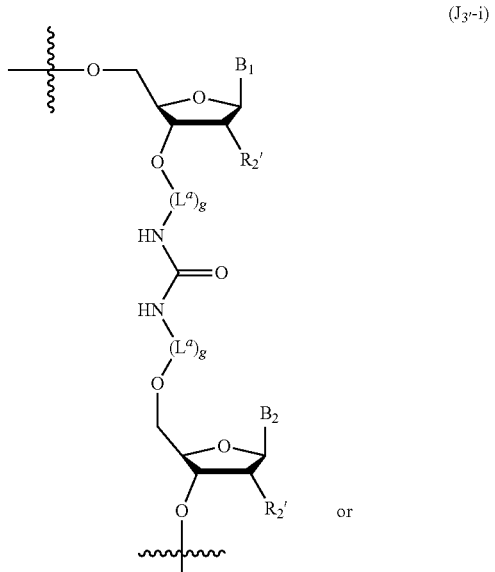

(J_{3'}-i)

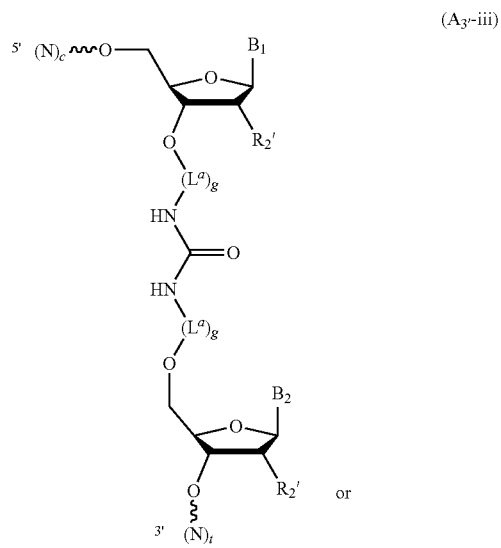

(A_{3'}-iii)

or

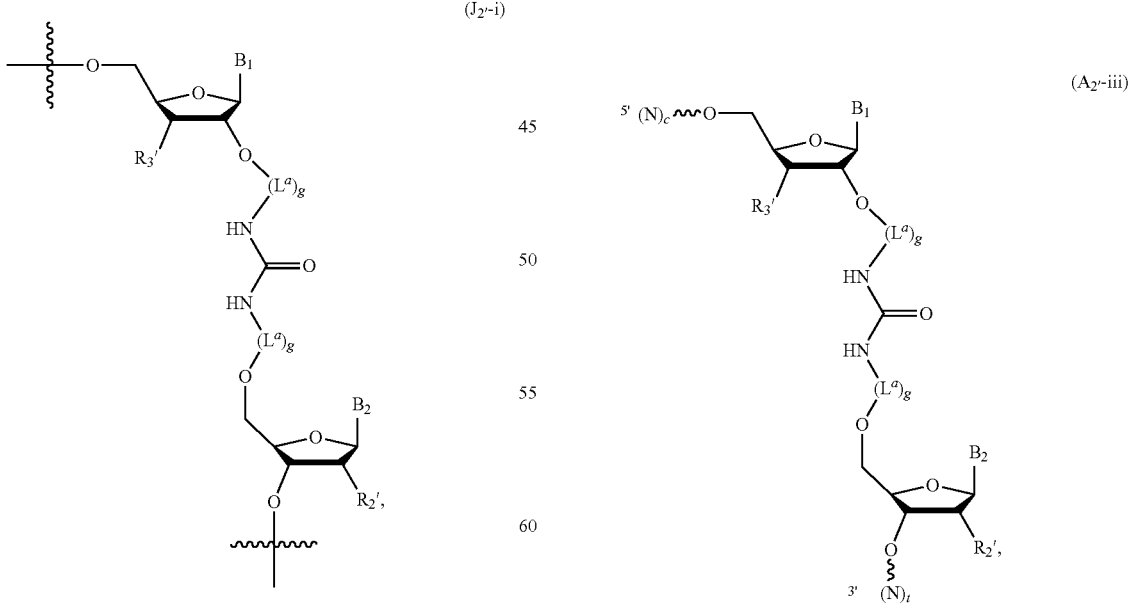

(J_{2'}-i)

(A_{2'}-iii)

wherein $B_1$, $B_2$, $R_2'$, and $R_3'$ are as defined in formulas $A_{3'}$-i and $A_{2'}$-i above; each g is independently 0, 1, 2, 3, 4, or 5; and $L^a$ is as described above and defined herein.

wherein N, $B_1$, $B_2$, $R_2'$, $R_3'$, c, and t are as defined above in formulas $A_{3'}$-i and $A_{2'}$-i; each g is independently 0, 1, 2, 3, 4, or 5; and $L^a$ is as described above and defined herein.

In some embodiments, the guide molecule comprising a urea is of formula $B_{3'}$-iii or $B_{2'}$-iii:

In some embodiments, the guide molecule comprising a urea is of formula $C_{3'}$-iii, $C_{2'}$-iii, $D_{3'}$-iii, or $D_{2'}$-iii:

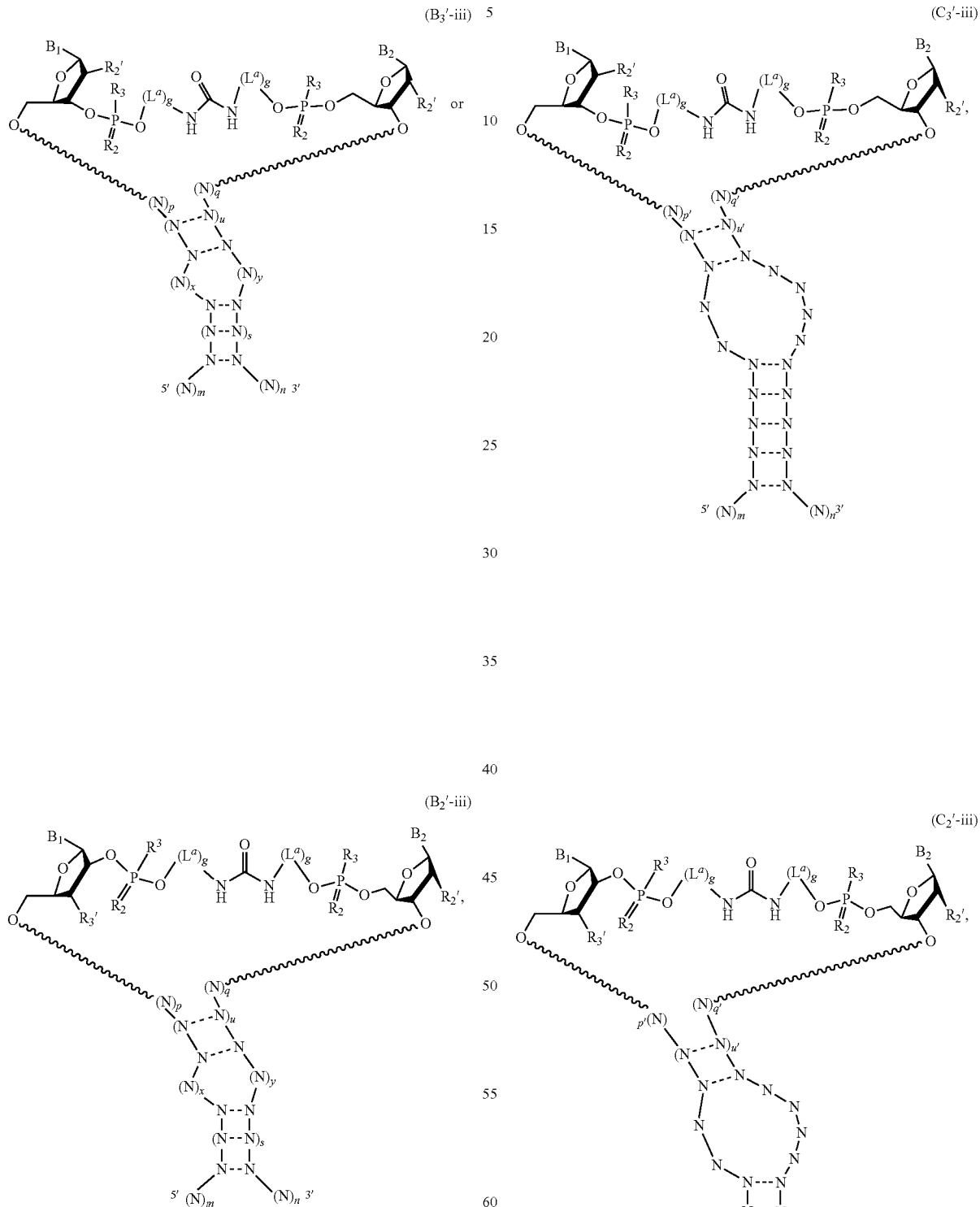

wherein N, $B_1$, $B_2$, $R_2'$, $R_3'$, p, q, u, x, y, s, n, m, and 〰 are as defined above in formulas $B_{3'}$-i and $B_{2'}$-i; each $R_2$ is independently O or S; each $R_3$ is independently OH or COOH; each g is independently 0, 1, 2, 3, 4, or 5; and $L^a$ is as described above and defined herein.

-continued

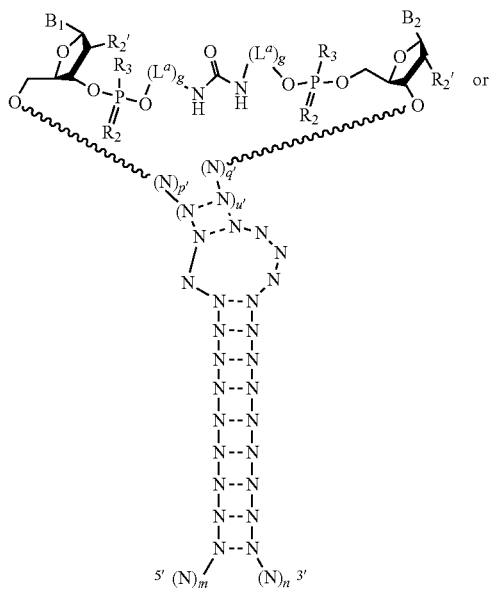

(D₃'-iii)

or

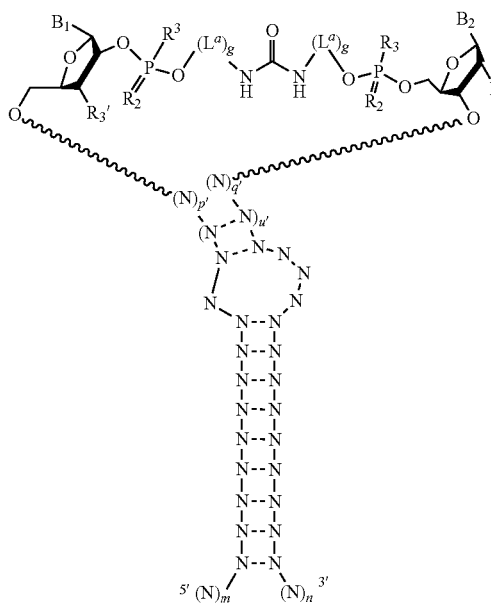

(D₂'-iii)

wherein N, B₁, B₂, R₂', R₃', p', q', u', n, m, and ∿∿∿ are as defined above in formulas C₃'-i and C₂'-i, D₃'-i, and D₂'-i; each R₂ is independently O or S; each R₃ is independently OH or COOH; each g is independently 0, 1, 2, 3, 4, or 5; and $L^a$ is as described above and defined herein.

In some embodiments, the chemical linkage of a cross-linked guide molecule comprises a thioether. In some embodiments, the guide molecule comprising a thioether is of formula J₃'-ii, J₂'-ii, J₃'-iii, or J₂'-iii:

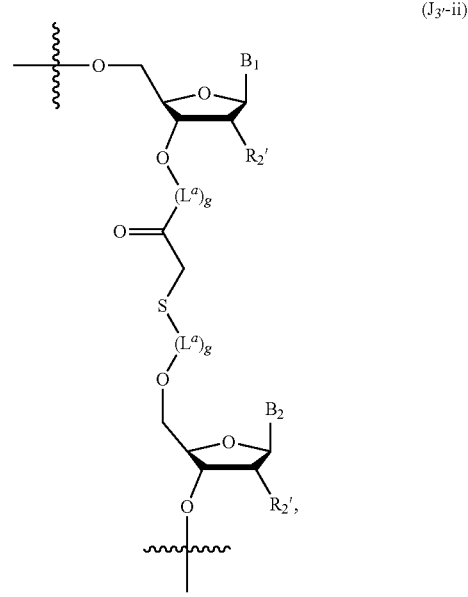

(J₃'-ii)

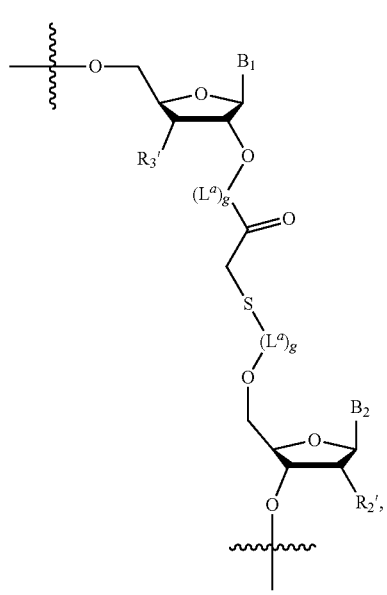

(J₂'-ii)

-continued
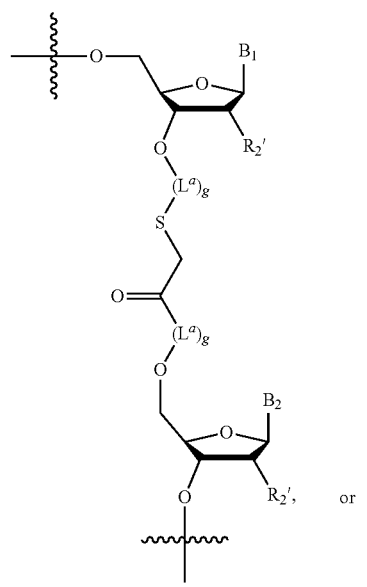
(J$_{3'}$-iii)
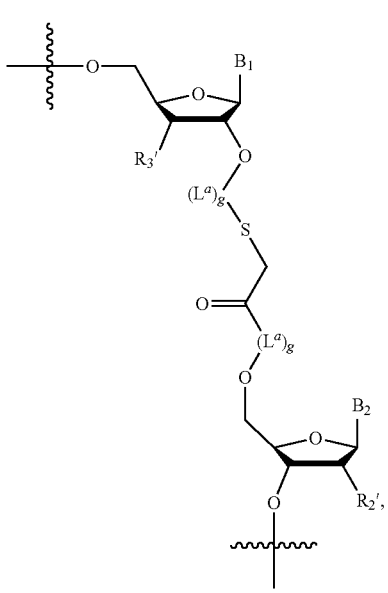
(J$_{2'}$-iii)
wherein B$_1$, B$_2$, R$_2'$, and R$_3'$ are as defined in formulas J$_{3'}$-i and J$_{2'}$-i above; each g is independently 0, 1, 2, 3, 4, or 5; and L$^a$ is as described above and defined herein.
In some embodiments, the guide molecule comprising a thioether is of formula A$_{3'}$-iv, A$_{2'}$-iv, A$_{3'}$-v, or A$_{2'}$-v:
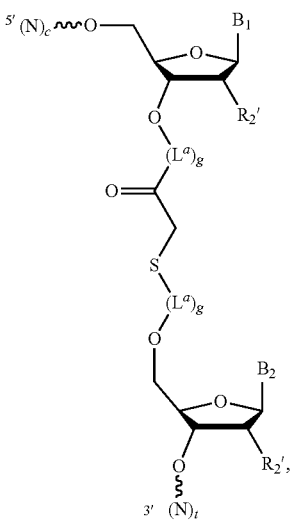
(A$_{3'}$-iv)
(A$_{2'}$-iv)
(A$_{3'}$-v)
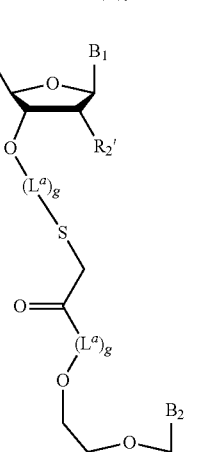

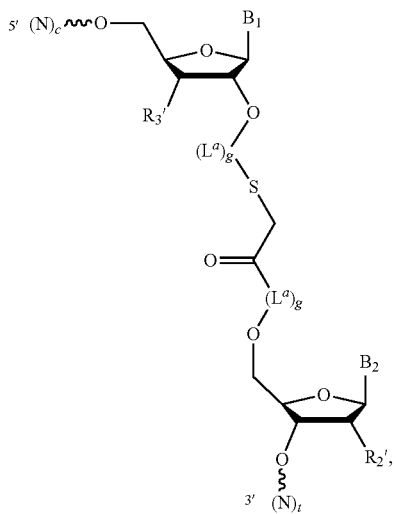

wherein N, $B_1$, $B_2$, $R_2'$, $R_3'$, c, and t are as defined above in formulas $A_3$-i and $A_2$-i; each g is independently 0, 1, 2, 3, 4, or 5; and $L^a$ is as described above and defined herein.

In some embodiments, the guide molecule comprising a thioether is of formula $B_3'$-iv, $B_2'$-iv, $B_3'$-v, or $B_2'$-v:

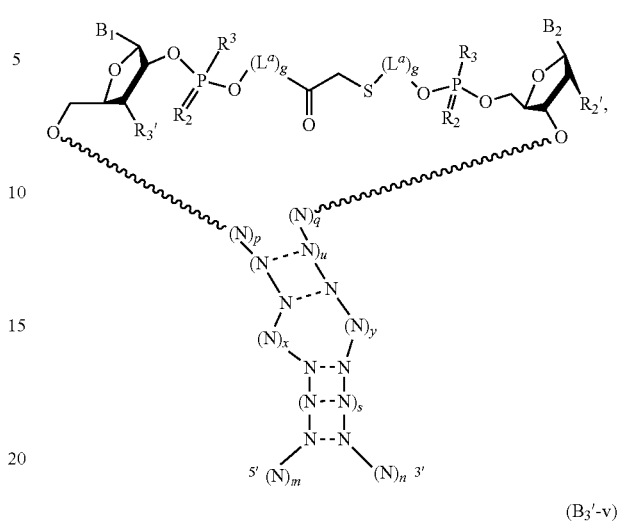

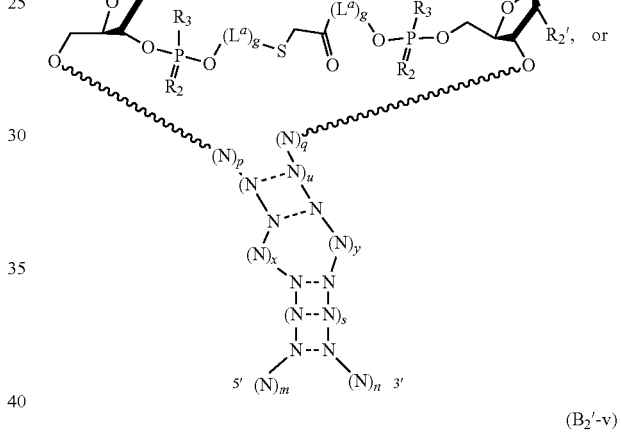

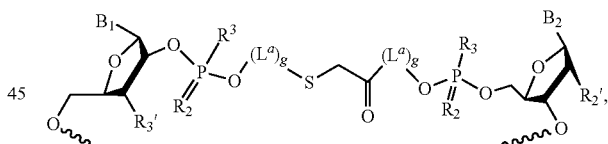

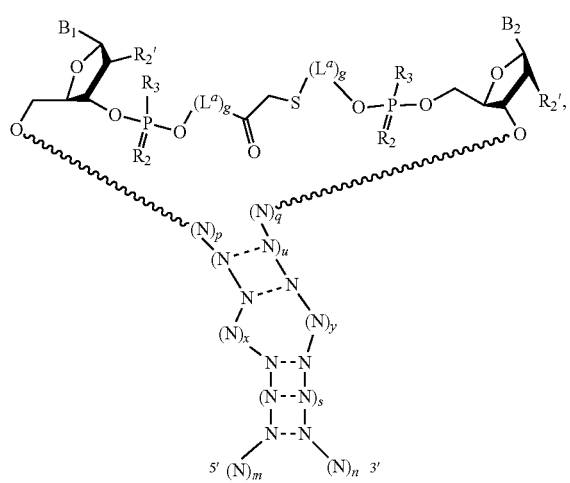

wherein N, $B_1$, $B_2$, $R_2'$, $R_3'$, p, q, u, x, y, s, n, m, and ∿∿∿ are as defined above in formulas $B_3$-i and $B_2$-i; each $R_2$ is independently O or S; each $R_3$ is independently OH or COOH; each g is independently 0, 1, 2, 3, 4, or 5; and $L^a$ is as described above and defined herein.

In some embodiments, the guide molecule comprising a thioether is of formula $C_{3'}$-iv, $C_{2'}$-iv, $C_{3'}$-v, $C_{2'}$-v, $D_{3'}$-iv, $D_{2'}$-iv, $D_{3'}$-v, or $D_{2'}$-v:
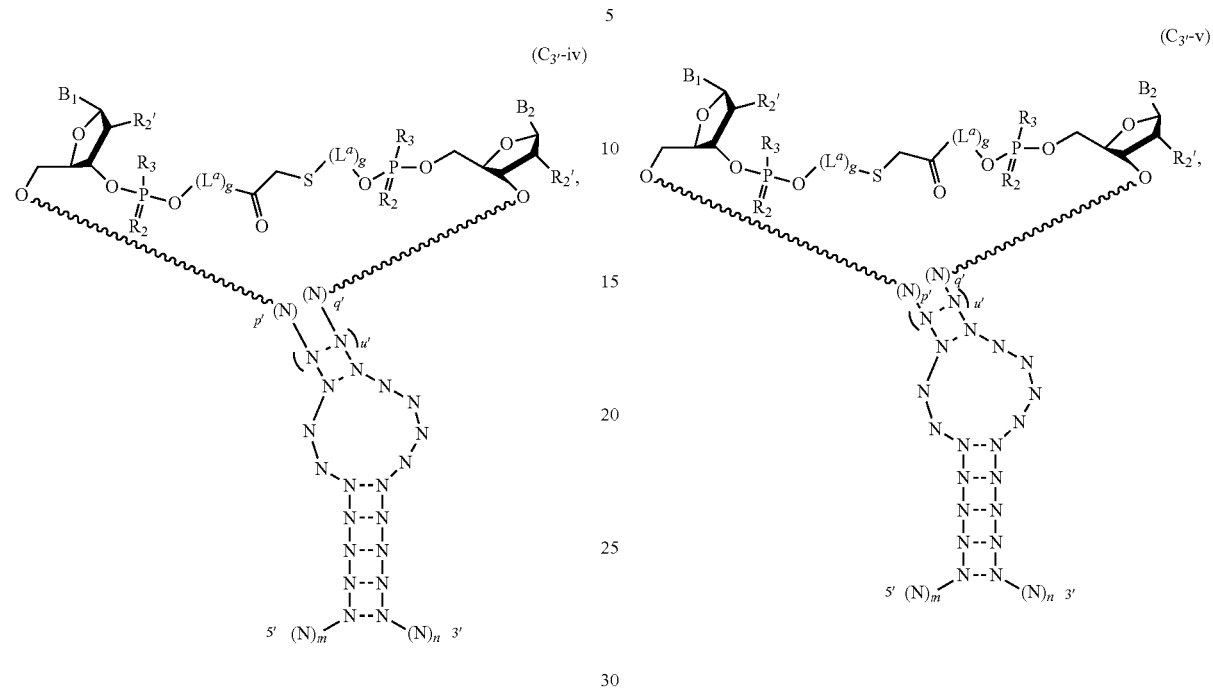
-continued
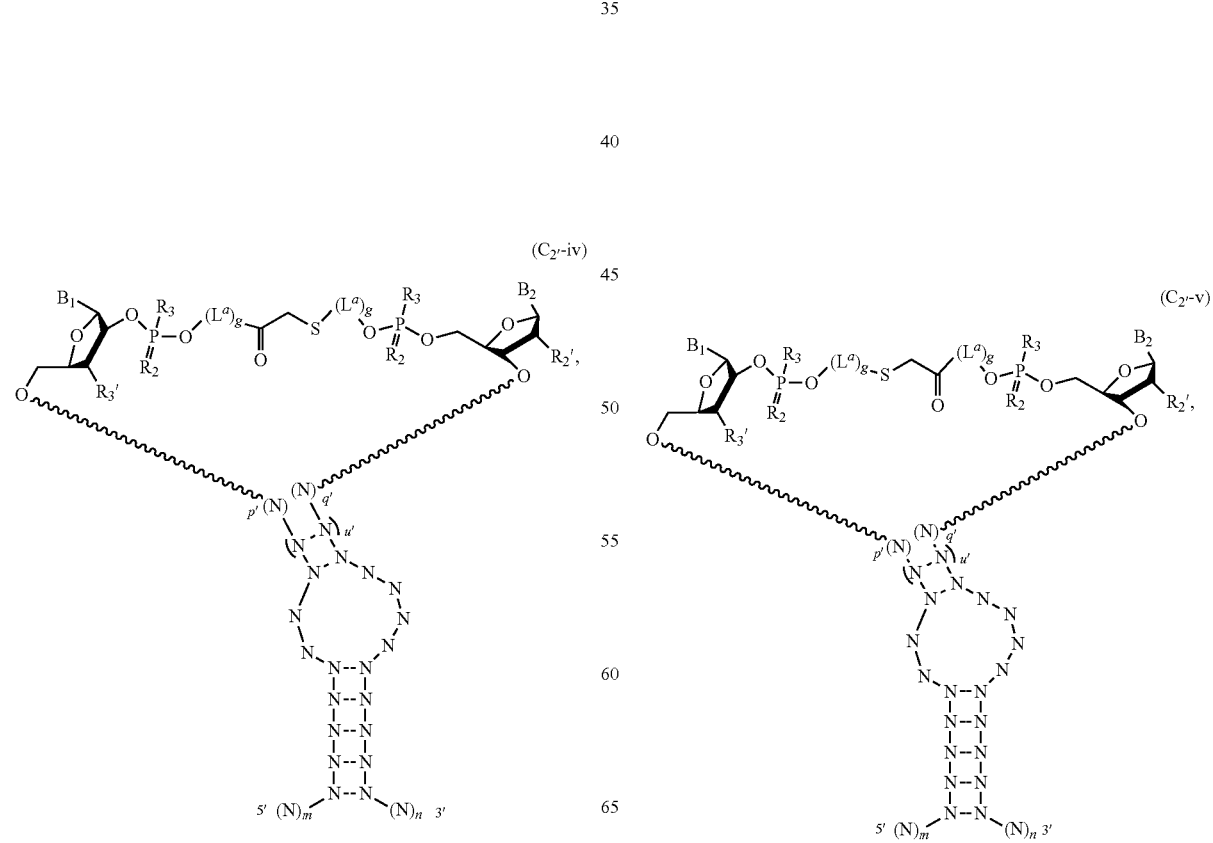

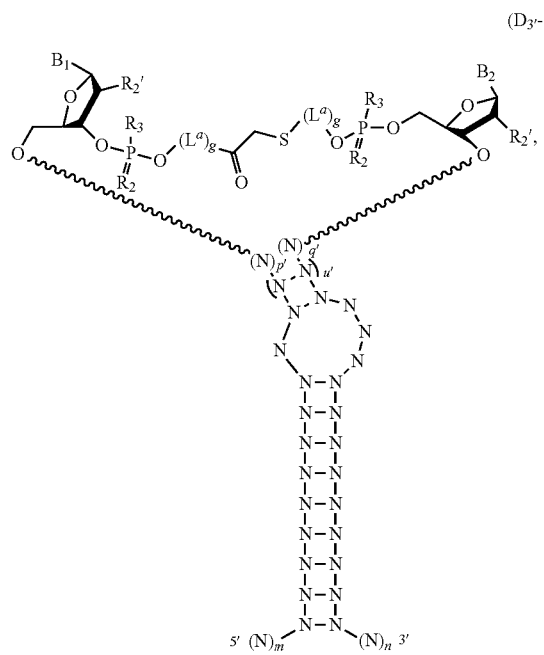

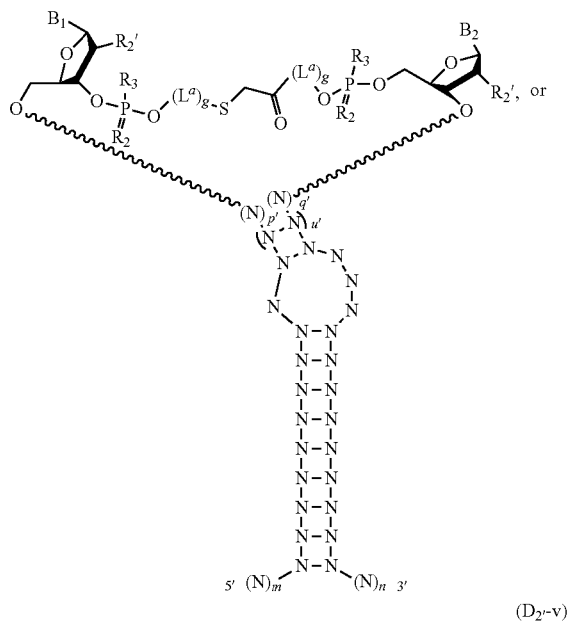

wherein N, $B_1$, $B_2$, $R_2'$, $R_3'$, p', q' u', n, m, and 〜 are as defined above in formulas $C_3$-i and $C_2$-i, $D_3$-i, and $D_2$-i; each $R_2$ is independently O or S; each $R_3$ is independently OH or COOH; each g is independently 0, 1, 2, 3, 4, or 5; and $L^a$ is as described above and defined herein.

In some embodiments, in any formulas of this application, $R_2'$ and $R_3'$ are each independently H, OH, fluoro, chloro, bromo, $NH_2$, SH, S—R', or O—R' wherein each R' is independently a protecting group or an optionally substituted alkyl group. In some embodiments, $R_2'$ and $R_3'$ are each independently H, OH, halogen, $NH_2$, or O—R' wherein each R' is independently a protecting group or an optionally substituted alkyl group. In some embodiments, $R_2'$ and $R_3'$ are each independently H, fluoro, and O—R', wherein R' is a protecting group or an optionally substituted alkyl group. In some embodiments, $R_2'$ is H. In some embodiments, $R_3'$ is H. In some embodiments, $R_2'$ is halogen. In some embodiments, $R_3'$ is halogen. In some embodiments, $R_2'$ is fluoro. In some embodiments, $R_3'$ is fluoro. In some embodiments, $R_2'$ is O—R'. In some embodiments, $R_3'$ is O—R'. In some embodiments, $R_2'$ is O-Me. In some embodiments, $R_3'$ is O-Me.

In some embodiments, in any formulas of this application, p and q are each independently 0, 1, 2, 3, 4, 5, or 6, and p+q is an integer between 0 and 6, inclusive. In some embodiments, p is 0, 1, 2, or 3. In some embodiments, q is 0, 1, 2, or 3. In some embodiments, p and q are each 2. In some embodiments, p and q are each 0. In some embodiments, p is 0 and q is 1. In some embodiments, p is 0 and q is 2. In some embodiments, p is 1 and q is 0. In some embodiments, p is 2 and q is 0.

In some embodiments, in any formulas of this application, p' and q' are each 0, 1, 2, 3, 4, 5, or 6, and p'+q' is an integer between 0 and 6, inclusive. In some embodiments, p' and q' are each independently 0, 1, 2, 3, or 4, and p'+q' is an integer between 0 and 4, inclusive. In some embodiments, p' and q' are each 2. In some embodiments, p' and q' are each 0. In some embodiments, p' is 0 and q' is 1. In some embodiments, p' is 0 and q' is 2. In some embodiments, p' is 1 and q' is 0. In some embodiments, p' is 2 and q' is 0.

In some embodiments, in any formulas of this application, u is an integer between 2 and 22, inclusive. In some embodiments, u is an integer between 3 and 22, inclusive. In some embodiments, u is an integer between 4 and 22, inclusive. In some embodiments, u is an integer between 8 and 22, inclusive. In some embodiments, u is an integer between 12 and 22, inclusive. In some embodiments, u is an integer between 0 and 22, inclusive. In some embodiments, u is an integer between 2 and 14, inclusive. In some embodiments, u is an integer between 4 and 14, inclusive. In some embodiments, u is an integer between 8 and 14, inclusive. In some embodiments, u is an integer between 0 and 14, inclusive. In some embodiments, u is an integer between 0 and 4, inclusive.

In some embodiments, in any formulas of this application, u' is an integer between 2 and 22, inclusive. In some embodiments, u' is an integer between 3 and 22, inclusive. In some embodiments, u' is an integer between 4 and 22, inclusive. In some embodiments, u' is an integer between 8 and 22, inclusive. In some embodiments, u' is an integer between 12 and 22, inclusive. In some embodiments, u' is an integer between 0 and 22, inclusive. In some embodiments, u' is an integer between 2 and 14, inclusive. In some embodiments, u' is an integer between 4 and 14, inclusive. In some embodiments, u' is an integer between 8 and 14, inclusive. In some embodiments, u' is an integer between 0 and 14, inclusive. In some embodiments, u' is an integer between 0 and 4, inclusive.

In some embodiments, in any formulas of this application, each N is independently a nucleotide residue. In some embodiments, N is a modified nucleotide residue. In some embodiments, N is an unmodified nucleotide residue. In some embodiments, each N is independently a ribonucleotide, a deoxyribonucleotide, a modified ribonucleotide, or a modified deoxyribonucleotide. Nucleotide modifications are discussed below. In some embodiments, each N is independently linked to its adjacent nucleotide(s) via a phosphodiester linkage, a phosphorothioate linkage, a phosphonoacetate linkage, a thiophosphonoacetate linkage, or a phosphoramidate linkage.

In some embodiments, in any formulas of this application, c is an integer 20 or greater. In some embodiments, c is an integer between 20 and 60, inclusive. In some embodiments, c is an integer between 20 and 40, inclusive. In some embodiments, c is an integer between 40 and 60, inclusive. In some embodiments, c is an integer between 30 and 60, inclusive. In some embodiments, c is an integer between 20 and 50, inclusive.

In some embodiments, in any formulas of this application, t is an integer 20 or greater. In some embodiments, t is an integer between 20 and 80, inclusive. In some embodiments, t is an integer between 20 and 50, inclusive. In some embodiments, t is an integer between 50 and 80, inclusive. In some embodiments, t is an integer between 20 and 70, inclusive. In some embodiments, t is an integer between 30 and 80, inclusive.

In some embodiments, in any formulas of this application, s is an integer between 1 and 10, inclusive. In some embodiments, s is an integer between 3 and 9, inclusive. In some embodiments, s is an integer between 1 and 8, inclusive. In some embodiments, s is an integer between 0 and 10, inclusive. In some embodiments, s is an integer between 2 and 6, inclusive.

In some embodiments, in any formulas of this application, x is an integer between 1 and 3, inclusive. In some embodiments, x is 1. In some embodiments, x is 2. In some embodiments, x is 3. In some embodiments, in any formulas of this application, y is greater than x. In some embodiments, y is an integer between 3 and 5, inclusive. In some embodiments, y is 3. In some embodiments, y is 4. In some embodiments, y is 5. In some embodiments, x is 1 and y is 3. In some embodiments, x is 2 and y is 4.

In some embodiments, in any formulas of this application, m is an integer 15 or greater. In some embodiments, m is an integer between 15 and 50, inclusive. In some embodiments, m is an integer 16 or greater. In some embodiments, m is an integer 17 or greater. In some embodiments, m is an integer 18 or greater. In some embodiments, m is an integer 19 or greater. In some embodiments, m is an integer 20 or greater. In some embodiments, m is an integer between 20 and 40, inclusive. In some embodiments, m is an integer between 30 and 50, inclusive. In some embodiments, m is an integer between 15 and 30, inclusive.

In some embodiments, in any formulas of this application, n is an integer 30 or greater. In some embodiments, n is an integer between 30 and 70, inclusive. In some embodiments, n is an integer between 30 and 60, inclusive. In some embodiments, n is an integer between 40 and 70, inclusive.

In some embodiments, in any formulas of this application, each $R_2$ is independently O or S. In some embodiments, $R_2$ is O. In some embodiments, $R_2$ is S.

In some embodiments, in any formulas of this application, each $R_3$ is independently OH or COOH. In some embodiments, $R_3$ is OH. In some embodiments, $R_3$ is COOH.

In some embodiments, $R_2$ is O and $R_3$ is OH. In some embodiments, $R_2$ is O and $R_3$ is COOH. In some embodiments, $R_2$ is S and $R_3$ is OH. In some embodiments, $R_2$ is S and $R_3$ is COOH.

It will be appreciated that provided guide molecules may exist as one or more neutral or salt forms, all of which are contemplated by the present disclosure. For example, a phosphodiester moiety drawn as such:

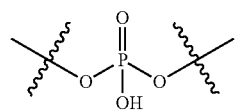 [SMILES: *OP(=O)(O)O*]

includes both protonated (i.e., neutral) or deprotonated (e.g., as a salt) forms, both of which are encompassed by the present disclosure.

In some embodiments, in any formulas of this application, each N—N independently represents two complementary nucleotides, optionally two complementary nucleotides that are hydrogen bonding base-paired. In some embodiments, all N—N represent two complementary nucleotides that are hydrogen bonding base-paired. In some embodiments, some N—N represent two complementary nucleotides and some N—N represent two complementary nucleotides that are hydrogen bonding base-paired.

In some embodiments, in any formulas of this application, $B_1$ and $B_2$ are each independently a nucleobase. In some embodiments, $B_1$ and $B_2$ are independently selected from guanine, cytosine, adenine, and uracil. In some embodiments, $B_1$ is guanine and $B_2$ is cytosine. In some embodiments, $B_1$ is cytosine and $B_2$ is guanine. In some embodiments, $B_1$ is adenine and $B_2$ is uracil. In some embodiments, $B_1$ is uracil and $B_2$ is adenine. In some embodiments, $B_1$ and $B_2$ are complementary. In some embodiments, $B_1$ and $B_2$ are complementary and base-paired through hydrogen bonding. In some embodiments, $B_1$ and $B_2$ are complementary and not base-paired through hydrogen bonding. In some embodiments, $B_1$ and $B_2$ are not complementary.

In some embodiments, in any formulas of this application, each ⌇ represents independently a phosphodiester linkage, a phosphorothioate linkage, a phosphonoacetate linkage, a thiophosphonoacetate linkage, or a phosphoroamidate linkage. In some embodiments, each ⌇ represents a phosphodiester linkage.

In some embodiments, in any formulas of this application, each R is independently hydrogen or an optionally substituted group selected from $C_{1-6}$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur. In some embodiments, R is hydrogen or an optionally substituted group selected from $C_{1-6}$ aliphatic and phenyl. In some embodiments, R is hydrogen or $C_{1-6}$ alkyl. In some embodiments, R is hydrogen.

Synthesis of Guide Molecules

The present disclosure also provides a method of synthesizing a unimolecular guide molecule, the method comprising the steps of:

providing a first oligonucleotide and a second oligonucleotide, capable of forming a duplex between a 3' region of the first oligonucleotide and a 5' region of the second oligonucleotide, wherein the first oligonucleotide comprises a first reactive group which is at least one of a 2' reactive group and a 3' reactive group, and wherein the second oligonucleotide comprises a second reactive group which is a 5' reactive group; and conjugating the first and second oligonucleotides via the first and second reactive groups to form a unimolecular guide molecule that includes a covalent bond linking the first and second oligonucleotides.

In some embodiments, the method of synthesizing a unimolecular guide molecule comprises the steps of:

providing a first oligonucleotide and a second oligonucleotide, capable of forming a duplex between a 3' region of the first oligonucleotide and a 5' region of the second oligonucleotide, wherein the first oligonucleotide comprises a first reactive group which is at least one of a 2' reactive group and a 3' reactive group, and wherein the second oligonucleotide comprises a second reactive group which is a 5' reactive group annealing the first oligonucleotide and the second oligonucleotide to form a duplex between a 3' region of the first oligonucleotide and a 5' region of the second oligonucleotide; and conjugating the annealed first and second oligonucleotides via the first and second reactive groups to form a unimolecular guide molecule that includes a covalent bond linking the first and second oligonucleotides.

In some embodiments, the first reactive group and the second reactive group are selected from the functional groups listed above under "Overview." In some embodiments, the first reactive group and the second reactive group are each independently an amine moiety, a sulfhydryl moiety, a haloacetyl (e.g., bromoacetyl or iodoacetyl) moiety, a hydroxyl moiety, or a phosphate moiety. In some embodiments, the first reactive group and the second reactive group are each independently an amine moiety, a hydroxyl moiety, a sulfhydryl moiety, a haloacetyl (e.g., bromoacetyl or iodoacetyl) moiety, a phosphate moiety, an aryl fluoride moiety, an imidoester moiety, a maleimide moiety, a carbonate moiety, an ester moiety, or an isocyanate moiety. In some embodiments, the first reactive group and the second reactive group are each independently an amine moiety, a hydroxyl moiety, a phosphate moiety, a sulfhydryl moiety, a haloacetyl (e.g., bromoacetyl or iodoacetyl) moiety, or a disulfide moiety.

In some embodiments, the first reactive group and the second reactive group are both amine moieties. In some embodiments, the first reactive group is a sulfhydryl moiety, and the second reactive group is a haloacetyl (e.g., bromoacetyl or iodoacetyl) moiety. In some embodiments, the first reactive group is a haloacetyl (e.g., bromoacetyl or iodoacetyl) moiety, and the second reactive group is a sulfhydryl moiety. In some embodiments, the first reactive group is a hydroxyl moiety and the second reactive group is a phosphate moiety. In some embodiments, the first reactive group is a phosphate moiety, and the second reactive group is a hydroxyl moiety. In some embodiments, the first reactive group is an amine moiety, and the second reactive group is a sulfhydryl moiety. In some embodiments, the first reactive group is a sulfhydryl moiety, and the second reactive group is an amine moiety. In some embodiments, the first reactive group is an amine moiety, and the second reactive group is a hydroxyl moiety. In some embodiments, the first reactive group is a hydroxyl moiety, and the second reactive group is an amine moiety. In some embodiments, the first reactive group and the second reactive group are both sulfhydryl moieties. In some embodiments, the first reactive group is an amine moiety, and the second reactive group is a phosphate moiety. In some embodiments, the first reactive group is a phosphate moiety, and the second reactive group is an amine moiety.

In some embodiments, the first reactive group and the second reactive group are not an azide moiety, an alkyne moiety, a tetrazine moiety, a sulfhydryl group, a maleimide moiety, or an alkene moiety. In some embodiments, the first reactive group and the second reactive group are not an azide moiety, a cycloalkyne moiety, a tetrazine moiety, a sulfhydryl group, a maleimide moiety, or a cycloalkene moiety.

In some embodiments, the step of conjugating comprises a concentration of first nucleotide in the range of 10 µM to 1 mM. In some embodiments, the step of conjugating comprises a concentration of second nucleotide in the range of 10 µM to 1 mM. In some embodiments, the concentration of either the first or second nucleotide is 10 µM, 50 µM, 100 µM, 200 µM, 400 µM, 600 µM, 800 µM, or 1 mM, or any range in between.

In some embodiments, the step of conjugating comprises a pH in the range of 5.0 to 9.0. In some embodiments, the pH is 5.0, 5.5, 6.0, 6.5, 7.0, 7.5, 8.0, 8.5, or 9.0. In some embodiments, the pH is 6.0. In some embodiments, the pH is 7.0. In some embodiments, the pH is 7.5. In some embodiments, the pH is 8.0. In some embodiments, the pH is 8.5. In some embodiments, the pH is 9.0.

In some embodiments, the step of conjugating is performed under argon. In some embodiments, the step of conjugating is performed under ambient atmosphere.

In some embodiments, the step of conjugating is performed in water. In some embodiments, the step of conjugating is performed in water with a cosolvent. In some embodiments, the cosolvent is DMSO, DMF, NMP, DMA, morpholine, pyridine, or MeCN. In some embodiments, the cosolvent is DMSO. In some embodiments, the cosolvent is DMF.

In some embodiments, the step of conjugating is performed at a temperature in the range of 0° C. to 40° C. In some embodiments, the temperature is 0° C., 4° C., 10° C., 20° C., 25° C., 30° C., 37° C., or 40° C. In some embodiments, the temperature is 25° C. In some embodiments, the temperature is 4° C.

In some embodiments, the step of conjugating is performed in the presence of a divalent metal cation. In some embodiments, the divalent metal cation is $Mg^{2+}$, $Ca^{2+}$, $Sr^{2+}$, $Ba^{2+}$, $Cr^{2+}$, $Mn^{2+}$, $Fe^{2+}$, $Co^{2+}$, $Ni^{2+}$, $Cu^{2+}$, or $Zn^{2+}$. In some embodiments, the divalent metal cation is $Mg^{2+}$.

In some embodiments, the step of conjugating comprises a cross-linking reagent or a cross-linker (see "Overview" above). In some embodiments, the cross-linker is multifunctional, and in some embodiments the cross-linker is bifunctional. In some embodiments, the multifunctional cross-linker is heterofunctional or homofunctional.

In some embodiments, the cross-linker contains a carbonate. In some embodiments, the carbonate-containing cross-linker is disuccinimidyl carbonate, diimidazole carbonate, or bis-(p-nitrophenyl) carbonate, or

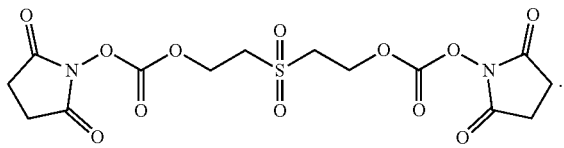 [SMILES: O=C(OCCS(=O)(=O)CCOC(=O)ON1C(=O)CCC1=O)ON1C(=O)CCC1=O]

In some embodiments, the carbonate-containing cross-linker is disuccinimidyl carbonate.

In some embodiments, the cross-linker contains an ester. In some embodiments, the ester-containing cross linker is selected from:

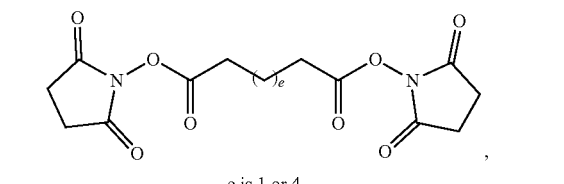

e is 1 or 4

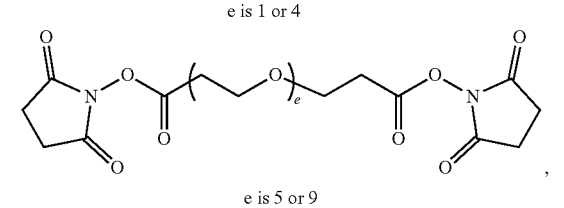

e is 5 or 9

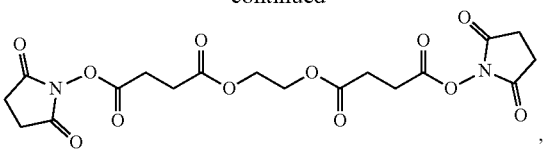

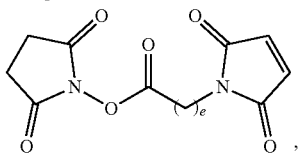

e is 1, 2, 3, 4, 5, or 6

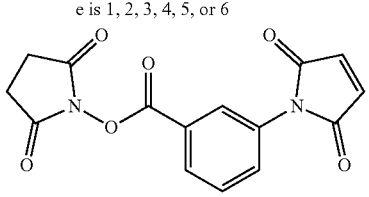

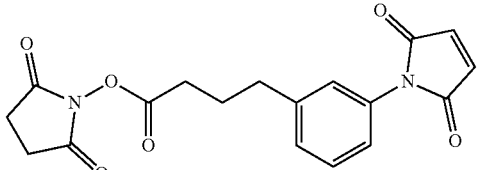

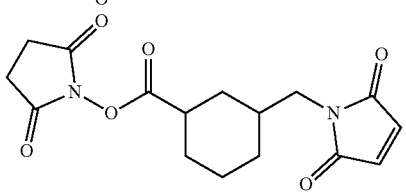

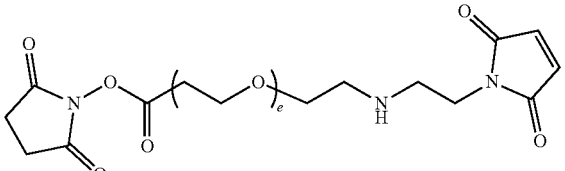

e is 2, 5, 6, 8, 12, or 24

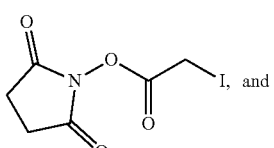

I, and

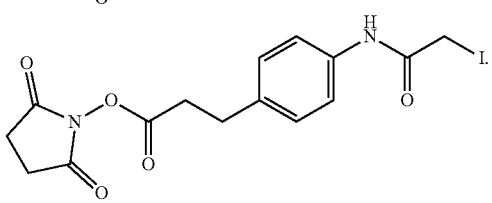

In some embodiments, the cross-linker is disuccinimidyl gluterate (DSG). In some embodiments, the cross-linker is disuccinimidyl suberate (DSS). In some embodiments, the cross-linker is bis(sulfosuccinimidyl) suberate (BS3). In some embodiments, the cross-linker is dithiobis(succinimidyl propionate) (DSP).

In some embodiments, the cross-linker contains an imidoester. In some embodiments, the imidoester-containing cross-linker is:

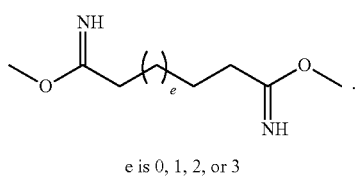

e is 0, 1, 2, or 3

In some embodiments, the cross-linker is dimethyl pimelimidate.

In some embodiments, the cross-linker contains an aryl fluoride. In some embodiments, the aryl fluoride-containing cross-linker is:

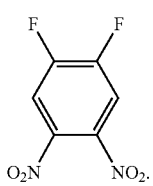

In some embodiments, the cross-linker contains a maleimide. In some embodiments, the maleimide-containing cross-linker is selected from:

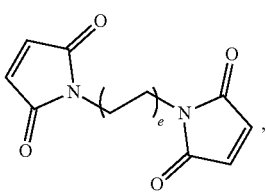

e is 1, 2, or 3

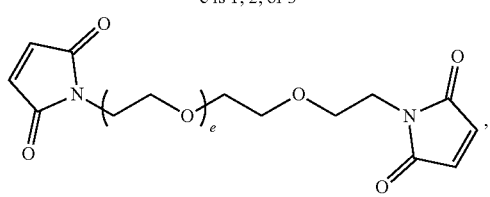

e is 1 or 2

e is 1, 2, 3, 4, 5, or 6

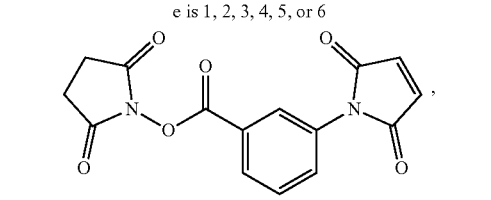

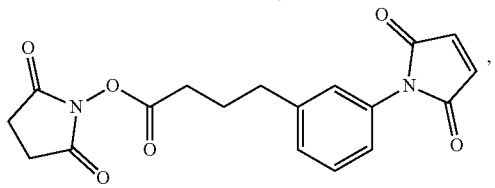

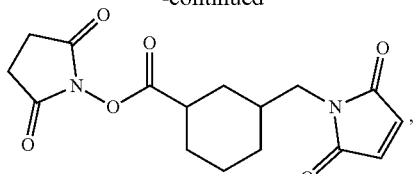

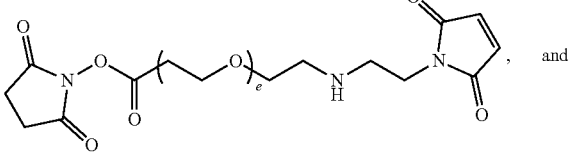

e is 2, 5, 6, 8, 12, or 24

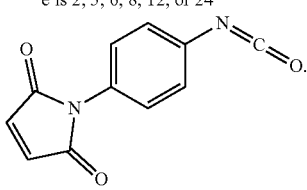

In some embodiments, the cross-linker is dibromomaleimide.

In some embodiments, the cross-linker contains a haloacetyl group. In some embodiments, the haloacetyl-containing cross-linker is selected from:

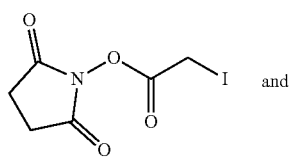
and

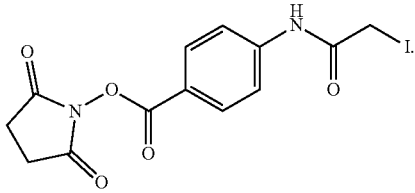

In some embodiments, the cross-linker contains an isocyanate group. In some embodiments, the isocyanate-containing cross-linker is selected from:

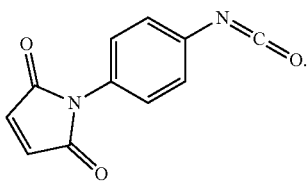 [SMILES: O=C=Nc1ccc(N2C(=O)C=CC2=O)cc1]

In some embodiments, the cross-linker contains an aldehyde. In some embodiments, the cross-linker is formaldehyde.

In some embodiments, the step of conjugating comprises a concentration of bifunctional crosslinking reagent in the range of 1 mM to 100 mM. In some embodiments, the concentration of bifunctional crosslinking reagent is 1 mM, 10 mM, 20 mM, 40 mM, 60 mM, 80 mM, or 100 mM. In some embodiments, the concentration of bifunctional crosslinking reagent is 100 to 1000 times greater than the concentration of each of the first and second oligonucleotides. In some embodiments, the concentration of bifunctional crosslinking reagent is 100, 200, 400, 600, 800, or 1000 times greater than the concentration of the first oligonucleotide. In some embodiments, the concentration of bifunctional crosslinking reagent is 100, 200, 400, 600, 800, or 1000 times greater than the concentration of the second oligonucleotide.

In some embodiments, the step of conjugating is performed in the presence of a chelating reagent. In some embodiments, the chelating reagent is ethylenediaminetetraacetic acid (EDTA), or a salt thereof.

In some embodiments, the step of conjugating is performed in the presence of an activating agent. In some embodiments, the activating agent is a carbodiimide, or salt thereof. In some embodiments, the carbodiimide is 1-ethyl-3-(3-dimethylaminopropyl) carbodiimide (EDC), N,N'-dicyclohexylcarbodiimide (DCC) or N,N'-diisopropylcarbodiimide (DIC), or a salt thereof. In some embodiments, the carbodiimide is 1-ethyl-3-(3-dimethylaminopropyl) carbodiimide (EDC), or a salt thereof.

In some embodiments, the step of conjugating comprises a concentration of activating agent that is in the range of 1 mM to 100 mM. In some embodiments, the concentration of activating agent is 1 mM, 10 mM, 20 mM, 40 mM, 60 mM, 80 mM, or 100 mM. In some embodiments, the concentration of activating agent is 100 to 1000 times greater than the concentration of each of the first and second oligonucleotides. In some embodiments, the concentration of activating agent is 100, 200, 400, 600, 800, or 1000 times greater than the concentration of the first oligonucleotide. In some embodiments, the concentration of activating agent is 100, 200, 400, 600, 800, or 1000 times greater than the concentration of the second oligonucleotide.

In some embodiments, the step of conjugating is performed in the presence of a stabilizing agent. In some embodiments, the stabilizing agent is imidazole, cyanoimidazole, pyridine, or dimethylaminopyridine, or a salt thereof. In some embodiments, the stabilizing agent is imidazole. In some embodiments, the step of conjugating is performed in the presence of both an activating agent and a stabilizing agent. In some embodiments, the step of conjugating is performed in the presence of 1-ethyl-3-(3-dimethylaminopropyl) carbodiimide (EDC) and imidazole, or salts thereof.

In some embodiments, the step of conjugating is performed in the presence of an RNA template. In some embodiments, the RNA template is about a 10-mer, 20-mer, 30-mer, 40-mer, or 50-mer. In some embodiments, the RNA template is complementary to the ligation site.

In some embodiments, the step of conjugating is performed in the presence of a reducing agent. In some embodiments, the reducing agent is tris(2-carboxyethyl)phosphine.

In some embodiments, the method of synthesizing a unimolecular guide molecule generates a guide molecule of any formula disclosed herein.

In some embodiments, the first oligonucleotide is of formula $K_{3'}\text{-i}$ or $K_{2'}\text{-i}$:

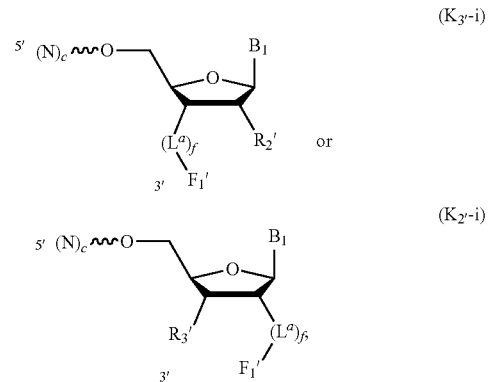

or a salt thereof,
wherein N, c, $B_1$, $R_2'$, $R_3'$, $L^a$, f, and ∼∼∼ are as described above and defined herein, and:
$F_1'$ is selected from —$NH_2$, —OH, —SH, —S—$SR^x$, —OP(O)(OH)OH, and —$CH_2X$;
X is a suitable leaving group, optionally halogen; and
$R^x$ is hydrogen or an optionally substituted group selected from $C_1$-$C_6$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur.

In some embodiments, the second oligonucleotide is of formula $K_{5'}\text{-i}$:

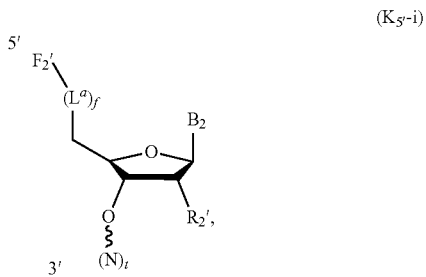

or a salt thereof,
wherein N, t, $B_2$, $R_2'$, $L^a$, f, and ∼∼∼ are as described above and defined herein, and:
$F_2'$ is selected from —$NH_2$, —OH, —SH, —S—$SR^x$, —OP(O)(OH)OH, and —$CH_2X$;
X is a suitable leaving group, optionally halogen; and
$R^x$ is hydrogen or an optionally substituted group selected from $C_1$-$C_6$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur.

In some embodiments of formula $K_{3'}\text{-i}$ or $K_{2'}\text{-i}$, $F_1'$ is selected from —$NH_2$, —OH, —SH, —S—$SR^x$, —OP(O)(OH)OH, and —$CH_2X$. In some embodiments, $F_1'$ is —$NH_2$. In some embodiments, $F_1'$ is —OH. In some embodiments, $F_1'$ is —SH. In some embodiments, $F_1'$ is —OP(O)(OH)OH.

In some embodiments, $F_1'$ is —$CH_2X$. In some such embodiments, X is halogen (e.g., iodo, bromo, or chloro). In some such embodiments, X is bromo. In some such embodiments, X is iodo.

In some embodiments, $F_1'$ is —S—$SR^x$. In some such embodiments, $F_1'$ is

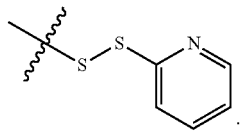 [SMILES: *SSc1ccccn1]

In some embodiments of formula $K_5'$-i, $F_2'$ is selected from —$NH_2$, —OH, —SH, —S—SRY, —OP(O)(OH)OH, and —$CH_2X$. In some embodiments, $F_2'$ is —$NH_2$. In some embodiments, $F_2'$ is —OH. In some embodiments, $F_2'$ is —SH. In some embodiments, $F_2'$ is —OP(O)(OH)OH.

In some embodiments, $F_2'$ is —$CH_2X$. In some such embodiments, X is halogen (e.g., iodo, bromo, or chloro). In some embodiments, X is bromo. In some such embodiments, X is iodo.

In some embodiments, $F_2'$ is —S—$SR^x$. In some such embodiments, F' is

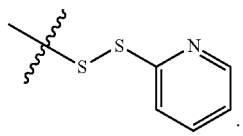 [SMILES: *SSc1ccccn1]

In some embodiments, the first oligonucleotide is of formula $K_3'$-i or $K_2'$-i, wherein $F_1'$ is —$NH_2$, and the second oligonucleotide is of formula $K_5'$-i, wherein $F_2'$ is —$NH_2$.

In some embodiments, the first oligonucleotide is of formula $K_3'$-i or $K_2'$-i, wherein $F_1'$ is —SH, and the second oligonucleotide is of formula $K_5'$-i, wherein $F_2'$ is —SH.

In some embodiments, the first oligonucleotide is of formula $K_3'$-i or $K_2'$-i, wherein $F_1'$ is —S—$SR^x$, and the second oligonucleotide is of formula $K_5'$-i, wherein $F_2'$ is —S—$SR^x$. In some such embodiments, $F_1'$ and $F_2'$ are both

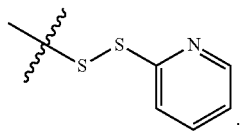 [SMILES: *SSc1ccccn1]

In some embodiments, the first oligonucleotide is of formula $K_3'$-i or $K_2'$-i, wherein Fr' is —OH, and the second oligonucleotide is of formula $K_5'$-i, wherein $F_2'$ is —OP(O)(OH)OH. In some embodiments, the first oligonucleotide is of formula $K_3'$-i or $K_2'$-i, wherein $F_1'$ is —OP(O)(OH)OH, and the second oligonucleotide is of formula $K_5'$-i, wherein $F_2'$ is —OH.

In some embodiments, the first oligonucleotide is of formula $K_3'$-i or $K_2'$-i, wherein $F_1'$ is —$NH_2$, and the second oligonucleotide is of formula $K_5'$-i, wherein $F_2'$ is —OP(O)(OH)OH. In some embodiments, the first oligonucleotide is of formula $K_3'$-i or $K_2'$-i, wherein $F_1'$ is —OP(O)(OH)OH, and the second oligonucleotide is of formula $K_5'$-i, wherein $F_2'$ is —$NH_2$.

In some embodiments, the first oligonucleotide is of formula $K_3'$-i or $K_2'$-i, wherein $F_1'$ is —SH, and the second oligonucleotide is of formula $K_5'$-i, wherein $F_2'$ is —$CH_2X$. In some such embodiments, X is bromo. In some such embodiments, X is iodo. In some embodiments, the first oligonucleotide is of formula $K_3'$-i or $K_2'$-i, wherein $F_1'$ is —$CH_2X$, and the second oligonucleotide is of formula $K_5'$-i, wherein $F_2'$ is —SH. In some such embodiments, X is bromo. In some such embodiments, X is iodo.

In some embodiments, the first oligonucleotide is of formula $K_3'$-i or $K_2'$-i, wherein $F_1'$ is —$NH_2$, and the second oligonucleotide is of formula $K_5'$-i, wherein $F_2'$ is —SH. In some embodiments, the first oligonucleotide is of formula $K_3'$-i or $K_2'$-i, wherein $F_1'$ is —SH, and the second oligonucleotide is of formula $K_5'$-i, wherein $F_2'$ is —$NH_2$.

In some embodiments, the first oligonucleotide is of formula $K_3'$-i or $K_2'$-i, wherein $F_1'$ is —$NH_2$, and the second oligonucleotide is of formula $K_5'$-i, wherein $F_2'$ is —OH. In some embodiments, the first oligonucleotide is of formula $K_3'$-i or $K_2'$-i, wherein $F_1'$ is —OH, and the second oligonucleotide is of formula $K_5'$-i, wherein $F_2'$ is —$NH_2$.

In some embodiments, the first oligonucleotide is of formula $K_3'$-i or $K_2'$-i, wherein $F_1'$ is —$NH_2$, and the second oligonucleotide is of formula $K_5'$-i, wherein $F_2'$ is —S—$SR^x$. In some such embodiments, $R^x$ is 2-pyridyl. In some embodiments, the first oligonucleotide is of formula $K_3'$-i or $K_2'$-i, wherein $F_1'$ is —S—$SR^x$, and the second oligonucleotide is of formula $K_5'$-i, wherein $F_2'$ is —$NH_2$. In some such embodiments, $R^x$ is 2-pyridyl.

In some embodiments, the method comprises a first oligonucleotide of formula:

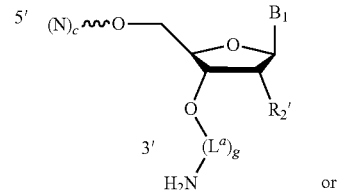

or

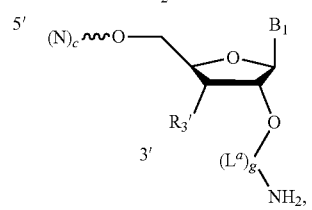

or a salt thereof, wherein $L^a$ is as described above and defined herein, and each g is independently 0, 1, 2, 3, 4, or 5. In some embodiments, the method comprises a second oligonucleotide of formula:

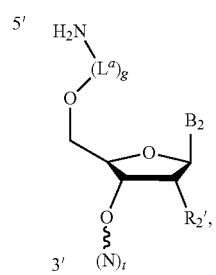

or a salt thereof, wherein $L^a$ is as described above and defined herein, and each g is independently 0, 1, 2, 3, 4, or 5.

In some embodiments, the method comprises a first oligonucleotide of formula:

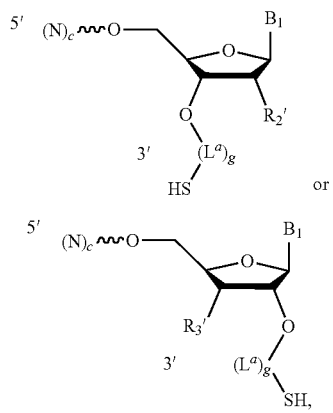

or a salt thereof, wherein $L^a$ is as described above and defined herein, and each g is independently 0, 1, 2, 3, 4, or 5. In some embodiments, the method comprises a second oligonucleotide of formula:

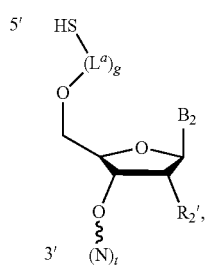

or a salt thereof, wherein $L^a$ is as described above and defined herein, and each g is independently 0, 1, 2, 3, 4, or 5.

In some embodiments, the method comprises a first oligonucleotide of formula:

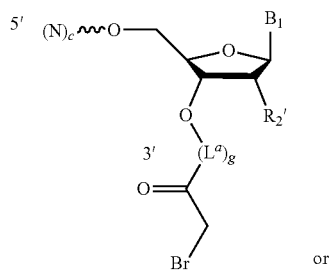

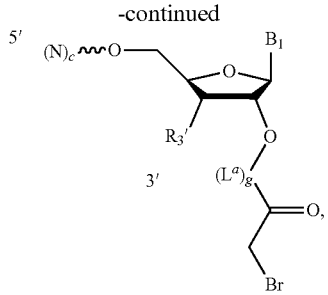

or a salt thereof, wherein $L^a$ is as described above and defined herein, and each g is independently 0, 1, 2, 3, 4, or 5, and the second oligonucleotide is of formula:

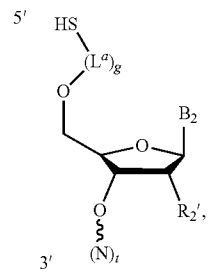

or a salt thereof, wherein $L^a$ is as described above and defined herein, and each g is independently 0, 1, 2, 3, 4, or 5; or the method comprises a first oligonucleotide of formula:

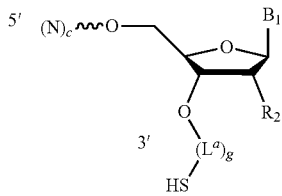

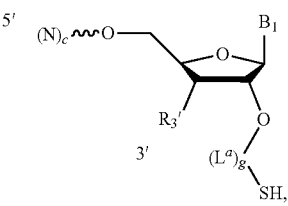

or a salt thereof, wherein $L^a$ is as described above and defined herein, and each g is independently 0, 1, 2, 3, 4, or 5; and the second oligonucleotide is of formula:

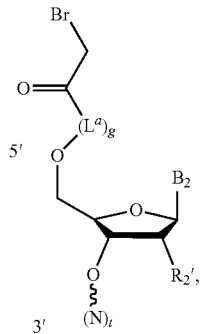

or a salt thereof, wherein $L^a$ is as described above and defined herein, and each g is independently 0, 1, 2, 3, 4, or 5.

In some embodiments, the method comprises a first oligonucleotide of formula:

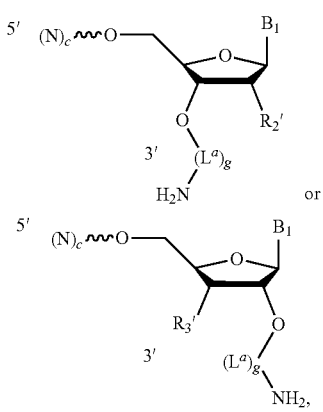

or a salt thereof, wherein $L^a$ is as described above and defined herein, and each g is independently 0, 1, 2, 3, 4, or 5, and the second oligonucleotide is of formula:

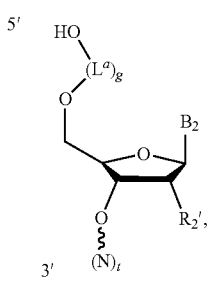

or a salt thereof, wherein $L^a$ is as described above and defined herein, and each g is independently 0, 1, 2, 3, 4, or 5; or the method comprises a first oligonucleotide of formula:

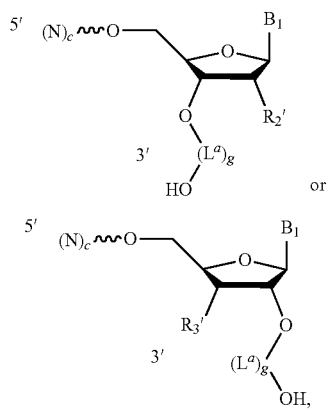

or a salt thereof, wherein $L^a$ is as described above and defined herein, and each g is independently 0, 1, 2, 3, 4, or 5; and the second oligonucleotide is of formula:

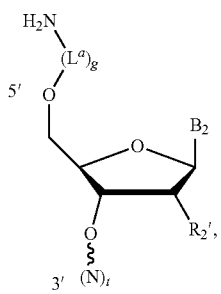

or a salt thereof, wherein $L^a$ is as described above and defined herein, and each g is independently 0, 1, 2, 3, 4, or 5.

In some embodiments, the method comprises a first oligonucleotide of formula:

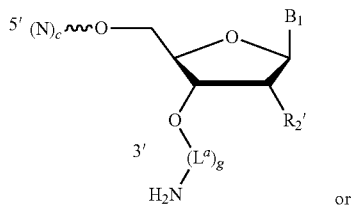

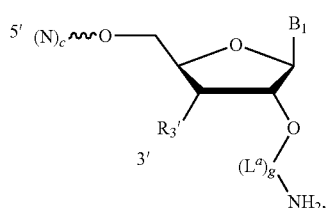

or a salt thereof, wherein $L^a$ is as described above and defined herein, and each g is independently 0, 1, 2, 3, 4, or 5; and the second oligonucleotide is of formula:

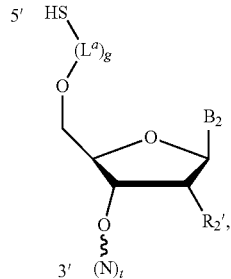

or a salt thereof, wherein $L^a$ is as described above and defined herein, and each g is independently 0, 1, 2, 3, 4, or 5; or the method comprises a first oligonucleotide of formula:

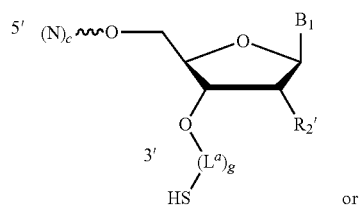

or

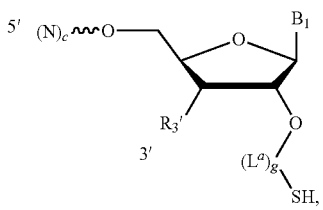

or a salt thereof, wherein $L^a$ is as described above and defined herein, and each g is independently 0, 1, 2, 3, 4, or 5; and the second oligonucleotide is of formula:

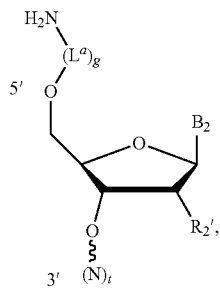

or a salt thereof, wherein $L^a$ is as described above and defined herein, and each g is independently 0, 1, 2, 3, 4, or 5.

In some embodiments, the method comprises a first oligonucleotide of formula:

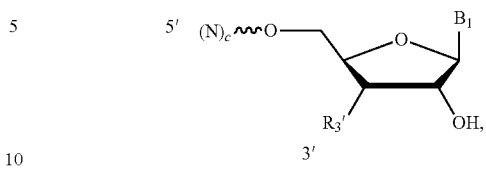

or a salt thereof; and
the second oligonucleotide is of formula:

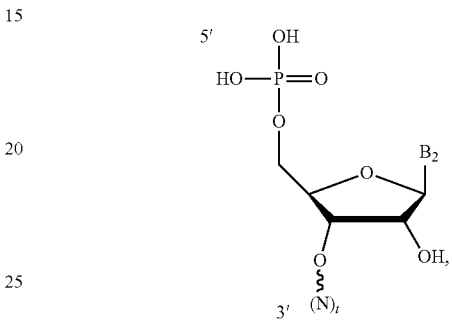

or a salt thereof.

In some embodiments, the method of synthesizing a unimolecular guide molecule results in a guide molecule with a linker comprising a urea. In some embodiments, the first reactive group and the second reactive group are both amines, and the first and second reactive groups are cross-linked with a carbonate-containing bifunctional crosslinking reagent to form a linker comprising a urea. In some embodiments, the carbonate-containing bifunctional crosslinking reagent is disuccinimidyl carbonate.

In some embodiments, the method of synthesizing a unimolecular guide molecule results in a guide molecule with a linker comprising an amidine. In some embodiments, the first reactive group and the second reactive group are both amines, and the first and second reactive groups are cross-linked with an imidoester-containing bifunctional crosslinking reagent to form a linker comprising an amidine. In some embodiments, the carbonate-containing bifunctional crosslinking reagent is dimethyl pimelimidate.

In some embodiments, the method of synthesizing a unimolecular guide molecule results in a guide molecule with a linker comprising an amide. In some embodiments, the first reactive group and the second reactive group are both amines, and the first and second reactive groups are cross-linked with an ester-containing bifunctional crosslinking reagent to form an amide linker. In some embodiments, the carbonate-containing bifunctional crosslinking reagent is disuccinimidyl glutarate, disuccinimidyl suberate, bis(sulfosuccinimidyl) suberate, or dithiobis(succinimidyl propionate).

In some embodiments, the method of synthesizing a unimolecular guide molecule results in a guide molecule with a linker comprising a thioether. In some embodiments, first reactive group is a sulfhydryl group and the second reactive group is a haloacetyl group (e.g., a bromoacetyl or iodoacetyal group), or the first reactive group is a haloacetyl group (e.g., a bromoacetyl or iodoacetyl group) and the second reactive group is a sulfhydryl group. In some embodiments, the first reactive group and the second reactive group react in the presence of a chelating agent to form a linker comprising a thioether. In some embodiments, the first reactive group and the second reactive group undergo a substitution reaction to form a linker comprising a thioether.

In some embodiments, the method of synthesizing a unimolecular guide molecule results in a guide molecule with a phosphodiester linker. In some embodiments, first reactive group comprises a 2' or 3' hydroxyl group and the second reactive group comprises a 5' phosphate moiety. In some embodiments, the first and second reactive groups are conjugated in the presence of an activating agent to form a phosphodiester linker. In some embodiments, the activating agent is EDC.

In some embodiments, the method of synthesizing a unimolecular guide molecule results in a guide molecule with a linker comprising a phosphoramidate. In some embodiments, the first reactive group is an amine and the second reactive group is a phosphate group, or the first reactive group is a phosphate group and the second reactive group is an amine. In some embodiments, the first and second reactive groups are cross-linked in the presence of an activating agent to form a linker comprising a phosphoramidate. In some embodiments, the activating agent is EDC.

In some embodiments, the method of synthesizing a unimolecular guide molecule results in a guide molecule with a linker comprising a carbamate. In some embodiments, the first reactive group is an amine and the second reactive group is a hydroxyl group, or the first reactive group is a hydroxyl group and the second reactive group is an amine. In some embodiments, the first and second reactive groups are cross-linked with carbonate-containing bifunctional crosslinker to form a linker comprising a carbamate. In some embodiments, the crosslinking reagent is disuccinimidyl carbonate.

In some embodiments, the method of synthesizing a unimolecular guide molecule results in a guide molecule with a linker comprising a disulfide. In some embodiments, the first reactive group and the second reactive group are both disulfide groups. In some embodiments, the first and second reactive groups are cross-linked in the presence of a reducing agent. In some embodiments, the reducing agent is tris(2-carboxyethyl)phosphine.

Additionally or alternatively, in some embodiments, the first reactive group is a sulfhydryl group and the second reactive group is a disulfide group. In some embodiments, the first reactive group is a disulfide group and the second reactive group is a thiol group. In some embodiments, the first and second reactive groups are cross-linked in the presence of a reducing agent. In some embodiments, the reducing agent is tris(2-carboxyethyl)phosphine.

In some embodiments, the method of synthesizing a unimolecular guide molecule results in a guide molecule with a linker comprising a maleimide. In some embodiments, the first reactive group and the second reactive group are both sulfhydryl groups. In some embodiments, the first and second reactive groups are cross-linked with dibromomaleimide to form a linker comprising a maleimide.

In some embodiments, the method of synthesizing a unimolecular guide molecule results in a guide molecule with a linker comprising an aminal group. In some embodiments, the first reactive group and the second reactive group are both amines. In some embodiments, the first and second reactive groups are cross-linked with an aldehyde to form an aminal. In some embodiments, the aldehyde is formaldehyde.

In some embodiments, the method of synthesizing a unimolecular guide molecule generates a unimolecular guide molecule with at least one 2'-5' phosphodiester linkage in a duplex region.

Oligonucleotide Intermediates

Certain embodiments of this disclosure are related to oligonucleotide intermediates that are useful for the synthesis of cross-linked synthetic guide molecules. In some embodiments, the oligonucleotide intermediates are useful for the synthesis of guide molecules comprising a urea linkage, a thioether linkage or a phosphodiester linkage. In some embodiments, the oligonucleotide intermediates are useful for the synthesis of guide molecules linkers comprising a urea, carbamate, amidine, amide, phosphoamidate, phosphodiester, disulfide, thioether, or maleimide. In some embodiments, the oligonucleotide intermediates comprise an annealed duplex.

In some embodiments, the oligonucleotide intermediates are of formula $K_{3'}\text{-}i$ or $K_{2'}\text{-}i$:

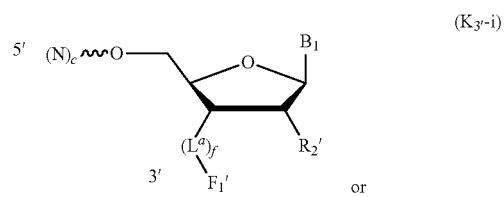

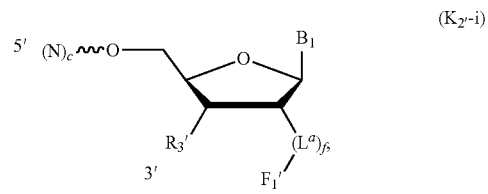

or a salt thereof, wherein N, c, $B_1$, $R_2'$, $R_3'$, $L^a$, f, $F_1'$, and ∿∿ are as described above and defined herein.

In some embodiments, the oligonucleotide intermediates are of formula $K_{5'}\text{-}i$:

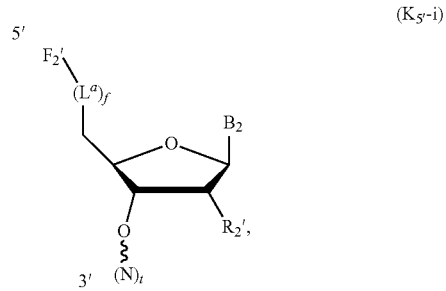

or a salt thereof, wherein N, t, $B_2$, $R_2'$, $L^a$, f, $F_2'$, and ∿∿ are as described above and defined herein.

In some embodiments, the oligonucleotide intermediates are of formula $B_3'$-ix or $B_2'$-ix:

In some embodiments, the oligonucleotide intermediates are of formula $C_3'$-xiv and $C_2'$-xiv:

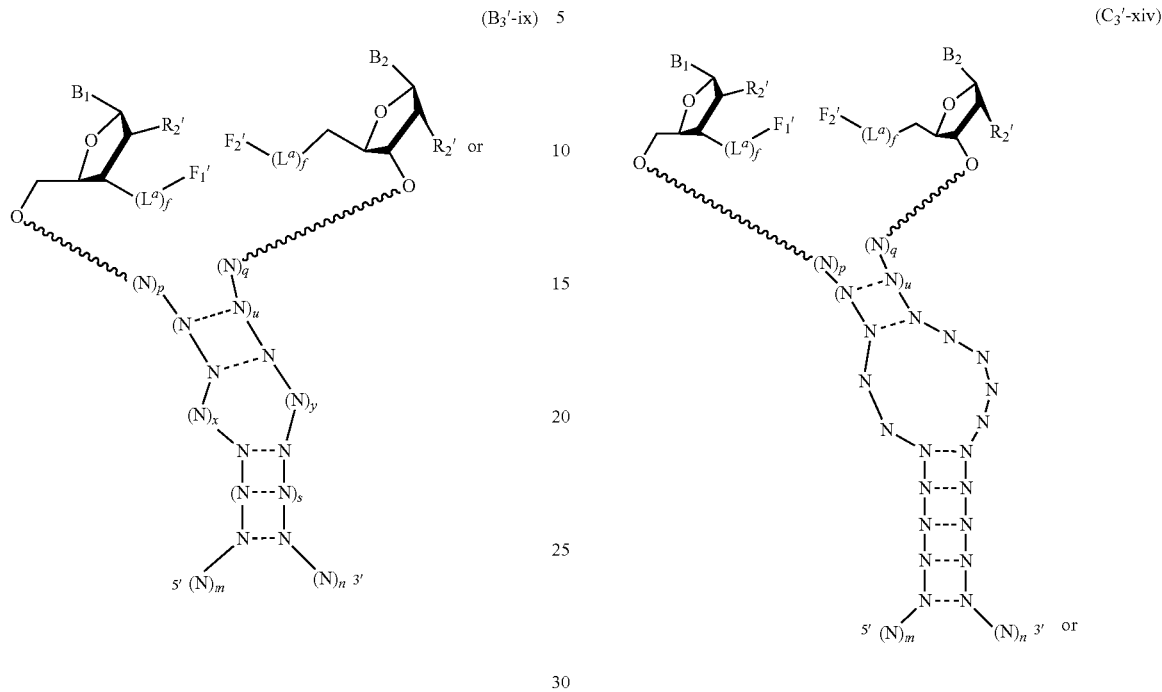

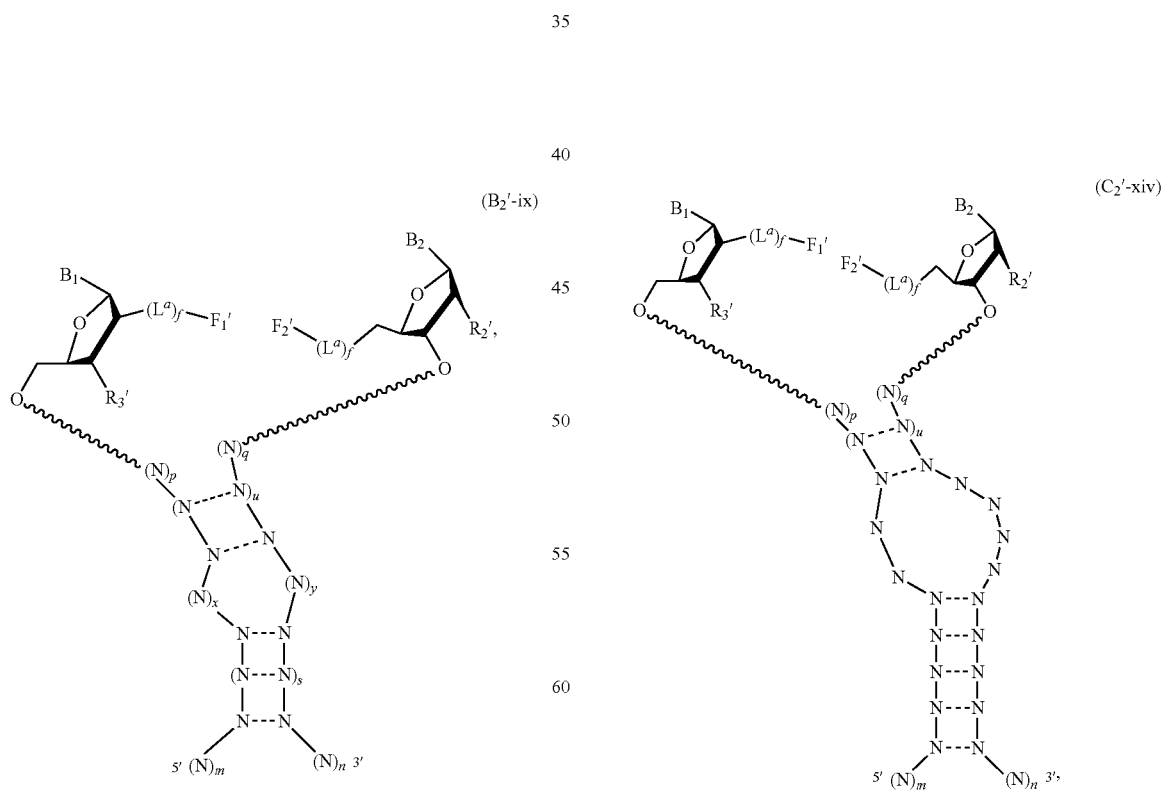

wherein N, $B_1$, $B_2$, $R_2'$, $R_3'$, $F_1'$, $F_2'$, $L^a$, f, p, q, u, x, y, s, m, and n are as described above and defined herein.

wherein N, $B_1$, $B_2$, $R_2'$, $R_3'$, $F_1'$, $F_2'$, $L^a$, f, p, q, u, m, and n are as described above and defined herein.

In some embodiments, the oligonucleotide intermediates are of formula $D_3'$-xiv and $D_2'$-xiv:

(D₃'-xiv)

(D₂'-xiv)

wherein N, $B_1$, $B_2$, $R_2'$, $R_3'$, $F_1'$, $F_2'$, $L^a$, f, p, q, u, m, and n are as described above and defined herein.

In certain embodiments, the oligonucleotide intermediates are of formula:

wherein N, $B_1$, $B_2$, $R_2'$, $R_3'$, c, and t are as defined in formulas $A_3'$-i and $A_2'$-i above, $L^a$ is as described above and defined herein, and each g is independently 0, 1, 2, 3, 4, or 5. In some embodiments, the oligonucleotide intermediates are of formula:

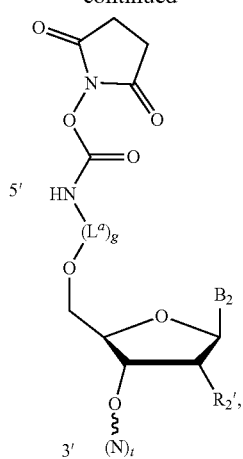

wherein N, $B_1$, $B_2$, $R_2'$, $R_3'$, c, and t are as defined in formulas $A_{3'}$-i and $A_{2'}$-i above, $L^a$ is as described above and defined herein, and each g is independently 0, 1, 2, 3, 4, or 5. In some embodiments, the oligonucleotide intermediates are of formula:

wherein N, $B_1$, $B_2$, $R_2'$, $R_3'$, c, and t are as defined in formulas $A_{3'}$-i and $A_{2'}$-i above, $L^a$ is as described above and defined herein, and each g is independently 0, 1, 2, 3, 4, or 5.

In some embodiments, the oligonucleotide intermediates are of formula $B_{3'}$-vi or $B_{2'}$-vi:

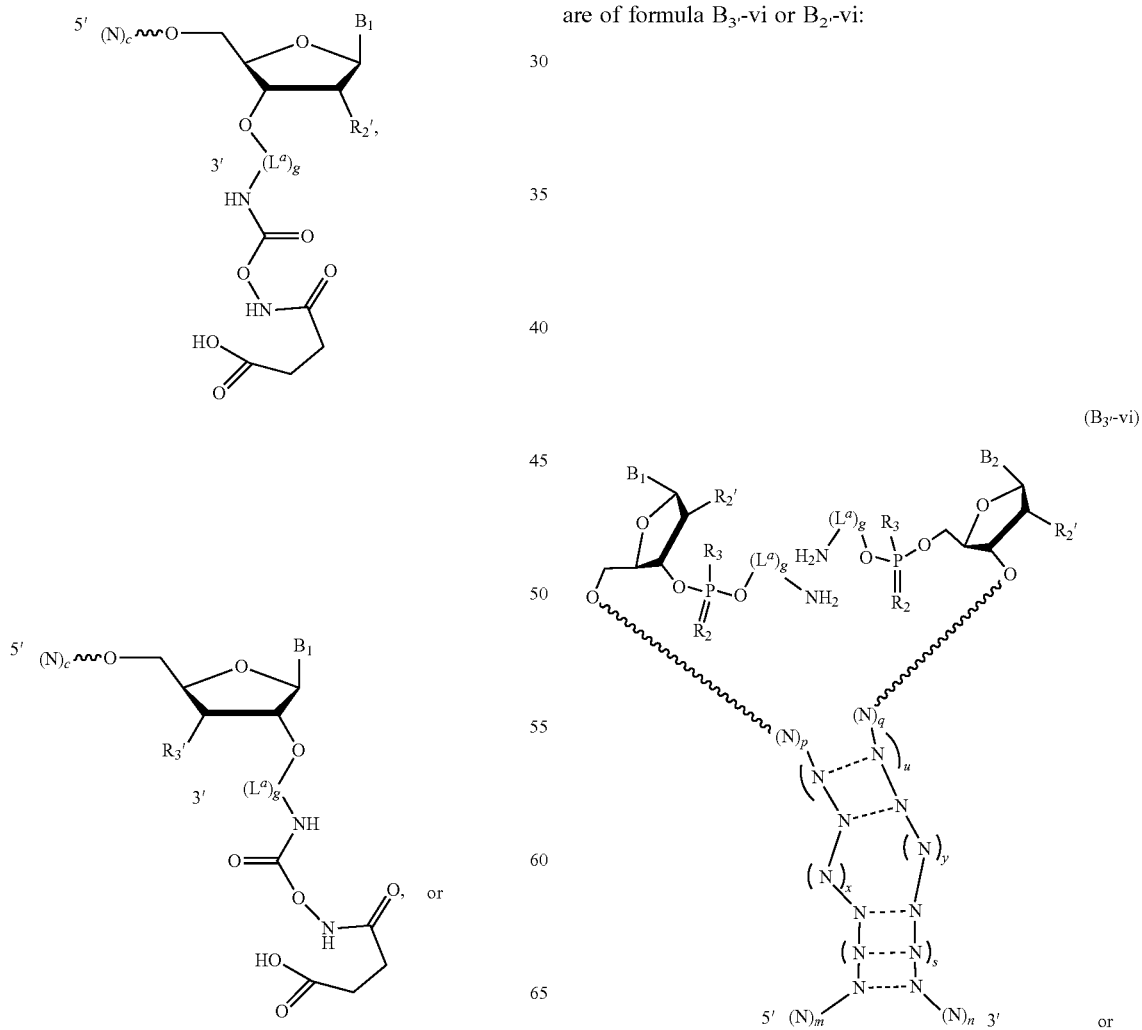

(B2'-vi)

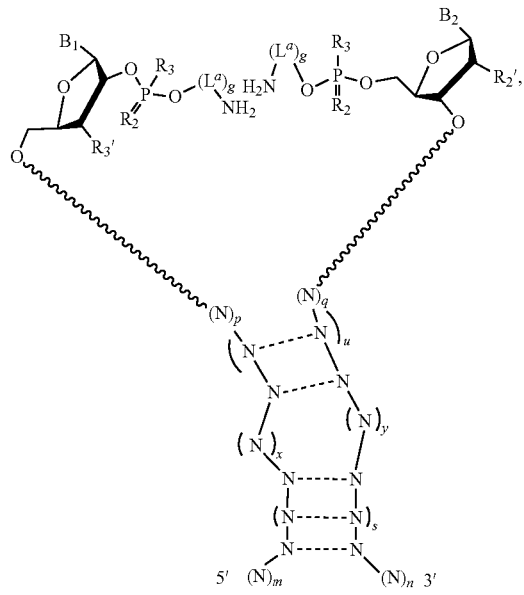

wherein N, $B_1$, $B_2$, $R_2'$, $R_3'$, p, q, u, x, y, s, m, and n are as defined in formulas $B_3$-i and $B_2$-i above, $L^a$ is as described above and defined herein, each g is independently 0, 1, 2, 3, 4, or 5, each $R_2$ is independently O or S, and each $R_3$ is independently OH or COOH.

In some embodiments, the oligonucleotide intermediates are of formula $C_3$-vi and $C_2$-vi:

(C2'-vi)

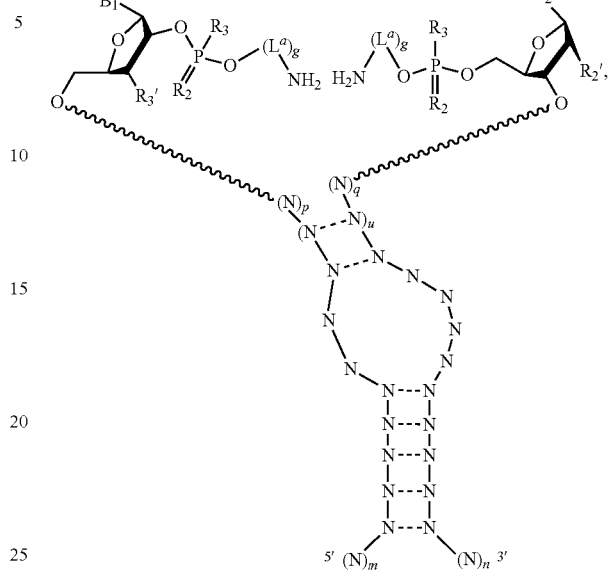

wherein N, $B_1$, $B_2$, $R_2'$, $R_3'$, p, q, u, m, and n are as defined in formulas $C_3$-i and $C_2$-i above, $L^a$ is as described above and defined herein, each g is independently 0, 1, 2, 3, 4, or 5, each $R_2$ is independently O or S, and each $R_3$ is independently OH or COOH.

In some embodiments, the oligonucleotide intermediates are of formula $D_3$-vi or $D_2$-vi:

(C3'-vi)

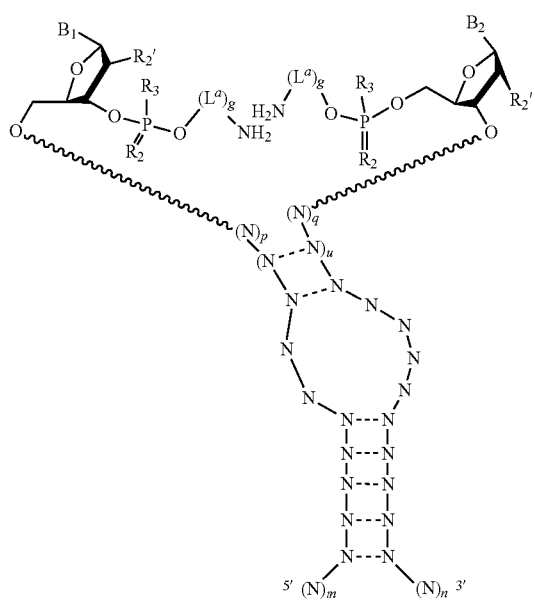

or (D3'-vi)

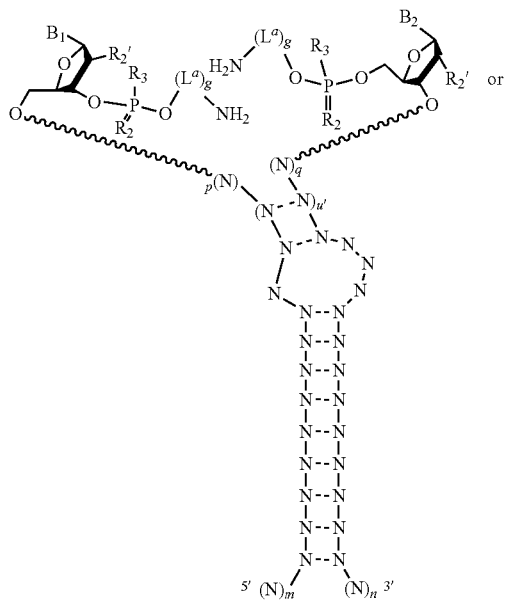

or

-continued

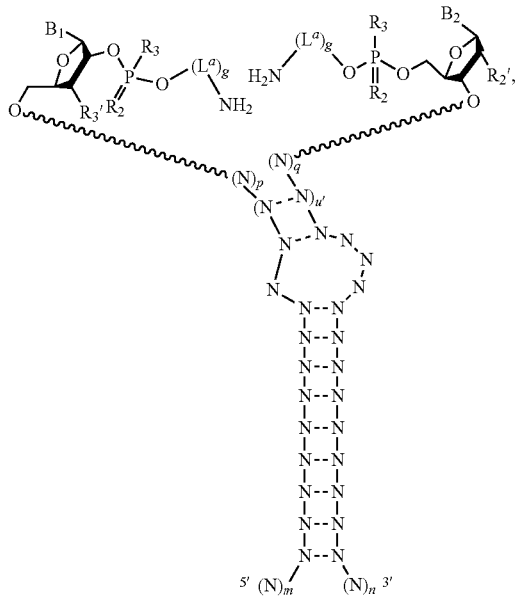

(D₂'-vi)

herein N, $B_1$, $B_2$, $R_2'$, $R_3'$, p, q, u, m, and n are as defined in formulas $D_3$-i and $D_2$-i above, $L^a$ is as described above and defined herein, each g is independently 0, 1, 2, 3, 4, or 5, each $R_2$ is independently O or S, and each $R_3$ is independently OH or COOH. In certain embodiments, the oligonucleotide intermediates are of formula:

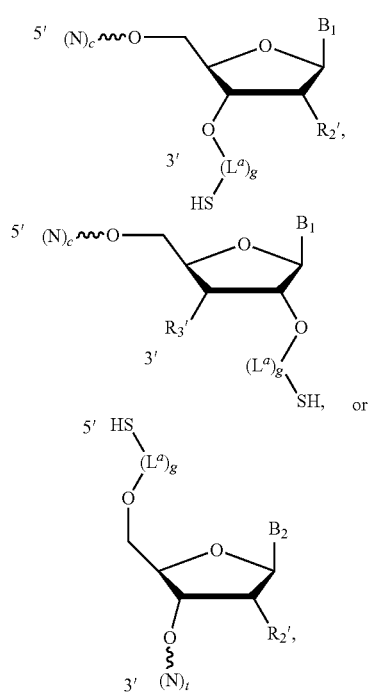

wherein N, $B_1$, $B_2$, $R_2'$, $R_3'$, c, and t are as defined in formulas $A_3$-i and $A_2$-i above, $L^a$ is as described above and defined herein, and each g is independently 0, 1, 2, 3, 4, or 5.

In some embodiments, the oligonucleotide intermediates are of formula $B_3$-ix or $B_2$-ix:

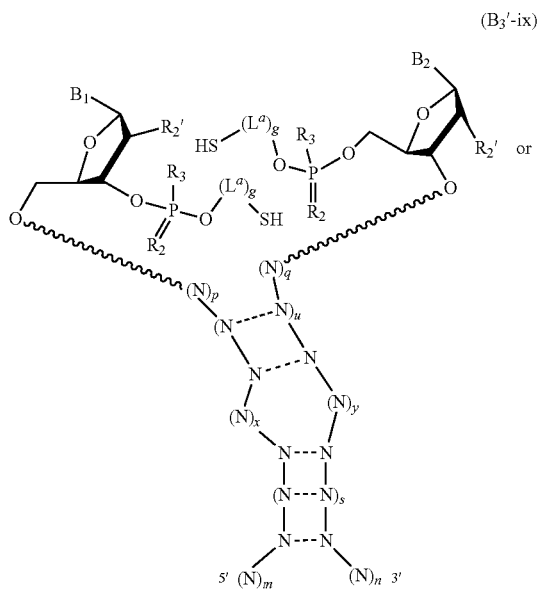

(B₃'-ix)

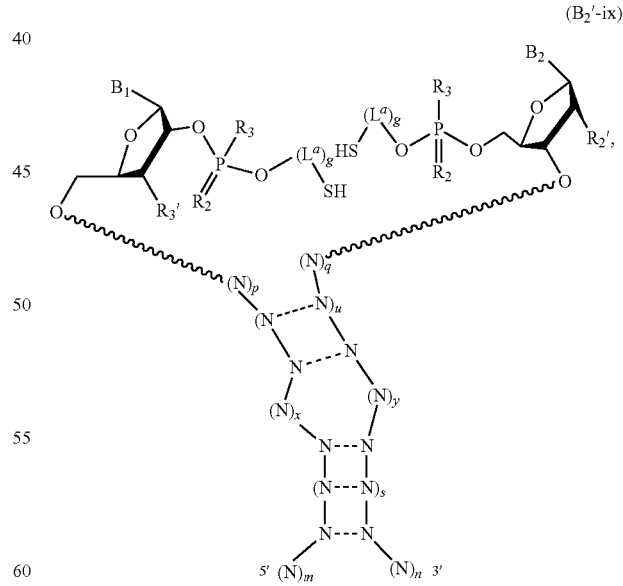

(B₂'-ix)

wherein N, $B_1$, $B_2$, $R_2'$, $R_3'$, p, q, u, x, y, s, m, and n are as defined in formulas $B_3$-i and $B_2$-i above, $L^a$ is as described above and defined herein, each g is independently 0, 1, 2, 3, 4, or 5, each $R_2$ is independently O or S, and each $R_3$ is independently OH or COOH.

In some embodiments, the oligonucleotide intermediates are of formula $C_{3'}$-ix and $C_{2'}$-ix:

In some embodiments, the oligonucleotide intermediates are of formula $D_{3'}$-ix or $D_{2'}$-ix:

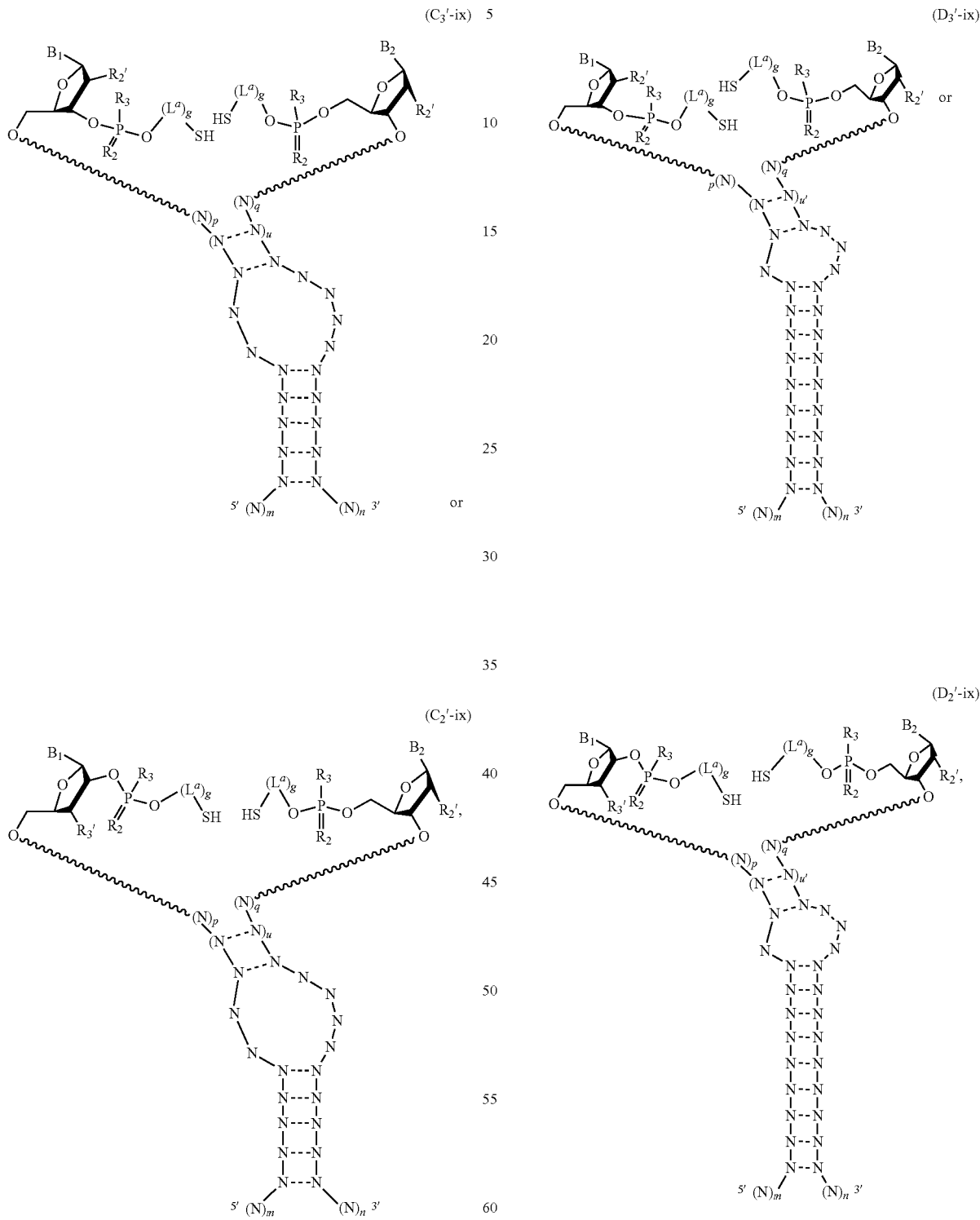

wherein N, $B_1$, $B_2$, $R_2'$, $R_3'$, p, q, u, m, and n are as defined in formulas $C_{3'}$-i and $C_{2'}$-i above, $L^a$ is as described above and defined herein, each g is independently 0, 1, 2, 3, 4, or 5, each $R_2$ is independently O or S, and each $R_3$ is independently OH or COOH.

wherein N, $B_1$, $B_2$, $R_2$, $R_3$, p, q, u, m, and n are as defined in formulas $D_{3'}$-i and $D_{2'}$-i above, $L^a$ is as described above and defined herein, each g is independently 0, 1, 2, 3, 4, or 5, each $R_2$ is independently O or S, and each $R_3$ is independently OH or COOH. In certain embodiments, the oligonucleotide intermediates are of formula:

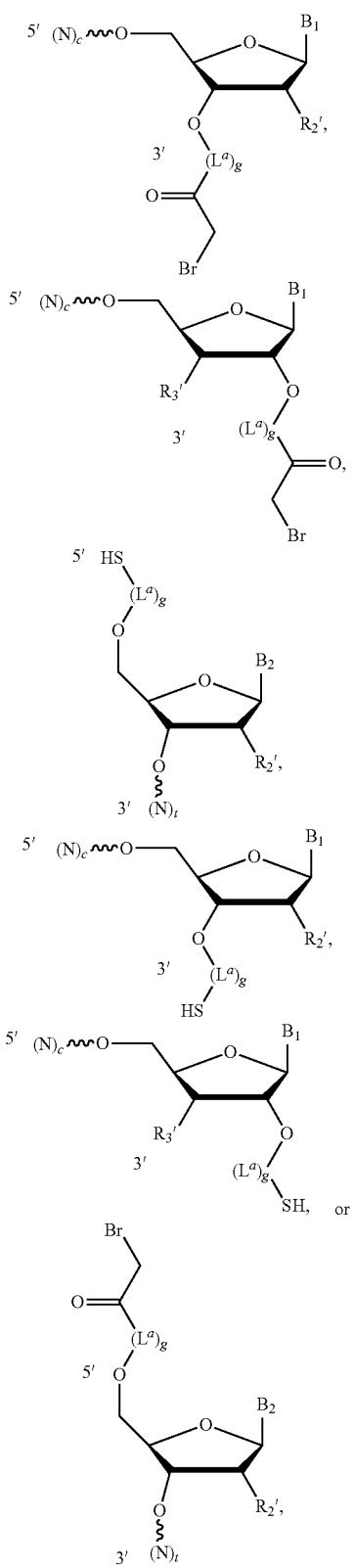
wherein N, $B_1$, $B_2$, $R_2'$, $R_3'$, c, and t are as defined in formulas $A_3$-i and $A_2$-i above, $L^a$ is as described above and defined herein, and each g is independently 0, 1, 2, 3, 4, or 5.
In some embodiments, the oligonucleotide intermediates are of formula $B_3'$-vii, $B_2'$-vii, $B_3'$-viii, or $B_2'$-viii:
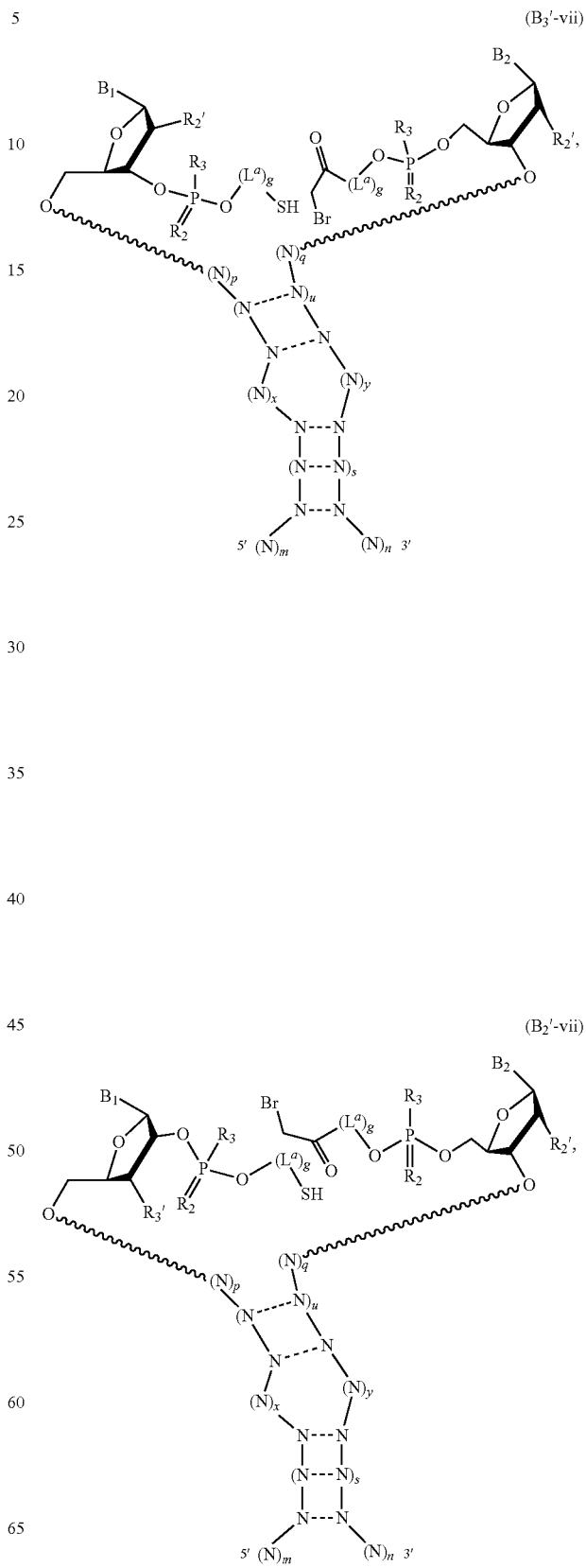

-continued (B₃'-viii)

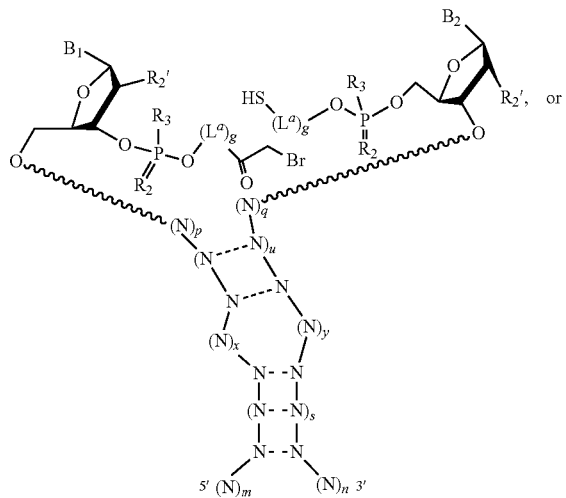

, or (B₂'-viii)

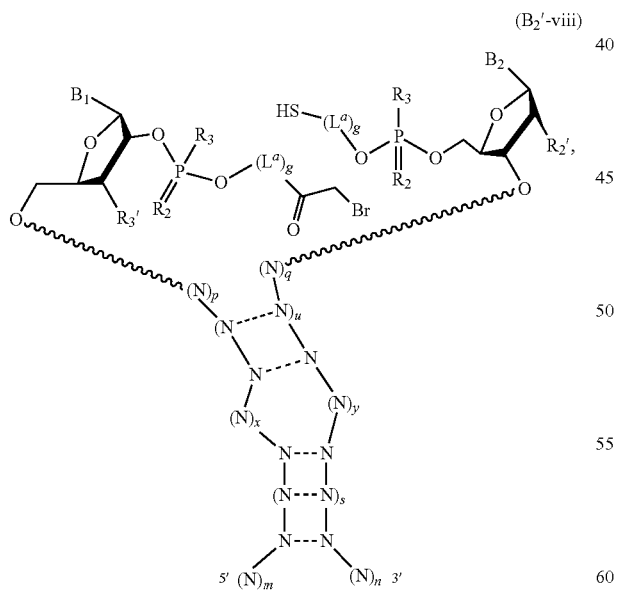

wherein N, $B_1$, $B_2$, $R_2'$, $R_3'$, p, q, u, x, y, s, m, and n are as defined in formulas $B_3'$-i and $B_2'$-i above, $L^a$ is as described above and defined herein, each g is independently 0, 1, 2, 3, 4, or 5, each $R_2$ is independently O or S, and each $R_3$ is independently OH or COOH.

In some embodiments, the oligonucleotide intermediates are of formula $C_3'$-vii, $C_2'$-vii, $C_3'$-viii, or $C_2'$-viii:

($C_3'$-vii)

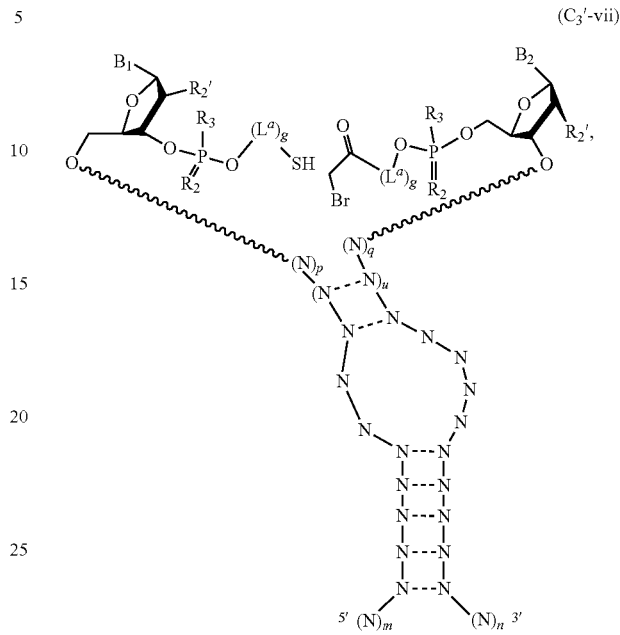

($C_2'$-vii)

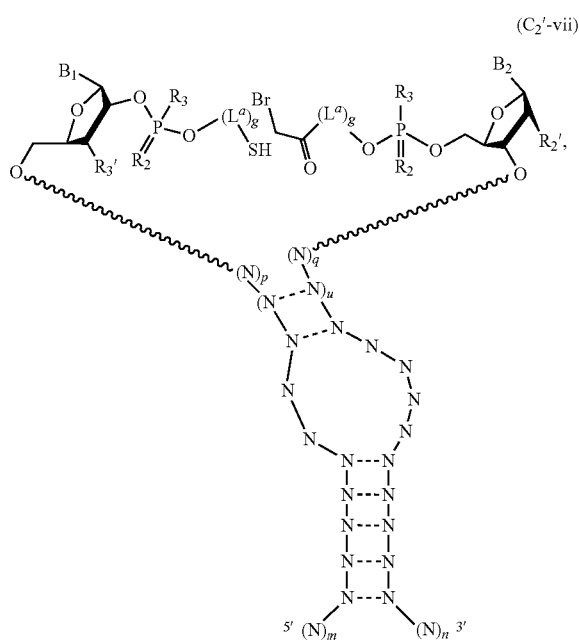

-continued (C₃'-viii)

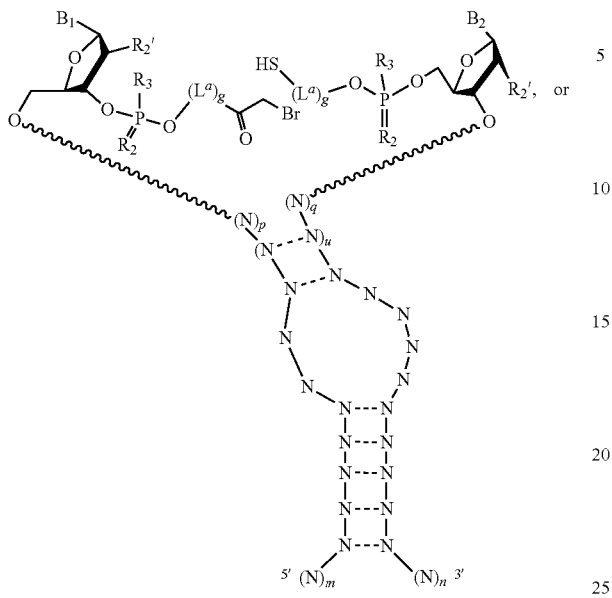

(C₂'-viii)

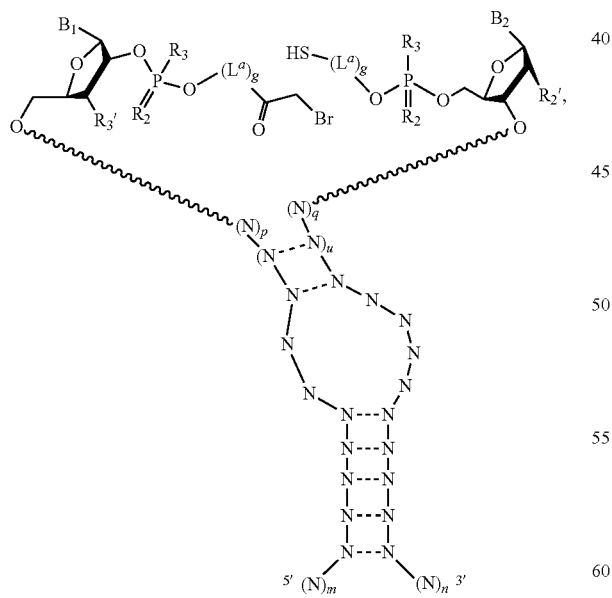

wherein N, B₁, B₂, R₂', R₃', p, q, u, m, and n are as defined in formulas C₃'-i and C₂'-i above, $L^a$ is as described above and defined herein, each g is independently 0, 1, 2, 3, 4, or 5, each R₂ is independently O or S, and each R₃ is independently OH or COOH.

In some embodiments, the oligonucleotide intermediates are of formula D₃'-vii, D₂'-vii, D₃'-viii, or D₂'-viii:

(D₃'-vii)

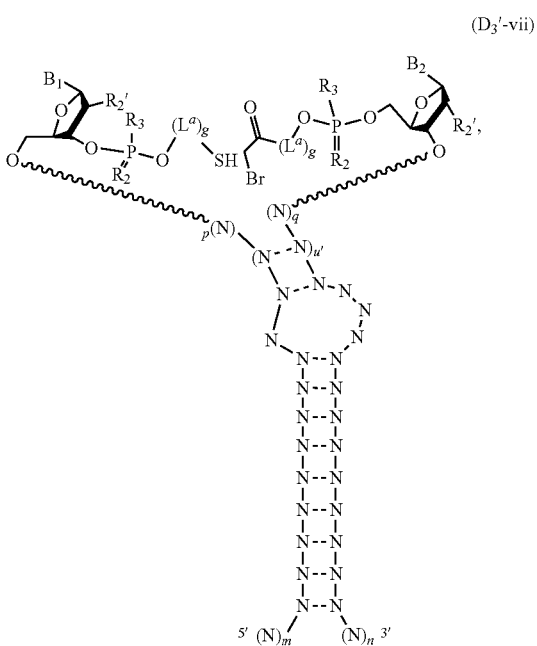

(D₂'-vii)

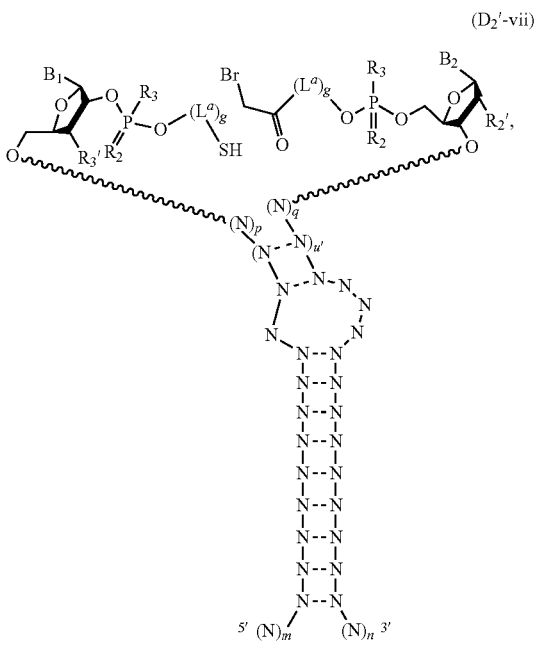

-continued (D₃'-viii)

(D₂'-viii)

wherein N, $B_1$, $B_2$, $R_2'$, $R_3'$, p, q, u, m, and n are as defined in formulas $D_3$-i and $D_2$-i above, $L^a$ is as described above and defined herein, each g is independently 0, 1, 2, 3, 4, or 5, each $R_2$ is independently O or S, and each $R_3$ is independently OH or COOH.

In certain embodiments, the oligonucleotide intermediates are of formula:

wherein N, $B_1$, $B_2$, $R_2'$, $R_3'$, c, and t are as defined in formulas $A_3$-i and $A_2$-i above, $L^a$ is as described above and defined herein, and each g is independently 0, 1, 2, 3, 4, or 5.

In some embodiments, the oligonucleotide intermediates are of formula B$_{3'}$-x, B$_{2'}$-x, B$_{3'}$-xi, or B$_{2'}$-xi:

(B$_{3'}$-x)
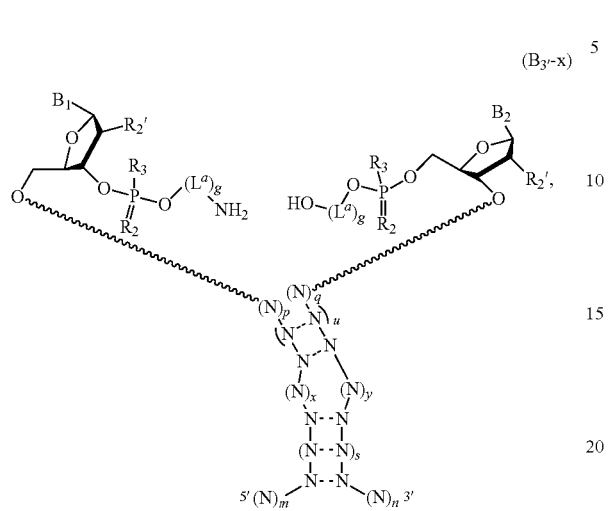

(B$_{2'}$-x)

(B$_{3'}$-xi)
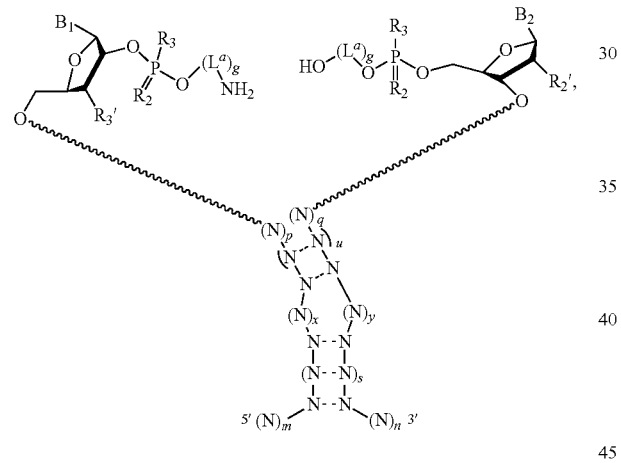

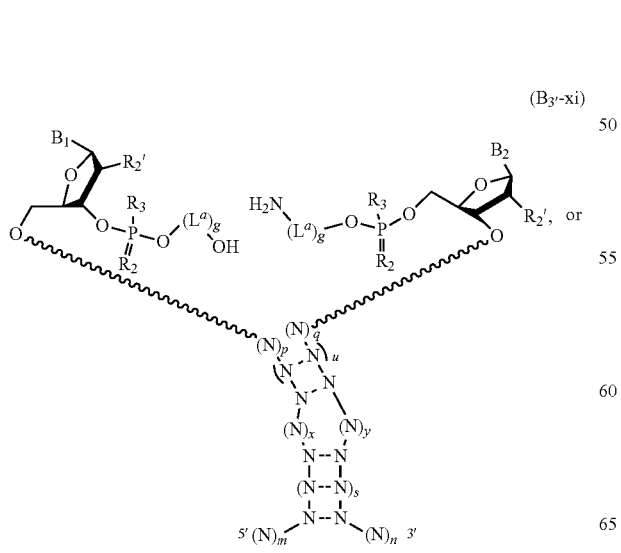

(B$_{2'}$-xi)
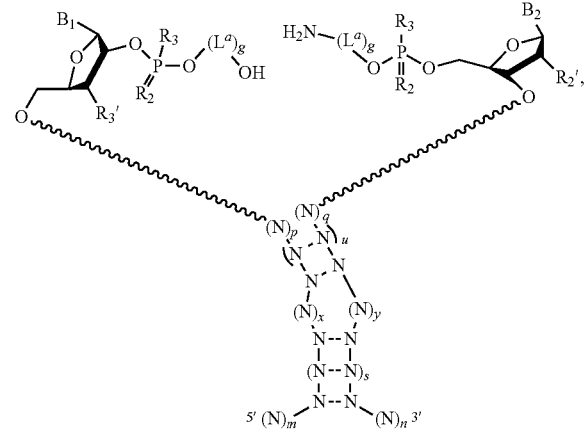

wherein N, B$_1$, B$_2$, R$_2'$, R$_3'$, p, q, u, x, y, s, m, and n are as defined in formulas B$_{3'}$-i and B$_{2'}$-i above, L$^a$ is as described above and defined herein, each g is independently 0, 1, 2, 3, 4, or 5, each R$_2$ is independently O or S, and each R$_3$ is independently OH or COOH.

In some embodiments, the oligonucleotide intermediates are of formula C$_{3'}$-x, C$_{2'}$-x, C$_{3'}$-xi, or C$_{2'}$-xi:

(C$_{3'}$-x)
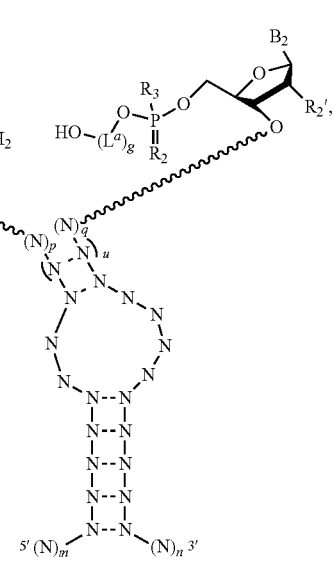

(C2'-x)
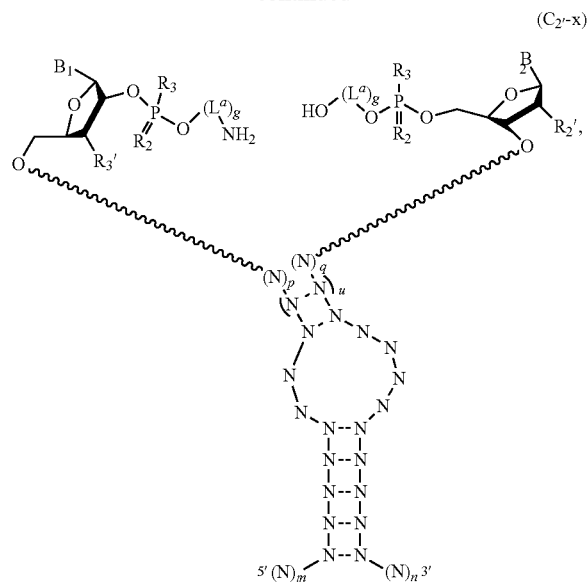
(C2'-xi)
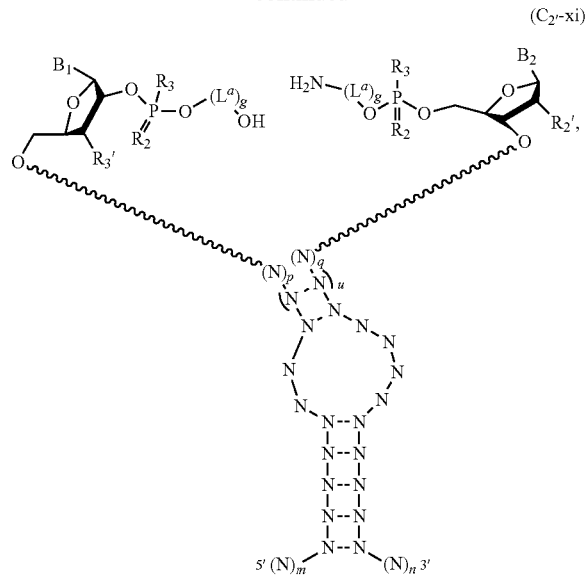
wherein N, $B_1$, $B_2$, $R_2'$, $R_3'$, p, q, u, m, and n are as defined in formulas $C_3$-i and $C_2$-i above, $L^a$ is as described above and defined herein, each g is independently 0, 1, 2, 3, 4, or 5, each $R_2$ is independently O or S, and each $R_3$ is independently OH or COOH.
In some embodiments, the oligonucleotide intermediates are of formula $D_{3'}$-x, $D_{2'}$-x, $D_{3'}$-xi, or $D_{2'}$-xi:

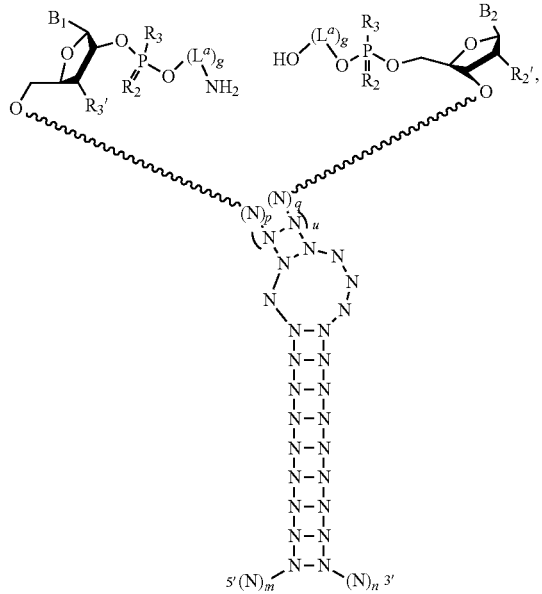
(D2'-x)
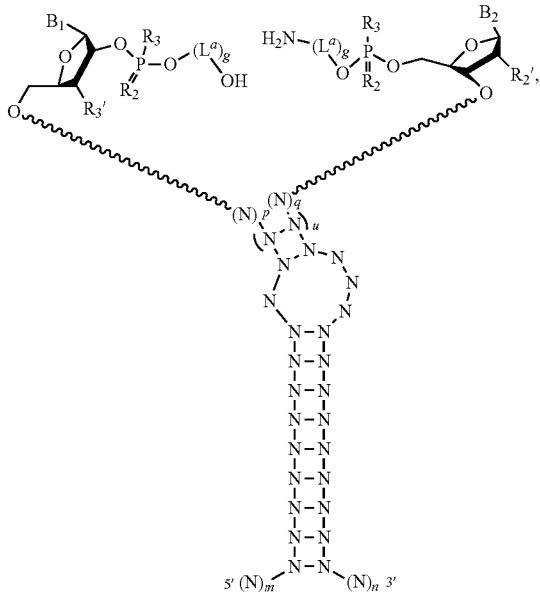
(D2'-xi)
wherein N, $B_1$, $B_2$, $R_2'$, $R_3'$, p, q, u, m, and n are as defined in formulas $D_3'$-i and $D_2'$-i above, $L^a$ is as described above and defined herein, each g is independently 0, 1, 2, 3, 4, or 5, each $R_2$ is independently O or S, and each $R_3$ is independently OH or COOH.
In certain embodiments, the oligonucleotide intermediates are of formula:
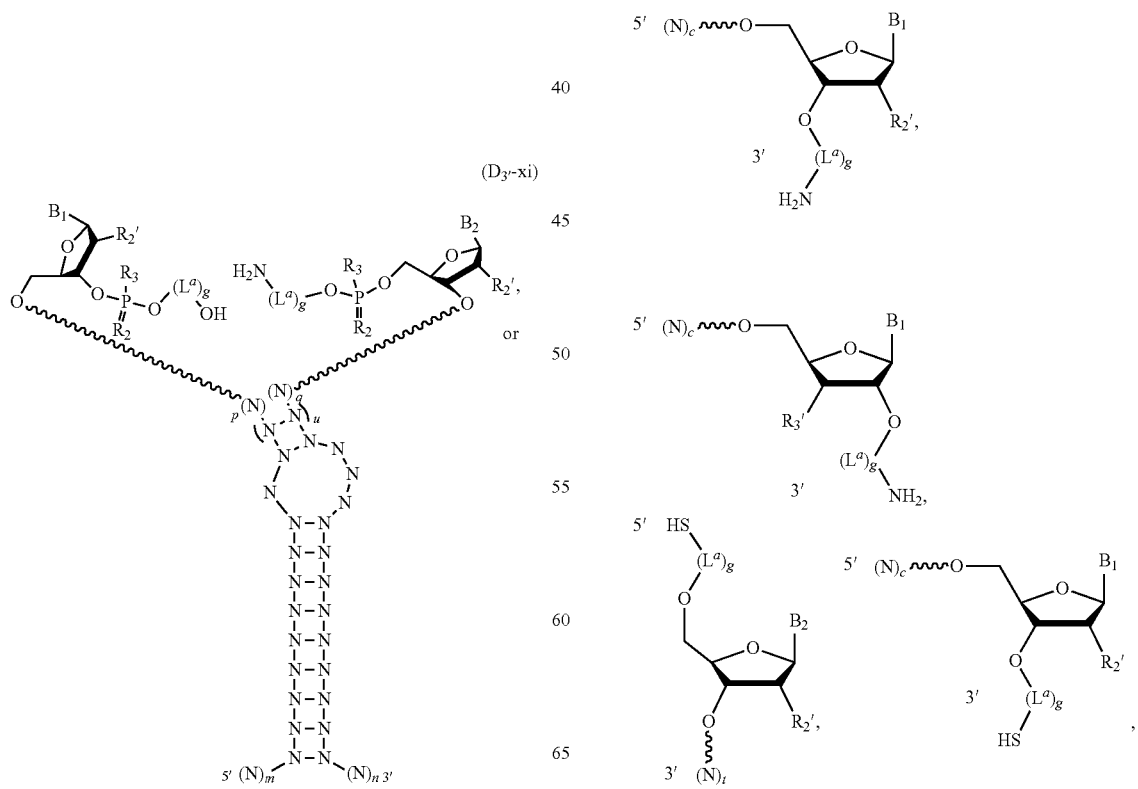
or -continued
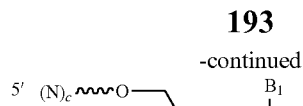
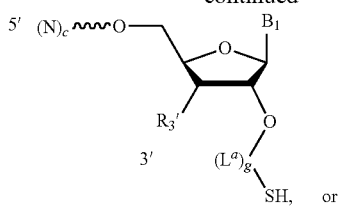
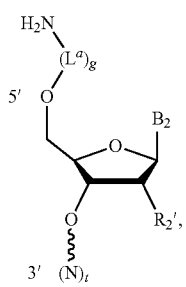
wherein N, $B_1$, $B_2$, $R_2'$, $R_3'$, c, and t are as defined in formulas $A_3'$-i and $A_2'$-i above, $L^a$ is as described above and defined herein, and each g is independently 0, 1, 2, 3, 4, or 5.
In some embodiments, the oligonucleotide intermediates are of formula $B_3'$-xii, $B_2'$-xii, $B_{31}$-xiii, or $B_2'$-xiii:
-continued
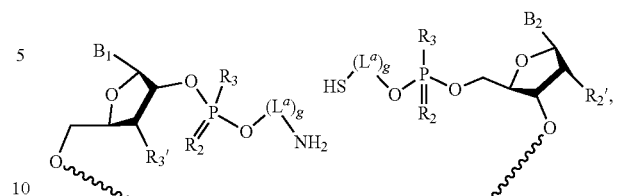
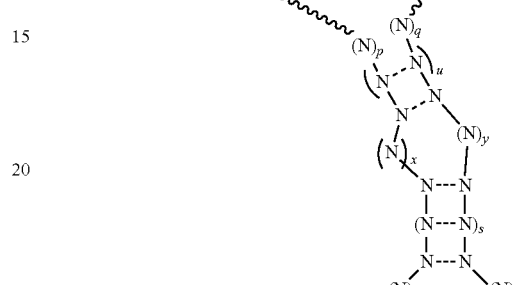
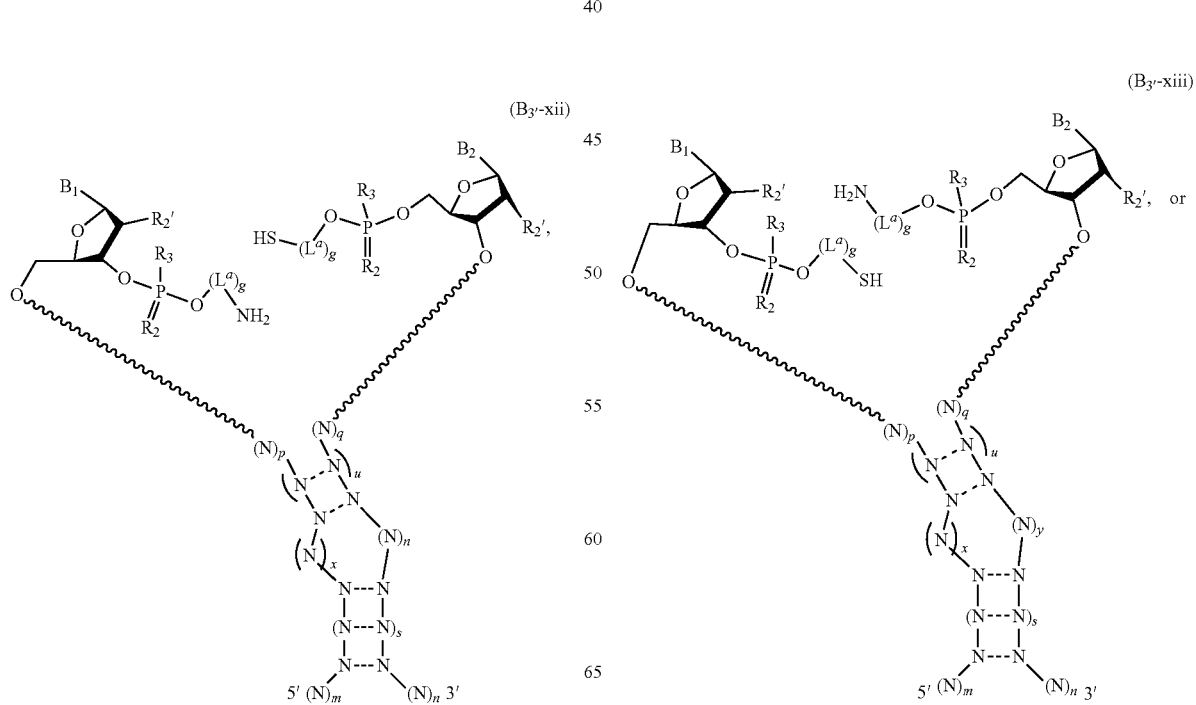

-continued

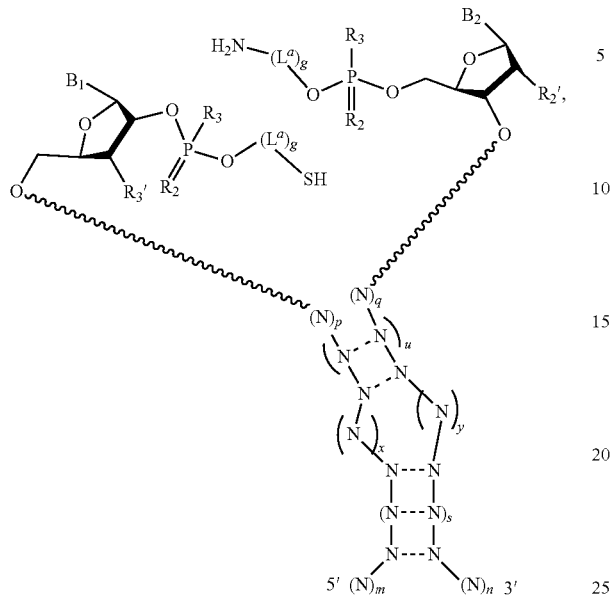
(B₂'-xiii)

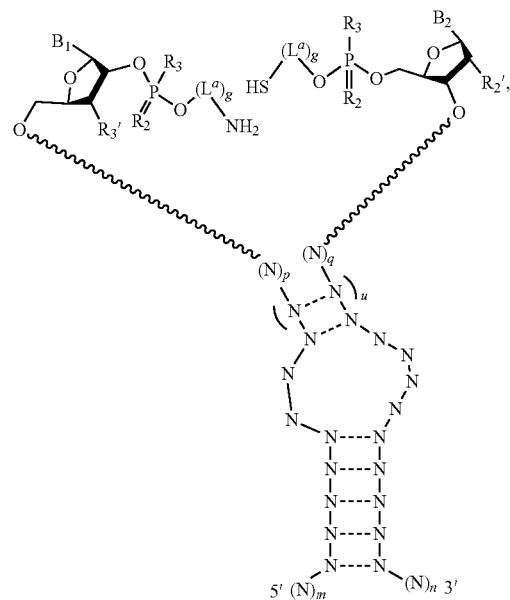
(C₂'-xii)

wherein N, $B_1$, $B_2$, $R_2'$, $R_3'$, p, q, u, x, y, s, m, and n are as defined in formulas $B_3$'-i and $B_2$'-i above, $L^a$ is as described above and defined herein, each g is independently 0, 1, 2, 3, 4, or 5, each $R_2$ is independently O or S, and each $R_3$ is independently OH or COOH.

In some embodiments, the oligonucleotide intermediates are of formula $C_3'$-xii, $C_2'$-xii, $C_3'$-xiii, or $C_2'$-xiii:

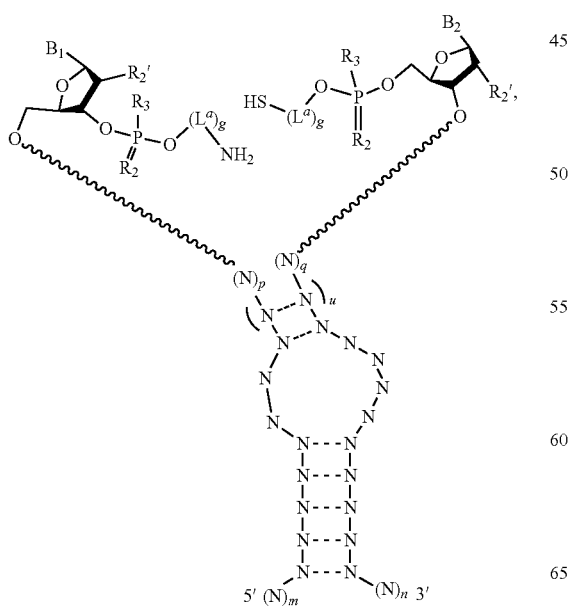
(C₃'-xii)

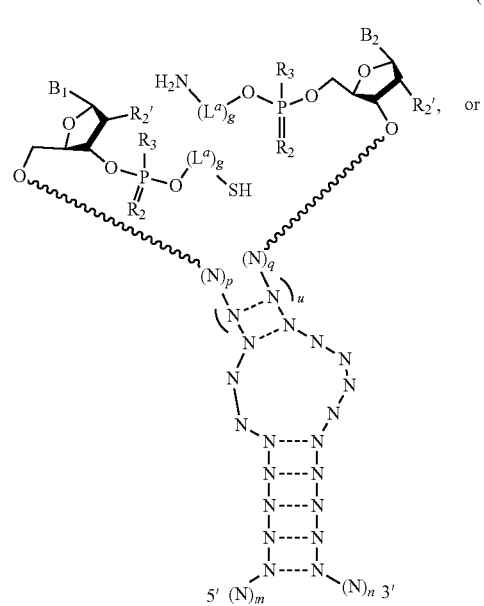
(C₃'-xiii)

or (C2'-xiii)

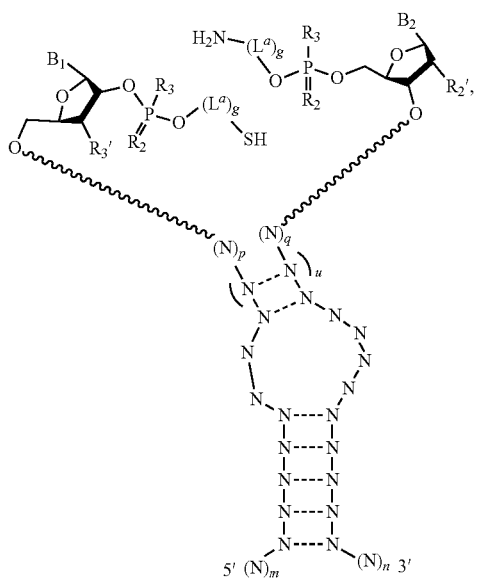

(D2'-xii)

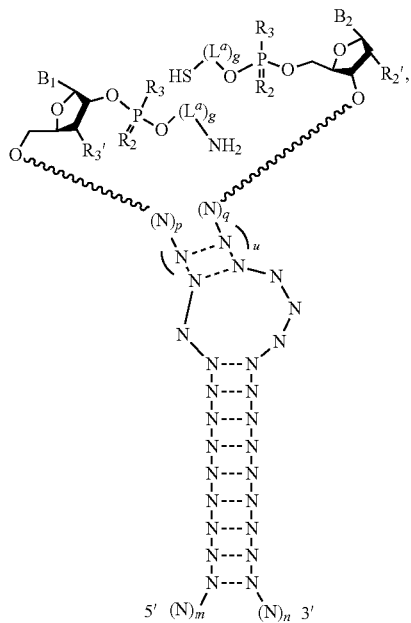

wherein N, $B_1$, $B_2$, $R_2'$, $R_3'$, p, q, u, m, and n are as defined in formulas $C_3'$-i and $C_2'$-i above, $L^a$ is as described above and defined herein, each g is independently 0, 1, 2, 3, 4, or 5, each $R_2$ is independently O or S, and each $R_3$ is independently OH or COOH.

In some embodiments, the oligonucleotide intermediates are of formula $D_3'$-xii, $D_2'$-xii, $D_3'$-xiii, or $D_2'$-xiii:

(D3'-xii)

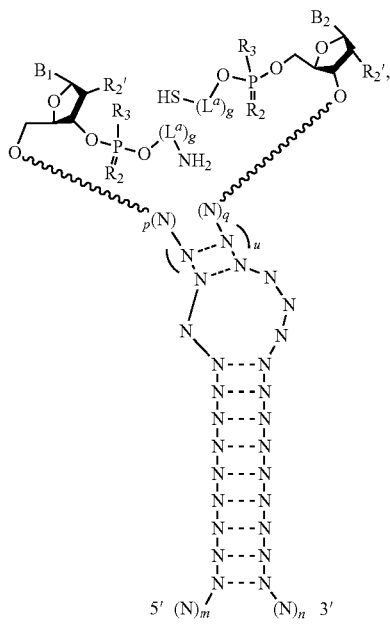

(D3'-xiii) or

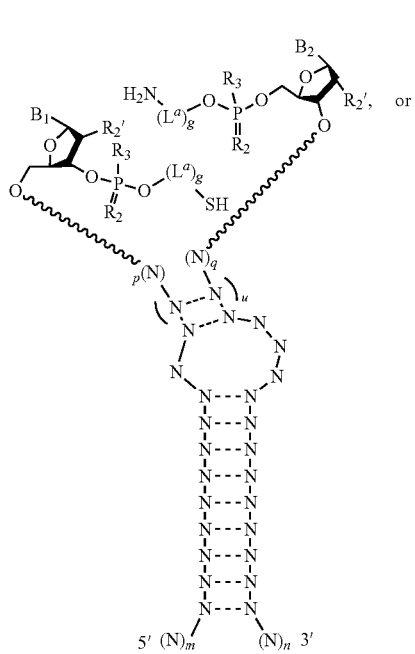

-continued (D₂′-xiii)

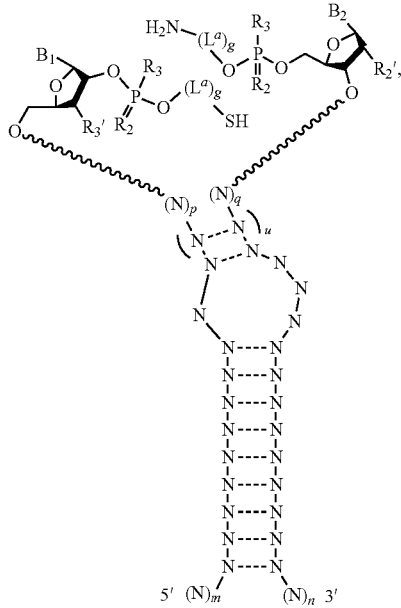

wherein N, B₁, B₂, R₂', R₃', p, q, u, m, and n are as defined in formulas D₃′-i and D₂′-i above, $L^a$ is as described above and defined herein, each g is independently 0, 1, 2, 3, 4, or 5, each R₂ is independently O or S, and each R₃ is independently OH or COOH.

In certain embodiments, the oligonucleotide intermediates are useful in the synthesis of guide molecules comprising a phosphodiester linkage. In some embodiments, the oligonucleotide intermediates are of formula:

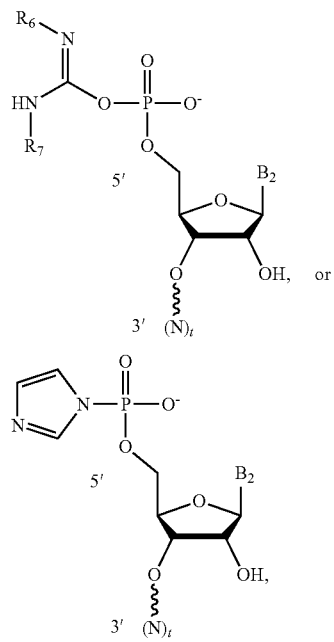

wherein R₆ and R₇ are each independently substituted or unsubstituted alkyl, or substituted or unsubstituted carbocyclyl. In some embodiments, the oligonucleotide intermediates are of formula:

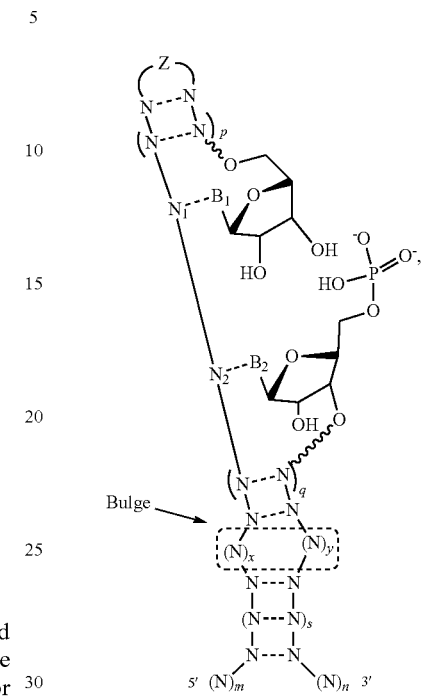

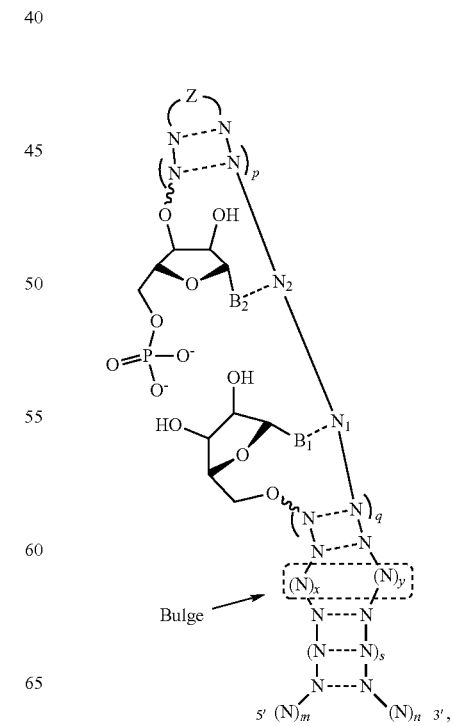

-continued

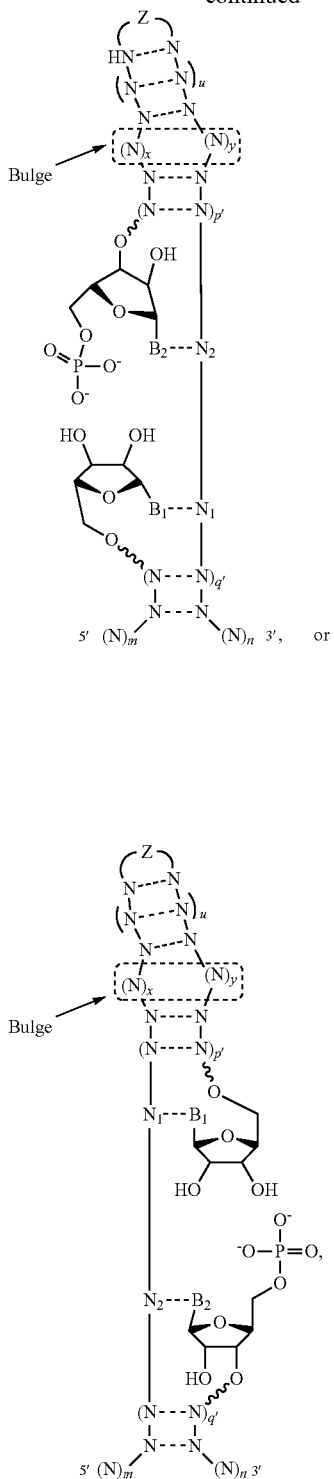

wherein Z represents a nucleotide loop which is 4-6 nucleotides long, optionally 4 or 6 nucleotides long.

Certain embodiments of this disclosure relate to oligonucleotide compounds that are formed as side products in a cross linking reaction. These oligonucleotide compounds may or may not be useful as guide molecules. In some embodiments, the oligonucleotide compound is of formula $A_{3'}$-vi or $A_{2'}$-vi:

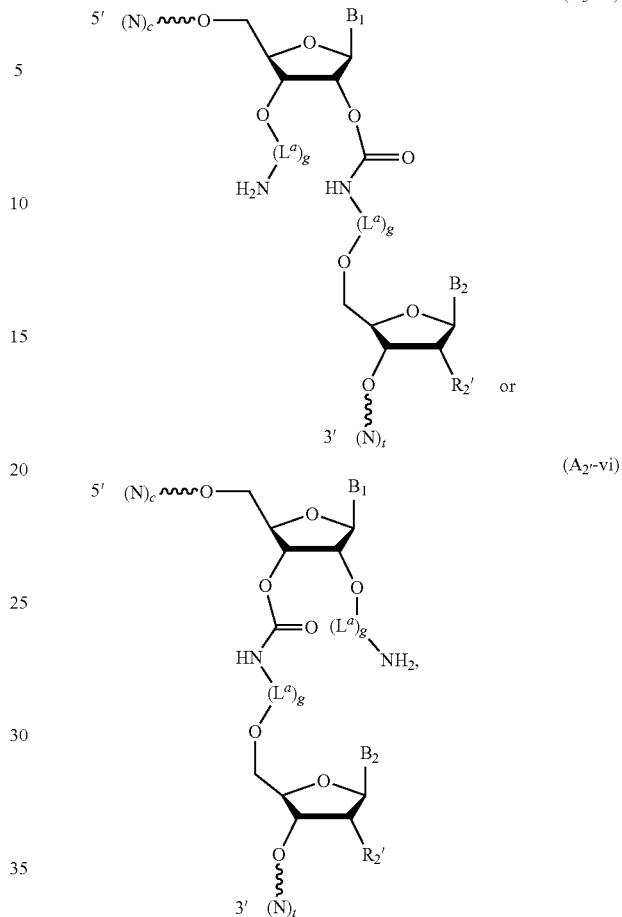

wherein N, $B_1$, $B_2$, $R_2'$, $R_3'$, c, and t are as defined in formulas $A_{3'}$-i and $A_{2'}$-i above, $L^a$ is as described above and defined herein, and each g is independently 0, 1, 2, 3, 4, or 5.

Compositions of Chemically Conjugated Guide Molecules

Certain embodiments of this disclosure are related to compositions comprising synthetic guide molecules described above and to compositions generated by the methods described above. In some embodiments, provided compositions are characterized in that greater than 90% of guide molecules in the composition are full length guide molecules. In some embodiments, provided compositions are characterized in that greater than 85% of guide molecules in the composition comprise an identical targeting domain sequence.

In some embodiments, provided compositions have not been subjected to a purification step. In some embodiments, provided compositions consists essentially of guide molecules of formula $A_{3'}$-i or $A_{2'}$-i, or any subgenera thereof. In some embodiments, provided compositions consist essentially of guide molecules of formula $B_{3'}$-i or $B_{2'}$-i, or any subgenera thereof. In some embodiments, provided compositions consist essentially of guide molecules of formula $C_{3'}$-i or $C_{2'}$-i, or any subgenera thereof. In some embodiments, provided compositions consist essentially of guide molecules of formula $D_{3'}$-i or $D_{2'}$-i, or any subgenera thereof. In some embodiments, provided compositions consist essentially of guide molecules of formula $E_{3'}$-$i_A$, $E_{2'}$-$i_A$, $E_{3'}$-$i_U$ or $E_{2'}$-$i_U$ or any subgenera thereof. In some embodiments, provided compositions consist essentially of guide molecules of formula $F_{3'}\text{-}i_A$, $F_{2'}\text{-}i_A$, $F_{3'}\text{-}i_U$ or $F_{2'}\text{-}i_U$ or any subgenera thereof.
In some embodiments, provided compositions consist essentially of guide molecules of formula:
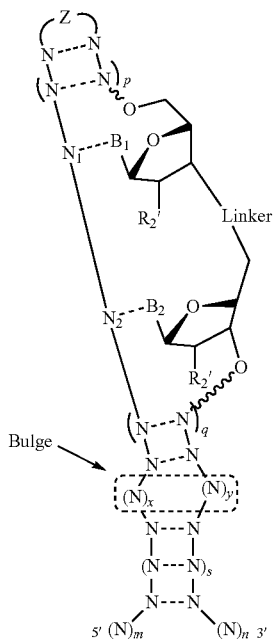
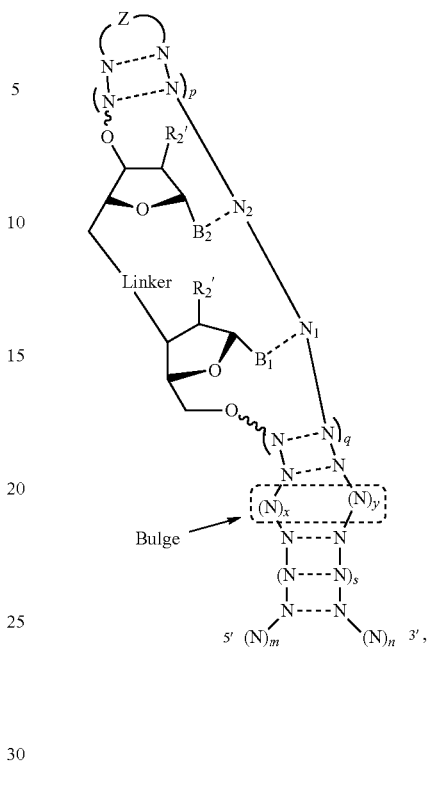
-continued
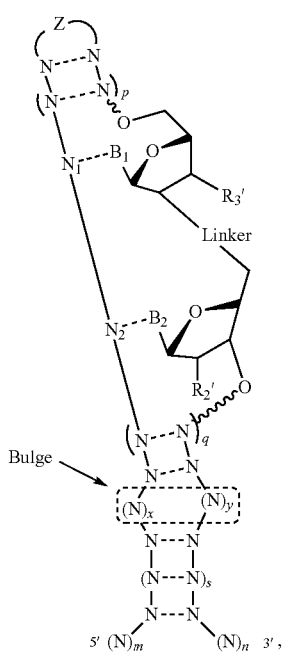
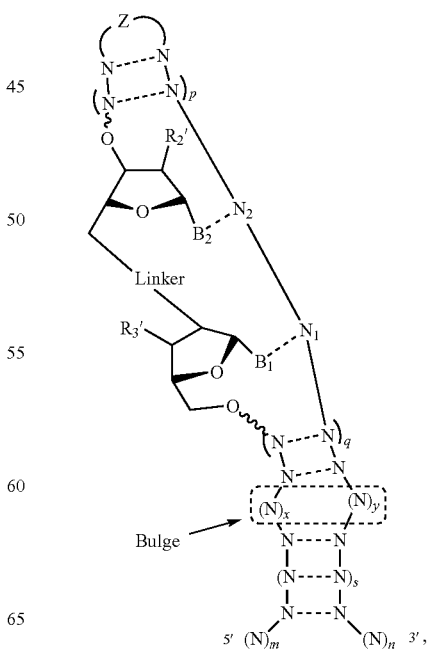

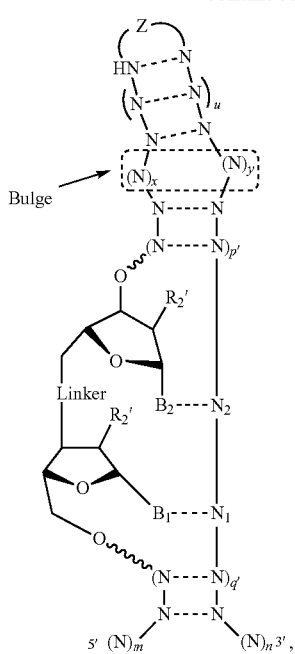
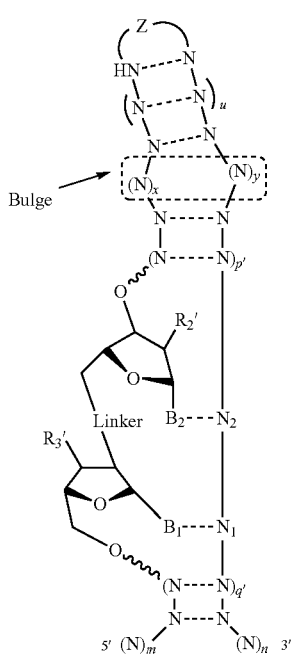
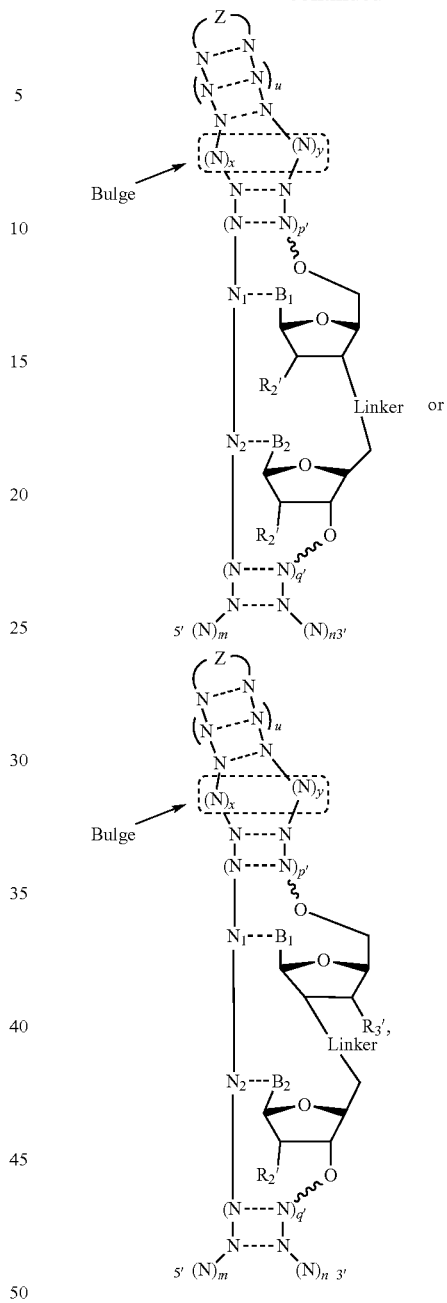

or a salt thereof.

In some embodiments, the present disclosure provides a composition comprising a guide molecule described herein and one or more oligonucleotide intermediates described herein. In some embodiments, the composition is substantially free of oligonucleotide intermediates. In some embodiments, the composition is not substantially free of oligonucleotide intermediates. In some embodiments, the composition comprises at least about 80%, 85%, 90%, 95%, 96%, 97%, 98%, 99%, or greater of the guide molecule. In some embodiments, the composition comprises no more than about 20%, 15%, 10%, 5%, 4%, 3%, 2%, 1%, or less of the one or more oligonucleotide intermediates.

In some embodiments, provided compositions comprise oligonucleotide intermediates (described above) in the presence or absence of a synthetic guide molecule. In some embodiments, the oligonucleotide intermediates of the composition are of formula:

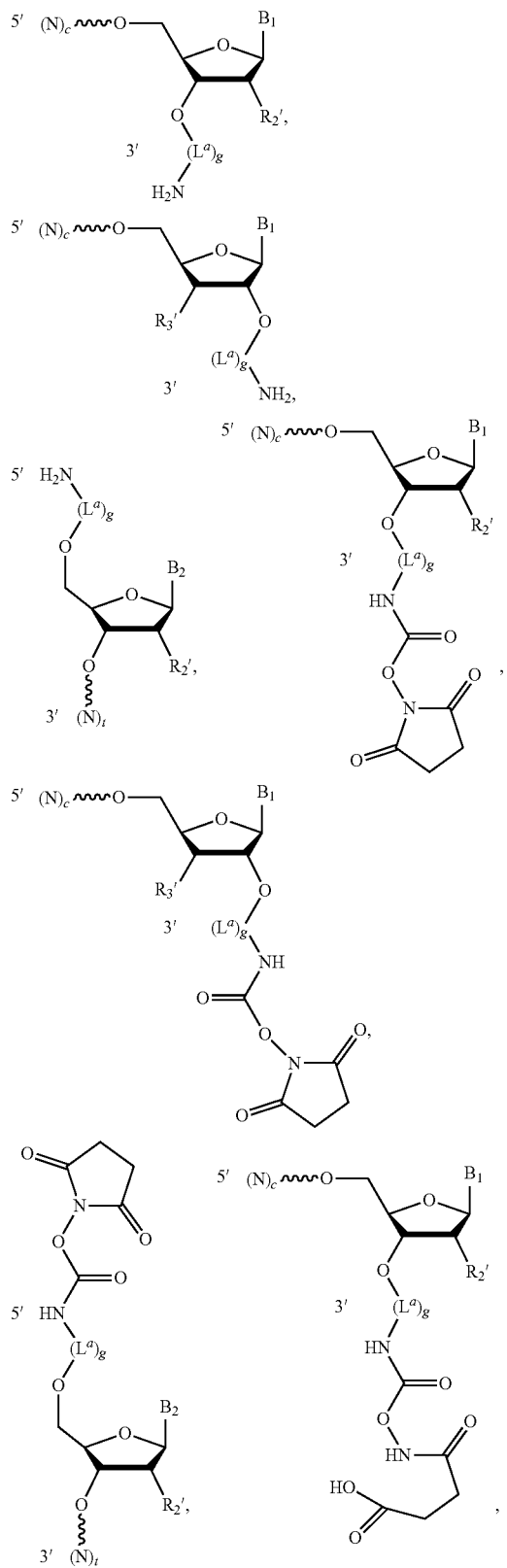

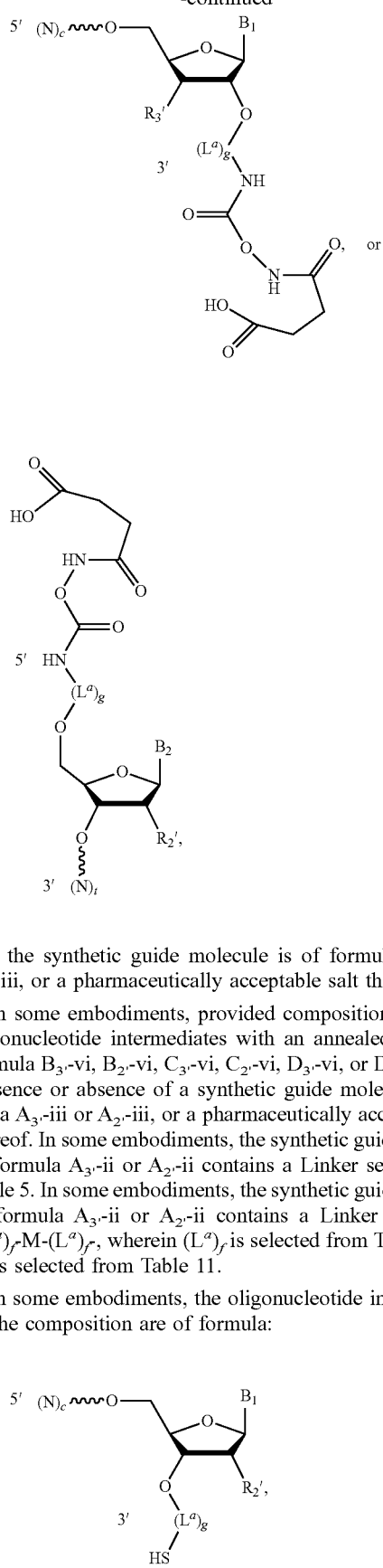

and the synthetic guide molecule is of formula $A_{3'}$-iii or $A_{2'}$-iii, or a pharmaceutically acceptable salt thereof.

In some embodiments, provided compositions comprise oligonucleotide intermediates with an annealed duplex of formula $B_{3'}$-vi, $B_{2'}$-vi, $C_{3'}$-vi, $C_{2'}$-vi, $D_{3'}$-vi, or $D_{2'}$-vi, in the presence or absence of a synthetic guide molecule of formula $A_{3'}$-iii or $A_{2'}$-iii, or a pharmaceutically acceptable salt thereof. In some embodiments, the synthetic guide molecule of formula $A_{3'}$-ii or $A_{2'}$-ii contains a Linker selected from Table 5. In some embodiments, the synthetic guide molecule of formula $A_{3'}$-ii or $A_{2'}$-ii contains a Linker of formula $-(L^a)_{f}\text{-}M\text{-}(L^a)_{f'}$, wherein $(L^a)_f$ is selected from Table 10 and M is selected from Table 11.

In some embodiments, the oligonucleotide intermediates of the composition are of formula:

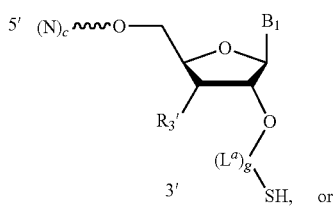

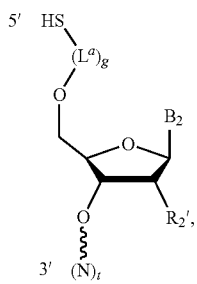

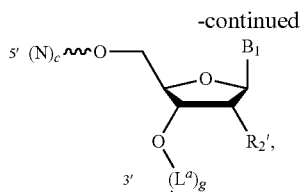

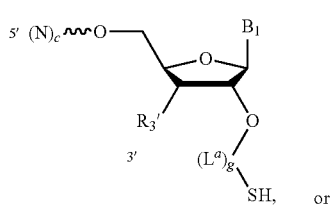

in the presence or absence of a synthetic guide molecule of formula $A_{3'}$-ii or $A_{2'}$-ii. In some embodiments, the synthetic guide molecule of formula $A_{3'}$-ii or $A_{2'}$-ii contains a Linker selected from Table 5. In some embodiments, the synthetic guide molecule of formula $A_{3'}$-ii or $A_{2'}$-ii contains a Linker of formula $-(L^a)_{f'}\text{-M-}(L^a)_{f'}$-, wherein $(L^a)_f$ is selected from Table 10 and M is selected from Table 11.

In some embodiments, provided compositions comprise oligonucleotide intermediates with an annealed duplex of formula $B_{3'}$-ix, $B_{2'}$-ix, $C_{3'}$-ix, $C_{2'}$-ix, $D_{3'}$-ix, or $D_{2'}$-ix, in the presence or absence of a synthetic guide molecule of formula $A_{3'}$-ii or $A_{2'}$-ii, or a pharmaceutically acceptable salt thereof. In some embodiments, the synthetic guide molecule of formula $A_{3'}$-ii or $A_{2'}$-ii contains a Linker selected from Table 5. In some embodiments, the synthetic guide molecule of formula $A_{3'}$-ii or $A_{2'}$-ii contains a Linker of formula $-(L^a)_{f'}\text{-M-}(L^a)_{f'}$-, wherein $(L^a)_f$ is selected from Table 10 and M is or is encompassed by a group selected from Table 11.

In some embodiments, the oligonucleotide intermediates in the composition are of formula:

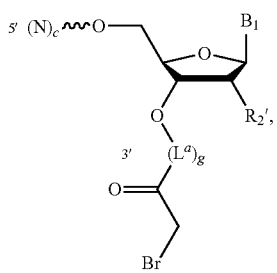

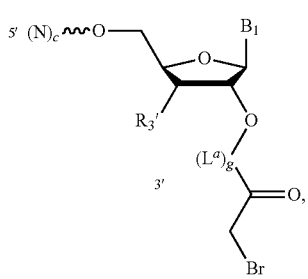 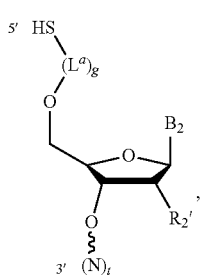

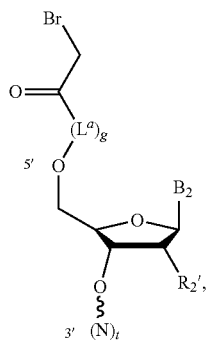

or a salt thereof, in the presence or absence of a synthetic guide molecule of formula $A_{3'}$-iv, $A_{2'}$-iv, $A_{3'}$-v, or $A_{2'}$-V.

In some embodiments, provided compositions comprise oligonucleotide intermediates with an annealed duplex of formula $B_{3'}$-vii, $B_{2'}$-vii, $B_{3'}$-viii, $B_{2'}$-viii, $C_{3'}$-vii, $C_{2'}$-vii, $C_{3'}$-viii, $C_{2'}$-viii, $D_{3'}$-vii, $D_{2'}$-vii, $D_{3'}$-viii, or $D_{2'}$-viii, in the presence or absence of a synthetic guide molecule of formula $A_{3'}$-iv, $A_{2'}$-iv, $A_{3'}$-v, or $A_{2'}$-v, or a pharmaceutically acceptable salt thereof.

In some embodiments, the oligonucleotide intermediates of the composition are of formula:

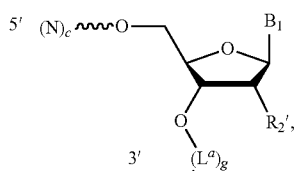

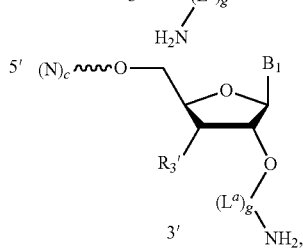

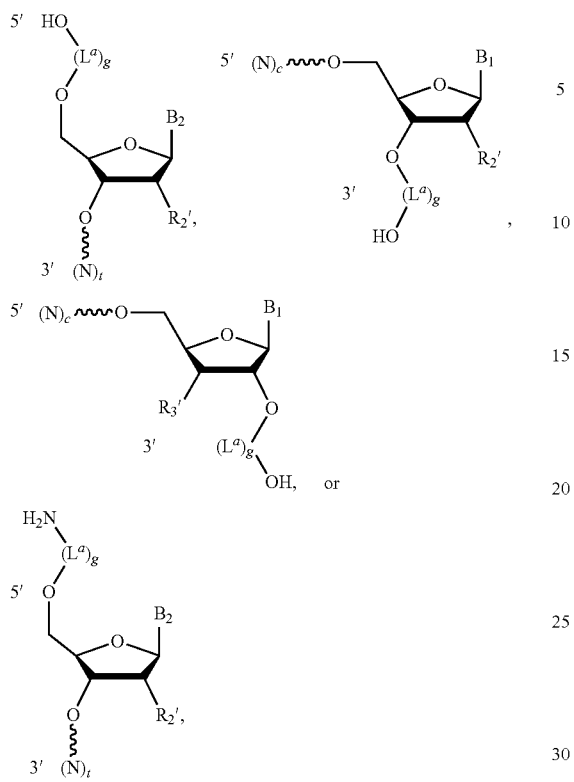

in the presence or absence of a synthetic guide molecule of formula $A_{3'}$-ii or $A_{2'}$-ii. In some embodiments, the synthetic guide molecule of formula $A_{3'}$-ii or $A_{2'}$-ii contains a Linker selected from Table 5. In some embodiments, the synthetic guide molecule of formula $A_{3'}$-ii or $A_{2'}$-ii contains a Linker of formula $-(L^a)_{f'}-M-(L^a)_{f'}-$, wherein $(L^a)_f$ is selected from Table 8 and M is or is encompassed by a group selected from Table 9.

In some embodiments, provided compositions comprise oligonucleotide intermediates with an annealed duplex of formula $B_{3'}$-x, $B_{2'}$-x, $B_{3'}$-xi, $B_{2'}$-xi, $C_{3'}$-x, $C_{2'}$-x, $C_{3'}$-xi, $C_{2'}$-xi, $D_{3'}$-x, $D_{2'}$-x, $D_{3'}$-xi, or $D_{2'}$-xi in the presence or absence of a synthetic guide molecule of formula $A_{3'}$-ii or $A_{2'}$-ii, or a pharmaceutically acceptable salt thereof. In some embodiments, the synthetic guide molecule of formula $A_{3'}$-ii or $A_{2'}$-ii contains a Linker selected from Table 5. In some embodiments, the synthetic guide molecule of formula $A_{3'}$-ii or $A_{2'}$-ii contains a Linker of formula $-(L^a)_{f'}-M-(L^a)_{f'}-$, wherein $(L^a)_f$ is selected from Table 8 and M is or is encompassed by a group selected from Table 9.

In some embodiments, the oligonucleotide intermediates of the composition are of formula:

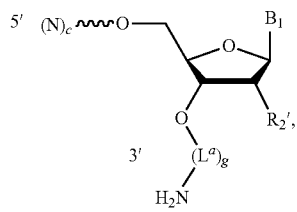

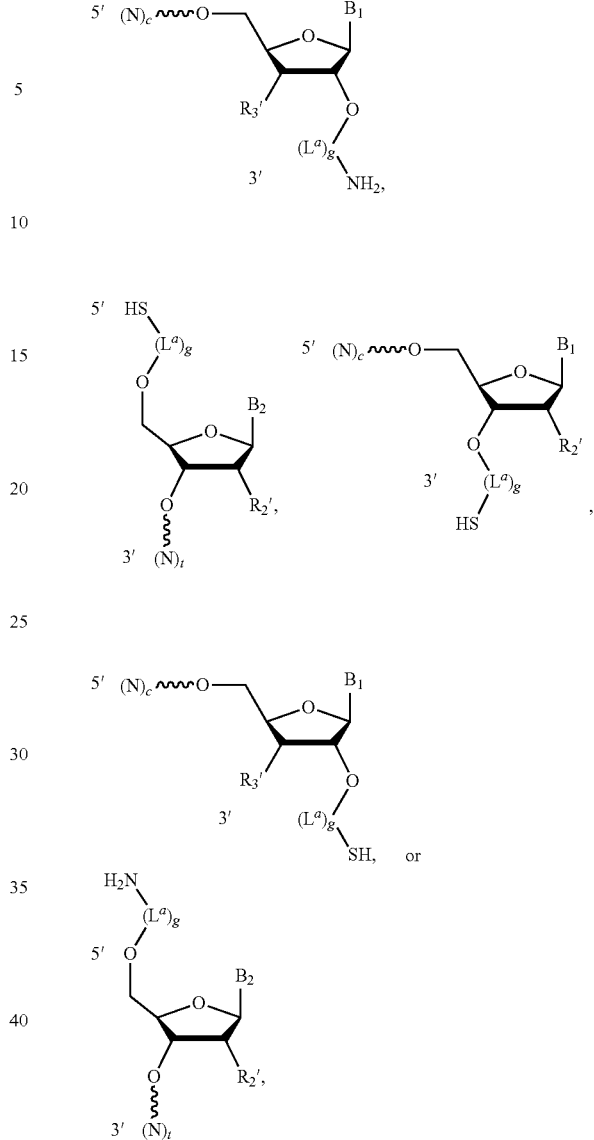

in the presence or absence of a synthetic guide molecule of formula $A_{3'}$-ii or $A_{2'}$-ii. In some embodiments, the synthetic guide molecule of formula $A_{3'}$-ii or $A_{2'}$-ii contains a Linker selected from Table 5. In some embodiments, the synthetic guide molecule of formula $A_{3'}$-ii or $A_{2'}$-ii contains a Linker of formula $-(L^a)_{f'}-M-(L^a)_{f'}-$, wherein $(L^a)_f$ is selected from Tables 8 or 10 and M is or is encompassed by a group selected from Tables 9 or 11.

In some embodiments, provided compositions comprise oligonucleotide intermediates with an annealed duplex of formula $B_{3'}$-xii, $B_{2'}$-xii, $B_{3'}$-xiii, $B_{2'}$-xiii, $C_{3'}$-xii, $C_{2'}$-xii, $C_{3'}$-xiii, $C_{2'}$-xiii, $D_{3'}$-xii, $D_{2'}$-xii, $D_{3'}$-xiii, or $D_{2'}$-xiii in the presence or absence of a synthetic guide molecule of formula $A_{3'}$-ii or $A_{2'}$-ii, or a pharmaceutically acceptable salt thereof. In some embodiments, the synthetic guide molecule of formula $A_{3'}$-ii or $A_{2'}$-ii contains a Linker selected from Table 5. In some embodiments, the synthetic guide molecule of formula $A_{3'}$-ii or $A_{2'}$-ii contains a Linker of formula $-(L^a)_{f'}-M-(L^a)_{f'}-$, wherein $(L^a)_f$ is selected from Tables 8 or 10 and M is or is encompassed by a group selected from Tables 9 or 11.

In some embodiments, the oligonucleotide intermediates of the composition are of formula:
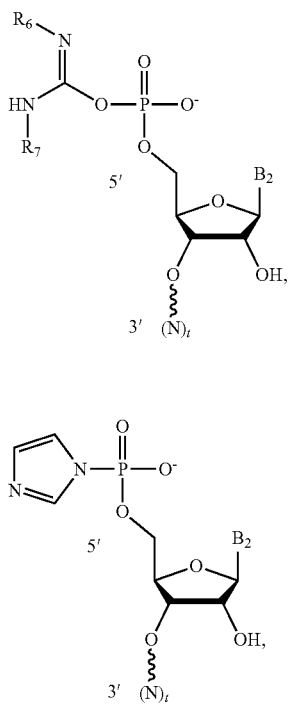
or, and the synthetic guide molecule is of formula:
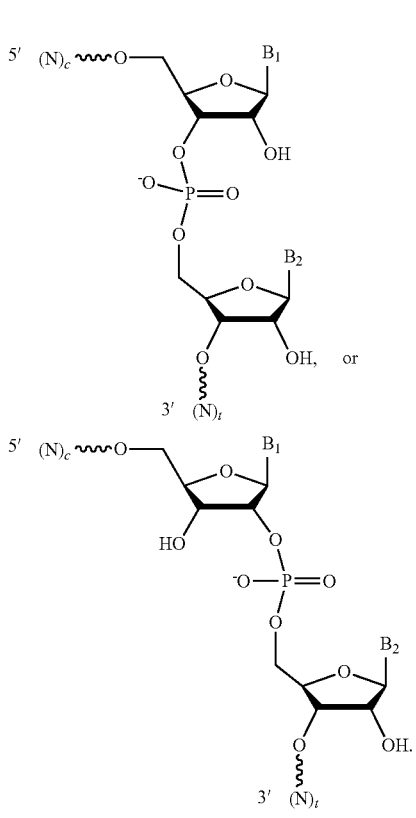
In some embodiments, the composition comprises oligonucleotide intermediates with an annealed duplex of formula:
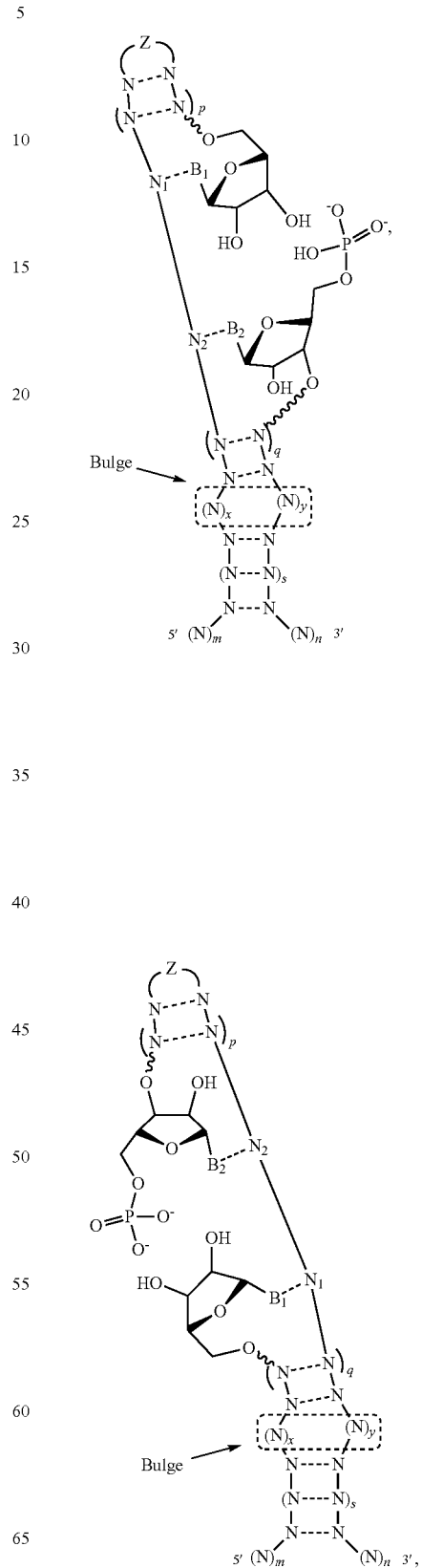

-continued

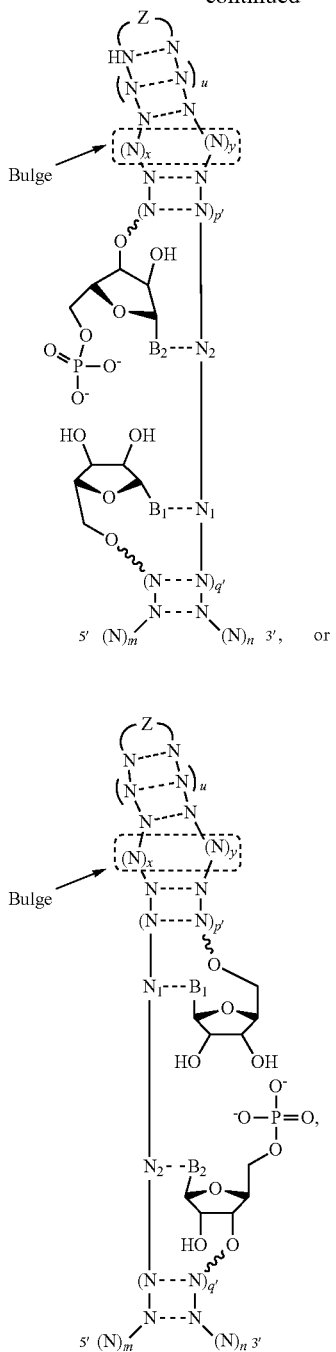

or a salt thereof.

In some embodiments, provided compositions are substantially free of homodimers. In some embodiments, provided compositions are substantially free of byproducts. In some embodiments, the composition that is substantially free of homodimers and/or byproducts comprises a guide molecule that was synthesized using a method comprising a homobifunctional cross linking reagent. In some embodiments, the composition that is substantially free of homodimers and/or byproducts comprises a guide molecule of formula $A_3$-ii, or a pharmaceutically acceptable salt thereof, and the composition is substantially free of molecules of formula:

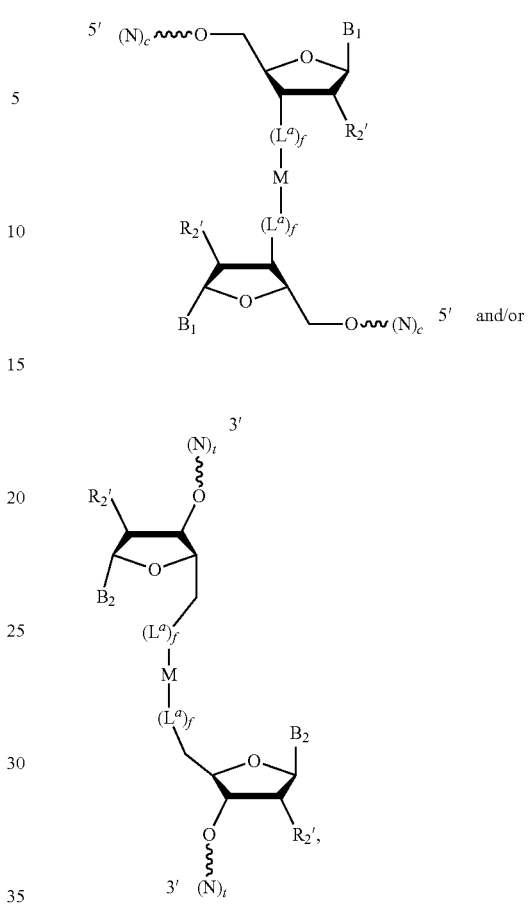

or a pharmaceutically acceptable salt thereof, wherein N, $B_1$, $B_2$, $R_2'$, $R_3'$, c, and t are as defined above in formula $A_3$-i; and $L^a$ and f are as described above and defined herein.

In some embodiments, in the composition that is substantially free of homodimers and/or byproducts, $-(L^a)_f$-M-$(L^a)_f$- is selected from Table 5. In some embodiments, in the composition that is substantially free of homodimers and/or byproducts, $(L^a)_f$ is selected from Tables 8 or 10 and M is or is encompassed by a group selected from Tables 9 or 11.

In some embodiments, the composition that is substantially free of homodimers and/or byproducts comprises a guide molecule of formula $A_2$-ii, or a pharmaceutically acceptable salt thereof, and the composition is substantially free of molecules of formula:

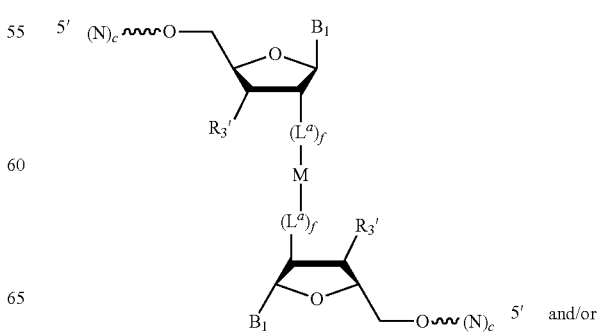

217
-continued

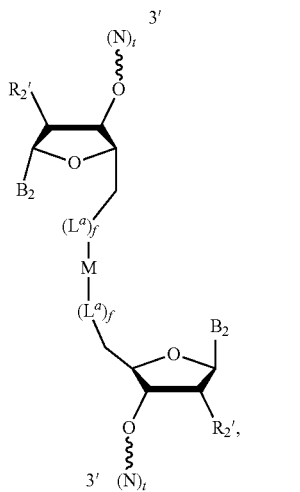

or a pharmaceutically acceptable salt thereof, wherein N, $B_1$, $B_2$, $R_2'$, $R_3'$, c, and t are as defined above in formula $A_2$-i; each f is independently 1, 2, 3, 4, 5, or 6; and $L^a$ is as described above and defined herein.

In some embodiments, in the composition that is substantially free of homodimers and/or byproducts, $-(L^a)_f\text{-}M\text{-}(L^a)_f\text{-}$ is selected from Table 5. In some embodiments, in the composition that is substantially free of homodimers and/or byproducts, $(L^a)_f$ is selected from Tables 8 or 10 and M is or is encompassed by a group selected from Tables 9 or 11.

In some embodiments, the composition that is substantially free of homodimers and/or byproducts comprises a guide molecule with a urea linkage. In some embodiments, the guide molecule is of formula $A_3$-iii, or a pharmaceutically acceptable salt thereof, and the composition is substantially free of molecules of formula:

218
-continued or a pharmaceutically acceptable salt thereof, wherein N, $B_1$, $B_2$, $R_2'$, $R_3'$, c, and t are as defined above in formula $A_3$-i; each g is independently 0, 1, 2, 3, 4, or 5; and $L^a$ is as described above and defined herein.

In some embodiments, the guide molecule is of formula $A_2$-iii, or a pharmaceutically acceptable salt thereof, wherein the composition is substantially free of molecules of formula:

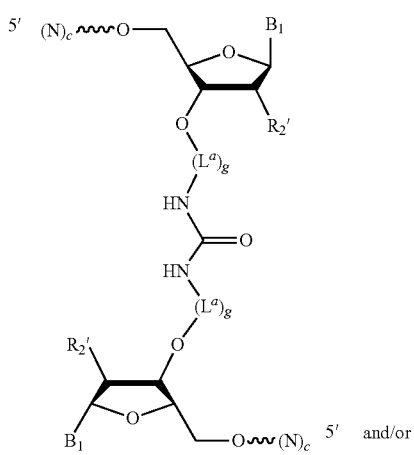

and/or

-continued

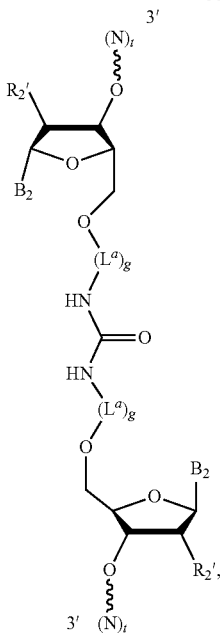

or a pharmaceutically acceptable salt thereof, wherein N, $B_1$, $B_2$, $R_2'$, $R_3'$, c, and t are as defined above in formula $A_2$-i; each g is independently 0, 1, 2, 3, 4, or 5; and $L^a$ is as described above and defined herein.

In some embodiments, provided compositions are substantially free of byproducts. In some embodiments, the composition that is substantially free of byproducts comprises a guide molecule comprising a urea linkage. In some embodiments, the composition comprises a guide molecule of formula $A_{3'}$-iii, or a pharmaceutically acceptable salt thereof, wherein the composition is substantially free of molecules of formula $A_{3'}$-vi. In some embodiments, the composition comprises a guide molecule of formula $A_{2'}$-iii, or a pharmaceutically acceptable salt thereof, wherein the composition is substantially free of molecules of formula $A_{2'}$-vi.

In some embodiments, the composition is not substantially free of byproducts. In some embodiments, the composition comprises (a) a synthetic unimolecular guide molecule for a CRISPR system, wherein the guide molecule is of formula:

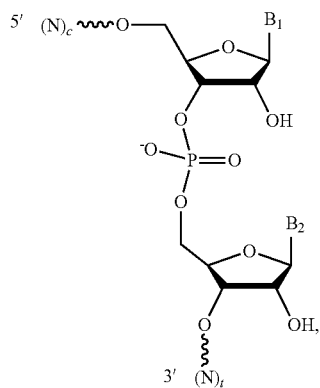

or a pharmaceutically acceptable salt thereof; and (b) one or more of: (i) a carbodiimide, or a salt thereof; (ii) imidazole, cyanoimidazole, pyridine, and dimethylaminopyridine, or a salt thereof; and (iii) a compound of formula:

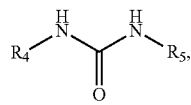

or a salt thereof, wherein $R^4$ and $R^5$ are each independently substituted or unsubstituted alkyl, or substituted or unsubstituted carbocyclyl. In some embodiments, the carbodiimide is EDC, DCC, or DIC. In some embodiments, the composition comprises EDC. In some embodiments, the composition comprises imidazole.

In some embodiments, provided compositions are substantially free of n+1 and/or n−1 species. In some embodiments, the composition comprises less than about 10%, 5%, 2%, 1%, or 0.1% of guide molecules comprising a truncation relative to a reference guide molecule sequence. In some embodiments, at least about 85%, 90%, 95%, 98%, or 99% of the guide molecules comprise a 5' sequence comprising nucleotides 1-20 of the guide molecule that is 100% identical to a corresponding 5' sequence of the reference guide molecule sequence.

In some embodiments, provided compositions comprise a guide molecule of formula $A_{3'}$-ii:

(A$_{3'}$-ii)

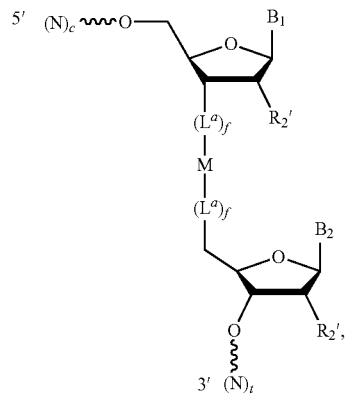

or a pharmaceutically acceptable salt thereof, wherein the composition is substantially free of molecules of formula $A_{3'}$-x:

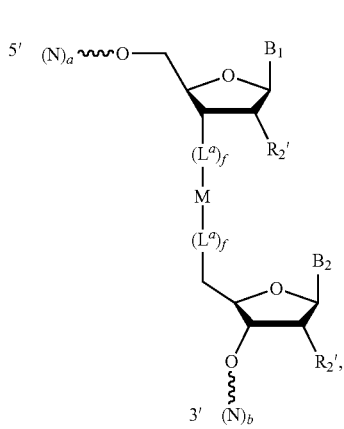

(A$_{3'}$-x)

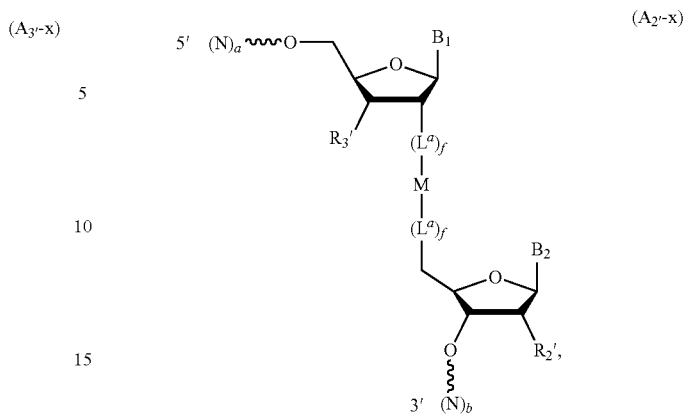

(A$_{2'}$-x)

or a pharmaceutically acceptable salt thereof, wherein a is not equal to c; and/or b is not equal to t, and N, B$_1$, B$_2$, R$_2'$, R$_3'$, c, and t are as defined above in formula A$_{3'}$-i; each f is independently 1, 2, 3, 4, 5, or 6; and L$^a$ is as described above and defined herein.

In some embodiments, in the composition that is free of molecules of formula A$_{3'}$-x, -(L$^a$)$_f$-M-(L$^a$)$_f$- is selected from Table 5. In some embodiments, in the composition that is free of molecules of formula A$_{3'}$-x, (L$^a$) is selected from Tables 8 or 10 and M is or is encompassed by a group selected from Tables 9 or 11.

In some embodiments, provided compositions comprise a guide molecule of formula A$_{2'}$-ii:

or a pharmaceutically acceptable salt thereof, wherein a is not equal to c; and/or b is not equal to t, and N, B$_1$, B$_2$, R$_2'$, R$_3'$, c, and t are as defined above in formula A$_{2'}$-i; each f is independently 1, 2, 3, 4, 5, or 6; and L$^a$ is as described above and defined herein.

In some embodiments, in the composition that is free of molecules of formula A$_{2'}$-x, -(L$^a$)$_f$-M-(L$^a$)$_f$- is selected from Table 5. In some embodiments, in the composition that is free of molecules of formula A$_{2'}$-x, (L$^a$), is selected from Tables 8 or 10 and M is or is encompassed by a group selected from Tables 9 or 11.

In some embodiments, provided compositions comprise a guide molecule of formula A$_{3'}$-iii:

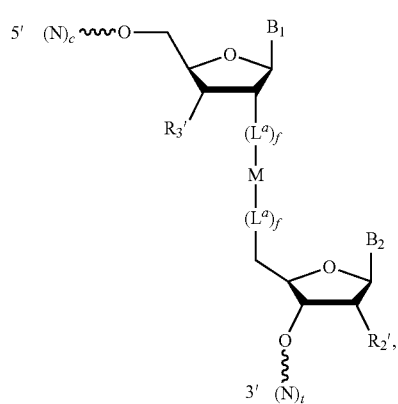

(A$_{2'}$-ii)

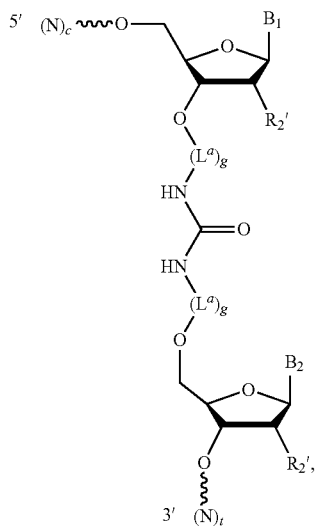

(A$_{3'}$-iii)

or a pharmaceutically acceptable salt thereof, wherein the composition is substantially free of molecules of formula A$_{2'}$-x:

or a pharmaceutically acceptable salt thereof, wherein the composition is substantially free of molecules of formula A$_{3'}$-vii:

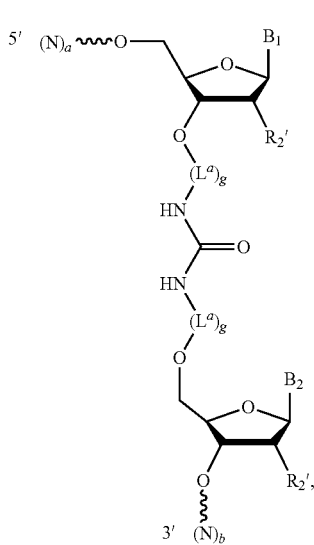

(A₃'-vii)

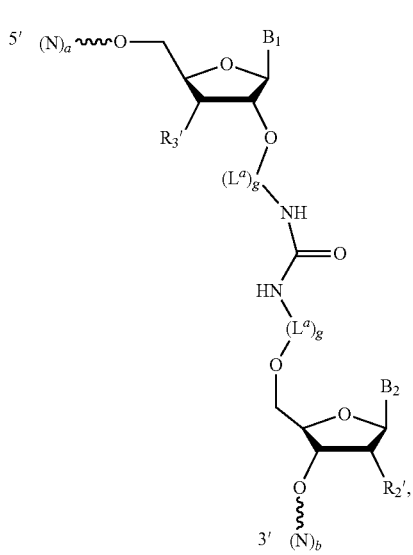

(A₂'-vii)

or a pharmaceutically acceptable salt thereof, wherein a is not equal to c; and/or b is not equal to t.

In some embodiments, provided compositions comprise a guide molecule of formula $A_{2'}$-iii:

or a pharmaceutically acceptable salt thereof, wherein a is not equal to c; and/or b is not equal to t.

In some embodiments, provided compositions comprise guide molecules of formula $A_{3'}$-iv:

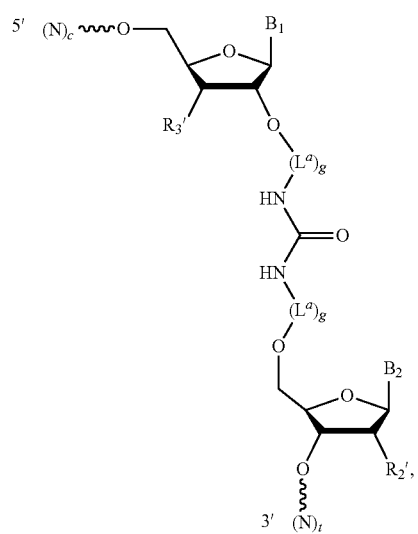

(A₂'-iii)

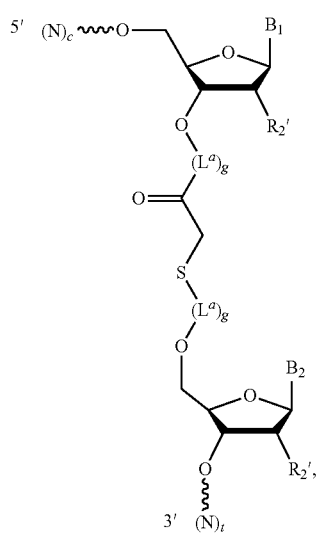

(A₃'-iv)

or a pharmaceutically acceptable salt thereof, wherein the composition is substantially free of molecules of formula $A_{2'}$-vii:

or a pharmaceutically acceptable salt thereof, wherein the composition is substantially free of molecules of formula $A_{3'}$-viii:

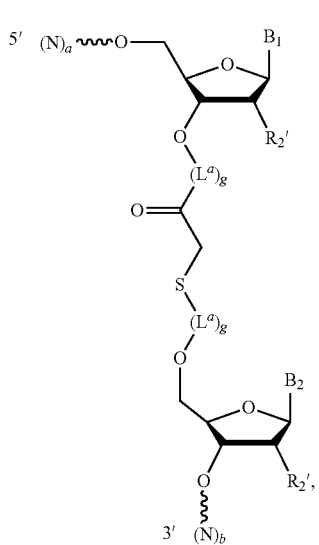

(A₃′-viii)

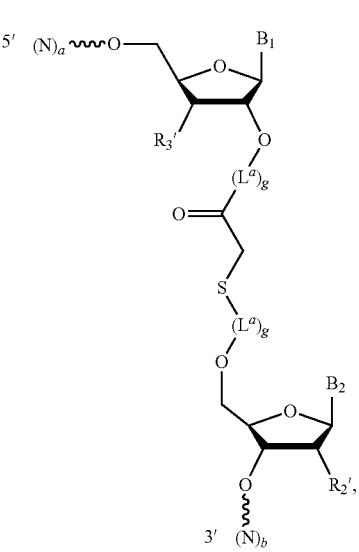

(A₂′-viii)

or a pharmaceutically acceptable salt thereof, wherein a is not equal to c; and/or b is not equal to t.

In some embodiments, provided compositions comprise guide molecules of formula $A_{2'}$-iv:

or a pharmaceutically acceptable salt thereof, wherein a is not equal to c; and/or b is not equal to t.

In some embodiments, provided compositions comprise guide molecules of formula $A_{3'}$-V:

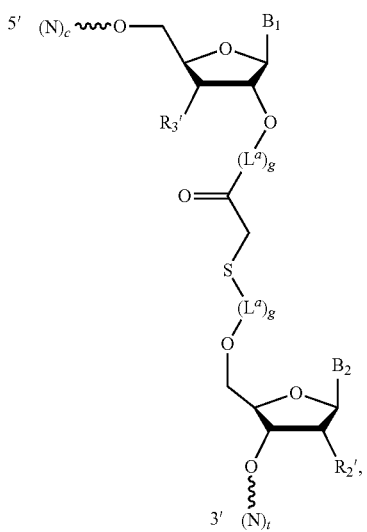

(A₂′-iv)

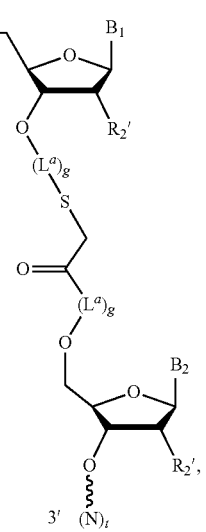

(A₃′-v)

or a pharmaceutically acceptable salt thereof, wherein the composition is substantially free of molecules of formula $A_{2'}$-viii:

or a pharmaceutically acceptable salt thereof, wherein the composition is substantially free of molecules of formula $A_{3'}$-ix:

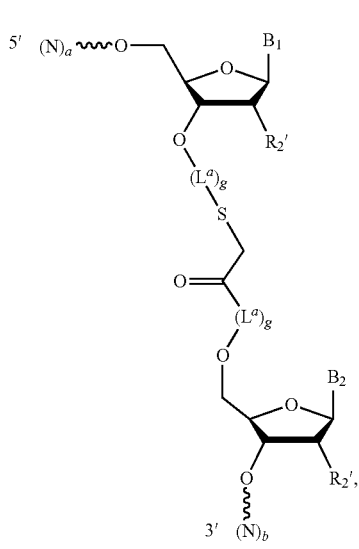

(A₃′-ix)

or a pharmaceutically acceptable salt thereof, wherein a is not equal to c; and/or b is not equal to t.

In some embodiments, provided compositions comprise guide molecules of formula A₂′-v:

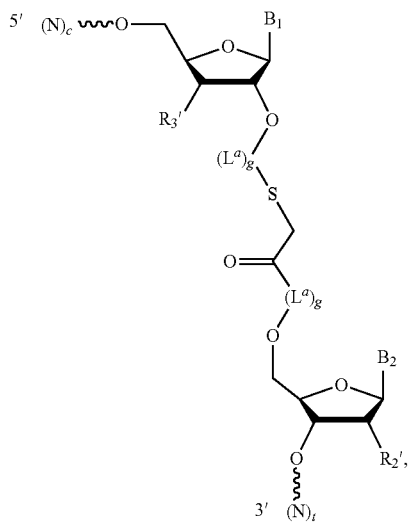

(A₂′-v)

or a pharmaceutically acceptable salt thereof, wherein the composition is substantially free of molecules of formula A₂′-ix:

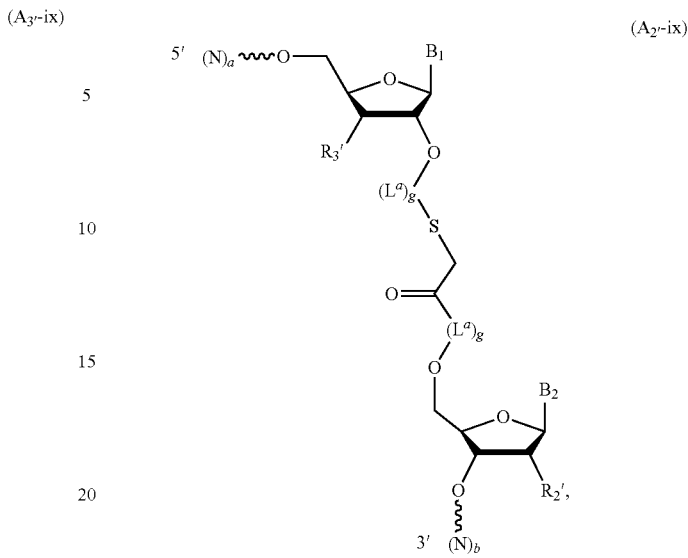

(A₂′-ix)

or a pharmaceutically acceptable salt thereof, wherein a is not equal to c; and/or b is not equal to t.

In some embodiments, provided compositions comprising a guide molecule of any of formulas A₃′-ii, A₂′-ii, A₃′-iii, A₂′-iii, A₃′-iv, A₂′-iv, A₃′-v, or A₂′-v are substantially free of molecules of formulas A₃′-x, A₂′-x, A₃′-vii, A₂′-vii, A₃′-viii, A₂′-viii, A₃′-ix, or A₂′-ix wherein a is less than c, and/or b is less than t.

The present disclosure also encompasses the recognition that linkers comprising a maleimide are susceptible to ring opening under aqueous conditions, particularly when R is hydrogen. Accordingly, in some embodiments, the present disclosure provides compositions comprising a mixture of two or more guide molecules of any of Formulas A₃′-ii, A₂′-ii, B₃′-ii, B₂′-ii, C₃′-ii, C₂′-ii, D₃′-ii, D₂′-ii, E₃′-ii_U, E₂′-ii_U, E₃′-ii_A, E₂′-ii_A, F₃′-ii_U, F₂′-ii_U, F₃′-ii_A, or F₂′-ii_A, wherein -(L^a)_f-M-(L^a)_f- is:

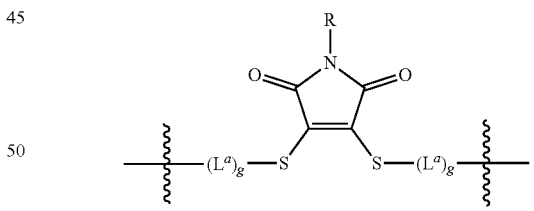

in at least one guide molecule, and

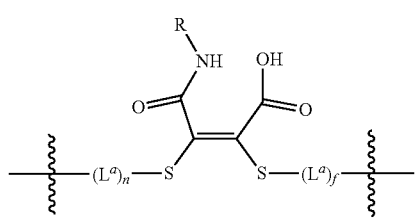

in at least one guide molecule.

In some embodiments, the composition comprises a guide molecule of formula:

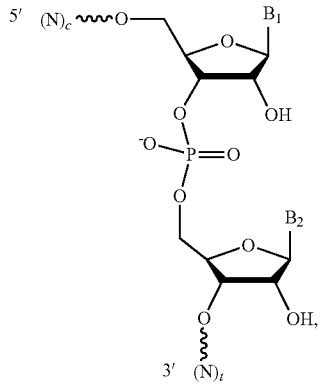

or a pharmaceutically acceptable salt thereof, wherein the composition is substantially free of molecules of formula:

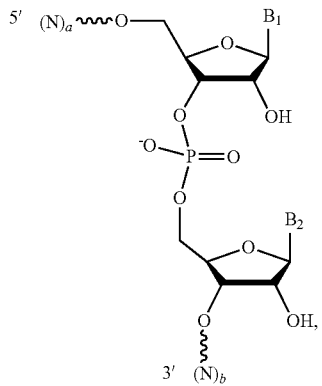

or a pharmaceutically acceptable salt thereof, wherein a+b is c+t−k, wherein k is an integer between 1 and 10, inclusive.

In one embodiment, the composition comprises a synthetic unimolecular guide molecule for a CRISPR system, wherein the guide molecule is of formula:

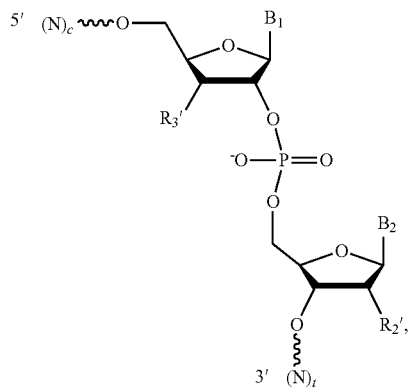

or a pharmaceutically acceptable salt thereof, wherein the 2'-5' phosphodiester linkage depicted in the formula is between two nucleotides in the duplex. In some embodiments, the guide molecule is of formula:

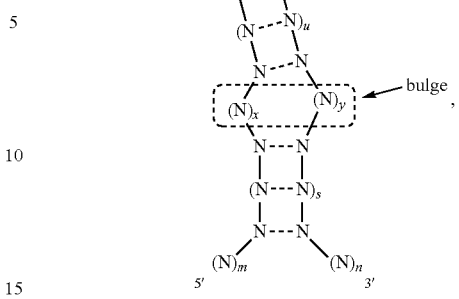

or a pharmaceutically acceptable salt thereof, wherein at least one phosphodiester linkage between two nucleotides in a duplex region depicted in the formula is a 2'-5' phosphodiester linkage. In some embodiments, the 2'-5' phosphodiester linkage is between two nucleotides that are located 5' of the bulge. In some embodiments, the 2'-5' phosphodiester linkage is between two nucleotides that are located 5' of the nucleotide loop Z and 3' of the bulge. In some embodiments, the 2'-5' phosphodiester linkage is between two nucleotides that are located 3' of the nucleotide loop Z and 5' of the bulge. In some embodiments, the 2'-5' phosphodiester linkage is between two nucleotides that are located 3' of the bulge.

Guide Molecule Design

Methods for selection and validation of target sequences as well as off-target analyses have been described previously, e.g., in Mali; Hsu; Fu et al., 2014 Nat biotechnol 32 (3): 279-84, Heigwer et al., 2014 Nat methods 11 (2): 122-3; Bae et al. (2014) Bioinformatics 30 (10): 1473-5; and Xiao A et al. (2014) Bioinformatics 30 (8): 1180-1182. Each of these references is incorporated by reference herein. As a non-limiting example, guide molecule design may involve the use of a software tool to optimize the choice of potential target sequences corresponding to a user's target sequence, e.g., to minimize total off-target activity across the genome. While off-target activity is not limited to cleavage, the cleavage efficiency at each off-target sequence can be predicted, e.g., using an experimentally-derived weighting scheme. These and other guide selection methods are described in detail in Maeder and Cotta-Ramusino.

The stem loop structure and position of a chemical linkage in a synthetic unimolecular guide molecule may also be designed. The inventors recognized the value of using Gibbs free energy differences (ΔG) to predict the ligation efficiency of chemical conjugation reactions. Calculation of ΔG is performed using OligoAnalyzer (available at www.idtdna.com/calc/analyzer) or similar tools. Comparison of ΔG of heterodimerization to form the desired annealed duplex and ΔG of homodimerization of two identical oligonucleotides may predict the experimental outcome of chemical conjugation. When ΔG of heterodimerization is less than ΔG of homodimerization, ligation efficiency is predicted to be high. This prediction method is explained further in Example 8.

Guide Molecule Modifications

The activity, stability, or other characteristics of guide molecules can be altered through the incorporation of certain modifications. As one example, transiently expressed or delivered nucleic acids can be prone to degradation by, e.g., cellular nucleases. Accordingly, the guide molecules described herein can contain one or more modified nucleosides or nucleotides which introduce stability toward nucleases. While not wishing to be bound by theory it is also believed that certain modified guide molecules described herein can exhibit a reduced innate immune response when introduced into cells. Those of skill in the art will be aware of certain cellular responses commonly observed in cells, e.g., mammalian cells, in response to exogenous nucleic acids, particularly those of viral or bacterial origin. Such responses, which can include induction of cytokine expression and release and cell death, may be reduced or eliminated altogether by the modifications presented herein.

Certain exemplary modifications discussed in this section can be included at any position within a guide molecule sequence including, without limitation at or near the 5' end (e.g., within 1-10, 1-5, 1-3, or 1-2 nucleotides of the 5' end) and/or at or near the 3' end (e.g., within 1-10, 1-5, 1-3, or 1-2 nucleotides of the 3' end). In some cases, modifications are positioned within functional motifs, such as the repeat-antirepeat duplex of a Cas9 guide molecule, a stem loop structure of a Cas9 or Cpf1 guide molecule, and/or a targeting domain of a guide molecule.

As one example, the 5' end of a guide molecule can include a eukaryotic mRNA cap structure or cap analog (e.g., a G(5')ppp(5')G cap analog, a m7G(5')ppp(5')G cap analog, or a 3'-O-Me-m7G(5')ppp(5')G anti reverse cap analog (ARCA)), as shown below:

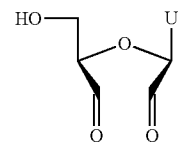

wherein "U" can be an unmodified or modified uridine.

The 3' terminal U ribose can be modified with a 2'3' cyclic phosphate as shown below:

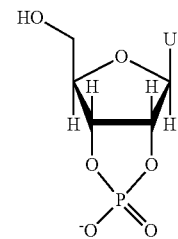

wherein "U" can be an unmodified or modified uridine.

Guide molecules can contain 3' nucleotides which can be stabilized against degradation, e.g., by incorporating one or more of the modified nucleotides described herein. In certain embodiments, uridines can be replaced with modified uridines, e.g., 5-(2-amino) propyl uridine, and 5-bromo uridine,

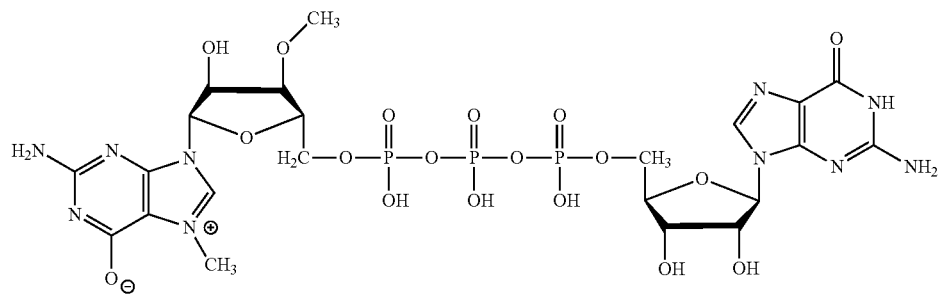

The cap or cap analog can be included during either chemical or enzymatic synthesis of the guide molecule.

Along similar lines, the 5' end of the guide molecule can lack a 5' triphosphate group. For instance, in vitro transcribed guide molecules can be phosphatase-treated (e.g., using calf intestinal alkaline phosphatase) to remove a 5' triphosphate group.

Another common modification involves the addition, at the 3' end of a guide molecule, of a plurality (e.g., 1-10, 10-20, or 25-200) of adenine (A) residues referred to as a polyA tract. The polyA tract can be added to a guide molecule during chemical or enzymatic synthesis, using a polyadenosine polymerase (e.g., E. coli Poly(A)Polymerase).

Guide RNAs can be modified at a 3' terminal U ribose. For example, the two terminal hydroxyl groups of the U ribose can be oxidized to aldehyde groups and a concomitant opening of the ribose ring to afford a modified nucleoside as shown below:

or with any of the modified uridines described herein; adenosines and guanosines can be replaced with modified adenosines and guanosines, e.g., with modifications at the 8-position, e.g., 8-bromo guanosine, or with any of the modified adenosines or guanosines described herein.

In some embodiments, sugar-modified ribonucleotides can be incorporated into the guide molecule, e.g., wherein the 2'-OH group is replaced by a group selected from H, —OR, —R (wherein R can be, e.g., alkyl, cycloalkyl, aryl, aralkyl, heteroaryl or sugar), halo, —SH, —SR (wherein R can be, e.g., alkyl, cycloalkyl, aryl, aralkyl, heteroaryl or sugar), amino (wherein amino can be, e.g., NH$_2$, alkylamino, dialkylamino, heterocyclyl, arylamino, diarylamino, heteroarylamino, diheteroarylamino, or amino acid), or cyano (—CN). In some embodiments, the phosphate backbone can be modified as described herein, e.g., with a phosphorothioate (PhTx) group. In some embodiments, one or more of the nucleotides of the guide molecule can each independently be a modified or unmodified nucleotide including, but not limited to 2'-sugar modified, such as, 2'-O-methyl, 2'-O-methoxyethyl, or 2'-Fluoro modified including, e.g., 2'-F or 2'-O-methyl, adenosine (A), 2'-F or 2'-O-methyl, cytidine (C), 2'-F or 2'-O-methyl, uridine (U), 2'-F or 2'-O-methyl, thymidine (T), 2'-F or 2'-O-methyl, guanosine (G), 2'-O-methoxyethyl-5-methyluridine (Teo), 2'-O-methoxyethyladenosine (Aeo), 2'-O-methoxyethyl-5-methylcytidine (m5Ceo), and any combinations thereof.

Guide molecules can also include "locked" nucleic acids (LNA) in which the 2'-OH group can be connected, e.g., by a $C_{1-6}$ alkylene or $C_{1-6}$ heteroalkylene bridge, to the 4' carbon of the same ribose sugar. Any suitable moiety can be used to provide such bridges, include without limitation methylene, propylene, ether, or amino bridges; O-amino (wherein amino can be, e.g., $NH_2$, alkylamino, dialkylamino, heterocyclyl, arylamino, diarylamino, heteroarylamino, or diheteroarylamino, ethylenediamine, or polyamino), aminoalkoxy and $O(CH_2)_n$-amino (wherein amino can be, e.g., $NH_2$, alkylamino, dialkylamino, heterocyclyl, arylamino, diarylamino, heteroarylamino, or diheteroarylamino, ethylenediamine, or polyamino).

In some embodiments, a guide molecule can include a modified nucleotide which is multicyclic (e.g., tricyclo and "unlocked" forms, such as glycol nucleic acid (GNA) (e.g., R-GNA or S-GNA, where ribose is replaced by glycol units attached to phosphodiester bonds), or threose nucleic acid (TNA, where ribose is replaced with α-L-threofuranosyl-(3'→2')).

Generally, guide molecules include a sugar group ribose, which is a 5-membered ring having an oxygen. Exemplary modified guide molecules can include, without limitation, replacement of the oxygen in ribose (e.g., with sulfur(S), selenium (Se), or alkylene, such as, e.g., methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for example, anhydrohexitol, altritol, mannitol, cyclohexanyl, cyclohexenyl, and morpholino that also has a phosphoramidate backbone). Although the majority of sugar analog alterations are localized to the 2' position, other sites are amenable to modification, including the 4' position. In certain embodiments, a guide molecule comprises a 4'-S, 4'-Se or a 4'-C-aminomethyl-2'-O-Me modification.

In some embodiments, deaza nucleotides, e.g., 7-deazaadenosine, can be incorporated into the guide molecule. In some embodiments, O- and N-alkylated nucleotides, e.g., N6-methyl adenosine, can be incorporated into the guide molecule. In certain embodiments, one or more, or all of the nucleotides in a guide molecule are deoxynucleotides.

Nucleotides of a guide molecule may also be modified at the phosphodiester linkage. Such modifications may include phosphonoacetate, phosphorothioate, thiophosphonoacetate, or phosphoroamidate linkages. In some embodiments, a nucleotide may be linked to its adjacent nucleotide via a phosphorothioate linkage. Furthermore, modifications to the phosphodiester linkage may be the sole modification to a nucleotide or may be combined with other nucleotide modifications described above. For example, a modified phosphodiester linkage can be combined with a modification to the sugar group of a nucleotide. In some embodiments, one or more 5' or 3' nucleotides comprise a 2'-OMe modified ribonucleotide residue that is linked to its adjacent nucleotide(s) via a phosphorothioate linkage.

RNA-Guided Nucleases

RNA-guided nucleases according to the present disclosure include, but are not limited to, naturally-occurring Class 2 CRISPR nucleases such as Cas9, and Cpf1, as well as other nucleases derived or obtained therefrom. In functional terms, RNA-guided nucleases are defined as those nucleases that: (a) interact with (e.g., complex with) a guide molecule (e.g., gRNA); and (b) together with the guide molecule (e.g., gRNA), associate with, and optionally cleave or modify, a target region of a DNA that includes (i) a sequence complementary to the targeting domain of the guide molecule (e.g., gRNA) and, optionally, (ii) an additional sequence referred to as a "protospacer adjacent motif," or "PAM," which is described in greater detail below. As the following examples will illustrate, RNA-guided nucleases can be defined, in broad terms, by their PAM specificity and cleavage activity, even though variations may exist between individual RNA-guided nucleases that share the same PAM specificity or cleavage activity. Skilled artisans will appreciate that some aspects of the present disclosure relate to systems, methods and compositions that can be implemented using any suitable RNA-guided nuclease having a certain PAM specificity and/or cleavage activity. For this reason, unless otherwise specified, the term RNA-guided nuclease should be understood as a generic term, and not limited to any particular type (e.g. Cas9 vs. Cpf1), species (e.g. S. pyogenes vs. S. aureus) or variation (e.g., full-length vs. truncated or split; naturally-occurring PAM specificity vs. engineered PAM specificity, etc.) of RNA-guided nuclease.

The PAM sequence takes its name from its sequential relationship to the "protospacer" sequence that is complementary to guide molecule targeting domains (or "spacers"). Together with protospacer sequences, PAM sequences define target regions or sequences for specific RNA-guided nuclease/guide molecule combinations.

Various RNA-guided nucleases may require different sequential relationships between PAMs and protospacers. In general, Cas9s recognize PAM sequences that are 3' of the protospacer as visualized relative to the guide molecule.

Cpf1, on the other hand, generally recognizes PAM sequences that are 5' of the protospacer as visualized relative to the guide molecule.

In addition to recognizing specific sequential orientations of PAMs and protospacers, RNA-guided nucleases can also recognize specific PAM sequences. S. aureus Cas9, for instance, recognizes a PAM sequence of NNGRRT or NNGRRV, wherein the N residues are immediately 3' of the region recognized by the guide molecule targeting domain. S. pyogenes Cas9 recognizes NGG PAM sequences. And F. novicida Cpf1 recognizes a TTN PAM sequence. PAM sequences have been identified for a variety of RNA-guided nucleases, and a strategy for identifying novel PAM sequences has been described by Shmakov et al., 2015, Molecular Cell 60, 385-397, Nov. 5, 2015. It should also be noted that engineered RNA-guided nucleases can have PAM specificities that differ from the PAM specificities of reference molecules (for instance, in the case of an engineered RNA-guided nuclease, the reference molecule may be the naturally occurring variant from which the RNA-guided nuclease is derived, or the naturally occurring variant having the greatest amino acid sequence homology to the engineered RNA-guided nuclease).

In addition to their PAM specificity, RNA-guided nucleases can be characterized by their DNA cleavage activity: naturally-occurring RNA-guided nucleases typically form DSBs in target nucleic acids, but engineered variants have been produced that generate only SSBs (discussed above) Ran & Hsu, et al., Cell 154 (6), 1380-1389 Sep. 12, 2013 (Ran), incorporated by reference herein), or that that do not cut at all.

Cas9

Crystal structures have been determined for S. pyogenes Cas9 (Jinek 2014), and for S. aureus Cas9 in complex with a unimolecular guide RNA and a target DNA (Nishimasu 2014; Anders 2014; and Nishimasu 2015).

A naturally occurring Cas9 protein comprises two lobes: a recognition (REC) lobe and a nuclease (NUC) lobe; each of which comprise particular structural and/or functional domains. The REC lobe comprises an arginine-rich bridge helix (BH) domain, and at least one REC domain (e.g. a REC1 domain and, optionally, a REC2 domain). The REC lobe does not share structural similarity with other known proteins, indicating that it is a unique functional domain. While not wishing to be bound by any theory, mutational analyses suggest specific functional roles for the BH and REC domains: the BH domain appears to play a role in guide molecule: DNA recognition, while the REC domain is thought to interact with the repeat:anti-repeat duplex of the guide molecule and to mediate the formation of the Cas9/guide molecule complex.

The NUC lobe comprises a RuvC domain, an HNH domain, and a PAM-interacting (PI) domain. The RuvC domain shares structural similarity to retroviral integrase superfamily members and cleaves the non-complementary (i.e. bottom) strand of the target nucleic acid. It may be formed from two or more split RuvC motifs (such as RuvC I, RuvCII, and RuvCIII in S. pyogenes and S. aureus). The HNH domain, meanwhile, is structurally similar to HNN endonuclease motifs, and cleaves the complementary (i.e. top) strand of the target nucleic acid. The PI domain, as its name suggests, contributes to PAM specificity.

While certain functions of Cas9 are linked to (but not necessarily fully determined by) the specific domains set forth above, these and other functions may be mediated or influenced by other Cas9 domains, or by multiple domains on either lobe. For instance, in S. pyogenes Cas9, as described in Nishimasu 2014, the repeat:antirepeat duplex of the guide molecule falls into a groove between the REC and NUC lobes, and nucleotides in the duplex interact with amino acids in the BH, PI, and REC domains. Some nucleotides in the first stem loop structure also interact with amino acids in multiple domains (PI, BH and REC1), as do some nucleotides in the second and third stem loops (RuvC and PI domains).

Cpf1

The crystal structure of Acidaminococcus sp. Cpf1 in complex with crRNA and a double-stranded (ds) DNA target including a TTTN PAM sequence has been solved by Yamano et al. (Cell. 2016 May 5; 165 (4): 949-962 (Yamano), incorporated by reference herein). Cpf1, like Cas9, has two lobes: a REC (recognition) lobe, and a NUC (nuclease) lobe. The REC lobe includes REC1 and REC2 domains, which lack similarity to any known protein structures. The NUC lobe, meanwhile, includes three RuvC domains (RuvC-I, -II and -III) and a BH domain. However, in contrast to Cas9, the Cpf1 REC lobe lacks an HNH domain, and includes other domains that also lack similarity to known protein structures: a structurally unique PI domain, three Wedge (WED) domains (WED-I, -II and -III), and a nuclease (Nuc) domain.

While Cas9 and Cpf1 share similarities in structure and function, it should be appreciated that certain Cpf1 activities are mediated by structural domains that are not analogous to any Cas9 domains. For instance, cleavage of the complementary strand of the target DNA appears to be mediated by the Nuc domain, which differs sequentially and spatially from the HNH domain of Cas9. Additionally, the non-targeting portion of Cpf1 guide molecule (the handle) adopts a pseudonot structure, rather than a stem loop structure formed by the repeat: antirepeat duplex in Cas9 guide molecules.

Modifications of RNA-Guided Nucleases

The RNA-guided nucleases described above have activities and properties that can be useful in a variety of applications, but the skilled artisan will appreciate that RNA-guided nucleases can also be modified in certain instances, to alter cleavage activity, PAM specificity, or other structural or functional features.

Turning first to modifications that alter cleavage activity, mutations that reduce or eliminate the activity of domains within the NUC lobe have been described above. Exemplary mutations that may be made in the RuvC domains, in the Cas9 HNH domain, or in the Cpf1 Nuc domain are described in Ran and Yamano, as well as in Cotta-Ramusino. In general, mutations that reduce or eliminate activity in one of the two nuclease domains result in RNA-guided nucleases with nickase activity, but it should be noted that the type of nickase activity varies depending on which domain is inactivated. As one example, inactivation of a RuvC domain of a Cas9 will result in a nickase that cleaves the complementary or top strand.

On the other hand, inactivation of a Cas9 HNH domain results in a nickase that cleaves the bottom or non-complementary strand.

Modifications of PAM specificity relative to naturally occurring Cas9 reference molecules has been described by Kleinstiver et al. for both S. pyogenes (Kleinstiver et al., Nature. 2015 Jul. 23; 523 (7561): 481-5 (Kleinstiver I) and S. aureus (Kleinstiver et al., Nat Biotechnol. 2015 December; 33 (12): 1293-1298 (Klienstiver II)). Kleinstiver et al. have also described modifications that improve the targeting fidelity of Cas9 (Nature, 2016 Jan. 28; 529, 490-495 (Kleinstiver III)). Each of these references is incorporated by reference herein.

RNA-guided nucleases have been split into two or more parts, as described by Zetsche et al. (Nat Biotechnol. 2015 February; 33 (2): 139-42 (Zetsche II), incorporated by reference), and by Fine et al. (Sci Rep. 2015 Jul. 1; 5:10777 (Fine), incorporated by reference).

RNA-guided nucleases can be, in certain embodiments, size-optimized or truncated, for instance via one or more deletions that reduce the size of the nuclease while still retaining guide molecule association, target and PAM recognition, and cleavage activities. In certain embodiments, RNA guided nucleases are bound, covalently or non-covalently, to another polypeptide, nucleotide, or other structure, optionally by means of a linker. Exemplary bound nucleases and linkers are described by Guilinger et al., Nature Biotechnology 32, 577-582 (2014), which is incorporated by reference for all purposes herein.

RNA-guided nucleases also optionally include a tag, such as, but not limited to, a nuclear localization signal to facilitate movement of RNA-guided nuclease protein into the nucleus. In certain embodiments, the RNA-guided nuclease can incorporate C- and/or N-terminal nuclear localization signals. Nuclear localization sequences are known in the art and are described in Maeder and elsewhere.

The foregoing list of modifications is intended to be exemplary in nature, and the skilled artisan will appreciate, in view of the instant disclosure, that other modifications may be possible or desirable in certain applications. For brevity, therefore, exemplary systems, methods and compositions of the present disclosure are presented with reference to particular RNA-guided nucleases, but it should be understood that the RNA-guided nucleases used may be modified in ways that do not alter their operating principles. Such modifications are within the scope of the present disclosure.
Nucleic Acids Encoding RNA-Guided Nucleases Nucleic acids encoding RNA-guided nucleases, e.g., Cas9, Cpf1 or functional fragments thereof, are provided herein. Exemplary nucleic acids encoding RNA-guided nucleases have been described previously (see, e.g., Cong 2013; Wang 2013; Mali 2013; Jinek 2012).

In some cases, a nucleic acid encoding an RNA-guided nuclease can be a synthetic nucleic acid sequence. For example, the synthetic nucleic acid molecule can be chemically modified. In certain embodiments, an mRNA encoding an RNA-guided nuclease will have one or more (e.g., all) of the following properties: it can be capped; polyadenylated; and substituted with 5-methylcytidine and/or pseudouridine.

Synthetic nucleic acid sequences can also be codon optimized, e.g., at least one non-common codon or less-common codon has been replaced by a common codon. For example, the synthetic nucleic acid can direct the synthesis of an optimized messenger mRNA, e.g., optimized for expression in a mammalian expression system, e.g., described herein. Examples of codon optimized Cas9 coding sequences are presented in Cotta-Ramusino.

In addition, or alternatively, a nucleic acid encoding an RNA-guided nuclease may comprise a nuclear localization sequence (NLS). Nuclear localization sequences are known in the art.
Functional Analysis of Candidate Molecules Candidate RNA-guided nucleases, guide molecules, and complexes thereof, can be evaluated by standard methods known in the art. See, e.g. Cotta-Ramusino. The stability of RNP complexes may be evaluated by differential scanning fluorimetry, as described below.
Differential Scanning Fluorimetry (DSF)

The thermostability of ribonucleoprotein (RNP) complexes comprising guide molecules and RNA-guided nucleases can be measured via DSF. The DSF technique measures the thermostability of a protein, which can increase under favorable conditions such as the addition of a binding RNA molecule, e.g., a guide molecule.

A DSF assay can be performed according to any suitable protocol, and can be employed in any suitable setting, including without limitation (a) testing different conditions (e.g., different stoichiometric ratios of guide molecule:RNA-guided nuclease protein, different buffer solutions, etc.) to identify optimal conditions for RNP formation; and (b) testing modifications (e.g. chemical modifications, alterations of sequence, etc.) of an RNA-guided nuclease and/or a guide molecule to identify those modifications that improve RNP formation or stability. One readout of a DSF assay is a shift in melting temperature of the RNP complex; a relatively high shift suggests that the RNP complex is more stable (and may thus have greater activity or more favorable kinetics of formation, kinetics of degradation, or another functional characteristic) relative to a reference RNP complex characterized by a lower shift. When the DSF assay is deployed as a screening tool, a threshold melting temperature shift may be specified, so that the output is one or more RNPs having a melting temperature shift at or above the threshold. For instance, the threshold can be 5-10° C. (e.g. 5° C., 6° C., 7° C., 8° C., 9° C., 10° C.) or more, and the output may be one or more RNPs characterized by a melting temperature shift greater than or equal to the threshold.

Two non-limiting examples of DSF assay conditions are set forth below:

To determine the best solution to form RNP complexes, a fixed concentration (e.g. 2 μM) of Cas9 in water+10× SYPRO OrangeR (Life Technologies cat #S-6650) is dispensed into a 384 well plate. An equimolar amount of guide molecule diluted in solutions with varied pH and salt is then added. After incubating at room temperature for 10' and brief centrifugation to remove any bubbles, a Bio-Rad CFX384™ Real-Time System C1000 Touch™ Thermal Cycler with the Bio-Rad CFX Manager software is used to run a gradient from 20° C. to 90° C. with a 1° C. increase in temperature every 10 seconds.

The second assay consists of mixing various concentrations of guide molecule with fixed concentration (e.g. 2 μM) Cas9 in optimal buffer from assay 1 above and incubating (e.g. at RT for 10') in a 384 well plate. An equal volume of optimal buffer+10×SYPRO Orange® (Life Technologies cat #S-6650) is added and the plate sealed with Microseal® B adhesive (MSB-1001). Following brief centrifugation to remove any bubbles, a Bio-Rad CFX384™ Real-Time System C1000 Touch™ Thermal Cycler with the Bio-Rad CFX Manager software is used to run a gradient from 20° C. to 90° C. with a 1° C. increase in temperature every 10 seconds.
Genome Editing Strategies The genome editing systems described above are used, in various embodiments of the present disclosure, to generate edits in (i.e. to alter) targeted regions of DNA within or obtained from a cell. Various strategies are described herein to generate particular edits, and these strategies are generally described in terms of the desired repair outcome, the number and positioning of individual edits (e.g. SSBs or DSBs), and the target sites of such edits.

Genome editing strategies that involve the formation of SSBs or DSBs are characterized by repair outcomes including: (a) deletion of all or part of a targeted region; (b) insertion into or replacement of all or part of a targeted region; or (c) interruption of all or part of a targeted region. This grouping is not intended to be limiting, or to be binding to any particular theory or model, and is offered solely for economy of presentation. Skilled artisans will appreciate that the listed outcomes are not mutually exclusive and that some repairs may result in other outcomes. The description of a particular editing strategy or method should not be understood to require a particular repair outcome unless otherwise specified.

Replacement of a targeted region generally involves the replacement of all or part of the existing sequence within the targeted region with a homologous sequence, for instance through gene correction or gene conversion, two repair outcomes that are mediated by HDR pathways. HDR is promoted by the use of a donor template, which can be single-stranded or double-stranded, as described in greater detail below. Single or double stranded templates can be exogenous, in which case they will promote gene correction, or they can be endogenous (e.g. a homologous sequence within the cellular genome), to promote gene conversion. Exogenous templates can have asymmetric overhangs (i.e. the portion of the template that is complementary to the site of the DSB may be offset in a 3' or 5' direction, rather than being centered within the donor template), for instance as described by Richardson et al. (Nature Biotechnology 34, 339-344 (2016), (Richardson), incorporated by reference). In instances where the template is single stranded, it can correspond to either the complementary (top) or non-complementary (bottom) strand of the targeted region.

Gene conversion and gene correction are facilitated, in some cases, by the formation of one or more nicks in or around the targeted region, as described in Ran and Cotta-Ramusino. In some cases, a dual-nickase strategy is used to form two offset SSBs that, in turn, form a single DSB having an overhang (e.g. a 5' overhang).

Interruption and/or deletion of all or part of a targeted sequence can be achieved by a variety of repair outcomes. As one example, a sequence can be deleted by simultaneously generating two or more DSBs that flank a targeted region, which is then excised when the DSBs are repaired, as is described in Maeder for the LCA10 mutation. As another example, a sequence can be interrupted by a deletion generated by formation of a double strand break with single-stranded overhangs, followed by exonucleolytic processing of the overhangs prior to repair.

One specific subset of target sequence interruptions is mediated by the formation of an indel within the targeted sequence, where the repair outcome is typically mediated by NHEJ pathways (including Alt-NHEJ). NHEJ is referred to as an "error prone" repair pathway because of its association with indel mutations. In some cases, however, a DSB is repaired by NHEJ without alteration of the sequence around it (a so-called "perfect" or "scarless" repair); this generally requires the two ends of the DSB to be perfectly ligated. Indels, meanwhile, are thought to arise from enzymatic processing of free DNA ends before they are ligated that adds and/or removes nucleotides from either or both strands of either or both free ends.

Because the enzymatic processing of free DSB ends may be stochastic in nature, indel mutations tend to be variable, occurring along a distribution, and can be influenced by a variety of factors, including the specific target site, the cell type used, the genome editing strategy used, etc. Even so, it is possible to draw limited generalizations about indel formation: deletions formed by repair of a single DSB are most commonly in the 1-50 bp range, but can reach greater than 100-200 bp. Insertions formed by repair of a single DSB tend to be shorter and often include short duplications of the sequence immediately surrounding the break site. However, it is possible to obtain large insertions, and in these cases, the inserted sequence has often been traced to other regions of the genome or to plasmid DNA present in the cells.

Indel mutations—and genome editing systems configured to produce indels—are useful for interrupting target sequences, for example, when the generation of a specific final sequence is not required and/or where a frameshift mutation would be tolerated. They can also be useful in settings where particular sequences are preferred, insofar as the certain sequences desired tend to occur preferentially from the repair of an SSB or DSB at a given site. Indel mutations are also a useful tool for evaluating or screening the activity of particular genome editing systems and their components. In these and other settings, indels can be characterized by (a) their relative and absolute frequencies in the genomes of cells contacted with genome editing systems and (b) the distribution of numerical differences relative to the unedited sequence, e.g. ±1, ±2, ±3, etc. As one example, in a lead-finding setting, multiple guide molecules can be screened to identify those guide molecules that most efficiently drive cutting at a target site based on an indel readout under controlled conditions. Guides that produce indels at or above a threshold frequency, or that produce a particular distribution of indels, can be selected for further study and development. Indel frequency and distribution can also be useful as a readout for evaluating different genome editing system implementations or formulations and delivery methods, for instance by keeping the guide molecule constant and varying certain other reaction conditions or delivery methods.

Multiplex Strategies

While exemplary strategies discussed above have focused on repair outcomes mediated by single DSBs, genome editing systems according to this disclosure may also be employed to generate two or more DSBs, either in the same locus or in different loci. Strategies for editing that involve the formation of multiple DSBs, or SSBs, are described in, for instance, Cotta-Ramusino.

Donor Template Design

Donor template design is described in detail in the literature, for instance in Cotta-Ramusino. DNA oligomer donor templates (oligodeoxynucleotides or ODNs), which can be single stranded (ssODNs) or double-stranded (dsODNs), can be used to facilitate HDR-based repair of DSBs, and are particularly useful for introducing alterations into a target DNA sequence, inserting a new sequence into the target sequence, or replacing the target sequence altogether.

Whether single-stranded or double stranded, donor templates generally include regions that are homologous to regions of DNA within or near (e.g. flanking or adjoining) a target sequence to be cleaved. These homologous regions are referred to here as "homology arms," and are illustrated schematically below:

[5' homology arm]—[replacement sequence]—[3' homology arm].

The homology arms can have any suitable length (including 0 nucleotides if only one homology arm is used), and 3' and 5' homology arms can have the same length, or can differ in length. The selection of appropriate homology arm lengths can be influenced by a variety of factors, such as the desire to avoid homologies or microhomologies with certain sequences such as Alu repeats or other very common elements. For example, a 5' homology arm can be shortened to avoid a sequence repeat element. In other embodiments, a 3' homology arm can be shortened to avoid a sequence repeat element. In some embodiments, both the 5' and the 3' homology arms can be shortened to avoid including certain sequence repeat elements. In addition, some homology arm designs can improve the efficiency of editing or increase the frequency of a desired repair outcome. For example, Richardson et al. Nature Biotechnology 34, 339-344 (2016) (Richardson), which is incorporated by reference, found that the relative asymmetry of 3' and 5' homology arms of single stranded donor templates influenced repair rates and/or outcomes.

Replacement sequences in donor templates have been described elsewhere, including in Cotta-Ramusino et al. A replacement sequence can be any suitable length (including zero nucleotides, where the desired repair outcome is a deletion), and typically includes one, two, three or more sequence modifications relative to the naturally-occurring sequence within a cell in which editing is desired. One common sequence modification involves the alteration of the naturally-occurring sequence to repair a mutation that is related to a disease or condition of which treatment is desired. Another common sequence modification involves the alteration of one or more sequences that are complementary to, or code for, the PAM sequence of the RNA-guided nuclease or the targeting domain of the guide molecule(s) being used to generate an SSB or DSB, to reduce or eliminate repeated cleavage of the target site after the replacement sequence has been incorporated into the target site.

Where a linear ssODN is used, it can be configured to (i) anneal to the nicked strand of the target nucleic acid, (ii) anneal to the intact strand of the target nucleic acid, (iii) anneal to the plus strand of the target nucleic acid, and/or (iv) anneal to the minus strand of the target nucleic acid. An ssODN may have any suitable length, e.g., about, at least, or no more than 150-200 nucleotides (e.g., 150, 160, 170, 180, 190, or 200 nucleotides).

It should be noted that a template nucleic acid can also be a nucleic acid vector, such as a viral genome or circular double stranded DNA, e.g., a plasmid. Nucleic acid vectors comprising donor templates can include other coding or non-coding elements. For example, a template nucleic acid can be delivered as part of a viral genome (e.g., in an AAV or lentiviral genome) that includes certain genomic backbone elements (e.g., inverted terminal repeats, in the case of an AAV genome) and optionally includes additional sequences coding for a guide molecule and/or an RNA-guided nuclease. In some embodiments, the donor template can be adjacent to, or flanked by, target sites recognized by one or more guide molecules, to facilitate the formation of free DSBs on one or both ends of the donor template that can participate in repair of corresponding SSBs or DSBs formed in cellular DNA using the same guide molecules. Exemplary nucleic acid vectors suitable for use as donor templates are described in Cotta-Ramusino.

Whatever format is used, a template nucleic acid can be designed to avoid undesirable sequences. In certain embodiments, one or both homology arms can be shortened to avoid overlap with certain sequence repeat elements, e.g., Alu repeats, LINE elements, etc.

Target Cells

Genome editing systems according to this disclosure can be used to manipulate or alter a cell, e.g., to edit or alter a target nucleic acid. The manipulating can occur, in various embodiments, in vivo or ex vivo.

A variety of cell types can be manipulated or altered according to the embodiments of this disclosure, and in some cases, such as in vivo applications, a plurality of cell types are altered or manipulated, for example by delivering genome editing systems according to this disclosure to a plurality of cell types. In other cases, however, it may be desirable to limit manipulation or alteration to a particular cell type or types. For instance, it can be desirable in some instances to edit a cell with limited differentiation potential or a terminally differentiated cell, such as a photoreceptor cell in the case of Maeder, in which modification of a genotype is expected to result in a change in cell phenotype. In other cases, however, it may be desirable to edit a less differentiated, multipotent or pluripotent, stem or progenitor cell. By way of example, the cell may be an embryonic stem cell, induced pluripotent stem cell (iPSC), hematopoietic stem/progenitor cell (HSPC), or other stem or progenitor cell type that differentiates into a cell type of relevance to a given application or indication.

As a corollary, the cell being altered or manipulated is, variously, a dividing cell or a non-dividing cell, depending on the cell type(s) being targeted and/or the desired editing outcome.

When cells are manipulated or altered ex vivo, the cells can be used (e.g. administered to a subject) immediately, or they can be maintained or stored for later use. Those of skill in the art will appreciate that cells can be maintained in culture or stored (e.g. frozen in liquid nitrogen) using any suitable method known in the art.

Implementation of Genome Editing Systems: Delivery, Formulations, and Routes of Administration As discussed above, the genome editing systems of this disclosure can be implemented in any suitable manner, meaning that the components of such systems, including without limitation the RNA-guided nuclease, guide molecule, and optional donor template nucleic acid, can be delivered, formulated, or administered in any suitable form or combination of forms that results in the transduction, expression or introduction of a genome editing system and/or causes a desired repair outcome in a cell, tissue or subject. Tables 12 and 13 set forth several, non-limiting examples of genome editing system implementations. Those of skill in the art will appreciate, however, that these listings are not comprehensive, and that other implementations are possible. With reference to Table 12 in particular, the table lists several exemplary implementations of a genome editing system comprising a single guide molecule and an optional donor template. However, genome editing systems according to this disclosure can incorporate multiple guide molecules, multiple RNA-guided nucleases, and other components such as proteins, and a variety of implementations will be evident to the skilled artisan based on the principles illustrated in the table. In the table, [N/A] indicates that the genome editing system does not include the indicated component.

TABLE 12

Genome Editing System Components

| RNA-guided Nuclease | Guide molecule | Donor Template | Comments |
|---|---|---|---|
| Protein | RNA | [N/A] | An RNA-guided nuclease protein complexed with a gRNA molecule (an RNP complex) |
| Protein | RNA | DNA | An RNP complex as described above plus a single-stranded or double stranded donor template. |
| Protein | DNA | [N/A] | An RNA-guided nuclease protein plus gRNA transcribed from DNA. |
| Protein | DNA | DNA | An RNA-guided nuclease protein plus gRNA-encoding DNA and a separate DNA donor template. |
| Protein | DNA | | An RNA-guided nuclease protein and a single DNA encoding both a gRNA and a donor template. |
| | DNA | | A DNA or DNA vector encoding an RNA-guided nuclease, a gRNA and a donor template. |
| DNA | DNA | [N/A] | Two separate DNAs, or two separate DNA vectors, encoding the RNA-guided nuclease and the gRNA, respectively. |
| DNA | DNA | DNA | Three separate DNAs, or three separate DNA vectors, encoding the RNA-guided nuclease, the gRNA and the donor template, respectively. |
| DNA | | [N/A] | A DNA or DNA vector encoding an RNA-guided nuclease and a gRNA |
| DNA | | DNA | A first DNA or DNA vector encoding an RNA-guided nuclease and a gRNA, and a second DNA or DNA vector encoding a donor template. |
| DNA | DNA | | A first DNA or DNA vector encoding an RNA-guided nuclease and second DNA or DNA vector encoding a gRNA and a donor template. |
| | DNA | DNA | A first DNA or DNA vector encoding an RNA-guided nuclease and a donor template, and a second DNA or DNA vector encoding a gRNA |
| | DNA | RNA | A DNA or DNA vector encoding an RNA-guided nuclease and a donor template, and a gRNA |
| RNA | | [N/A] | An RNA or RNA vector encoding an RNA-guided nuclease and comprising a gRNA |

TABLE 12-continued

Genome Editing System Components

| RNA-guided Nuclease | Guide molecule | Donor Template | Comments |
|---|---|---|---|
| RNA | | DNA | An RNA or RNA vector encoding an RNA-guided nuclease and comprising a gRNA, and a DNA or DNA vector encoding a donor template. |

Table 13 summarizes various delivery methods for the components of genome editing systems, as described herein. Again, the listing is intended to be exemplary rather than limiting.

TABLE 13

| Delivery Vector/Mode | | Delivery into Non-Dividing Cells | Duration of Expression | Genome Integration | Type of Molecule Delivered |
|---|---|---|---|---|---|
| Physical (e.g., electroporation, particle gun, Calcium Phosphate transfection, cell compression or squeezing) | | YES | Transient | NO | Nucleic Acids and Proteins |
| Viral | Retrovirus | NO | Stable | YES | RNA |
| | Lentivirus | YES | Stable | YES/NO with modifications | RNA |
| | Adenovirus | YES | Transient | NO | DNA |
| | Adeno-Associated Virus (AAV) | YES | Stable | NO | DNA |
| | Vaccinia Virus | YES | Very Transient | NO | DNA |
| | Herpes Simplex Virus | YES | Stable | NO | DNA |
| Non-Viral | Cationic Liposomes | YES | Transient | Depends on what is delivered | Nucleic Acids and Proteins |
| | Polymeric Nanoparticles | YES | Transient | Depends on what is delivered | Nucleic Acids and Proteins |
| Biological Non-Viral Delivery Vehicles | Attenuated Bacteria | YES | Transient | NO | Nucleic Acids |
| | Engineered Bacteriophages | YES | Transient | NO | Nucleic Acids |
| | Mammalian Virus-like Particles | YES | Transient | NO | Nucleic Acids |
| | Biological liposomes: Erythrocyte Ghosts and Exosomes | YES | Transient | NO | Nucleic Acids |

Nucleic Acid-Based Delivery of Genome Editing Systems

Nucleic acids encoding the various elements of a genome editing system according to the present disclosure can be administered to subjects or delivered into cells by art-known methods or as described herein. For example, RNA-guided nuclease-encoding and/or guide molecule-encoding DNA, as well as donor template nucleic acids can be delivered by, e.g., vectors (e.g., viral or non-viral vectors), non-vector based methods (e.g., using naked DNA or DNA complexes), or a combination thereof.

Nucleic acids encoding genome editing systems or components thereof can be delivered directly to cells as naked DNA or RNA, for instance by means of transfection or electroporation, or can be conjugated to molecules (e.g., N-acetylgalactosamine) promoting uptake by the target cells (e.g., erythrocytes, HSCs). Nucleic acid vectors, such as the vectors summarized in Table 13, can also be used.

Nucleic acid vectors can comprise one or more sequences encoding genome editing system components, such as an RNA-guided nuclease, a guide molecule and/or a donor template. A vector can also comprise a sequence encoding a signal peptide (e.g., for nuclear localization, nucleolar localization, or mitochondrial localization), associated with (e.g., inserted into or fused to) a sequence coding for a protein. As one example, nucleic acid vectors can include a Cas9 coding sequence that includes one or more nuclear localization sequences (e.g., a nuclear localization sequence from SV40).

The nucleic acid vector can also include any suitable number of regulatory/control elements, e.g., promoters, enhancers, introns, polyadenylation signals, Kozak consensus sequences, or internal ribosome entry sites (IRES). These elements are well known in the art, and are described in Cotta-Ramusino.

Nucleic acid vectors according to this disclosure include recombinant viral vectors. Exemplary viral vectors are set forth in Table 13, and additional suitable viral vectors and their use and production are described in Cotta-Ramusino. Other viral vectors known in the art can also be used. In addition, viral particles can be used to deliver genome editing system components in nucleic acid and/or peptide form. For example, "empty" viral particles can be assembled to contain any suitable cargo. Viral vectors and viral particles can also be engineered to incorporate targeting ligands to alter target tissue specificity.

In addition to viral vectors, non-viral vectors can be used to deliver nucleic acids encoding genome editing systems according to the present disclosure. One important category of non-viral nucleic acid vectors are nanoparticles, which can be organic or inorganic. Nanoparticles are well known in the art, and are summarized in Cotta-Ramusino. Any suitable nanoparticle design can be used to deliver genome editing system components or nucleic acids encoding such components. For instance, organic (e.g. lipid and/or polymer) nanoparticles can be suitable for use as delivery vehicles in certain embodiments of this disclosure. Exemplary lipids for use in nanoparticle formulations, and/or gene transfer are shown in Table 14, and Table 15 lists exemplary polymers for use in gene transfer and/or nanoparticle formulations.

TABLE 14

Lipids Used for Gene Transfer

| Lipid | Abbreviation | Feature |
|---|---|---|
| 1,2-Dioleoyl-sn-glycero-3-phosphatidylcholine | DOPC | Helper |
| 1,2-Dioleoyl-sn-glycero-3-phosphatidylethanolamine | DOPE | Helper |
| Cholesterol | | Helper |
| N-[1-(2,3-Dioleyloxy)propyl]N,N,N-trimethylammonium chloride | DOTMA | Cationic |
| 1,2-Dioleoyloxy-3-trimethylammonium-propane | DOTAP | Cationic |
| Dioctadecylamidoglycylspermine | DOGS | Cationic |
| N-(3-Aminopropyl)-N,N-dimethyl-2,3-bis(dodecyloxy)-1-propanaminium bromide | GAP-DLRIE | Cationic |
| Cetyltrimethylammonium bromide | CTAB | Cationic |
| 6-Lauroxyhexyl ornithinate | LHON | Cationic |
| 1-(2,3-Dioleoyloxypropyl)-2,4,6-trimethylpyridinium | 2Oc | Cationic |
| 2,3-Dioleyloxy-N-[2(sperminecarboxamido-ethyl]-N,N-dimethyl-1-propanaminium trifluoroacetate | DOSPA | Cationic |
| 1,2-Dioleyl-3-trimethylammonium-propane | DOPA | Cationic |
| N-(2-Hydroxyethyl)-N,N-dimethyl-2,3-bis(tetradecyloxy)-1-propanaminium bromide | MDRIE | Cationic |
| Dimyristooxypropyl dimethyl hydroxyethyl ammonium bromide | DMRI | Cationic |
| 3B-[N-(N',N'-Dimethylaminoethane)-carbamoyl]cholesterol | DC-Chol | Cationic |
| Bis-guanidium-tren-cholesterol | BGTC | Cationic |
| 1,3-Diodeoxy-2-(6-carboxy-spermyl)-propylamide | DOSPER | Cationic |
| Dimethyloctadecylammonium bromide | DDAB | Cationic |
| Dioctadecylamidoglicylspermidin | DSL | Cationic |
| rac-[(2,3-Dioctadecyloxypropyl)(2-hydroxyethyl)]-dimethylammonium chloride | CLIP-1 | Cationic |
| rac-[2(2,3-Dihexadecyloxypropyl-oxymethyloxy)ethyl]trimethylammonium bromide | CLIP-6 | Cationic |
| Ethyldimyristoylphosphatidylcholine | EDMPC | Cationic |
| 1,2-Distearyloxy-N,N-dimethyl-3-aminopropane | DSDMA | Cationic |
| 1,2-Dimyristoyl-trimethylammonium propane | DMTAP | Cationic |
| O,O'-Dimyristyl-N-lysyl aspartate | DMKE | Cationic |
| 1,2-Distearoyl-sn-glycero-3-ethylphosphocholine | DSEPC | Cationic |
| N-Palmitoyl D-erythro-sphingosyl carbamoyl-spermine | CCS | Cationic |
| N-t-Butyl-N0-tetradecyl-3-tetradecylaminopropionamidine | diC14-amidine | Cationic |
| Octadecenolyoxy[ethyl-2-heptadeceny1-3 hydroxyethyl] imidazolinium chloride | DOTIM | Cationic |
| N1-Cholesteryloxycarbonyl-3,7-diazanonane-1,9-diamine | CDAN | Cationic |
| 2-(3-[Bis(3-amino-propyl)-amino]propylamino)-N-ditetradecylcarbamoylme-ethyl-acetamide | RPR209120 | Cationic |
| 1,2-dilinoleyloxy-3- dimethylaminopropane | DLinDMA | Cationic |
| 2,2-dilinoley1-4-dimethylaminoethyl-[1,3]- dioxolane | DLin-KC2-DMA | Cationic |
| dilinoleyl- methyl-4-dimethylaminobutyrate | DLin-MC3-DMA | Cationic |

TABLE 15

Polymers Used for Gene Transfer

| Polymer | Abbreviation |
|---|---|
| Poly(ethylene)glycol | PEG |
| Polyethylenimine | PEI |
| Dithiobis(succinimidylpropionate) | DSP |
| Dimethyl-3,3'-dithiobispropionimidate | DTBP |
| Poly(ethylene imine) biscarbamate | PEIC |
| Poly(L-lysine) | PLL |
| Histidine modified PLL | |
| Poly(N-vinylpyrrolidone) | PVP |
| Poly(propylenimine) | PPI |
| Poly(amidoamine) | PAMAM |
| Poly(amido ethylenimine) | SS-PAEI |
| Triethylenetetramine | TETA |
| Poly(β-aminoester) | |
| Poly(4-hydroxy-L-proline ester) | PHP |
| Poly(allylamine) | |
| Poly(α-[4-aminobutyl]-L-glycolic acid) | PAGA |
| Poly(D,L-lactic-co-glycolic acid) | PLGA |
| Poly(N-ethyl-4-vinylpyridinium bromide) | |
| Poly(phosphazene)s | PPZ |
| Poly(phosphoester)s | PPE |
| Poly(phosphoramidate)s | PPA |
| Poly(N-2-hydroxypropylmethacrylamide) | pHPMA |
| Poly (2-(dimethylamino) ethyl methacrylate) | pDMAEMA |
| Poly(2-aminoethyl propylene phosphate) | PPE-EA |
| Chitosan | |
| Galactosylated chitosan | |
| N-Dodacylated chitosan | |

TABLE 15-continued

Polymers Used for Gene Transfer

| Polymer | Abbreviation |
|---|---|
| Histone | |
| Collagen | |
| Dextran-spermine | D-SPM |

Non-viral vectors optionally include targeting modifications to improve uptake and/or selectively target certain cell types. These targeting modifications can include e.g., cell specific antigens, monoclonal antibodies, single chain antibodies, aptamers, polymers, sugars (e.g., N-acetylgalactosamine (GalNAc)), and cell penetrating peptides. Such vectors also optionally use fusogenic and endosome-destabilizing peptides/polymers, undergo acid-triggered conformational changes (e.g., to accelerate endosomal escape of the cargo), and/or incorporate a stimuli-cleavable polymer, e.g., for release in a cellular compartment. For example, disulfide-based cationic polymers that are cleaved in the reducing cellular environment can be used.

In some embodiments, one or more nucleic acid molecules (e.g., DNA molecules) other than the components of a genome editing system, e.g., the RNA-guided nuclease component and/or the guide molecule component described herein, are delivered. In certain embodiments, the nucleic acid molecule is delivered at the same time as one or more of the components of the genome editing system. In some embodiments, the nucleic acid molecule is delivered before or after (e.g., less than about 30 minutes, 1 hour, 2 hours, 3 hours, 6 hours, 9 hours, 12 hours, 1 day, 2 days, 3 days, 1 week, 2 weeks, or 4 weeks) one or more of the components of the genome editing system are delivered. In some embodiments, the nucleic acid molecule is delivered by a different means than one or more of the components of the genome editing system, e.g., the RNA-guided nuclease component and/or the guide molecule component, are delivered. The nucleic acid molecule can be delivered by any of the delivery methods described herein. For example, the nucleic acid molecule can be delivered by a viral vector, e.g., an integration-deficient lentivirus, and the RNA-guided nuclease molecule component and/or the guide molecule component can be delivered by electroporation, e.g., such that the toxicity caused by nucleic acids (e.g., DNAs) can be reduced. In certain embodiments, the nucleic acid molecule encodes a therapeutic protein, e.g., a protein described herein. In certain embodiments, the nucleic acid molecule encodes an RNA molecule, e.g., an RNA molecule described herein.

Delivery of RNPs and/or RNA Encoding Genome Editing System Components

RNPs (complexes of guide molecules and RNA-guided nucleases) and/or RNAs encoding RNA-guided nucleases and/or guide molecules, can be delivered into cells or administered to subjects by art-known methods, some of which are described in Cotta-Ramusino. In vitro, RNA-guided nuclease-encoding and/or guide molecule-encoding RNA can be delivered, e.g., by microinjection, electroporation, transient cell compression or squeezing (see, e.g., Lee 2012). Lipid-mediated transfection, peptide-mediated delivery, GalNAc- or other conjugate-mediated delivery, and combinations thereof, can also be used for delivery in vitro and in vivo.

In vitro, delivery via electroporation comprises mixing the cells with the RNA encoding RNA-guided nucleases and/or guide molecules, with or without donor template nucleic acid molecules, in a cartridge, chamber or cuvette and applying one or more electrical impulses of defined duration and amplitude. Systems and protocols for electroporation are known in the art, and any suitable electroporation tool and/or protocol can be used in connection with the various embodiments of this disclosure.

Route of Administration

Genome editing systems, or cells altered or manipulated using such systems, can be administered to subjects by any suitable mode or route, whether local or systemic. Systemic modes of administration include oral and parenteral routes. Parenteral routes include, by way of example, intravenous, intramarrow, intrarterial, intramuscular, intradermal, subcutaneous, intranasal, and intraperitoneal routes. Components administered systemically can be modified or formulated to target, e.g., HSCs, hematopoietic stem/progenitor cells, or erythroid progenitors or precursor cells.

Local modes of administration include, by way of example, intramarrow injection into the trabecular bone or intrafemoral injection into the marrow space, and infusion into the portal vein. In certain embodiments, significantly smaller amounts of the components (compared with systemic approaches) can exert an effect when administered locally (for example, directly into the bone marrow) compared to when administered systemically (for example, intravenously). Local modes of administration can reduce or eliminate the incidence of potentially toxic side effects that may occur when therapeutically effective amounts of a component are administered systemically.

Administration can be provided as a periodic bolus (for example, intravenously) or as continuous infusion from an internal reservoir or from an external reservoir (for example, from an intravenous bag or implantable pump). Components can be administered locally, for example, by continuous release from a sustained release drug delivery device.

In addition, components can be formulated to permit release over a prolonged period of time. A release system can include a matrix of a biodegradable material or a material which releases the incorporated components by diffusion. The components can be homogeneously or heterogeneously distributed within the release system. A variety of release systems can be useful, however, the choice of the appropriate system will depend upon rate of release required by a particular application. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, synthetic release systems are preferred because generally they are more reliable, more reproducible and produce more defined release profiles. The release system material can be selected so that components having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly (caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly (ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly (vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

Poly(lactide-co-glycolide) microsphere can also be used. Typically the microspheres are composed of a polymer of lactic acid and glycolic acid, which are structured to form hollow spheres. The spheres can be approximately 15-30 microns in diameter and can be loaded with components described herein.

Multi-Modal or Differential Delivery of Components

Skilled artisans will appreciate, in view of the instant disclosure, that different components of genome editing systems disclosed herein can be delivered together or separately and simultaneously or nonsimultaneously. Separate and/or asynchronous delivery of genome editing system components can be particularly desirable to provide temporal or spatial control over the function of genome editing systems and to limit certain effects caused by their activity.

Different or differential modes as used herein refer to modes of delivery that confer different pharmacodynamic or pharmacokinetic properties on the subject component molecule, e.g., a RNA-guided nuclease molecule, guide molecule, template nucleic acid, or payload. For example, the modes of delivery can result in different tissue distribution, different half-life, or different temporal distribution, e.g., in a selected compartment, tissue, or organ.

Some modes of delivery, e.g., delivery by a nucleic acid vector that persists in a cell, or in progeny of a cell, e.g., by autonomous replication or insertion into cellular nucleic acid, result in more persistent expression of and presence of a component. Examples include viral, e.g., AAV or lentivirus, delivery.

By way of example, the components of a genome editing system, e.g., a RNA-guided nuclease and a guide molecule, can be delivered by modes that differ in terms of resulting half-life or persistent of the delivered component in the body, or in a particular compartment, tissue or organ. In certain embodiments, a guide molecule can be delivered by such modes. The RNA-guided nuclease molecule component can be delivered by a mode which results in less persistence or less exposure to the body or a particular compartment or tissue or organ.

More generally, in some embodiments, a first mode of delivery is used to deliver a first component and a second mode of delivery is used to deliver a second component. The first mode of delivery confers a first pharmacodynamic or pharmacokinetic property. The first pharmacodynamic property can be, e.g., distribution, persistence, or exposure, of the component, or of a nucleic acid that encodes the component, in the body, a compartment, tissue or organ. The second mode of delivery confers a second pharmacodynamic or pharmacokinetic property. The second pharmacodynamic property can be, e.g., distribution, persistence, or exposure, of the component, or of a nucleic acid that encodes the component, in the body, a compartment, tissue or organ.

In some embodiments, the first pharmacodynamic or pharmacokinetic property, e.g., distribution, persistence or exposure, is more limited than the second pharmacodynamic or pharmacokinetic property.

In some embodiments, the first mode of delivery is selected to optimize, e.g., minimize, a pharmacodynamic or pharmacokinetic property, e.g., distribution, persistence or exposure.

In some embodiments, the second mode of delivery is selected to optimize, e.g., maximize, a pharmacodynamic or pharmacokinetic property, e.g., distribution, persistence or exposure.

In some embodiments, the first mode of delivery comprises the use of a relatively persistent element, e.g., a nucleic acid, e.g., a plasmid or viral vector, e.g., an AAV or lentivirus. As such vectors are relatively persistent, and a product transcribed from them would be relatively persistent.

In some embodiments, the second mode of delivery comprises a relatively transient element, e.g., an RNA or protein.

In some embodiments, the first component comprises a guide molecule, and the delivery mode is relatively persistent, e.g., the guide molecule is transcribed from a plasmid or viral vector, e.g., an AAV or lentivirus. Transcription of these genes would be of little physiological consequence because the genes do not encode for a protein product, and the guide molecules are incapable of acting in isolation. The second component, a RNA-guided nuclease molecule, is delivered in a transient manner, for example as mRNA or as protein, ensuring that the full RNA-guided nuclease molecule/guide molecule complex is only present and active for a short period of time.

Furthermore, the components can be delivered in different molecular form or with different delivery vectors that complement one another to enhance safety and tissue specificity.

Use of differential delivery modes can enhance performance, safety, and/or efficacy, e.g., the likelihood of an eventual off-target modification can be reduced. Delivery of immunogenic components, e.g., Cas9 molecules, by less persistent modes can reduce immunogenicity, as peptides from the bacterially-derived Cas enzyme are displayed on the surface of the cell by MHC molecules. A two-part delivery system can alleviate these drawbacks.

Differential delivery modes can be used to deliver components to different, but overlapping target regions. The formation active complex is minimized outside the overlap of the target regions. Thus, in some embodiments, a first component, e.g., a guide molecule is delivered by a first delivery mode that results in a first spatial, e.g., tissue, distribution. A second component, e.g., a RNA-guided nuclease molecule is delivered by a second delivery mode that results in a second spatial, e.g., tissue, distribution. In some embodiments, the first mode comprises a first element selected from a liposome, nanoparticle, e.g., polymeric nanoparticle, and a nucleic acid, e.g., viral vector. The second mode comprises a second element selected from the group. In some embodiments, the first mode of delivery comprises a first targeting element, e.g., a cell specific receptor or an antibody, and the second mode of delivery does not include that element. In some embodiments, the second mode of delivery comprises a second targeting element, e.g., a second cell specific receptor or second antibody.

When the RNA-guided nuclease molecule is delivered in a virus delivery vector, a liposome, or polymeric nanoparticle, there is the potential for delivery to and therapeutic activity in multiple tissues, when it may be desirable to only target a single tissue. A two-part delivery system can resolve this challenge and enhance tissue specificity. If the guide molecule and the RNA-guided nuclease molecule are packaged in separated delivery vehicles with distinct but overlapping tissue tropism, the fully functional complex is only be formed in the tissue that is targeted by both vectors.

Exemplary Embodiments

The following numbered embodiments, while non-limiting, are exemplary of certain aspects of the present disclosure:

1. A synthetic unimolecular guide molecule for a CRISPR system, wherein the guide molecule comprises a group of formula $J_{3'}$-i or $J_{2'}$-i:

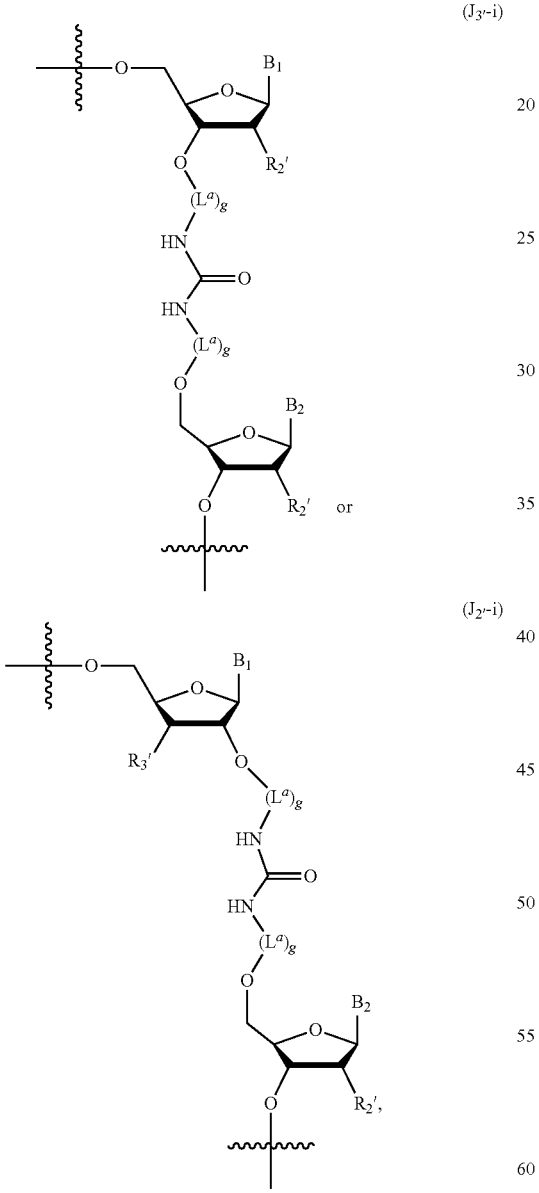

wherein:
each of $R_2'$ and $R_3'$ is independently H, OH, fluoro, chloro, bromo, $NH_2$, SH, S—R', or O—R' wherein each R' is independently a protection group or an alkyl group, wherein the alkyl group may be optionally each $L^a$ is independently a non-nucleotide linker;
each g is independently 0, 1, 2, 3, 4, or 5; and
$B_1$ and $B_2$ are each independently a nucleobase.

2. The guide molecule of embodiment 1, wherein $R_2'$ is selected from the group consisting of H, fluoro, and O—R' wherein R' is a protecting group or an optionally substituted alkyl group.

3. The guide molecule of embodiment 1 or 2, wherein the guide molecule is of formula $A_{3'}$-iii or $A_{2'}$-iii:

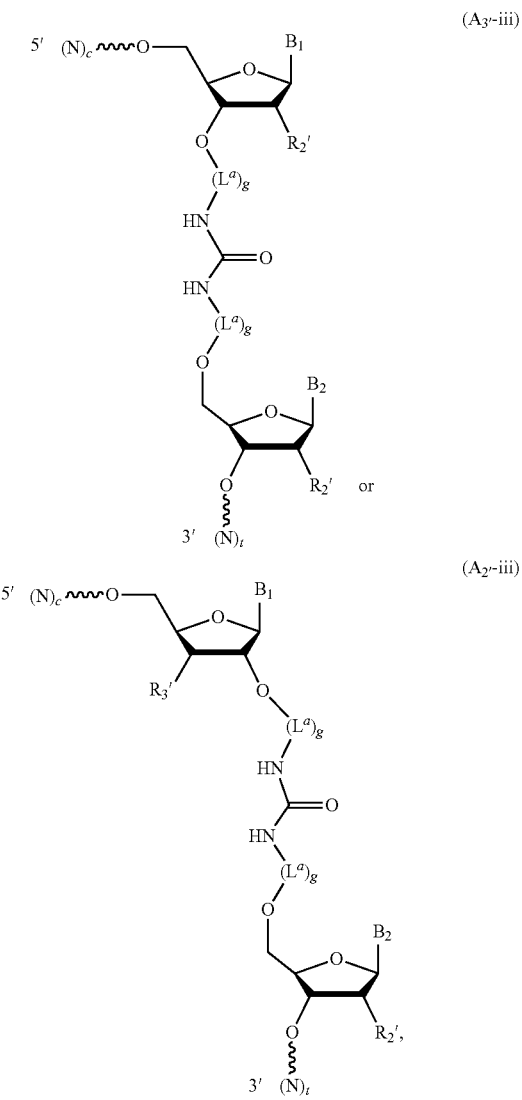

wherein:
each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;

$(N)_c$ includes a 3' region that is complementary or partially complementary to, and forms a duplex with, a 5' region of $(N)_t$;

c is an integer 20 or greater;
t is an integer 20 or greater; and each ∿∿ represents independently a phosphodiester linkage, a phosphorothioate linkage, a phosphonoacetate linkage, a thiophosphonoacetate linkage, or a phosphoroamidate linkage.

4. The guide molecule of embodiment 3, wherein each N in $(N)_c$ and $(N)_t$ is independently a ribonucleotide residue or a sugar-modified ribonucleotide residue.

5. The guide molecule of embodiment 3 or 4, wherein $(N)_c$ or $(N)_t$ comprise one or more deoxyribonucleotide residues.

6. The guide molecule of any one of embodiments 3-5, wherein $(N)_c$ or $(N)_t$ comprise one or more 2'-O-methyl modified ribonucleotide residues.

7. The guide molecule of any one of embodiments 3-6, wherein each of the three nucleotides at the 5' end of $(N)_c$ and/or each of the three nucleotides at the 3' end of $(N)_t$ comprise a 2'-O-methyl modified ribonucleotide residue that is linked to its adjacent nucleotide(s) via a phosphorothioate linkage.

8. The guide molecule of any one of embodiments 1-7, wherein each $L^a$ is independently a non-nucleotide linker comprising a moiety selected from the group consisting of polyethylene, polypropylene, polyethylene glycol, and polypropylene glycol.

9. The guide molecule of any one of embodiments 3-8, wherein the guide molecule is for a Type II CRISPR system and $(N)_c$ includes a 5' region that comprises a targeting domain that is fully or partially complementary to a target domain within a target sequence.

10. The guide molecule of any one of embodiments 3-9, wherein $(N)_t$ includes a 3' region that comprises one or more stem-loop structures.

11. The guide molecule of any one of embodiments 1-10, wherein the guide molecule is capable of interacting with a Cas9 molecule and mediating the formation of a Cas9/guide ribonucleoprotein complex.

12. The guide molecule of any one of embodiments 3-11, wherein $(N)_c$ comprises a 3' region that comprises at least a portion of a repeat from a Type II CRISPR system.

13. The guide molecule of any one of embodiments 1-12, wherein the guide molecule is of formula $B_{3'}$-iii or $B_{2'}$-iii:

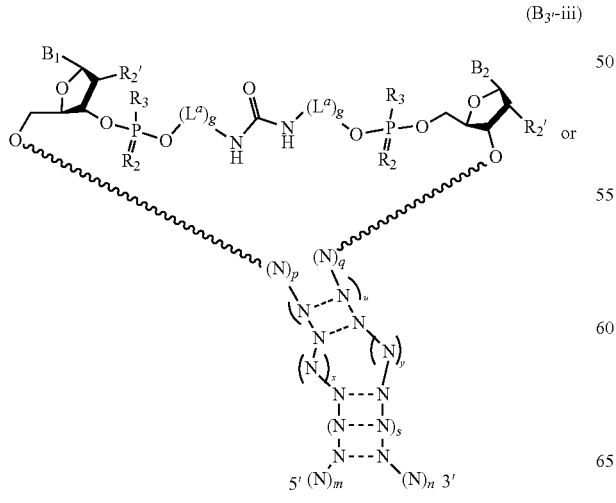

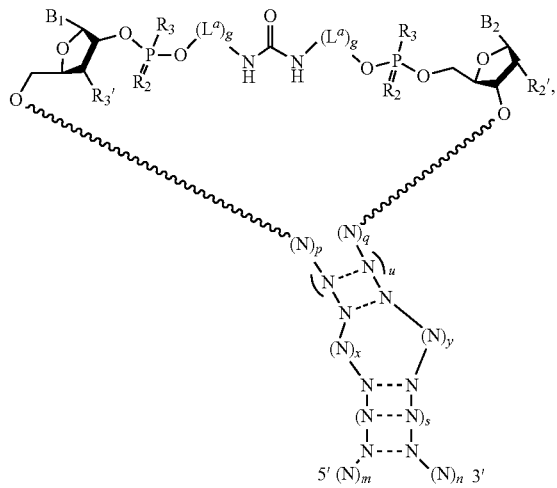

wherein:

each $L^a$ is independently a non-nucleotide linker;

each g is independently 0, 1, 2, 3, 4, or 5;

each $R_2$ is independently O or S;

each $R_3$ is independently O or COO;

p and q are each independently an integer between 0 and 6, inclusive, and p+q is an integer between 0 and 6, inclusive;

u is an integer between 2 and 22, inclusive;

s is an integer between 1 and 10, inclusive;

x is an integer between 1 and 3, inclusive;

y is >x and an integer between 3 and 5, inclusive;

m is an integer 15 or greater;

n is an integer 30 or greater;

each N is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;

each N—N independently represents two complementary nucleotides, optionally two complementary nucleotides that are hydrogen bonding base-paired; and each ∿∿ represents independently a phosphodiester linkage, a phosphorothioate linkage, a phosphonoacetate linkage, a thiophosphonoacetate linkage, or a phosphoroamidate linkage.

14. The guide molecule of embodiment 13, wherein p and q are each 0.

15. The guide molecule of embodiment 13 or 14, wherein u is an integer between 3 and 22, inclusive.

16. The guide molecule of any one of embodiments 1-15, wherein the guide molecule is of formula $C_{3'}$-iii or $C_{2'}$-iii:

(C$_{3'}$-iii)

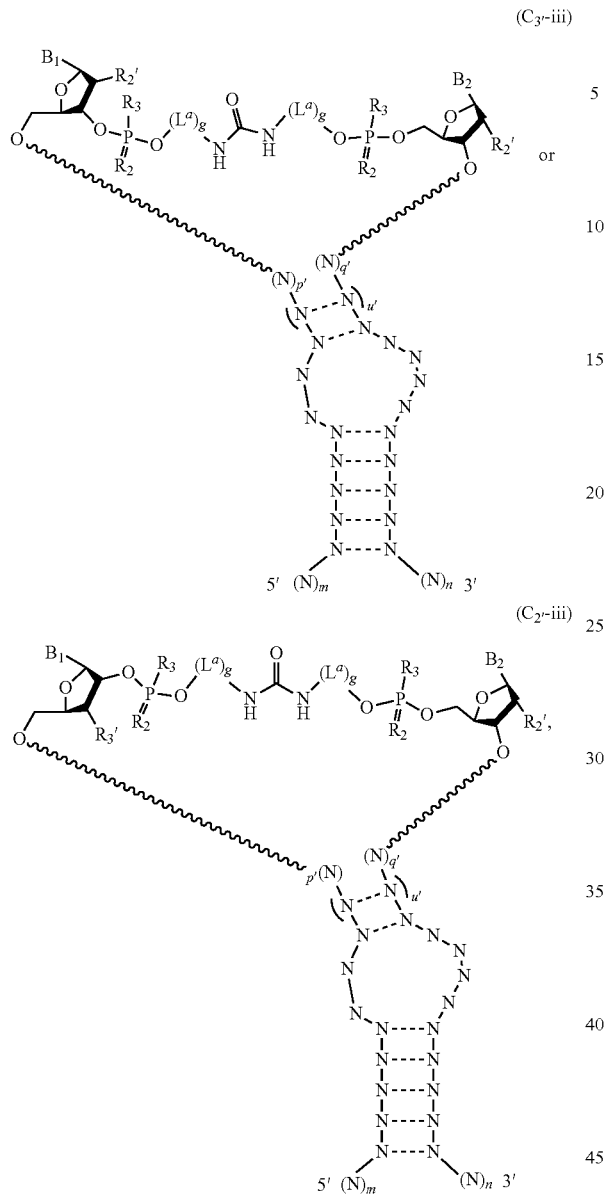

(C$_{2'}$-iii)

-continued (D$_{2'}$-iii)

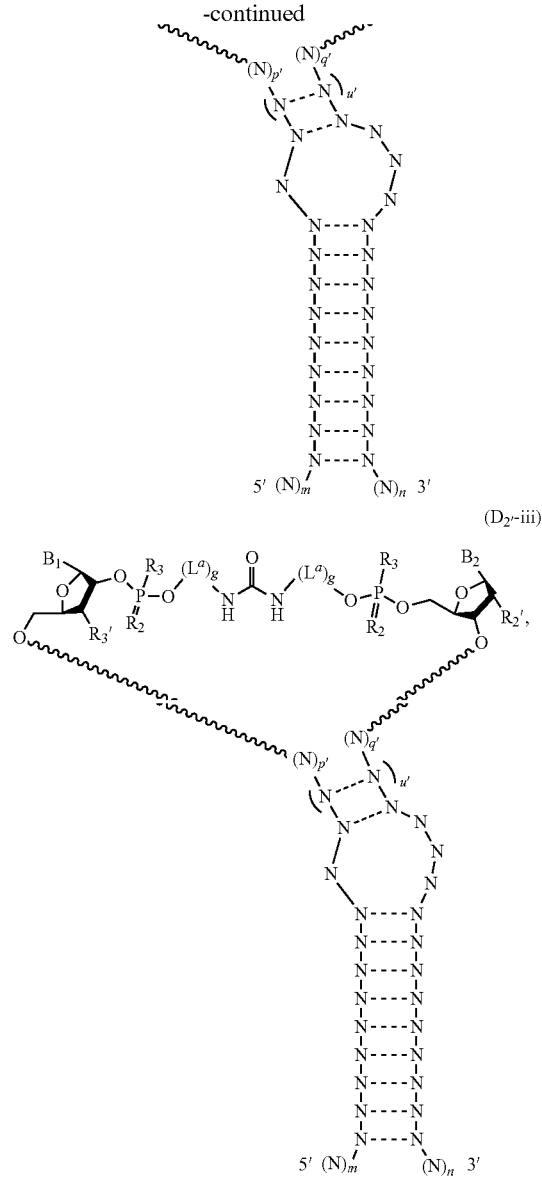

wherein:
u' is an integer between 2 and 22, inclusive; and
p' and q' are each independently an integer between 0 and 4, inclusive, and p'+q' is an integer between 0 and 4, inclusive.

17. The guide molecule of any one of embodiments 1-15, wherein the guide molecule is of formula D$_{3'}$-iii or D$_{2'}$-iii:

(D$_{3'}$-iii)

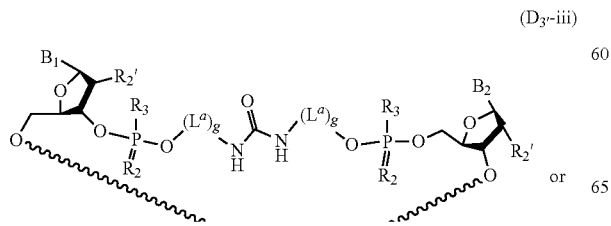

wherein:
u' is an integer between 2 and 22, inclusive; and
p' and q' are each independently an integer between 0 and 4, inclusive, and p'+q' is an integer between 0 and 4, inclusive.

18. The guide molecule of embodiment 16 or 17, wherein p' and q' are each 0.

19. The guide molecule of any one of embodiments 16-18, wherein u' is an integer between 3 and 22, inclusive.

20. The guide molecule of any one of embodiments 13-19, wherein one -(L$^a$)$_g$- is —(CH$_2$)$_w$—, and w is an integer between 1-20, inclusive.

21. The guide molecule of any one of embodiments 13-20, wherein one -(L$^a$)$_g$- is —(CH$_2$CH$_2$O)$_v$CH$_2$CH$_2$—, and v is an integer between 1-10, inclusive.

22. The guide molecule of embodiment 20 or 21, wherein one -(L$^a$)$_g$- is —(CH$_2$)$_w$- and w is 6, and the other -(L$^a$)$_g$- is —(CH$_2$CH$_2$O)$_v$CH$_2$CH$_2$- and v is 3.

23. The guide molecule of any of the preceding embodiments, wherein the guide molecule comprises a sequence selected from Table 17.

24. A synthetic unimolecular guide molecule for a CRISPR system, wherein the guide molecule comprises a chemical linkage of formula J$_{3'}$-ii, J$_{2'}$-ii, J$_{3'}$-iii, or J$_{2'}$-iii:

(J$_{3'}$-ii)

(J$_{2'}$-ii)

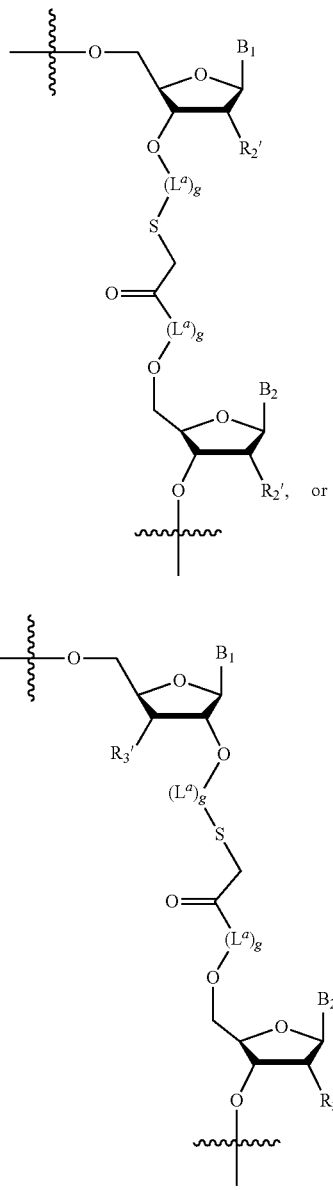

(J$_{3'}$-iii)

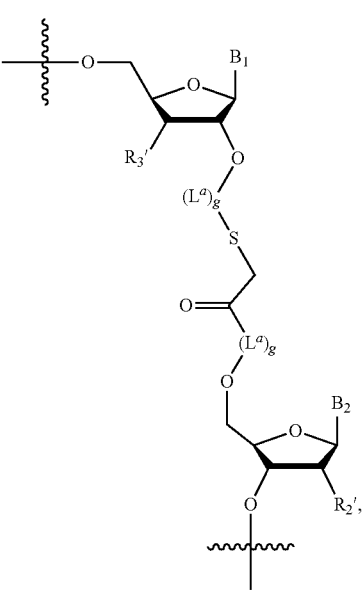

(J$_{2'}$-iii)

wherein:
each of R$_2$' and R$_3$' is independently H, OH, fluoro, chloro, bromo, NH$_2$, SH, S—R', or O—R' wherein each R' is independently a protection group or an alkyl group, wherein the alkyl group may be optionally substituted;

each L$^a$ is independently a non-nucleotide linker;

each g is independently 0, 1, 2, 3, 4, or 5; and

B$_1$ and B$_2$ are each independently a nucleobase.

25. The guide molecule of embodiment 24, wherein R$_2$' is selected from the group consisting of H, fluoro, and O—R' wherein R' is a protecting group or an optionally substituted alkyl group.

26. The guide molecule of embodiment 24 or 25, wherein the guide molecule is of formula A$_{3'}$-iv, A$_{2'}$-iv, A$_{3'}$-v, or A$_{2'}$-v:

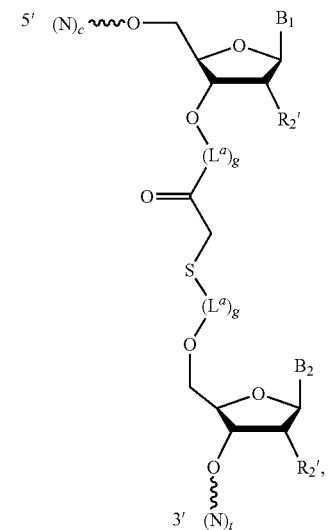

(A3'-iv)

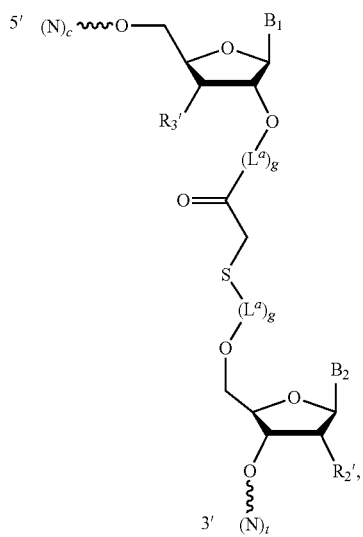

(A2'-iv)

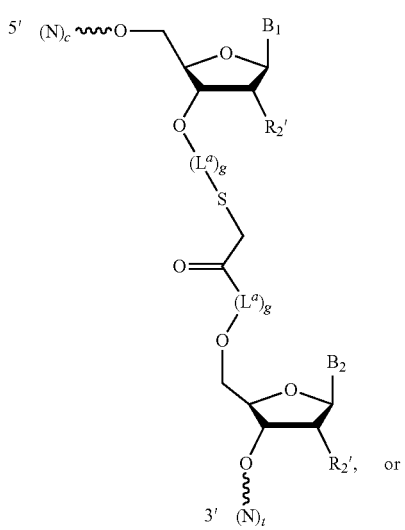

(A3'-v)

or

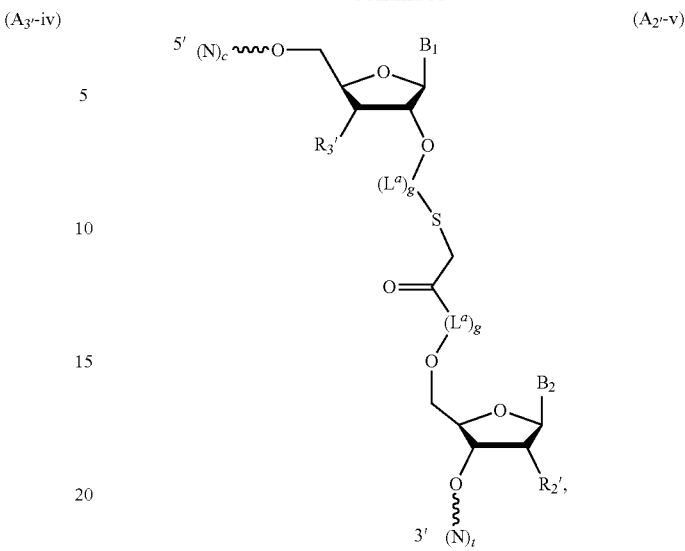

(A2'-v)

wherein:
each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;
$(N)_c$ includes a 3' region that is complementary or partially complementary to, and forms a duplex with, a 5' region of $(N)_t$;
c is an integer 20 or greater;
t is an integer 20 or greater; and
each ∿∿∿ represents independently a phosphodiester linkage, a phosphorothioate linkage, a phosphonoacetate linkage, a thiophosphonoacetate linkage, or a phosphoroamidate linkage.

27. The guide molecule of embodiment 26, wherein each N in $(N)_c$ and $(N)_t$ is independently a ribonucleotide residue or a sugar-modified ribonucleotide residue.

28. The guide molecule of embodiment 26 or 27, wherein $(N)_c$ or $(N)_t$ comprise one or more deoxyribonucleotide residues.

29. The guide molecule of any one of embodiments 26-28, wherein $(N)_c$ or $(N)_t$ comprise one or more 2'-O-methyl modified ribonucleotide residues.

30. The guide molecule of any one of embodiments 26-29, wherein each of the three nucleotides at the 5' end of $(N)_c$ and/or each of the three nucleotides at the 3' end of $(N)_t$ comprise a 2'-O-methyl modified ribonucleotide residue that is linked to its adjacent nucleotide(s) via a phosphorothioate linkage.

31. The guide molecule of any one of embodiments 24-30, wherein each $-(L^a)_{f-1}-$ is independently a non-nucleotide non-nucleotide linker comprising a moiety selected from the group consisting of polyethylene, polypropylene, polyethylene glycol, and polypropylene glycol.

32. The guide molecule of any one of embodiments 26-31, wherein the guide molecule is for a Type II CRISPR system and $(N)_c$ includes a 5' region that comprises a targeting domain that is fully or partially complementary to a target domain within a target sequence.

33. The guide molecule of any one of embodiments 26-32, wherein $(N)_t$ includes a 3' region that comprises one or more stem-loop structures.

34. The guide molecule of any one of embodiments 24-33, wherein the guide molecule is capable of interacting with a Cas9 molecule and mediating the formation of a Cas9/guide ribonucleoprotein complex.

35. The guide molecule of any one of embodiments 26-34, wherein $(N)_t$ comprises a 3' region that comprises at least a portion of a repeat from a Type II CRISPR system.

36. The guide molecule of any one of embodiments 24-35, wherein the guide molecule is of formula:

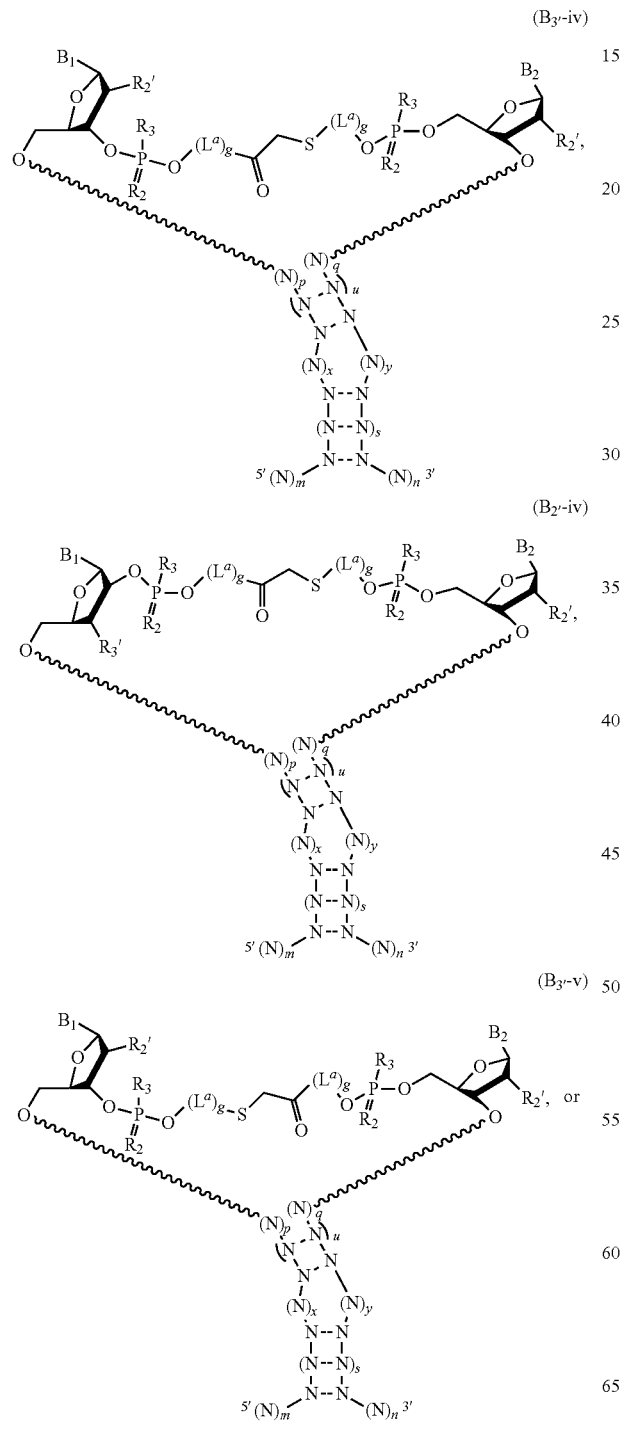

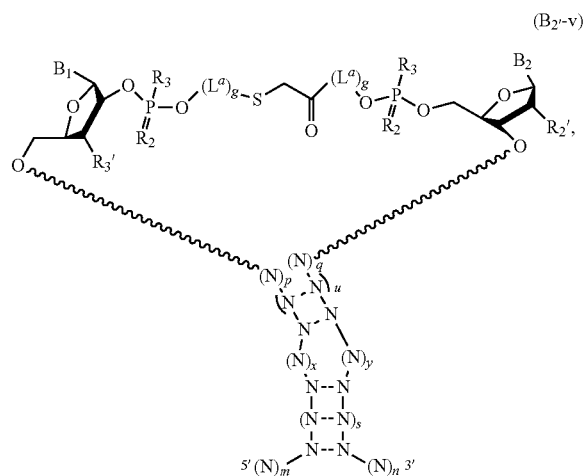

wherein:

each $-(L^a)_{f-1}-$ is independently a non-nucleotide linker;

each g is independently 0, 1, 2, 3, 4, or 5;

each $R_2$ is independently O or S;

each $R_3$ is independently $O^-$ or COO;

p and q are each independently an integer between 0 and 6, inclusive, and p+q is an integer between 0 and 6, inclusive;

u is an integer between 2 and 22, inclusive;

s is an integer between 1 and 10, inclusive;

x is an integer between 1 and 3, inclusive;

y is >x and an integer between 3 and 5, inclusive;

m is an integer 15 or greater;

n is an integer 30 or greater;

each N is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;

each N—N independently represents two complementary nucleotides, optionally two complementary nucleotides that are hydrogen bonding base-paired; and each ∿∿ represents independently a phosphodiester linkage, a phosphorothioate linkage, a phosphonoacetate linkage, a thiophosphonoacetate linkage, or a phosphoroamidate linkage.

37. The guide molecule of any one of embodiments 24-36, wherein the guide molecule is of formula $C_{3'}$-iv, $C_{2'}$-iv, $C_{3'}$-v, or $C_{2'}$-v:

($C_{3'}$-iv)
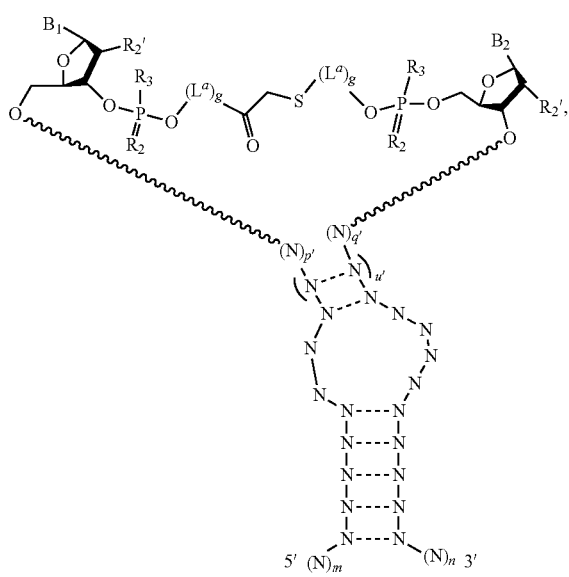
($C_{3'}$-v)
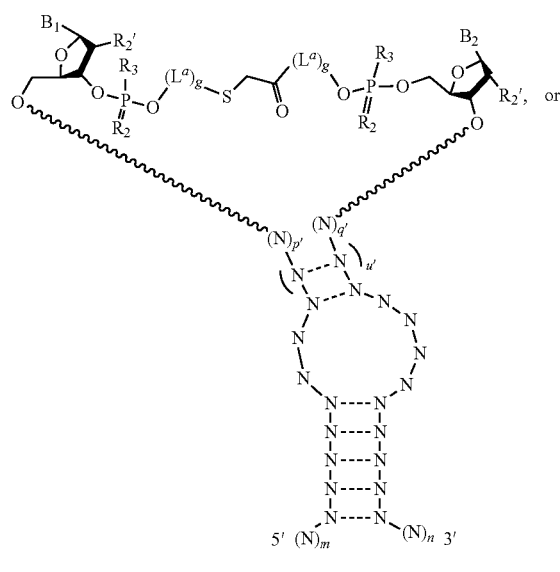
or
($C_{2'}$-v)
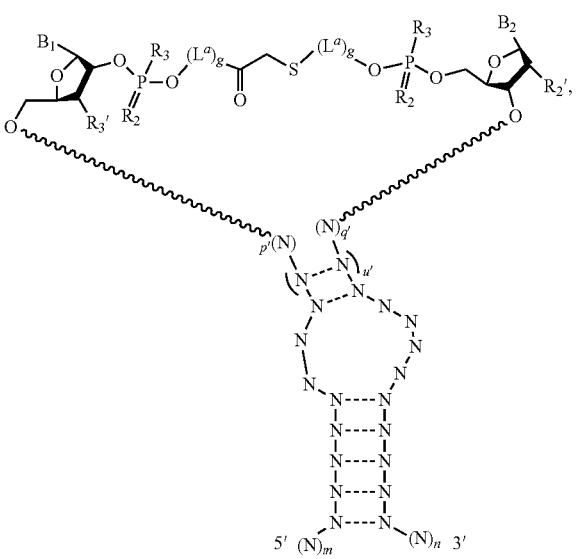
($C_{2'}$-iv)
wherein:
u' is an integer between 2 and 22, inclusive; and
p' and q' are each independently an integer between 0 and 4, inclusive, and p'+q' is an integer between 0 and 4, inclusive.
38. The guide molecule of any one of embodiments 24-36, wherein the guide molecule is of formula $D_{3'}$-iv, $D_{2'}$-iv, $D_{3'}$-v, or $D_{2'}$-v:

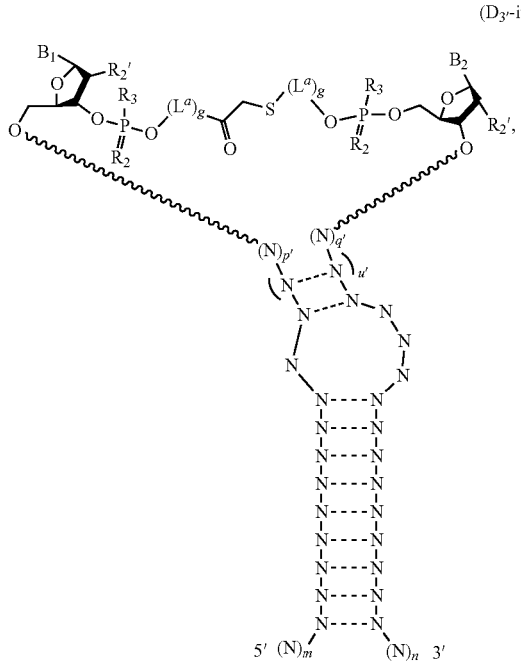

(D3'-iv)

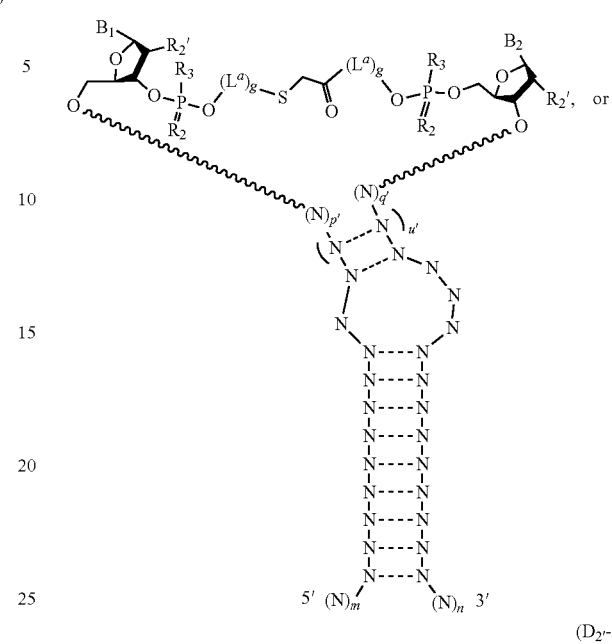

(D3'-v)

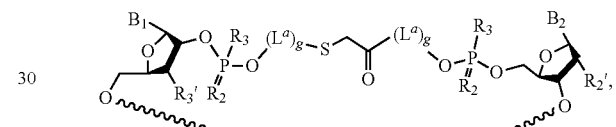

(D2'-v)

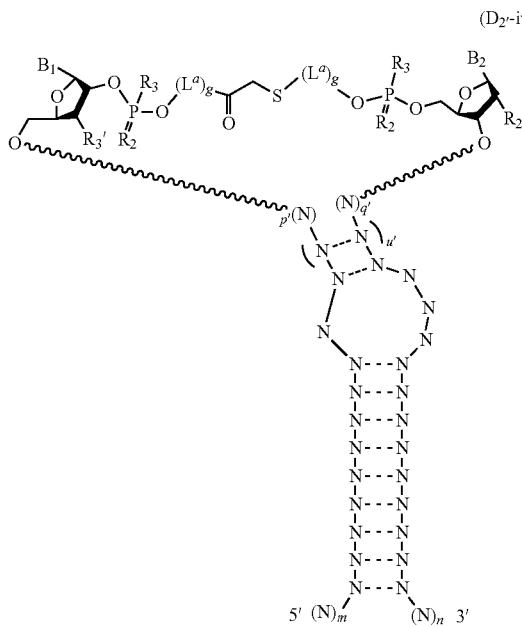

(D2'-iv)

wherein:
u' is an integer between 2 and 22, inclusive; and
p' and q' are each independently an integer between 0 and 4, inclusive, and p'+q' is an integer between 0 and 4, inclusive.

39. The guide molecule of any one of embodiments 36-38, wherein one -(L$^a$)$_g$- is —(CH$_2$)$_w$—NHC(O)—(CH$_2$)$_w$—NH—; each w is independently 1-20; and each v is independently 1-10.

40. The guide molecule of any one of embodiments 36-39, wherein one -(L$^a$)$_g$- is -CH$_2$CH$_2$—(OCH$_2$CH$_2$)$_v$—NH—C(O)—(CH$_2$)$_w$—; each w is independently 1-20; and each v is independently 1-10.

41. The guide molecule of embodiment any one of embodiments 36-40, wherein one -(L$^a$)$_g$- is —(CH$_2$)$_6$-NHC(O)—(CH$_2$)$_2$—NH—, and the other-(L$^a$)$_g$- is-CH$_2$CH$_2$—(OCH$_2$CH$_2$)$_3$—NHC(O)—(CH$_2$)$_2$—.

42. The guide molecule of any of embodiments 24-41, wherein the guide molecule comprises a sequence selected from Table 16.

43. A composition comprising a plurality of synthetic guide molecules of any of the preceding embodiments, wherein less than about 10% of the guide molecules comprise a truncation at a 5' end, relative to a reference guide molecule sequence.

44. The composition of embodiment 39, wherein at least about 99% of the guide molecules comprise a 5' sequence comprising nucleotides 1-20 of the guide molecule that is 100% identical to a corresponding 5' sequence of the reference guide molecule sequence.

45. A composition comprising, or consisting essentially of, a guide molecule of any one of embodiments 1-23 of formula $A_{3'}$-iii, or a pharmaceutically acceptable salt thereof, wherein the composition is substantially free of molecules of formula:

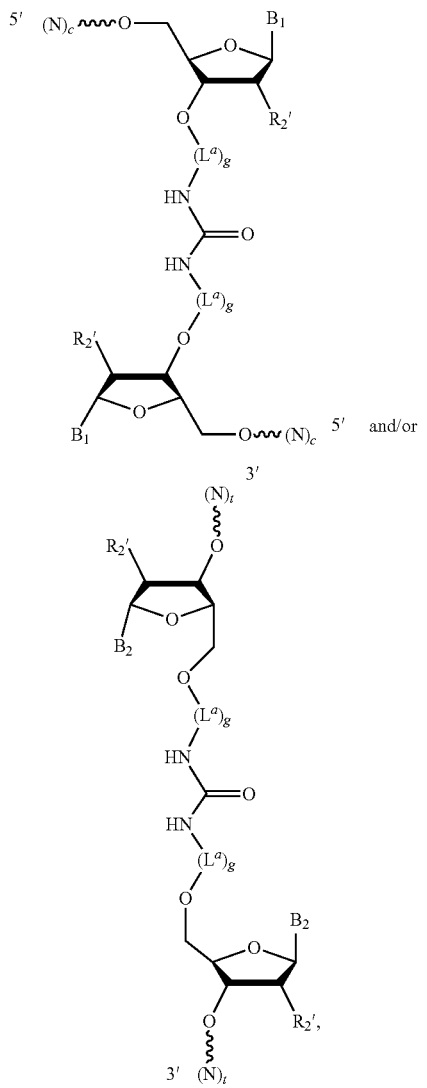

or a pharmaceutically acceptable salt thereof.

46. A composition comprising, or consisting essentially of, a guide molecule of any one of embodiments 1-23 of formula $A_{2'}$-iii, or a pharmaceutically acceptable salt thereof, wherein the composition is substantially free of molecules of formula:

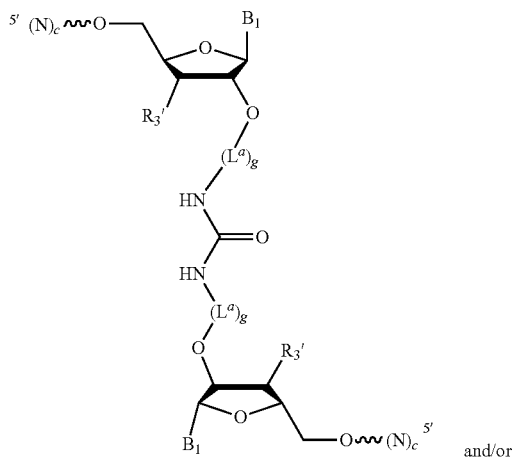 and/or

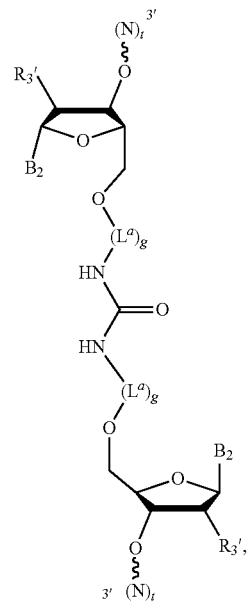

or a pharmaceutically acceptable salt thereof.

47. The composition of embodiment 45 or 46, wherein the composition has not been subjected to any purification steps.

48. A composition comprising, or consisting essentially of, a guide molecule of any one of embodiments 1-23 of formula $A_{3'}$-iii, or a pharmaceutically acceptable salt thereof, wherein the composition is substantially free of molecules of formula $A_{3'}$-vii:

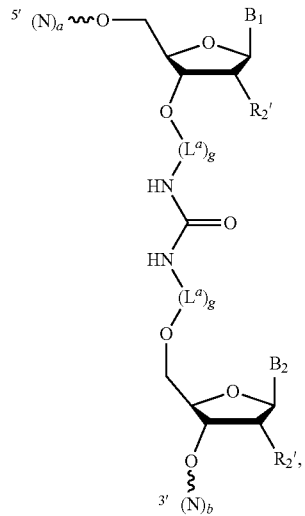

($A_{3'}$-vii)

or a pharmaceutically acceptable salt thereof,
wherein:
   a is not equal to c; and/or
   b is not equal to t.

49. A composition comprising, or consisting essentially of, a guide molecule of any one of embodiments 1-23 of formula $A_{2'}$-iii, or a pharmaceutically acceptable salt thereof,
   wherein the composition is substantially free of molecules of formula $A_{2'}$-vii:

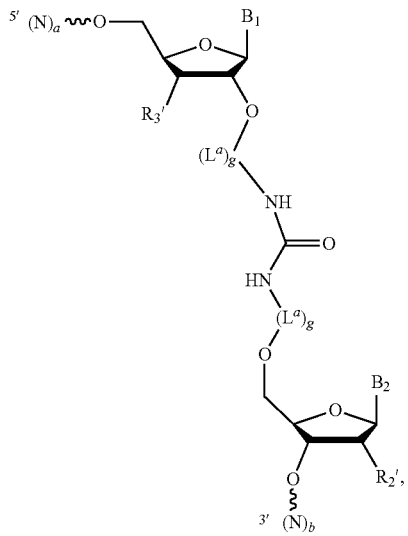

($A_{2'}$-vii)

or a pharmaceutically acceptable salt thereof,
wherein:
   a is not equal to c; and/or
   b is not equal to t.

50. The composition of embodiment 48 or 49, wherein a is less than c, and/or b is less than t.

51. The composition of any one of embodiments 48-50, wherein the composition has not been subjected to any purification steps.

52. The composition of any one of embodiments 45-51, comprising a complex of the guide molecule with a Cas9 or an RNA-guided nuclease.

53. The composition of any one of embodiments 45-52, wherein the guide molecule is suspended in solution or in a pharmaceutically acceptable carrier.

54. The composition of any one of embodiments 45-53, wherein $(N)_c$ comprises a 3' region that comprises at least a portion of a repeat from a Type II CRISPR system.

55. A composition comprising, or consisting essentially of, a guide molecule of any one of embodiments 24-42 of formula $A_{3'}$-iv, or a pharmaceutically acceptable salt thereof,
   wherein the composition is substantially free of molecules of formula:

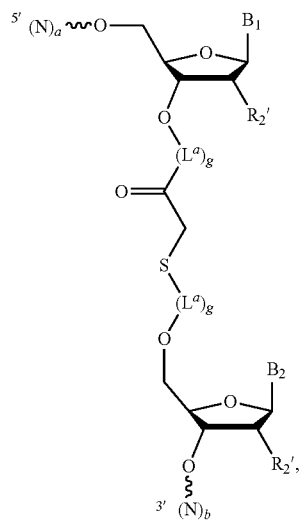

($A_{3'}$-viii)

or a pharmaceutically acceptable salt thereof,
wherein:
   a is not equal to c; and/or
   b is not equal to t.

56. A composition comprising, or consisting essentially of, a guide molecule of any one of embodiments 24-42 of formula $A_{2'}$-iv, or a pharmaceutically acceptable salt thereof, wherein the composition is substantially free of molecules of formula:

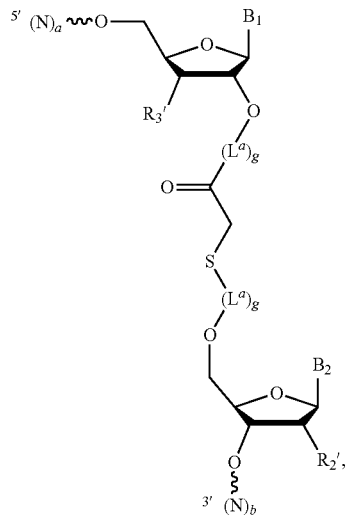

(A$_{2'}$-viii)

or a pharmaceutically acceptable salt thereof,
wherein:
a is not equal to c; and/or
b is not equal to t.

57. A composition comprising, or consisting essentially of, a guide molecule of any one of embodiments 24-42 of formula A$_{3'}$-v, or a pharmaceutically acceptable salt thereof,
wherein the composition is substantially free of molecules of formula:

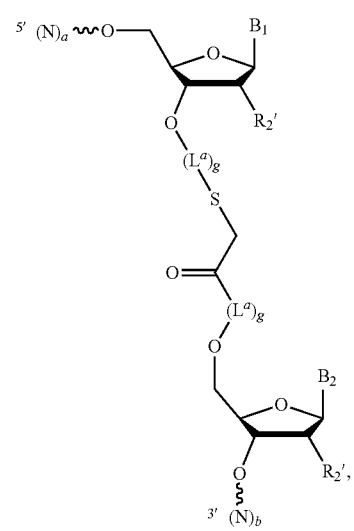

(A$_{3'}$-ix)

or a pharmaceutically acceptable salt thereof,
wherein:
a is not equal to c; and/or
b is not equal to t.

58. A composition comprising, or consisting essentially of, a guide molecule of any one of embodiments 24-42 of formula A$_{2'}$-v, or a pharmaceutically acceptable salt thereof,
wherein the composition is substantially free of molecules of formula:

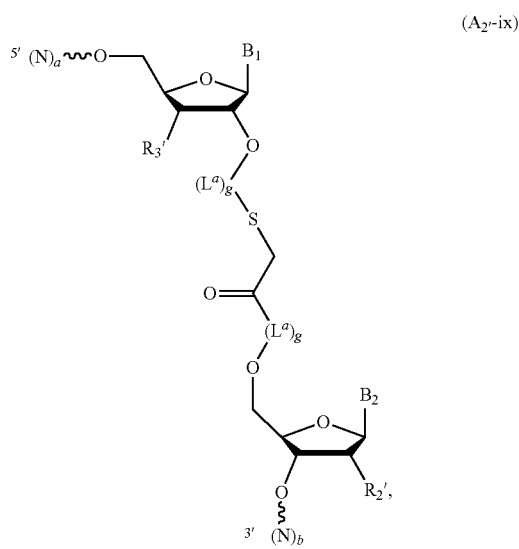

(A$_{2'}$-ix)

or a pharmaceutically acceptable salt thereof,
wherein:
a is not equal to c; and/or
b is not equal to t.

59. The composition of any one of embodiments 55-58, wherein a is less than c, and/or b is less than t.

60. The composition of any one of embodiments 55-58, wherein the composition has not been subjected to any purification steps.

61. The composition of any one of embodiments 55-60, comprising a complex of the guide molecule with a Cas9 or an RNA-guided nuclease.

62. The composition of any one of embodiments 55-61, wherein the guide molecule is suspended in solution or in a pharmaceutically acceptable carrier.

63. The composition of any one of embodiments 55-62, wherein (N)$_c$ comprises a 3' region that comprises at least a portion of a repeat from a Type II CRISPR system.

64. A composition comprising
(a) a synthetic unimolecular guide molecule for a CRISPR system, wherein the guide molecule is of formula:

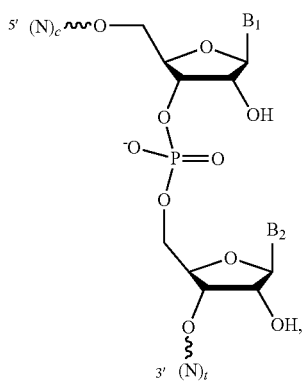

or a pharmaceutically acceptable salt thereof,
wherein:
each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;

$(N)_c$ includes a 3' region that is complementary or partially complementary to, and forms a duplex with, a 5' region of $(N)_t$;

c is an integer 20 or greater;

t is an integer 20 or greater;

$B_1$ and $B_2$ are each independently a nucleobase; and each ∿∿ represents independently a phosphodiester linkage, a phosphorothioate linkage, a phosphonoacetate linkage, a thiophosphonoacetate linkage, or a phosphoroamidate linkage; and (b) one or more of:

(i) a carbodiimide, or a salt thereof;

(ii) imidazole, cyanoimidazole, pyridine, and dimethylaminopyridine, or a salt thereof; and (iii) a compound of formula:

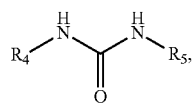

or a salt thereof, wherein $R^4$ and $R^5$ are each independently substituted or unsubstituted alkyl, or substituted or unsubstituted carbocyclyl.

65. The composition of embodiment 64, wherein the carbodiimide is EDC, DCC or DIC.

66. A composition comprising
a synthetic unimolecular guide molecule for a CRISPR system, wherein the guide molecule is of formula:

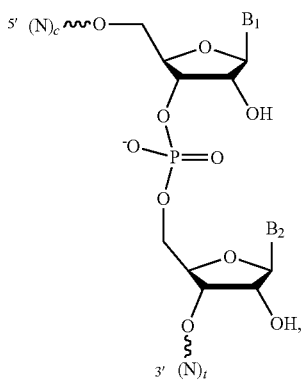

or a pharmaceutically acceptable salt thereof,
wherein:
each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;

$(N)_c$ (includes a 3' region that is complementary or partially complementary to, and forms a duplex with, a 5' region of $(N)_t$;

c is an integer 20 or greater;

t is an integer 20 or greater;

$B_1$ and $B_2$ are each independently a nucleobase; and each ∿∿ represents independently a phosphodiester linkage, a phosphorothioate linkage, a phosphonoacetate linkage, a thiophosphonoacetate linkage, or a phosphoroamidate linkage;

wherein the composition is substantially free of molecules of formula:

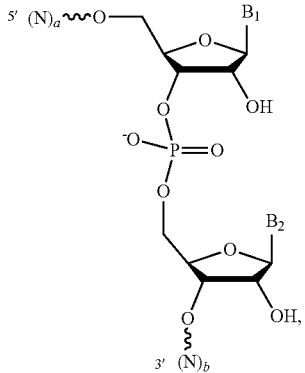

or a pharmaceutically acceptable salt thereof,
wherein:
a+b is c+t-k, wherein k is an integer between 1 and 10, inclusive.

67. A composition comprising, or consisting essentially of, a synthetic unimolecular guide molecule for a CRISPR system, wherein the guide molecule is of formula:

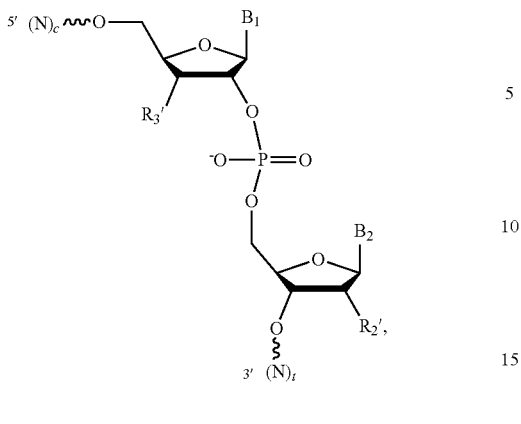

or a pharmaceutically acceptable salt thereof,
wherein:
- each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;
- $(N)_c$ (includes a 3' region that is complementary or partially complementary to, and forms a duplex with, a 5' region of (N);
- the 2'-5' phosphodiester linkage depicted in the formula is between two nucleotides in said duplex;
- c is an integer 20 or greater;
- t is an integer 20 or greater;
- $B_1$ and $B_2$ are each independently a nucleobase;
- each of $R_{2'}$ and $R_3'$ is independently H, OH, fluoro, chloro, bromo, $NH_2$, SH, S—R', or O—R' wherein each R' is independently a protection group or an alkyl group, wherein the alkyl group may be optionally substituted; and
- each ∿∿ represents independently a phosphodiester linkage, a phosphorothioate linkage, a phosphonoacetate linkage, a thiophosphonoacetate linkage, or a phosphoroamidate linkage.

68. The composition of embodiment 67, wherein the guide molecule is for a Type II CRISPR system and $(N)_c$ includes a 5' region that comprises a targeting domain that is fully or partially complementary to a target domain within a target sequence.

69. The composition of embodiment 67 or 68, wherein $(N)_t$ includes a 3' region that comprises one or more stem-loop structures.

70. The composition of any one of embodiments 67-69, wherein the guide molecule is capable of interacting with a Cas9 molecule and mediating the formation of a Cas9/guide molecule complex.

71. The composition of any one of embodiments 67-70, wherein the guide molecule is of formula:

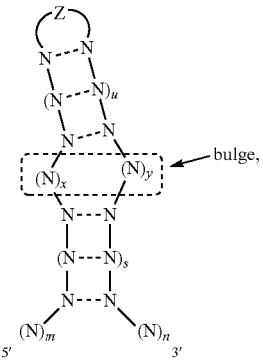

or a pharmaceutically acceptable salt thereof,
wherein:
- Z represents a nucleotide loop which is 4-6 nucleotides long, optionally 4 or 6 nucleotides long;
- u is an integer between 0 and 22, inclusive, optionally 2;
- s is an integer between 1 and 10, inclusive, optionally 4;
- x is an integer between 1 and 3, inclusive, optionally 2;
- y is >x and an integer between 3 and 5, inclusive, optionally 4;
- m is an integer 15 or greater;
- n is an integer 30 or greater;
- each N—N independently represents two complementary nucleotides, optionally two complementary nucleotides that are hydrogen bonding base-paired; and
- at least one phosphodiester linkage between two nucleotides in a duplex region depicted in the formula is a 2'-5' phosphodiester linkage; and
- each N is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage.

72. The composition of any one of embodiments 67-71, wherein the 2'-5' phosphodiester linkage is between two nucleotides that are located 5' of the bulge depicted in the formula of embodiment 71.

73. The composition of any one of embodiments 67-71, wherein the 2'-5' phosphodiester linkage is between two nucleotides that are located 5' of the nucleotide loop Z and 3' of the bulge depicted in the formula of embodiment 71.

74. The composition of any one of embodiments 67-71, wherein the 2'-5' phosphodiester linkage is between two nucleotides that are located 3' of the nucleotide loop Z and 5' of the bulge depicted in the formula of embodiment 71.

75. The composition of any one of embodiments 67-71, wherein the 2'-5' phosphodiester linkage is between two nucleotides that are located 3' of the bulge depicted in the formula of embodiment 71.

76. The composition of any one of embodiments 45-75, wherein less than about 10% of the guide molecules comprise a truncation at a 5' end, relative to a reference guide molecule sequence.

77. The composition of embodiment 76, wherein at least about 99% of the guide molecules comprise a 5' sequence comprising nucleotides 1-20 of the guide molecule that is 100% identical to a corresponding 5' sequence of the reference guide molecule sequence.

78. A composition of guide molecules for a CRISPR system, wherein the composition consists essentially of guide molecules of formula $A_{3'}$-i or $A_{2'}$-i:

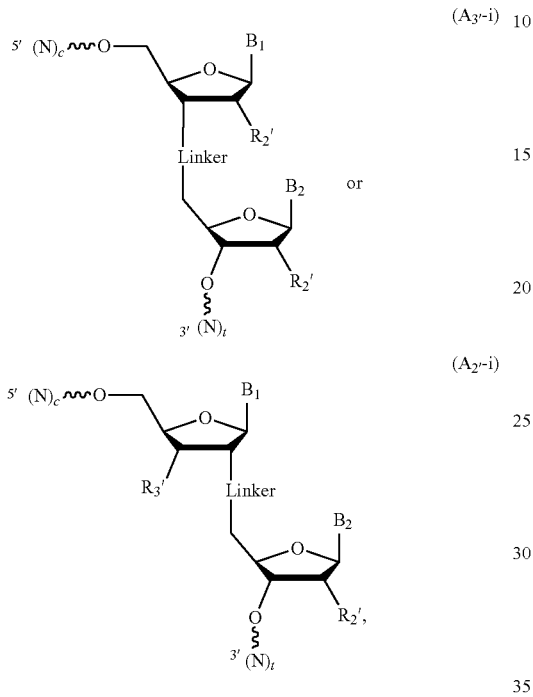

or a pharmaceutically acceptable salt thereof, wherein:

- each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;
- $(N)_c$ (includes a 3' region that is complementary or partially complementary to, and forms a duplex with, a 5' region of $(N)_t$;
- c is an integer 20 or greater;
- t is an integer 20 or greater; and
- each ⁓ represents independently a phosphodiester linkage, a phosphorothioate linkage, a phosphonoacetate linkage, a thiophosphonoacetate linkage, or a phosphoroamidate linkage;
- Linker is a non-nucleotide chemical linkage;
- $B_1$ and $B_2$ are each independently a nucleobase; and
- each of $R_2'$ and $R_3'$ is independently H, OH, fluoro, chloro, bromo, $NH_2$, SH, S—R', or O—R' wherein each R' is independently a protection group or an alkyl group, wherein the alkyl group may be optionally substituted.

79. The composition of guide molecules of embodiment 78, consisting essentially of guide molecules of formula $C_{3'}$-i or $C_{2'}$-i:

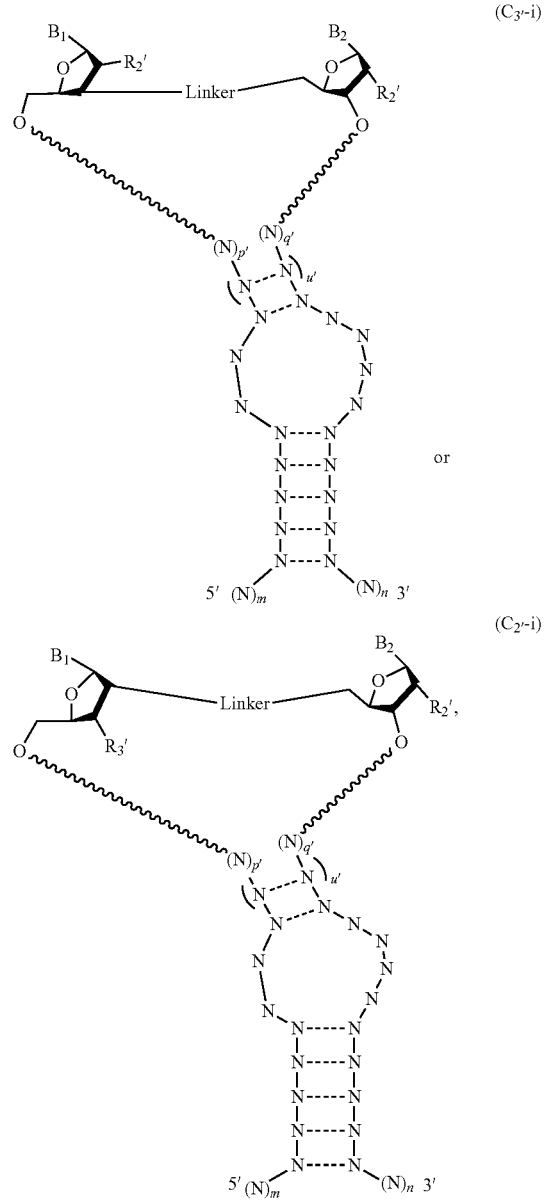

or a salt thereof, wherein:
- p and q are each independently an integer between 0 and 6, inclusive, and p+q is an integer between 0 and 6, inclusive;
- u' is an integer between 2 and 22, inclusive;
- m is an integer 15 or greater;
- n is an integer 30 or greater;
- each N—N independently represents two complementary nucleotides, optionally two complementary nucleotides that are hydrogen bonding base-paired; and
- each N is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage.

80. The composition of guide molecules of embodiment 78, consisting essentially of guide molecules of formula $D_{3'}$-i or $D_{2'}$-i:

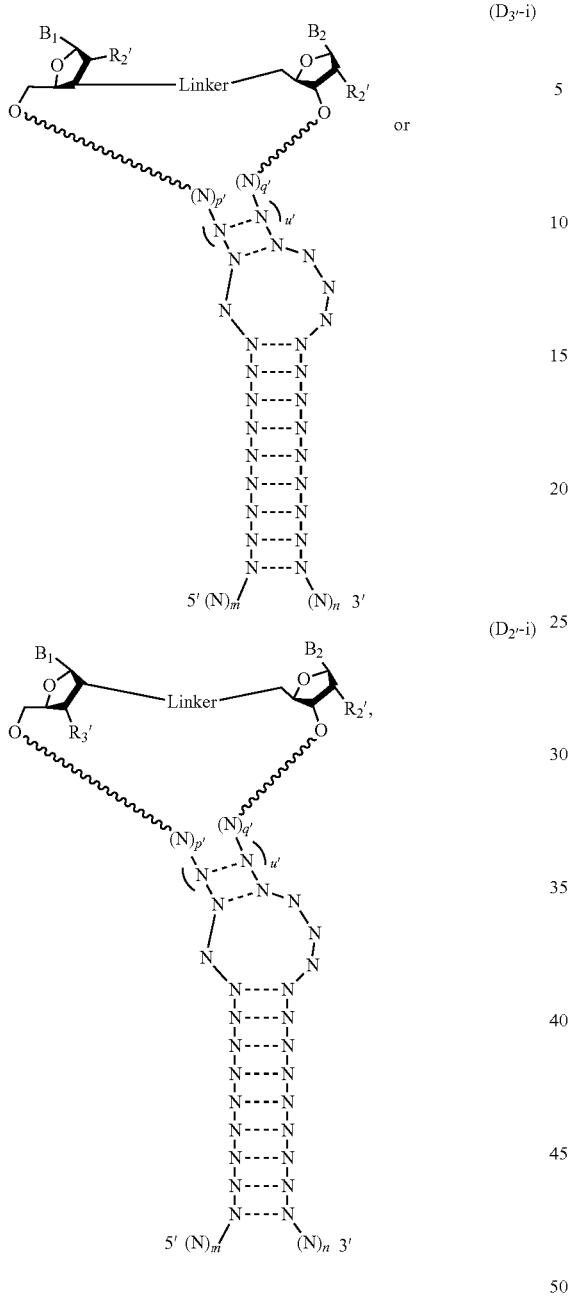

or a salt thereof, wherein:
  p and q are each independently an integer between 0 and 6, inclusive, and p+q is an integer between 0 and 6, inclusive;
  u' is an integer between 2 and 22, inclusive;
  m is an integer 15 or greater;
  n is an integer 30 or greater;
  each N—N independently represents two complementary nucleotides, optionally two complementary nucleotides that are hydrogen bonding base-paired; and
each N is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage.

81. The composition of guide molecules of embodiment 78, consisting essentially of guide molecules of formula:

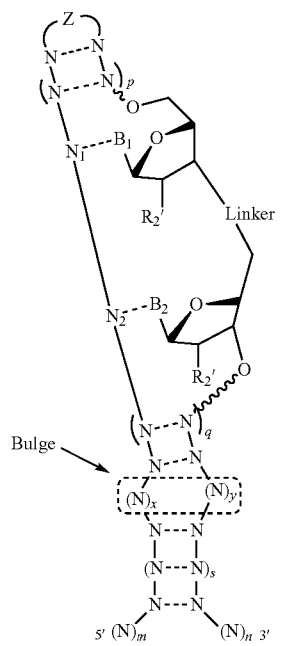

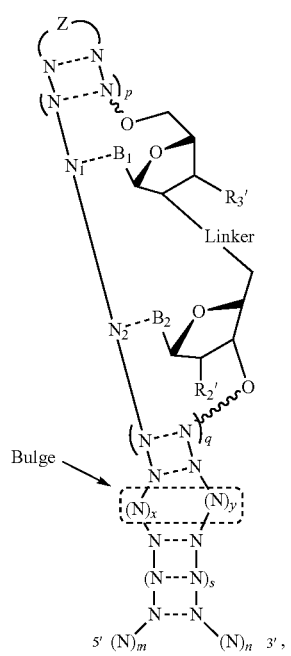

281
-continued
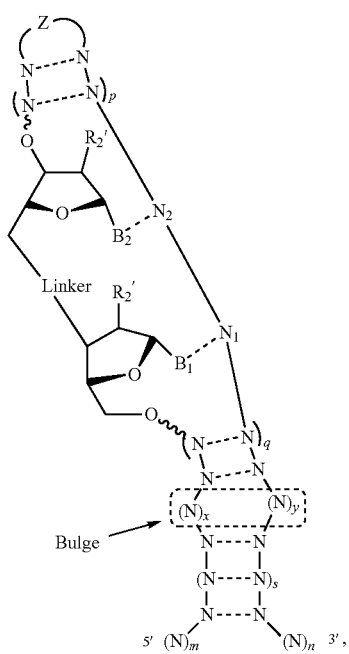
282
-continued
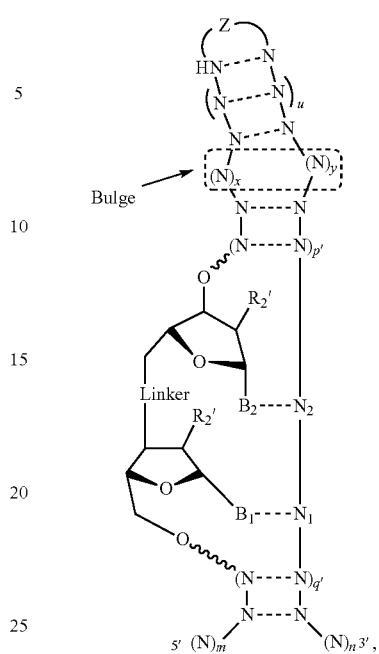
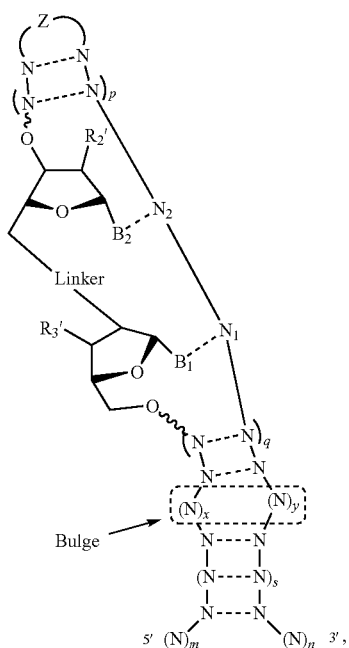
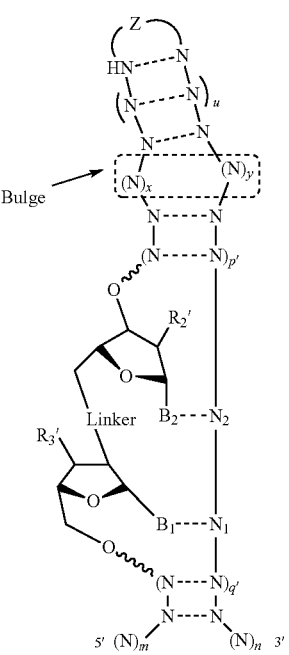

-continued

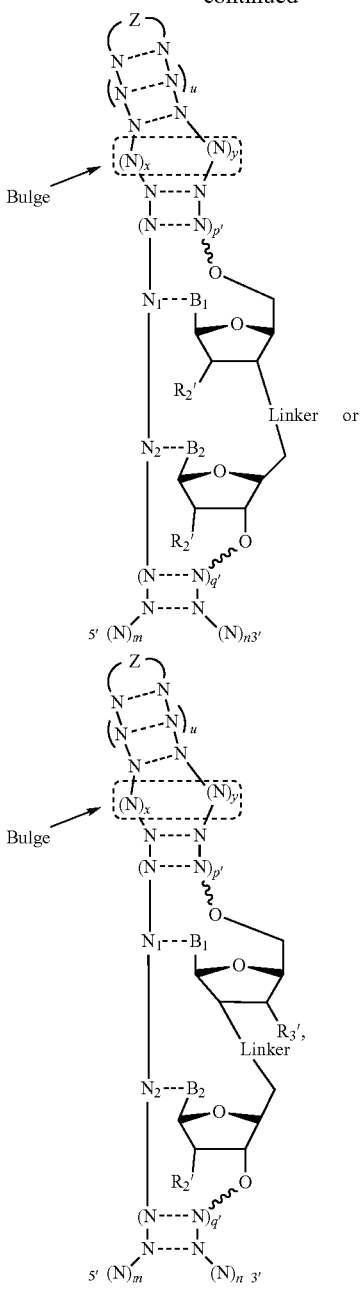

or a salt thereof,
wherein:
Z represents a nucleotide loop which is 4-6 nucleotides long, optionally 4 or 6 nucleotides long;
p and q are each independently an integer between 0 and 2, inclusive, optionally 0;
p' is an integer between 0 and 4, inclusive, optionally 0;
q' is an integer between 0 and 4, inclusive, optionally 2;
x is an integer between 1 and 3, inclusive optionally 2;
y is >x and an integer between 3 and 5, inclusive, optionally 4;
u is an integer between 2 and 22, inclusive, optionally 2;

s is an integer between 1 and 10, inclusive, optionally 4;
m is an integer 15 or greater;
n is an integer 30 or greater;
$B_1$ and $B_2$ are each independently a nucleobase;
each N is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;
$N_1$ and $N_2$ are each independently a nucleotide residue;
each N—N independently represents two complementary nucleotides, optionally two complementary nucleotides that are hydrogen bonding base-paired; and
each ∿∿ represents independently a phosphodiester linkage, a phosphorothioate linkage, a phosphonoacetate linkage, a thiophosphonoacetate linkage, or a phosphoroamidate linkage.

82. A composition of guide molecules for a CRISPR system, wherein the guide molecules are of formula $A_{3'}$-i or $A_{2'}$-i:

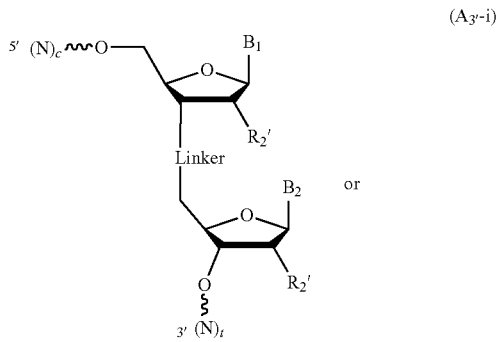

(A$_{3'}$-i)

or

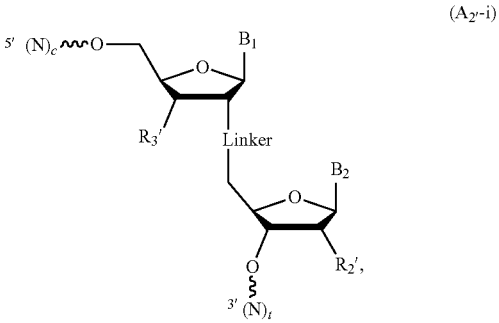

(A$_{2'}$-i)

or a pharmaceutically acceptable salt thereof, wherein:

each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;

$(N)_c$ includes a 3' region that is complementary or partially complementary to, and forms a duplex with, a 5' region of $(N)_t$;

c is an integer 20 or greater;

t is an integer 20 or greater; and each ∿∿∿ represents independently a phosphodiester linkage, a phosphorothioate linkage, a phosphonoacetate linkage, a thiophosphonoacetate linkage, or a phosphoroamidate linkage;

Linker is a non-nucleotide chemical linkage;

$B_1$ and $B_2$ are each independently a nucleobase; and each of $R_2'$ and $R_3'$ is independently H, OH, fluoro, chloro, bromo, $NH_2$, SH, S—R', or O—R' wherein each R' is independently a protection group or an alkyl group, wherein the alkyl group may be optionally substituted, wherein less than about 10% of the guide molecules comprise a truncation at a 5' end, relative to a reference guide molecule sequence, and wherein at least about 99% of the guide molecules comprise a 5' sequence comprising nucleotides 1-20 of the guide molecule that is 100% identical to a corresponding 5' sequence of the reference guide molecule sequence.

83. The composition of guide molecules of embodiment 82, wherein the guide molecules are of formula $C_{3'}$-i or $C_{2'}$-i:

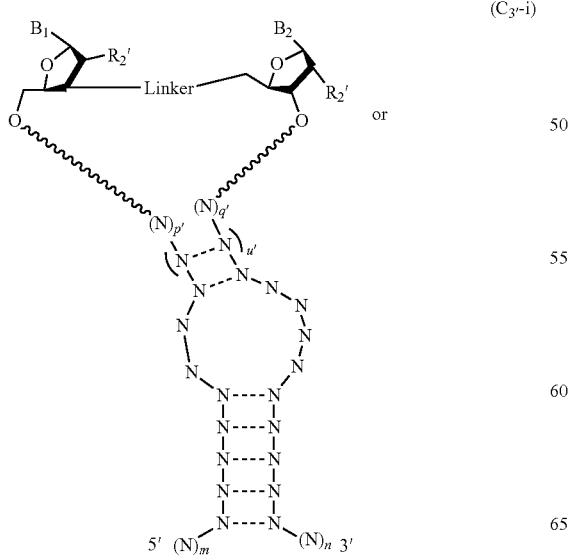

(C$_{3'}$-i)

or

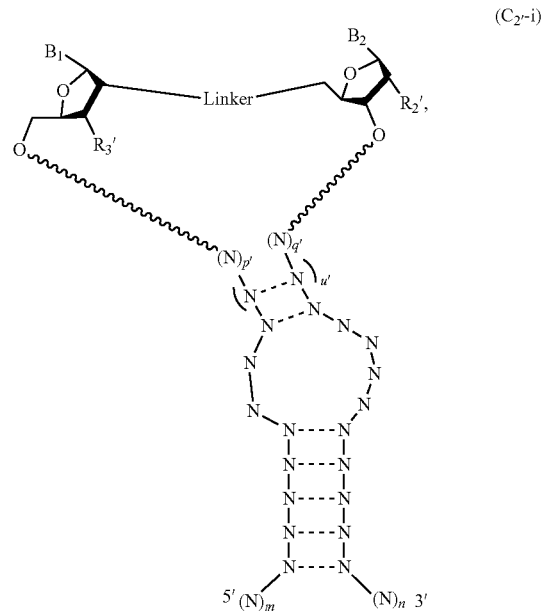

(C$_{2'}$-i)

or a salt thereof, wherein:

p and q are each independently an integer between 0 and 6, inclusive, and p+q is an integer between 0 and 6, inclusive;

u' is an integer between 2 and 22, inclusive;

m is an integer 15 or greater;

n is an integer 30 or greater;

each N—N independently represents two complementary nucleotides, optionally two complementary nucleotides that are hydrogen bonding base-paired; and each N is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage.

84. The composition of guide molecules of embodiment 82, wherein the guide molecules are of formula $D_{3'}$-i or $D_{2'}$-i:

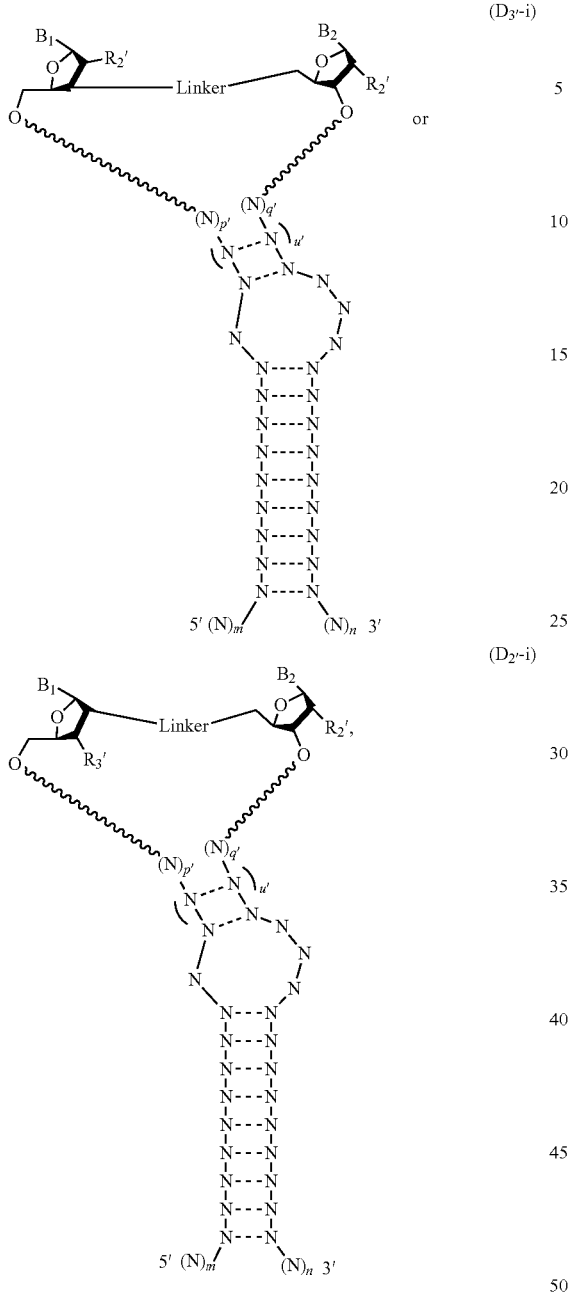

(D3'-i)

(D2'-i)

or a salt thereof, wherein:
p and q are each independently an integer between 0 and 6, inclusive, and p+q is an integer between 0 and 6, inclusive;
u' is an integer between 2 and 22, inclusive;
m is an integer 15 or greater;
n is an integer 30 or greater;
each N—N independently represents two complementary nucleotides, optionally two complementary nucleotides that are hydrogen bonding base-paired; and
each N is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage.

85. The composition of guide molecules of embodiment 82, wherein the guide molecules are of formula:

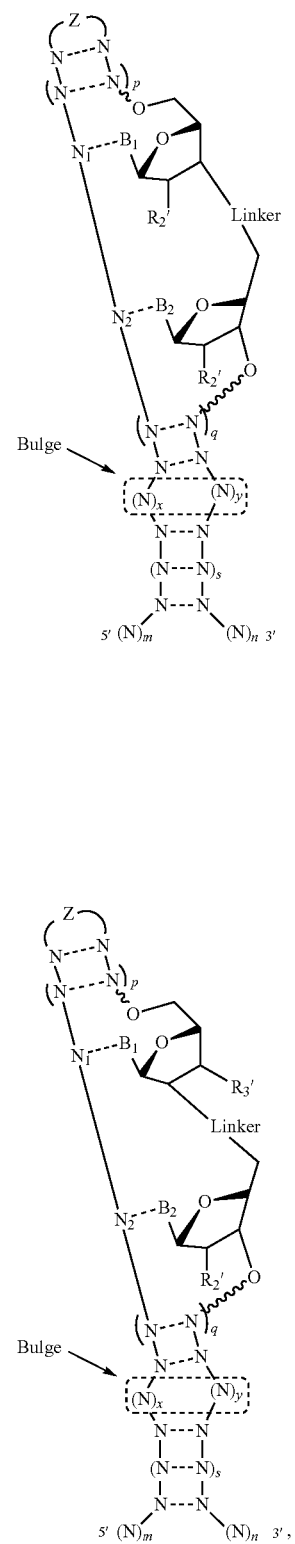

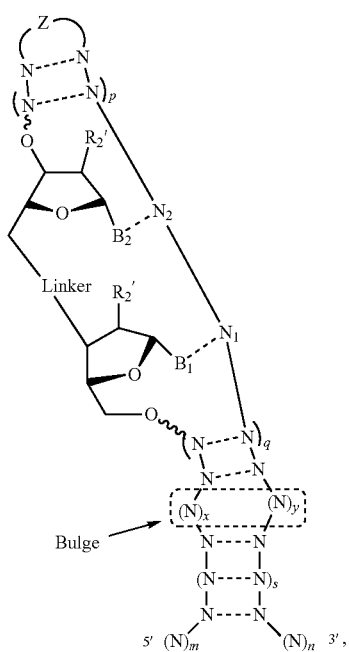
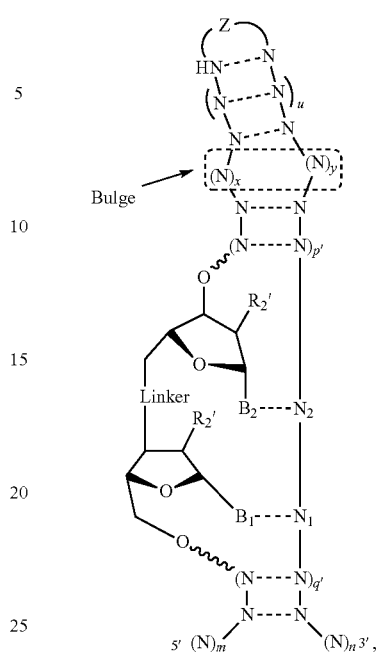
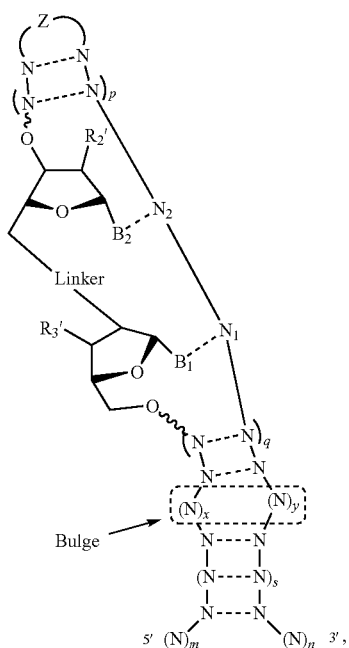
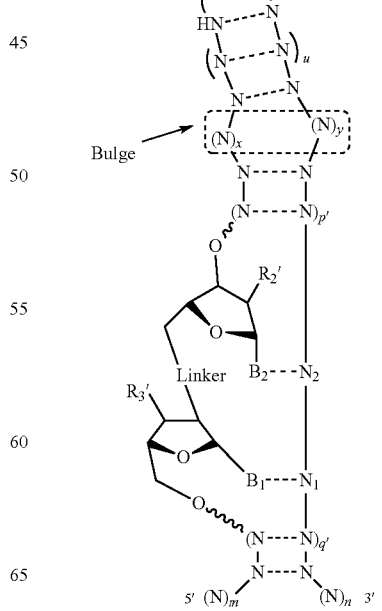

-continued

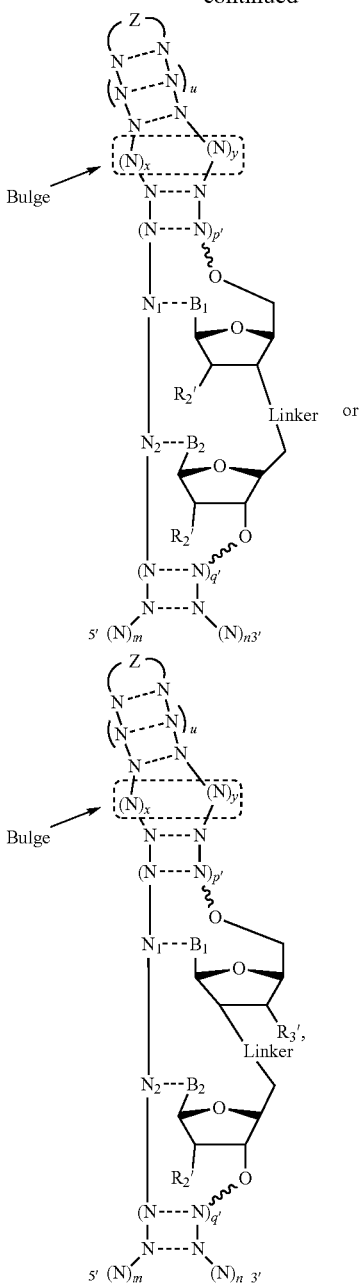

or a salt thereof,
wherein:
Z represents a nucleotide loop which is 4-6 nucleotides long, optionally 4 or 6 nucleotides long;
p and q are each independently an integer between 0 and 2, inclusive, optionally 0;
p' is an integer between 0 and 4, inclusive, optionally 0;
q' is an integer between 0 and 4, inclusive, optionally 2;
x is an integer between 1 and 3, inclusive optionally 2;
y is >x and an integer between 3 and 5, inclusive, optionally 4;
u is an integer between 2 and 22, inclusive, optionally 2;

s is an integer between 1 and 10, inclusive, optionally 4;
m is an integer 15 or greater;
n is an integer 30 or greater;
$B_1$ and $B_2$ are each independently a nucleobase;
each N is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;
$N_1$ and $N_2$ are each independently a nucleotide residue;
each N—N independently represents two complementary nucleotides, optionally two complementary nucleotides that are hydrogen bonding base-paired; and
each ⌇⌇⌇ represents independently a phosphodiester linkage, a phosphorothioate linkage, a phosphonoacetate linkage, a thiophosphonoacetate linkage, or a phosphoroamidate linkage.

86. A method of synthesizing a unimolecular guide molecule for a CRISPR system, the method comprising the steps of:
annealing a first oligonucleotide and a second oligonucleotide to form a duplex between a 3' region of the first oligonucleotide and a 5' region of the second oligonucleotide, wherein the first oligonucleotide comprises a first reactive group which is at least one of a 2' reactive group and a 3' reactive group, and wherein the second oligonucleotide comprises a second reactive group which is a 5' reactive group; and
conjugating the annealed first and second oligonucleotides via the first and second reactive groups to form a unimolecular guide molecule that includes a covalent bond linking the first and second oligonucleotides.

87. The method of embodiment 86, wherein the guide molecule is for a Type II CRISPR system and a 5' region of the first oligonucleotide comprises a targeting domain that is fully or partially complementary to a target domain within a target sequence.

88. The method of embodiment 86 or 87, wherein a 3' region of the second oligonucleotide comprises one or more stem-loop structures.

89. The method of any one of embodiments 86-88, wherein the guide molecule is capable of interacting with a Cas9 molecule and mediating the formation of a Cas9/guide molecule complex.

90. The method of any one of embodiments 86-89, wherein the first and second reactive groups both comprise an amine moiety and the step of conjugating comprises crosslinking the amine moieties of the first and second reactive groups with a carbonate-containing bifunctional crosslinking reagent to form a urea linkage.

91. The method of embodiment 90, wherein the carbonate-containing bifunctional crosslinking reagent is disuccinimidyl carbonate, diimidazole carbonate, or bis-(p-nitrophenyl) carbonate.

92. The method of any one of embodiments 86-91, wherein the concentration of each of the first and second oligonucleotides is in the range of 10 μM to 1 mM.

93. The method of any one of embodiments 90-92, wherein the concentration of carbonate-containing bifunctional crosslinking reagent is in the range of 1 mM to 100 mM.
94. The method of any one of embodiments 90-93, wherein the concentration of carbonate-containing bifunctional crosslinking reagent is 100-1,000 times greater than the concentration of each of the first and second oligonucleotides.
95. The method of any one of embodiments 86-94, wherein the step of conjugating is performed at a pH in the range of 7-9.
96. The method of any one of embodiments 86-95, wherein the step of conjugating is performed in water with DMSO, DMF, NMP, DMA, morpholine, pyridine or MeCN as a co-solvent.
97. The method of any one of embodiments 86-96, wherein the step of conjugating is performed in the presence of a divalent metal cation.
98. The method of any one of embodiments 86-97, wherein the step of conjugating is performed at a temperature in the range of 0° C. to 40° C.
99. The method of any one of embodiments 86-98, wherein the first oligonucleotide is of formula:

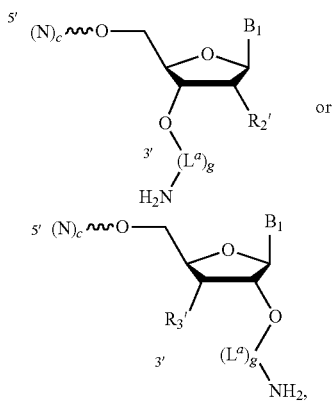

or a salt thereof; and
the second oligonucleotide is of formula:

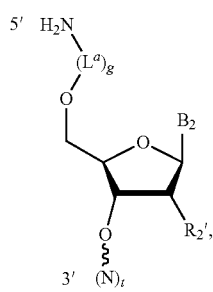

or a salt thereof;
wherein:
each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;

$(N)_c$ includes a 3' region that is complementary or partially complementary to, and forms a duplex with, a 5' region of $(N)_t$;

c is an integer 20 or greater;

t is an integer 20 or greater;

each of $R_2'$ and $R_3'$ is independently H, OH, fluoro, chloro, bromo, $NH_2$, SH, S—R', or O—R' wherein each R' is independently a protection group or an alkyl group, wherein the alkyl group may be optionally substituted;

each $L^a$ is independently a non-nucleotide linker;

each g is independently 0, 1, 2, 3, 4, or 5; and $B_1$ and $B_2$ are each independently a nucleobase; and each ∿∿ represents independently a phosphodiester linkage, a phosphorothioate linkage, a phosphonoacetate linkage, a thiophosphonoacetate linkage, or a phosphoroamidate linkage.

100. The method of any one of embodiments 86-99, wherein the unimolecular guide molecule is of formula $A_{3'}$-iii or $A_{2'}$-iii, or a salt thereof.
101. The method of any one of embodiments 82-96, wherein the unimolecular guide molecule is of formula $B_{3'}$-iii or $B_{2'}$-iii, or a salt thereof.
102. The method of any one of embodiments 86-101, wherein the unimolecular guide molecule is of formula $C_{3'}$-iii or $C_{2'}$-iii, or a salt thereof.
103. The method of any one of embodiments 86-101, wherein the unimolecular guide molecule is of formula $D_{3'}$-iii or $D_{2'}$-iii, or a salt thereof.
104. The method of embodiment 102 or 103, wherein p'=q', optionally wherein p'=q'=0, p'=q'=1, or p'=q'=2.
105. The method of any one of embodiments 101-104, wherein one $-(L^a)_g-$ is $—(CH_2)_w—$, and w is 1-20.
106. The method of any one of embodiments 101-104, wherein one $-(L^a)_g-$ is $—(CH_2CH_2O)_vCH_2CH_2—$, and v is 1-10.
107. The method of any one of embodiments 99-102, wherein the unimolecular guide molecule is of formula:

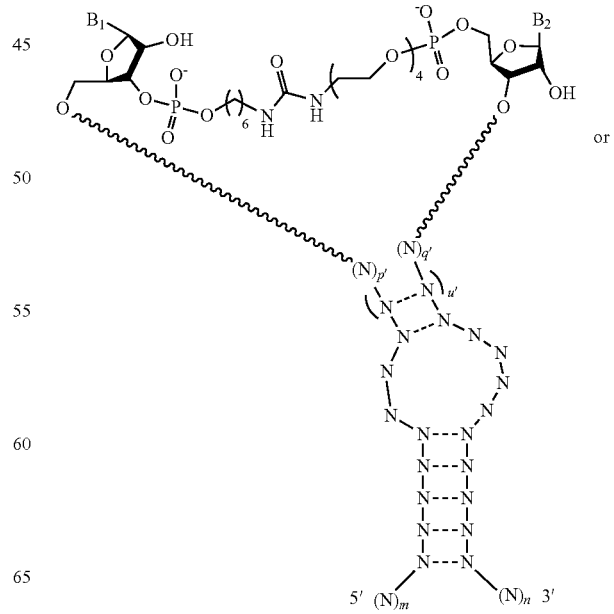

-continued

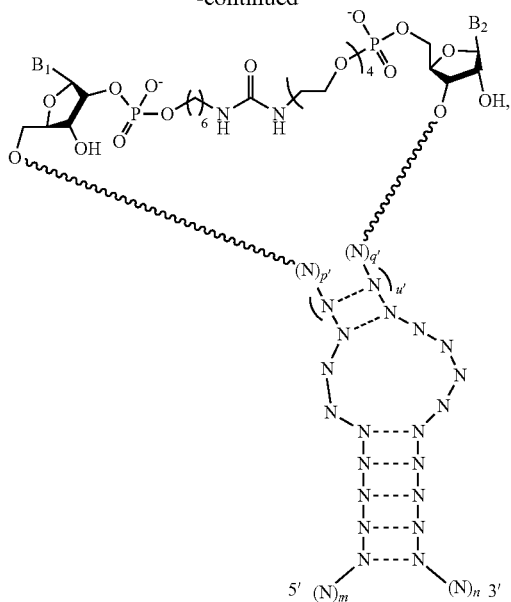

or a salt thereof,
wherein:
p' and q' are each independently an integer between 0 and 4, inclusive;
p'+q' is an integer between 0 and 4, inclusive; and
u' is an integer between 2 and 14, inclusive.

108. The method of any one of embodiments 99-102, wherein the unimolecular guide molecule is of formula:

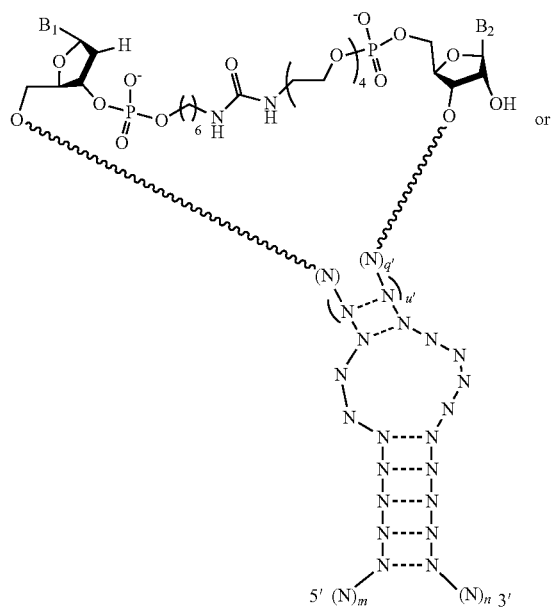

-continued

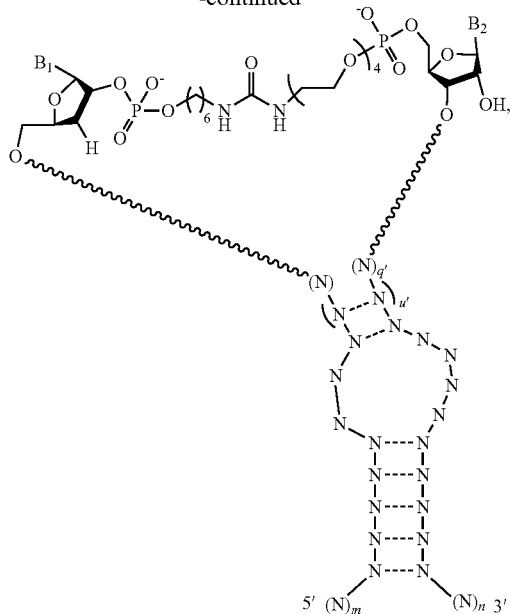

or a salt thereof,
wherein:
p' and q' are each independently an integer between 0 and 4, inclusive;
p'+q' is an integer between 0 and 4, inclusive; and
u' is an integer between 2 and 14, inclusive.

109. The method of any one of embodiments 86-89, wherein (a) the first reactive group comprises a bromoacetyl moiety and the second reactive group comprises a sulfhydryl moiety, or (b) the first reactive group comprises a sulfhydryl moiety and the second reactive group comprises a bromoacetyl moiety, and the step of conjugating comprises reacting the bromoacetyl moiety with the sulfhydryl moiety to form a bromoacetyl-thiol linkage.

110. The method of embodiment 109, wherein the concentration of each of the first and second oligonucleotides is in the range of 10 μM to 1 mM.

111. The method of embodiment 109 or 110, wherein the step of conjugating is performed at a pH in the range of 7-9.

112. The method of any one of embodiments 109-111, wherein the step of conjugating is performed under argon.

113. The method of any one of embodiments 109-112, wherein the step of conjugating is performed in the presence of a chelating reagent, optionally ethylenediaminetetraacetic acid (EDTA), or a salt thereof.

114. The method of any one of embodiments 109-113, wherein the step of conjugating is performed at a temperature in the range of 0° C. to 40° C.

115. The method of any one of embodiments 109-114, wherein:

(a) the first oligonucleotide is of formula:

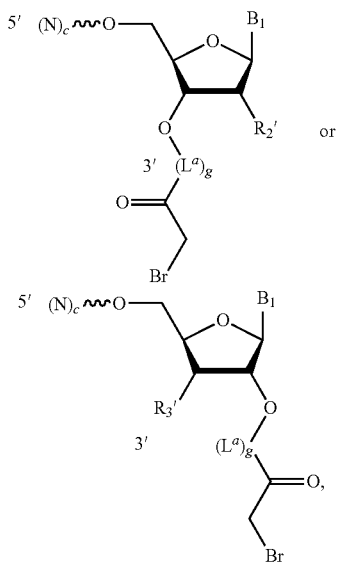

or a salt thereof, and
the second oligonucleotide is of formula:

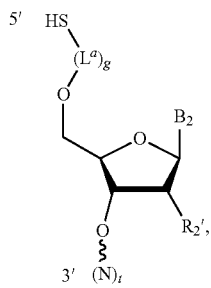

or a salt thereof; or (b) the first oligonucleotide is of formula:

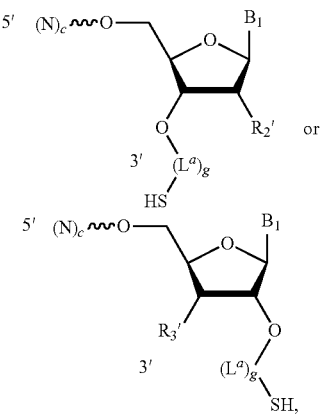

or a salt thereof, and
the second oligonucleotide is of formula:

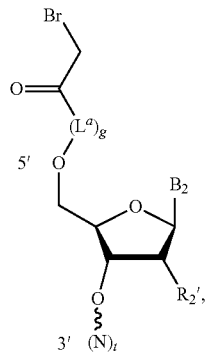

or a salt thereof;
wherein:
  each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;
  $(N)_c$ includes a 3' region that is complementary or partially complementary to, and forms a duplex with, a 5' region of $(N)_t$;
  c is an integer 20 or greater;
  t is an integer 20 or greater;
  each of $R_2'$ and $R_3'$ is independently H, OH, fluoro, chloro, bromo, $NH_2$, SH, S—R', or O—R' wherein each R' is independently a protection group or an alkyl group, wherein the alkyl group may be optionally substituted;
  each $L^a$ is independently a non-nucleotide linker;
  each g is independently 0, 1, 2, 3, 4, or 5; and
  $B_1$ and $B_2$ are each independently a nucleobase; and
  each ∿∿ represents independently a phosphodiester linkage, a phosphorothioate linkage, a phosphonoacetate linkage, a thiophosphonoacetate linkage, or a phosphoroamidate linkage.

116. The method of any one of embodiments 109-115, wherein the unimolecular guide molecule is of formula $A_{3'}$-iv, $A_{2'}$-iv, $A_{3'}$-v, or $A_{2'}$-v, or a salt thereof.

117. The method of any one of embodiments 109-116, wherein the unimolecular guide molecule is of formula $B_{3'}$-iv, $B_{2'}$-iv, $B_{3'}$-v, or $B_{2'}$-v, or a salt thereof.

118. The method of any one of embodiments 109-117, wherein the unimolecular guide molecule is of formula $C_{3'}$-iv, $C_{2'}$-iv, $C_{3'}$-v, or $C_{2'}$-v, or a salt thereof.

119. The method of any one of embodiments 109-117, wherein the unimolecular guide molecule is of formula $D_{3'}$-iv, $D_{2'}$-iv, $D_{3'}$-v, or $D_{2'}$-v, or a salt thereof.

120. The method of embodiment 118 or 119, wherein p'=q', optionally wherein p'=q'=0, p'=q'=1, or p'=q'=2.

121. The method of any one of embodiments 117-120, wherein $-(L^a)_g-$ are each independently $-(CH_2)_w-NHC(O)-(CH_2)_w-NH-$ or $-CH_2CH_2-(OCH_2CH_2)_v-NH-C(O)-(CH_2)_w-$; each w is independently 1-20; and each v is independently 1-10.

122. The method of any one of embodiments 115-121, wherein the unimolecular guide molecule is of formula:

299 300
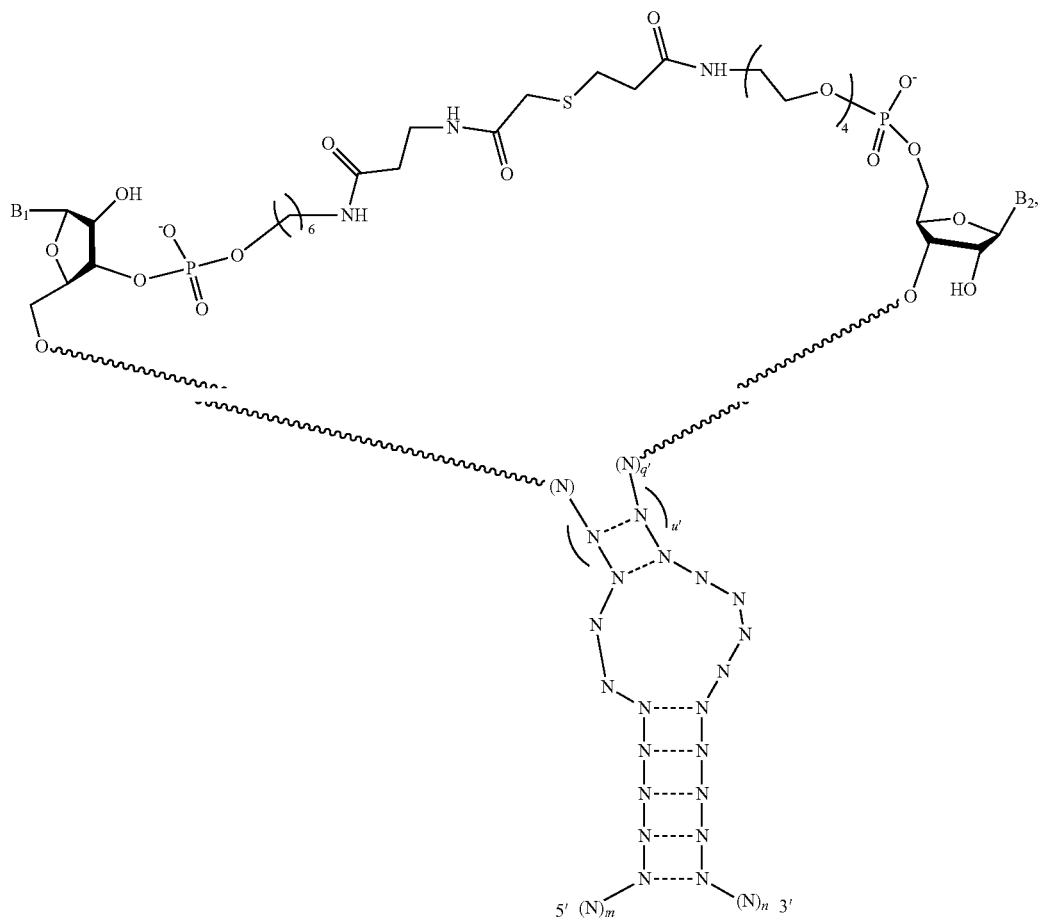
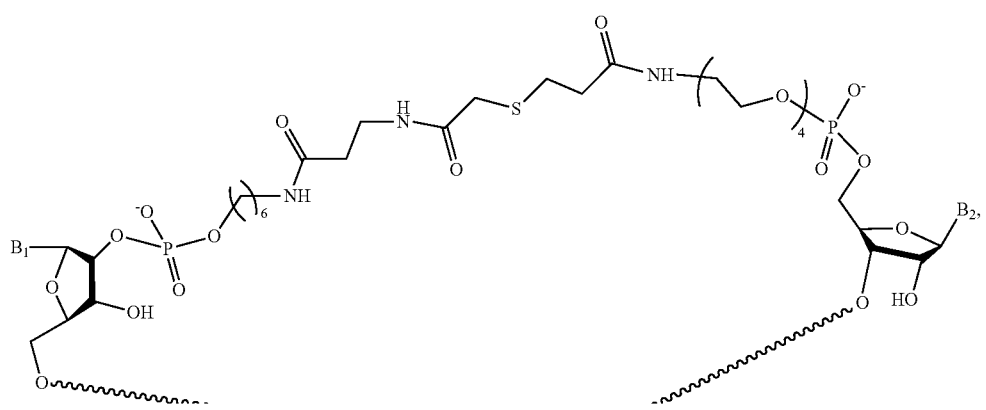

-continued
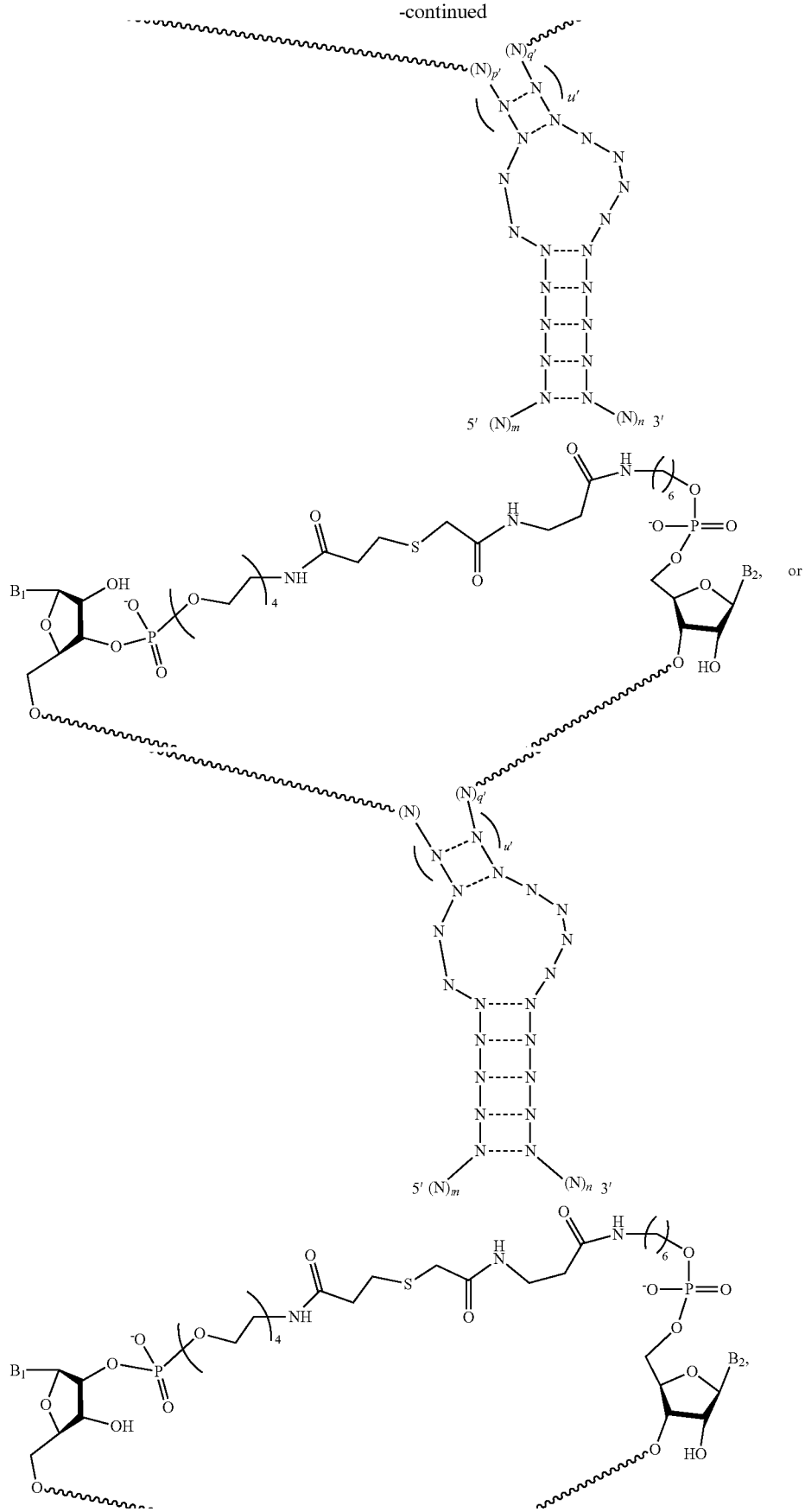
or

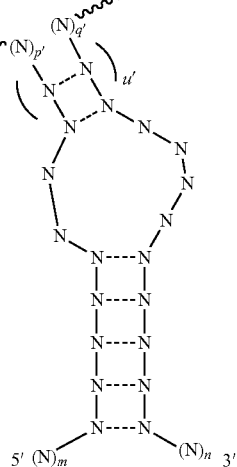

or a salt thereof, wherein p' and q' are each independently an integer between 0 and 4, inclusive, and p'+q' is an integer between 0 and 4, inclusive; and u' is an integer between 2 and 14, inclusive.

123. The method of any one of embodiments 86-89, wherein (a) the first reactive group comprises a 2' or 3' hydroxyl moiety and the second reactive group comprises a 5' phosphate moiety or (b) the first reactive group comprises a 5' phosphate moiety and the second reactive group comprises a 2' or 3' hydroxyl moiety, and the step of conjugating comprises reacting the hydroxyl and phosphate moieties in the presence of an activating agent to form a phosphodiester linkage.

124. The method of embodiment 123, wherein the activating agent is a carbodiimide, or a salt thereof.

125. The method of embodiment 124, wherein the carbodiimide is 1-ethyl-3-(3-dimethylaminopropyl) carbodiimide (EDC), N,N'-dicyclohexylcarbodiimide (DCC) or N,N'-diisopropylcarbodiimide (DIC), or a salt thereof.

126. The method of any one of embodiments 123-125, wherein the step of conjugating comprises reacting the hydroxyl and phosphate moieties in the presence of an activating agent and a stabilizing agent.

127. The method of embodiment 126, wherein the stabilizing agent is imidazole, cyanoimidazole, pyridine, or dimethylaminopyridine, or a salt thereof.

128. The method of any one of embodiments 123-127, wherein the concentration of each of the first and second oligonucleotides is in the range of 10 μM to 1 mM.

129. The method of any one of embodiments 123-128, wherein the concentration of the activating agent is in the range of 1 mM to 100 mM.

130. The method of any one of embodiments 123-129, wherein the concentration of the activating agent is 100-1,000 times greater than the concentration of each of the first and second oligonucleotides.

131. The method of any one of embodiments 123-130, wherein the step of conjugating is performed at a pH in the range of 5-9.

132. The method of any one of embodiments 123-131, wherein the step of conjugating is performed in the presence of a divalent metal cation.

133. The method of any one of embodiments 123-132, wherein the step of conjugating is performed at a temperature in the range of 0° C. to 40° C.

134. The method of any one of embodiments 123-133, wherein the first oligonucleotide is of formula:

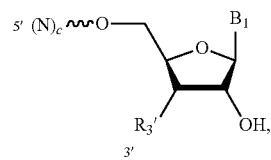

or a salt thereof; and
the second oligonucleotide is of formula:

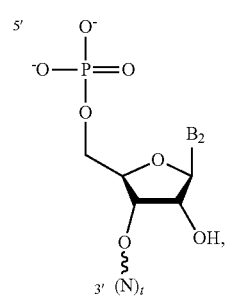

or a salt thereof;
wherein:
each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;
$(N)_c$ includes a 3' region that is complementary or partially complementary to, and forms a duplex with, a 5' region of (N);
$B_1$ and $B_2$ are each independently a nucleobase;
c is an integer 20 or greater;

t is an integer 20 or greater;

R$_3$' is independently H, OH, fluoro, chloro, bromo, NH$_2$, SH, S—R', or O—R' wherein each R' is independently a protection group or an alkyl group, wherein the alkyl group may be optionally substituted; and each ∿∿ represents independently a phosphodiester linkage, a phosphorothioate linkage, a phosphonoacetate linkage, a thiophosphonoacetate linkage, or a phosphoroamidate linkage.

135. The method of any one of embodiments 123-134, wherein the unimolecular guide molecule is of formula:

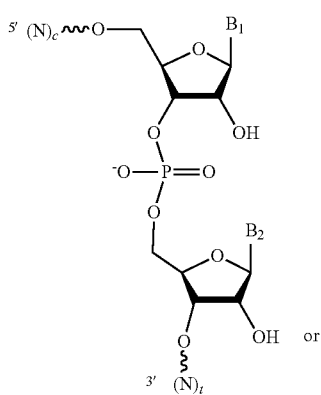

or

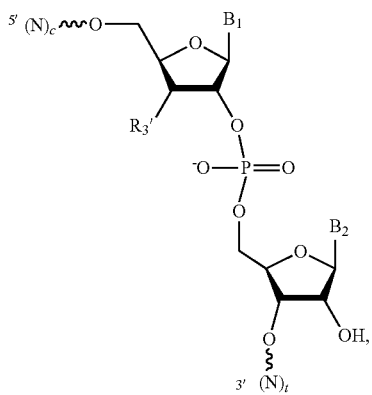

or a pharmaceutically acceptable salt thereof.

136. The method of any one of embodiments 123-135, wherein the unimolecular guide molecule is of formula:

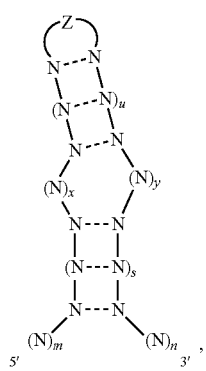

or a pharmaceutically acceptable salt thereof,
wherein:
Z represents a nucleotide loop which is 4-6 nucleotides long, optionally 4 or 6 nucleotides long;
u is an integer between 2 and 22, inclusive;
s is an integer between 1 and 10, inclusive;
x is an integer between 1 and 3, inclusive;
y is >x and an integer between 3 and 5, inclusive;
m is an integer 15 or greater;
n is an integer 30 or greater;
each N is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage; and
each N—N independently represents two complementary nucleotides, optionally two complementary nucleotides that are hydrogen bonding base-paired, optionally comprising at least one 2'-5' phosphodiester linkage in a duplex region.

137. A composition comprising a plurality of guide molecules produced by the method of any one of embodiments 86-136, wherein less than about 10% of the guide molecules comprise a truncation at a 5' end, relative to a reference guide molecule sequence.

138. The composition of embodiment 137, wherein at least about 99% of the guide molecules comprise a 5' sequence comprising nucleotides 1-20 of the guide molecule that is 100% identical to a corresponding 5' sequence of the reference guide molecule sequence.

139. A composition comprising a synthetic unimolecular guide molecule for a CRISPR system of formula:

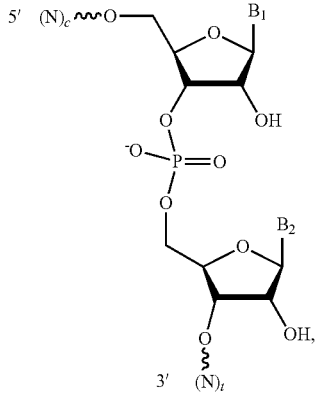

or a pharmaceutically acceptable salt thereof,
prepared by a process comprising a reaction between

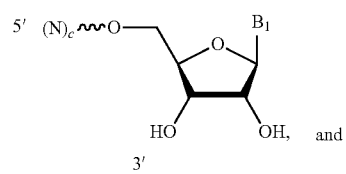

and

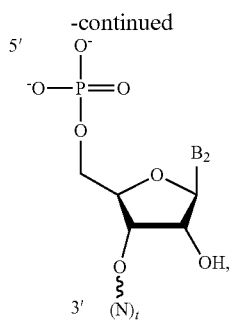

or salts thereof, in the presence of an activating agent to form a phosphodiester linkage,
wherein:
each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;
$(N)_c$ includes a 3' region that is complementary or partially complementary to, and forms a duplex with, a 5' region of $(N)_t$;
c is an integer 20 or greater;
t is an integer 20 or greater;
$B_1$ and $B_2$ are each independently a nucleobase; and
each ∿∿ represents independently a phosphodiester linkage, a phosphorothioate linkage, a phosphonoacetate linkage, a thiophosphonoacetate linkage, or a phosphoroamidate linkage.

140. An oligonucleotide for synthesizing a unimolecular guide molecule for a Type II CRISPR system, wherein the oligonucleotide is of formula:

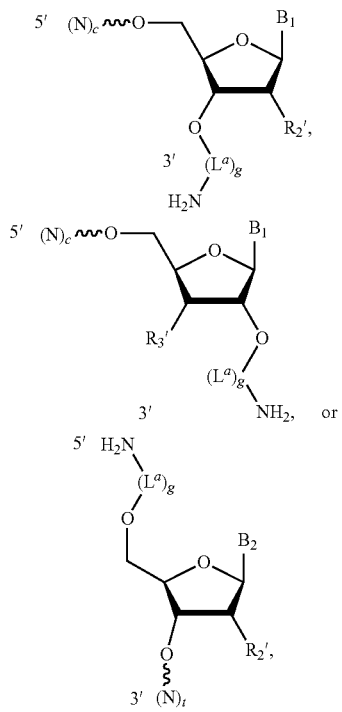

or a salt thereof, wherein:
each of $R_2'$ and $R_3'$ is independently H, OH, fluoro, chloro, bromo, $NH_2$, SH, S—R', or O—R' wherein each R' is independently a protection group or an alkyl group, wherein the alkyl group may be optionally substituted;
each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;
$(N)_c$ includes a 5' region that comprises a targeting domain that is fully or partially complementary to a target domain within a target sequence and a 3' region that comprises at least a portion of a repeat from a Type II CRISPR system;
$(N)_t$ includes a 5' region that comprises at least a portion of an anti-repeat from a Type II CRISPR system;
c is an integer 20 or greater;
t is an integer 20 or greater;
each $L^a$ is independently a non-nucleotide linker;
each g is independently 0, 1, 2, 3, 4, or 5;
$B_1$ and $B_2$ are each independently a nucleobase; and
each ∿∿ represents independently a phosphodiester linkage, a phosphorothioate linkage, a phosphonoacetate linkage, a thiophosphonoacetate linkage, or a phosphoroamidate linkage.

141. The oligonucleotide of embodiment 140, wherein $(N)_c$ comprises a 3' region that comprises at least a portion of a repeat from a Type II CRISPR system.

142. The oligonucleotide of embodiments 140 or 141, wherein $(N)_t$ includes a 3' region that comprises one or more stem-loop structures.

143. An oligonucleotide intermediate for synthesizing a unimolecular guide molecule for a Type II CRISPR system, wherein the oligonucleotide intermediate is of formula:

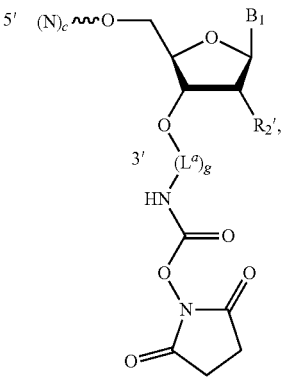

309

-continued

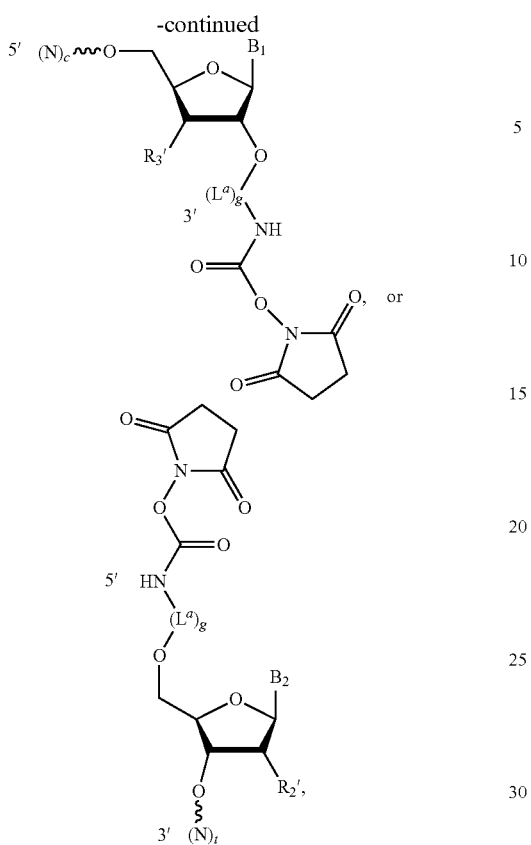

or a salt thereof, wherein:
  each of $R_2'$ and $R_3'$ is independently H, OH, fluoro, chloro, bromo, $NH_2$, SH, S—R', or O—R' wherein each R' is independently a protection group or an alkyl group, wherein the alkyl group may be optionally substituted;
  each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;
  $(N)_c$ includes a 5' region that comprises a targeting domain that is fully or partially complementary to a target domain within a target sequence and a 3' region that comprises at least a portion of a repeat from a Type II CRISPR system;
  $(N)_t$ includes a 5' region that comprises at least a portion of an anti-repeat from a Type II CRISPR system;
  c is an integer 20 or greater;
  t is an integer 20 or greater;
  each $L^a$ is independently a non-nucleotide linker;
  each g is independently 0, 1, 2, 3, 4, or 5;
  $B_1$ and $B_2$ are each independently a nucleobase; and
  each ∿∿ represents independently a phosphodiester linkage, a phosphorothioate linkage, a phosphonoacetate linkage, a thiophosphonoacetate linkage, or a phosphoroamidate linkage.
144. The oligonucleotide of embodiment 143, wherein $(N)_t$ includes a 3' region that comprises one or more stem-loop structures.

310

145. An oligonucleotide intermediate for synthesizing a unimolecular guide molecule for a Type II CRISPR system, wherein the oligonucleotide intermediate is of formula:

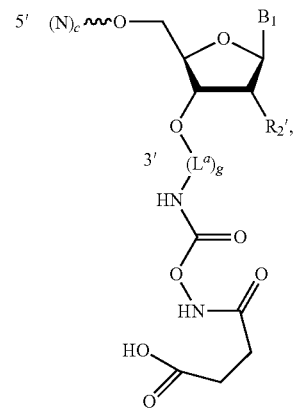

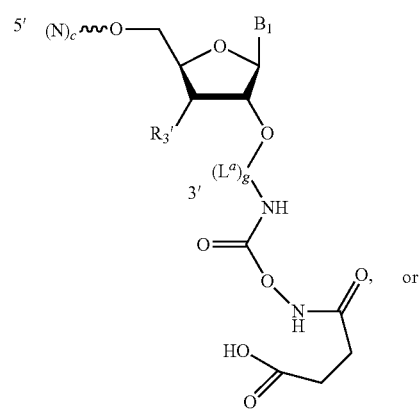

or

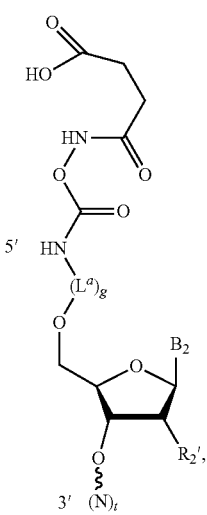

or a pharmaceutically acceptable salt thereof, wherein:

each of $R_2'$ and $R_3'$ is independently H, OH, fluoro, chloro, bromo, $NH_2$, SH, S—R', or O—R' wherein each R' is independently a protection group or an alkyl group, wherein the alkyl group may be optionally substituted;

each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;

$(N)_t$ includes a 5' region that comprises a targeting domain that is fully or partially complementary to a target domain within a target sequence and a 3' region that comprises at least a portion of a repeat from a Type II CRISPR system;

$(N)_t$ includes a 5' region that comprises at least a portion of an anti-repeat from a Type II CRISPR system;

c is an integer 20 or greater;

t is an integer 20 or greater;

each $L^a$ is independently a non-nucleotide linker;

each g is independently 0, 1, 2, 3, 4, or 5;

$B_1$ and $B_2$ are each independently a nucleobase; and each ⁓⁓ represents independently a phosphodiester linkage, a phosphorothioate linkage, a phosphonoacetate linkage, a thiophosphonoacetate linkage, or a phosphoroamidate linkage.

146. The oligonucleotide of embodiment 145, wherein $(N)_t$ includes a 3' region that comprises one or more stem-loop structures.

147. A composition comprising an intermediate with an annealed duplex for synthesizing a unimolecular guide molecule for a Type II CRISPR system, wherein the intermediate is of formula $B_3'$-vi or $B_2'$-vi:

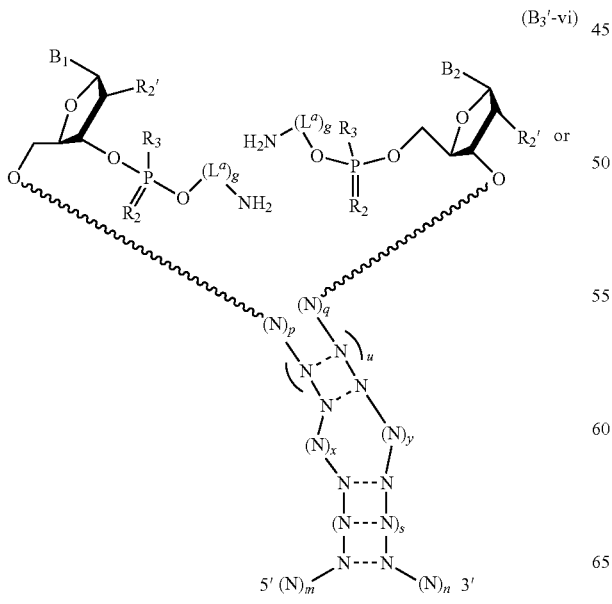

(B₃'-vi)

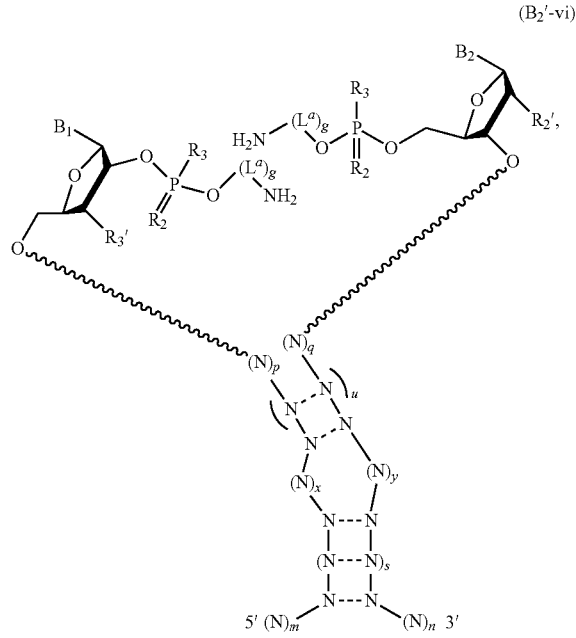

(B₂'-vi)

or a salt thereof, wherein:

each $L^a$ is independently a non-nucleotide linker;

each g is independently 0, 1, 2, 3, 4, or 5;

each $R_2$ is independently O or S;

each $R_3$ is independently O or COO;

p and q are each independently an integer between 0 and 6, inclusive, and p+q is an integer between 0 and 6, inclusive;

u is an integer between 2 and 22, inclusive;

s is an integer between 1 and 10, inclusive;

x is an integer between 1 and 3, inclusive;

y is >x and an integer between 3 and 5, inclusive;

m is an integer 15 or greater;

n is an integer 30 or greater;

each N is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;

each N—N independently represents two complementary nucleotides, optionally two complementary nucleotides that are hydrogen bonding base-paired; and each ⁓⁓ represents independently a phosphodiester linkage, a phosphorothioate linkage, a phosphonoacetate linkage, a thiophosphonoacetate linkage, or a phosphoroamidate linkage.

148. The composition of embodiment 147, wherein p and q are each 0.

149. The composition of embodiment 147, wherein u is an integer between 3 and 22.

150. A composition of any one of embodiments 147-149, wherein the intermediate is of formula $C_3'$-vi or $C_2'$-vi:

or a salt thereof.

151. A composition of any one of embodiments 147-149, wherein the intermediate is of formula $D_{3'}$-vi or $D_{2'}$-vi:

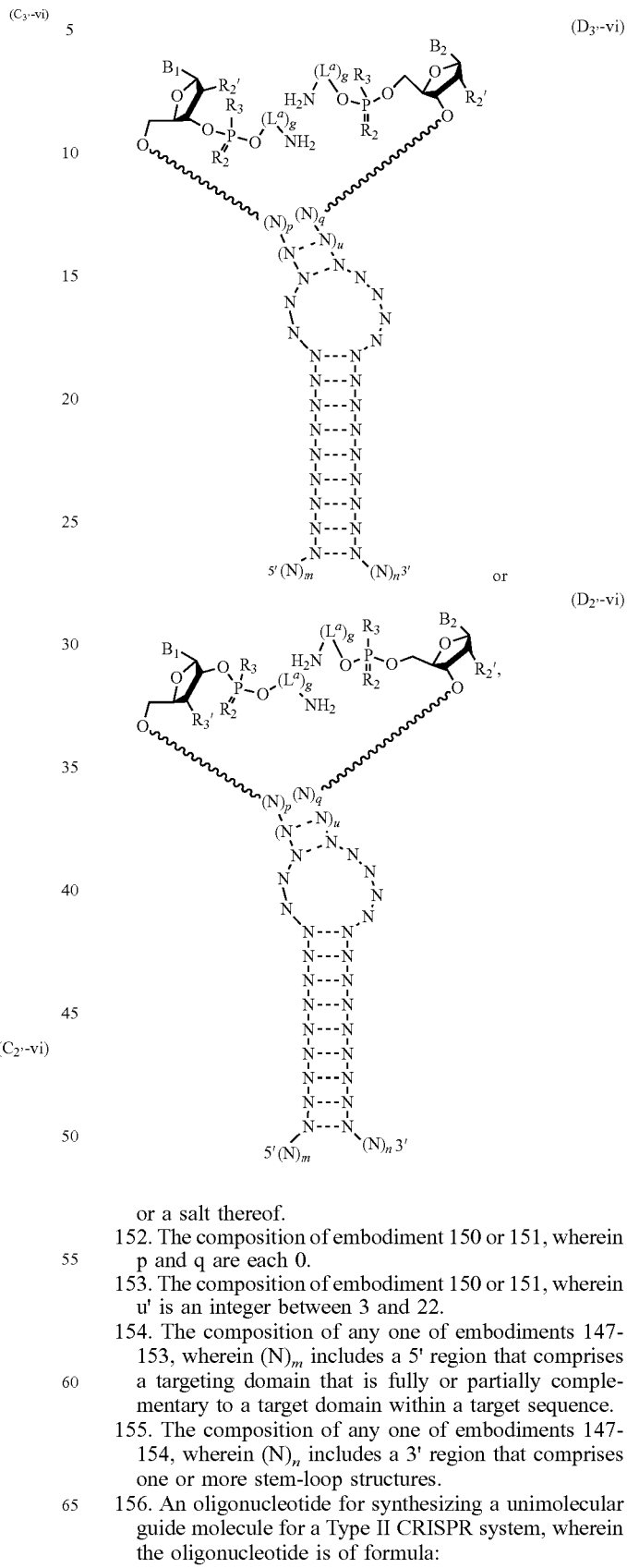

or a salt thereof.

152. The composition of embodiment 150 or 151, wherein p and q are each 0.

153. The composition of embodiment 150 or 151, wherein u' is an integer between 3 and 22.

154. The composition of any one of embodiments 147-153, wherein $(N)_m$ includes a 5' region that comprises a targeting domain that is fully or partially complementary to a target domain within a target sequence.

155. The composition of any one of embodiments 147-154, wherein $(N)_n$ includes a 3' region that comprises one or more stem-loop structures.

156. An oligonucleotide for synthesizing a unimolecular guide molecule for a Type II CRISPR system, wherein the oligonucleotide is of formula:

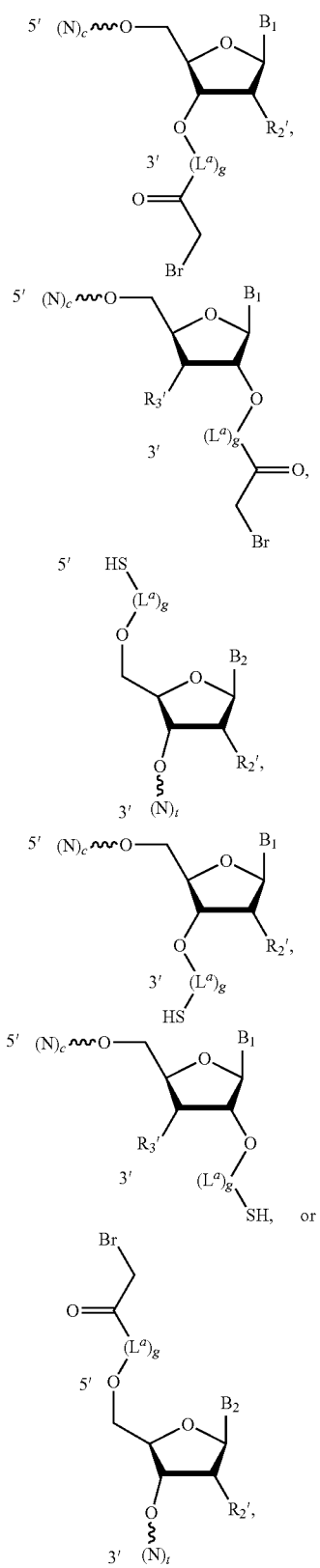

or a salt thereof, wherein:
each of $R_2'$ and $R_3'$ is independently H, OH, fluoro, chloro, bromo, $NH_2$, SH, S—R', or O—R' wherein each R' is independently a protection group or an alkyl group, wherein the alkyl group may be optionally substituted;
each $L^a$ is independently a non-nucleotide linker;
each g is independently 0, 1, 2, 3, 4, or 5;
$B_1$ and $B_2$ are each independently a nucleobase;
each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;
$(N)_c$ includes a 3' region that is complementary or partially complementary to, and forms a duplex with, a 5' region of $(N)_t$;
c is an integer 20 or greater;
t is an integer 20 or greater; and
each ∿∿ represents independently a phosphodiester linkage, a phosphorothioate linkage, a phosphonoacetate linkage, a thiophosphonoacetate linkage, or a phosphoroamidate linkage.

157. The oligonucleotide of embodiment 156, wherein $(N)_c$ comprises a 3' region that comprises at least a portion of a repeat from a Type II CRISPR system.

158. The oligonucleotide of embodiment 156 or 157, wherein $(N)_t$ includes a 3' region that comprises one or more stem-loop structures.

159. An oligonucleotide intermediate for synthesizing a unimolecular guide molecule for a Type II CRISPR system, wherein the oligonucleotide intermediate is of formula:

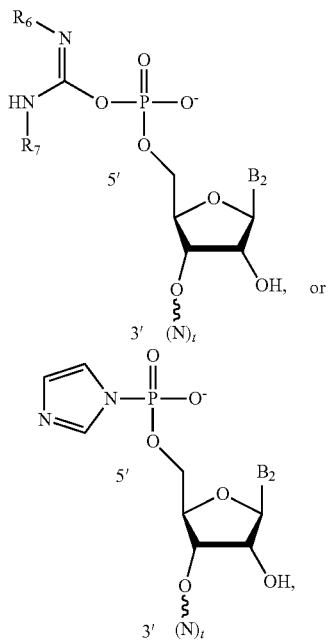

or a salt thereof,
wherein:
$R_6$ and $R_7$ are each independently substituted or unsubstituted alkyl, or substituted or unsubstituted carbocyclyl;
$(N)_t$ includes a 5' region that comprises at least a portion of an anti-repeat from a Type II CRISPR system, wherein each N in $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;

t is an integer 20 or greater;

$B_2$ is a nucleobase; and each ⌇ represents independently a phosphodiester linkage, a phosphorothioate linkage, a phosphonoacetate linkage, a thiophosphonoacetate linkage, or a phosphoroamidate linkage.

160. A composition comprising an intermediate with an annealed duplex for synthesizing a unimolecular guide molecule for a Type II CRISPR system, wherein the intermediate is of formula:

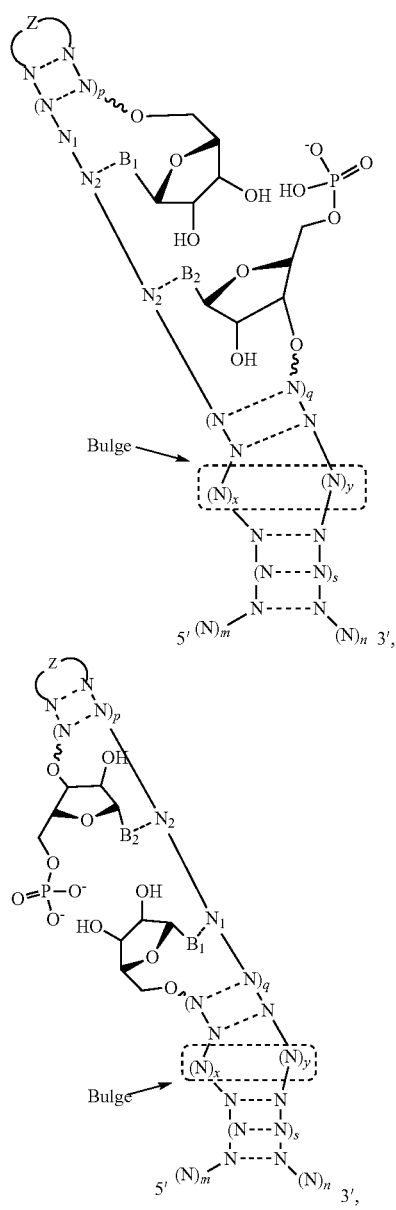

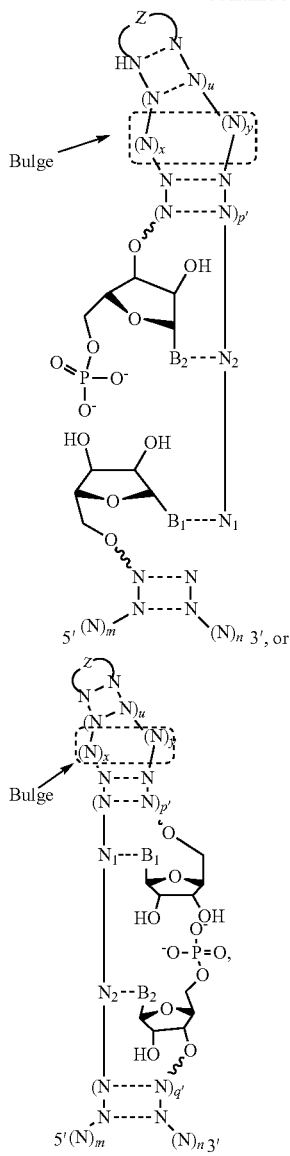

or a salt thereof,
wherein:
  Z represents a nucleotide loop which is 4-6 nucleotides long, optionally 4 or 6 nucleotides long;
  p and q are each independently an integer between 0 and 6, inclusive, and p+q is an integer between 0 and 6, inclusive;
  u is an integer between 2 and 22, inclusive;
  s is an integer between 1 and 10, inclusive;
  x is an integer between 1 and 3, inclusive;
  y is >x and an integer between 3 and 5, inclusive;
  m is an integer 15 or greater;
  n is an integer 30 or greater;
  each N is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;
  each ⌇ represents independently a phosphodiester linkage, a phosphorothioate linkage, a phosphonoacetate linkage, a thiophosphonoacetate linkage, or a phosphoroamidate linkage; and
each N—N independently represents two complementary nucleotides, optionally two complementary nucleotides that are hydrogen bonding base-paired.

161. The composition of embodiment 160, wherein $(N)_m$ includes a 5' region that comprises a targeting domain that is fully or partially complementary to a target domain within a target sequence.

162. The composition of embodiment 160 or 161, wherein $(N)_n$ includes a 3' region that comprises one or more stem-loop structures.

163. The composition of any one of embodiments 160-162, wherein the composition further comprises a carbodiimide or a salt thereof, and/or imidazole, cyanoimidazole, pyridine and dimethylaminopyridine, or a salt thereof.

164. The composition of embodiment 163, wherein the carbodiimide is EDC, DCC or DIC.

165. The composition of any one of embodiments 160-164, wherein the composition comprises a carbodiimide, or a salt thereof, and imidazole, or a salt thereof.

166. A compound of formula:

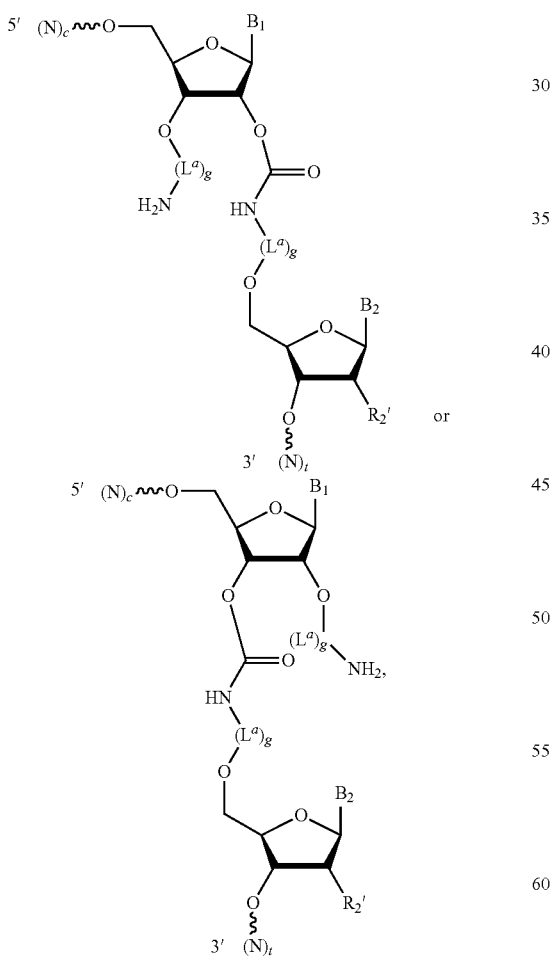

wherein:
each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;

$(N)_c$ includes a 3' region that is complementary or partially complementary to, and forms a duplex with, a 5' region of $(N)_t$;

c is an integer 20 or greater;

t is an integer 20 or greater; and each ～ represents independently a phosphodiester linkage, a phosphorothioate linkage, a phosphonoacetate linkage, a thiophosphonoacetate linkage, or a phosphoroamidate linkage;

each $L^a$ is independently a non-nucleotide linker;

each g is independently 0, 1, 2, 3, 4, or 5; and $B_1$ and $B_2$ are each independently a nucleobase.

167. A composition comprising, or consisting essentially of, a guide molecule of any one of embodiments 1-23 of formula $A_3$-iii, or a pharmaceutically acceptable salt thereof, wherein the composition is substantially free of molecules of formula:

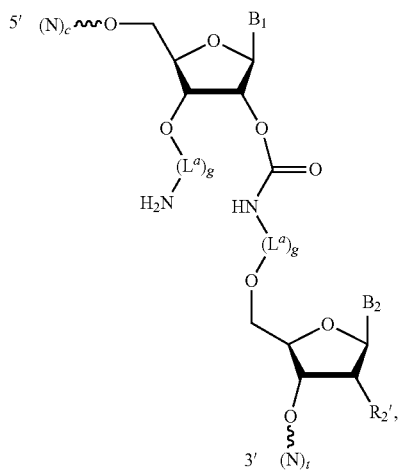

wherein:
each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;

$(N)_c$ includes a 3' region that is complementary or partially complementary to, and forms a duplex with, a 5' region of $(N)_t$;

c is an integer 20 or greater;

t is an integer 20 or greater; and each ～ represents independently a phosphodiester linkage, a phosphorothioate linkage, a phosphonoacetate linkage, a thiophosphonoacetate linkage, or a phosphoroamidate linkage;

each $L^a$ is independently a non-nucleotide linker;

each g is independently 0, 1, 2, 3, 4, or 5; and $B_1$ and $B_2$ are each independently a nucleobase, and/or, or a pharmaceutically acceptable salt thereof.

168. A composition comprising, or consisting essentially of, a guide molecule of any one of embodiments 1-23 of formula A$_2$'-iii, or a pharmaceutically acceptable salt thereof, wherein the composition is substantially free of molecules of formula:

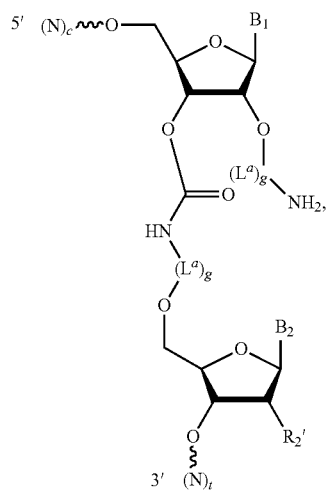

wherein:
each N in (N)$_c$ and (N)$_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;
(N)$_c$ includes a 3' region that is complementary or partially complementary to, and forms a duplex with, a 5' region of (N)$_t$;
c is an integer 20 or greater;
t is an integer 20 or greater; and
each ∽ represents independently a phosphodiester linkage, a phosphorothioate linkage, a phosphonoacetate linkage, a thiophosphonoacetate linkage, or a phosphoroamidate linkage;
each L$^a$ is independently a non-nucleotide linker;
each g is independently 0, 1, 2, 3, 4, or 5; and
B$_1$ and B$_2$ are each independently a nucleobase, and/or, or a pharmaceutically acceptable salt thereof.

169. A synthetic unimolecular guide molecule for a CRISPR system of formula B$_3$'-i or B$_2$'-i:

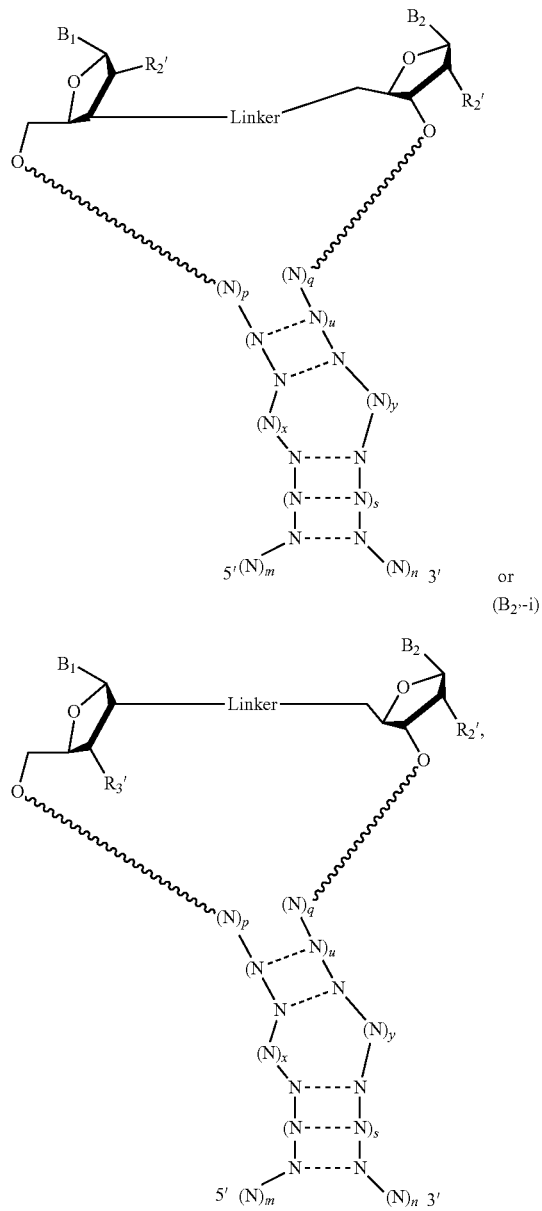

wherein:
each N is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage; and
each N—N independently represents two complementary nucleotides, optionally two complementary nucleotides that are hydrogen bonding base-paired
each ∽ represents independently a phosphodiester linkage, a phosphorothioate linkage, a phosphonoacetate linkage, a thiophosphonoacetate linkage, or a phosphoroamidate linkage;
p and q are each 0;

u is an integer between 2 and 22, inclusive;
s is an integer between 1 and 10, inclusive;
x is an integer between 1 and 3, inclusive;
y is >x and an integer between 3 and 5, inclusive;
m is an integer 15 or greater;
n is an integer 30 or greater;
Linker is a non-nucleotide chemical linkage;
$B_1$ and $B_2$ are each independently a nucleobase; and
each of $R_2'$ and $R_3'$ is independently H, OH, fluoro, chloro, bromo, $NH_2$, SH, S—R', or O—R' wherein each R' is independently a protection group or an alkyl group, wherein the alkyl group may be optionally substituted.

170. The guide molecule of embodiment 169, wherein each of $R_2'$ and $R_3'$ is independently selected from the group consisting of H, fluoro, and O—R' wherein R' is a protecting group or an optionally substituted alkyl group.

171. The guide molecule of embodiment 169 or 170, wherein each N is independently a ribonucleotide residue or a sugar-modified ribonucleotide residue.

172. The guide molecule of any one of embodiments 169-171, wherein one or more N is a deoxyribonucleotide residue.

173. The guide molecule of any one of embodiments 169-172, wherein one or more N is a 2'-O-methyl modified ribonucleotide residue.

174. The guide molecule of any one of embodiments 169-173, wherein each of the three nucleotides at the 5' end of $(N)_m$ and/or each of the three nucleotides at the 3' end of $(N)_n$ comprise a 2'-O-methyl modified ribonucleotide residue that is linked to its adjacent nucleotide(s) via a phosphorothioate linkage.

175. The guide molecule of any one of embodiments 169-174, wherein the guide molecule is for a Type II CRISPR system and $(N)_m$ includes a 5' region that comprises a targeting domain that is fully or partially complementary to a target domain within a target sequence.

176. The guide molecule of any one of embodiments 169-175, wherein $(N)_n$ includes a 3' region that comprises one or more stem-loop structures.

177. The guide molecule of any one of embodiments 169-176, wherein the guide molecule is capable of interacting with a Cas9 molecule and mediating the formation of a Cas9/guide ribonucleoprotein complex.

178. The guide molecule of any one of embodiments 169-177, wherein $(N)_m$ comprises a 3' region that comprises at least a portion of a repeat from a Type II CRISPR system.

179. The guide molecule of any one of embodiments 169-178, wherein $(N-N)_y$ and $(N-N)_s$ do not comprise an identical sequence of 3 or more nucleotides.

180. The guide molecule of embodiment 179, wherein $(N-N)_y$ and $(N-N)_s$ do not comprise an identical sequence of 4 or more nucleotides.

181. The guide molecule of embodiment 180, wherein $(N-N)_s$ comprises a N'UUU, UN'UU, UUN'U or UUUN' sequence and $(N-N)_y$ comprises a UUUU sequence, wherein N' is A, G or C.

182. The guide molecule of embodiment 181, wherein N' is A.

183. The guide molecule of embodiment 180, wherein the lower stem sequence of $(N-N)_s$ comprises a UUUU sequence and $(N-N)_y$ comprises a N'UUU, UN'UU, UUN'U or UUUN' sequence, wherein N' is A, G or C.

184. The guide molecule of embodiment 183, wherein N' is A.

185. The guide molecule of any one of embodiments 169-184, wherein the guide molecule is of formula $C_{3'}$-i or $C_{2'}$-i:

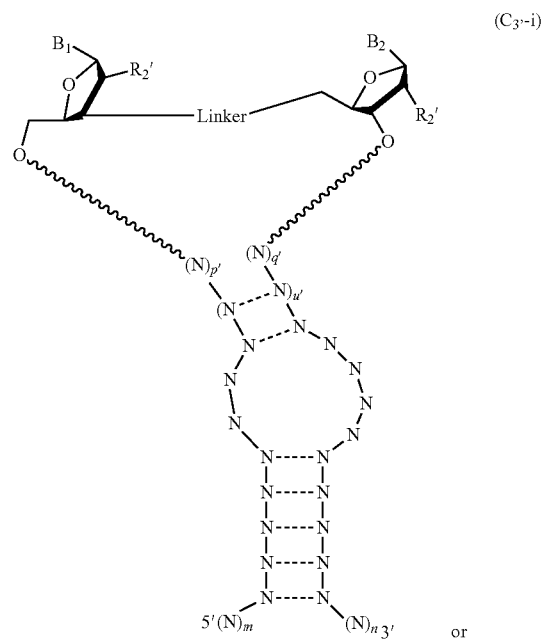

($C_{3'}$-i)

or

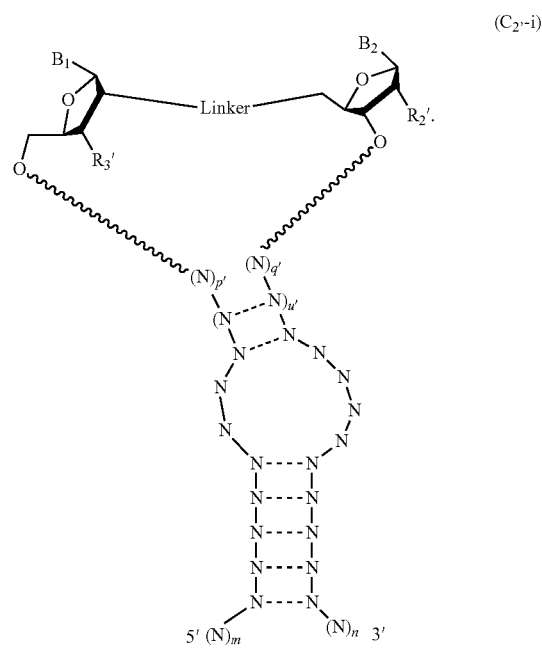

($C_{2'}$-i)

186. The guide molecule of embodiment 185, wherein the guide molecule is of formula:

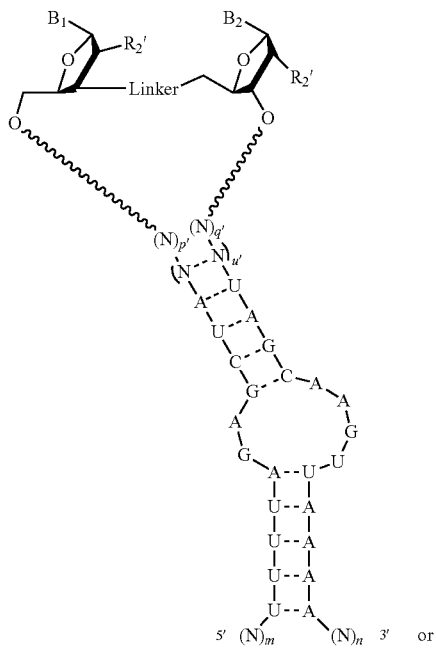

or

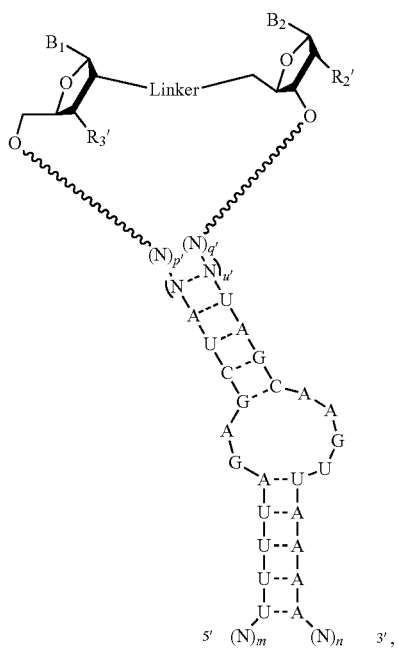

or a covariant thereof, wherein:
p' and q' are each 0; and
u' is an integer between 0 and 15, inclusive.

187. The guide molecule of embodiment 186, wherein $(N-N)_{u'}$ is of formula:

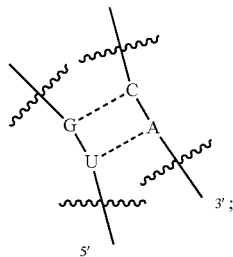

and
wherein $B_1$ is a cytosine residue and $B_2$ is a guanine residue; or a covariant thereof.

188. The guide molecule of embodiment 186, wherein $(N-N)_{u'}$ is of formula:

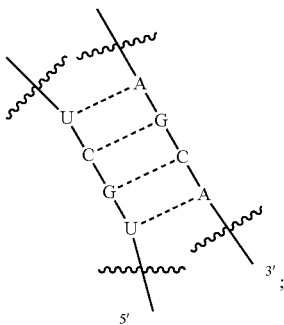

and
wherein $B_1$ is a guanine residue and $B_2$ is a cytosine residue; or a covariant thereof.

189. The guide molecule of embodiment 186, wherein $(N-N)_{u'}$ is of formula:

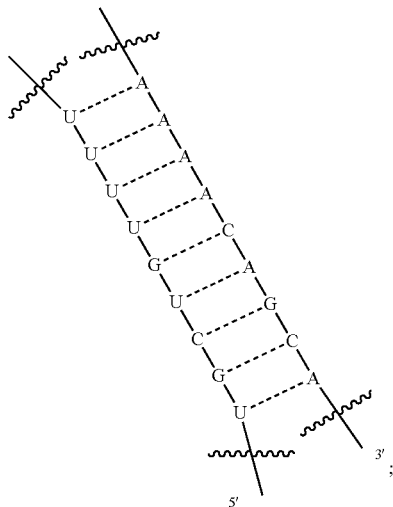

and
wherein $B_1$ is a guanine residue and $B_2$ is a cytosine residue; or a covariant thereof.

190. The guide molecule of embodiment 185, wherein the guide molecule is of formula:

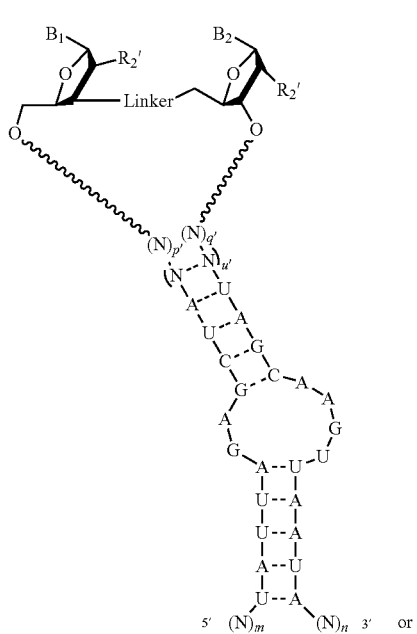

(C$_{3'}$-i)

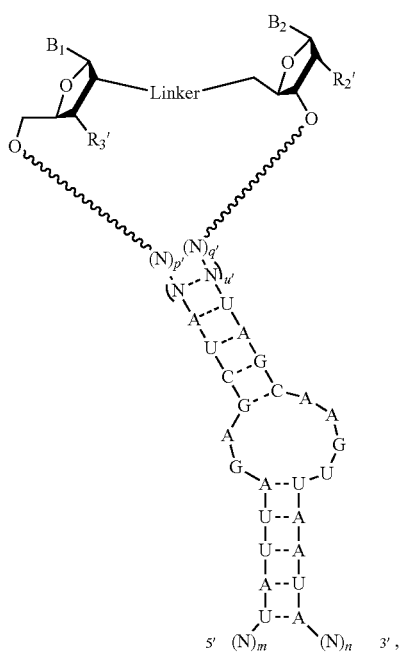

(C$_{2'}$-i)

or a covariant thereof, wherein:
p' and q' are each 0; and
u' is an integer between 0 and 15, inclusive.

191. The guide molecule of embodiment 190, wherein $(N-N)_{u'}$ is of formula:

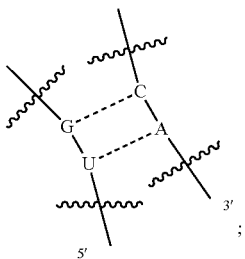

and
wherein $B_1$ is a cytosine residue and $B_2$ is a guanine residue; or a covariant thereof.

192. The guide molecule of embodiment 190, wherein $(N-N)_{u'}$ is of formula:

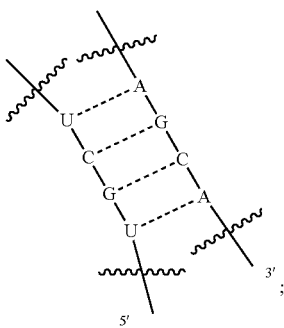

and
wherein $B_1$ is a guanine residue and $B_2$ is a cytosine residue; or a covariant thereof.

193. The guide molecule of embodiment 190, wherein $(N-N)_{u'}$ is of formula:

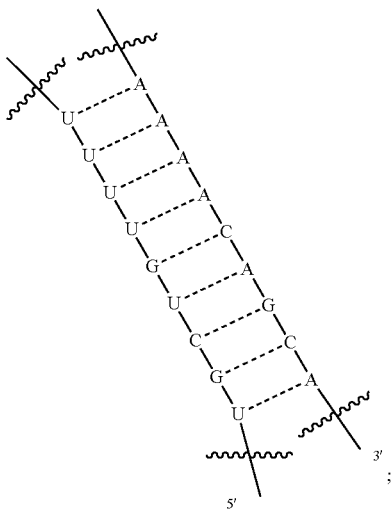

and
wherein $B_1$ is a guanine residue and $B_2$ is a cytosine residue; or a covariant thereof.

194. The guide molecule of any one of embodiments 169-184, wherein the guide molecule is of formula $D_{3'}$-i or $D_{2'}$-i:
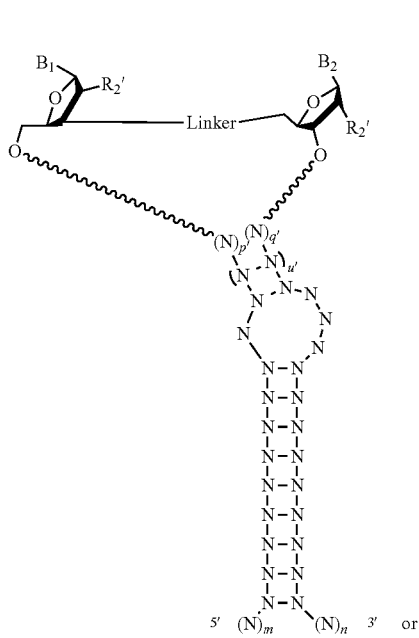
(D$_{3'}$-i)
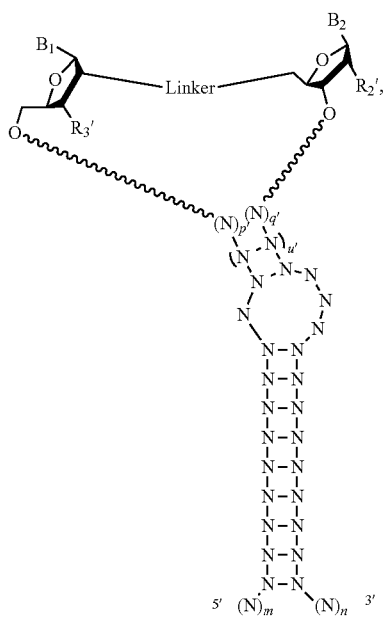
(D$_{2'}$-i)
wherein:
u' is an integer between 2 and 22, inclusive; and
p' and q' are each 0.
195. The guide molecule of embodiment 194, wherein the guide molecule is of formula:
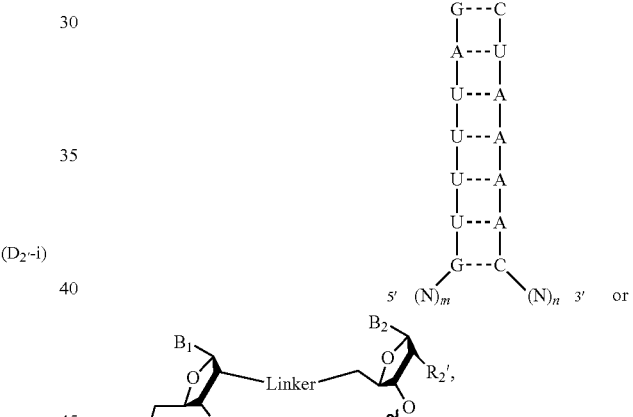
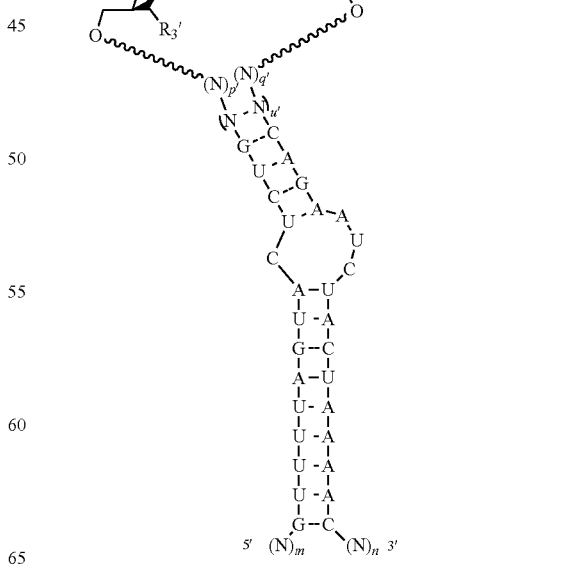

or a covariant thereof, wherein:

u' is an integer between 0 and 19, inclusive; and p' and q' are each 0.

196. The guide molecule of embodiment 195, wherein $(N—N)_{u'}$ is of formula:

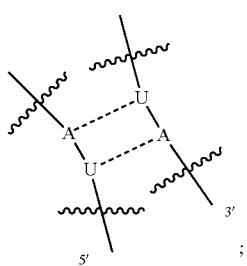

and wherein $B_1$ is an adenine residue and $B_2$ is a uracil residue; or a covariant thereof.

197. The guide molecule of embodiment 195, wherein $(N—N)_{u'}$ is of formula:

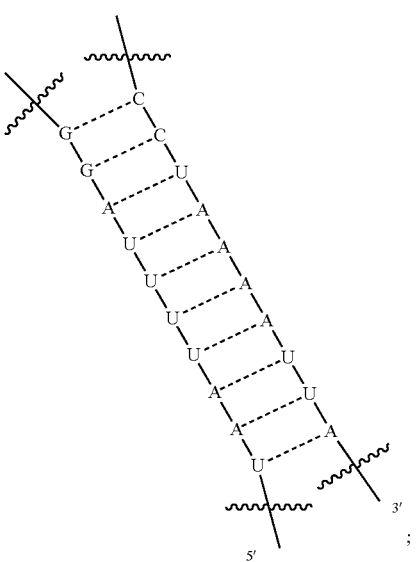

and wherein $B_1$ is a uracil residue and $B_2$ is an adenine residue; or a covariant thereof.

198. The guide molecule of embodiment 195, wherein $(N—N)_{u'}$ is of formula:

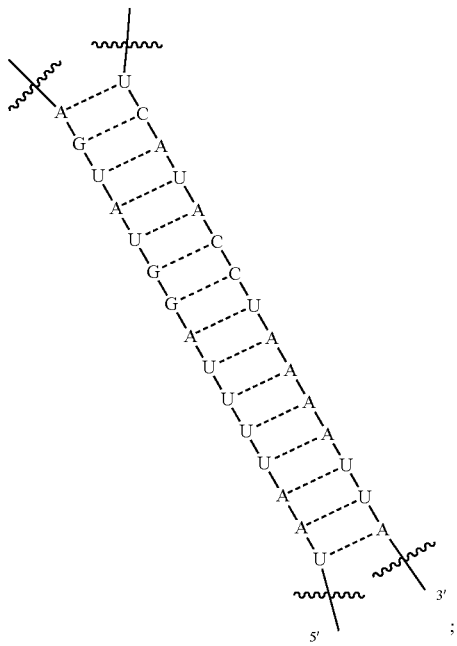

and wherein $B_1$ is a guanine residue and $B_2$ is a cytosine residue; or a covariant thereof.

199. The guide molecule of any of embodiments 169-184, wherein the guide molecule is of formula:

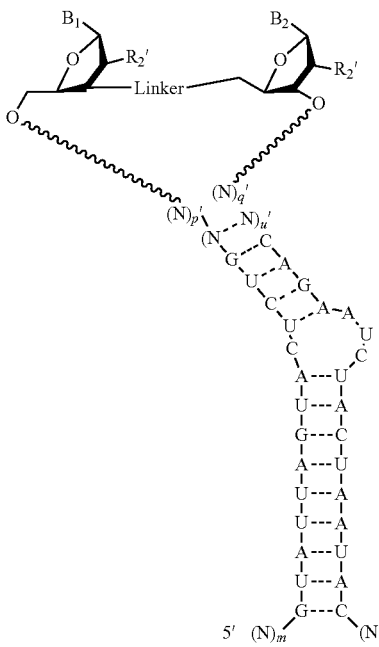

333
-continued

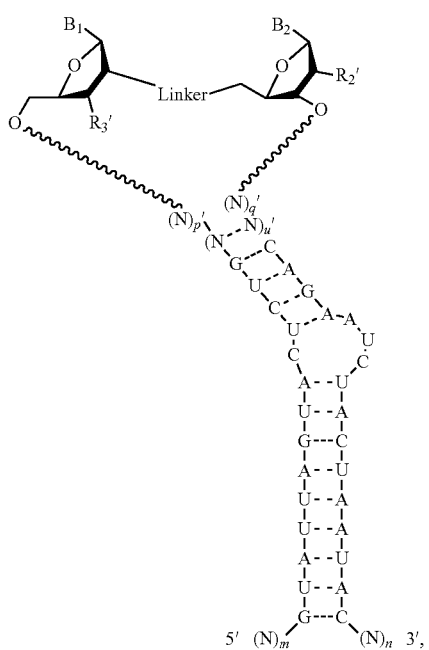

or a covariant thereof,
wherein:
u' is an integer between 0 and 19, inclusive; and
p' and q' are each 0.

200. The guide molecule of embodiment 199, wherein $(N-N)_{u'}$ is of formula:

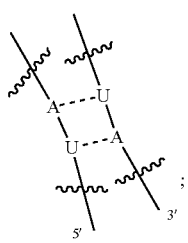

and
wherein $B_1$ is an adenine residue and $B_2$ is a uracil residue; or a covariant thereof.

334

201. The guide molecule of embodiment 199, wherein $(N-N)_{u'}$ is of formula:

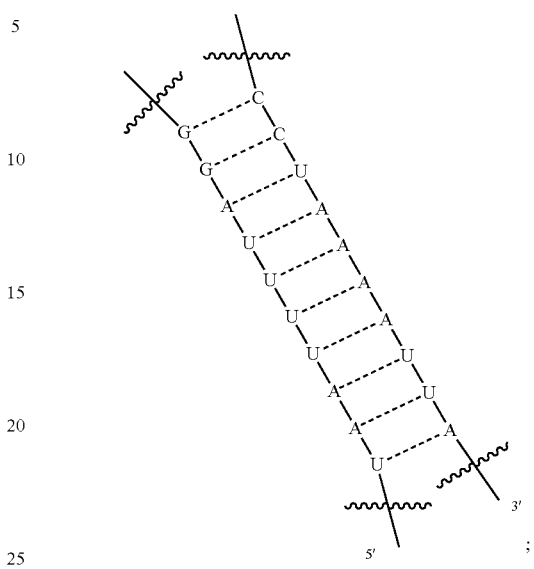

and
wherein $B_1$ is a uracil residue and $B_2$ is an adenine residue; or a covariant thereof.

202. The guide molecule of embodiment 199, wherein $(N-N)_{u'}$ is of formula:

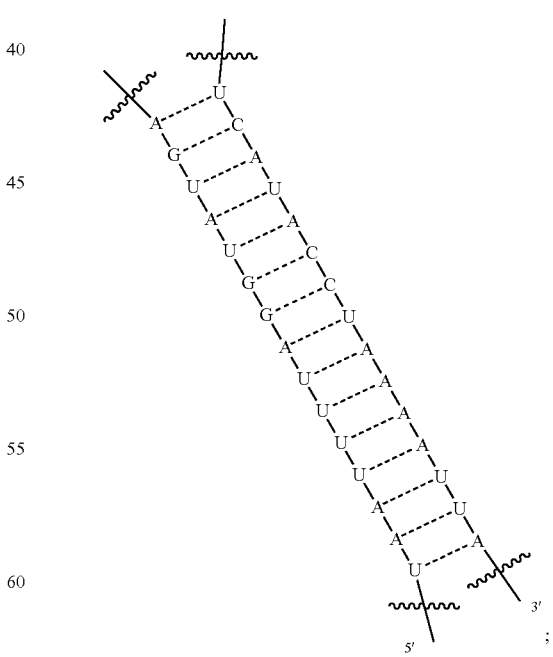

and
wherein $B_1$ is a guanine residue and $B_2$ is a cytosine residue; or a covariant thereof.

203. The guide molecule of any one of embodiments 169-184, wherein the guide molecule is of formula B₃'-iii or B₂'-iii:

204. The guide molecule of embodiment 203, wherein the guide molecule is of formula C₃'-iii or C₂'-

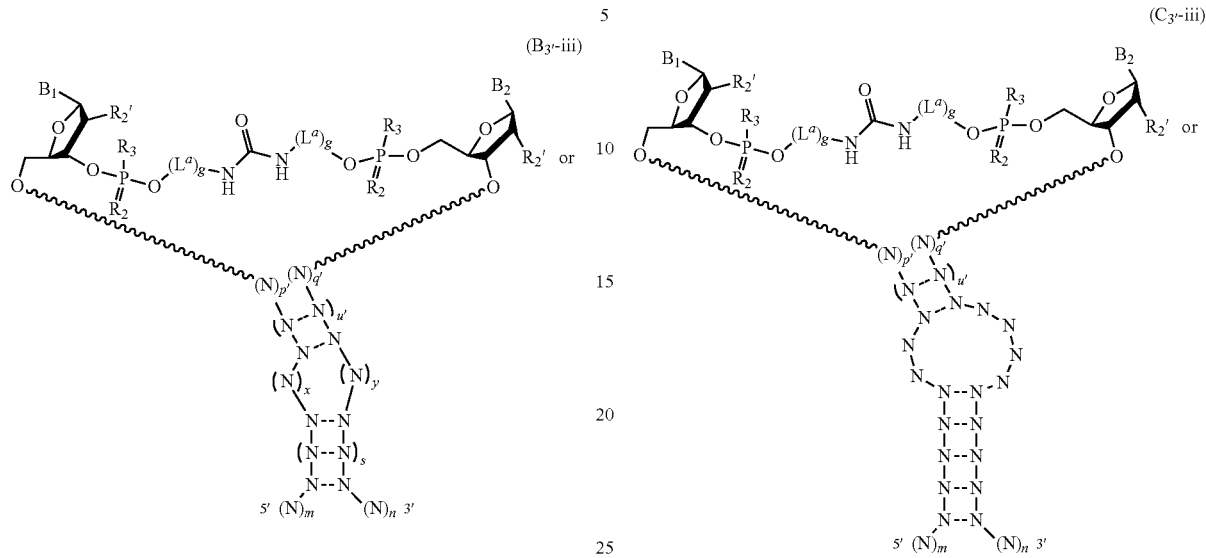

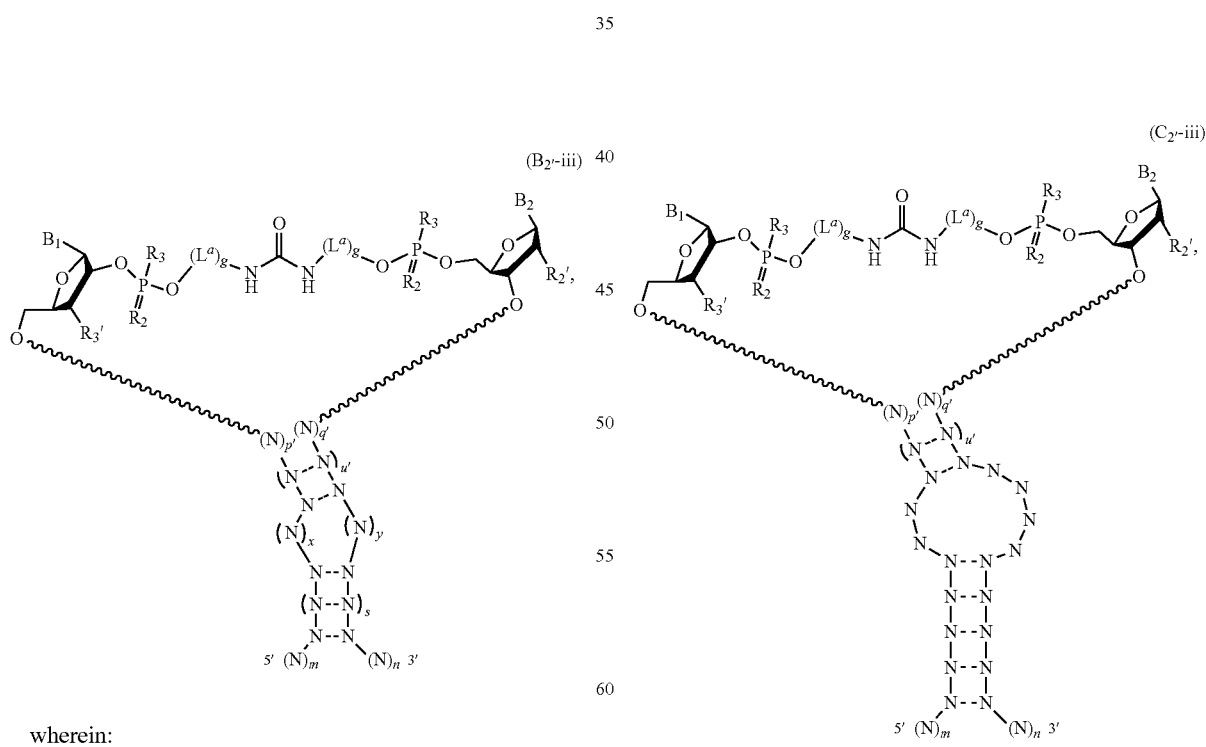

wherein:
    each $L^a$ is independently a non-nucleotide linker;
    each g is independently 0, 1, 2, 3, 4, or 5;
    each $R_2$ is independently O or S;
    each $R_3$ is independently O⁻ or COO⁻.

wherein:
    u' is an integer between 2 and 22, inclusive; and
    p' and q' are each 0.

205. The guide molecule of embodiment 204, wherein the guide molecule is of formula $D_{3'}$-iii or $D_{2'}$-

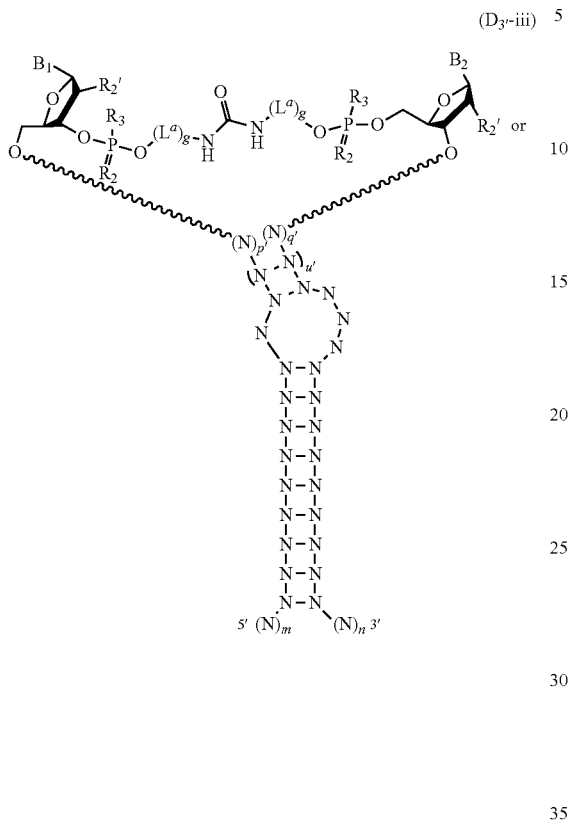

(D$_{3'}$-iii)

(D$_{2'}$-iii)

wherein:
p' and q' are each 0; and
u' is an integer between 0 and 19, inclusive.

206. The guide molecule of embodiment 205, wherein $(N-N)_{u'}$ is of formula:

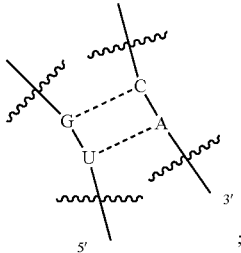

and
wherein $B_1$ is a cytosine residue and $B_2$ is a guanine residue; or a covariant thereof.

207. The guide molecule of embodiment 205, wherein $(N-N)_{u'}$ is of formula:

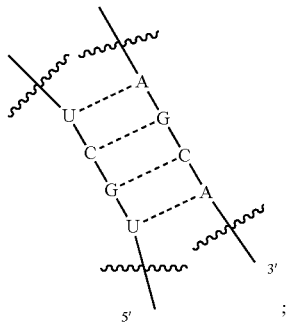

and
wherein $B_1$ is a guanine residue and $B_2$ is a cytosine residue; or a covariant thereof.

208. The guide molecule of embodiment 205, wherein $(N-N)_{u'}$ is of formula:

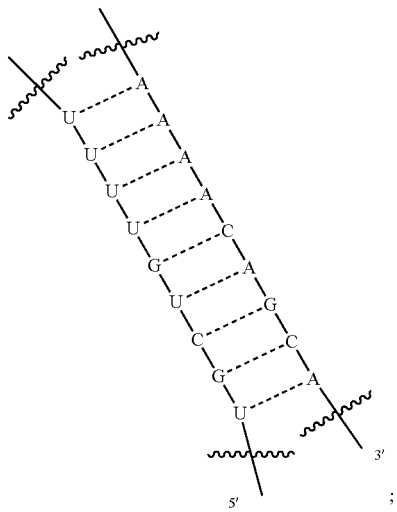

and
wherein $B_1$ is a guanine residue and $B_2$ is a cytosine residue; or a covariant thereof.

209. The guide molecule of embodiment 203, wherein the guide molecule is of formula:

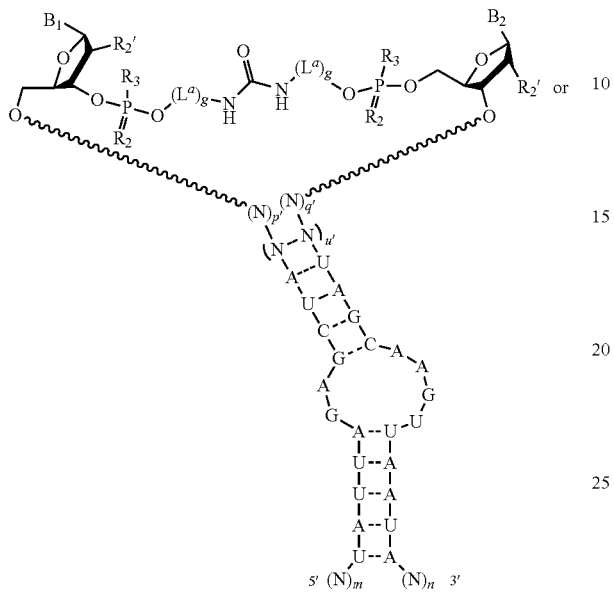 or

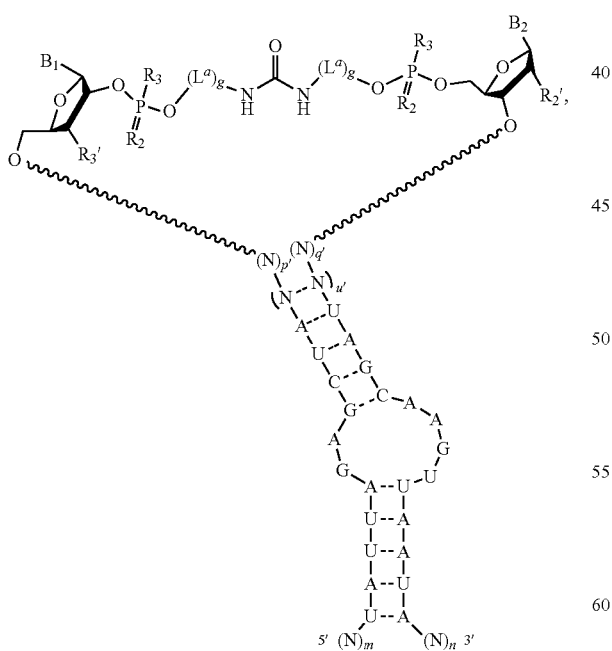, or a covariant thereof, wherein:

p' and q' are each 0; and u' is an integer between 0 and 19, inclusive.

210. The guide molecule of embodiment 209, wherein $(N\text{—}N)_{u'}$ is of formula:

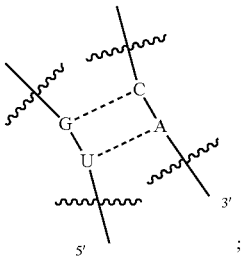;

and wherein $B_1$ is a cytosine residue and $B_2$ is a guanine residue; or a covariant thereof.

211. The guide molecule of embodiment 209, wherein $(N\text{—}N)_{u'}$ is of formula:

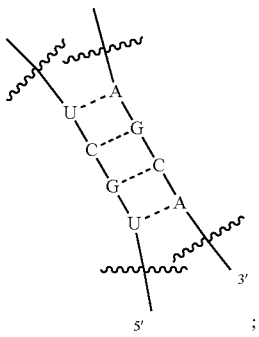;

and wherein $B_1$ is a guanine residue and $B_2$ is a cytosine residue; or a covariant thereof.

212. The guide molecule of embodiment 209, wherein $(N\text{—}N)_{u'}$ is of formula:

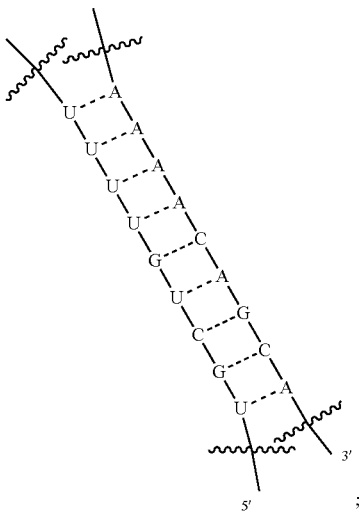;

and wherein $B_1$ is a guanine residue and $B_2$ is a cytosine residue; or a covariant thereof.

213. The guide molecule of any of embodiment 203, wherein the guide molecule is of formula
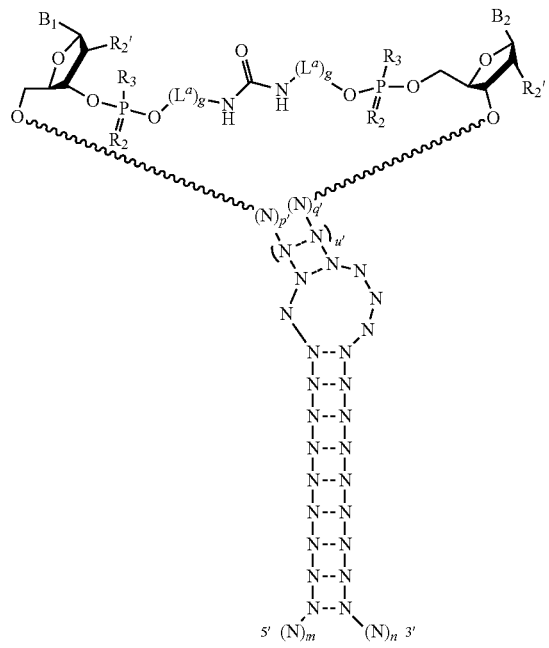
or
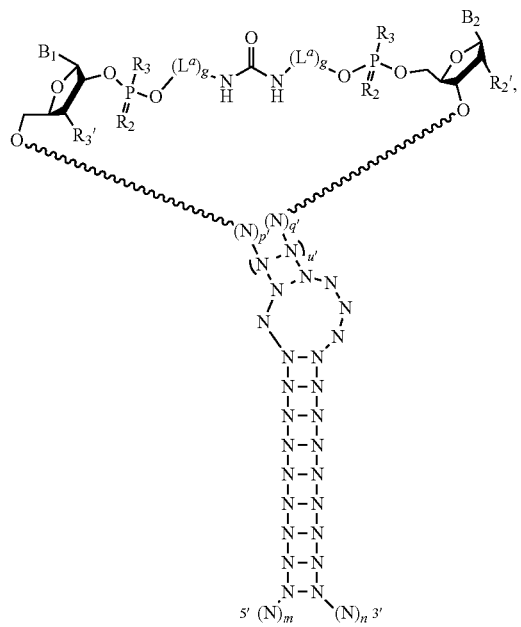
or a covariant thereof, wherein:
u' is an integer between 2 and 22, inclusive; and
p' and q' are each 0.
214. The guide molecule of embodiment 213, wherein the guide molecule is of formula:
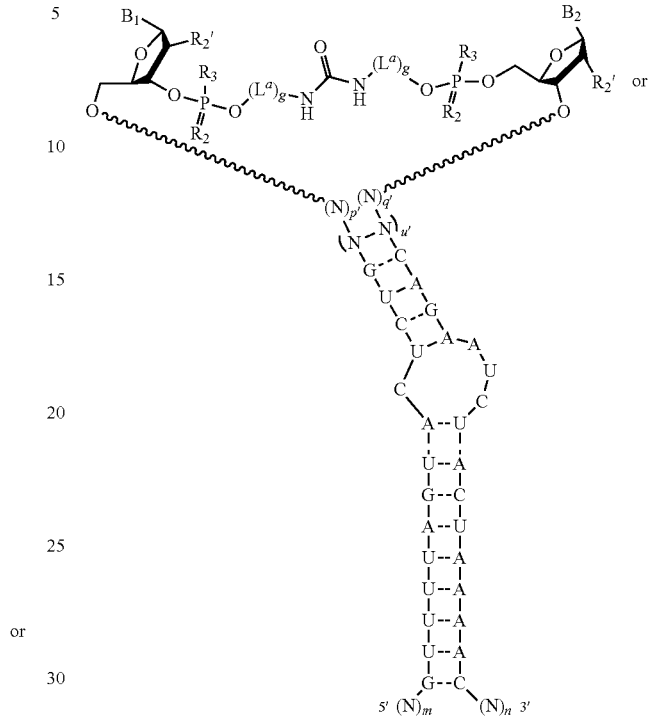
or
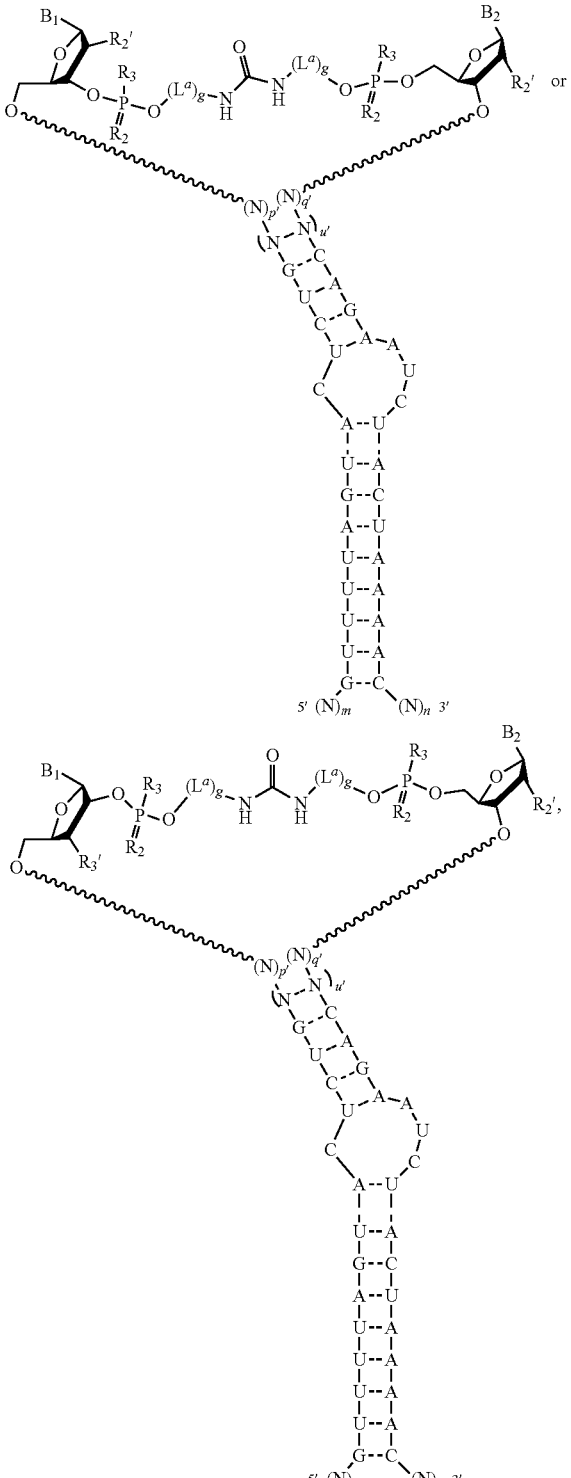
or a covariant thereof,
wherein:
u' is an integer between 0 and 19, inclusive; and
p' and q' are each 0.

215. The guide molecule of embodiment 214, wherein $(N-N)_{u'}$ is of formula:

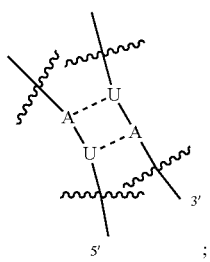

and wherein $B_1$ is an adenine residue and $B_2$ is a uracil residue; or a covariant thereof.

216. The guide molecule of embodiment 214, wherein $(N-N)_{u'}$ is of formula:

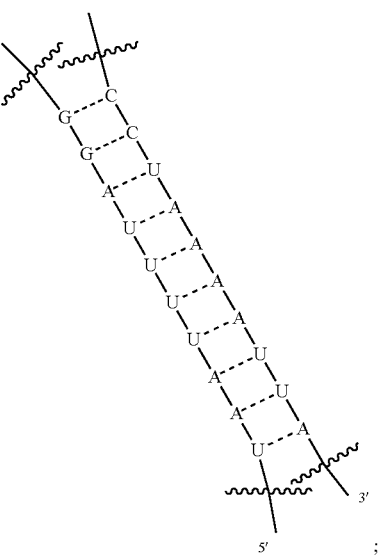

and wherein $B_1$ is a uracil residue and $B_2$ is an adenine residue; or a covariant thereof.

217. The guide molecule of embodiment 214, wherein $(N-N)_{u'}$ is of formula:

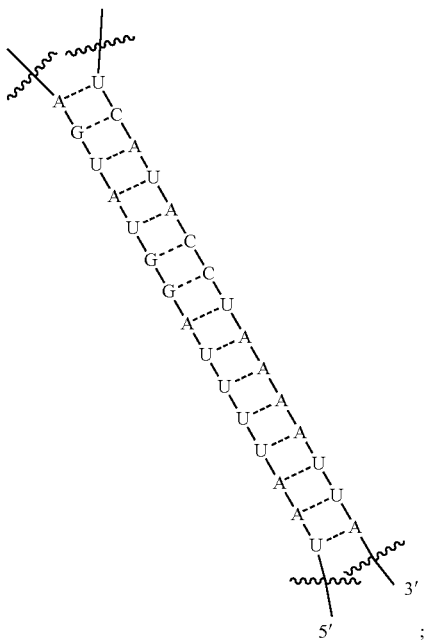

and wherein $B_1$ is a guanine residue and $B_2$ is a cytosine residue; or a covariant thereof.

218. The guide molecule of embodiment 203, wherein the guide molecule is of formula:

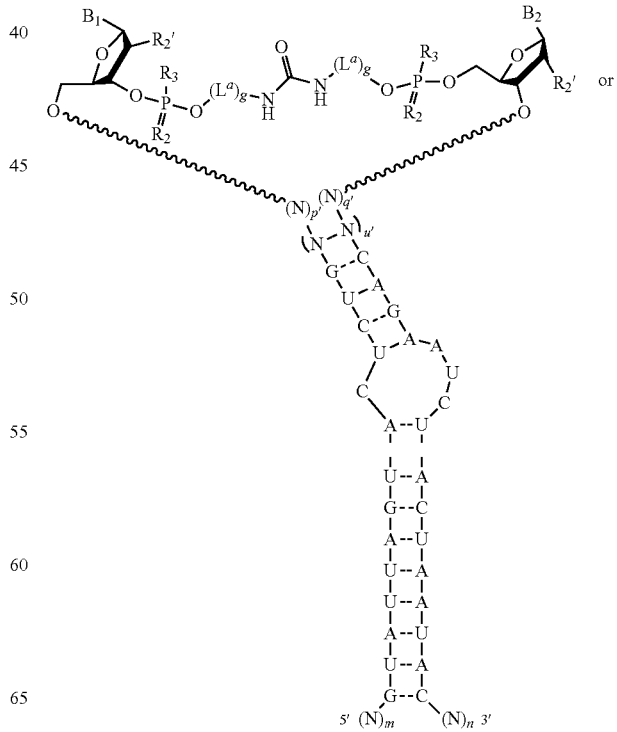

-continued

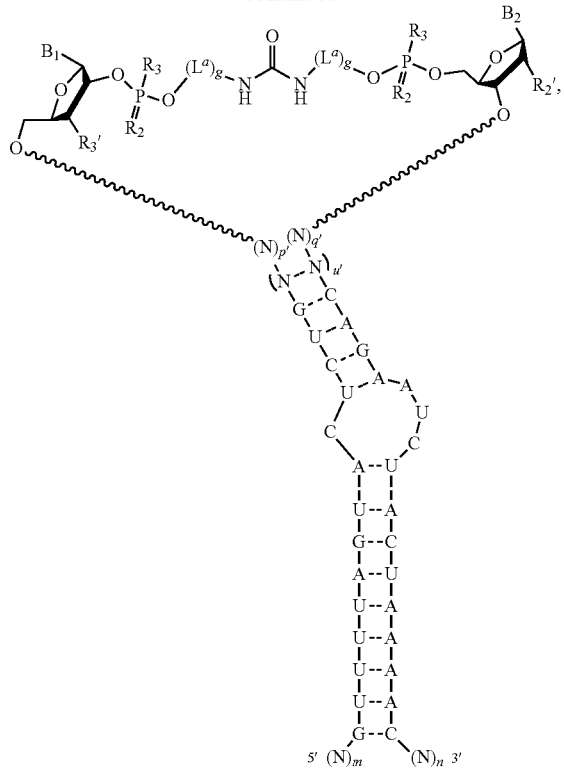

or a covariant thereof,
wherein:
u' is an integer between 0 and 19, inclusive; and
p' and q' are each 0.

219. The guide molecule of embodiment 218, wherein $(N—N)_{u'}$ is of formula:

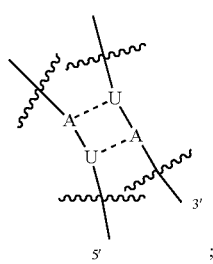

and
wherein $B_1$ is an adenine residue and $B_2$ is a uracil residue; or a covariant thereof.

220. The guide molecule of embodiment 218, wherein $(N—N)_{u'}$ is of formula:

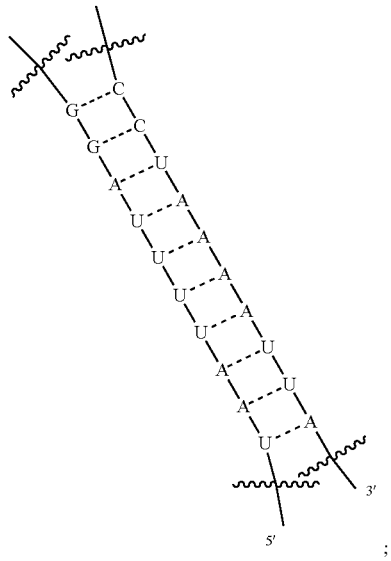

and
wherein $B_1$ is a uracil residue and $B_2$ is an adenine residue; or a covariant thereof.

221. The guide molecule of embodiment 218, wherein $(N—N)_{u'}$ is of formula:

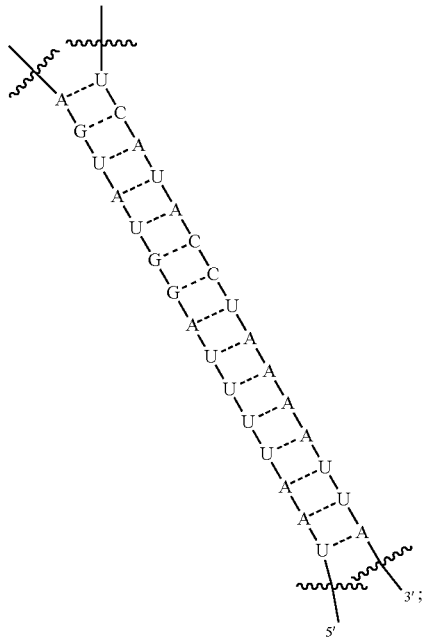

and
wherein $B_1$ is a guanine residue and $B_2$ is a cytosine residue; or a covariant thereof.

222. A composition comprising a plurality of synthetic guide molecules of any of embodiments 169-221, wherein less than about 10% of the guide molecules comprise a truncation at a 5' end, relative to a reference guide molecule sequence.

223. The composition of embodiment 222, wherein at least about 99% of the guide molecules comprise a 5' sequence comprising nucleotides 1-20 of the guide molecule that is 100% identical to a corresponding 5' sequence of the reference guide molecule sequence.

224. A guide molecule comprising, from 5' to 3':
   a first guide molecule fragment, comprising:
      a targeting domain sequence;
      a first lower stem sequence;
      a first bulge sequence;
      a first upper stem sequence;
   a non-nucleotide chemical linkage; and
   a second guide molecule fragment, comprising
      a second upper stem sequence;
      a second bulge sequence; and
      a second lower stem sequence,
   wherein (a) at least one nucleotide in the first lower stem sequence is base paired with a nucleotide in the second lower stem sequence, and (b) at least one nucleotide in the first upper stem sequence is base paired with a nucleotide in the second upper stem sequence.

225. The guide molecule according to embodiment 224, wherein (c) the guide molecule does not include a tetraloop sequence between the first and second upper stem sequences.

226. The guide molecule of embodiment 224 or 225, wherein the first and/or second upper stem sequence comprises nucleotides that number from 4 to 22, inclusive.

227. The guide molecule according to any of embodiments 224-226, characterized in that a Gibbs free energy ($\Delta G$) for the formation of a duplex between the first and second guide molecule fragments is less than a $\Delta G$ for the formation of a duplex between two first guide molecule fragments.

228. The guide molecule according to embodiment 227, wherein a $\Delta G$ for the formation of a duplex between the first and second guide molecule fragments is characterized by greater than 50%, 60%, 70%, 80%, 90% or 95% base pairing between each of (i) the first and second upper stem sequences and (ii) the first and second lower stem sequences is less than a $\Delta G$ for the formation of a duplex characterized by less than 50%, 60%, 70%, 80%, 90% or 95% base pairing between (i) and (ii).

229. The guide molecule according to embodiment 224 or 225, wherein the non-nucleotide chemical linkage covalently links a first nucleotide at or near a 3' terminus of the first upper stem sequence with a second nucleotide at or near a 5' terminus of the second upper stem sequence.

230. The guide molecule according to embodiment 229, wherein the first and second nucleotides are base paired.

231. The guide molecule according to embodiment 229, wherein a Gibbs free energy ($\Delta G$) for the formation of a duplex between the first and second guide molecule fragments that includes base pairing of the first and second nucleotides is less than $\Delta G$ for the formation of a duplex between the first and second guide molecule fragments in which the first and second nucleotides are not base paired.

232. The guide molecule according to any of embodiments 224-231, wherein the non-nucleotide chemical linkage comprises a urea.

233. A composition comprising a guide molecule according to any of embodiments 224-232.

234. The composition of embodiment 233, characterized in that greater than 90% of guide molecules in the composition are full length guide molecules.

235. The composition of embodiment 233 or 234, characterized in that greater than 85% of guide molecules in the composition comprise an identical targeting domain sequence.

236. The composition of any one of embodiments 233-235, wherein the targeting domain sequence is a predetermined targeting sequence.

237. The composition of any of embodiments 233-236, further comprising a Cas9 protein, wherein the guide molecule and the Cas9 protein form a complex capable of interacting with a target nucleic acid comprising (x) a sequence complementary to the targeting domain sequence, and (y) a protospacer adjacent motif (PAM) sequence that is recognized by the Cas9 protein.

238. The composition of embodiment 237, wherein the complex forms a single- or double-strand break in the target nucleic acid.

239. The composition of embodiment 237, wherein the complex chemically modifies the target nucleic acid or a protein associated with the target nucleic acid.

240. A genome editing system comprising a guide molecule according to any of embodiments 224-232.

241. The guide molecule of any of embodiments 224-232, the composition of any of embodiments 233-239 or the genome editing system of embodiment 240, for use in therapy.

242. The guide molecule of any of embodiments 224-232, the composition of any of embodiments 233-239 or the genome editing system of embodiment 240, for use in the production of a medicament.

243. The guide molecule of any of embodiments 224-232, the composition of any of embodiments 233-239 or the genome editing system of embodiment 240, for use in the modification a cell of a subject ex vivo.

244. The guide molecule of any of embodiments 224-232, the composition of any of embodiments 233-239 or the genome editing system of embodiment 240, for use in the modification a cell of a subject in vivo.

245. A method of altering a nucleic acid in a cell or subject comprising administering to the subject a guide molecule of embodiments 1-42, 169-221, or 224-232 or a composition of embodiments 43-85, 137-139, 147-155, 161-165, 222, 223, or 233-239.

246. A composition consisting essentially of a plurality of synthetic molecular guide molecules of any of embodiments 1-42, 169-221, or 224-232.

247. A composition consisting essentially of a plurality of guide molecules produced by the method of any one of embodiments 86-137 and a pharmaceutically acceptable carrier.

248. The method of any one of embodiments 86-137, wherein the guide molecule can act as a substrate for an enzyme that acts on RNA.

249. The method of embodiment 248, wherein the enzyme is a reverse transcriptase.

250. A synthetic unimolecular guide molecule for a CRISPR system, wherein the guide molecule is of formula $A_{3'}$-ii or $A_{2'}$-ii:

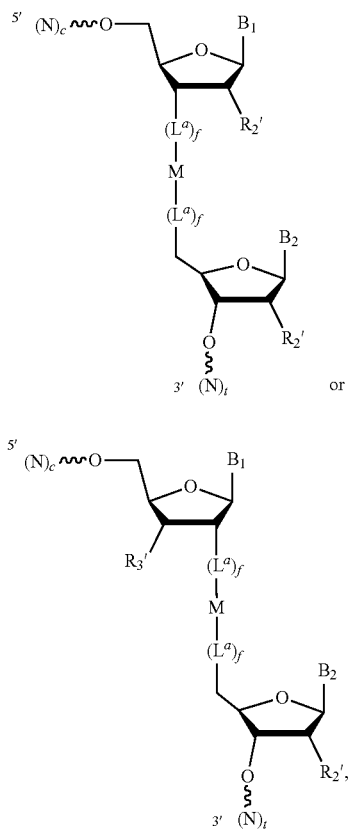

(A₃'-ii)

(A₂'-ii)

or a pharmaceutically acceptable salt thereof,
wherein:
each N in (N)$_c$ and (N)$_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;
(N)$_c$ includes a 3' region that is complementary or partially complementary to, and forms a duplex with, a 5' region of (N)$_t$;
c is an integer 20 or greater;
t is an integer 20 or greater;
B$_1$ and B$_2$ are each independently a nucleobase;
each of R$_2$' and R$_3$' is independently H, OH, fluoro, chloro, bromo, NH$_2$, SH, S—R', or O—R' wherein each R' is independently a protection group or an alkyl group, wherein the alkyl group may be optionally
each ∿∿ represents independently a phosphodiester linkage, a phosphorothioate linkage, a phosphonoacetate linkage, a thiophosphonoacetate linkage, or a phosphoroamidate linkage;
(L$^a$)$_f$-M-(L$^a$)$_f$- is a non-nucleotide linker;
each L$^a$ is independently a covalent bond or an optionally substituted, bivalent, straight or branched, saturated or unsaturated C$_1$-C$_{50}$ hydrocarbon chain, wherein one or more methylene units are optionally replaced by —O—, —S—, —N(R)—, —C(O)—, —C(S)—, —C(NR)—, —C(NOR)—, —C(NNR$_2$)—, —OC(O)—, —C(O)O—, —C(O)N(R)—, —N(R')C(O)—, —C(NR)O—, —OC(NR)—, —C(NR)NR—, —N(R)C(NR)—, —N(R)C(O)N(R)—, —N(R)C(O)O—, —OC(O)N(R)—, —N(R)C(O)S—, —SC(O)N(R)—, —N(R)C(NR)N(R)—, —SO$_2$—, —SO$_2$N(R)—, —N(R)SO$_2$—, —OP(O)(OH)O—, —OP(S)(OH)O—, —OP(S)(SH)O—, —OP(S)(COOH)O—, —OP(O)(COOH)O—, —OP(O)(NR$_2$)O—, or -Cy-;

M is —O—, —S—, —N(R)—, —C(O)—, —C(S)—, —C(NR)—, —C(NOR)—, —C(NNR$_2$)—, —OC(O)—, —C(O)O—, —C(O)N(R)—, —N(R)C(O)—, —C(NR)O—, —OC(NR)—, —C(NR)NR—, —N(R)C(NR)—, —N(R)C(O)N(R)—, —N(R)C(O)O—, —OC(O)N(R)—, —N(R)C(O)S—, —SC(O)N(R)—, —N(R)C(NR)N(R)—, —SO$_2$—, —SO$_2$N(R)—, —N(R)SO$_2$—, —OP(O)(OH)O—, —OP(S)(OH)O—, —OP(S)(SH)O—, —OP(S)(COOH)O—, —OP(O)(COOH)O—, —OP(O)(NR$_2$)O—, or -Cy-;

each R is independently hydrogen or an optionally substituted group selected from C$_{1-6}$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur;

Cy is an optionally substituted, mono- or multicyclic, 3- to 20-membered, bivalent ring system, wherein the ring system is fully or partially saturated, fully or partially unsaturated, or aromatic, and wherein the ring system contains 0-6 heteroatoms selected from the group consisting of O, N, and S; and each f is independently 0, 1, 2, 3, 4, 5, or 6.

251. The guide molecule of embodiment 250, wherein R$_2$' is selected from the group consisting of H, fluoro, and O—R' wherein R' is a protecting group or an optionally substituted alkyl group.

252. The guide molecule of embodiment 250 or 251, wherein each N in (N)$_c$ and (N)$_t$ is independently a ribonucleotide residue or a sugar-modified ribonucleotide residue.

253. The guide molecule of any one of embodiments 250-252, wherein (N)$_c$ or (N)$_t$ comprise one or more deoxyribonucleotide residues.

254. The guide molecule of any one of embodiments 250-253, wherein (N)$_c$ or (N)$_t$ comprise one or more 2'-O-methyl modified ribonucleotide residues.

255. The guide molecule of any one of embodiments 250-254, wherein each of the three nucleotides at the 5' end of (N)$_c$ and/or each of the three nucleotides at the 3' end of (N)$_t$ comprise a 2'-O-methyl modified ribonucleotide residue that is linked to its adjacent nucleotide(s) via a phosphorothioate linkage.

256. The guide molecule of any one of embodiments 250-255, wherein the guide molecule is for a Type II CRISPR system and (N)$_c$ includes a 5' region that comprises a targeting domain that is fully or partially complementary to a target domain within a target sequence.

257. The guide molecule of any one of embodiments 250-256, wherein (N)$_t$ includes a 3' region that comprises one or more stem-loop structures.

258. The guide molecule of any one of embodiments 250-257, wherein the guide molecule is capable of interacting with a Cas9 molecule and mediating the formation of a Cas9/guide ribonucleoprotein complex.

259. The guide molecule of any one of embodiments 250-258, wherein (N)$_c$ comprises a 3' region that comprises at least a portion of a repeat from a Type II CRISPR system.

260. The guide molecule of any one of embodiments 250-259, wherein the guide molecule is of formula $B_{3'}$-ii or $B_{2'}$-ii:

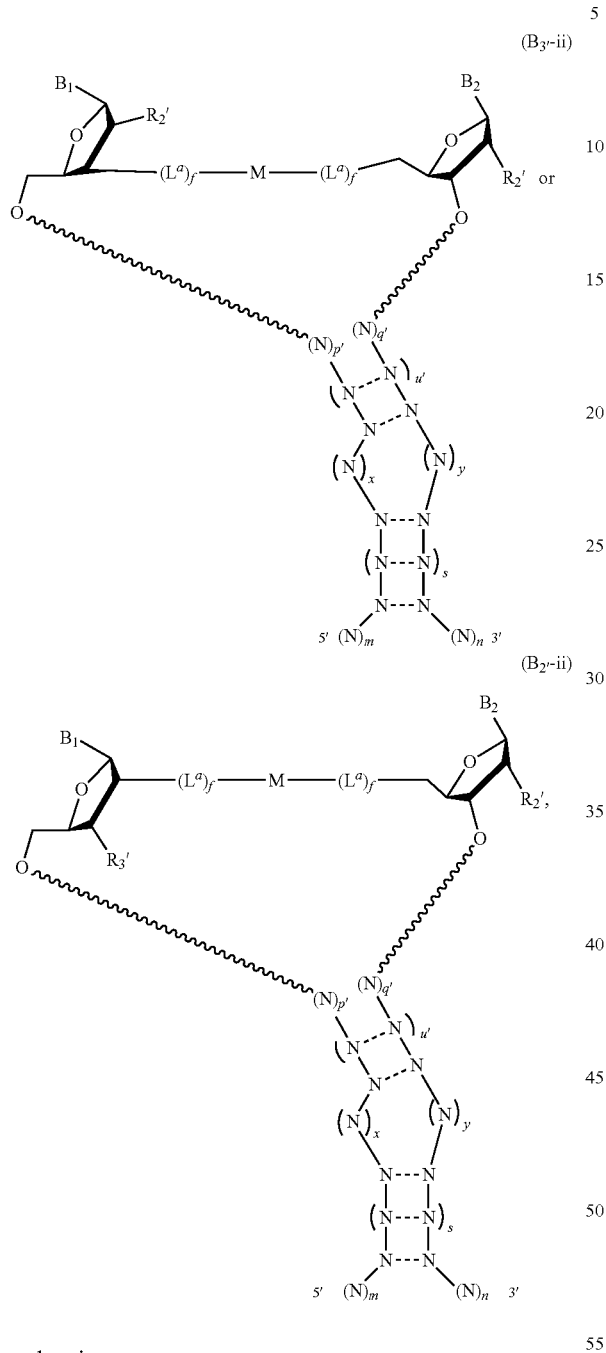

wherein:
p and q are each independently an integer between 0 and 6, inclusive, and p+q is an integer between 0 and 6, inclusive;
u is an integer between 2 and 22, inclusive;
s is an integer between 1 and 10, inclusive;
x is an integer between 1 and 3, inclusive;
y is >x and an integer between 3 and 5, inclusive;
m is an integer 15 or greater;
n is an integer 30 or greater;
each N is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage; and
each N—N independently represents two complementary nucleotides, optionally two complementary nucleotides that are hydrogen bonding base-paired.

261. The guide molecule of embodiment 260, wherein p and q are each 0.
262. The guide molecule of embodiment 260 or 261, wherein u is an integer between 3 and 22, inclusive.
263. The guide molecule of any one of embodiments 250-262, wherein the guide molecule is of formula $C_{3'}$-ii or $C_{2'}$-ii:

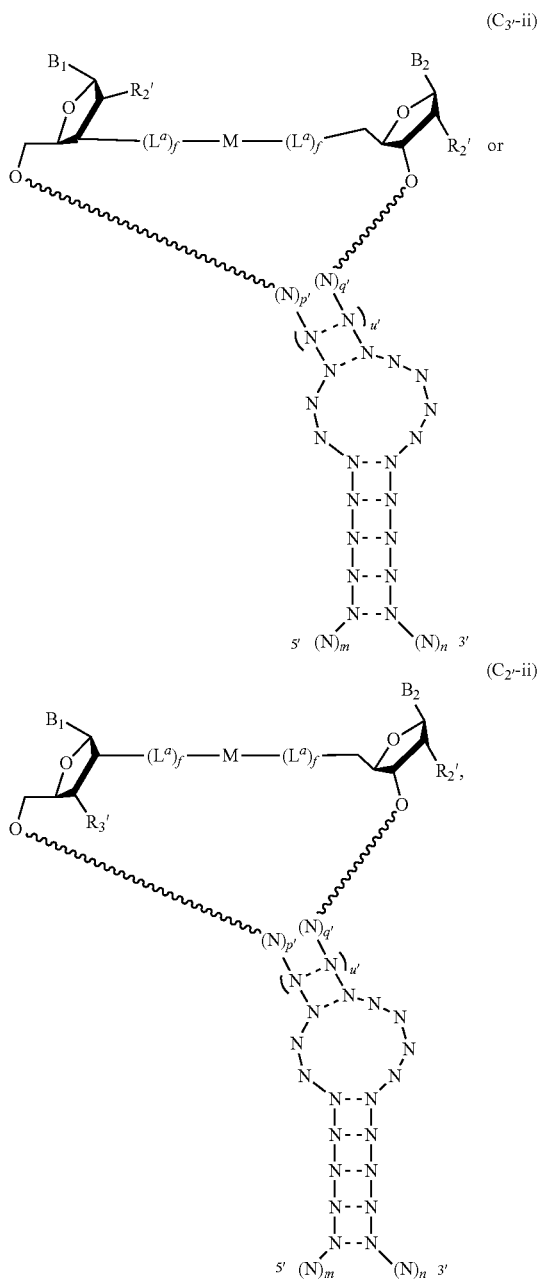

wherein:
u' is an integer between 2 and 22, inclusive; and
p' and q' are each independently an integer between 0 and 4, inclusive, and p'+q' is an integer between 0 and 4, inclusive.

264. The guide molecule of any one of embodiments 250-262, wherein the guide molecule is of formula $D_{3'}$-ii or $D_{2'}$-ii:

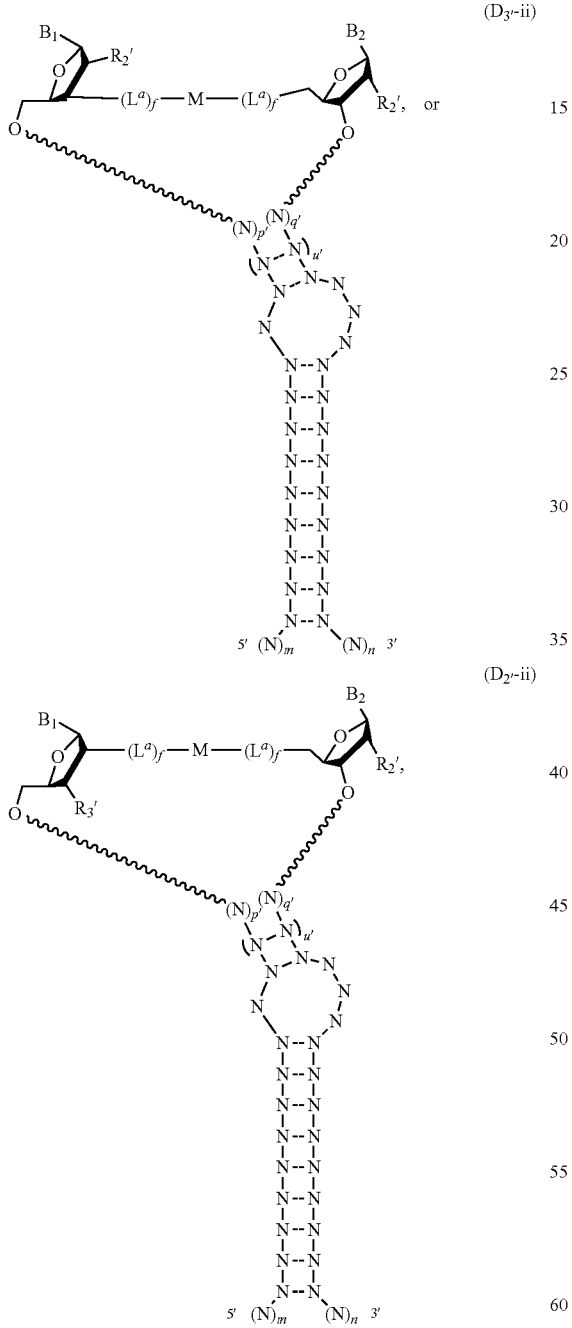

wherein:
u' is an integer between 2 and 22, inclusive; and
p' and q' are each independently an integer between 0 and 4, inclusive, and p'+q' is an integer between 0 and 4, inclusive.

265. The guide molecule of embodiment 263 or 264, wherein p' and q' are each 0.

266. The guide molecule of any one of embodiments 263-265, wherein u' is an integer between 3 and 22, inclusive.

267. The guide molecule of any one of embodiments 250-266, wherein the guide molecule comprises a sequence selected from Table 16 or Table 17.

268. The guide molecule of any one of embodiments 250-267, wherein at least one -(L$^a$)$_f$- is not selected from:

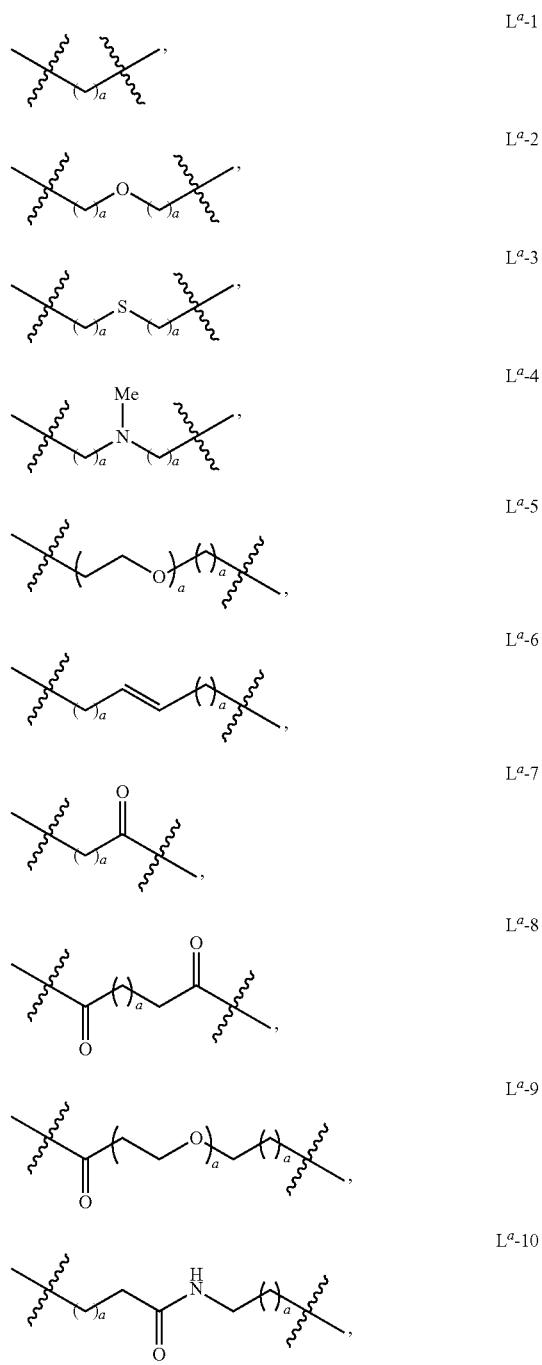

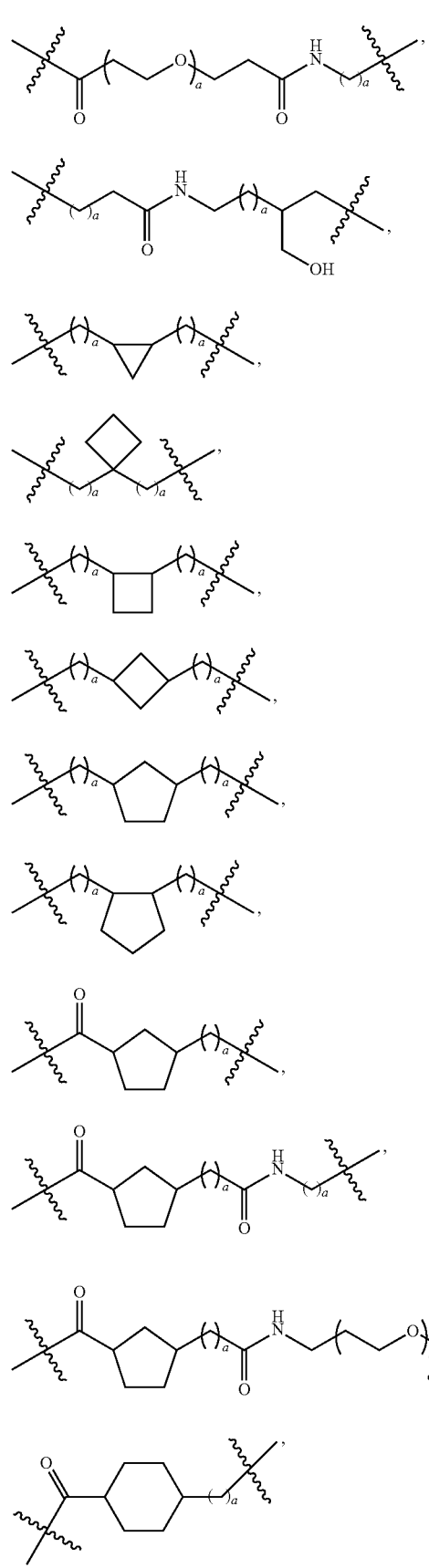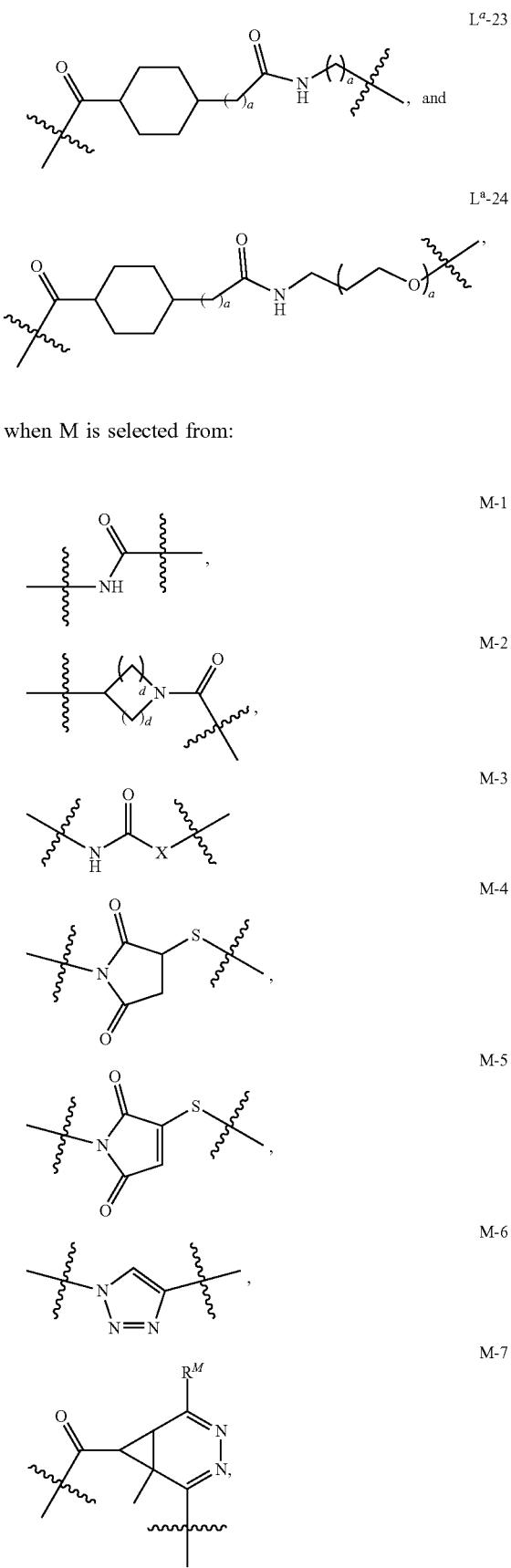

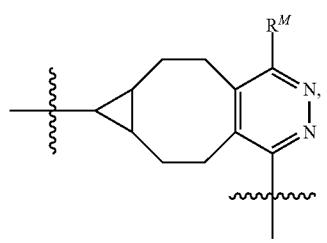
M-8
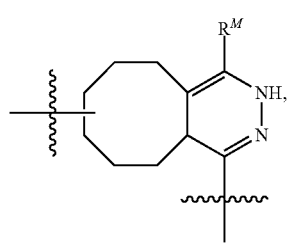
M-9
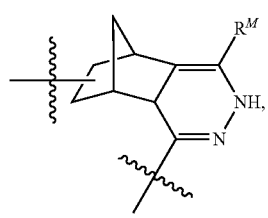
M-10
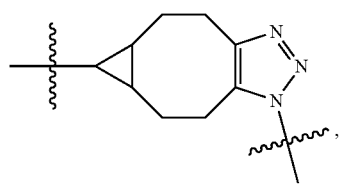
M-11
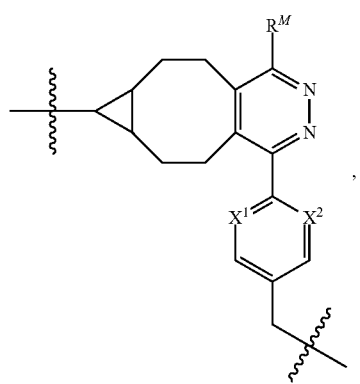
M-12
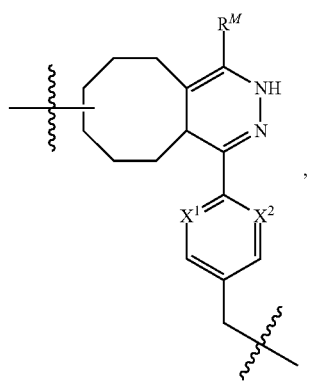
M-13
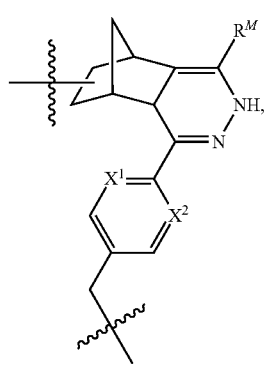
M-14
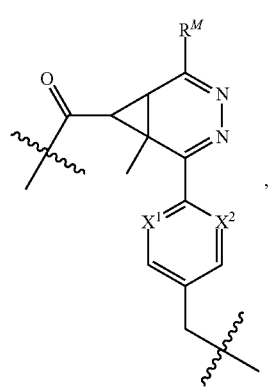
M-15
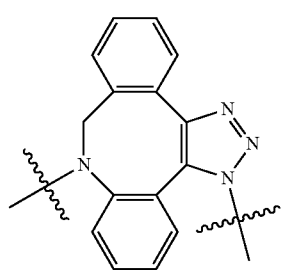
M-16

M-17
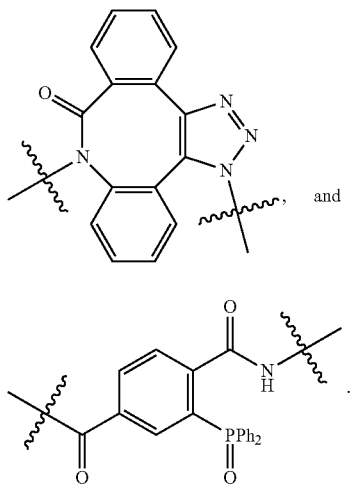, and
M-18
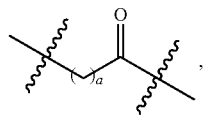
269. The guide molecule of any one of embodiments 250-267, wherein:
each $-(L^a)_f-$ is $-(L^a\text{-}28)-(L^a)_g-$, wherein $L^a\text{-}28$ is:
$L^a$-28
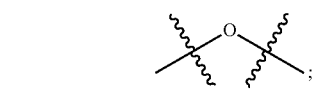;
each g is 0, 1, 2, 3, 4, or 5; and
at least one $-(L^a)_g-$ is not:
$L^a$-1
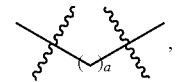,
$L^a$-2
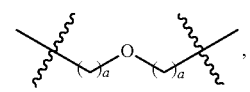,
$L^a$-3
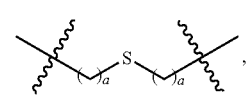,
$L^a$-4
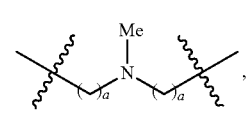,
$L^a$-5
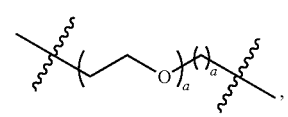,
$L^a$-6
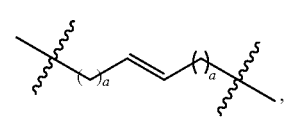,
$L^a$-7
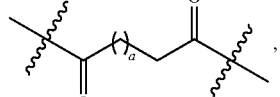,
$L^a$-8
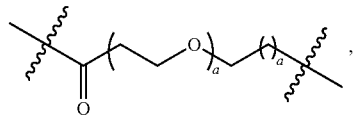,
$L^a$-9
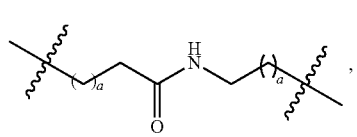,
$L^a$-10
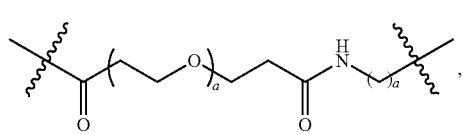,
$L^a$-11
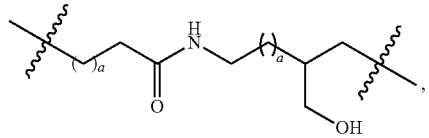,
$L^a$-12
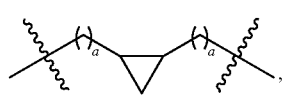,
$L^a$-13
,
$L^a$-14
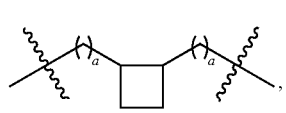,
$L^a$-15
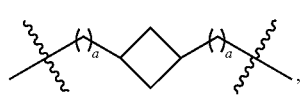,
$L^a$-16
$L^a$-17
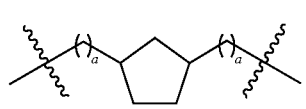,
$L^a$-18
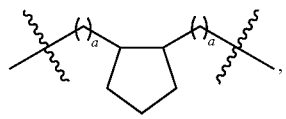,

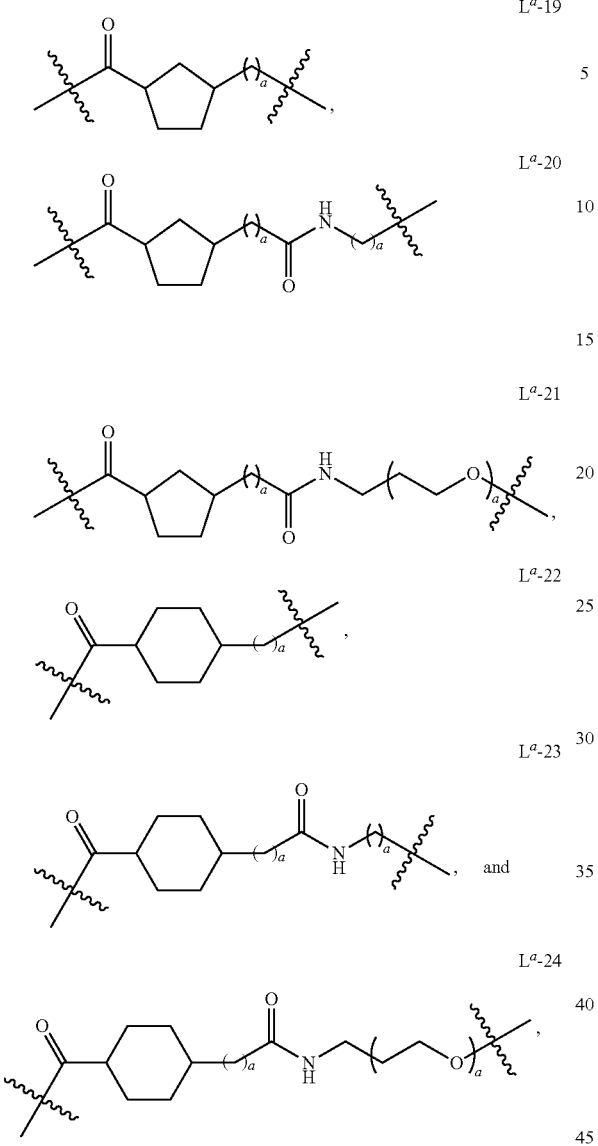
when M is selected from:
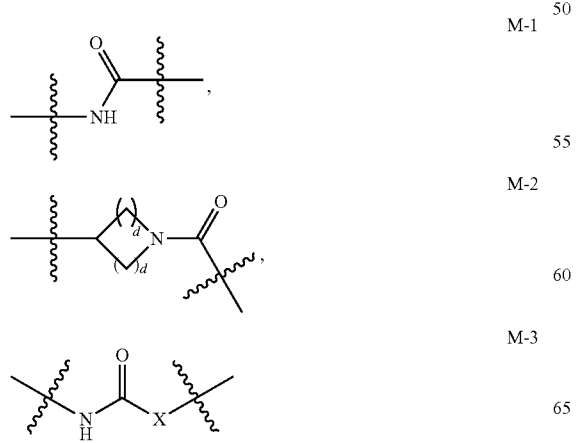
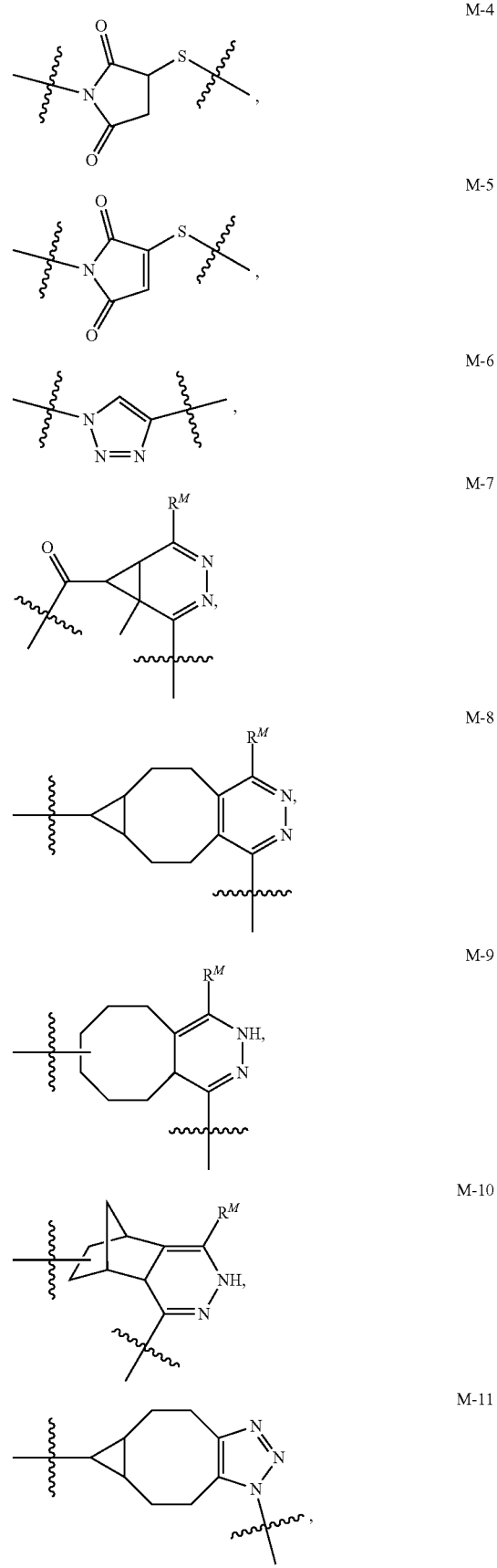

-continued
M-12
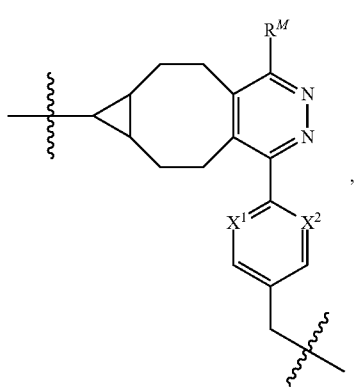
M-13
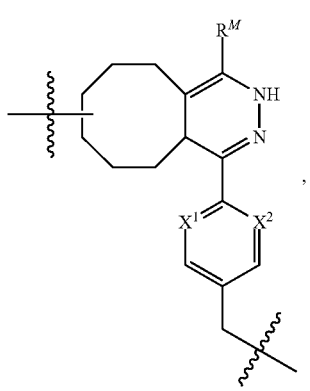
M-14
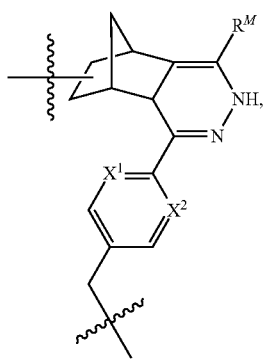
M-15
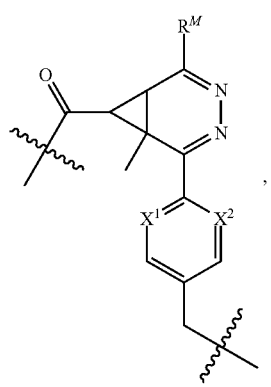
-continued
M-16
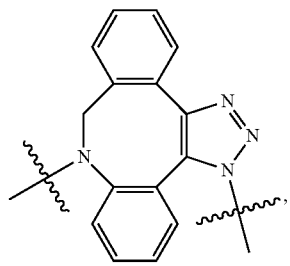
M-17
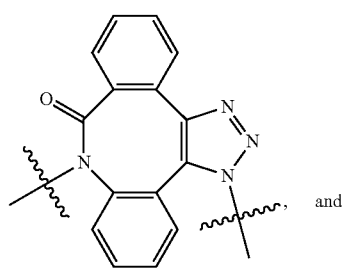
and
M-18
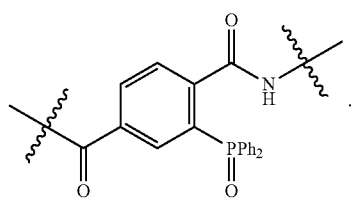
270. The guide molecule of any one of embodiments 250-267, wherein:
each $-(L^a)_f-$ is $-(L^a\text{-}26)-(L^a)_g-$, wherein $L^a\text{-}26$ is:
L$^a$-26
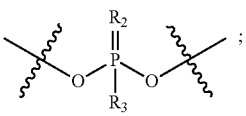
each $R_2$ is independently O or S;
each $R_3$ is independently $O^-$ or $COO^-$;
each g is 0, 1, 2, 3, 4, or 5; and
at least one $-(L^a)_g-$ is not:
L$^a$-1
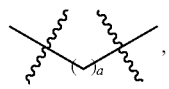
L$^a$-2
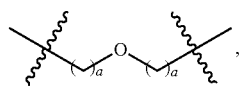
L$^a$-3
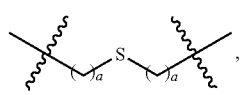
L$^a$-4
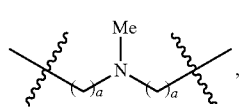

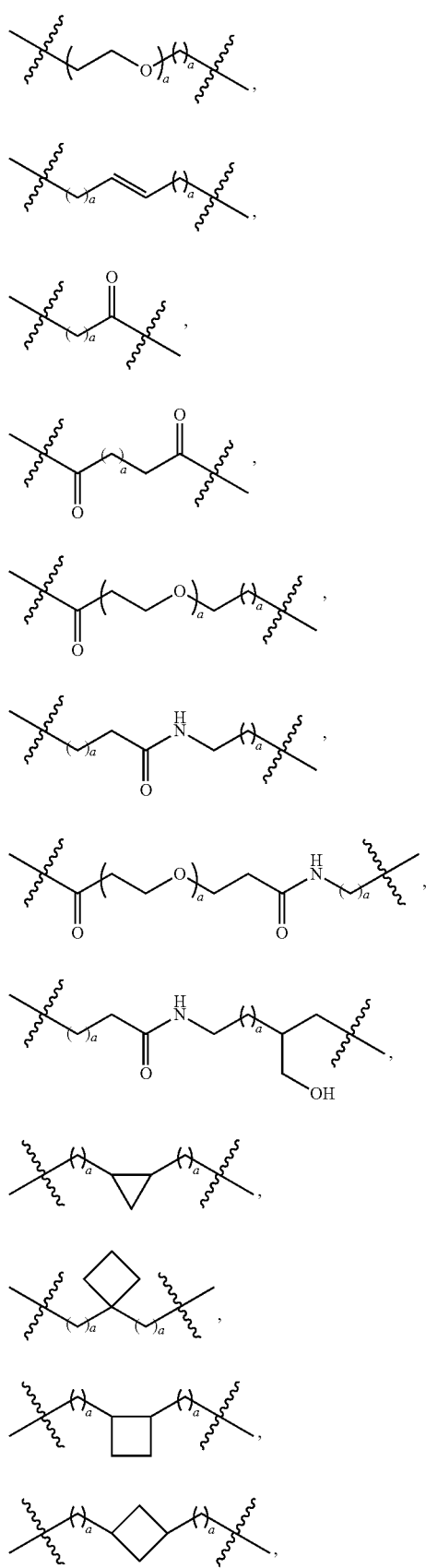
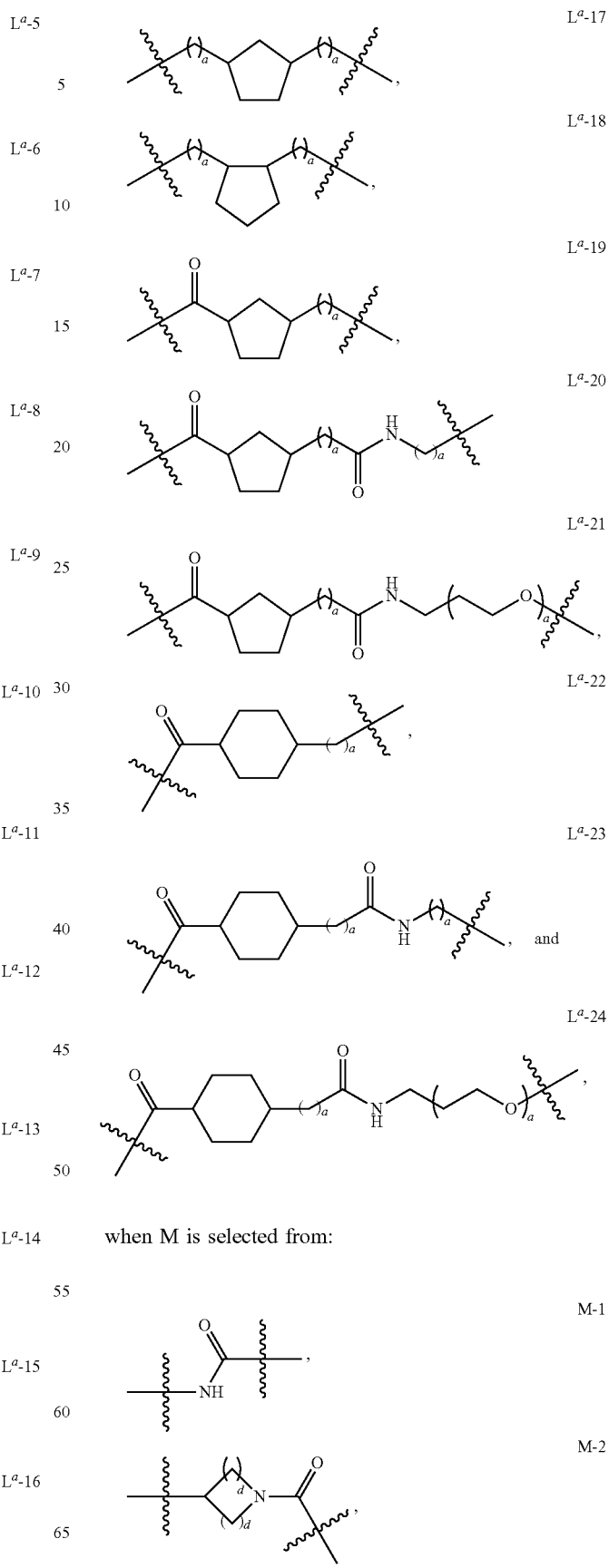
when M is selected from:

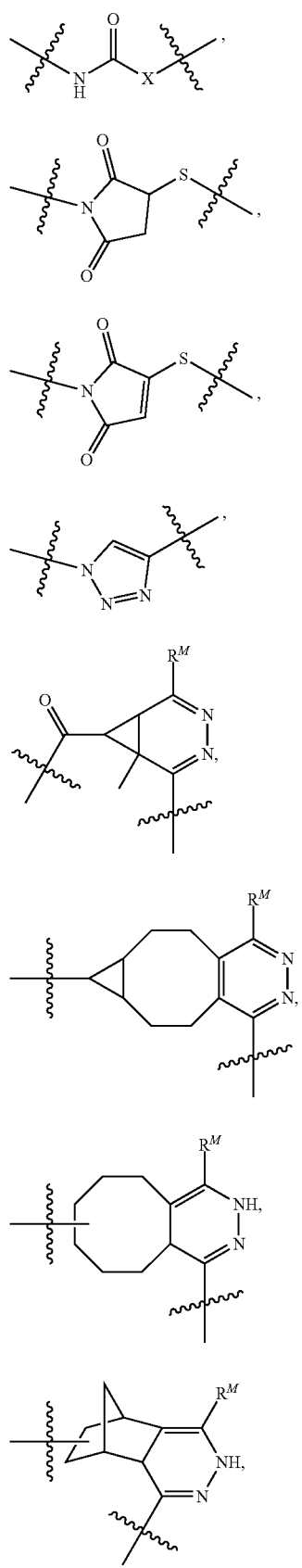
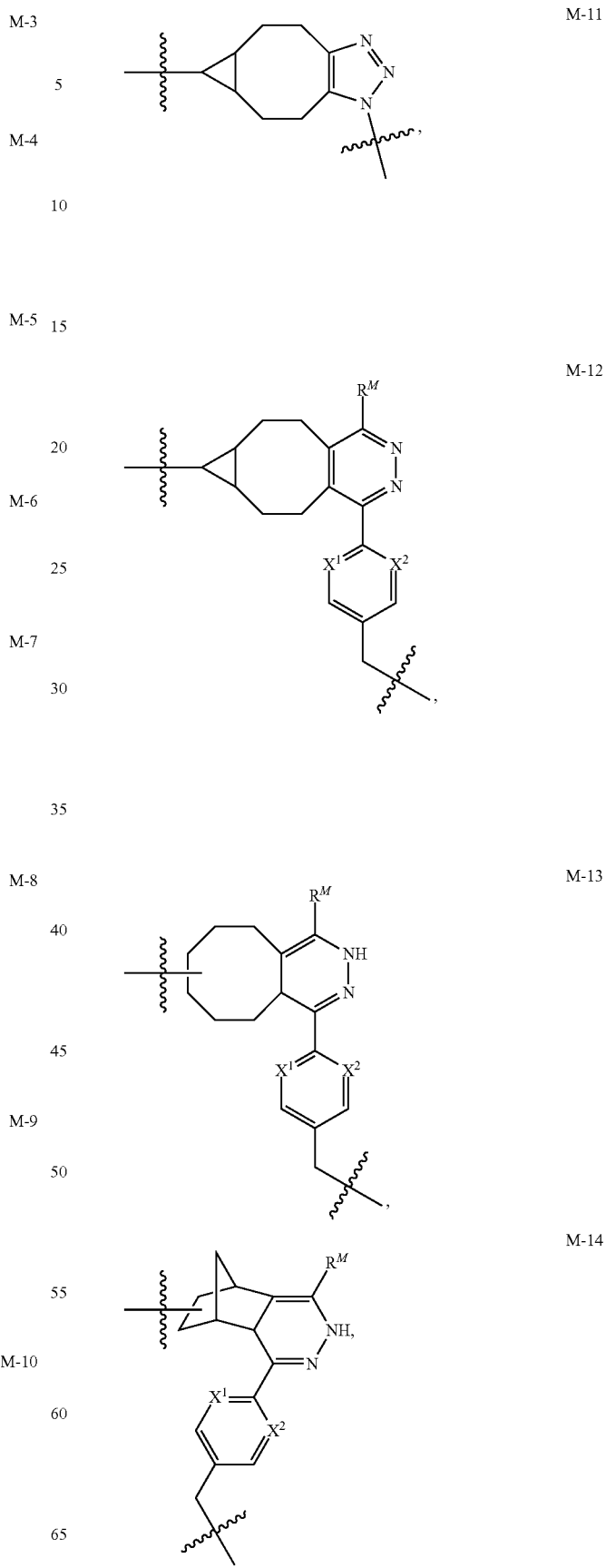

M-15
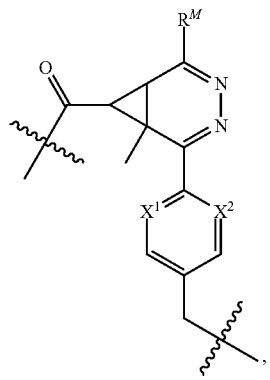
M-16
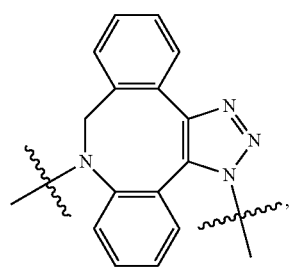
M-17
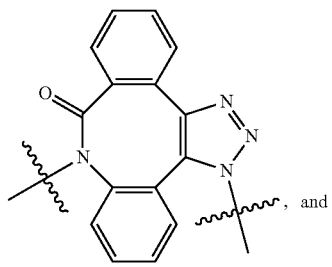, and
M-18
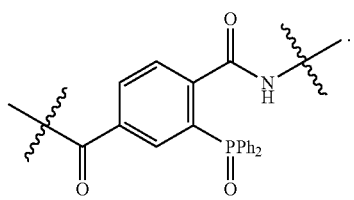
271. The guide molecule of any one of embodiments 250-270, wherein -(L$^a$)$_f$-M-(L$^a$)$_f$- is not:
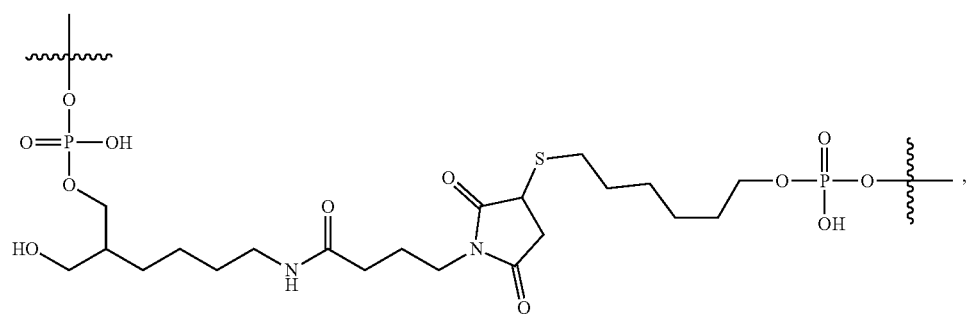,
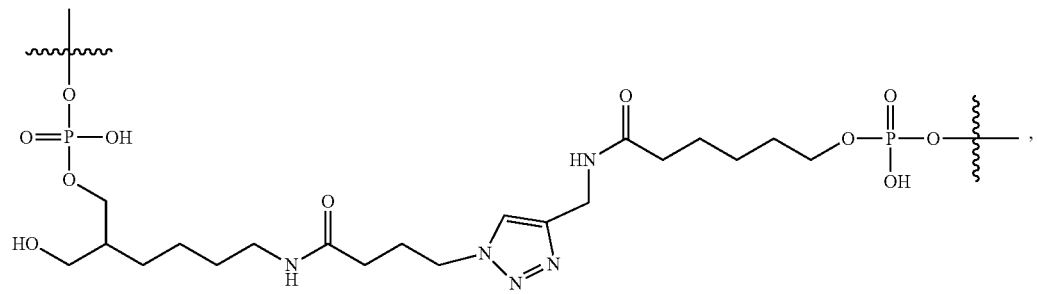,
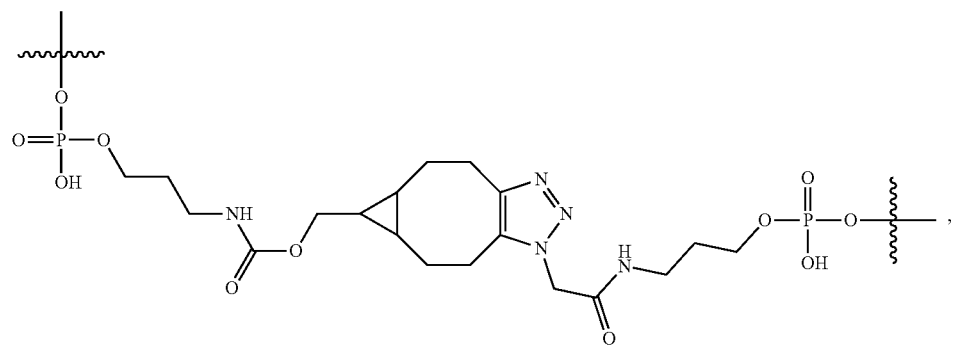, -continued

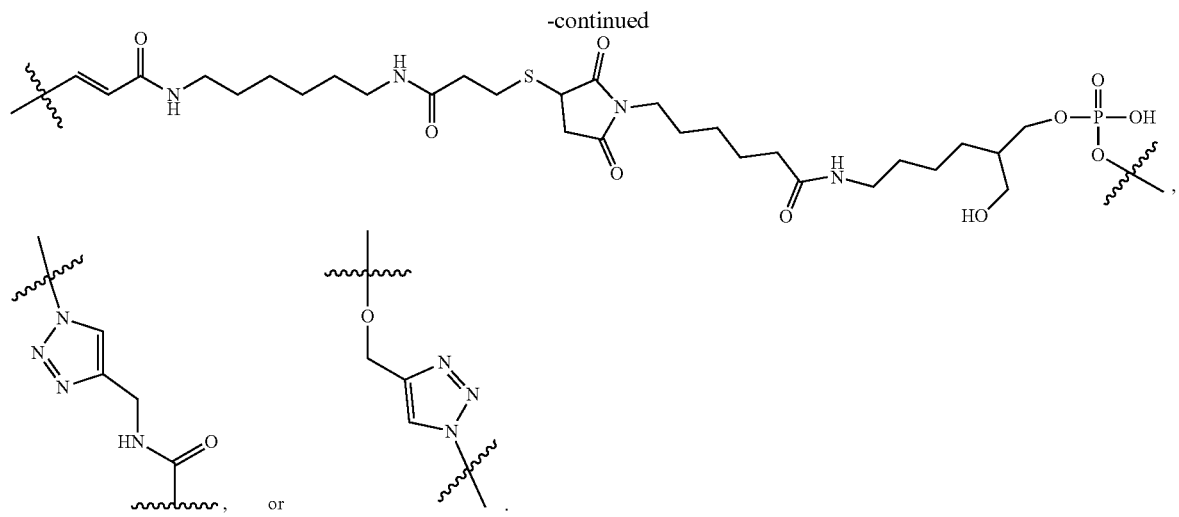

272. The guide molecule of any one of embodiments 250-271, wherein each $L^a$ is independently selected from the group consisting of:

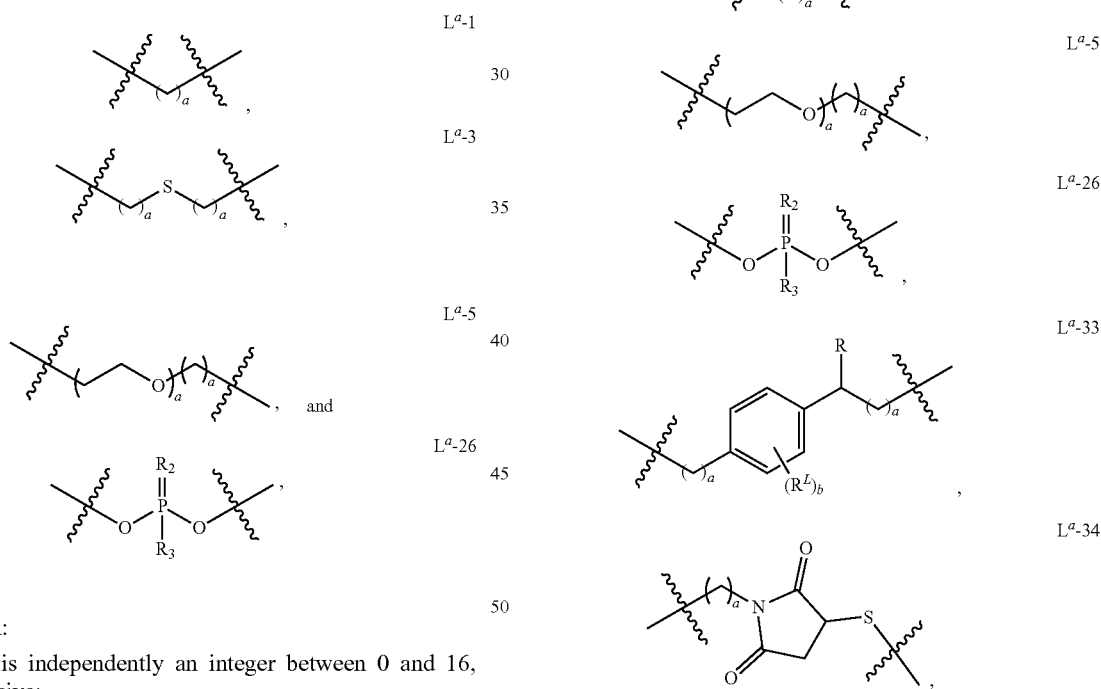

wherein:

each a is independently an integer between 0 and 16, inclusive;

each $R_2$ is independently O or S;

each $R_3$ is independently O$^-$ or COO$^-$; and each R is independently hydrogen or an optionally substituted group selected from $C_1$-$C_6$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur.

273. The guide molecule of any one of embodiments 250-271, wherein each $L^a$ is independently selected from the group consisting of:

wherein:

each a is independently an integer between 0 and 16, inclusive;

each b is independently an integer between 0 and 4, inclusive;

each $R_2$ is independently O or S;

each $R_3$ is independently $O^-$ or $COO^-$;

each $R^L$ is independently selected from R, halogen, —OR, —$NR_2$, —SR, —$NO_2$, —CN, —$SO_2R$, —$CO_2R$, and —$CONR_2$; and each R is independently hydrogen or an optionally substituted group selected from $C_1$-$C_6$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur.

274. The guide molecule of any one of embodiments 250-273, wherein M is selected from the group consisting of:

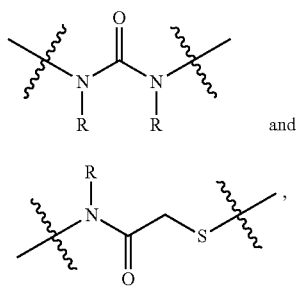

M-19 and

M-21 wherein each R is independently hydrogen or an optionally substituted group selected from $C_1$-$C_6$ aliphatic, phenyl, a 4-7 membered heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

275. The guide molecule of any one of embodiments 250-273, wherein M is selected from the group consisting of:

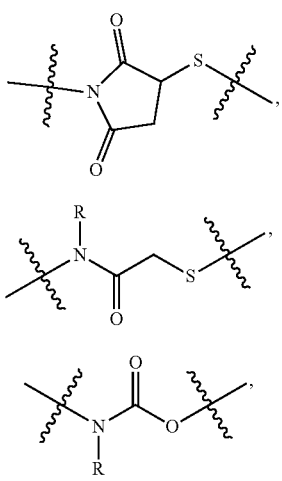

M-4

M-21

M-22

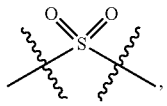

M-23

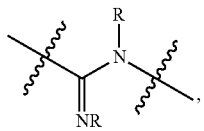

M-25

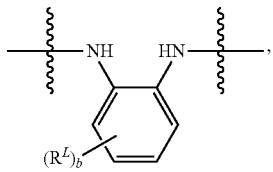

M-26

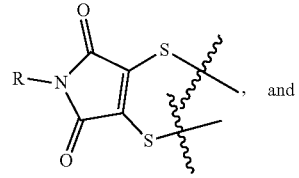

M-29

, and

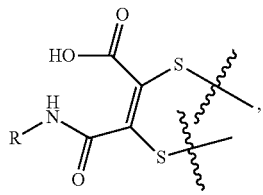

M-30 wherein:

each b is independently an integer between 0 and 4, inclusive;

each $R^L$ is independently selected from R, halogen, —OR, —$NR_2$, —SR, —$NO_2$, —CN, —$SO_2R$, —$CO_2R$, and —$CONR_2$; and each R is independently hydrogen or an optionally substituted group selected from $C_1$-$C_6$ aliphatic, phenyl, a 4-7 membered heterocyclic ring having 1-2 heteroatoms independently selected from nitrogen, oxygen, and sulfur, and a 5-6 membered monocyclic heteroaryl ring having 1-4 heteroatoms independently selected from nitrogen, oxygen, and sulfur.

276. The guide molecule of any one of embodiments 250-271, wherein -$(L^a)_f$-M-$(L^a)_f$- is selected from Table 5.

277. The guide molecule of any one of embodiments 250-271, wherein each -$(L^a)_f$- is selected from Table 8 and M is selected from Table 9.

278. The guide molecule of any one of embodiments 250-271, wherein each -$(L^a)_f$- is selected from Table 10 and M is selected from Table 11.

279. A composition of guide molecules for a CRISPR system, wherein the composition consists essentially of guide molecules of any one of embodiments 250-278.

280. A composition comprising, or consisting essentially of, a guide molecule of any one of embodiments 250-278 of formula $A_3$-ii, or a pharmaceutically acceptable salt thereof, wherein the composition is substantially free of molecules of formula:

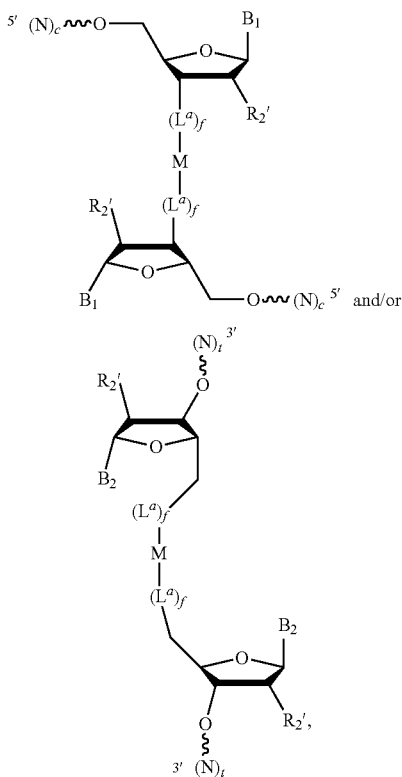

wherein:
each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;

$(N)_c$ includes a 3' region that is complementary or partially complementary to, and forms a duplex with, a 5' region of $(N)_t$;

c is an integer 20 or greater;

t is an integer 20 or greater;

$B_1$ and $B_2$ are each independently a nucleobase;

each of $R_2'$ and $R_3'$ is independently H, OH, fluoro, chloro, bromo, $NH_2$, SH, S—R', or O—R' wherein each R' is independently a protection group or an alkyl group, wherein the alkyl group may be optionally substituted;

each ⁓ represents independently a phosphodiester linkage, a phosphorothioate linkage, a phosphonoacetate linkage, a thiophosphonoacetate linkage, or a phosphoroamidate linkage;

$-(L^a)_f-M-(L^a)_f-$ is a non-nucleotide linker;

each $L^a$ is independently a covalent bond or an optionally substituted, bivalent, straight or branched, saturated or unsaturated $C_1$-$C_{50}$ hydrocarbon chain, wherein one or more methylene units are optionally replaced by —O—, —S—, —N(R)—, —C(O)—, —C(S)—, —C(NR)—, —C(NOR)—, —C(NNR$_2$)—, —OC(O)—, —C(O)O—, —C(O)N(R)—, —N(R')C(O)—, —C(NR)O—, —OC(NR)—, —C(NR)NR—, —N(R)C(NR)—, —N(R)C(O)N(R)—, —N(R)C(O)O—, —OC(O)N(R)—, —N(R)C(O)S—, —SC(O)N(R)—, —N(R)C(NR)N(R)—, —SO$_2$—, —SO$_2$N(R)—, —N(R)SO$_2$—, —OP(O)(OH)O—, —OP(S)(OH)O—, —OP(S)(SH)O—, —OP(S)(COOH)O—, —OP(O)(COOH)O—, —OP(O)(NR$_2$)O—, or -Cy-;

M is —O—, —S—, —N(R)—, —C(O)—, —C(S)—, —C(NR)—, —C(NOR)—, —C(NNR$_2$)—, —OC(O)—, —C(O)O—, —C(O)N(R)—, —N(R)C(O)—, —C(NR)O—, —OC(NR)—, —C(NR)NR—, —N(R)C(NR)—, —N(R)C(O)N(R)—, —N(R)C(O)O—, —OC(O)N(R)—, —N(R)C(O)S—, —SC(O)N(R)—, —N(R)C(NR)N(R)—, —SO$_2$—, —SO$_2$N(R)—, —N(R)SO$_2$—, —OP(O)(OH)O—, —OP(S)(OH)O—, —OP(S)(SH)O—, —OP(S)(COOH)O—, —OP(O)(COOH)O—, —OP(O)(NR$_2$)O—, or -Cy-;

each R is independently hydrogen or an optionally substituted group selected from $C_{1-6}$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur;

Cy is an optionally substituted, mono- or multicyclic, 3- to 20-membered, bivalent ring system, wherein the ring system is fully or partially saturated, fully or partially unsaturated, or aromatic, and wherein the ring system contains 0-6 heteroatoms selected from the group consisting of O, N, and S; and each f is independently 0, 1, 2, 3, 4, 5, or 6.

281. A composition comprising, or consisting essentially of, a guide molecule of any one of embodiments 250-278 of formula $A_2$-ii, or a pharmaceutically acceptable salt thereof, wherein the composition is substantially free of molecules of formula:

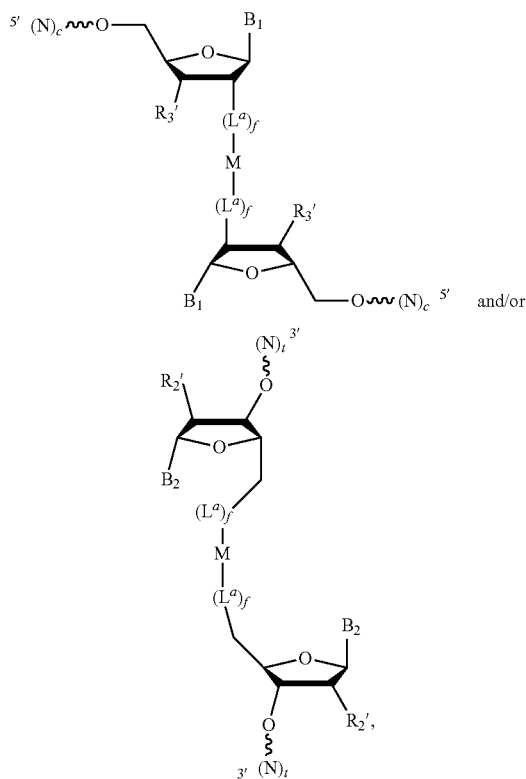

wherein:
each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;

$(N)_c$ includes a 3' region that is complementary or partially complementary to, and forms a duplex with, a 5' region of $(N)_t$;

c is an integer 20 or greater;

t is an integer 20 or greater;

$B_1$ and $B_2$ are each independently a nucleobase;

each of $R_2'$ and $R_3'$ is independently H, OH, fluoro, chloro, bromo, $NH_2$, SH, S—R', or O—R' wherein each R' is independently a protection group or an alkyl group, wherein the alkyl group may be optionally substituted;

each ⁓⁓⁓ represents independently a phosphodiester linkage, a phosphorothioate linkage, a phosphonoacetate linkage, a thiophosphonoacetate linkage, or a phosphoroamidate linkage;

$-(L^a)_f\text{-}M\text{-}(L^a)_f\text{-}$ is a non-nucleotide linker;

each $L^a$ is independently a covalent bond or an optionally substituted, bivalent, straight or branched, saturated or unsaturated $C_1\text{-}C_{50}$ hydrocarbon chain, wherein one or more methylene units are optionally replaced by —O—, —S—, —N(R)—, —C(O)—, —C(S)—, —C(NR)—, —C(NOR)—, —C(NNR$_2$)—, —OC(O)—, —C(O)O—, —C(O)N(R)—, —N(R')C(O)—, —C(NR)O—, —OC(NR)—, —C(NR)NR—, —N(R)C(NR)—, —N(R)C(O)N(R)—, —N(R)C(O)O—, —OC(O)N(R)—, —N(R)C(O)S—, —SC(O)N(R)—, —N(R)C(NR)N(R)—, —SO$_2$—, —SO$_2$N(R)—, —N(R)SO$_2$—, —OP(O)(OH)O—, —OP(S)(OH)O—, —OP(S)(SH)O—, —OP(S)(COOH)O—, —OP(O)(COOH)O—, —OP(O)(NR$_2$)O—, or -Cy-;

M is —O—, —S—, —N(R)—, —C(O)—, —C(S)—, —C(NR)—, —C(NOR)—, —C(NNR$_2$)—, —OC(O)—, —C(O)O—, —C(O)N(R)—, —N(R)C(O)—, —C(NR)O—, —OC(NR)—, —C(NR)NR—, —N(R)C(NR)—, —N(R)C(O)N(R)—, —N(R)C(O)O—, —OC(O)N(R)—, —N(R)C(O)S—, —SC(O)N(R)—, —N(R)C(NR)N(R)—, —SO$_2$—, —SO$_2$N(R)—, —N(R)SO$_2$—, —OP(O)(OH)O—, —OP(S)(OH)O—, —OP(S)(SH)O—, —OP(S)(COOH)O—, —OP(O)(COOH)O—, —OP(O)(NR$_2$)O—, or -Cy-;

each R is independently hydrogen or an optionally substituted group selected from $C_{1-6}$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur;

Cy is an optionally substituted, mono- or multicyclic, 3- to 20-membered, bivalent ring system, wherein the ring system is fully or partially saturated, fully or partially unsaturated, or aromatic, and wherein the ring system contains 0-6 heteroatoms selected from the group consisting of O, N, and S; and each f is independently 0, 1, 2, 3, 4, 5, or 6.

282. A composition comprising, or consisting essentially of, a guide molecule of any one of embodiments 250-278 of formula $A_3\text{-iii}$, or a pharmaceutically acceptable salt thereof, wherein the composition is substantially free of molecules of formula $A_3\text{-x}$:

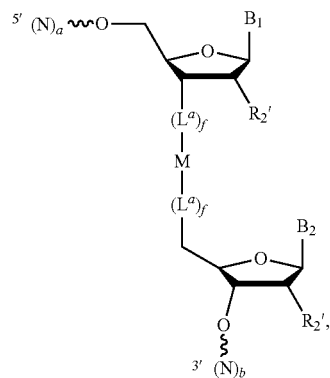

($A_3\text{-x}$)

wherein:

each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;

$(N)_c$ includes a 3' region that is complementary or partially complementary to, and forms a duplex with, a 5' region of $(N)_t$;

c is an integer 20 or greater;

t is an integer 20 or greater;

$B_1$ and $B_2$ are each independently a nucleobase;

each of $R_2'$ and $R_3'$ is independently H, OH, fluoro, chloro, bromo, $NH_2$, SH, S—R', or O—R' wherein each R' is independently a protection group or an alkyl group, wherein the alkyl group may be optionally substituted;

each ⁓⁓⁓ represents independently a phosphodiester linkage, a phosphorothioate linkage, a phosphonoacetate linkage, a thiophosphonoacetate linkage, or a phosphoroamidate linkage;

$-(L^a)_f\text{-}M\text{-}(L^a)_f\text{-}$ is a non-nucleotide linker;

each $L^a$ is independently a covalent bond or an optionally substituted, bivalent, straight or branched, saturated or unsaturated $C_1\text{-}C_{50}$ hydrocarbon chain, wherein one or more methylene units are optionally replaced by —O—, —S—, —N(R)—, —C(O)—, —C(S)—, —C(NR)—, —C(NOR)—, —C(NNR$_2$)—, —OC(O)—, —C(O)O—, —C(O)N(R)—, —N(R')C(O)—, —C(NR)O—, —OC(NR)—, —C(NR)NR—, —N(R)C(NR)—, —N(R)C(O)N(R)—, —N(R)C(O)O—, —OC(O)N(R)—, —N(R)C(O)S—, —SC(O)N(R)—, —N(R)C(NR)N(R)—, —SO$_2$—, —SO$_2$N(R)—, —N(R)SO$_2$—, —OP(O)(OH)O—, —OP(S)(OH)O—, —OP(S)(SH)O—, —OP(S)(COOH)O—, —OP(O)(COOH)O—, —OP(O)(NR$_2$)O—, or -Cy-;

M is —O—, —S—, —N(R)—, —C(O)—, —C(S)—, —C(NR)—, —C(NOR)—, —C(NNR$_2$)—, —OC(O)—, —C(O)O—, —C(O)N(R)—, —N(R)C(O)—, —C(NR)O—, —OC(NR)—, —C(NR)NR—, —N(R)C(NR)—, —N(R)C(O)N(R)—, —N(R)C(O)O—, —OC(O)N(R)—, —N(R)C(O)S—, —SC(O)N(R)—, —N(R)C(NR)N(R)—, —SO$_2$—, —SO$_2$N(R)—, —N(R)SO$_2$—, —OP(O)(OH)O—, —OP(S)(OH)O—, —OP(S)(SH)O—, —OP(S)(COOH)O—, —OP(O)(COOH)O—, —OP(O)(NR$_2$)O—, or -Cy-;

each R is independently hydrogen or an optionally substituted group selected from $C_{1-6}$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur;

Cy is an optionally substituted, mono- or multicyclic, 3- to 20-membered, bivalent ring system, wherein the ring system is fully or partially saturated, fully or partially unsaturated, or aromatic, and wherein the ring system contains 0-6 heteroatoms selected from the group consisting of O, N, and S; and each f is independently 0, 1, 2, 3, 4, 5, or 6.

283. A composition comprising, or consisting essentially of, a guide molecule of any one of embodiments 250-278 of formula $A_{3'}$-ii, or a pharmaceutically acceptable salt thereof, wherein the composition is substantially free of molecules of formula $A_{2'}$-x:

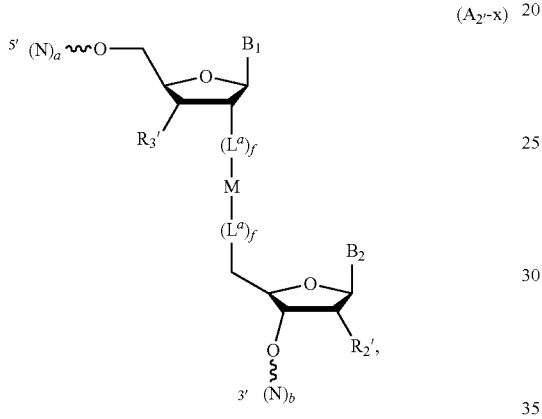

($A_{2'}$-x)

wherein:
each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;

$(N)_c$ includes a 3' region that is complementary or partially complementary to, and forms a duplex with, a 5' region of $(N)_t$;

c is an integer 20 or greater;
t is an integer 20 or greater;
$B_1$ and $B_2$ are each independently a nucleobase;
each of $R_2'$ and $R_3'$ is independently H, OH, fluoro, chloro, bromo, $NH_2$, SH, S—R', or O—R' wherein each R' is independently a protection group or an alkyl group, wherein the alkyl group may be optionally substituted;

each ∼∼∼ represents independently a phosphodiester linkage, a phosphorothioate linkage, a phosphonoacetate linkage, a thiophosphonoacetate linkage, or a phosphoroamidate linkage;

-$(L^a)_f$-M-$(L^a)_f$- is a non-nucleotide linker;

each $L^a$ is independently a covalent bond or an optionally substituted, bivalent, straight or branched, saturated or unsaturated $C_1$-$C_{50}$ hydrocarbon chain, wherein one or more methylene units are optionally replaced by —O—, —S—, —N(R)—, —C(O)—, —C(S)—, —C(NR)—, —C(NOR)—, —C(NNR$_2$)—, —OC(O)—, —C(O)O—, —C(O)N(R)—, —N(R')C(O)—, —C(NR)O—, —OC(NR)—, —C(NR)NR—, —N(R)C(NR)—, —N(R)C(O)N(R)—, —N(R)C(O)O—, —OC(O)N(R)—, —N(R)C(O)S—, —SC(O)N(R)—, —N(R)C(NR)N(R)—, —SO$_2$—, —SO$_2$N(R)—, —N(R)SO$_2$—, —OP(O)(OH)O—, —OP(S)(OH)O—, —OP(S)(SH)O—, —OP(S)(COOH)O—, —OP(O)(COOH)O—, —OP(O)(NR$_2$)O—, or -Cy-;

M is —O—, —S—, —N(R)—, —C(O)—, —C(S)—, —C(NR)—, —C(NOR)—, —C(NNR$_2$)—, —OC(O)—, —C(O)O—, —C(O)N(R)—, —N(R)C(O)—, —C(NR)O—, —OC(NR)—, —C(NR)NR—, —N(R)C(NR)—, —N(R)C(O)N(R)—, —N(R)C(O)O—, —OC(O)N(R)—, —N(R)C(O)S—, —SC(O)N(R)—, —N(R)C(NR)N(R)—, —SO$_2$—, —SO$_2$N(R)—, —N(R)SO$_2$—, —OP(O)(OH)O—, —OP(S)(OH)O—, —OP(S)(SH)O—, —OP(S)(COOH)O—, —OP(O)(COOH)O—, —OP(O)(NR$_2$)O—, or -Cy-;

each R is independently hydrogen or an optionally substituted group selected from $C_{1-6}$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur;

Cy is an optionally substituted, mono- or multicyclic, 3- to 20-membered, bivalent ring system, wherein the ring system is fully or partially saturated, fully or partially unsaturated, or aromatic, and wherein the ring system contains 0-6 heteroatoms selected from the group consisting of O, N, and S; and each f is independently 0, 1, 2, 3, 4, 5, or 6.

284. The composition of embodiment 282 or 283, wherein a is less than c and/or b is less than t.

285. The composition of any one of embodiments 279-284, wherein the composition has not been subjected to any purification steps.

286. The composition of any one of embodiments 279-285, comprising a complex of the guide molecule with a Cas9 or an RNA-guided nuclease.

287. The composition of any one of embodiments 279-286, wherein the guide molecule is suspended in solution or in a pharmaceutically acceptable carrier.

288. The composition of any one of embodiments 279-287, wherein $(N)_c$ comprises a 3' region that comprises at least a portion of a repeat from a Type II CRISPR system.

289. The composition of any one of embodiments 279-288, wherein less than about 10% of the guide molecules comprise a truncation at a 5' end, relative to a reference guide molecule sequence, and wherein at least about 99% of the guide molecules comprise a 5' sequence comprising nucleotides 1-20 of the guide molecule that is 100% identical to a corresponding 5' sequence of the reference guide molecule sequence.

290. The method of any one of embodiments 86-89, wherein the first and second reactive groups both comprise a sulfhydryl moiety.

291. The method of embodiment 290, wherein the first oligonucleotide is of formula:

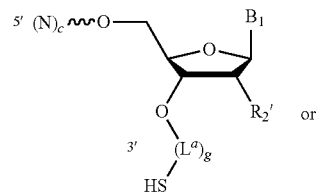

or

-continued

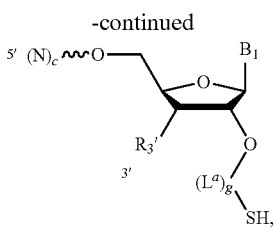

or a salt thereof; and the second oligonucleotide is of formula:

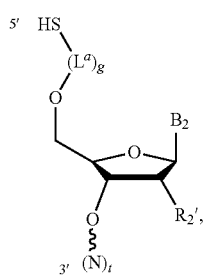

or a salt thereof,
wherein:
each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;
$(N)_c$ includes a 3' region that is complementary or partially complementary to, and forms a duplex with, a 5' region of $(N)_t$;
c is an integer 20 or greater;
t is an integer 20 or greater;
$B_1$ and $B_2$ are each independently a nucleobase;
each of $R_2'$ and $R_3'$ is independently H, OH, fluoro, chloro, bromo, $NH_2$, SH, S—R', or O—R' wherein each R' is independently a protection group or an alkyl group, wherein the alkyl group may be optionally substituted;
each ∿∿ represents independently a phosphodiester linkage, a phosphorothioate linkage, a phosphonoacetate linkage, a thiophosphonoacetate linkage, or a phosphoroamidate linkage;
each $L^a$ is independently a covalent bond or an optionally substituted, bivalent, straight or branched, saturated or unsaturated $C_1$-$C_{50}$ hydrocarbon chain, wherein one or more methylene units are optionally replaced by —O—, —S—, —N(R)—, —C(O)—, —C(S)—, —C(NR)—, —C(NOR)—, —C(NNR$_2$)—, —OC(O)—, —C(O)O—, —C(O)N(R)—, —N(R')C(O)—, —C(NR)O—, —OC(NR)—, —C(NR)NR—, —N(R)C(NR)—, —N(R)C(O)N(R)—, —N(R)C(O)O—, —OC(O)N(R)—, —N(R)C(O)S—, —SC(O)N(R)—, —N(R)C(NR)N(R)—, —SO$_2$—, —SO$_2$N(R)—, —N(R)SO$_2$—, —OP(O)(OH)O—, —OP(S)(OH)O—, —OP(S)(SH)O—, —OP(S)(COOH)O—, —OP(O)(COOH)O—, —OP(O)(NR$_2$)O—, or -Cy-;
each R is independently hydrogen or an optionally substituted group selected from $C_{1-6}$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur;
Cy is an optionally substituted, mono- or multicyclic, 3- to 20-membered, bivalent ring system, wherein the ring system is fully or partially saturated, fully or partially unsaturated, or aromatic, and wherein the ring system contains 0-6 heteroatoms selected from the group consisting of O, N, and S; and each g is 0, 1, 2, 3, 4, or 5.

292. The method of any one of embodiments 86-89, wherein the first reactive group comprises an amine moiety and the second reactive group comprises a hydroxyl moiety, or the first reactive group comprises a hydroxyl moiety and the second reactive group comprises an amine moiety.

293. The method of embodiment 292, wherein (a) the first oligonucleotide is of formula:

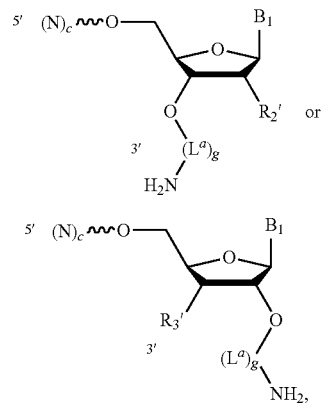

or a salt thereof; and the second oligonucleotide is of formula:

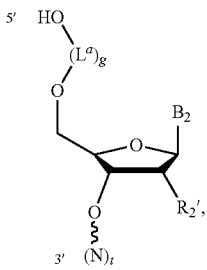

or a salt thereof; or
(b) the first oligonucleotide is of formula:

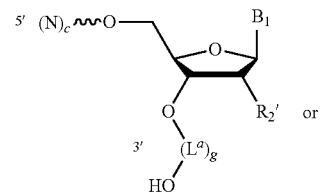

-continued

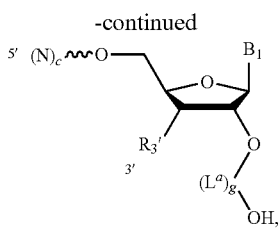

or a salt thereof; and the second oligonucleotide is of formula:

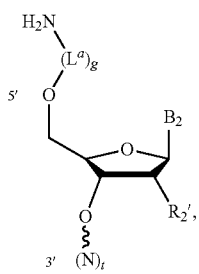

or a salt thereof,
wherein:
each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;
$(N)_c$ includes a 3' region that is complementary or partially complementary to, and forms a duplex with, a 5' region of $(N)_t$;
c is an integer 20 or greater;
t is an integer 20 or greater;
$B_1$ and $B_2$ are each independently a nucleobase;
each of $R_2'$ and $R_3'$ is independently H, OH, fluoro, chloro, bromo, $NH_2$, SH, S—R', or O—R' wherein each R' is independently a protection group or an alkyl group, wherein the alkyl group may be optionally substituted;
each ⁓⁓⁓ represents independently a phosphodiester linkage, a phosphorothioate linkage, a phosphonoacetate linkage, a thiophosphonoacetate linkage, or a phosphoroamidate linkage;
each $L^a$ is independently a covalent bond or an optionally substituted, bivalent, straight or branched, saturated or unsaturated $C_1$-$C_{50}$ hydrocarbon chain, wherein one or more methylene units are optionally replaced by —O—, —S—, —N(R)—, —C(O)—, —C(S)—, —C(NR)—, —C(NOR)—, —C(NNR_2)—, —OC(O)—, —C(O)O—, —C(O)N(R)—, —N(R')C(O)—, —C(NR)O—, —OC(NR)—, —C(NR)NR—, —N(R)C(NR)—, —N(R)C(O)N(R)—, —N(R)C(O)O—, —OC(O)N(R)—, —N(R)C(O)S—, —SC(O)N(R)—, —N(R)C(NR)N(R)—, —$SO_2$—, —$SO_2$N(R)—, —N(R)$SO_2$—, —OP(O)(OH)O—, —OP(S)(OH)O—, —OP(S)(SH)O—, —OP(S)(COOH)O—, —OP(O)(COOH)O—, —OP(O)($NR_2$)O—, or -Cy-;
each R is independently hydrogen or an optionally substituted group selected from $C_{1-6}$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur;
Cy is an optionally substituted, mono- or multicyclic, 3- to 20-membered, bivalent ring system, wherein the ring system is fully or partially saturated, fully or partially unsaturated, or aromatic, and wherein the ring system contains 0-6 heteroatoms selected from the group consisting of O, N, and S; and
each g is 0, 1, 2, 3, 4, or 5.

294. The method of any one of embodiments 86-89, wherein the first reactive group comprises an amine moiety and the second reactive group comprises a sulfhydryl moiety, or the first reactive group comprises a sulfhydryl moiety and the second reactive group comprises an amine moiety.

295. The method of embodiment 294, wherein (a) the first oligonucleotide is of formula:

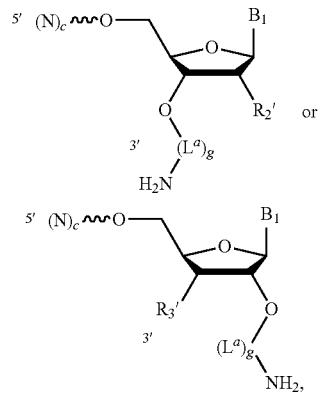

or a salt thereof; and the second oligonucleotide is of formula:

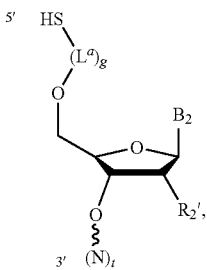

or a salt thereof; or
(b) the first oligonucleotide is of formula:

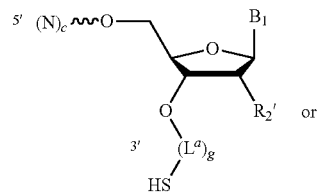

385
-continued

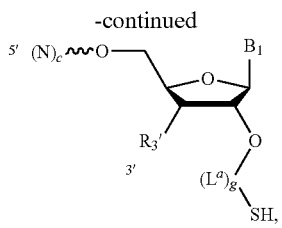

or a salt thereof; and the second oligonucleotide is of formula:

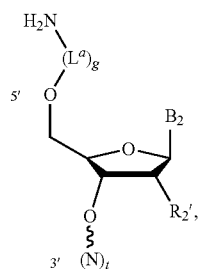

or a salt thereof,
wherein:
each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;
$(N)_c$ includes a 3' region that is complementary or partially complementary to, and forms a duplex with, a 5' region of (N);
c is an integer 20 or greater;
t is an integer 20 or greater;
$B_1$ and $B_2$ are each independently a nucleobase;
each of $R_2'$ and $R_3'$ is independently H, OH, fluoro, chloro, bromo, $NH_2$, SH, S—R', or O—R' wherein each R' is independently a protection group or an alkyl group, wherein the alkyl group may be optionally substituted;
each ∿ represents independently a phosphodiester linkage, a phosphorothioate linkage, a phosphonoacetate linkage, a thiophosphonoacetate linkage, or a phosphoroamidate linkage;
each $L^a$ is independently a covalent bond or an optionally substituted, bivalent, straight or branched, saturated or unsaturated $C_1$-$C_{50}$ hydrocarbon chain, wherein one or more methylene units are optionally replaced by —O—, —S—, —N(R)—, —C(O)—, —C(S)—, —C(NR)—, —C(NOR)—, —C(NNR_2)—, —OC(O)—, —C(O)O—, —C(O)N(R)—, —N(R')C(O)—, —C(NR)O—, —OC(NR)—, —C(NR)NR—, —N(R)C(NR)—, —N(R)C(O)N(R)—, —N(R)C(O)O—, —OC(O)N(R)—, —N(R)C(O)S—, —SC(O)N(R)—, —N(R)C(NR)N(R)—, —SO_2—, —SO_2N(R)—, —N(R)SO_2—, —OP(O)(OH)O—, —OP(S)(OH)O—, —OP(S)(SH)O—, —OP(S)(COOH)O—, —OP(O)(COOH)O—, —OP(O)(NR_2)O—, or -Cy-;
each R is independently hydrogen or an optionally substituted group selected from $C_{1-6}$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur;
Cy is an optionally substituted, mono- or multicyclic, 3- to 20-membered, bivalent ring system, wherein the ring system is fully or partially saturated, fully or partially unsaturated, or aromatic, and wherein the ring system contains 0-6 heteroatoms selected from the group consisting of O, N, and S; and
each g is 0, 1, 2, 3, 4, or 5.
296. The method of any one of embodiments 290-295, wherein the unimolecular guide molecule is of any one of embodiments 250-278.
297. An oligonucleotide for synthesizing a unimolecular guide molecule for a Type II CRISPR system, wherein the oligonucleotide is of formula:

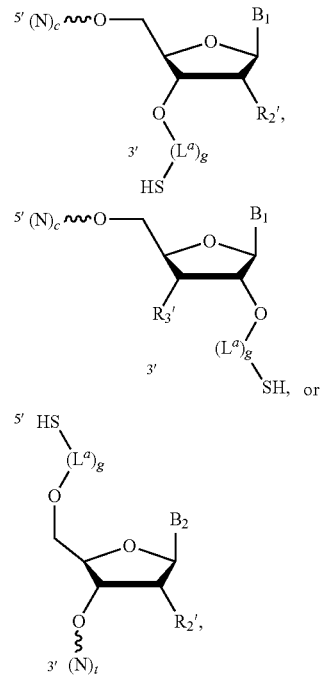

wherein:
each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;
$(N)_c$ includes a 3' region that is complementary or partially complementary to, and forms a duplex with, a 5' region of $(N)_t$;
c is an integer 20 or greater;
t is an integer 20 or greater;
$B_1$ and $B_2$ are each independently a nucleobase;
each of $R_2'$ and $R_3'$ is independently H, OH, fluoro, chloro, bromo, $NH_2$, SH, S—R', or O—R' wherein each R' is independently a protection group or an alkyl group, wherein the alkyl group may be optionally substituted;
each ∿ represents independently a phosphodiester linkage, a phosphorothioate linkage, a phosphonoacetate linkage, a thiophosphonoacetate linkage, or a phosphoroamidate linkage;

each $L^a$ is independently a covalent bond or an optionally substituted, bivalent, straight or branched, saturated or unsaturated $C_1$-$C_{50}$ hydrocarbon chain, wherein one or more methylene units are optionally replaced by —O—, —S—, —N(R)—, —C(O)—, —C(S)—, —C(NR)—, —C(NOR)—, —C(NNR$_2$)—, —OC(O)—, —C(O)O—, —C(O)N(R)—, —N(R')C(O)—, —C(NR)O—, —OC(NR)—, —C(NR)NR—, —N(R)C(NR)—, —N(R)C(O)N(R)—, —N(R)C(O)O—, —OC(O)N(R)—, —N(R)C(O)S—, —SC(O)N(R)—, —N(R)C(NR)N(R)—, —SO$_2$—, —SO$_2$N(R)—, —N(R)SO$_2$—, —OP(O)(OH)O—, —OP(S)(OH)O—, —OP(S)(SH)O—, —OP(S)(COOH)O—, —OP(O)(COOH)O—, —OP(O)(NR$_2$)O—, or -Cy-;

each R is independently hydrogen or an optionally substituted group selected from $C_{1-6}$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur;

Cy is an optionally substituted, mono- or multicyclic, 3- to 20-membered, bivalent ring system, wherein the ring system is fully or partially saturated, fully or partially unsaturated, or aromatic, and wherein the ring system contains 0-6 heteroatoms selected from the group consisting of O, N, and S; and each g is 0, 1, 2, 3, 4, or 5.

298. An oligonucleotide for synthesizing a unimolecular guide molecule for a Type II CRISPR system, wherein the oligonucleotide is of formula:

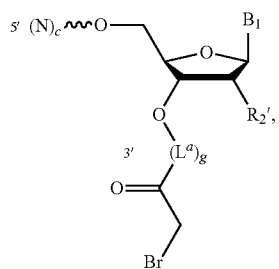

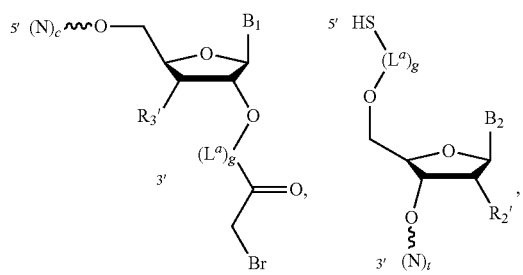

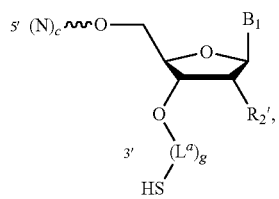

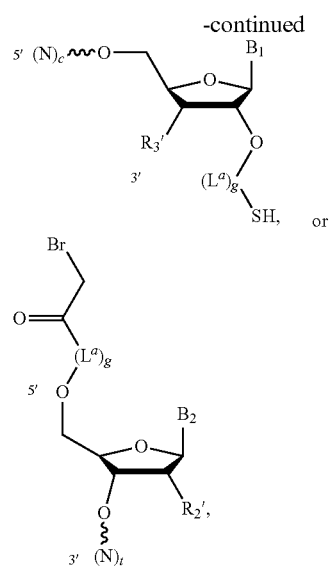

wherein:

each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;

$(N)_c$ includes a 3' region that is complementary or partially complementary to, and forms a duplex with, a 5' region of $(N)_t$;

c is an integer 20 or greater;

t is an integer 20 or greater;

$B_1$ and $B_2$ are each independently a nucleobase;

each of $R_2'$ and $R_3'$ is independently H, OH, fluoro, chloro, bromo, NH$_2$, SH, S—R', or O—R' wherein each R' is independently a protection group or an alkyl group, wherein the alkyl group may be optionally substituted;

each ∿∿ represents independently a phosphodiester linkage, a phosphorothioate linkage, a phosphonoacetate linkage, a thiophosphonoacetate linkage, or a phosphoroamidate linkage;

each $L^a$ is independently a covalent bond or an optionally substituted, bivalent, straight or branched, saturated or unsaturated $C_1$-$C_{50}$ hydrocarbon chain, wherein one or more methylene units are optionally replaced by —O—, —S—, —N(R)—, —C(O)—, —C(S)—, —C(NR)—, —C(NOR)—, —C(NNR$_2$)—, —OC(O)—, —C(O)O—, —C(O)N(R)—, —N(R')C(O)—, —C(NR)O—, —OC(NR)—, —C(NR)NR—, —N(R)C(NR)—, —N(R)C(O)N(R)—, —N(R)C(O)O—, —OC(O)N(R)—, —N(R)C(O)S—, —SC(O)N(R)—, —N(R)C(NR)N(R)—, —SO$_2$—, —SO$_2$N(R)—, —N(R)SO$_2$—, —OP(O)(OH)O—, —OP(S)(OH)O—, —OP(S)(SH)O—, —OP(S)(COOH)O—, —OP(O)(COOH)O—, —OP(O)(NR$_2$)O—, or -Cy-;

each R is independently hydrogen or an optionally substituted group selected from $C_{1-6}$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur;

Cy is an optionally substituted, mono- or multicyclic, 3- to 20-membered, bivalent ring system, wherein the ring system is fully or partially saturated, fully or partially unsaturated, or aromatic, and wherein the ring system contains 0-6 heteroatoms selected from the group consisting of O, N, and S; and each g is 0, 1, 2, 3, 4, or 5.

299. An oligonucleotide for synthesizing a unimolecular guide molecule for a Type II CRISPR system, wherein the oligonucleotide is of formula:

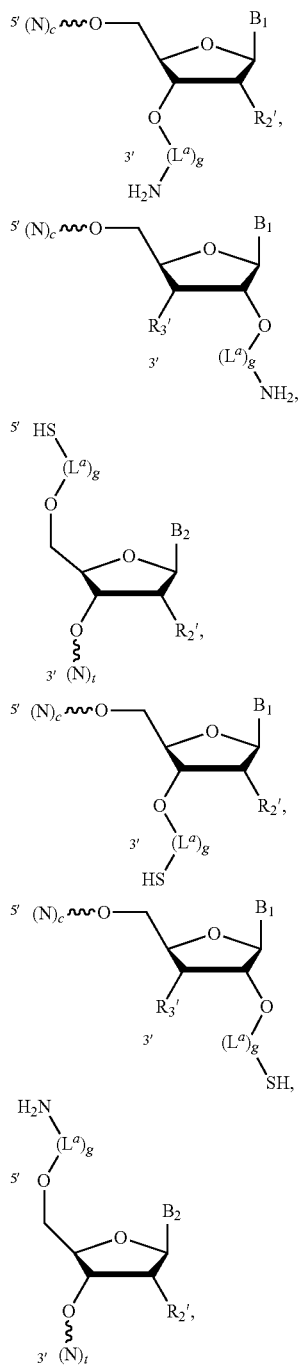

wherein:

each N in $(N)_c$ and $(N)_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;

$(N)_c$ includes a 3' region that is complementary or partially complementary to, and forms a duplex with, a 5' region of (N);

c is an integer 20 or greater;

t is an integer 20 or greater;

$B_1$ and $B_2$ are each independently a nucleobase;

each of $R_2'$ and $R_3'$ is independently H, OH, fluoro, chloro, bromo, $NH_2$, SH, S—R', or O—R' wherein each R' is independently a protection group or an alkyl group, wherein the alkyl group may be optionally substituted;

each ∿∿ represents independently a phosphodiester linkage, a phosphorothioate linkage, a phosphonoacetate linkage, a thiophosphonoacetate linkage, or a phosphoroamidate linkage;

each $L^a$ is independently a covalent bond or an optionally substituted, bivalent, straight or branched, saturated or unsaturated $C_1$-$C_{50}$ hydrocarbon chain, wherein one or more methylene units are optionally replaced by —O—, —S—, —N(R)—, —C(O)—, —C(S)—, —C(NR)—, —C(NOR)—, —C(NNR$_2$)—, —OC(O)—, —C(O)O—, —C(O)N(R)—, —N(R')C(O)—, —C(NR)O—, —OC(NR)—, —C(NR)NR—, —N(R)C(NR)—, —N(R)C(O)N(R)—, —N(R)C(O)O—, —OC(O)N(R)—, —N(R)C(O)S—, —SC(O)N(R)—, —N(R)C(NR)N(R)—, —SO$_2$—, —SO$_2$N(R)—, —N(R)SO$_2$—, —OP(O)(OH)O—, —OP(S)(OH)O—, —OP(S)(SH)O—, —OP(S)(COOH)O—, —OP(O)(COOH)O—, —OP(O)(NR$_2$)O—, or -Cy-;

each R is independently hydrogen or an optionally substituted group selected from $C_{1-6}$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur;

Cy is an optionally substituted, mono- or multicyclic, 3- to 20-membered, bivalent ring system, wherein the ring system is fully or partially saturated, fully or partially unsaturated, or aromatic, and wherein the ring system contains 0-6 heteroatoms selected from the group consisting of O, N, and S; and each g is 0, 1, 2, 3, 4, or 5.

300. The oligonucleotide of any one of embodiments 297-299, wherein $(N)_c$ comprises a 3' region that comprises at least a portion of a repeat from a Type II CRISPR system.

301. The oligonucleotide of any one of embodiments 297-300, wherein $(N)_t$ includes a 3' region that comprises one or more stem-loop structures.

302. A composition comprising an intermediate with an annealed duplex for synthesizing a unimolecular guide molecule for a Type II CRISPR system, wherein the intermediate is of formula $B_3$-ix or $B_2$-ix:

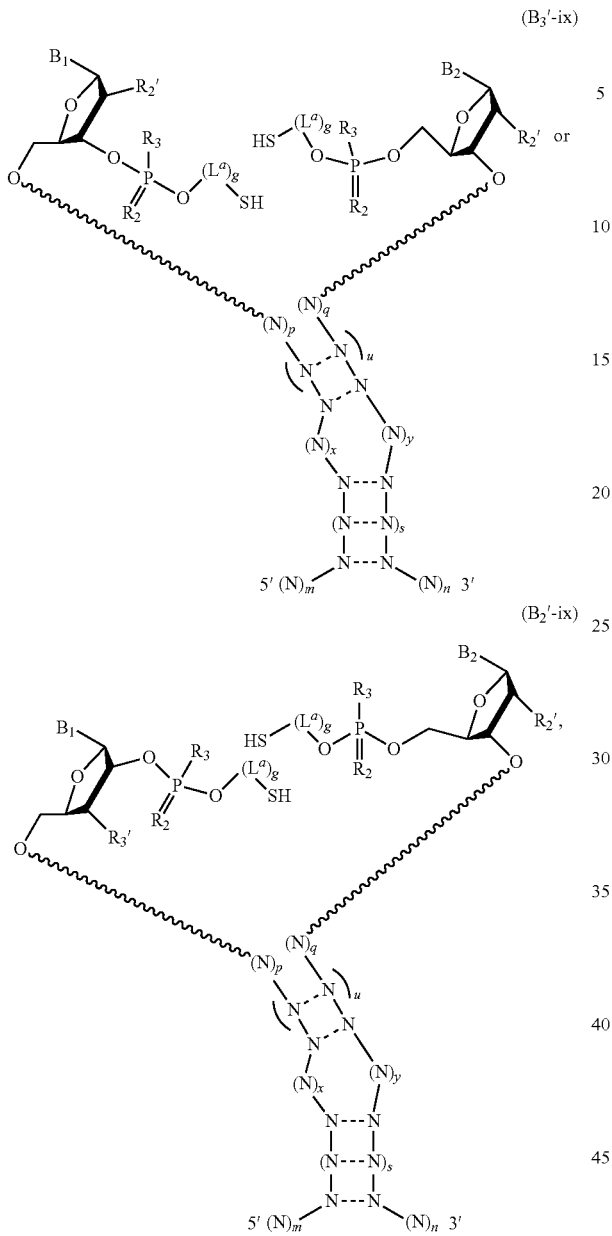

(B₃'-ix)

(B₂'-ix)

wherein:

B₁ and B₂ are each independently a nucleobase;

each of $R_2'$ and $R_3'$ is independently H, OH, fluoro, chloro, bromo, NH₂, SH, S—R', or O—R' wherein each R' is independently a protection group or an alkyl group, wherein the alkyl group may be optionally substituted;

each ∿∿∿ represents independently a phosphodiester linkage, a phosphorothioate linkage, a phosphonoacetate linkage, a thiophosphonoacetate linkage, or a phosphoroamidate linkage;

each $L^a$ is independently a covalent bond or an optionally substituted, bivalent, straight or branched, saturated or unsaturated $C_1$-$C_{50}$ hydrocarbon chain, wherein one or more methylene units are optionally replaced by —O—, —S—, —N(R)—, —C(O)—, —C(S)—, —C(NR)—, —C(NOR)—, —C(NNR₂)—, —OC(O)—, —C(O)O—, —C(O)N(R)—, —N(R')C(O)—, —C(NR)O—, —OC(NR)—, —C(NR)NR—, —N(R)C(NR)—, —N(R)C(O)N(R)—, —N(R)C(O)O—, —OC(O)N(R)—, —N(R)C(O)S—, —SC(O)N(R)—, —N(R)C(NR)N(R)—, —SO₂—, —SO₂N(R)—, —N(R)SO₂—, —OP(O)(OH)O—, —OP(S)(OH)O—, —OP(S)(SH)O—, —OP(S)(COOH)O—, —OP(O)(COOH)O—, —OP(O)(NR₂)O—, or -Cy-;

each R is independently hydrogen or an optionally substituted group selected from $C_{1-6}$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur;

Cy is an optionally substituted, mono- or multicyclic, 3- to 20-membered, bivalent ring system, wherein the ring system is fully or partially saturated, fully or partially unsaturated, or aromatic, and wherein the ring system contains 0-6 heteroatoms selected from the group consisting of O, N, and S;

p and q are each independently an integer between 0 and 6, inclusive, and p+q is an integer between 0 and 6, inclusive;

u is an integer between 2 and 22, inclusive;

s is an integer between 1 and 10, inclusive;

x is an integer between 1 and 3, inclusive;

y is >x and an integer between 3 and 5, inclusive;

m is an integer 15 or greater;

n is an integer 30 or greater;

each N is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage; and each N—N independently represents two complementary nucleotides, optionally two complementary nucleotides that are hydrogen bonding base-paired.

303. The composition of embodiment 302, wherein the intermediate is of formula $C_3'$-ix or $C_2'$-ix:

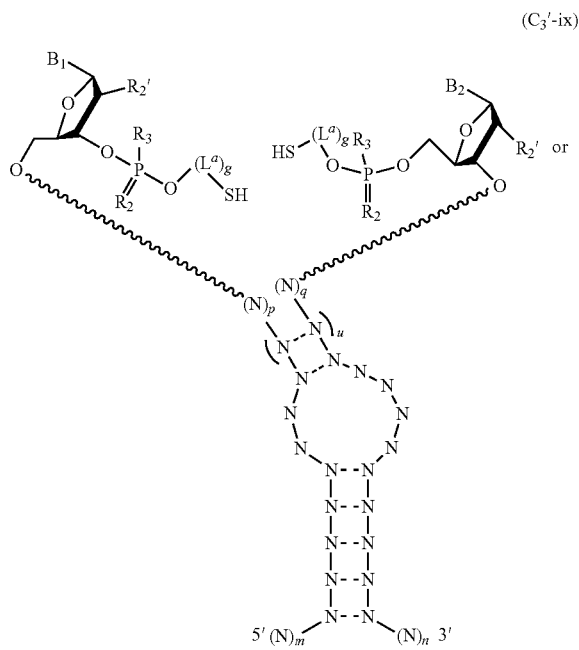

(C₃'-ix)

393
-continued
(C₂′-ix)
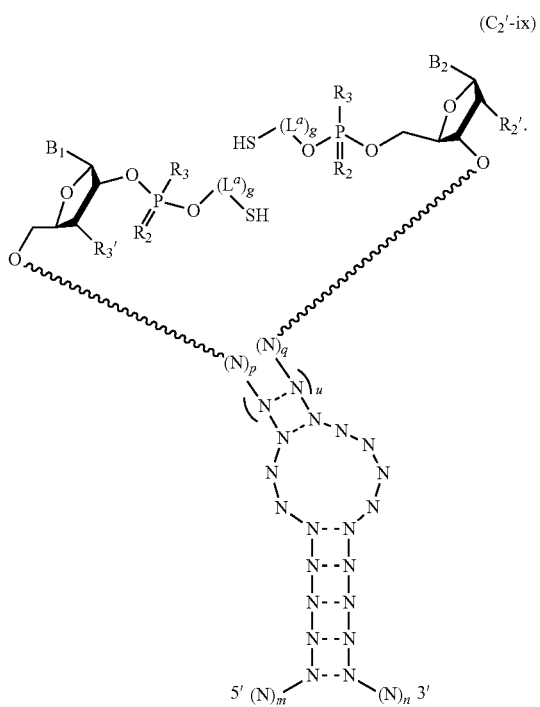
304. The composition of embodiment 302, wherein the intermediate is of formula $D_{3'}$-ix or $D_{2'}$-ix:
(D₃′-ix)
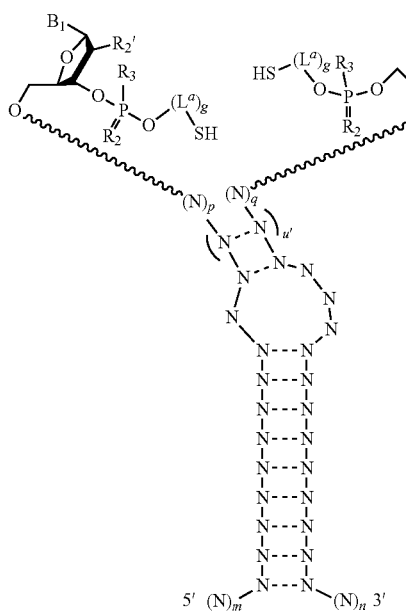
394
-continued
(D₂′-ix)
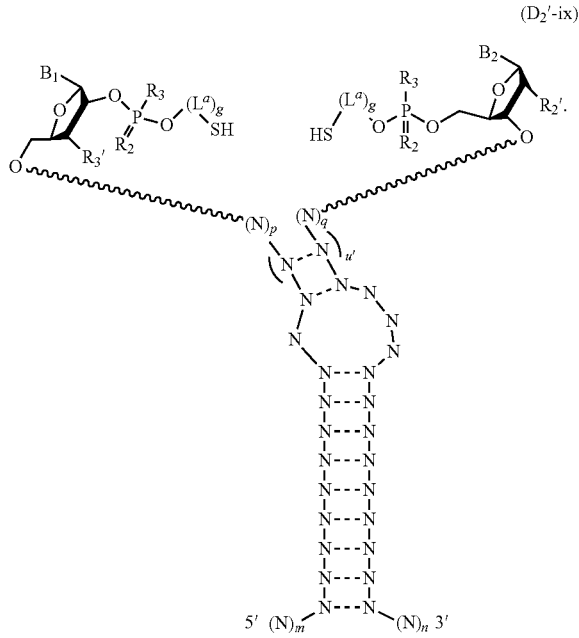
305. A composition comprising an intermediate with an annealed duplex for synthesizing a unimolecular guide molecule for a Type II CRISPR system, wherein the intermediate is of formula $B_{3'}$-x, $B_{2'}$-x, $B_{3'}$-xi, or $B_{2'}$-xi:
(B₃′-x)
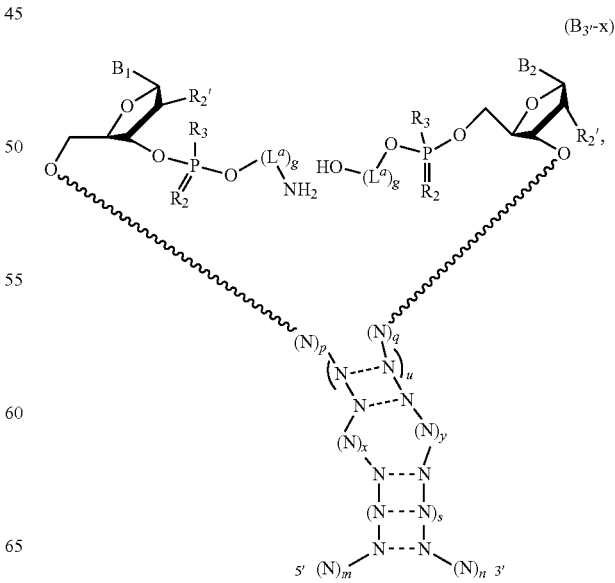

-continued (B$_{2'}$-x)

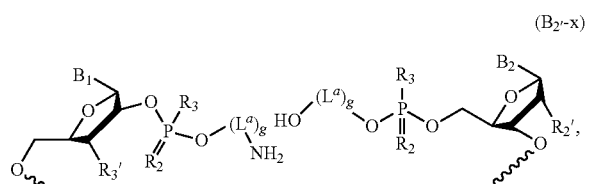
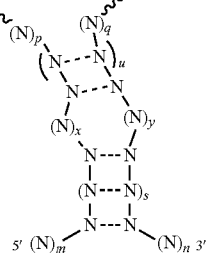

(B$_{3'}$-xi)

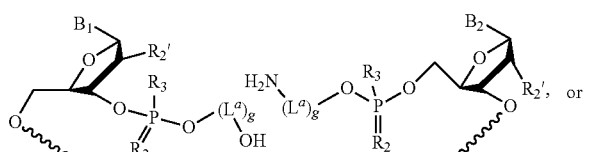
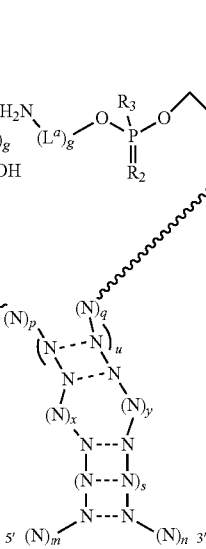

(B$_{2'}$-xi)

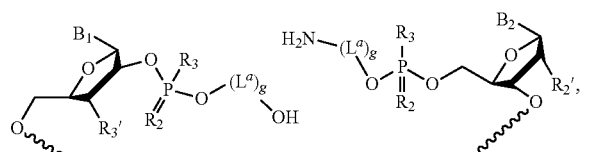
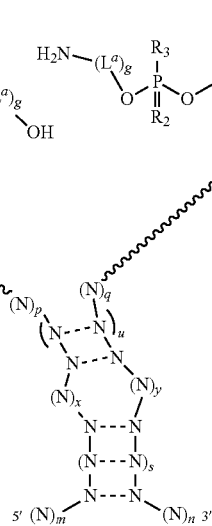

wherein:

B$_1$ and B$_2$ are each independently a nucleobase;

each of R$_2$' and R$_3$' is independently H, OH, fluoro, chloro, bromo, NH$_2$, SH, S—R', or O—R' wherein each R' is independently a protection group or an alkyl group, wherein the alkyl group may be optionally substituted;

each ∿ represents independently a phosphodiester linkage, a phosphorothioate linkage, a phosphonoacetate linkage, a thiophosphonoacetate linkage, or a phosphoroamidate linkage;

each L$^a$ is independently a covalent bond or an optionally substituted, bivalent, straight or branched, saturated or unsaturated C$_1$-C$_{50}$ hydrocarbon chain, wherein one or more methylene units are optionally replaced by —O—, —S—, —N(R)—, —C(O)—, —C(S)—, —C(NR)—, —C(NOR)—, —C(NNR$_2$)—, —OC(O)—, —C(O)O—, —C(O)N(R)—, —N(R')C(O)—, —C(NR)O—, —OC(NR)—, —C(NR)NR—, —N(R)C(NR)—, —N(R)C(O)N(R)—, —N(R)C(O)O—, —OC(O)N(R)—, —N(R)C(O)S—, —SC(O)N(R)—, —N(R)C(NR)N(R)—, —SO$_2$—, —SO$_2$N(R)—, —N(R)SO$_2$—, —OP(O)(OH)O—, —OP(S)(OH)O—, —OP(S)(SH)O—, —OP(S)(COOH)O—, —OP(O)(COOH)O—, —OP(O)(NR$_2$)O—, or -Cy-;

each R is independently hydrogen or an optionally substituted group selected from C$_{1-6}$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur;

Cy is an optionally substituted, mono- or multicyclic, 3- to 20-membered, bivalent ring system, wherein the ring system is fully or partially saturated, fully or partially unsaturated, or aromatic, and wherein the ring system contains 0-6 heteroatoms selected from the group consisting of O, N, and S;

p and q are each independently an integer between 0 and 6, inclusive, and p+q is an integer between 0 and 6, inclusive;

u is an integer between 2 and 22, inclusive;

s is an integer between 1 and 10, inclusive;

x is an integer between 1 and 3, inclusive;

y is >x and an integer between 3 and 5, inclusive;

m is an integer 15 or greater;

n is an integer 30 or greater;

each N is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage; and each N—N independently represents two complementary nucleotides, optionally two complementary nucleotides that are hydrogen bonding base-paired.

306. The composition of embodiment 305, wherein the intermediate is of formula C$_{3'}$-x, C$_{2'}$-x, C$_{3'}$-xi, or C$_{2'}$-xi:

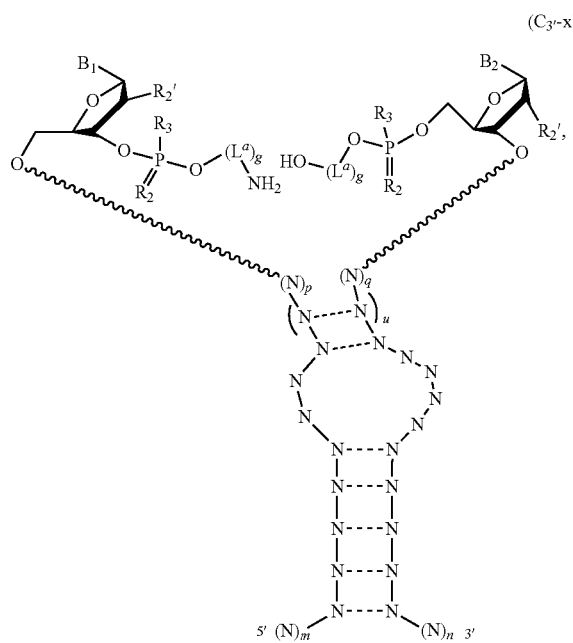
(C3'-x)
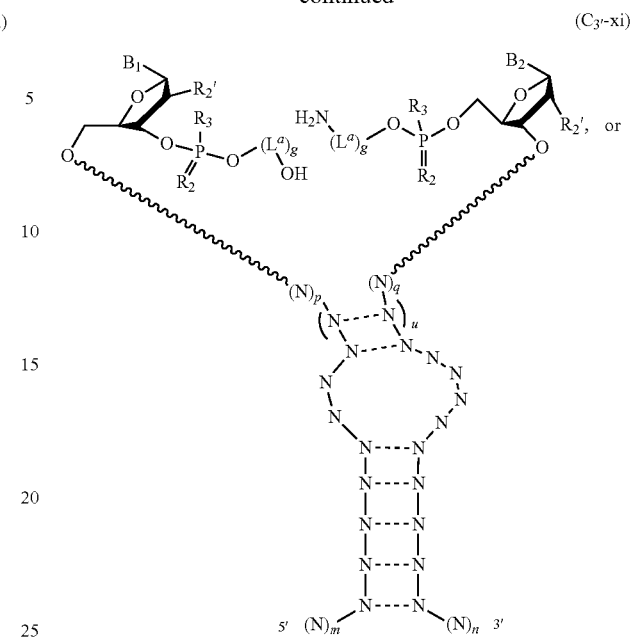
(C3'-xi), or
-continued
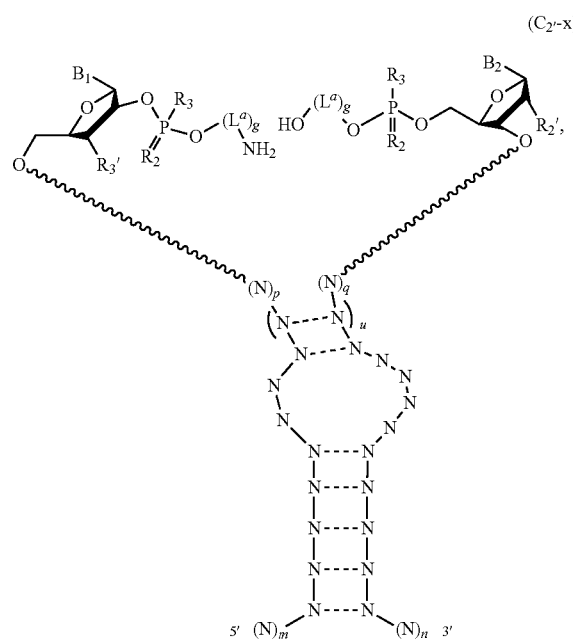
(C2'-x)
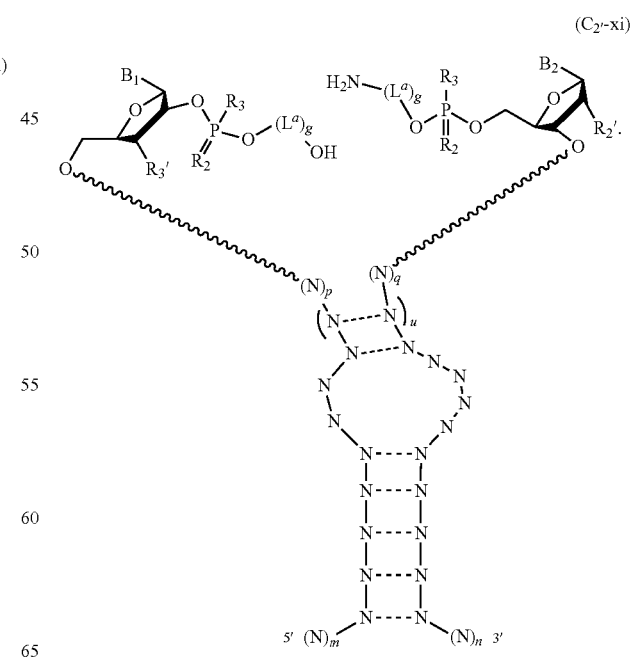
(C2'-xi).

307. The composition of embodiment 305, wherein the intermediate is of formula D$_{3'}$-x, D$_{2'}$-x, D$_{3'}$-xi, or D$_{2'}$-xi:
(D$_{3'}$-x)
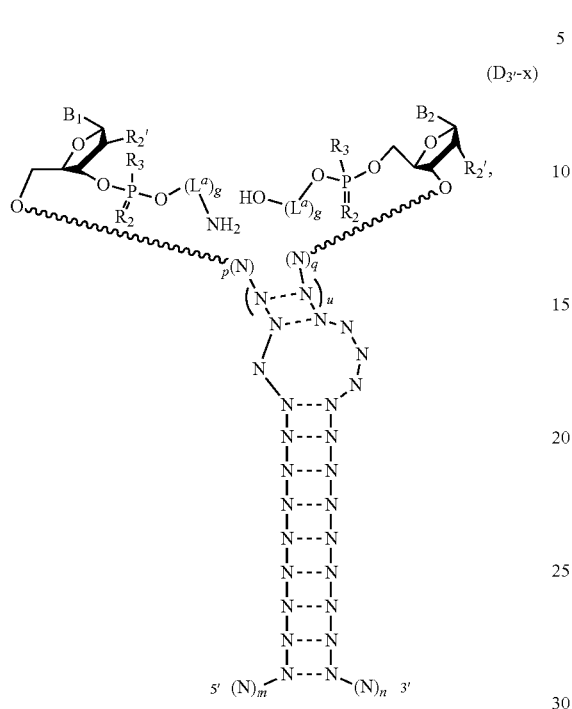
(D$_{2'}$-x)
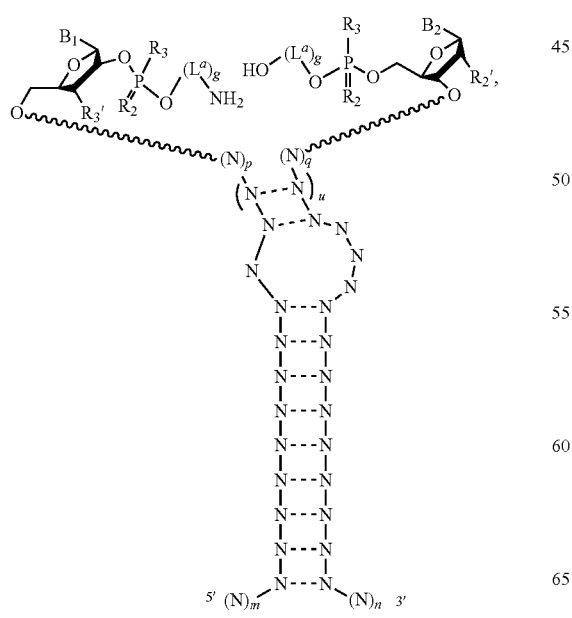
(D$_{3'}$-xi)
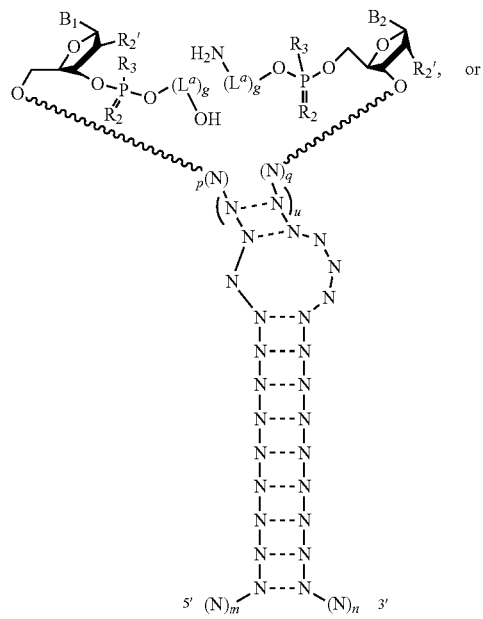
or
(D$_{2'}$-xi)
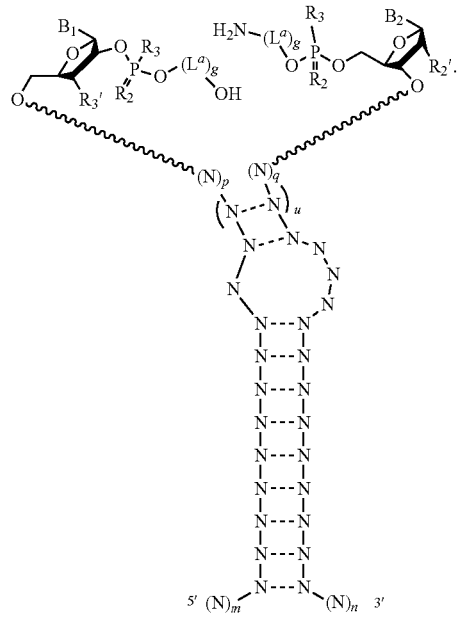
308. A composition comprising an intermediate with an annealed duplex for synthesizing a unimolecular guide molecule for a Type II CRISPR system, wherein the intermediate is of formula B$_{3'}$-xii, B$_{2'}$-xii, B$_{3'}$-xiii, or B$_{2'}$-xiii:

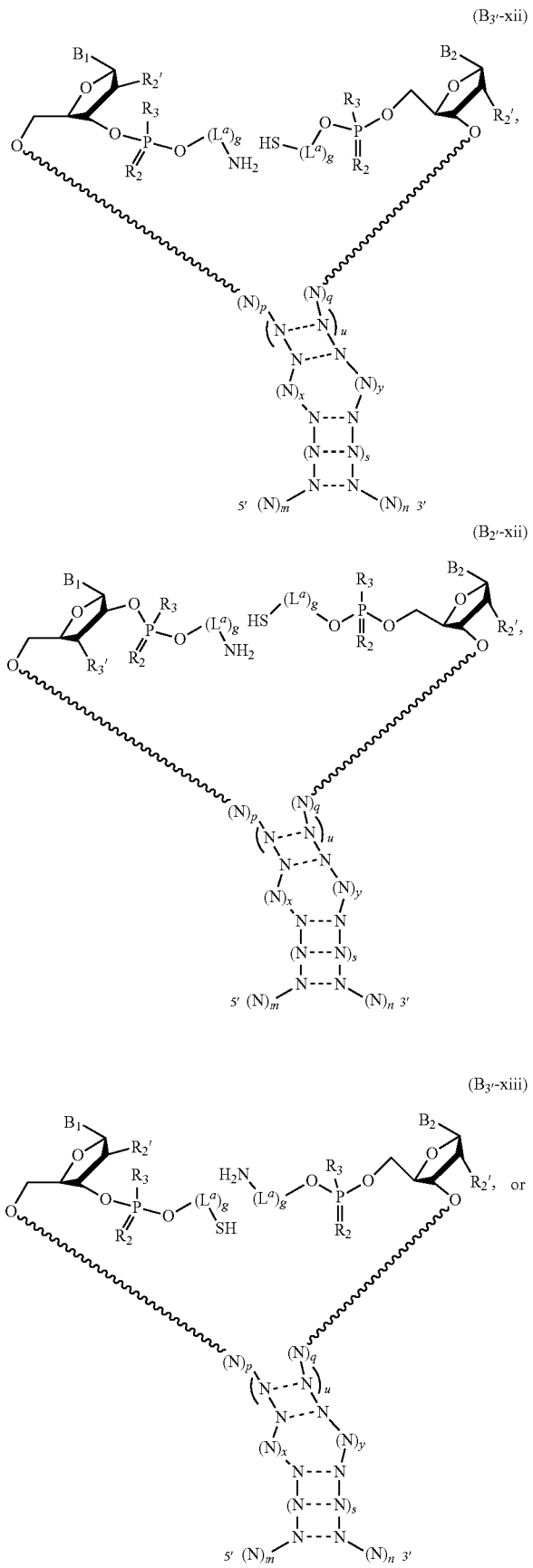

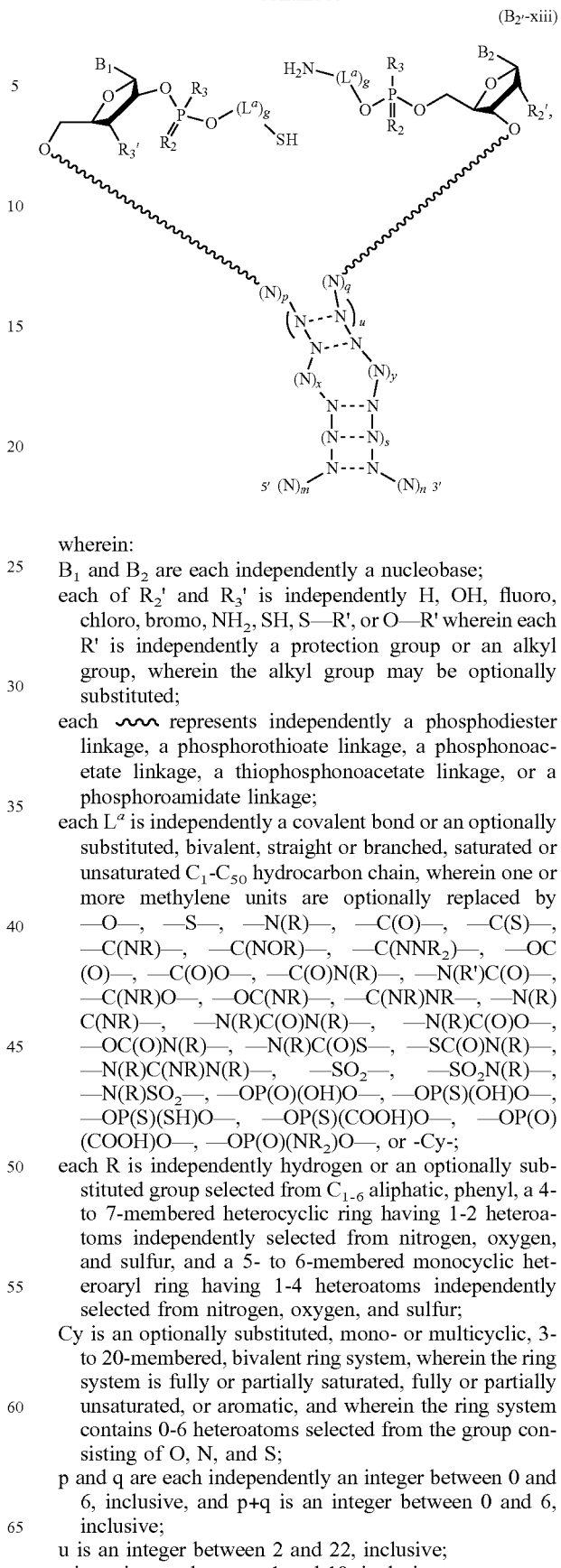

wherein:

B₁ and B₂ are each independently a nucleobase;

each of $R_2'$ and $R_3'$ is independently H, OH, fluoro, chloro, bromo, NH₂, SH, S—R', or O—R' wherein each R' is independently a protection group or an alkyl group, wherein the alkyl group may be optionally substituted;

each ∿∿ represents independently a phosphodiester linkage, a phosphorothioate linkage, a phosphonoacetate linkage, a thiophosphonoacetate linkage, or a phosphoroamidate linkage;

each $L^a$ is independently a covalent bond or an optionally substituted, bivalent, straight or branched, saturated or unsaturated $C_1$-$C_{50}$ hydrocarbon chain, wherein one or more methylene units are optionally replaced by —O—, —S—, —N(R)—, —C(O)—, —C(S)—, —C(NR)—, —C(NOR)—, —C(NNR₂)—, —OC(O)—, —C(O)O—, —C(O)N(R)—, —N(R')C(O)—, —C(NR)O—, —OC(NR)—, —C(NR)NR—, —N(R)C(NR)—, —N(R)C(O)N(R)—, —N(R)C(O)O—, —OC(O)N(R)—, —N(R)C(O)S—, —SC(O)N(R)—, —N(R)C(NR)N(R)—, —SO₂—, —SO₂N(R)—, —N(R)SO₂—, —OP(O)(OH)O—, —OP(S)(OH)O—, —OP(S)(SH)O—, —OP(S)(COOH)O—, —OP(O)(COOH)O—, —OP(O)(NR₂)O—, or -Cy-;

each R is independently hydrogen or an optionally substituted group selected from $C_{1-6}$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur;

Cy is an optionally substituted, mono- or multicyclic, 3- to 20-membered, bivalent ring system, wherein the ring system is fully or partially saturated, fully or partially unsaturated, or aromatic, and wherein the ring system contains 0-6 heteroatoms selected from the group consisting of O, N, and S;

p and q are each independently an integer between 0 and 6, inclusive, and p+q is an integer between 0 and 6, inclusive;

u is an integer between 2 and 22, inclusive;

s is an integer between 1 and 10, inclusive;

x is an integer between 1 and 3, inclusive;
y is >x and an integer between 3 and 5, inclusive;
m is an integer 15 or greater;
n is an integer 30 or greater;
each N is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage; and
each N—N independently represents two complementary nucleotides, optionally two complementary nucleotides that are hydrogen bonding base-paired.

309. The composition of embodiment 308, wherein the intermediate is of formula $C_{3'}$-xii, $C_{2'}$-xii, $C_{3'}$-xiii, or $C_{2'}$-xiii:

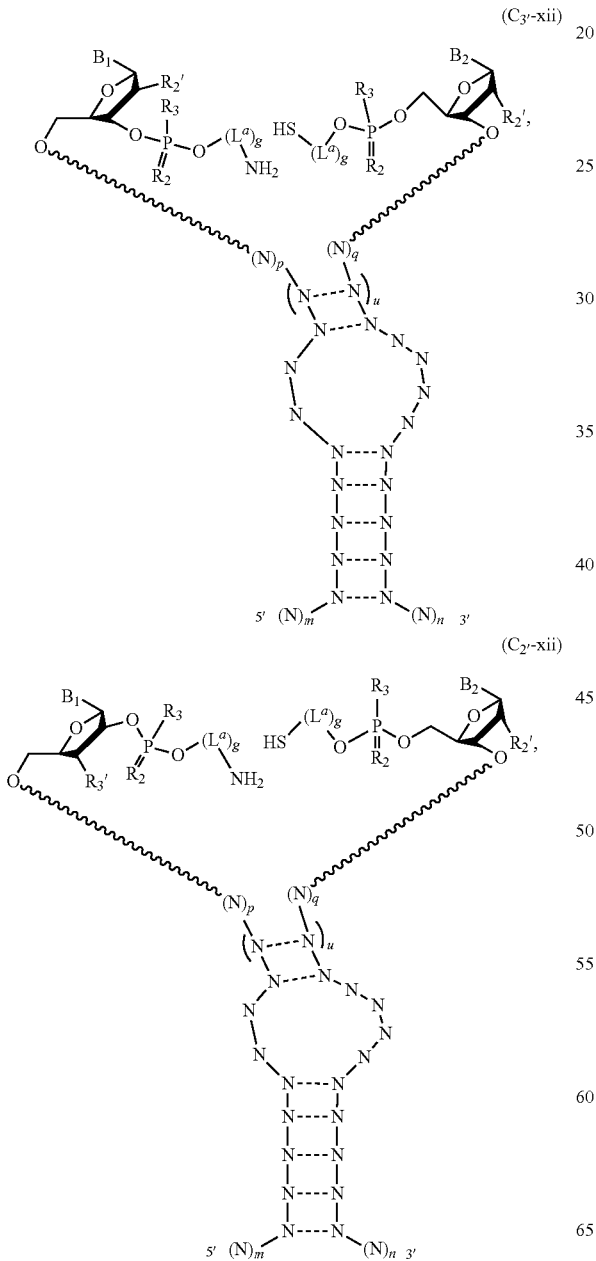

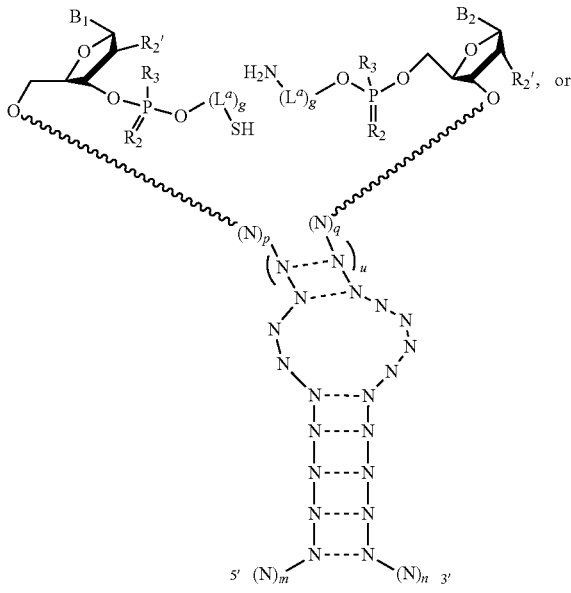

-continued

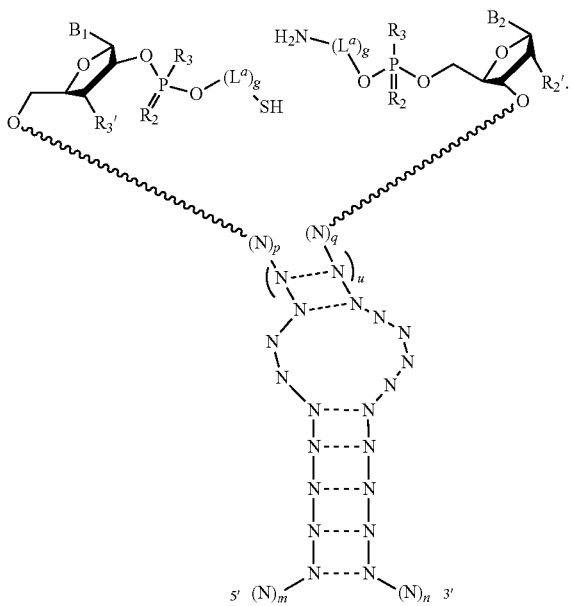

310. The composition of embodiment 309, wherein the intermediate is of formula $D_{3'}$-xii, $D_{2'}$-xii, $D_{3'}$-xiii, or $D_{2'}$-xiii:

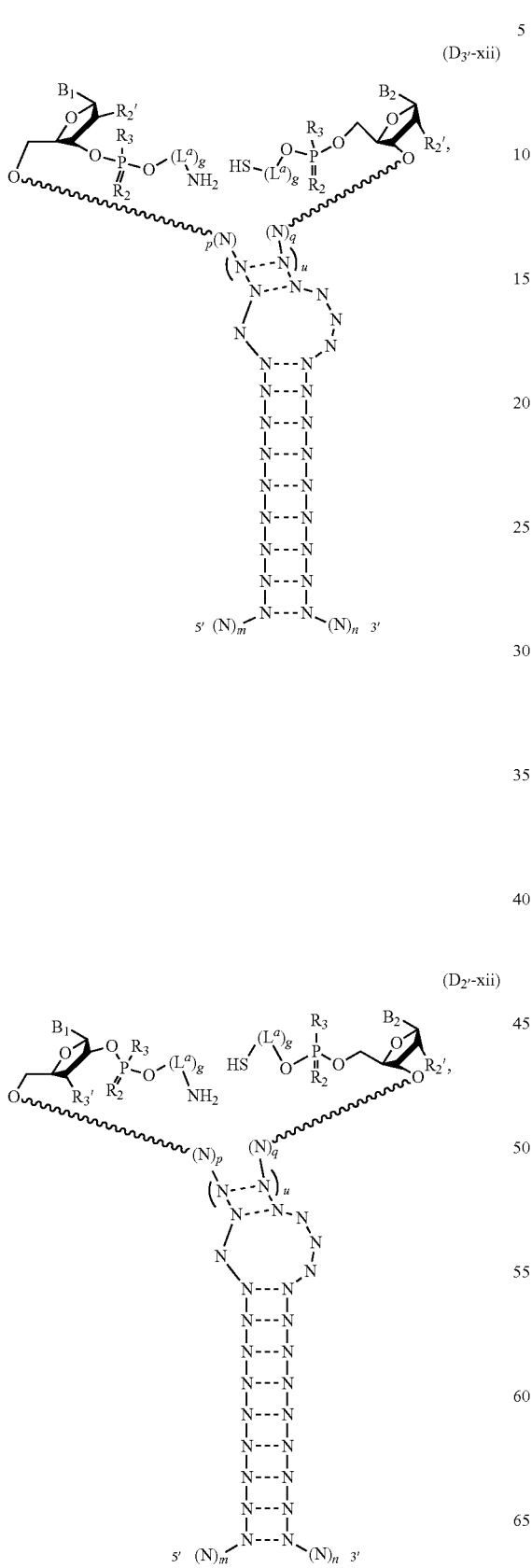

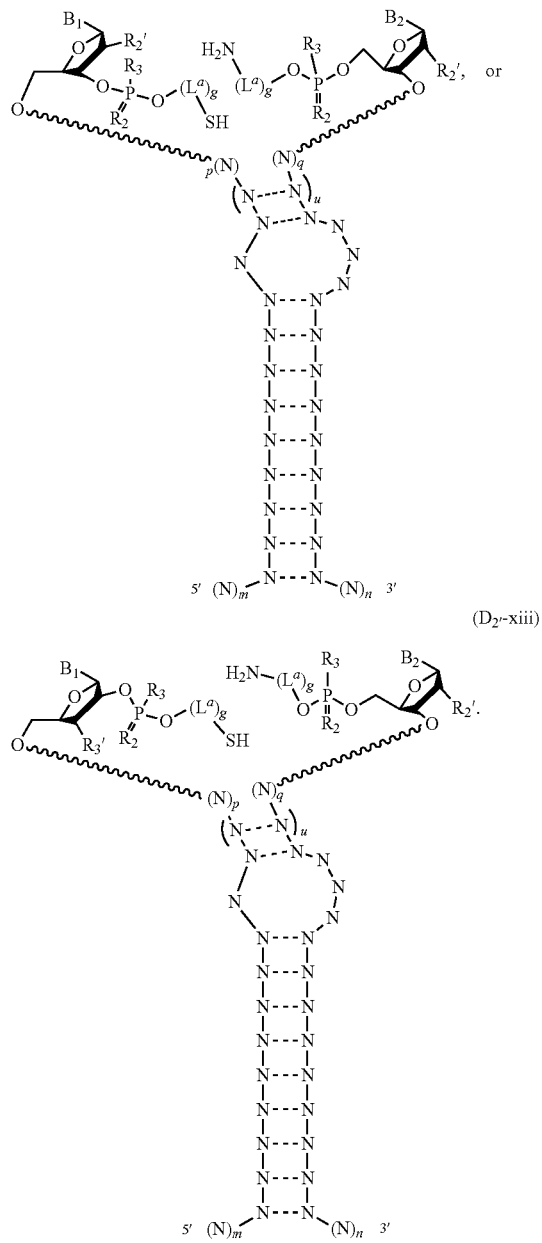

311. The composition of any one of embodiments 302-310, wherein p and q are each 0.
312. The composition of any one of embodiments 302-311, wherein u is an integer between 3 and 22, inclusive.
313. The composition of any one of embodiments 301-312, wherein $(N)_m$ includes a 5' region that comprises a targeting domain that is fully or partially complementary to a target domain within a target sequence.
314. The composition of any one of embodiments 301-313, wherein $(N)_n$ includes a 3' region that comprises one or more stem-loop structures.
315. A method of altering a nucleic acid in a cell or subject comprising administering to the subject a guide molecule of embodiments 250-278 or a composition of embodiments 279-289 or 302-314.

EXAMPLES

Certain principles of the present disclosure are illustrated by the non-limiting examples that follow.

Example 1: Exemplary Process for Conjugation of Amine-Functionalized Guide Molecule Fragments with Disuccinimidyl Carbonate As illustrated in FIG. 1A, a first 5' guide molecule fragment (e.g., a 34mer) was synthesized with a $(C_6)$—$NH_2$ linker at the 3' end, and a second 3' guide molecule fragment (e.g., a 66mer) was synthesized with a TEG-$NH_2$ linker at the 5' end. The two guide molecule fragments were mixed at a molar ratio of 1:1 in a pH 8.5 buffer comprising 10 mM sodium borate, 150 mM NaCl, and 5 mM $MgCl_2$. The resulting guide molecule concentration was about 50 to 100 µM. The two guide molecule fragments were annealed, followed by addition of disuccinimidyl carbonate (DSC) in DMF (2.5 mM final concentration). The reaction mixture was vortexed briefly and then mixed at room temperature for 1 hour, followed by removal of excess disuccinimidyl carbonate, and anion-exchange HPLC purification.

Figure 2A:
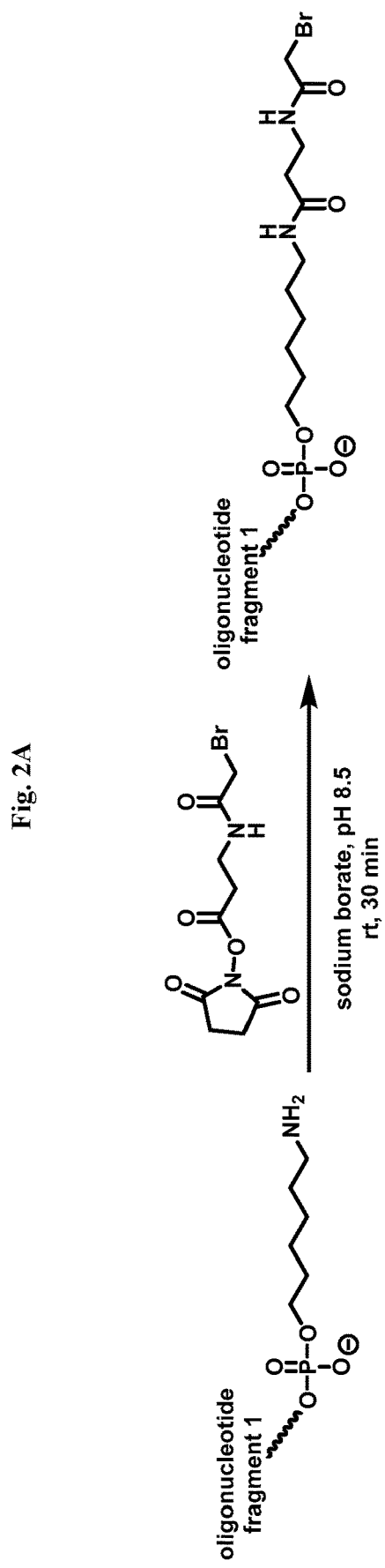
FIG. 2A depicts a step in an exemplary cross-linking reaction process according to certain embodiments of this disclosure.

Example 2: Exemplary Process for Conjugation of Thiol-Functionalized Guide Molecule Fragment to Bromoacetyl-Functionalized Guide Molecule Fragment As illustrated in FIG. 2A, a first 5' guide molecule fragment (e.g., a 34mer) was synthesized with a $(C_6)$—$NH_2$ linker at the 3' end. It was suspended in 100 mM borate buffer at pH 8.5. The guide molecule concentration was about 100 µM to 1 mM. 0.2 volumes of succinimidyl-3-(bromoacetamido) propionate (SBAP) in DMSO (50 equivalents) were added to the guide molecule solution. After mixing for 30 minutes at room temperature, 10 volumes of 100 mM phosphate buffer at pH 7.0 is added. The mixture was concentrated 10× or more on 10,000 MW Amicon. The mixture was further processed by (a) adding 10 volumes of water, and (b) concentrating 10× or more on 10,000 MW Amicon. Steps (a) and (b) were repeated 3 times to afford a first 5' guide molecule fragment (e.g., 34mer) with a bromoacetyl moiety at the 3' end.

Figure 2B:
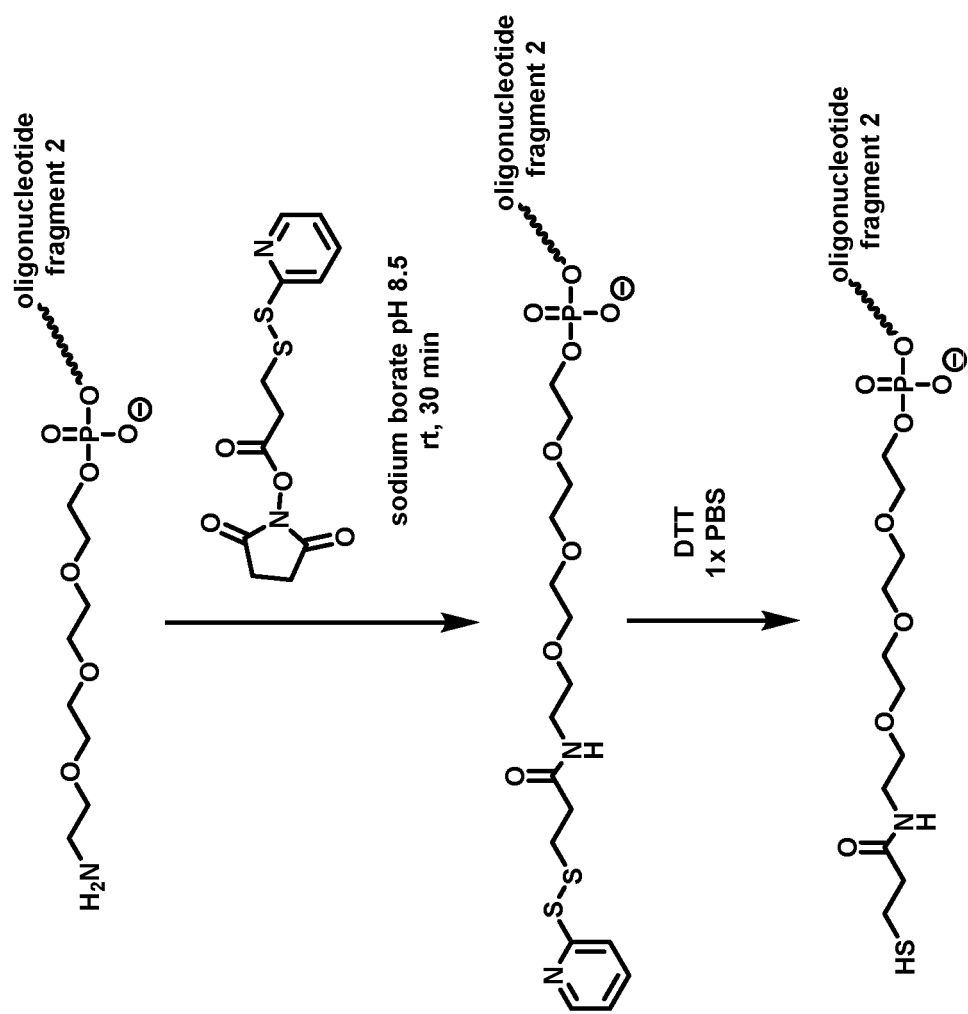
FIG. 2B depicts a step in an exemplary cross-linking reaction process according to certain embodiments of this disclosure.

As illustrated in FIG. 2B, a second 3' guide molecule fragment (e.g., a 66mer) was synthesized with a TEG-$NH_2$ linker at the 5' end. It was suspended in 100 mM borate buffer at pH 8.5 comprising 1 mM EDTA. The guide molecule concentration was about 100 µM to 1 mM. 0.2 volumes of succinimidyl-3-(2-pyridyldithio) propionate (SPDP) in DMSO (50 equivalents) were added to the guide molecule solution. After mixing for 1 hour at room temperature, 1 M dithiothreitol (DTT) was added in 1×PBS. The final concentration of DTT in the mixture was 20 mM. After mixing for 30 minutes at room temperature, 5 M NaCl was added to result in a final concentration of 0.3 M NaCl in the mixture followed by addition of 3 volumes of ethanol. The mixture was further processed by: (a) cooling to −20° C. for 15 minutes; (b) centrifuging at 17,000 g (preferably at 4° C.) for 5 minutes; (c) removing the supernatant; (d) suspending the residue in 0.3 M NaCl (sparged with argon); and (e) adding 3 volumes of ethanol. Steps (a)-(e) were repeated 3 times. The resulting pellet (i.e., second 3' guide molecule fragment with a thiol at the 5' end) was dried under vacuum.

Figure 2C:
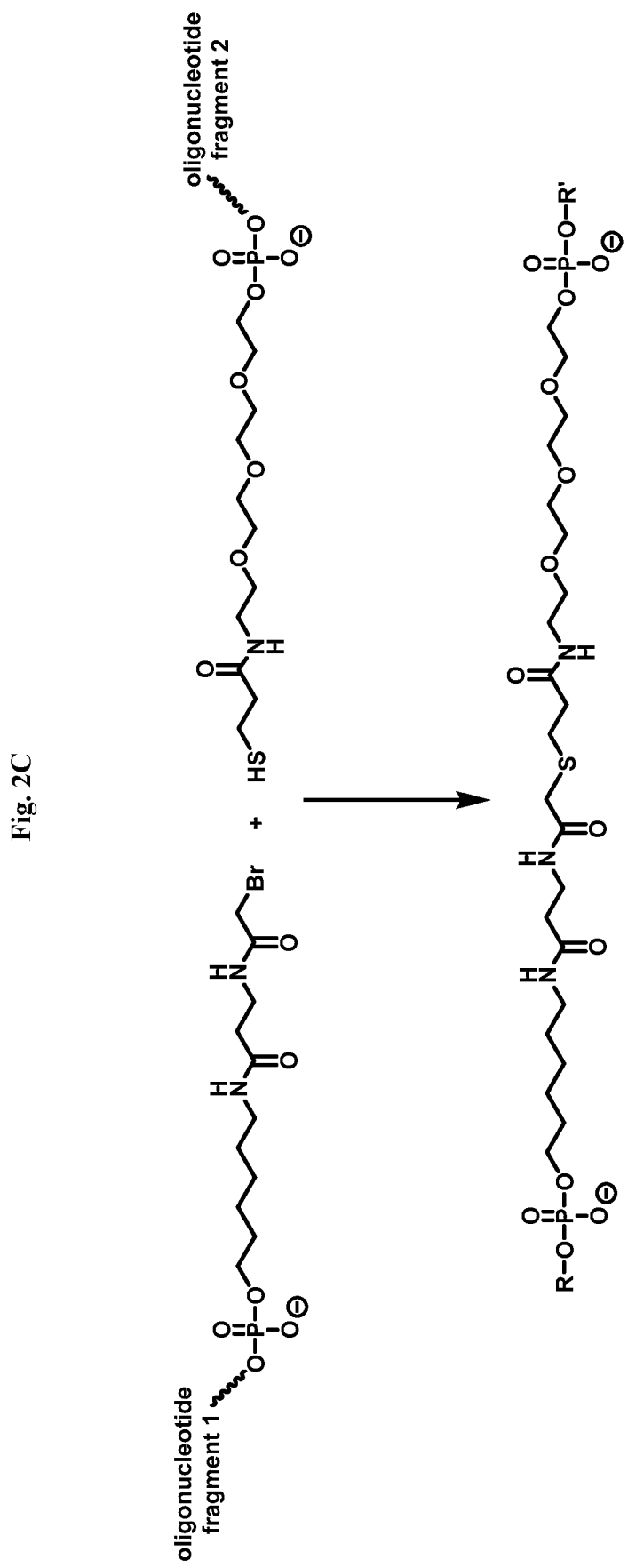
FIG. 2C depicts an additional step in the exemplary cross-linking reaction process using the reaction products from FIGS. 2A and 2B.

As illustrated in FIG. 2C, the second 3' guide molecule fragment (e.g., 66mer) with a thiol at the 5' end was suspended in 100 mM phosphate buffer at pH 8 comprising 2 mM EDTA (sparged with argon). The guide molecule concentration was about 100 µM to 1 mM. The first 5' guide molecule fragment (e.g., 34mer) with a bromoacetyl moiety at the 3' end was suspended in water (about 0.1 volumes relative to the volume of the second 3' guide molecule fragment mixture). The guide molecule concentration was about 100 µM to 1 mM. The first 5' guide molecule fragment mixture was added to the second 3' guide molecule fragment mixture (sparged with argon). The reaction mixture was mixed overnight at room temperature, followed by an anion-exchange HPLC purification.

Example 3: Exemplary Process for Conjugation of Phosphate Guide Molecule Fragments to 3' Hydroxyl Guide Molecule Fragments with Carbodiimide As illustrated in FIGS. 3A and 3B, a first 5' guide molecule fragment (e.g., a 34mer) was synthesized using standard phosphoramidite chemistry. A second 3' guide molecule fragment (e.g., a 66mer) comprising a 5'-phosphate was also synthesized. The first and second guide molecule fragments were mixed at a molar ratio of 1:1 in a coupling buffer (100 mM 2-(N-morpholino) ethanesulfonic acid (MES), pH 6, 150 mM NaCl, 5 mM $MgCl_2$, and 10 mM $ZnCl_2$). The two guide molecule fragments were annealed, followed by addition of 100 mM 1-ethyl-3-(3-dimethylaminopropyl) carbodiimide (EDC) and 90 mM imidazole. The reaction mixture was mixed at 4° C. for 1-5 days, followed by desalting and anion-exchange HPLC purification.

Example 4: Assessment of Guide Molecule Activity in HEK293T Cells

The activity of guide molecules conjugated in accordance with the process of Example 2 was assessed in HEK293T cells via a $T7E_1$ cutting assay. For clarity, all guide molecules used in this Example contained identical targeting domain sequences, and substantially similar RNA backbone sequences, as shown in Table 16, below. In the table, targeting domain sequences are denoted as degenerate sequences by "N"s, while the position of a cross-link between two guide molecule fragments is denoted by an [L].

In some embodiments, the guide molecule comprising a thioether is of sequence listed in Table 16 below, wherein [L] is a thioether linkage. In some embodiments, [L] indicates the following linkage:

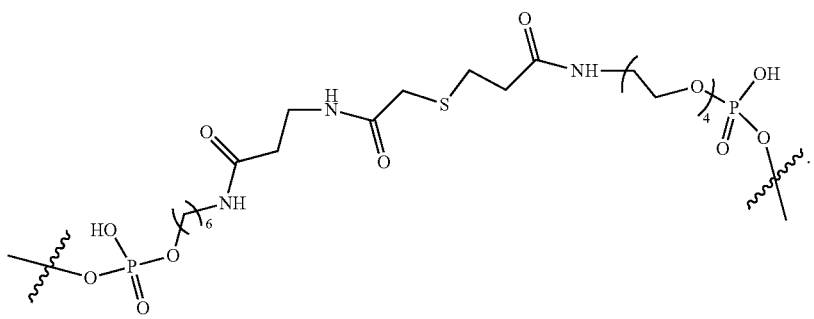

TABLE 16

| Guide molecule or guide molecule fragment | SEQ ID NO. | Sequence |
|---|---|---|
| 100mer gRNA | 32 | NNNNNNNNNNNNNNNNNNNNGUUUUAGAGCUAGAAAU AGCAAGUUAAAAUAAGGCUAGUCCGUUAUCAACUUGA AAAAGUGGCACCGAGUCGGUGCUUUU |
| 34mer 5' gRNA fragment | 33 | NNNNNNNNNNNNNNNNNNNNGUUUUAGAGCUAGA |
| 66mer 3' gRNA fragment | 34 | AAUAGCAAGUUAAAAUAAGGCUAGUCCGUUAUCAACU UGAAAAAGUGGCACCGAGUCGGUGCUUUU |
| Guide molecule or guide molecule fragment | SEQ ID NO. (Seq. A) SEQ ID NO. (Seq. B) | 5' - Seq. A - [L] - Seq. B - 3' |
| 100mer conjugated gRNA | 35 36 | NNNNNNNNNNNNNNNNNNNNGUUUUAGAGCUAGA[L] AAUAGCAAGUUAAAAUAAGGCUAGUCCGUUAUCAACU UGAAAAAGUGGCACCGAGUCGGUGCUUUU |

Figure 4:
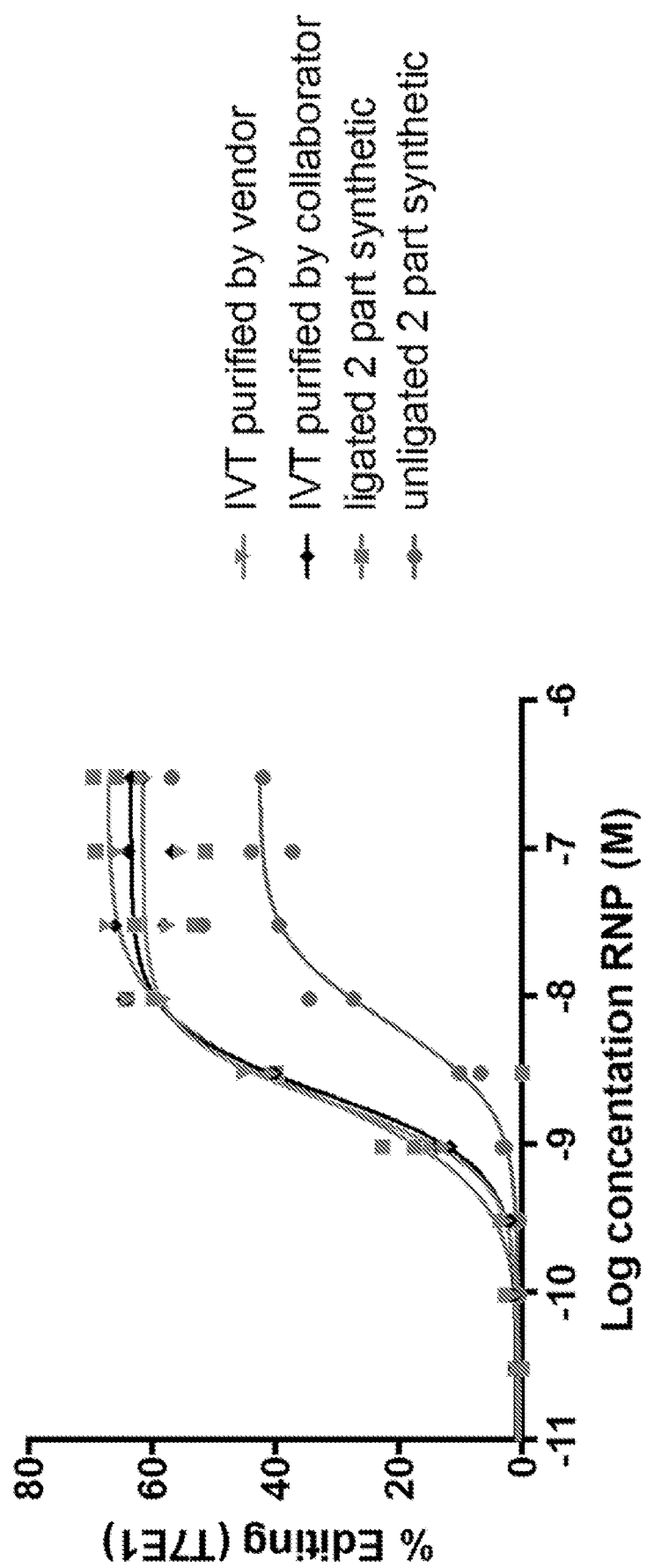
FIG. 4 shows DNA cleavage dose-response curves for synthetic unimolecular guide molecules according to certain embodiments of this disclosure as compared to unligated, annealed guide molecule fragments and guide molecules prepared by IVT obtained from a commercial vendor. DNA cleavage was assayed by T7E1 assays as described herein. As the graph shows, the conjugated guide molecule supported cleavage in HEK293 cells in a dose-dependent manner that was consistent with that observed with the unimolecular guide molecule generated by IVT or the synthetic unimolecular guide molecule. It should be noted that unconjugated annealed guide molecule fragments supported a lower level of cleavage, though in a similar dose-dependent manner.

Varying concentrations of ribonucleoprotein complexes comprising, variously, a unimolecular guide molecule generated by IVT, a synthetic unimolecular guide molecule (i.e., prepared without conjugation), or a synthetic unimolecular guide molecule conjugated by the bromoacetyl-thiol process of Example 2 were introduced into HEK293T cells by lipofection (CRISPR-Max, Thermo Fisher Scientific, Waltham, MA), and genomic DNA was harvested later. Cleavage was assessed using a standard T7E$_1$ cutting assay, using a commercial kit (Surveyor™ commercially available from Integrated DNA Systems, Coralville, Iowa). Results are presented in FIG. 4.

As the results show, the conjugated guide molecule supported cleavage in HEK293 cells in a dose-dependent manner that was consistent with that observed with the unimolecular guide molecule generated by IVT or the synthetic unimolecular guide molecule. It should be noted that unconjugated annealed guide molecule fragments supported a lower level of cleavage, though in a similar dose-dependent manner. These results suggest that guide molecules conjugated according to the methods of this disclosure support high levels of DNA cleavage in substantially the same manner as unimolecular guide molecules generated by IVT or synthetic unimolecular guide molecules.

Example 5: Evaluation of Guide Molecule Purity by Gel Electrophoresis and Mass Spectrometry The purity of a composition of guide molecules conjugated with a urea linker according to the process of Example 1 was compared by total ion current chromatography and mass spectrometry with the purity of a composition of commercially prepared synthetic unimolecular guide molecules (i.e., prepared without conjugation). 100 pmol of an analyte was injected for mass analysis. The analysis was achieved by LC-MS on a Bruker microTOF-QII mass spectrometer equipped with a Waters ACQUITY UPLC system. A ThermoDNAPac C18 column was used for separation. Results are shown in FIG. 5.

Figure 5A:
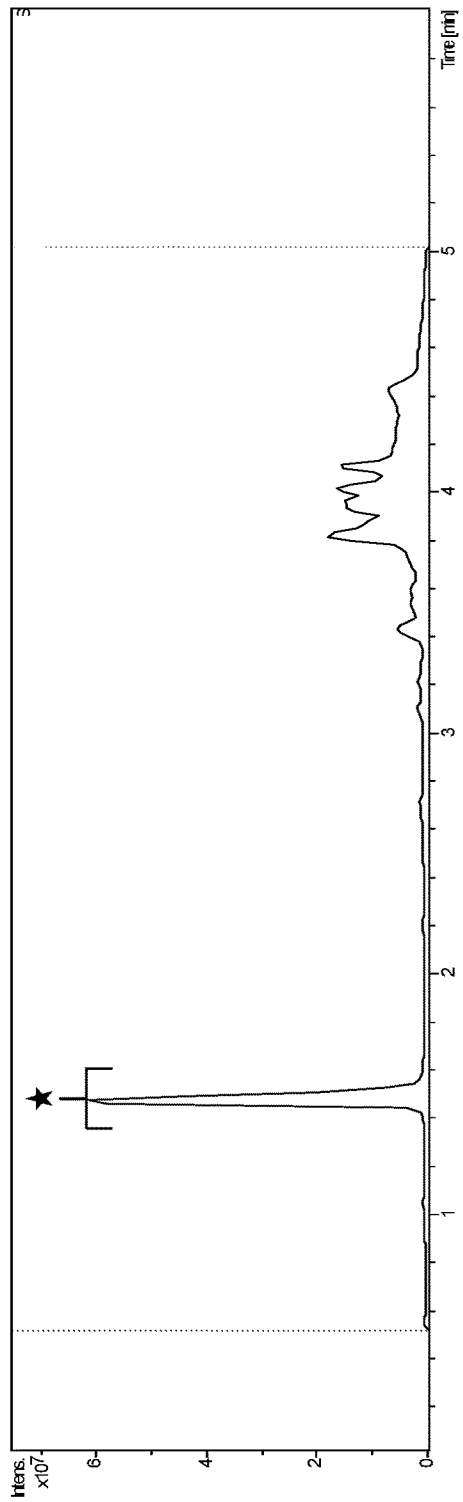
FIG. 5A shows a representative ion chromatograph and FIG. 5B shows a deconvoluted mass spectrum of an ion-exchange purified guide molecule conjugated with a urea linker according to the process of Example 1.
Figure 5B:
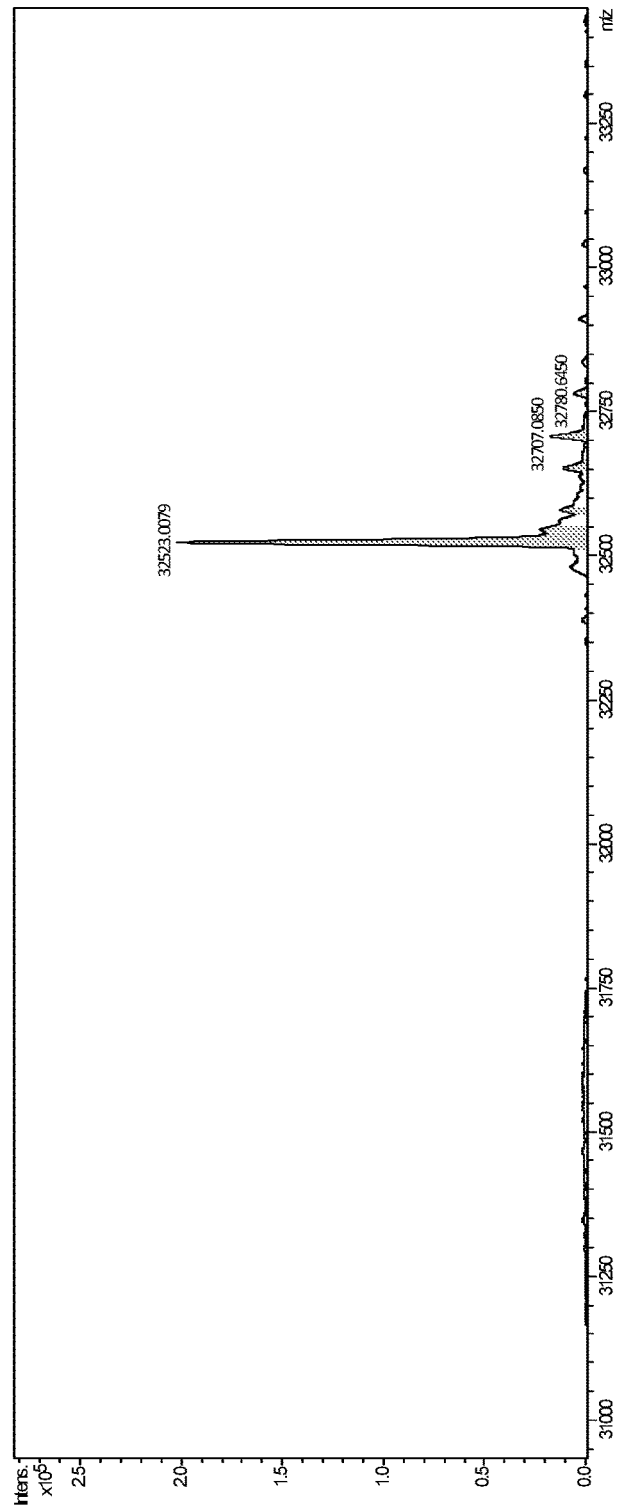
Figure 5C:
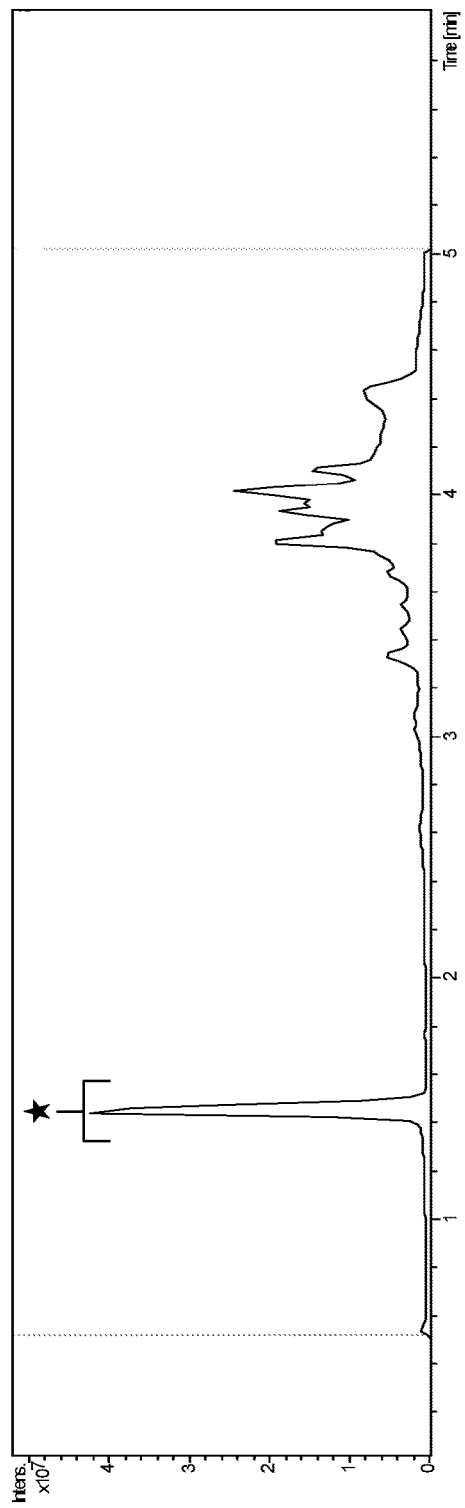
FIG. 5C shows a representative ion chromatograph and FIG. 5D shows a deconvoluted mass spectrum of a commercially prepared synthetic unimolecular guide molecule. Mass spectra were assessed for the highlighted peaks in the ion chromatographs.
Figure 5D:
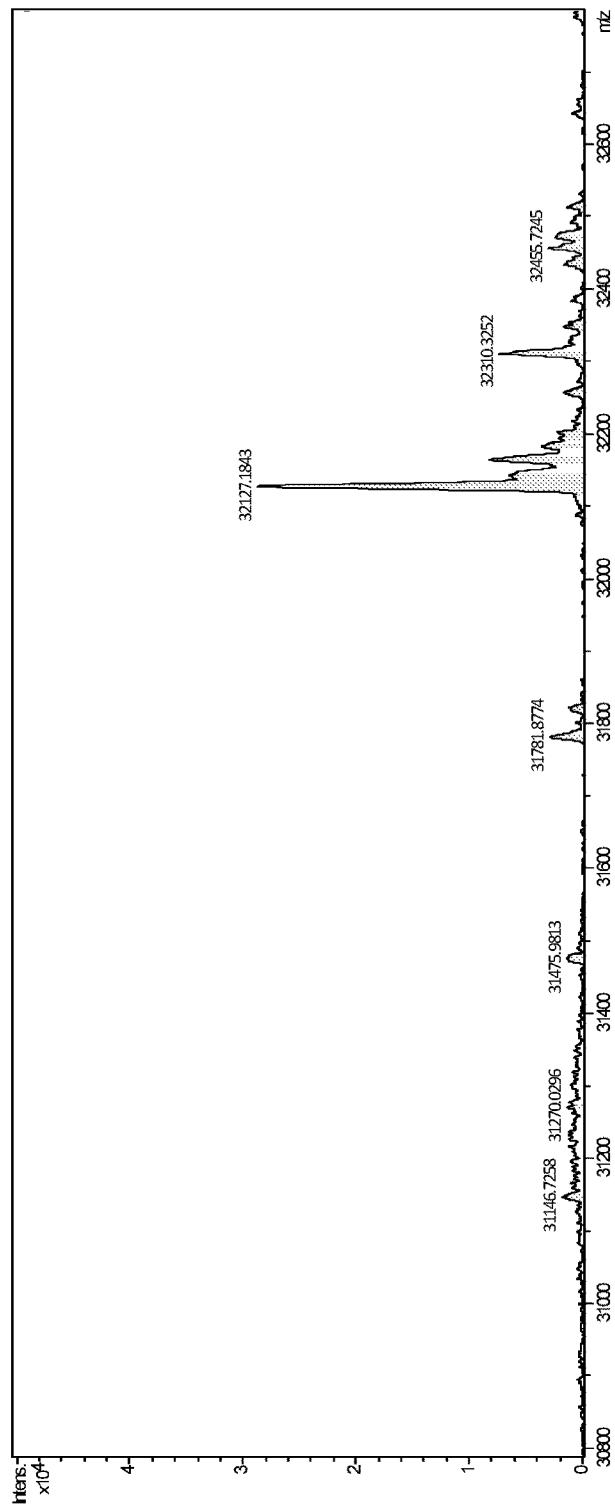

FIG. 5A shows a representative ion chromatograph and FIG. 5B shows a deconvoluted mass spectrum of an ion-exchange purified guide molecule conjugated with a urea linker according to the process of Example 1. FIG. 5C shows a representative ion chromatograph and FIG. 5D shows a deconvoluted mass spectrum of a commercially prepared synthetic unimolecular guide molecule. Mass spectra were assessed for the highlighted peaks in the ion chromatographs. FIG. 5E shows expanded versions of the mass spectra. The mass spectrum for the commercially prepared synthetic unimolecular guide molecule is on the left side (34% purity by total mass) while the mass spectrum for the guide molecule conjugated with a urea linker according to the process of Example 1 is on the right side (72% purity by total mass).

Example 6: Evaluation of Guide Molecule Purity by Sequence Analysis

The purity of a composition of guide molecules conjugated with a urea linkage, as described in Example 1, was compared with the purity of a composition of commercially prepared synthetic unimolecular guide molecules (i.e., prepared without conjugation) and a composition of guide molecules conjugated with a thioether linkage, as described in Example 2. All compositions of guide molecules were based on the same predetermined guide molecule sequence.

Figure 6A:
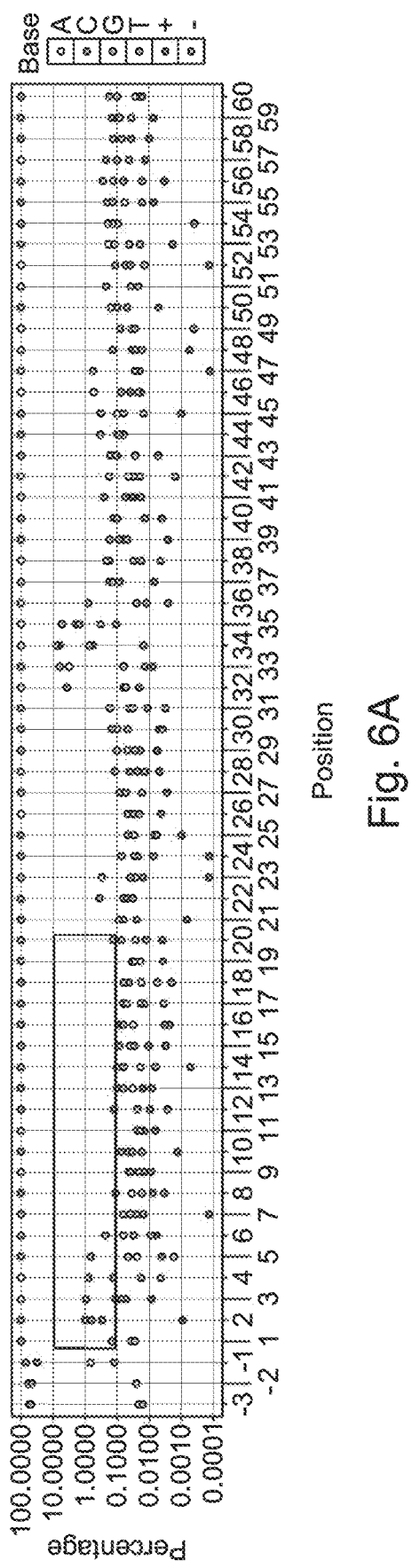
FIG. 6A shows a plot depicting the frequency with which individual bases and length variances occurred at each position from the 5' end of complementary DNAs (cDNAs) generated from synthetic unimolecular guide molecules that included a urea linkage.
Figure 6B:
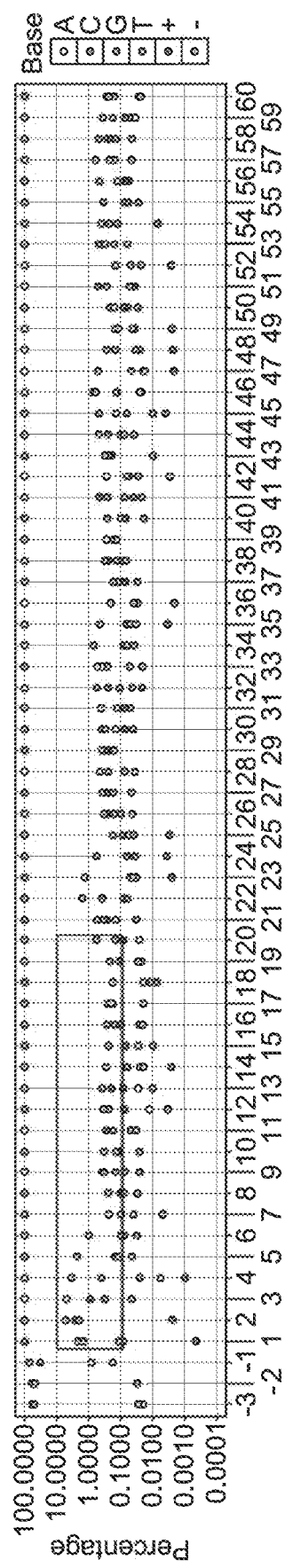
FIG. 6B shows a plot depicting the frequency with which individual bases and length variances occurred at each position from the 5' end of cDNAs generated from commercially prepared synthetic unimolecular guide molecules (i.e., prepared without conjugation). Boxes surround the 20 bp targeting domain of the guide molecule.

FIG. 6A shows a plot depicting the frequency with which individual bases and length variances occurred at each position from the 5' end of complementary DNAs (cDNAs) generated from synthetic unimolecular guide molecules that included a urea linkage, and FIG. 6B shows a plot depicting the frequency with which individual bases and length variances occurred at each position from the 5' end of cDNAs generated from commercially prepared synthetic unimolecular guide molecules (i.e., prepared without conjugation). Boxes surround the 20 bp targeting domain of the guide molecule. In this example, guide molecules that included the urea linkage resulted in greater sequence fidelity in the targeting domain (i.e., less than 1% of guide molecules included a deletion at any given position, and less than 1% of guide molecules included a substitution at any given position) compared to the guide molecules from the commercially prepared synthetic unimolecular guide molecules (in which less than 10% of guide molecules included a deletion at any given position, and less than 5% included a substitution at any given position).

Figure 6C:
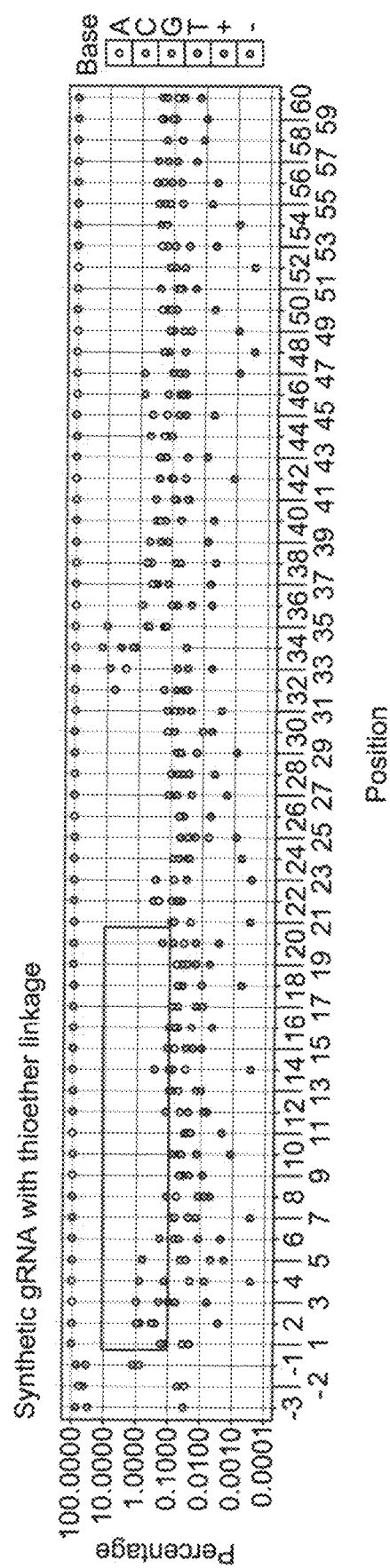
FIG. 6C shows a plot depicting the frequency with which individual bases and length variances occurred at each position from the 5' end of cDNAs generated from synthetic unimolecular guide molecules that included a thioether linkage.

FIG. 6C shows a plot depicting the frequency with which individual bases and length variances occurred at each position from the 5' end of cDNAs generated from synthetic unimolecular guide molecules that included the thioether linkage. As shown in FIG. 6C, high levels of 5' sequence fidelity were seen, demonstrating production of compositions of guide molecules with a high level of sequence fidelity and purity. The alignments in FIG. 6A (urea linkage) and FIG. 6C (thioether linkage) also showed a region of relatively high frequency of mismatches/indels at the linkage site (position 34). These data suggest that guide molecules synthesized by the methods of this disclosure demonstrate decreased frequency of deletions and substitutions as compared to commercially available guide molecules.

Figure 7A:
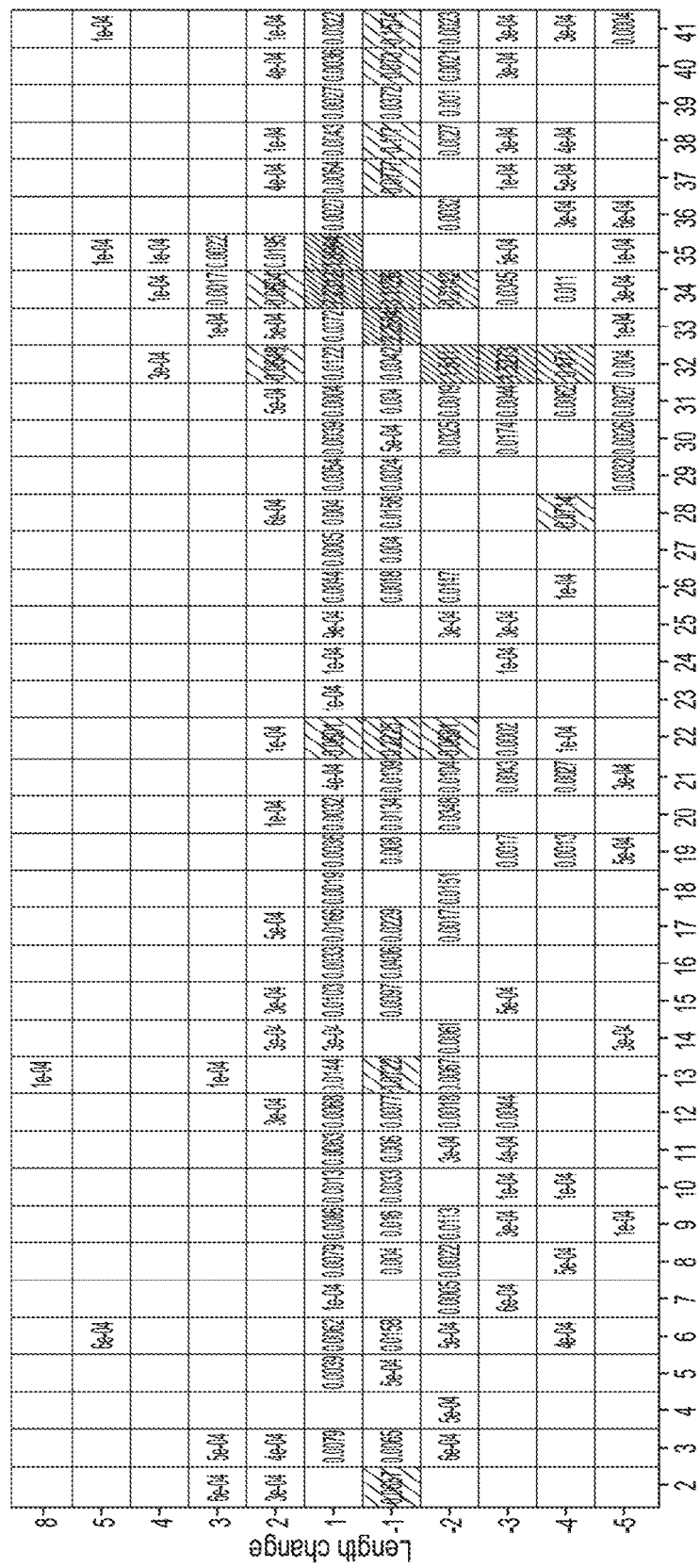
FIG. 7A and FIG. 7B are graphs depicting internal sequence length variances (+5 to −5) at the first 41 positions from the 5' ends of cDNAs generated from various synthetic unimolecular guide molecules that included the urea linkage (FIG. 7A), and from commercially prepared synthetic unimolecular guide molecules (i.e., prepared without conjugation) (FIG. 7B).
Figure 7B:
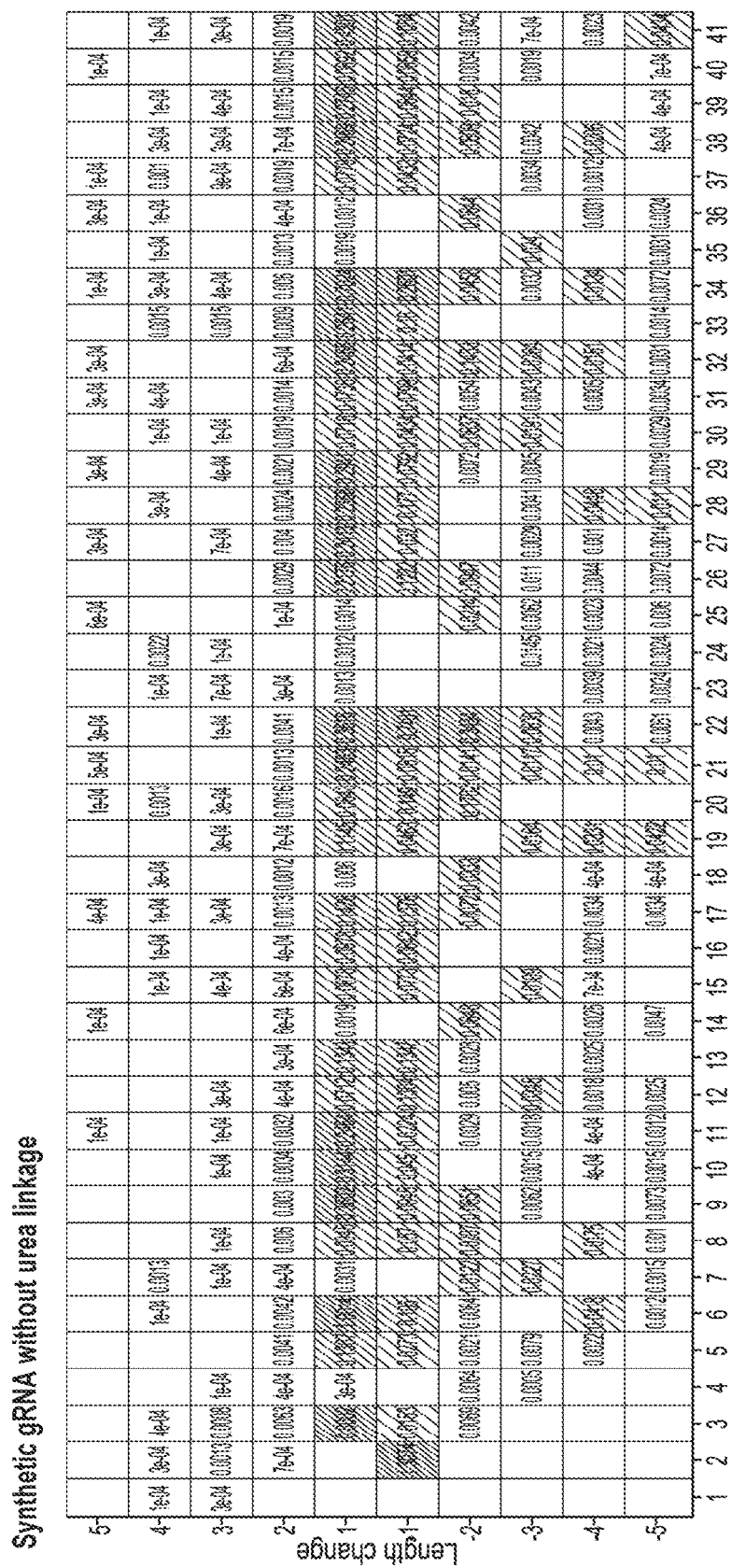
Figure 8A:
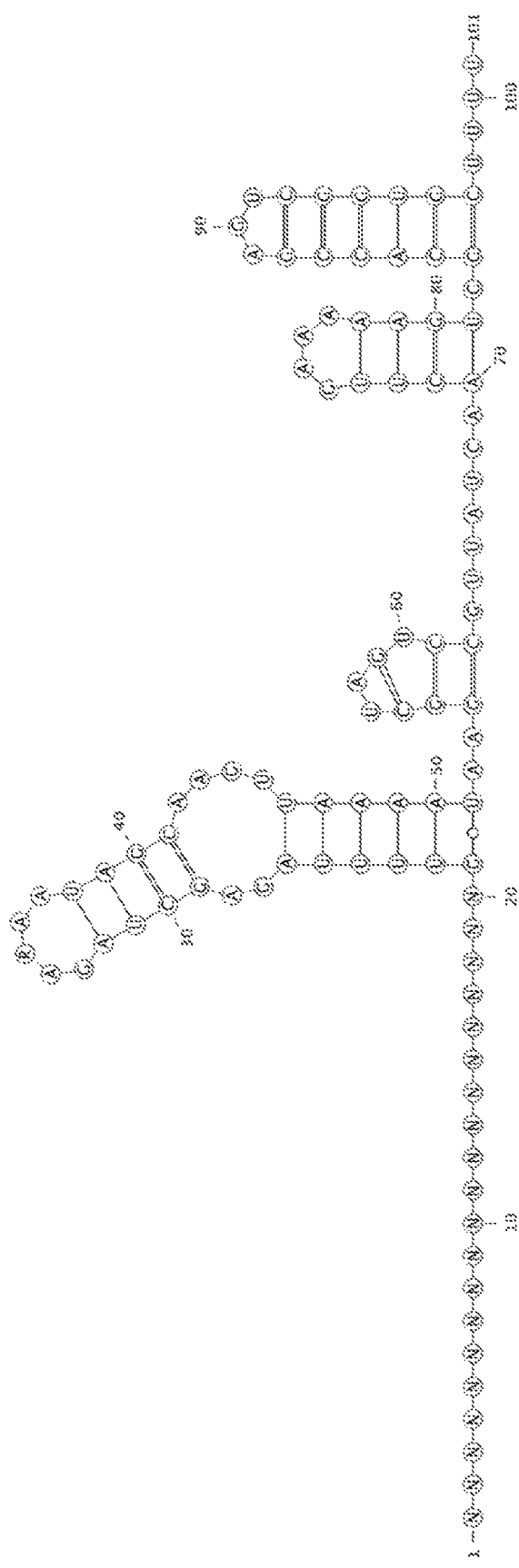
FIGS. 8A-8H depict, in two-dimensional schematic form, the structures of certain exemplary guide molecules according to various embodiments of this disclosure. Complementary bases capable of base pairing are denoted by one (A-U or A-T pairing) or two (G-C) horizontal lines between bases. Bases capable of non-Watson-Crick pairing are denoted by a single horizontal line with a circle.
Figure 8B:
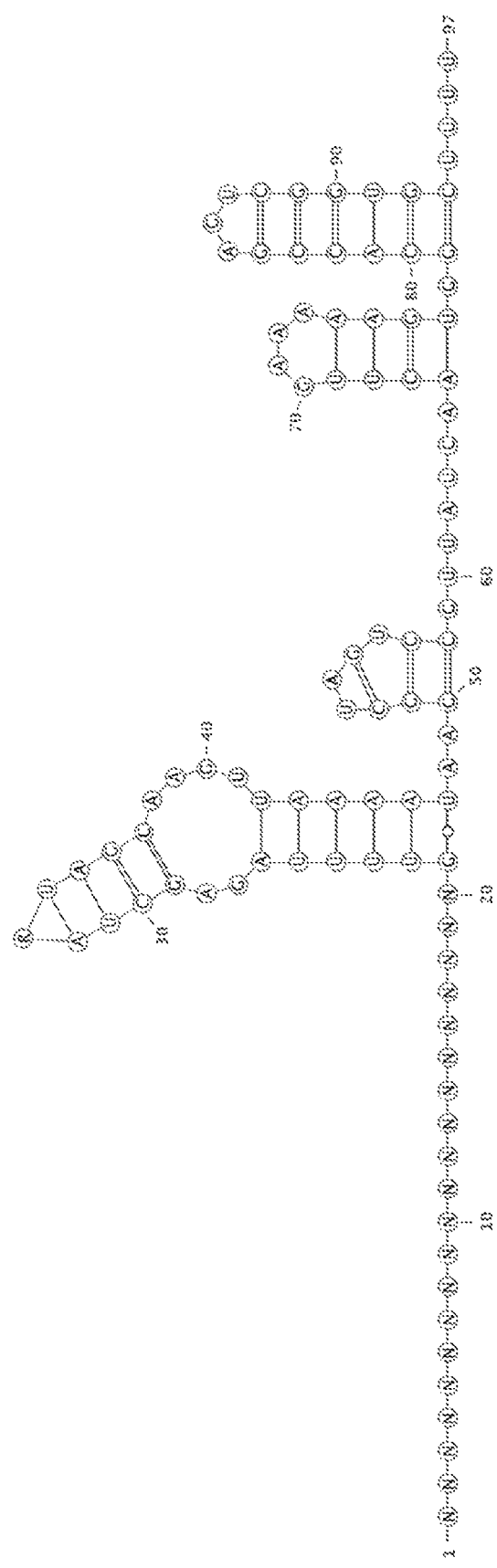
Figure 8C:
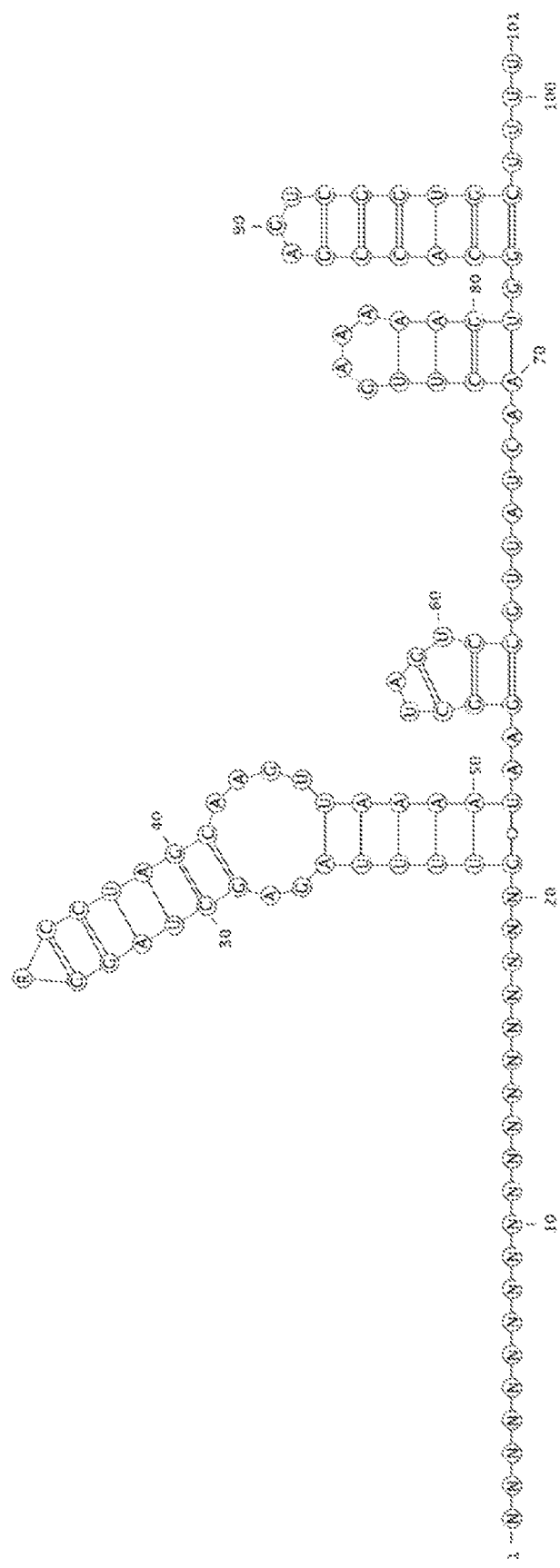
Figure 8D:
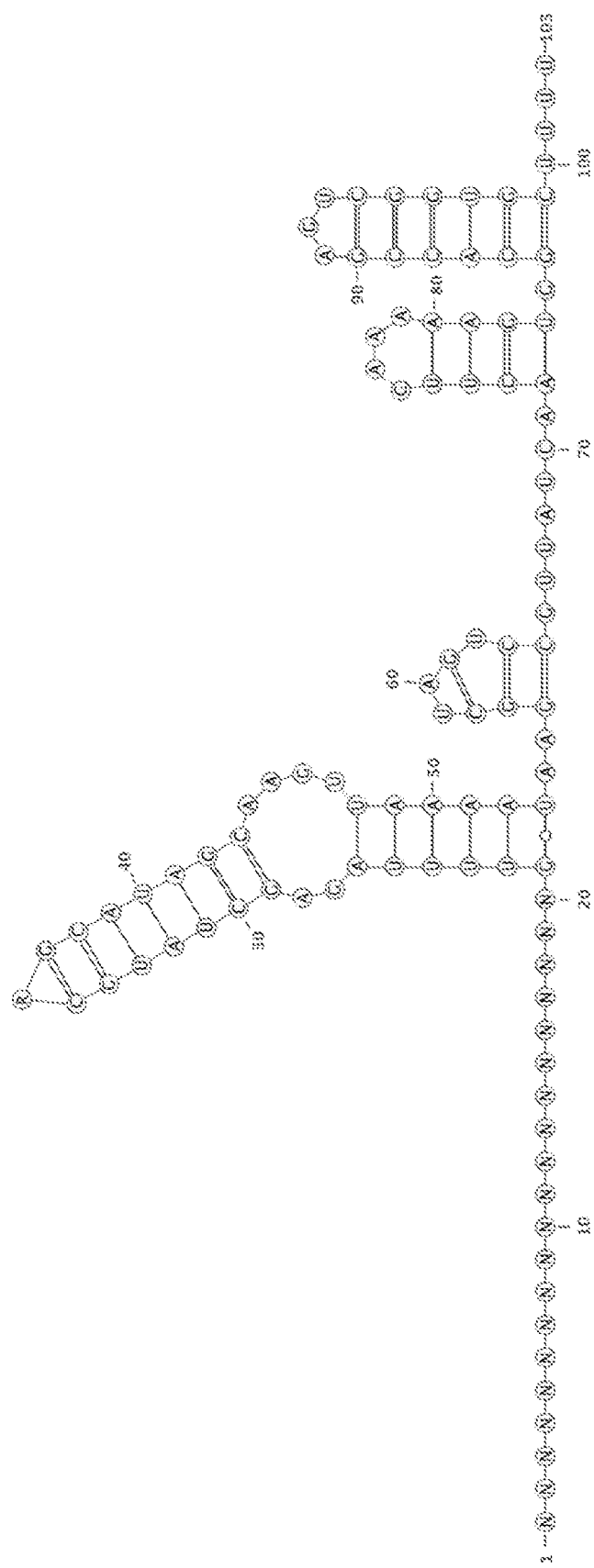
Figure 8E:
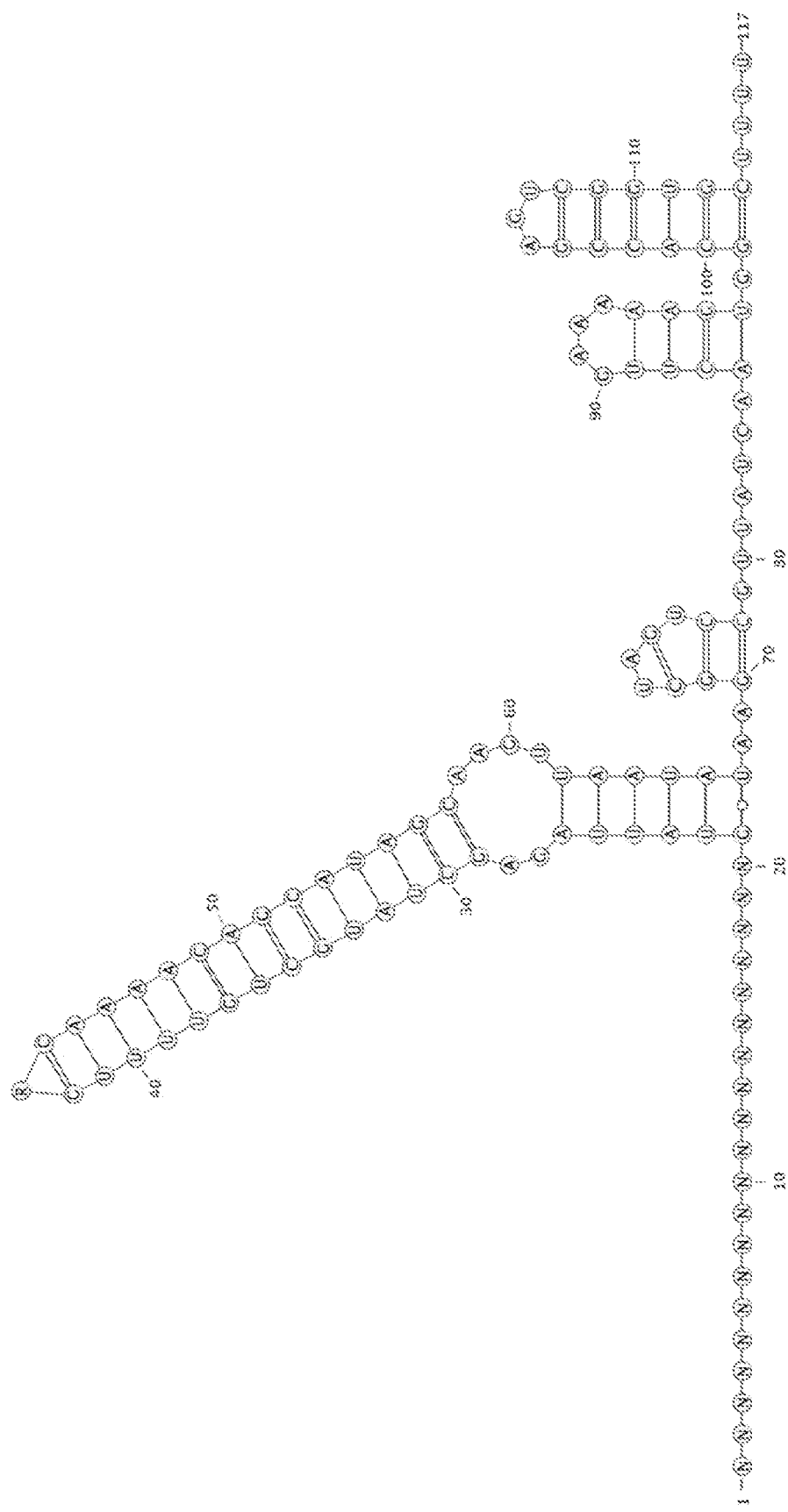
Figure 8F:
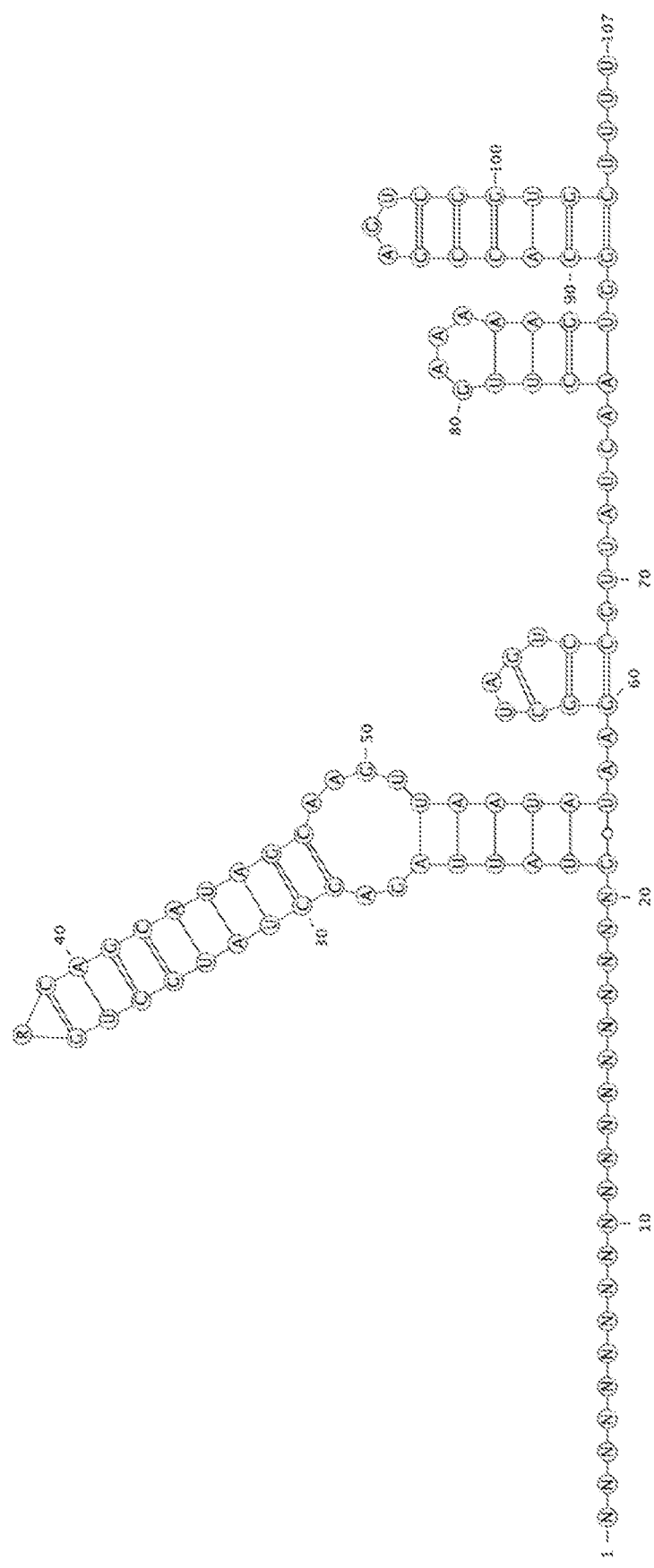
Figure 8G:
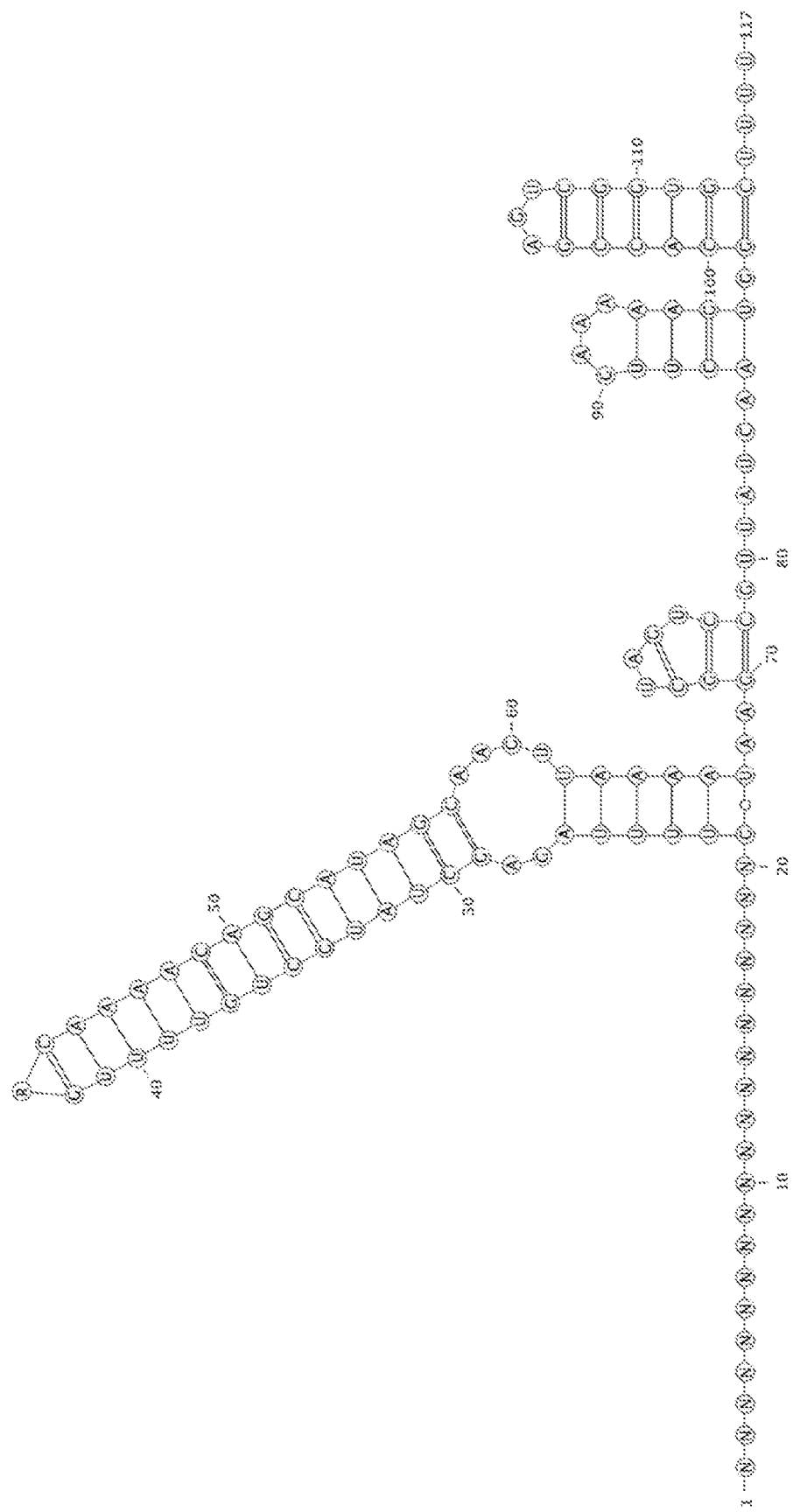
Figure 8H:
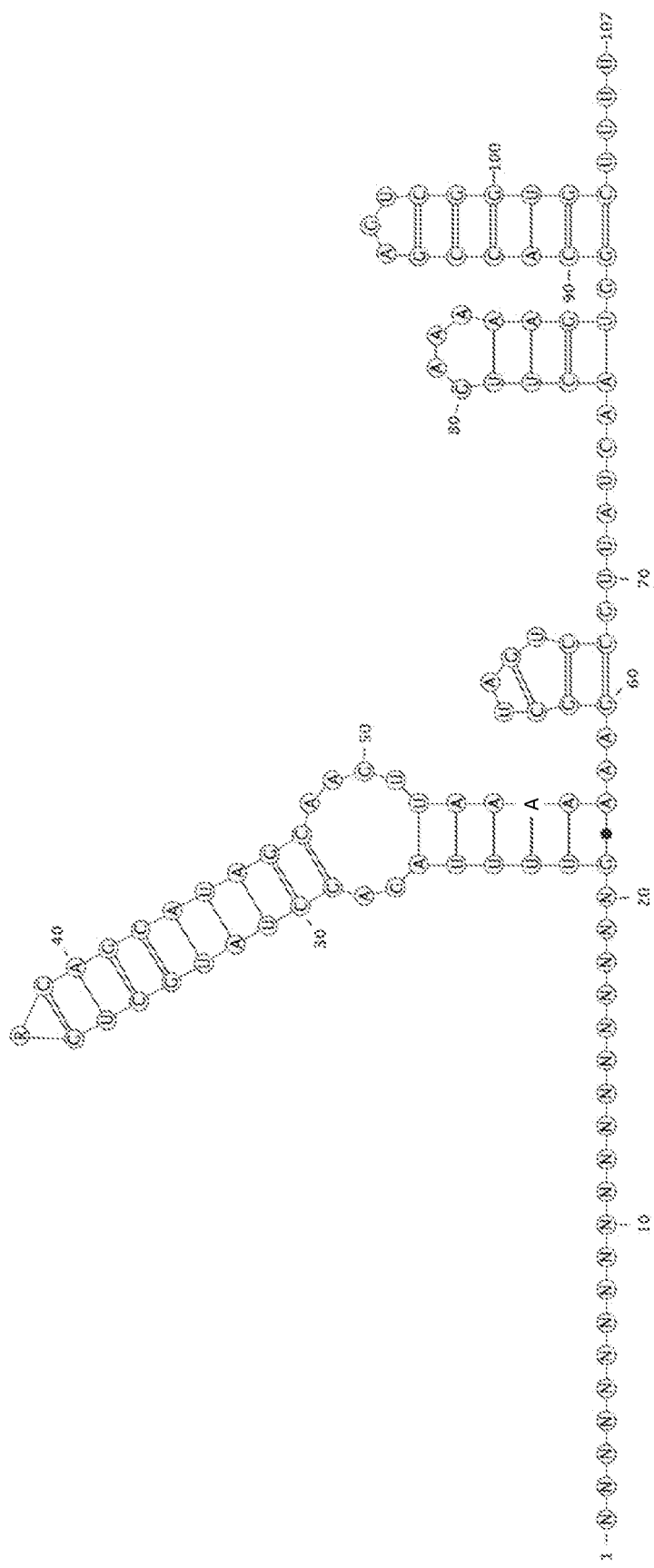
Figure 9A:
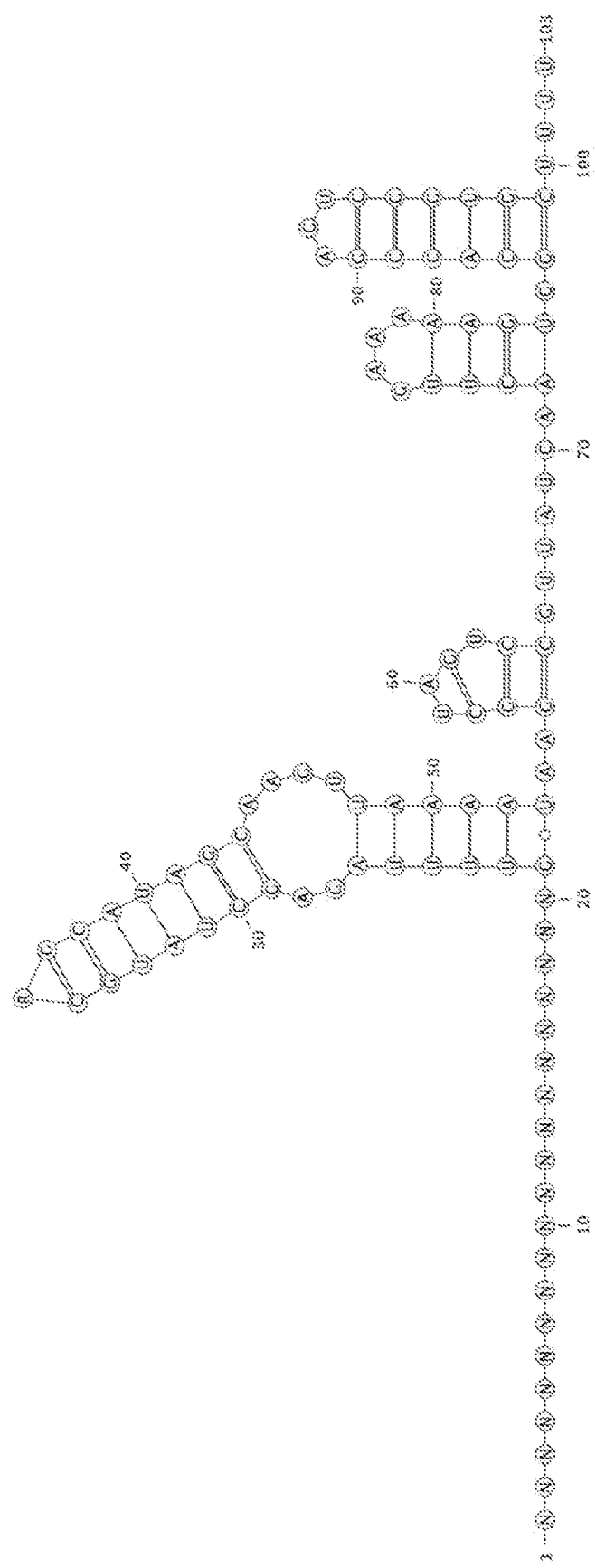
FIGS. 9A-9D depict, in two-dimensional schematic form, the structures of certain exemplary guide molecules according to various embodiments of this disclosure. Complementary bases capable of base pairing are denoted by one (A-U or A-T pairing) or two (G-C) horizontal lines between bases. Bases capable of non-Watson-Crick pairing are denoted by a single horizontal line with a circle.
Figure 9B:
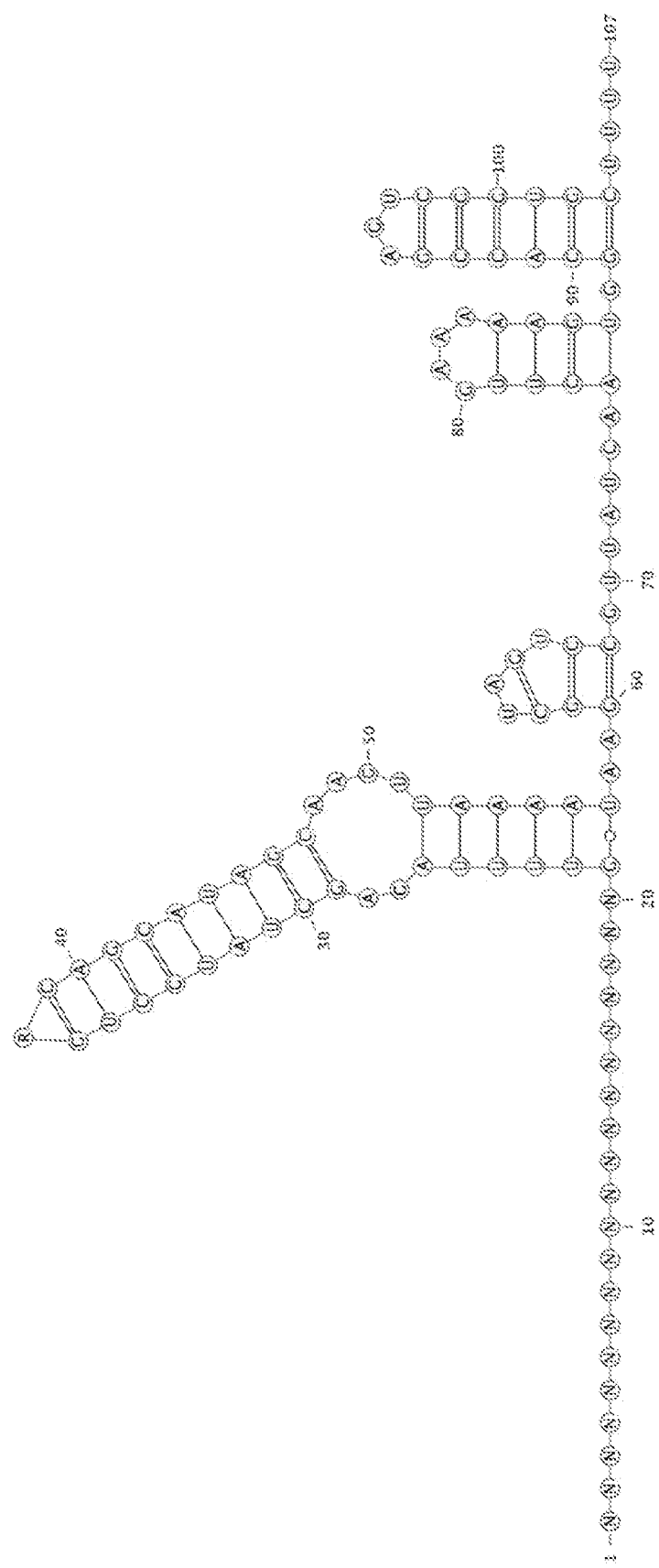
Figure 9C:
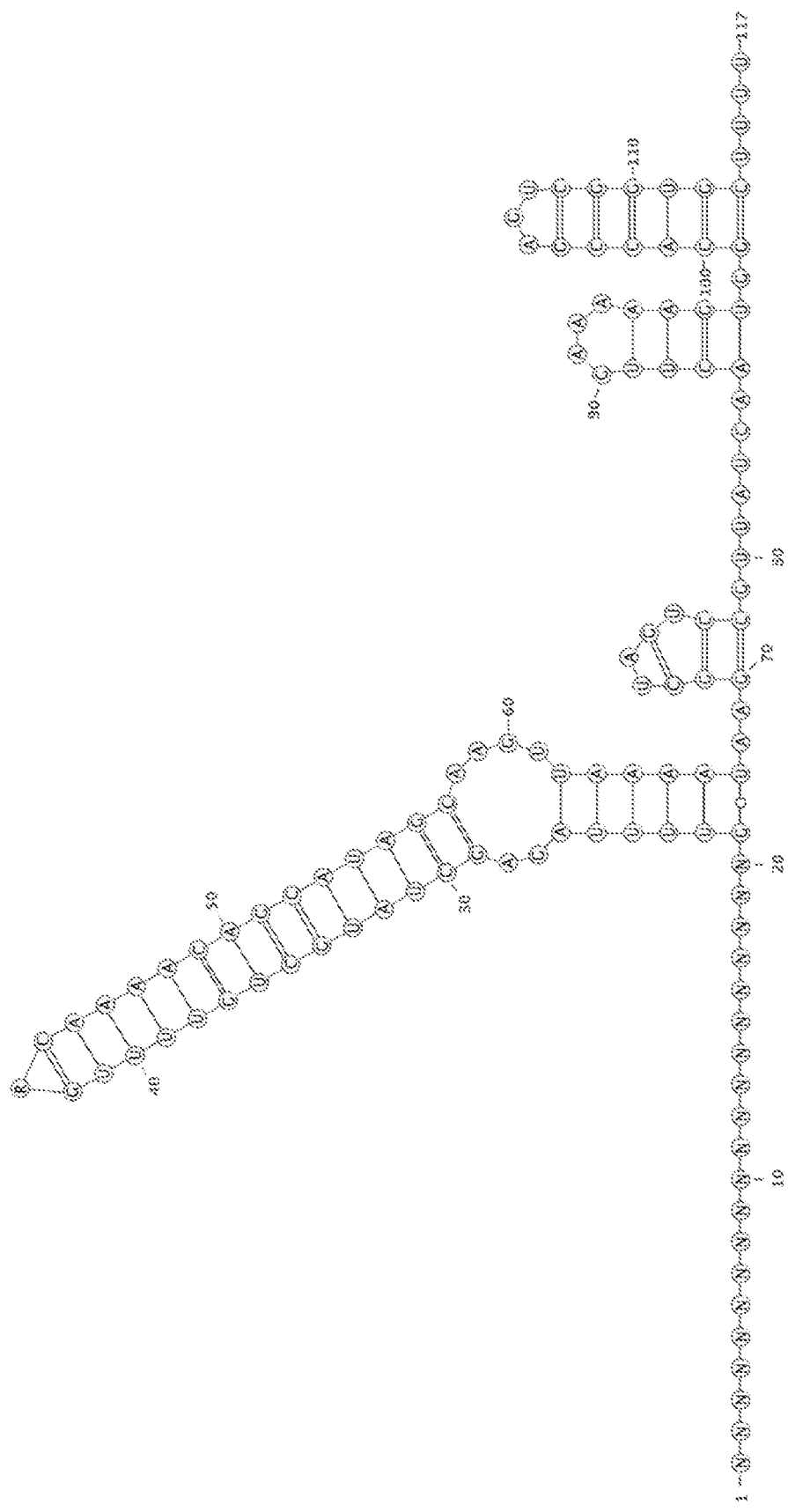
Figure 9D:
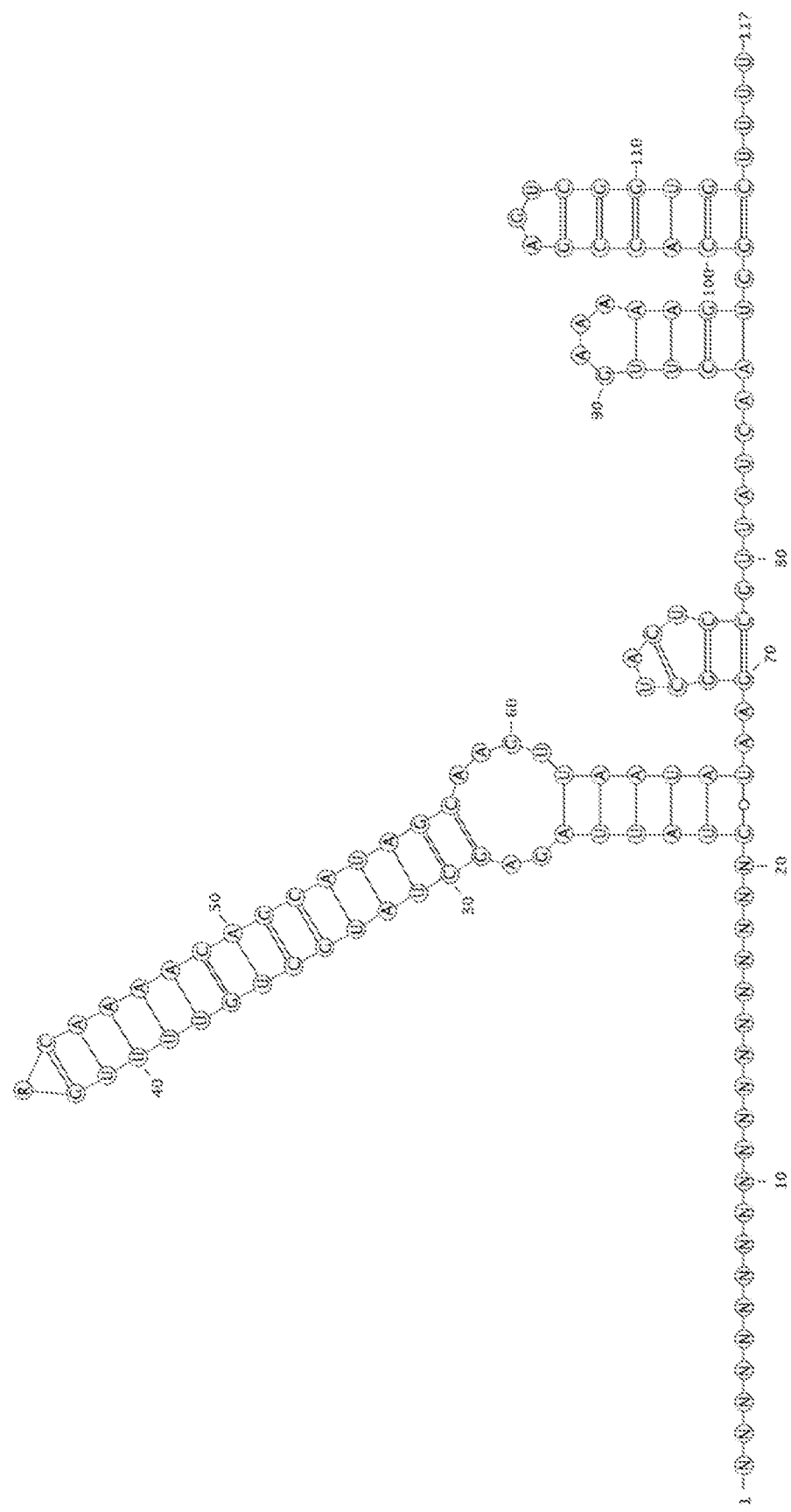
Figure 10A:
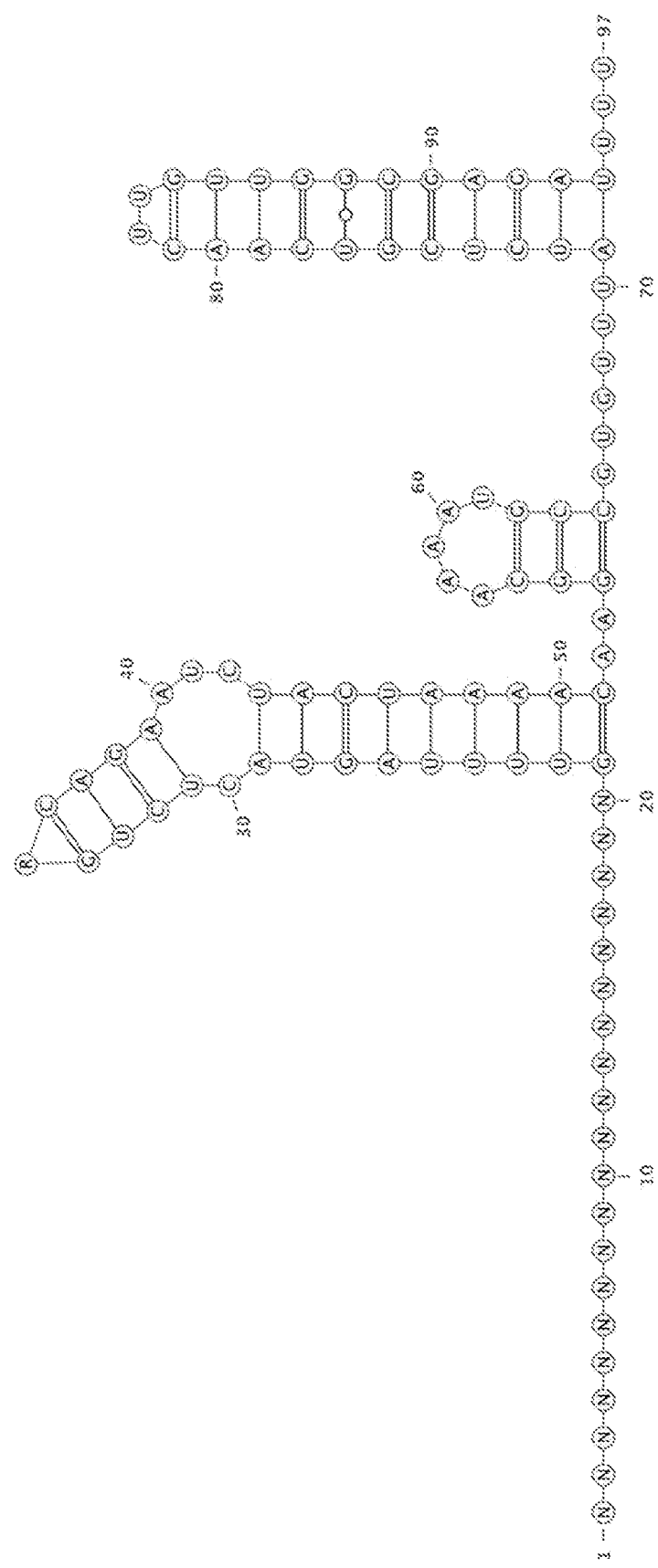
FIGS. 10A-10D depict, in two-dimensional schematic form, the structures of certain exemplary guide molecules according to various embodiments of this disclosure. Complementary bases capable of base pairing are denoted by one (A-U or A-T pairing) or two (G-C) horizontal lines between bases. Bases capable of non-Watson-Crick pairing are denoted by a single horizontal line with a circle.
Figure 10B:
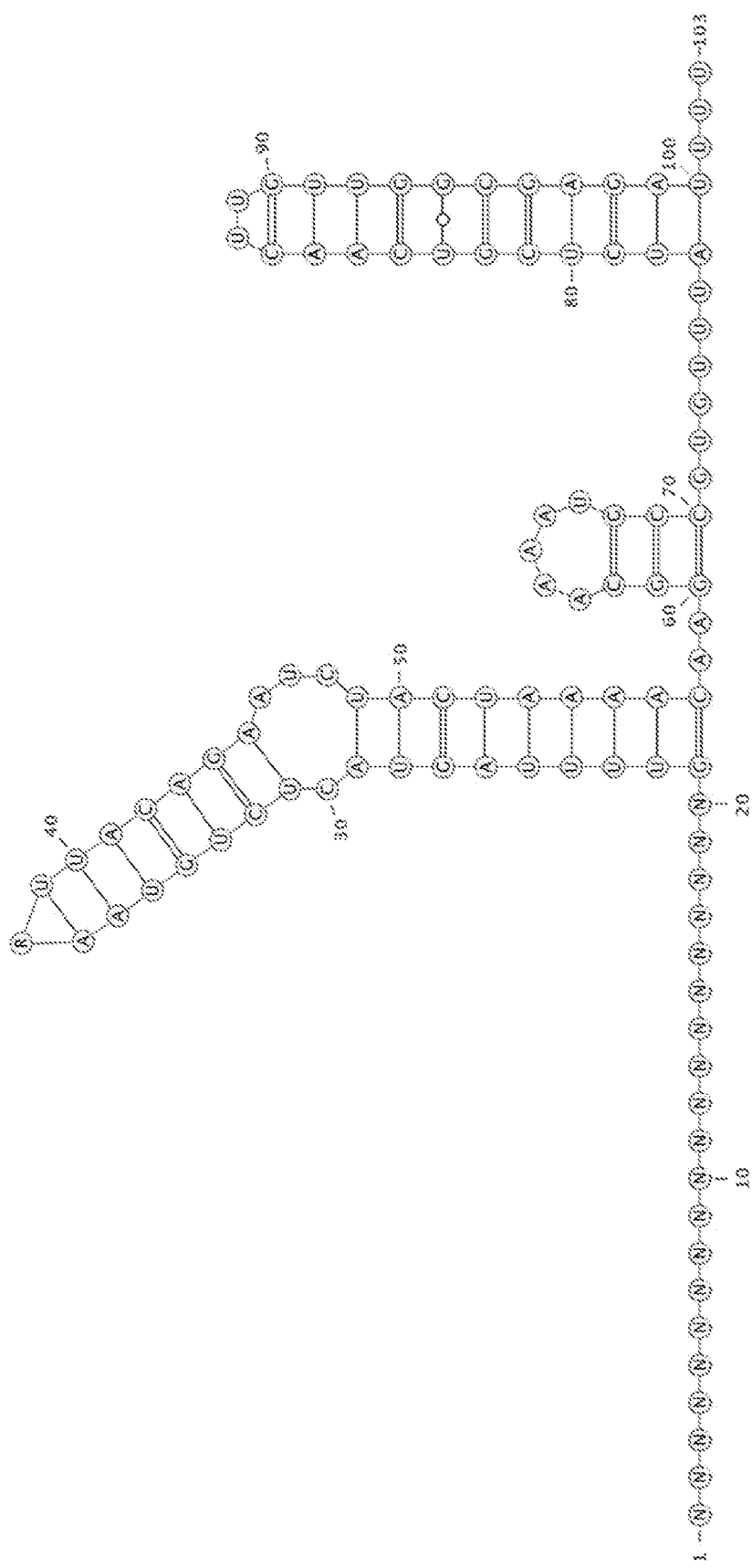
Figure 10C:
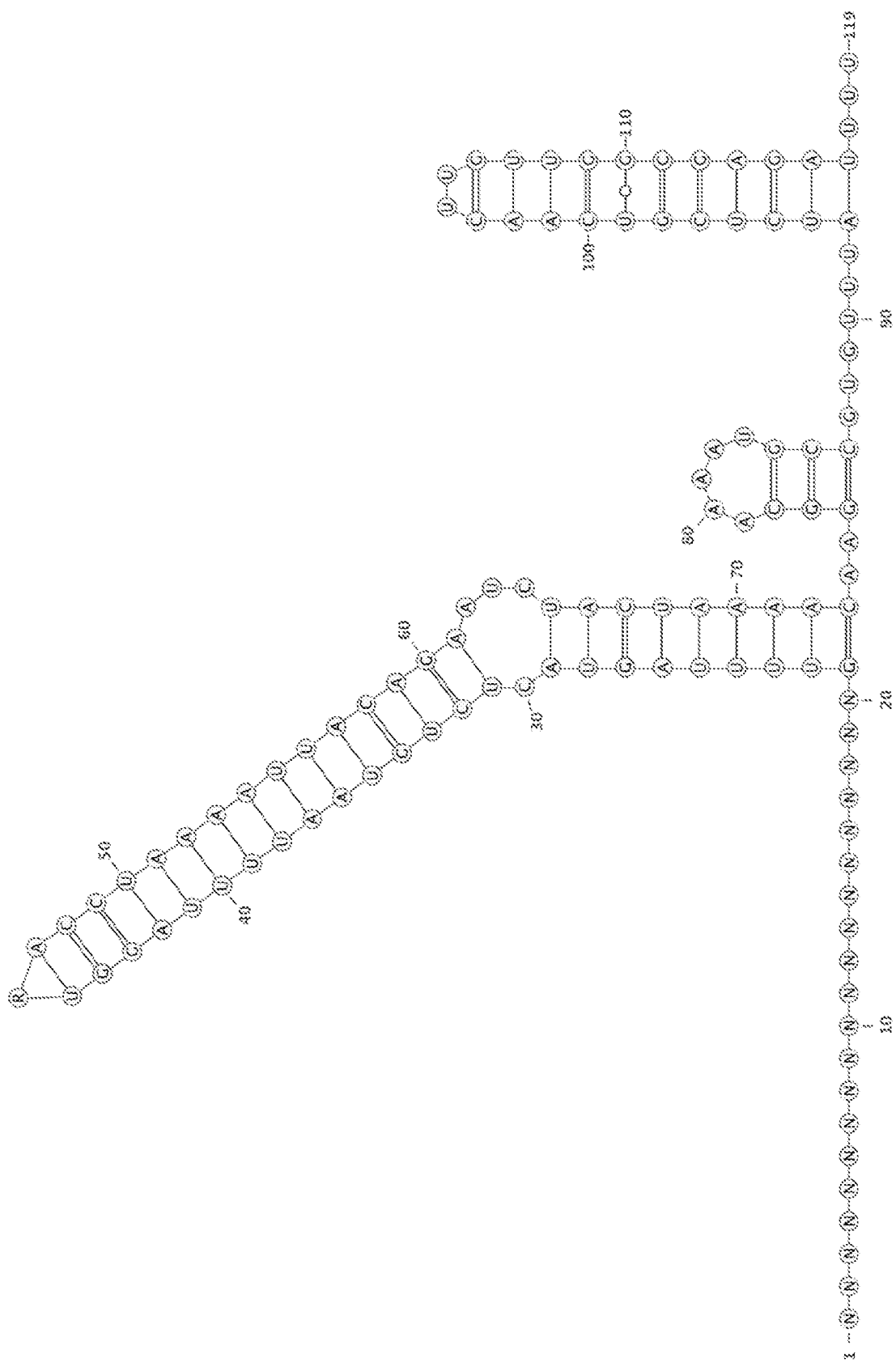
Figure 10D:
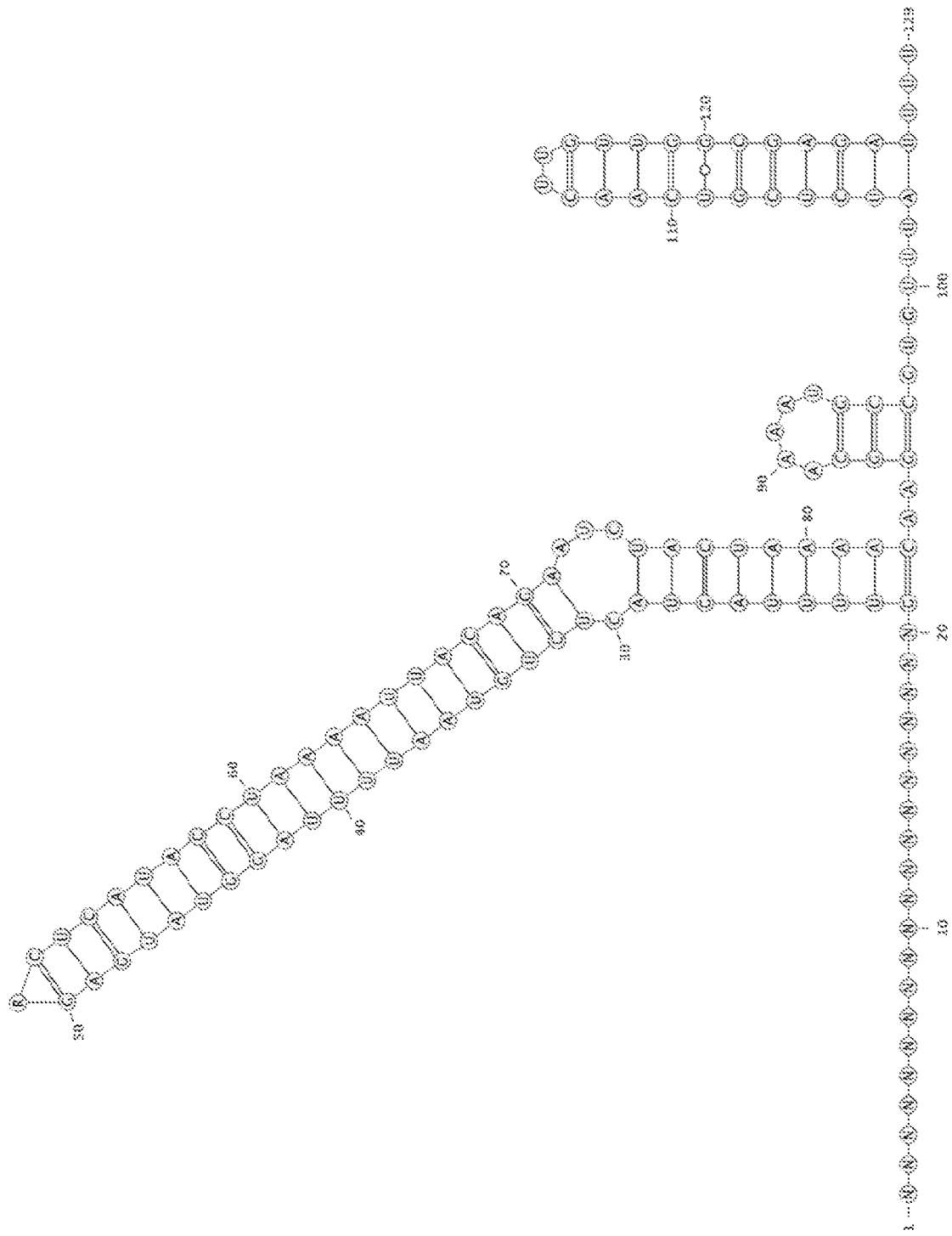

FIGS. 7A and 7B are graphs depicting internal sequence length variances (+5 to −5) at the first 41 positions from the 5' ends of cDNAs generated from synthetic unimolecular guide molecules that included the urea linkage (FIG. 7A), and from commercially prepared synthetic unimolecular guide molecules (i.e., prepared without conjugation) (FIG. 7B). As shown, guide molecules that included the urea linkage had a reduction in the frequency and length of insertions/deletions, relative to the commercially prepared synthetic unimolecular guide molecules (i.e., prepared without conjugation).

Example 7: Assessment of Guide Molecule Activity in CD34+ Cells

The activity of guide molecules with urea linkages conjugated in accordance with the process of Example 1 was assessed in CD34+ cells via next generation sequencing techniques. Guide molecules discussed in this Example contained one of three targeting domain sequences and various guide molecule backbone sequences, as shown in Table 17, below and FIGS. 8A-L, 9A-E, and 10A-D. The position of the urea linkage between two guide molecule fragments is denoted by [UR] in Table 17 and ® in FIGS. 8A-L, 9A-E, and 10A-D. The guide molecules with the first two targeting domain sequences (denoted gRNA 1 followed by a letter or gRNA 2 followed by a letter) were based on a S. pyogenes gRNA backbone while the guide molecules with the third targeting domain sequence (denoted gRNA 3 followed by a letter) were based on a S. aureus gRNA backbone.

The conjugated guide molecules were resuspended in pH 7.5 buffer, melted and reannealed, and then added to a suspension of S. pyogenes Cas9 to yield a solution with 55 µM fully-complexed ribonucleoprotein.

Human CD34+ cells were counted, centrifuged to a pellet and resuspended in P3 Nucleofection Buffer, then dispensed to each well of a 96-well Nucleocuvette Plate that was pre-filled with human HSC media (StemSpan™ Serum-Free Expansion Medium, StemCell Technologies, Vancouver, British Columbia, Canada) to yield 50,000 cells/well. A fully-complexed ribonucleoprotein solution as described above was added to each well in the Nucleocuvette Plate, followed by gentle mixing. Nucleofection was performed on an Amaxa Nucleofector System (Lonza, Basel, Switzerland). Nucleofected cells were incubated for 72 h at 37° C. and 5% $CO_2$ to allow editing to plateau. Genomic DNA was then extracted from nucleofected cells using the DNAdvance DNA isolation Kit according to manufacturer's instructions. Cleavage was assessed using next generation sequencing techniques to quantify % insertions and deletions (indels) relative to the wild-type human reference sequence. Results for gRNAs in Table 17 that were tested in CD34+ cells are presented in FIG. 11.

Figure 11:
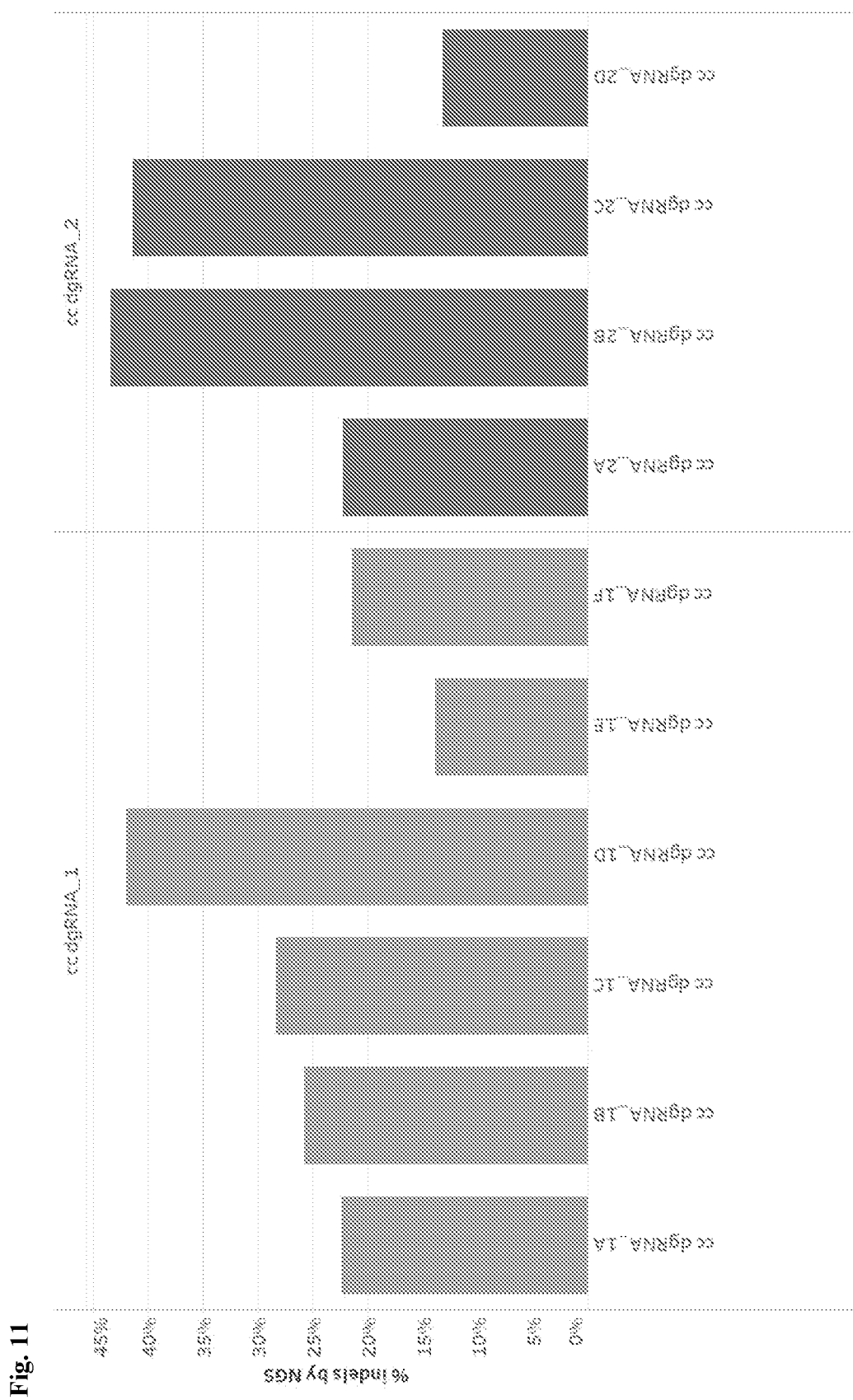
FIG. 11 shows a graph of DNA cleavage in CD34+ cells with a series of ribonucleoprotein complexes comprising conjugated guide molecules from Table 17. Cleavage was assessed using next generation sequencing techniques to quantify % insertions and deletions (indels) relative to a wild-type human reference sequence. Ligated guide molecules generated according to Example 1 support DNA cleavage in CD34+ cells. % indels were found to increase with increasing stemloop length, but incorporation of a U-A swap adjacent to the stemloop sequence (see gRNAs 1E, 1F, and 2D) mitigates the effect.

As the results in FIG. 11 show, ligated guide molecules generated according to Example 1 support DNA cleavage in CD34+ cells. % indels were found to increase with increasing stemloop length, but incorporation of a U-A swap adjacent to the stemloop sequence (see gRNA 1E, gRNA 1F, and gRNA 2D) mitigates the effect. These data suggest chemically conjugated synthetic unimolecular guide molecules with a longer stemloop feature result in higher levels of DNA cleavage in cells. In addition, DNA cleavage activity is independent of ligation efficiency and must be determined empirically.

In some embodiments, the guide molecule comprising a urea is of sequence listed in Table 17 below, wherein [UR] is a non-nucleotide linkage comprising a urea. In some embodiments, [UR] indicates the following linkage:

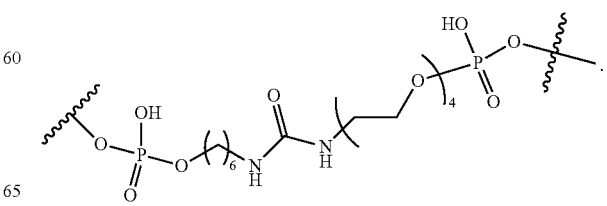

TABLE 17

| Guide molecule | SEQ ID NO. (Seq. A) SEQ ID NO. (Seq. B) | 5' - Seq. A - [UR] - Seq. B - 3' |
|---|---|---|
| gRNA 1A | 37 38 | GUAACGGCAGACUUCUCCUCGUUUUAGAGCUAGA[UR]AAUAGCAAGUU AAAAUAAGGCUAGUCCGUUAUCAACUUGAAAAAGUGGCACCGAGUCGGU GCUUUU |
| gRNA 1B | 39 40 | GUAACGGCAGACUUCUCCUCGUUUUAGAGCUA[UR]UAGCAAGUUAAAA UAAGGCUAGUCCGUUAUCAACUUGAAAAAGUGGCACCGAGUCGGUGCUU UU |
| gRNA 1C | 41 42 | GUAACGGCAGACUUCUCCUCGUUUUAGAGCUAGG[UR]CCUAGCAAGUU AAAAUAAGGCUAGUCCGUUAUCAACUUGAAAAAGUGGCACCGAGUCGGU GCUUUU |
| gRNA 1D | 43 44 | GUAACGGCAGACUUCUCCUCGUUUUAGAGCUAUGC[UR]GCAUAGCAAG UUAAAAUAAGGCUAGUCCGUUAUCAACUUGAAAAAGUGGCACCGAGUCG GUGCUUUU |
| gRNA 1E | 45 46 | GUAACGGCAGACUUCUCCUCGUAUUAGAGCUAUGCUGUUUUG[UR]CAA AACAGCAUAGCAAGUUAAUAUAAGGCUAGUCCGUUAUCAACUUGAAAAA GUGGCACCGAGUCGGUGCUUUU |
| gRNA 1F | 47 48 | GUAACGGCAGACUUCUCCUCGUAUUAGAGCUAUGCUG[UR]CAGCAUAG CAAGUUAAUAUAAGGCUAGUCCGUUAUCAACUUGAAAAAGUGGCACCGA GUCGGUGCUUUU |
| gRNA 1G | 49 50 | GUAACGGCAGACUUCUCCUCGUUUUAGAGCUAUGCUGUUUUG[UR]CAA AACAGCAUAGCAAGUUAAAAUAAGGCUAGUCCGUUAUCAACUUGAAAAA GUGGCACCGAGUCGGUGCUUUU |
| gRNA 1H | 51 52 | GUAACGGCAGACUUCUCCUCGUUUUAGAGCUAUGCUG[UR]CAGCAUAG CAAGUUAAAAAAGGCUAGUCCGUUAUCAACUUGAAAAAGUGGCACCGA GUCGGUGCUUUU |
| gRNA 1I | 53 54 | GUAACGGCAGACUUCUCCUCGUUUUAGAGCUAAAGA[UR]AAUUUAGCA AGUUAAAAUAAGGCUAGUCCGUUAUCAACUUGAAAAAGUGGCACCGAGU CGGUGCUUUU |
| gRNA 1J | 55 56 | GUAACGGCAGACUUCUCCUCGUUUUAGAGCUAAAA[UR]UUUUAGCAAGUU AAAAUAAGGCUAGUCCGUUAUCAACUUGAAAAAGUGGCACCGAGUCGGU GCUUUU |
| gRNA 1K | 57 58 | GUAACGGCAGACUUCUCCUCGUUUUAGAGCUAAAGGGA[UR]AACCUUU AGCAAGUUAAAAUAAGGCUAGUCCGUUAUCAACUUGAAAAAGUGGCACC GAGUCGGUGCUUUU |
| gRNA 1L | 59 60 | GUAACGGCAGACUUCUCCUCGUUUUAGAGCUAGdA[UR]AAUAGCAAGU UAAAAUAAGGCUAGUCCGUUAUCAACUUGAAAAAGUGGCACCGAGUCGG UGCUUUU |
| gRNA 2A | 61 62 | CUAACAGUUGCUUUUAUCACGUUUUAGAGCUAUGC[UR]GCAUAGCAAG UUAAAAUAAGGCUAGUCCGUUAUCAACUUGAAAAAGUGGCACCGAGUCG GUGCUUUU |
| gRNA 2B | 63 64 | CUAACAGUUGCUUUUAUCACGUUUUAGAGCUAUGCUG[UR]CAGCAUAG CAAGUUAAAAUAAGGCUAGUCCGUUAUCAACUUGAAAAAGUGGCACCGA GUCGGUGCUUUU |
| gRNA 2C | 65 66 | CUAACAGUUGCUUUUAUCACGUUUUAGAGCUAUGCUGUUUUG[UR]CAA AACAGCAUAGCAAGUUAAAAUAAGGCUAGUCCGUUAUCAACUUGAAAAA GUGGCACCGAGUCGGUGCUUUU |
| gRNA 2D | 67 68 | CUAACAGUUGCUUUUAUCACGUAUUAGAGCUAUGCUGUUUUG[UR]CAA AACAGCAUAGCAAGUUAAUAUAAGGCUAGUCCGUUAUCAACUUGAAAAA GUGGCACCGAGUCGGUGCUUUU |
| gRNA 2E | 69 70 | CUAACAGUUGCUUUUAUCACGUUUUAGAGCUAGA[UR]AAUAGCAAGUU AAAAUAAGGCUAGUCCGUUAUCAACUUGAAAAAGUGGCACCGAGUCGGU GCUUUU |
| gRNA 3A | 71 72 | GUAACGGCAGACUUCUCCUCGUUUUAGUACUCUG[UR]CAGAAUCUACU AAAACAAGGCAAAAUGCCGUGUUUAUCUCGUCAACUUGUUGGCGAGAUU UU |
| gRNA 3B | 73 74 | GUAACGGCAGACUUCUCCUCGUUUUAGUACUCUGUAA[UR]UUACAGAA UCUACUAAAACAAGGCAAAAUGCCGUGUUUAUCUCGUCAACUUGUUGGC GAGAUUUU |

TABLE 17-continued

| Guide molecule | SEQ ID NO. (Seq. A) SEQ ID NO. (Seq. B) | 5' - Seq. A - [UR] - Seq. B - 3' |
|---|---|---|
| gRNA 3C | 75 76 | GUAACGGCAGACUUCUCCUCGUUUUAGUACUCUGUAAUUUUAGGU[UR] ACCUAAAAUUACAGAAUCUACUAAAACAAGGCAAAAUGCCGUGUUUAUC UCGUCAACUUGUUGGCGAGAUUUU |
| gRNA 3D | 77 78 | GUAACGGCAGACUUCUCCUCGUUUUAGUACUCUGUAAUUUUAGGUAUGA G[UR]CUCAUACCUAAAAUUACAGAAUCUACUAAAACAAGGCAAAAUGC CGUGUUUAUCUCGUCAACUUGUUGGCGAGAUUUU |

Example 8: Evaluation of Computational Model of Ligation Efficiency

The ligation efficiency of the reaction described in Example 1 is one measure of the suitability of a particular guide molecule structure. Since the reactive functional group of the first and second guide molecule fragments in Example 1 is the same (an amine), competitive homo-coupling is a potential side product. This Example evaluated whether ligation efficiency (i.e., the % of hetero-coupled product in the reaction product) can be predicted through computational modeling of the free energy difference of the homo-coupling reaction ($\Delta G_1$), compared to the free energy difference of the hetero-coupling reaction ($\Delta G_2$) using the OligoAnalyzer 3.1 tool available at http://www.idtdna.com/calc/analyzer. Results of this analysis are shown in Table 18.

TABLE 18

| Guide molecule | Ligation efficiency | $\Delta G_1$ (kcal/mol) | $\Delta G_2$ (kcal/mol) | $\Delta G_2 - \Delta G_1$ (kcal/mol) |
|---|---|---|---|---|
| gRNA 1A | ~55% | −6.90 | −10.93 | −4.03 |
| gRNA 1C | 18% | −6.90 | −10.93 | −4.03 |
| gRNA 1D | 50% | −6.90 | −12.27 | −5.37 |
| gRNA 1E | 50% | −6.34 | −24.95 | −18.61 |
| gRNA 1F | 31% | −6.34 | −15.82 | −9.48 |
| gRNA 1G | 12% | −6.90 | −24.95 | −18.05 |
| gRNA 1H | 60% | −6.90 | −15.82 | −8.92 |
| gRNA 1I | ~50% | −6.90 | −10.93 | −4.03 |
| gRNA 1J | ~50% | −6.90 | −10.93 | −4.03 |
| gRNA 1K | ~55% | −6.90 | −10.93 | −4.03 |
| gRNA 2A | 18% | −6.34 | −12.27 | −5.93 |
| gRNA 2C | 48% | −6.84 | −24.95 | −18.11 |
| gRNA 2D | 45% | −6.84 | −24.95 | −18.11 |
| gRNA 2E | 5% | −6.34 | −8.64 | −2.30 |

As shown in Table 18, ligation efficiency (as measured by densitometry following gel analysis) was well predicted for most sequences with a more negative $\Delta G_2 - \Delta G_1$ value corresponding to a more favorable ligation efficiency (e.g., compare gRNAs 2A and 2C). However, the ligation efficiency to form certain guide molecules was not always correlated with the $\Delta G_2 - \Delta G_1$ value (e.g., see gRNA 1G where a more negative $\Delta G_2 - \Delta G_1$ value did not lead to higher ligation efficiency), indicating that modifications and experimentation may be required for conjugating certain guide molecule fragments. For example, ligation efficiency of gRNA 1G was improved by implementing a U-A swap in the sequence of the lower stem (compare ligation efficiency of gRNA 1G with gRNA 1E), where the U-A swap was designed to prevent staggered annealing of two guide molecule fragments before ligation.

Example 9: Characterization of Urea Linkage by Mass Spectrometry

Figure 12A:
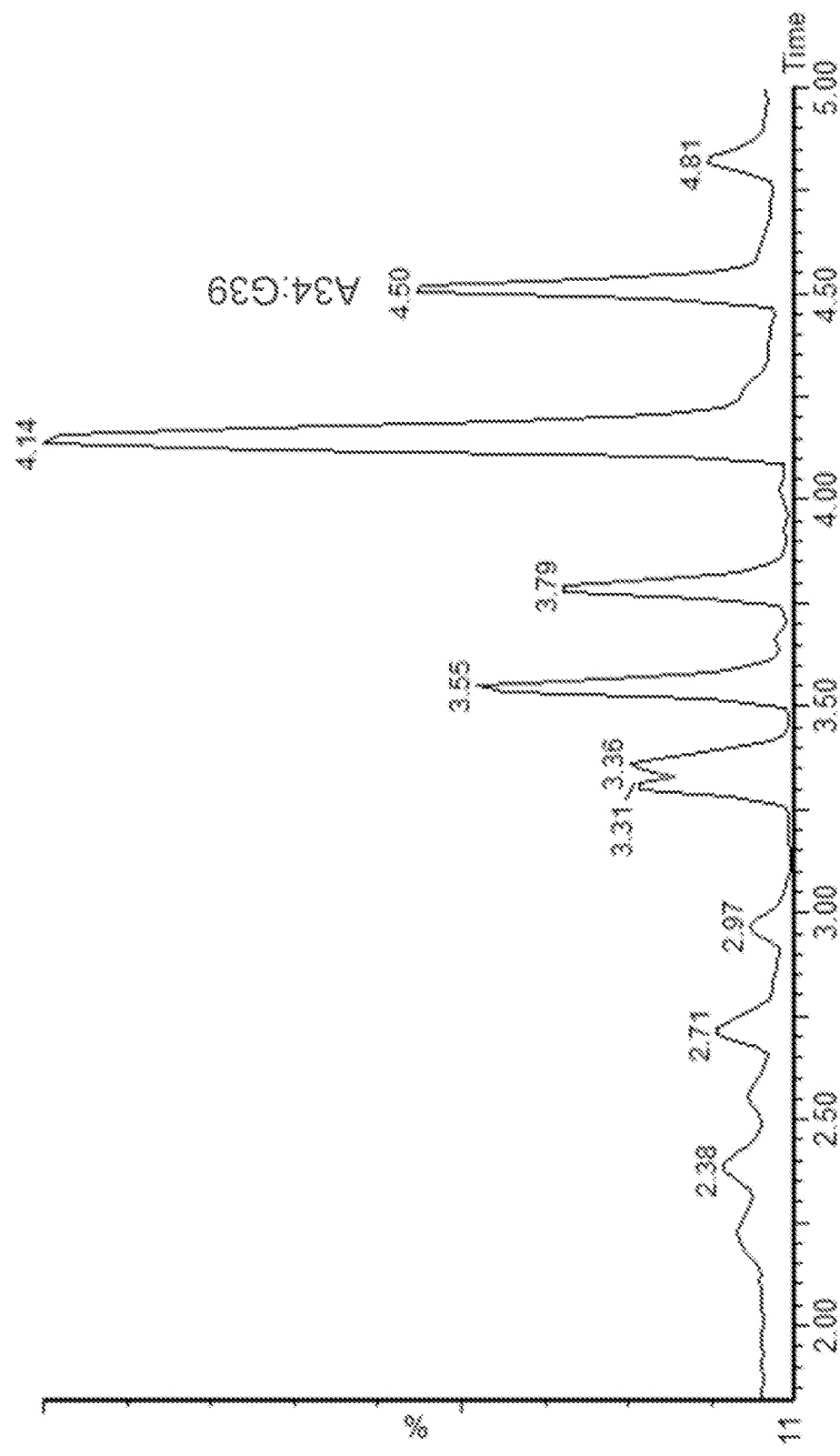
FIG. 12A shows a liquid chromatography-mass spectrometry (LC-MS) trace after T1 endonuclease digestion of gRNA 1A.
Figure 12B:
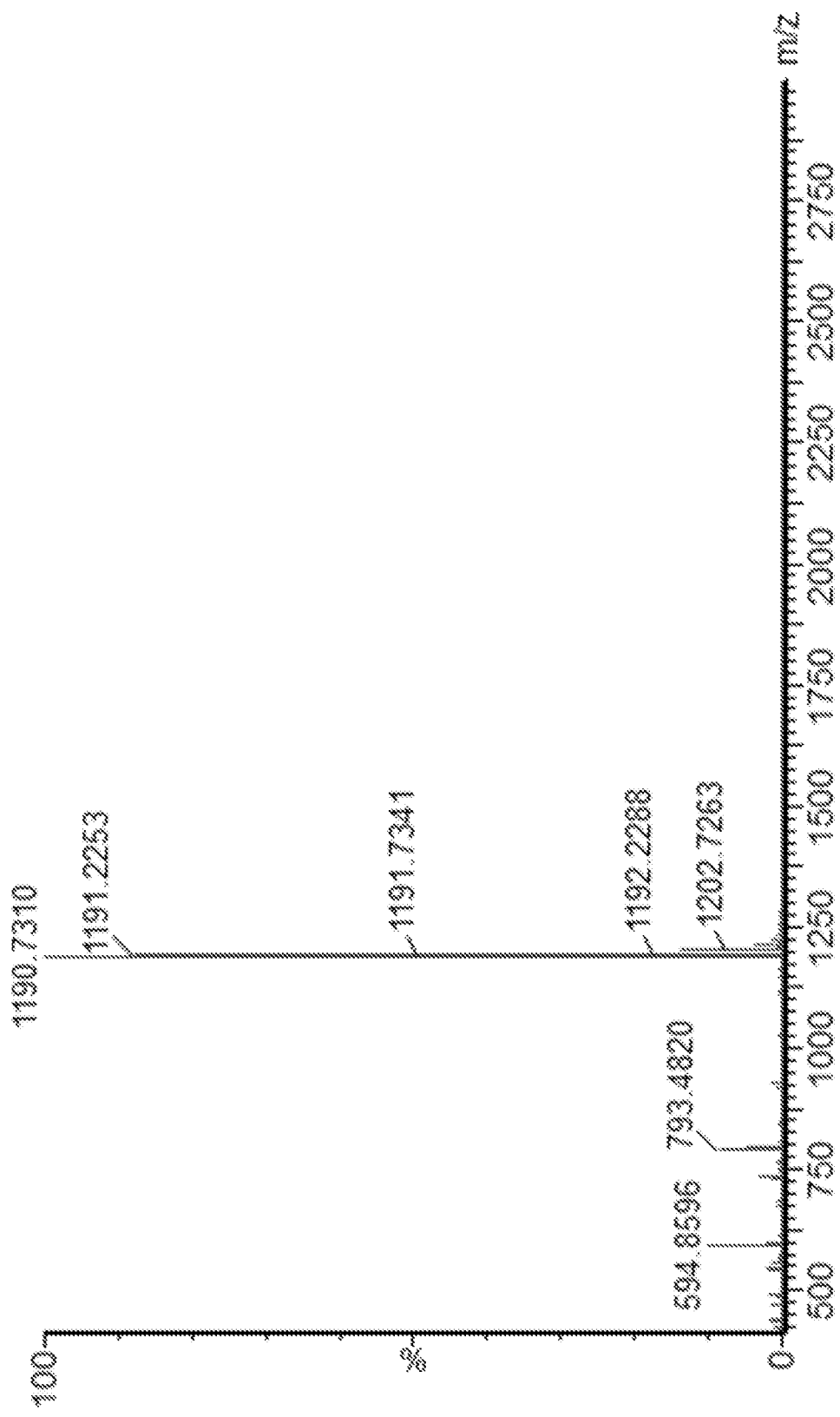
FIG. 12B shows a mass spectrum of the peak with a retention time of 4.50 min (A34:G39). In particular, the fragment containing the urea linkage, A-[UR]-AAUAG (A34:G39), was detected at a retention time of 4.50 min with m/z=1190.7.

A chemically conjugated guide molecule, containing a urea linkage and synthesized as described in Example 1, was characterized by mass spectrometry. After synthesis, chemical ligation, and purification, gRNA 1A (see Table 17) was cleaved into fragments at the 3'-end of each G nucleotide in the primary sequence using the T1 endonuclease. These fragments were analyzed using LC-MS. In particular, the fragment containing the urea linkage, A-[UR]-AAUAG (A34:G39), was detected at a retention time of 4.50 min with m/z=1190.7 (FIG. 12A and FIG. 12B). LC/MS-MS analysis of this precursor ion revealed collision-induced dissociation fragment ions consistent with a urea linkage in gRNA 1A.

Example 10: Characterization of a Carbamate Side Product

Figure 13A:
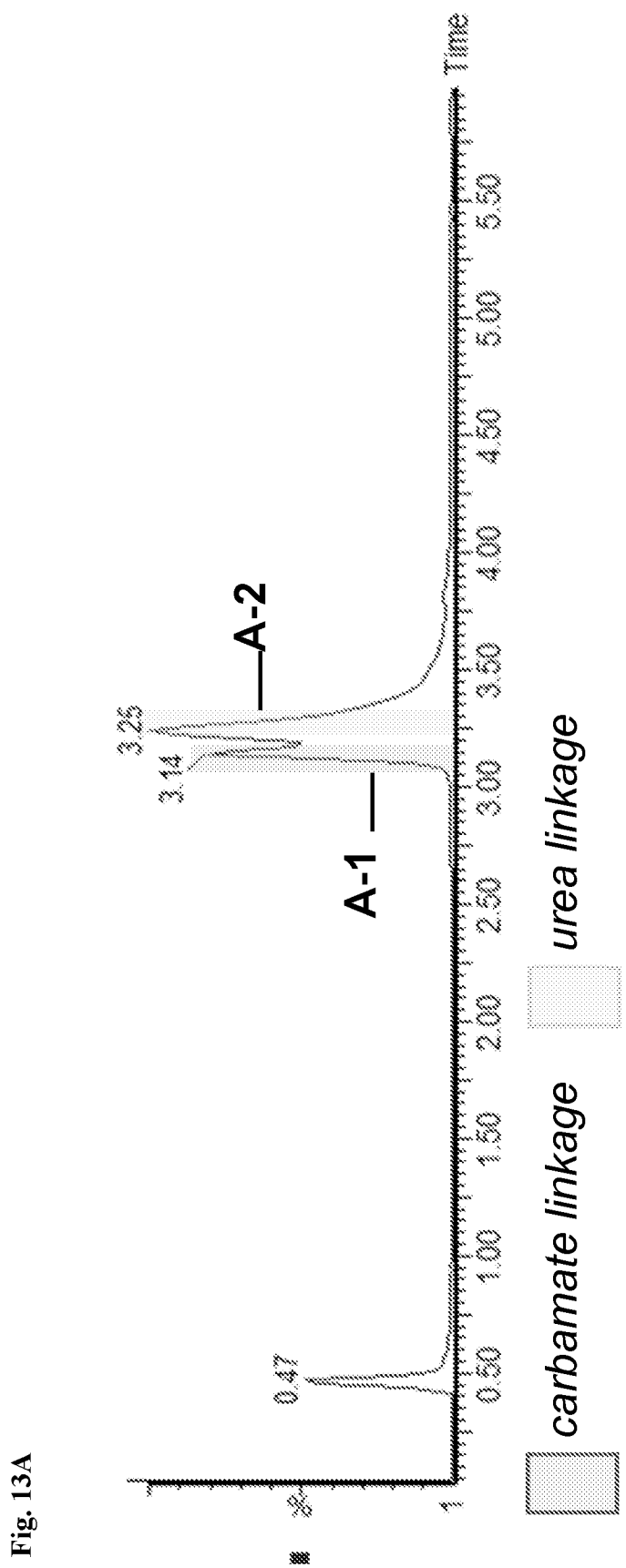
FIG. 13A shows LC-MS data for an unpurified composition of urea-linked guide molecules with both a major product (A-2, retention time of 3.25 min) and a minor product (A-1, retention time of 3.14 min) present. We note that the minor product (A-1) in FIG. 13A was enriched for purposes of illustration and is typically detected in up to 10% yield in the synthesis of guide molecules in accordance with the process of Example 1.
Figure 13B:
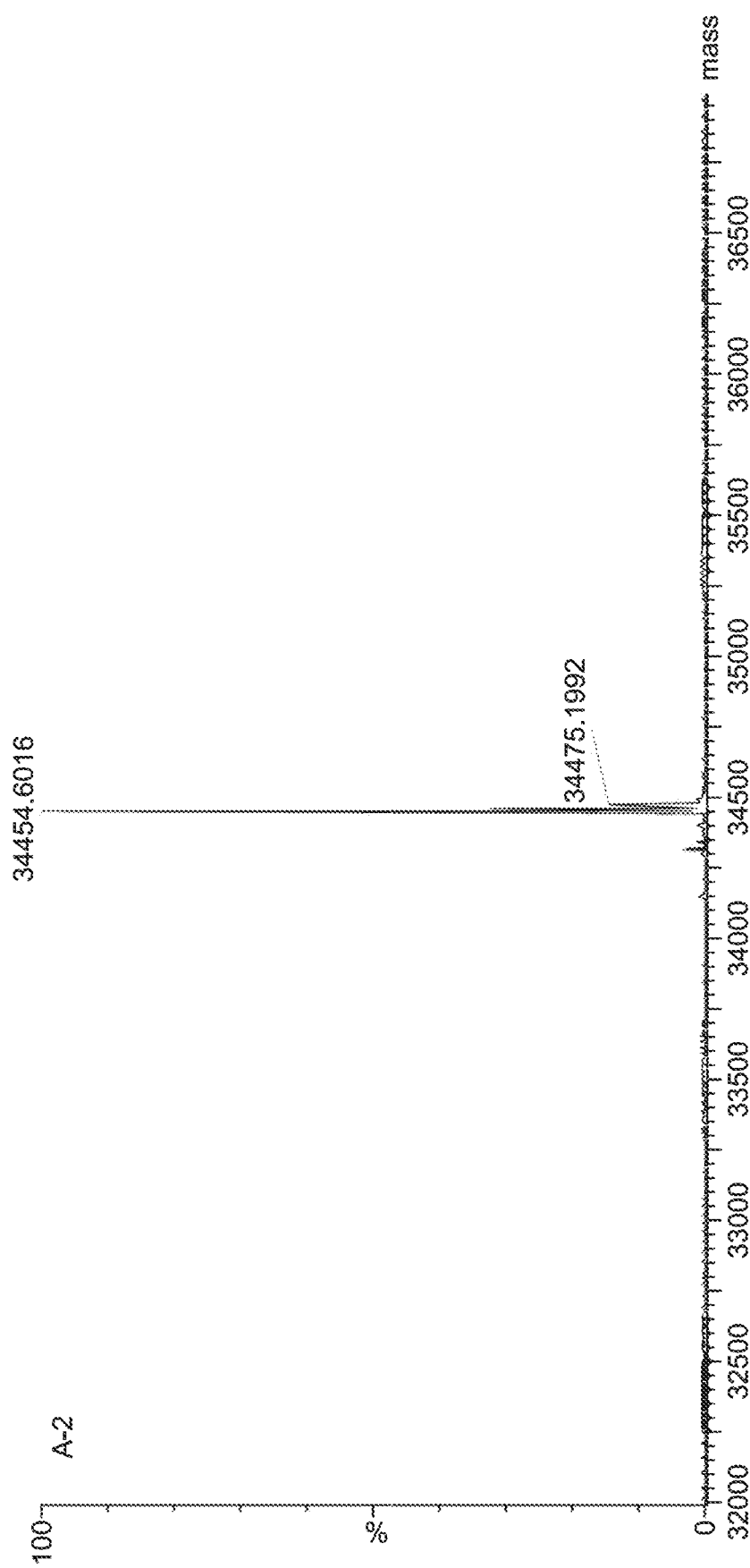
FIG. 13B shows a deconvoluted mass spectrum of peak A-2 (retention time of 3.25 min)
Figure 13C:
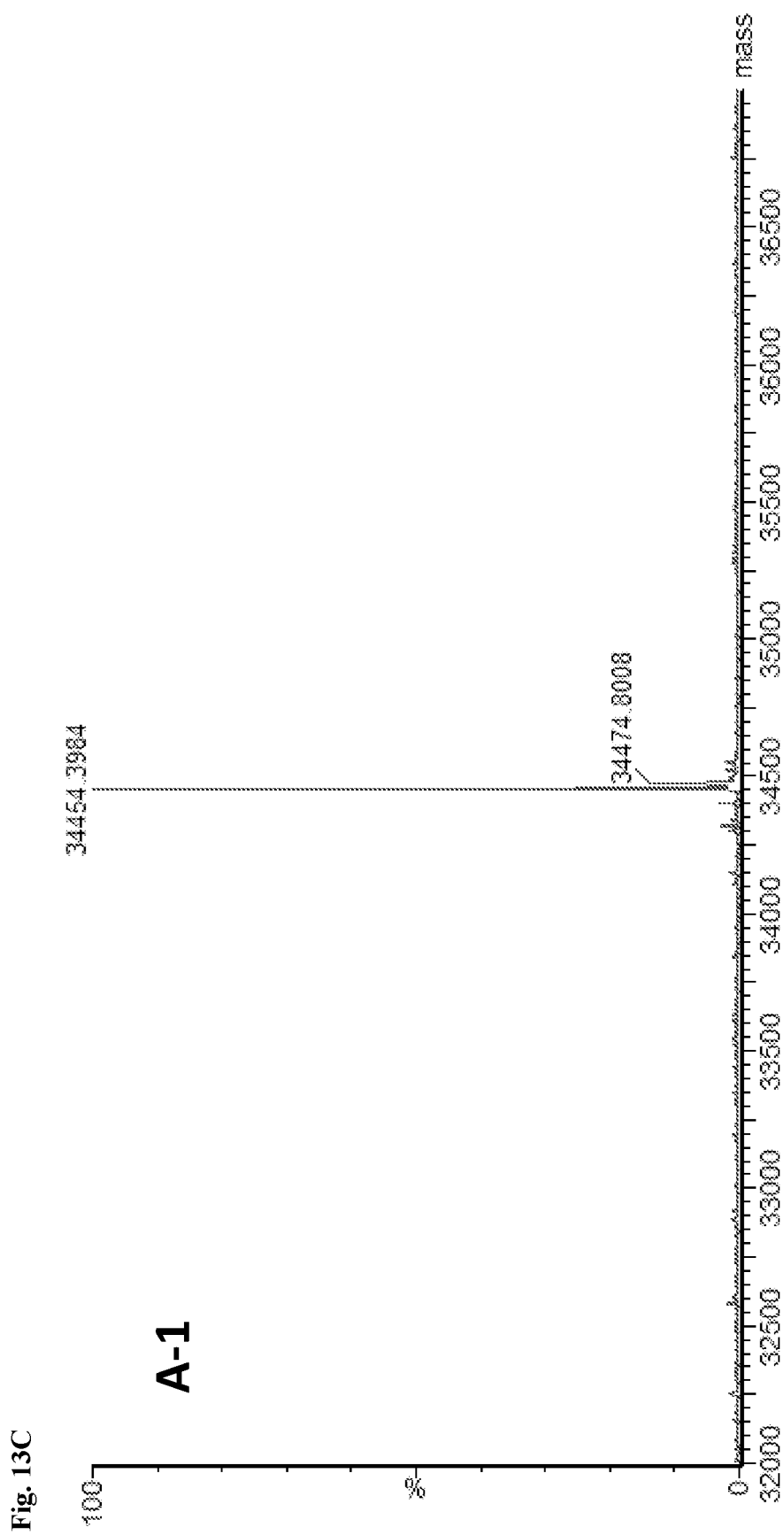
FIG. 13C shows a deconvoluted mass spectrum of peak A-1 (retention time of 3.14 min). Analysis of each peak by mass spectrometry indicated that both products have the same molecular weight.

FIG. 13A shows LC-MS data for an unpurified composition of urea-linked guide molecules with both a major product (A-2, retention time of 3.25 min) and a minor product (A-1, retention time of 3.14 min) present. We note that the minor product (A-1) in FIG. 13A was enriched by combining fractions from the anion exchange purification that contained a higher percentage of carbamate minor product for purposes of illustration. The side product is typically detected in up to 10% yield in the synthesis of guide molecules in accordance with the process of Example 1. Analysis of each peak by mass spectrometry indicated that both products have the same molecular weight (see FIG. 13B and FIG. 13C).

In light of this, we hypothesized that the minor product was a carbamate side product resulting from a reaction between the 5'-NH$_2$ on the 5' end of the 3' guide molecule fragment and the 2'-OH on the 3' end of the 5' guide molecule fragment, as follows:

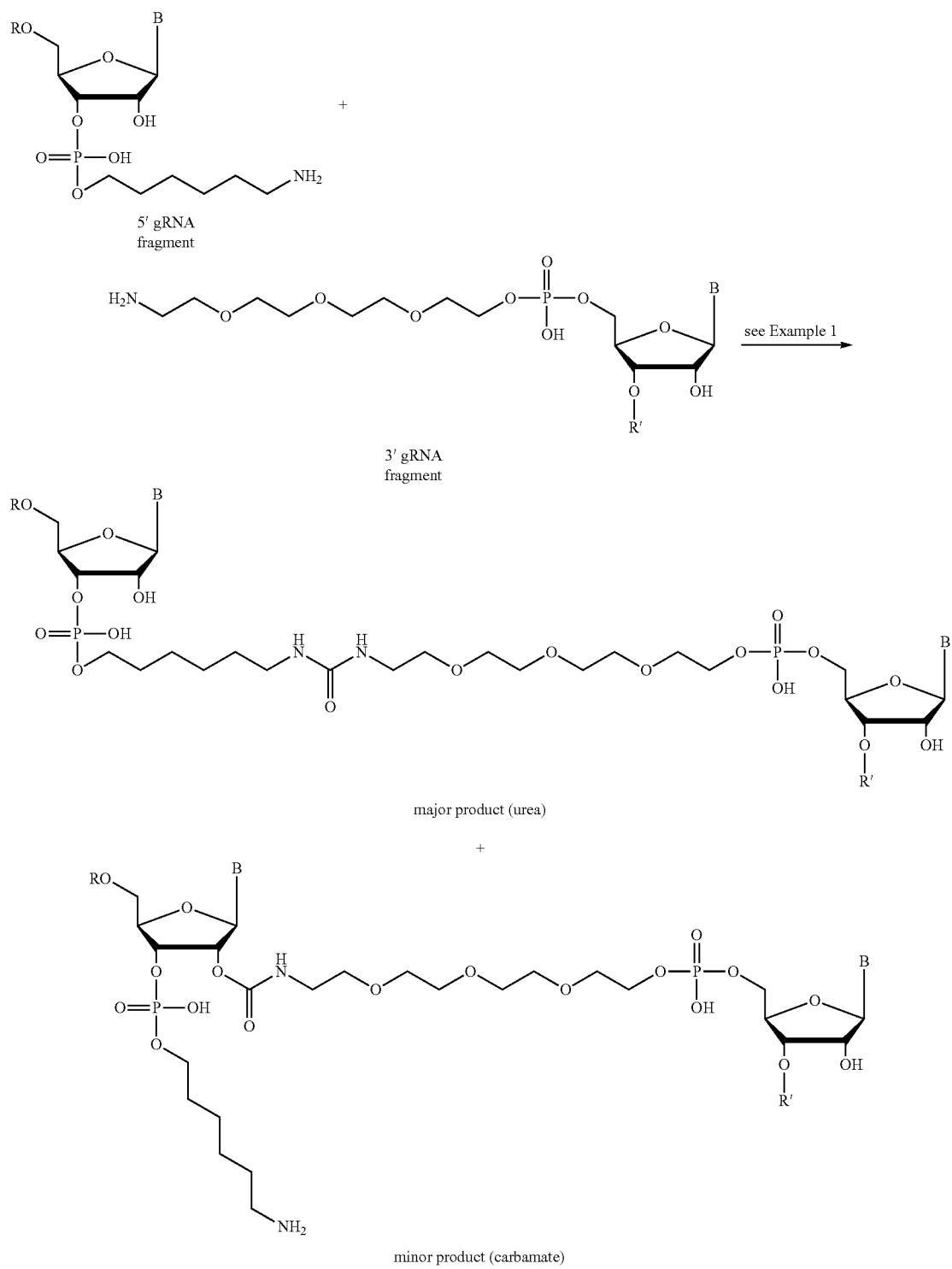

To further confirm the assignment of the carbamate side product, chemical modification with phenoxyacetic acid N-hydroxysuccinimide ester was performed. Basic chemical principles predict that only the minor product (carbamate) has a reactive nucleophilic center (free amine), and therefore only the minor product will be chemically functionalized. Addition of phenoxyacetic acid N-hydroxysuccinimide ester to the crude composition of urea-linked guide molecules should therefore result in a mixture of the major product (urea) and a chemically modified minor product (carbamate):

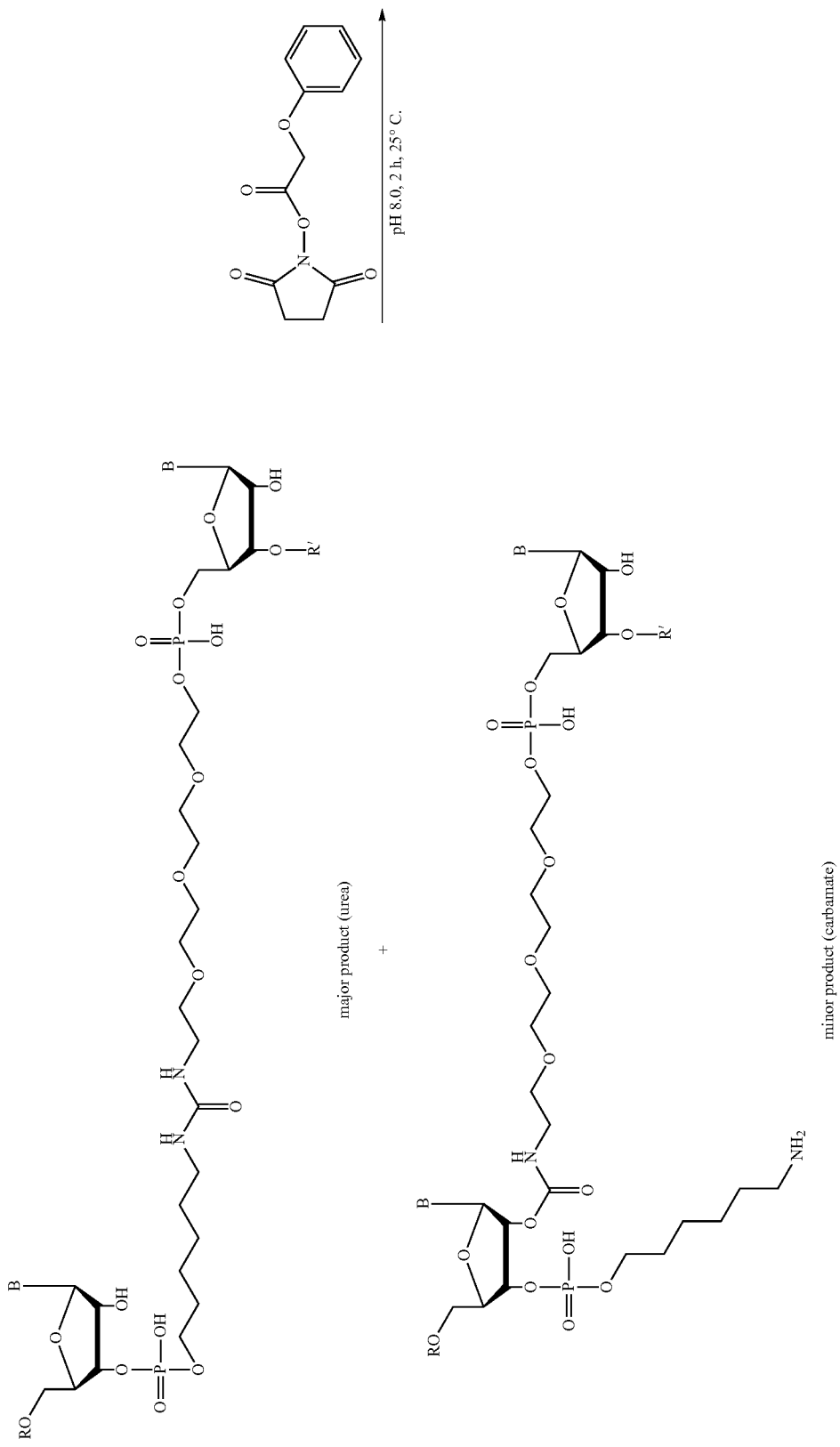

-continued
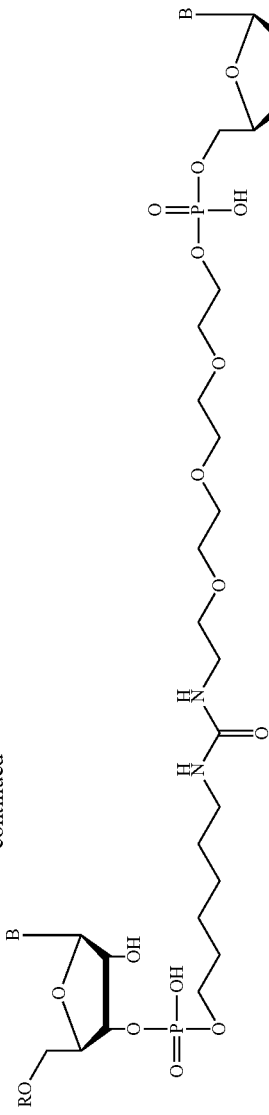
major product (urea)
+
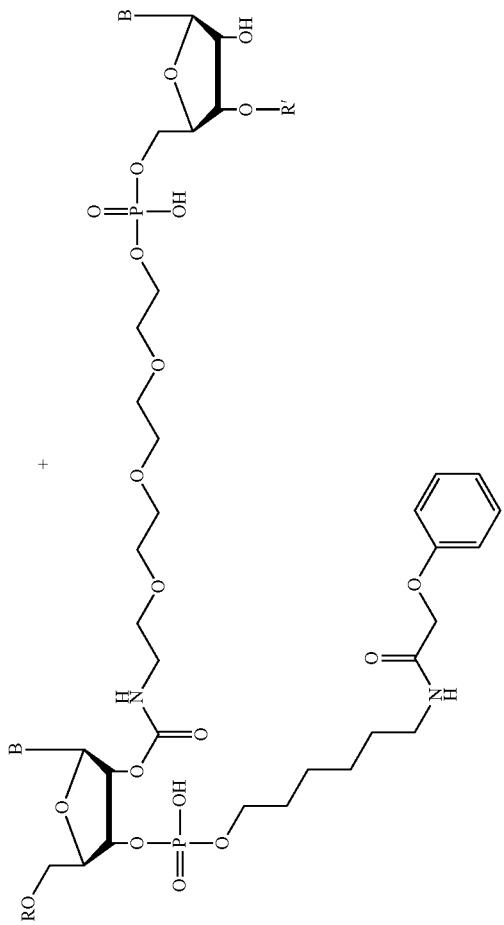
chemically modified minor product (carbamate)

Figure 14A:
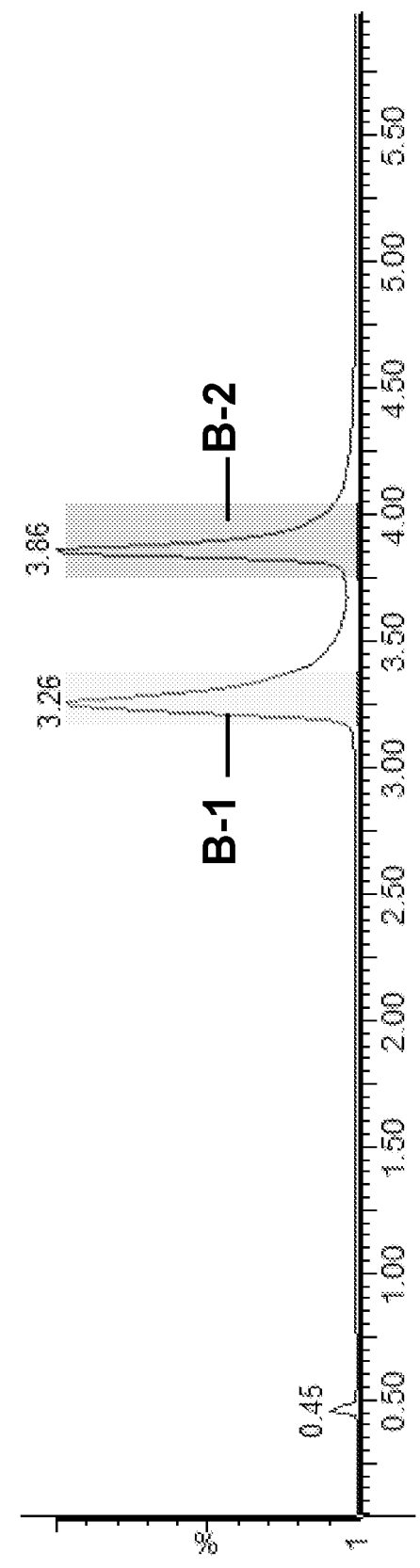
FIG. 14A shows LC-MS data for the guide molecule composition after chemical modification as described in Example 10. The major product (B-1, urea) has the same retention time as in the original analysis (3.26 min), while the retention time of minor product (B-2, carbamate) has shifted to 3.86 min, consistent with chemical functionalization of the free amine moiety.
Figure 14B:
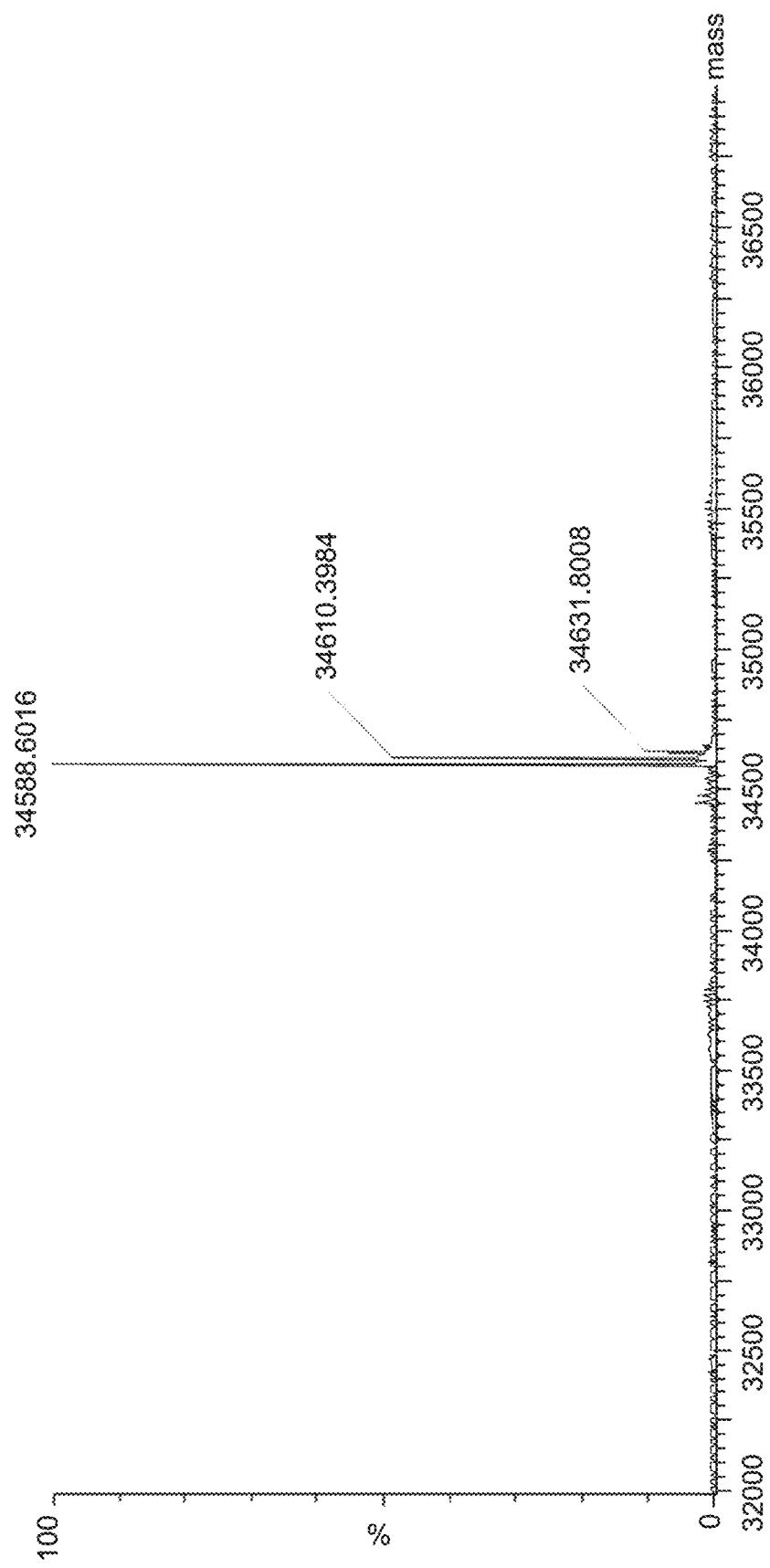
FIG. 14B shows a mass spectrum of peak B-2 (retention time of 3.86 min). Analysis of the peak at 3.86 min (M+134) indicates the predicted functionalization has occurred.

FIG. 14A shows LC-MS data for the guide molecule composition after chemical modification. The major product (B-1, urea) has the same retention time as in the original analysis (3.26 min, FIG. 13A), while the retention time of minor product (B-1, carbamate) has shifted to 3.86 min, consistent with chemical functionalization of the free amine moiety. Furthermore, mass spectrometric analysis of the peak at 3.86 min (M+134) indicates the predicted functionalization has occurred (see FIG. 14B). These results suggest the minor product is indeed a carbamate side product.

Figure 15A:
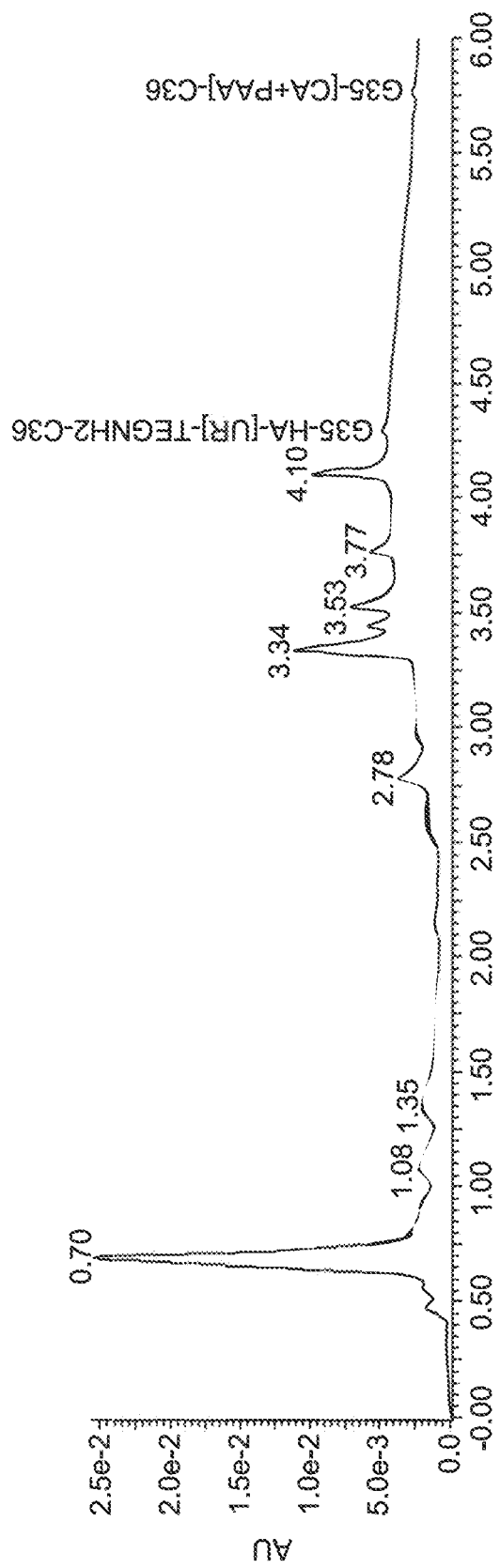
FIG. 15A shows the LC-MS trace of the fragment mixture after digestion with T1 endonuclease of a reaction mixture containing both major product (urea) and chemically modified minor product (carbamate). Both the urea linkage (G35-[UR]-C36) and the chemically modified carbamate linkage (G35-[CA+PAA]-C36) were detected at retention times of 4.31 min and 5.77 min, respectively.
Figure 15B:
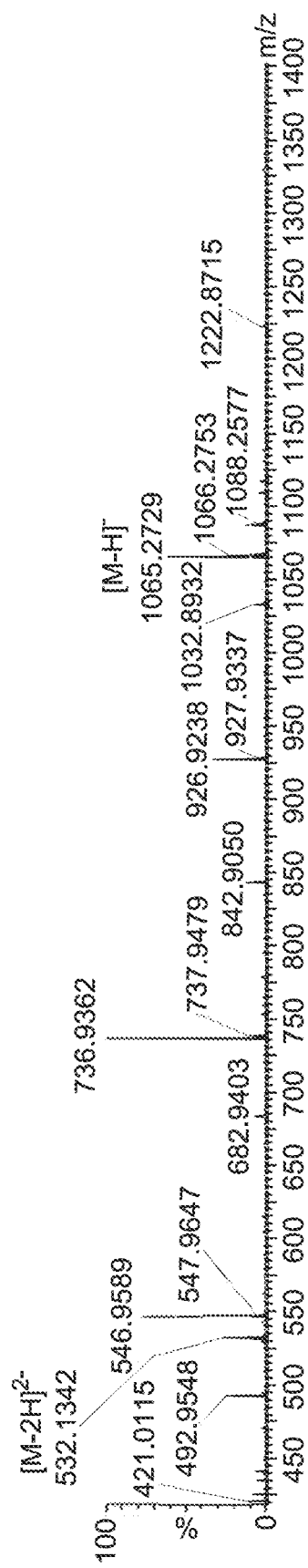
FIG. 15B shows the mass spectrum of the peak at 4.31 min, where m/z=532.13 is assigned to $[M-2H]^{2-}$.
Figure 15C:
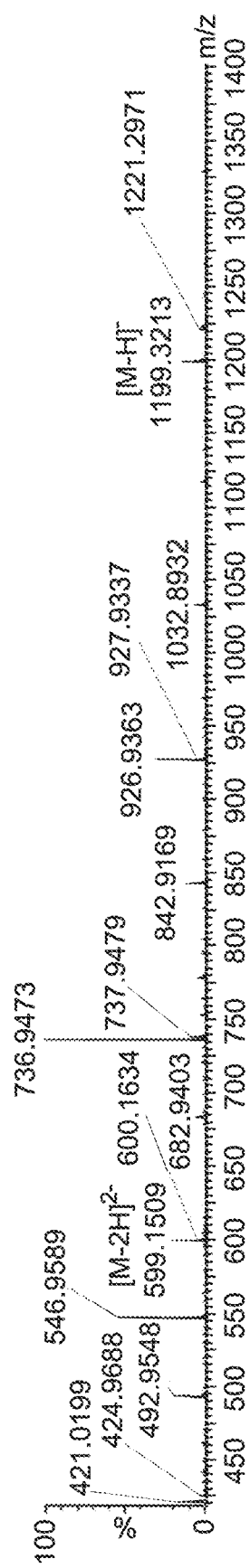
FIG. 15C shows the mass spectrum of the peak at 5.77 min, where m/z=599.15 is assigned to $[M-2H]^{2-}$.
Figure 15D:
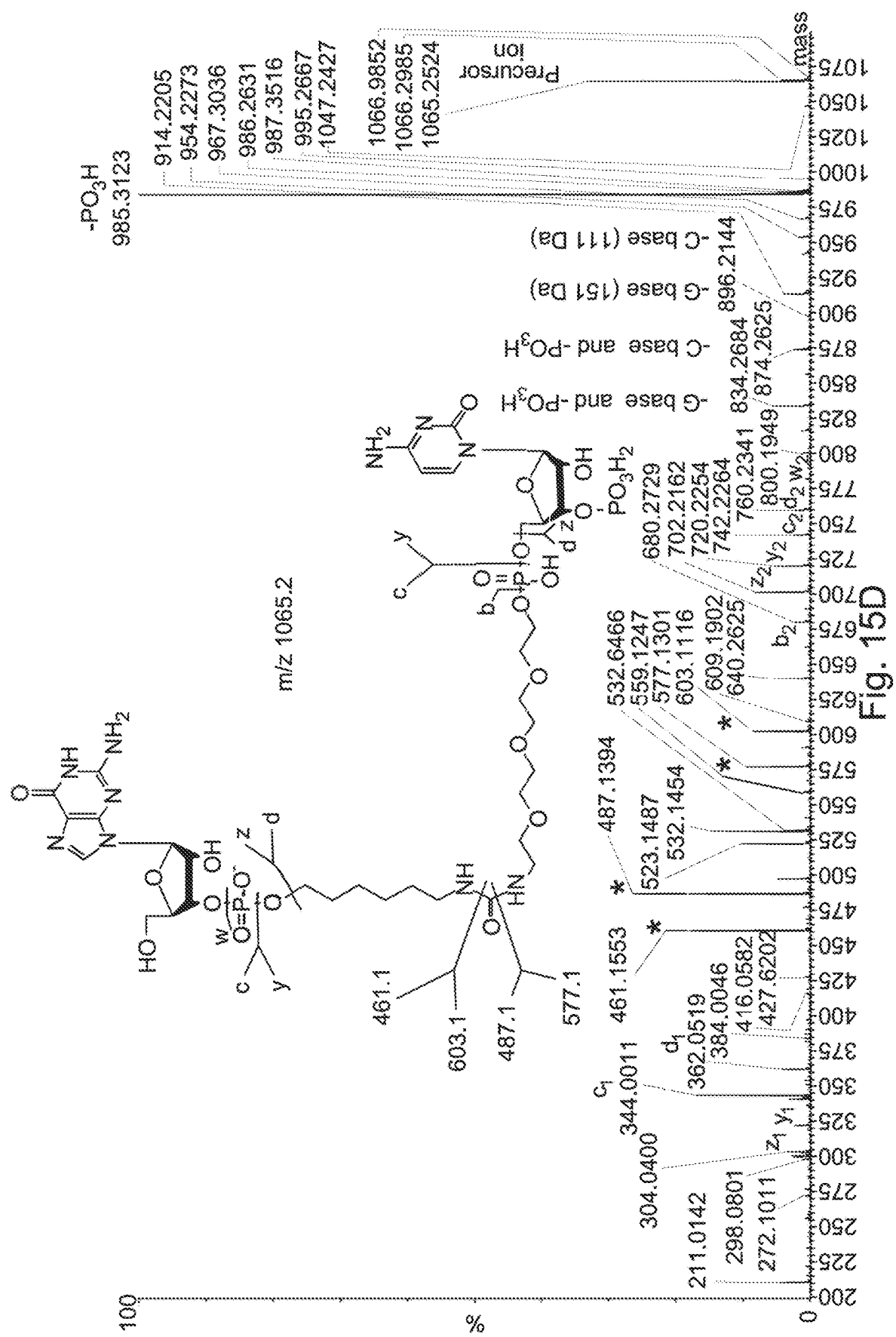
FIG. 15D and FIG. 15E show LC/MS-MS collision-induced dissociation (CID) experiments of m/z=532.1 from FIG. 15B and of m/z=599.1 from FIG. 15C.
Figure 15E:
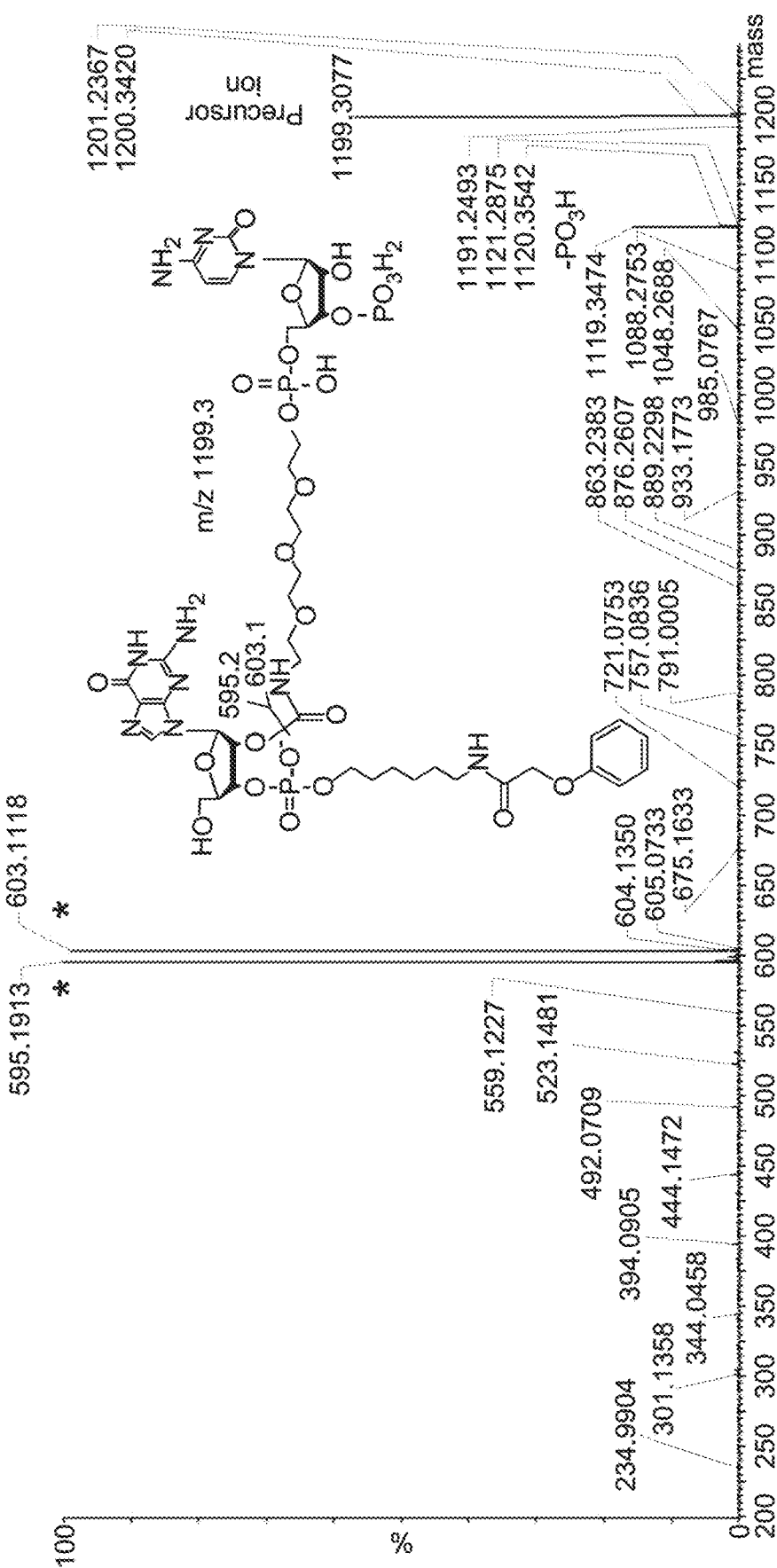

To further confirm the identity of the carbamate side product, the mixture of major product (urea) and chemically modified minor product (carbamate) were subjected to digestion with ribonuclease A (see Example 9), which cleaved the guide molecules at the 3'-end of each G nucleotide in the primary sequence. The fragments were then analyzed by LC-MS, and both the urea linkage (G35-[UR]—$C_{36}$) and the chemically modified carbamate linkage (G35-[CA+PAA]-$C_{36}$) were detected. FIG. 15A shows the LC-MS trace of the fragment mixture with the urea linkage at a retention time of 4.31 min and the chemically modified carbamate linkage at a retention time of 5.77 min. FIG. 15B shows the mass spectrum of the peak at 4.31 min, where m/z=532.1 is assigned to $[M-2H]^2$, and FIG. 15C shows the mass spectrum of the peak at 5.77 min, where m/z=599.1 is assigned to $[M-2H]^2$. The mass spectra were further analyzed using LC-MS/MS techniques. The LC-MS/MS spectrum (FIG. 15D) of the urea linked product at m/z 532.1, $[M-2H]^2$, contains the typical a-d and x-z ions that are observed in oligonucleotide collision-induced dissociation (CID) experiments. In addition, MS/MS fragment ions on either side of the UR linkage from the 5'-end (m/z=487.1 and 461.1) and the 3'-end (m/z=603.1 and 577.1) were observed. In contrast, only two product ions were observed in the LC-MS/MS spectrum (FIG. 15E) of the chemically modified carbamate linked product at m/z 599.1, $[M-2H]^{2-}$, including a MS/MS fragment ion from the 5'-end of the carbamate linkage (m/z=595.2) and the 3'-end of the carbamate linkage (m/z=603.1).

Example 11: Nucleotide Modifications for Single Product Formation

We hypothesized that formation of the carbamate side product as described in Example 10 could be prevented through strategic 2'-modifications in the nucleotide at the 3' end of the 5' guide molecule fragment. For example, replacing the 2'-OH in the nucleotide at the 3' end of the 5' guide molecule fragment with a 2'-H, synthesis of a urea-linked guide molecule in accordance with the process of Example 1 was hypothesized to yield a single urea-linked product with no carbamate side product:

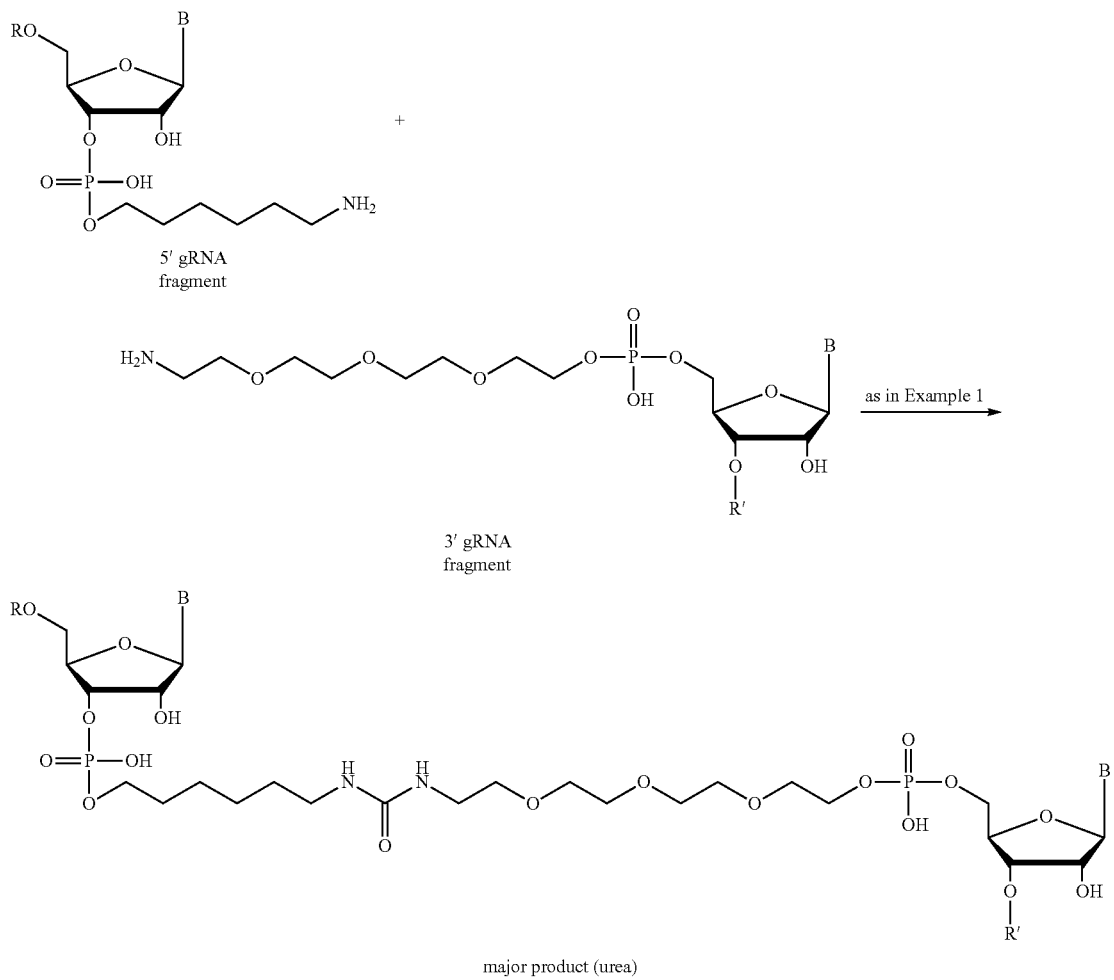

Figure 16A:
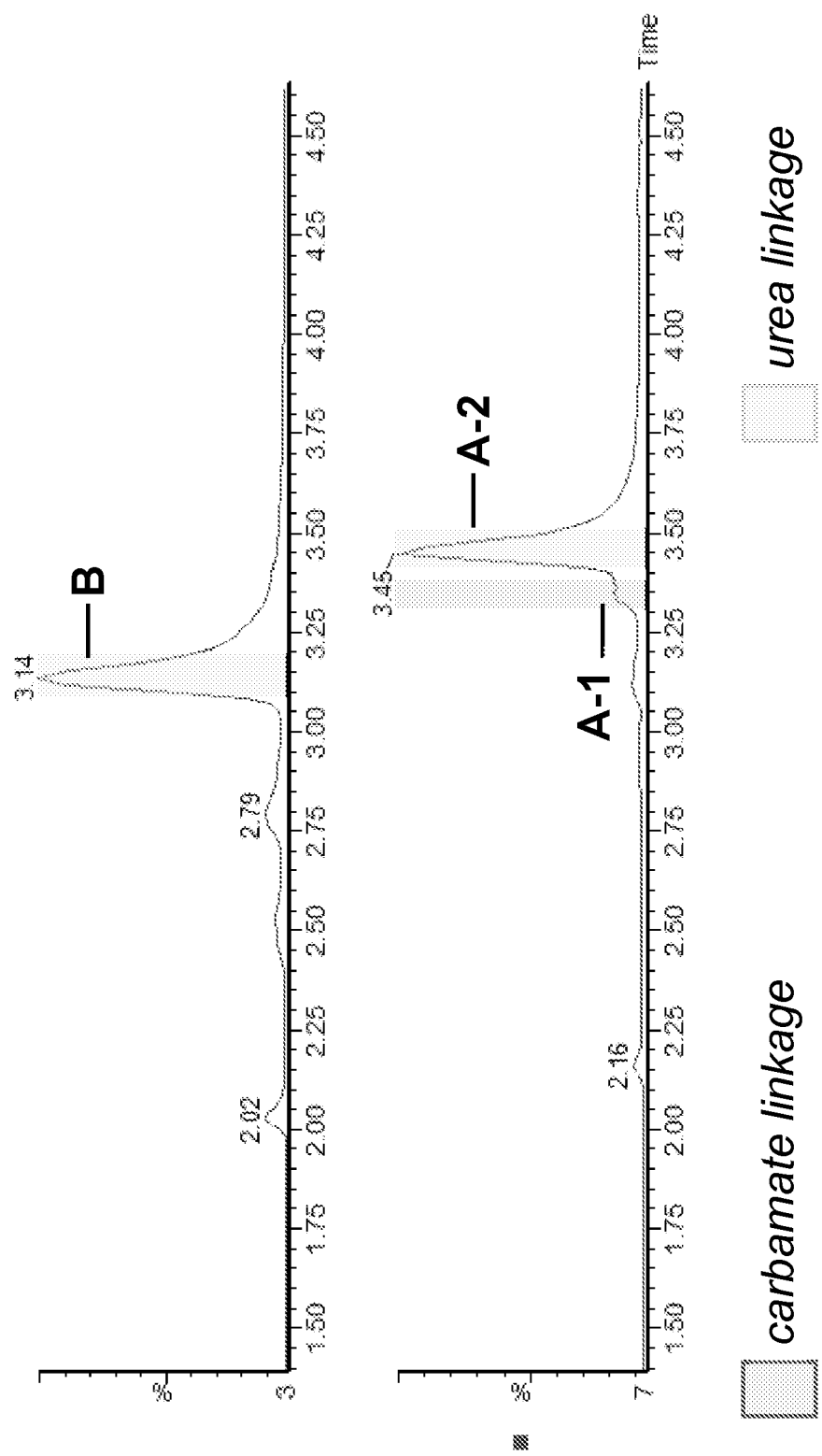
FIG. 16A shows LC-MS data of the crude reaction mixture for a reaction with a 2'-H modified 5' guide molecule fragment (upper spectrum), compared to a crude reaction mixture for a reaction with an unmodified version of the same 5' guide molecule (lower spectrum). There is no carbamate side product formation observed with the 2'-H modified 5' guide molecule fragment (upper spectrum). In contrast, the crude reaction mixture for a reaction with an unmodified version of the same 5' guide molecule fragment (lower spectrum) included a mixture of the major urea-linked product (A-2) and the minor carbamate side product (A-1). We note that, unlike in Example 10, the carbamate side product was not enriched and was therefore detected at much lower levels than in FIG. 13A of Example 10.
Figure 16B:
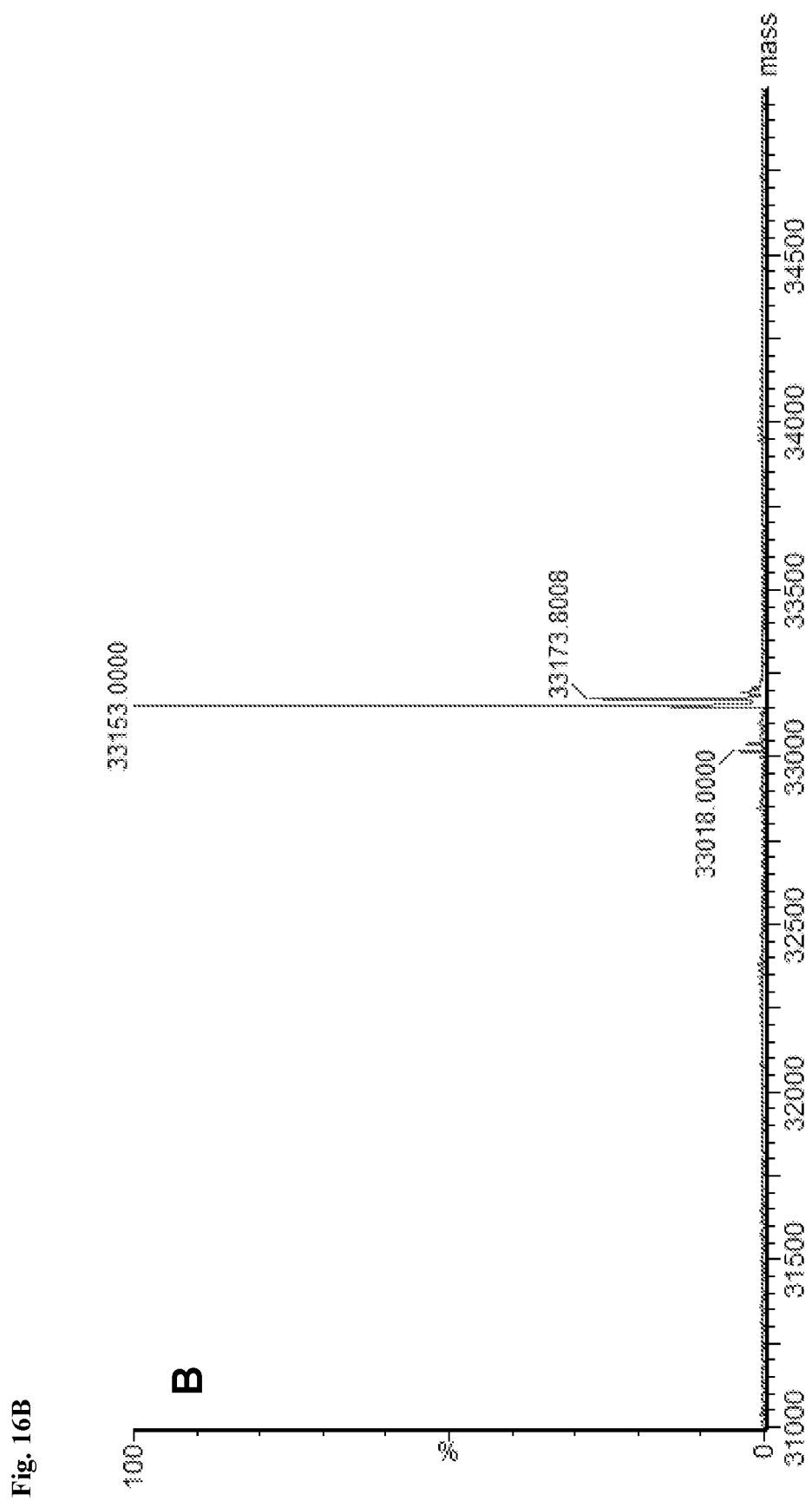
FIG. 16B shows a deconvoluted mass spectrum of peak B (retention time of 3.14 min, upper spectrum of FIG. 16A)
Figure 16C:
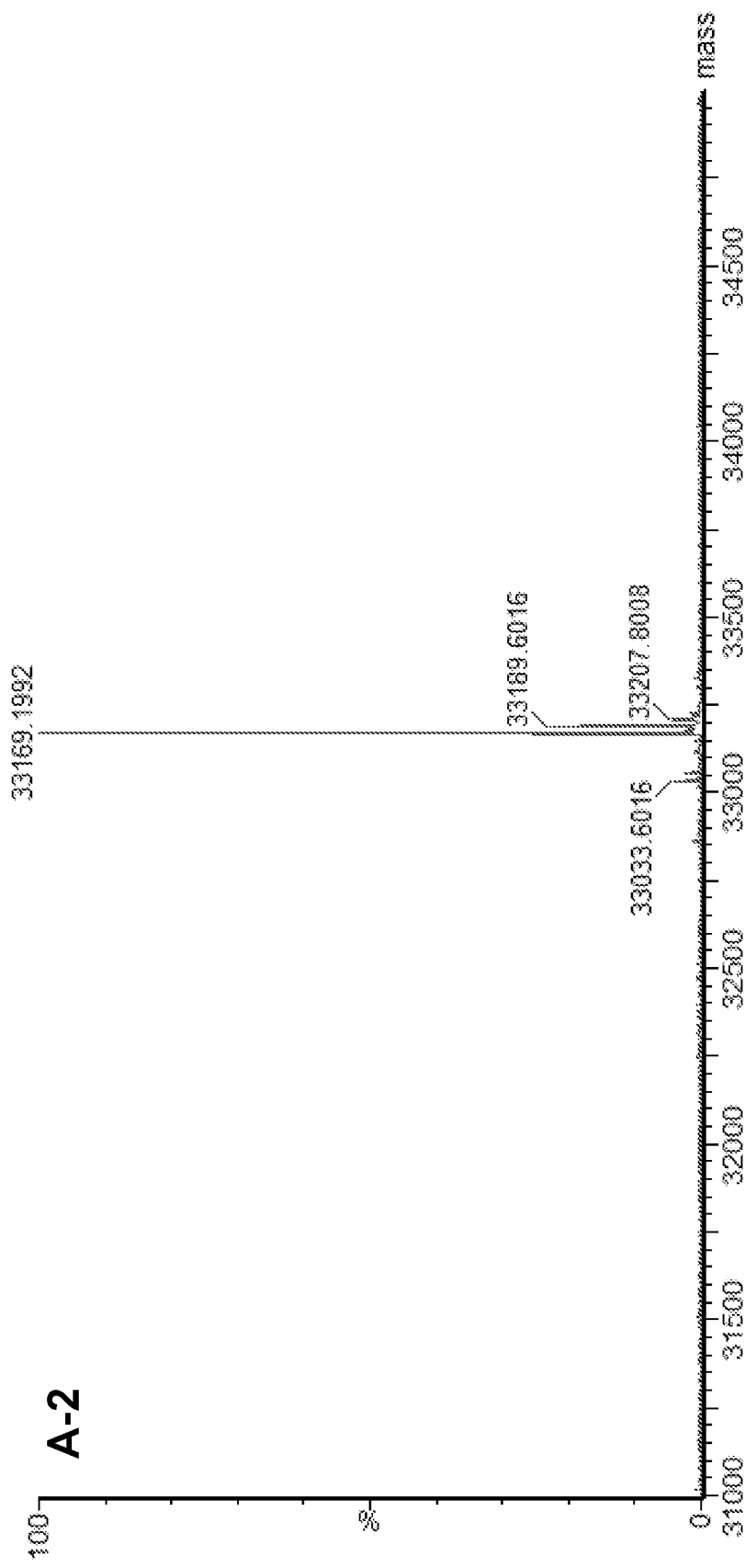
FIG. 16C shows a deconvoluted mass spectrum of peak A-2 (retention time of 3.45 min, lower spectrum of FIG. 16A). Analysis of the product of the reaction with the 2'-H modified 5' guide molecule fragment (B) gave M-16 (compared to A-2, the major unmodified urea-linked product), as expected for a molecule where a 2'-OH has been replaced with a 2'-H (see FIG. 16B and FIG. 16C).

FIG. 16A shows LC-MS data of the crude reaction mixture for a reaction with a 2'-H modified 5' guide molecule fragment (upper spectrum), compared to a crude reaction mixture for a reaction with an unmodified version of the same 5' guide molecule (lower spectrum). There is no carbamate side product formation observed with the 2'-H modified 5' guide molecule fragment (upper spectrum). In contrast, the crude reaction mixture for a reaction with an unmodified version of the same 5' guide molecule fragment (lower spectrum) included a mixture of the major urea-linked product (A-2) and the minor carbamate side product (A-1). We note that, unlike in Example 10, the carbamate side product was not enriched and was therefore detected at much lower levels than in FIG. 13A of Example 10. Furthermore, mass spectrometric analysis of the product of the reaction with the 2'-H modified 5' guide molecule fragment (B) gave M-16 (compared to A-2, the major unmodified urea-linked product), as expected for a molecule where a 2'-OH has been replaced with a 2'-H (see FIG. 16B and FIG. 16C).

Figure 17A:
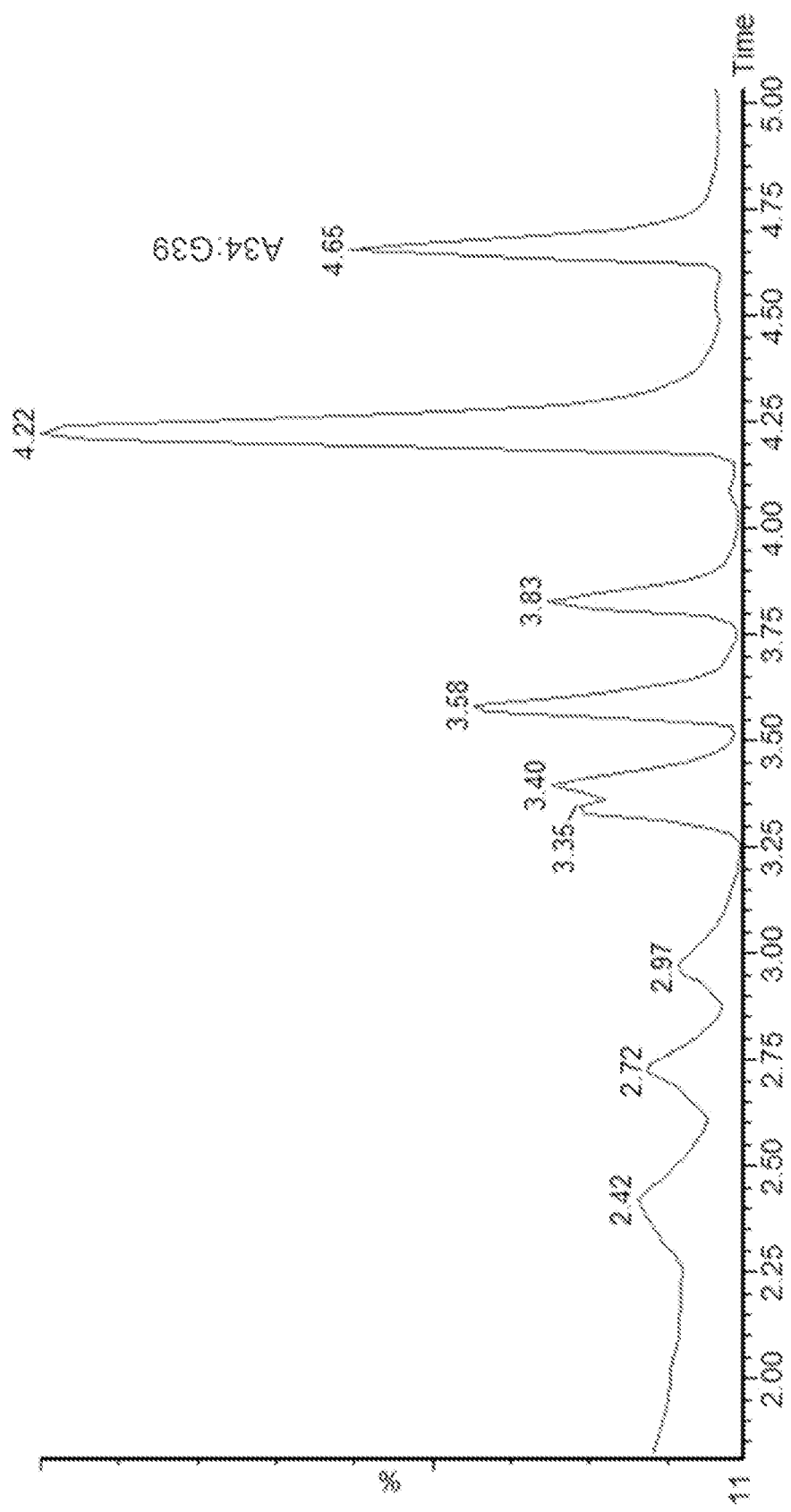
FIG. 17A shows a LC-MS trace after T1 endonuclease digestion of gRNA 1L.
Figure 17B:
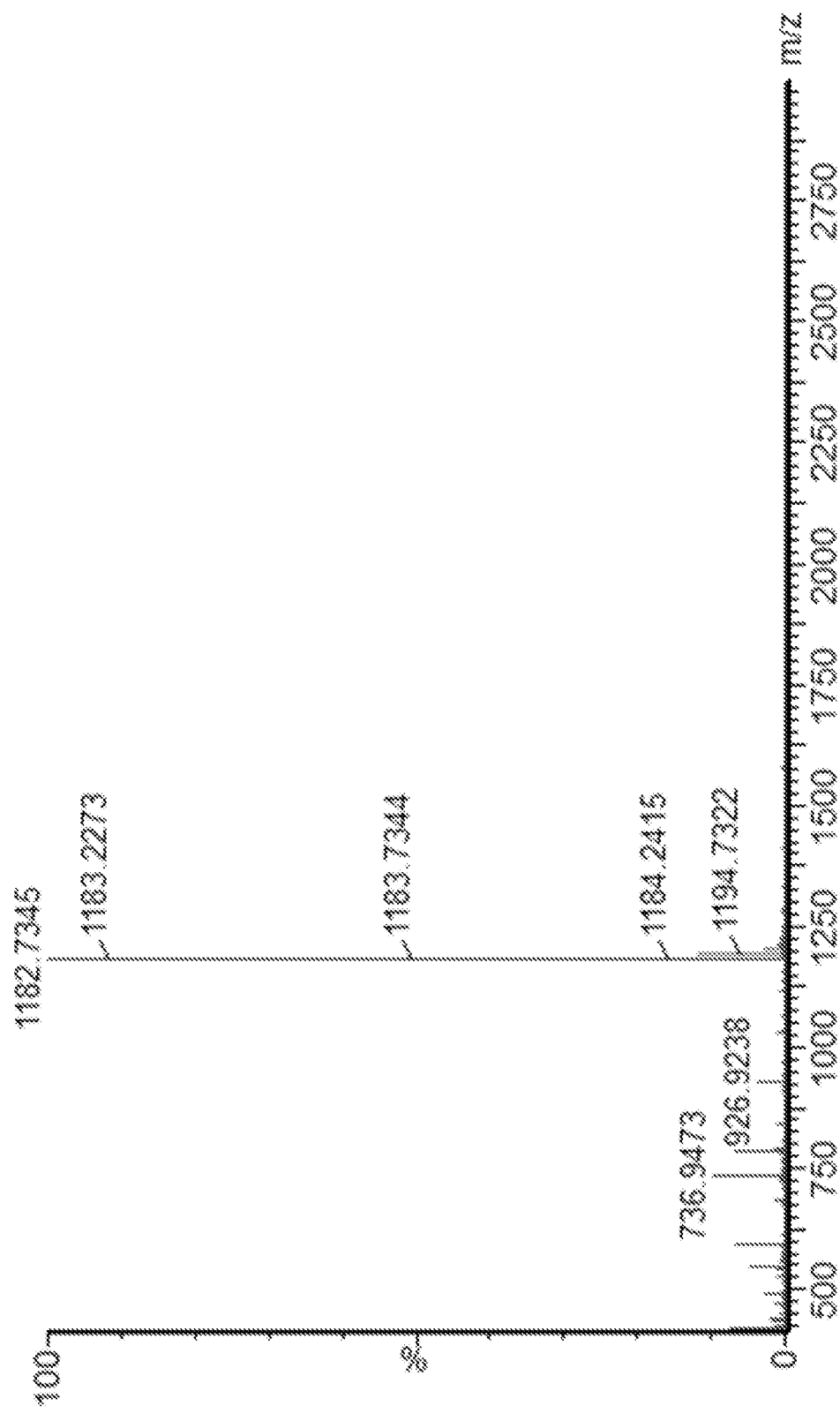
FIG. 17B shows a mass spectrum of the peak with a retention time of 4.65 min (A34:G39). In particular, the fragment containing the urea linkage, A-[UR]-AAUAG (A34:G39), was detected at a retention time of 4.65 min with m/z=1182.7.

An analogous experiment was performed using gRNA 1L of Table 17, which contains the same 2'-H modification. The formation of a 2'-H modified, urea-linked guide molecule was confirmed by T1 endonuclease digestion, followed by mass spectrometric analysis (see Example 9). The fragment containing the urea linkage, (2'-H-A)-[UR]-AAUAG (A34:G39), was detected at a retention time of 4.65 min (FIG. 17A) with m/z=1182.7 (FIG. 17B). LC-MS/MS analysis of this precursor ion revealed fragment ions consistent with a urea linkage in the reaction with the 2'-H modified nucleotide.

These results suggest that through 2'-OH modifications in the nucleotide at the 3' end of the 5' guide molecule fragment, the formation of the carbamate side product can be avoided. Consequently, the urea-ligated guide molecule is synthesized in high purity, which streamlines the overall process of producing a conjugated guide molecule.

Example 12: Upper Stem Variants

Figure 18:
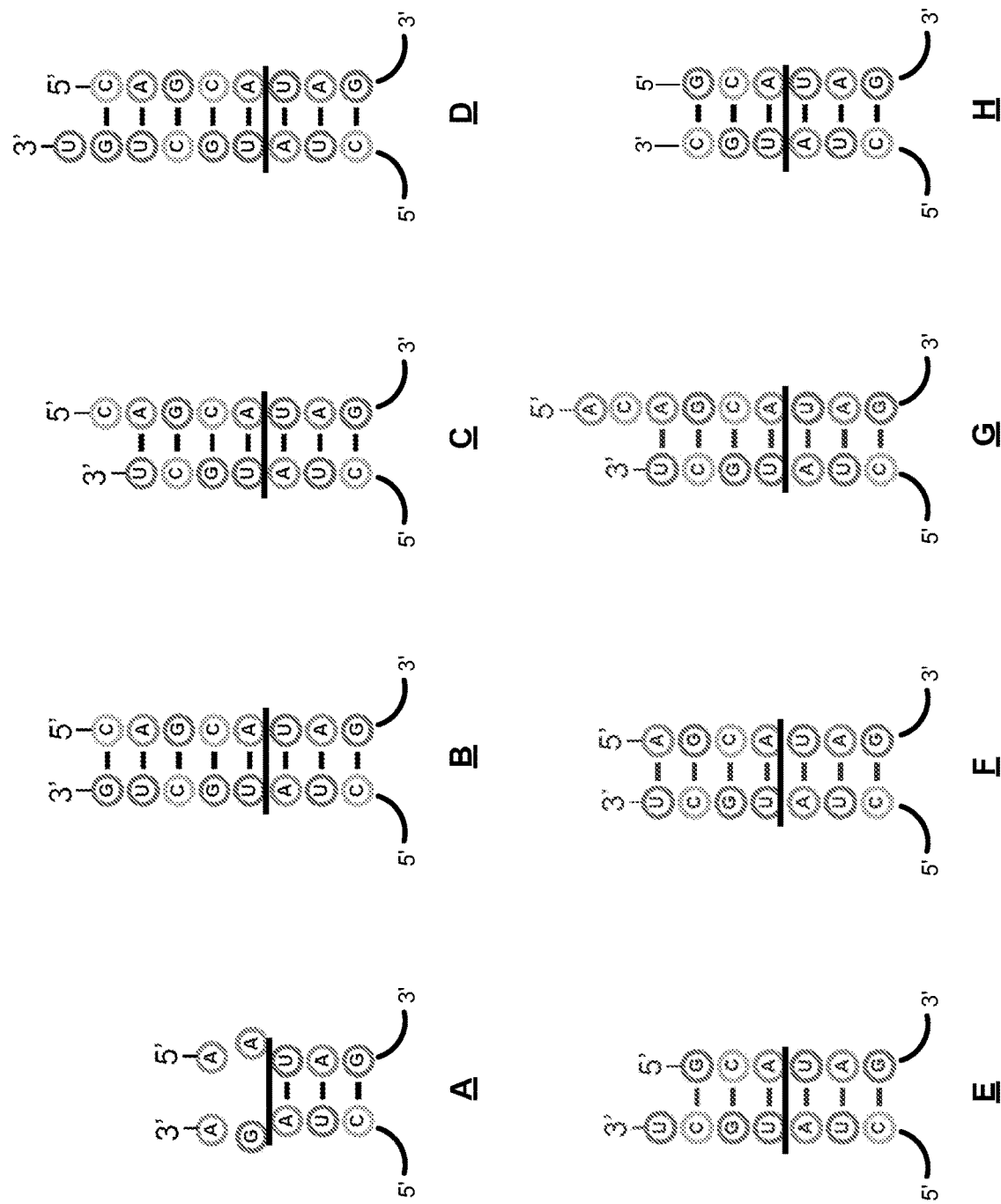
FIG. 18 shows exemplary upper stem variants as described in Example 12.

In the following Examples, guide molecules are prepared through conjugation of a 5' guide molecule fragment and a 3' guide molecule fragment. The guide molecule fragments used were substantially the same in each experiment, except for variations in the upper stem region in proximity to the linkage site (FIG. 18).

Example 13: Exemplary Process for Conjugation Through Carbamate Linkage

A first 5' guide molecule fragment (e.g. a 36-mer) was synthesized with a $C_6$—$NH_2$ linker at the 3' end, and a second 3' guide molecule fragment (e.g. a 69-mer) was synthesized with a hydroxyl group at the 5' end. The two guide molecule fragments were mixed at a molar ratio of 1:1 in a pH 9.0 buffer comprising 10 mM sodium borate, 150 mM NaCl, and 5 mM $MgCl_2$. The resulting guide molecule concentration was 50-100 µM. The two guide molecule fragments were annealed, followed by three additions of disuccinimidyl carbonate (DSC) in DMF (2.2 mM final concentration). Each addition of DSC was separated by 45 minutes. Following the addition of DSC, the reaction mixture was vortexed briefly and kept at room temperature for 1 h, followed by removal of excess DSC, and HPLC purification. Using upper stem variant C, a guide molecule with the following carbamate linkage was detected by LCMS (calculated: 33812.3 Da, observed: 33812.8 Da):

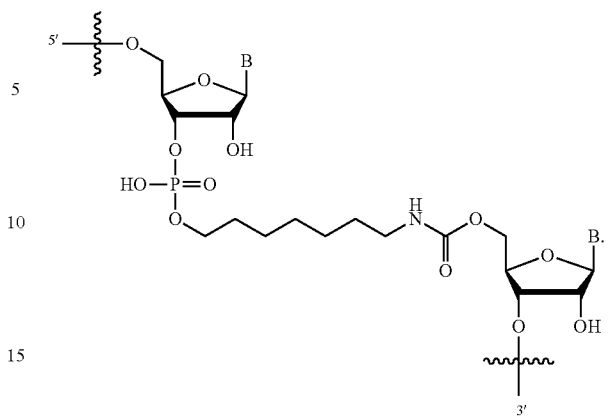

LC-MS/MS analysis (e.g., as described in Example 9) of RNAse T1 and RNAse A digestion products confirms the assignment of the above linkage.

Table 19 summarizes results from conjugation with carbamate linkages.

TABLE 19

| | % Conversion |
| --- | --- |
| Upper Stem Variant | % Conversion[a] |
| A | ND |
| B | 1% |
| B[b] | — |
| C | 14% |
| D | — |

[a]ND = not determined; a dash indicates conversion was not detected.
[b]Upper stem variant B with a 3'-DNA base was used.

Example 14: Exemplary Process for Conjugation Through Urea Linkage

A first 5' guide molecule fragment (e.g. a 36-mer) was synthesized with a 2' amino functionality on the 3' end of the guide molecule, and a second 3' guide molecule fragment (e.g. a 67-mer) was synthesized with a TEG-$NH_2$ linker at the 5' end. The two guide molecule fragments were mixed at a molar ratio of 1:1 in pH 8.5 buffer with 10 mM sodium borate, 150 mM NaCl, and 5 mM $MgCl_2$. The resulting guide molecule concentration was about 50-100 µM. The two guide molecule fragments were annealed, followed by addition of disuccinimidyl carbonate (DSC) in DMF (2.2 mM final concentration). The reaction mixture was vortexed briefly and kept at room temperature for 1 h, followed by removal of excess DSC, and HPLC purification. Using upper stem variant E, a guide molecule with the following urea linkage was detected by LCMS (calculated: 33294.9 Da, observed: 33294.0 Da):

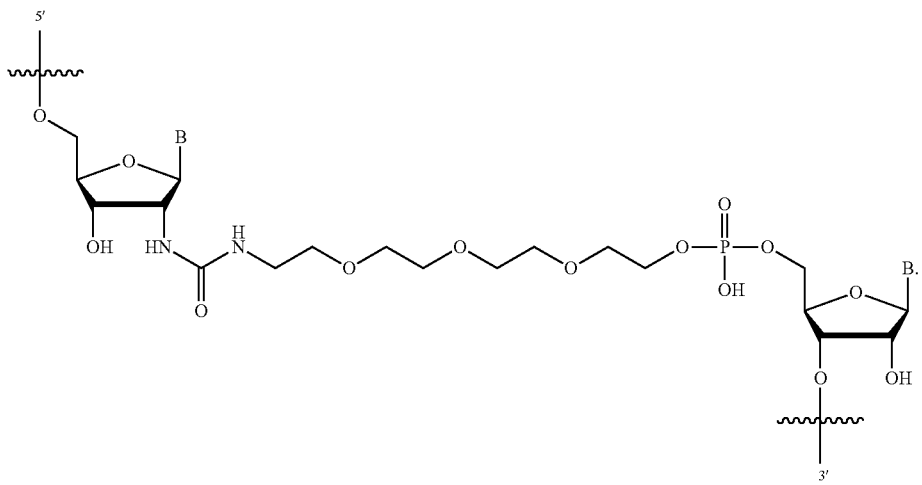

LC-MS/MS analysis (e.g., as described in Example 9) of RNAse T1 digestion products confirms the assignment of the above linkage.

Table 20 summarizes results from conjugation with urea linkages.

TABLE 20

| Upper Stem Variant | % Conversion |
|---|---|
| C | 30% |
| E | 35% |
| F | 30% |
| G | 26% |

Example 15: Exemplary Process for Conjugation Through Amidine Linkage

A first 5' guide molecule fragment (e.g. a 37-mer) was synthesized with a $C_6$—$NH_2$ linker at the 3' end, and a second 3' guide molecule fragment (e.g. a 69-mer) was synthesized with a TEG-$NH_2$ linker at the 5' end. The two guide molecule fragments were mixed at a molar ratio of 1:1 in pH 9.0 buffer with 10 mM sodium borate, 150 mM NaCl, and 5 mM $MgCl_2$. The resulting guide molecule concentration was about 50-100 µM. The two guide molecule fragments were annealed, followed by addition of dimethyl pimelimidate (DMP) in DMSO (2.2 mM final concentration). The reaction mixture was vortexed briefly and kept at room temperature for 1 h, followed by removal of excess DMP, and HPLC purification. Using upper stem variant B, a guide molecule with the following amidine linkage was detected by LCMS (calculated: 34509.9 Da, observed: 34509.6 Da):

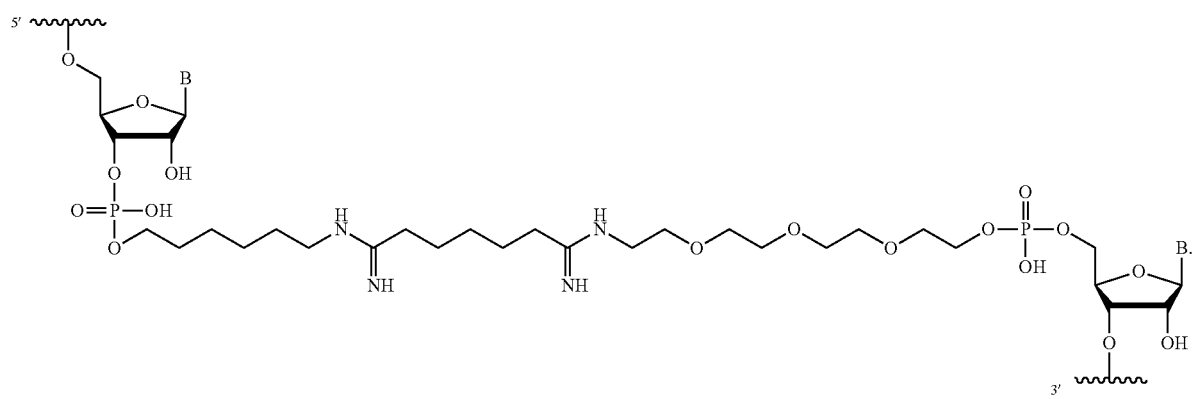

LC-MS/MS analysis (e.g., as described in Example 9) of RNAse A digestion products confirms the assignment of the above linkage.

Example 16: Exemplary Process for Conjugation Through Amide Linkage (I)

A first 5' guide molecule fragment (e.g. a 37-mer) was synthesized with a $C_6$—$NH_2$ linker at the 3' end, and a second 3' guide molecule fragment (e.g. a 69-mer) was synthesized with a TEG-$NH_2$ linker at the 5' end. The two guide molecule fragments were mixed at a molar ratio of 1:1 in pH 8.5 buffer with 10 mM sodium borate, 150 mM NaCl, and 5 mM $MgCl_2$. The resulting guide molecule concentration was about 50-100 µM. The two guide molecule fragments were annealed, followed by addition of disuccimidyl gluterate (DSG) in DMF (2.2 mM final concentration). The reaction mixture was vortexed briefly and kept at room temperature for 1 h, followed by removal of excess DSG, and HPLC purification. Using upper stem variant B, a guide molecule with the following amidine linkage was detected by LCMS (calculated: 34481.8 Da, observed: 34483.5 Da):

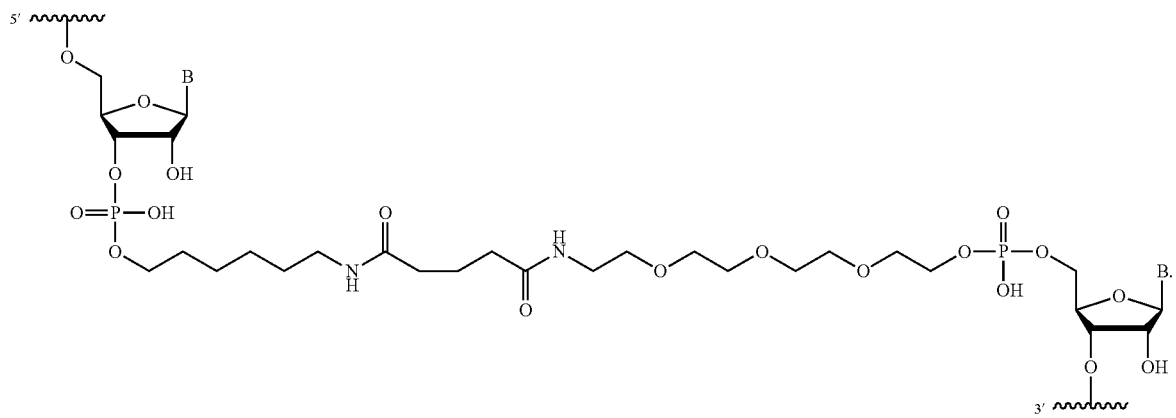

Example 17: Exemplary Process for Conjugation Through Amide Linkage (II)

A first 5' guide molecule fragment (e.g. a 37-mer) was synthesized with a $C_6$—$NH_2$ linker at the 3' end, and a second 3' guide molecule fragment (e.g. a 69-mer) was synthesized with a TEG-$NH_2$ linker at the 5' end. The two guide molecule fragments were mixed at a molar ratio of 1:1 in pH 8.5 buffer with 10 mM sodium borate, 150 mM NaCl, and 5 mM $MgCl_2$. The resulting guide molecule concentration was about 50-100 µM. The two guide molecule fragments were annealed, followed by addition of disuccimidyl suberate (DSS) in DMF (2.2 mM final concentration). The reaction mixture was vortexed briefly and kept at room temperature for 1 h, followed by removal of excess DSS, and HPLC purification. Using upper stem variant B, a guide molecule with the following amidine linkage was detected by LCMS (calculated: 34523.9 Da, observed: 34524.0 Da):

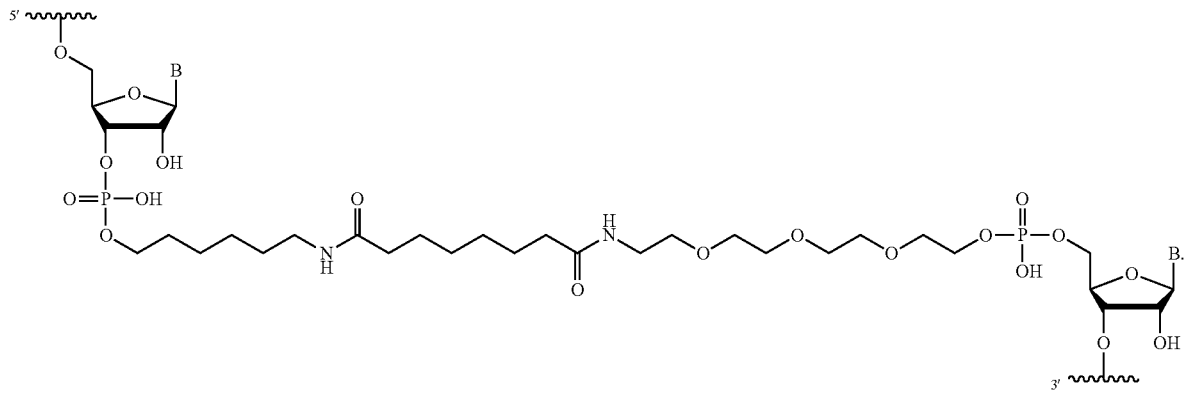

LC-MS/MS analysis (e.g., as described in Example 9) of RNAse A digestion products confirms the assignment of the above linkage.

Example 18: Exemplary Process for Conjugation Through Amide Linkage (III)

A first 5' guide molecule fragment (e.g. a 37-mer) was synthesized with a $C_6$—$NH_2$ linker at the 3' end, and a second 3' guide molecule fragment (e.g. a 69-mer) was synthesized with a TEG-$NH_2$ linker at the 5' end. The two guide molecule fragments were mixed at a molar ratio of 1:1 in pH 8.5 buffer with 10 mM sodium borate, 150 mM NaCl, and 5 mM $MgCl_2$. The resulting guide molecule concentration was about 50-100 µM. The two guide molecule fragments were annealed, followed by addition of bis(sulfosuccinimidyl) suberate (BS3) in water (2.2 mM final concentration). The reaction mixture was vortexed briefly and kept at room temperature for 1 h, followed by removal of excess BS3, and HPLC purification. Using upper stem variant B, a guide molecule with the following amidine linkage was detected by LCMS (calculated: 34523.9 Da, observed: 34524.0 Da):

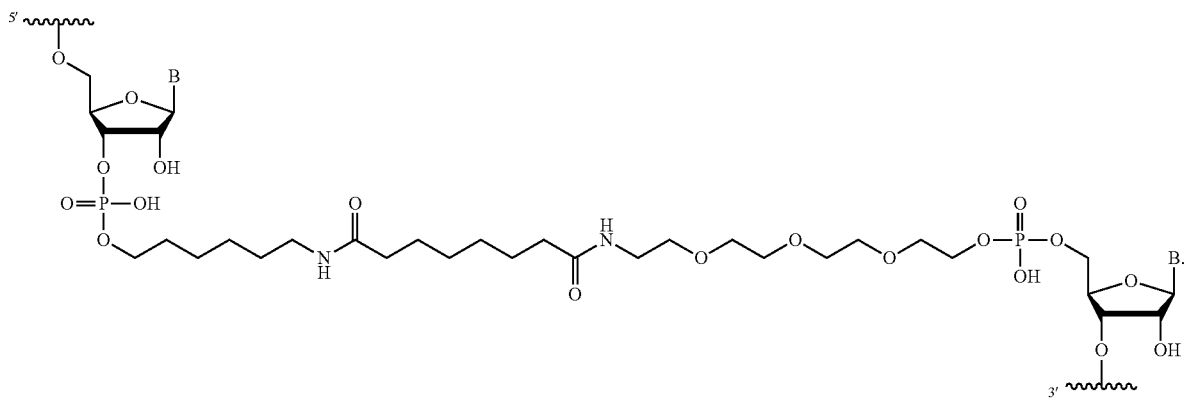

LC-MS/MS analysis (e.g., as described in Example 9) of RNAse A digestion products confirms the assignment of the above linkage.

Example 19: Exemplary Process for Conjugation Through Phosphoramidate Linkage (I)

The first 5' guide molecule fragment (e.g. a 37-mer) was synthesized with a $C_6$—$NH_2$ linker at the 3' end, and a second 3' guide molecule fragment (e.g. a 69-mer) was synthesized with a phosphate group at the 5' end. The two fragments were incubated at a molar ratio of 2:1 in pH 6.0 buffer with 50 mM 2-(N-morpholino) ethanesulfonic acid (MES), 50 mM imidazole, 150 mM NaCl, 10 mM $MgCl_2$, and 10 mM $ZnCl_2$. The resulting guide concentration was about 40-100 µM. The two guide fragments were either annealed in the presence or absence of a 30-mer RNA template at a concentration between 40-100 µM. The RNA template is complementary to the ligation site. After annealing these components, 1-ethyl-3-(3-dimethylaminopropyl) carbodiimide hydrochloride (EDC) in water (100 mM final concentration) was added. The reaction mixture was vortexed briefly and kept at 4° C. for 12 h-3 days, followed by removal of excess EDC, and HPLC purification. Using upper stem variant B in the presence of a 30-mer RNA template, a guide molecule with the following phosphoramidate linkage was detected by LCMS (calculated: 34193.5 Da, observed: 34193.4 Da):

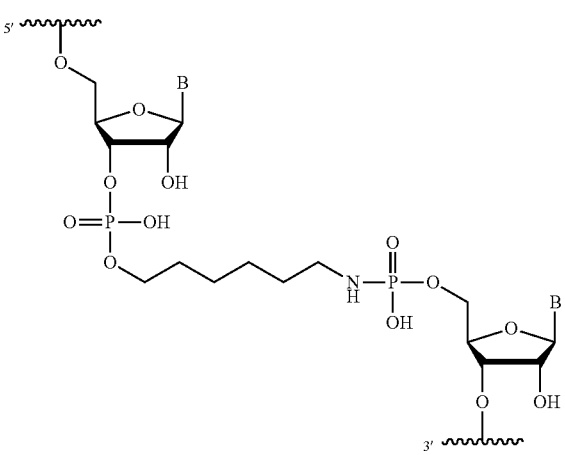

Table 21 summarizes results from conjugation with phosphoramidate linkages.

TABLE 21

| Upper Stem Variant[a] | % Conversion[b] |
|---|---|
| B (+) | 8% |
| B (−) | <1% |
| C (+) | <1% |
| C (−) | <1% |
| D (+) | <1% |
| D (−) | <1% |

[a](+) indicates a 30-mer RNA template was added; (−) indicates no RNA template was added;
[b]ND = not determined.

Example 20: Exemplary Process for Conjugation Through Phosphoramidate Linkage (II)

The first 5' guide molecule fragment (e.g. a 36-mer) was synthesized with a 2' amino moiety at the 3' end, and a second 3' guide molecule fragment (e.g. a 69-mer) was synthesized with a phosphate group at the 5' end. The two fragments were incubated at a molar ratio of 2:1 in pH 6.0 buffer with 50 mM 2-(N-morpholino) ethanesulfonic acid (MES), 50 mM imidazole, 150 mM NaCl, 10 mM MgCl$_2$, and 10 mM ZnCl$_2$. The resulting guide concentration was about 40 to 100 μM. The two guide fragments were either annealed in the presence or absence of a 30-mer RNA sequence at a concentration between 40-100 μM. The RNA template was complementary to the ligation site. After annealing these components, 1-ethyl-3-(3-dimethylaminopropyl) carbodiimide hydrochloride (EDC) in water (100 mM final concentration) was added. The reaction mixture was vortexed briefly and kept at 4° C. for 12 h-3 days, followed by removal of excess EDC, and HPLC purification. Using upper stem variant C in the presence of a 30-mer RNA template, a guide molecule with the following phosphoramidate linkage was provided in 37% conversion and was detected by LCMS (calculated: 33403.9 Da, observed: 33405.4 Da):

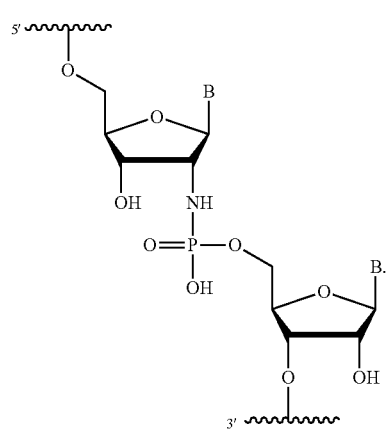

Example 21: Exemplary Process for Conjugation Through Phosphodiester Linkage The first 5' guide molecule fragment (e.g. a 37-mer) was synthesized with an RNA base at the 3' end, and a second 3' guide molecule fragment (e.g. a 69-mer) was synthesized with a phosphate group at the 5' end. The two fragments were incubated at a molar ratio of 2:1 in pH 6.0 buffer with 50 mM 2-(N-morpholino) ethanesulfonic acid (MES), 50 mM imidazole, 150 mM NaCl, 10 mM MgCl$_2$, and 10 mM ZnCl$_2$. The resulting guide concentration was about 40 to 100 μM. The two guide fragments were annealed in the presence of a 30-mer RNA template at a concentration between 40 and 100 μM. The RNA template was complementary to the ligation site. After annealing these components, 1-ethyl-3-(3-dimethylaminopropyl) carbodiimide hydrochloride (EDC) in water (100 mM final concentration) was added. The reaction mixture was vortexed briefly and kept at 4° C. for 12 h-3 days, followed by removal of excess EDC, and HPLC purification. Using upper stem variant B in the presence of a 30-mer RNA template, a guide molecule with the following mixture of phosphodiester linkages was provided in 13% conversion and was detected by LCMS (calculated: 34014.3 Da, observed: 34014.4 Da):

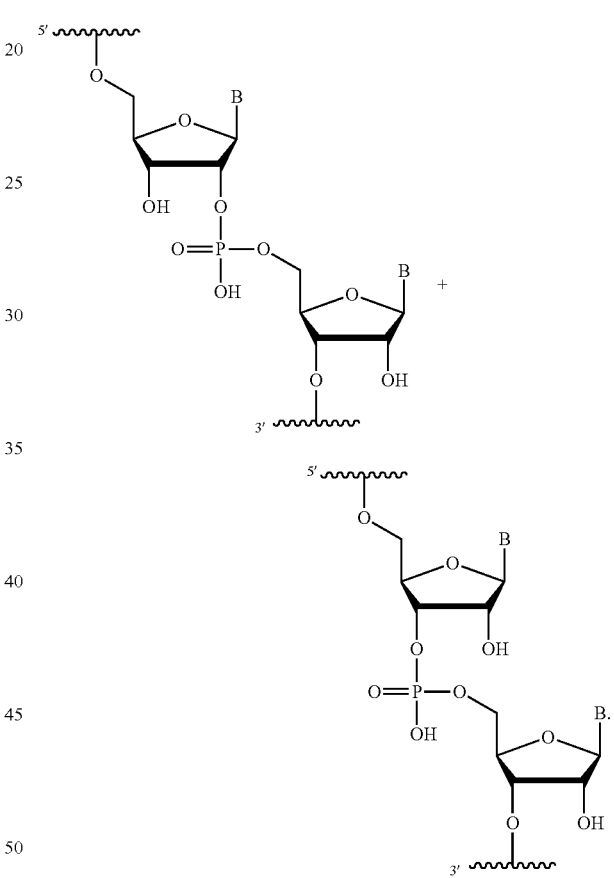

Table 22 summarizes results from conjugation with phosphoramidate linkages.

TABLE 22

| Upper Stem Variant[a] | % Conversion[b] |
|---|---|
| B (+) | 13% |
| B (−) | <1% |
| C (+) | <1% |
| C (−) | <1% |

[a](+) indicates a 30-mer RNA template was added; (−) indicates no RNA template was added;
[b]ND = not determined.

Example 22: Exemplary Process for Conjugation Through Disulfide Linkage (I)

A first 5' guide molecule fragment (e.g. a 37-mer) was synthesized with a $C_6$—$NH_2$ linker at the 3' end, and a second 3' guide molecule fragment (e.g. a 69-mer) was synthesized with a TEG-$NH_2$ linker at the 5' end. The two guide molecule fragments were mixed at a molar ratio of 1:1 in pH 8.5 buffer with 10 mM sodium borate, 150 mM NaCl, and 5 mM $MgCl_2$. The resulting guide molecule concentration was about 50 to 100 µM. The two guide molecule fragments were annealed, followed by addition of dithiobis (succinimidyl propionate) (DSP) in DMF (2.2 mM final concentration). The reaction mixture was vortexed briefly and kept at room temperature for 1 h, followed by removal of excess DSP. Using upper stem variant B, a guide molecule with the following disulfide linkage was detected by LCMS (calculated: 34560.0 Da, observed: 34561.5 Da):

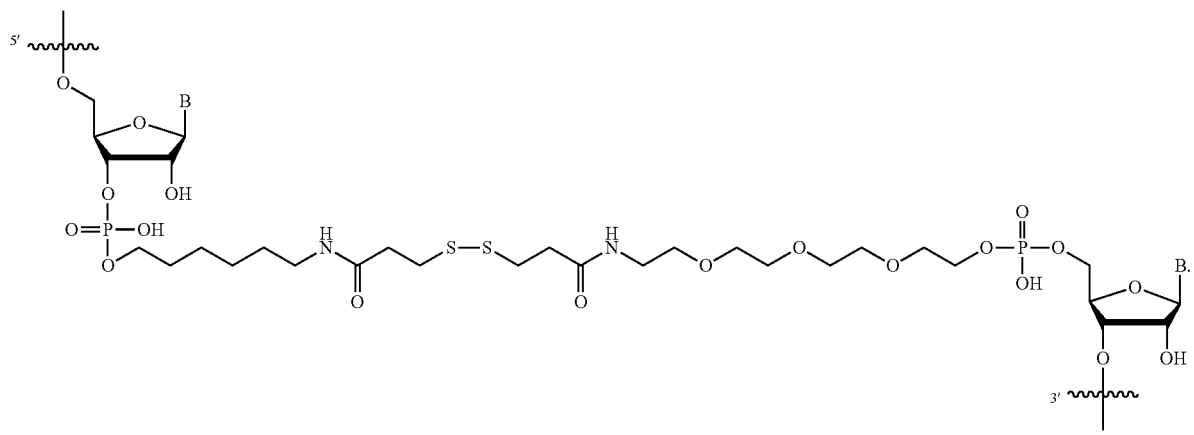

Example 23: Exemplary Process for Conjugation Through Disulfide Linkage (II)

A first 5' guide molecule fragment (e.g. a 37-mer) was synthesized with a $C_6$—$NH_2$ linker at the 3' end. A solution of this oligonucleotide fragment (100 µM final concentration) in pH 8.0 buffer with 20 mM phosphate buffer with 40% DMF was added to succinimidyl 3-(2-pyridyldithio) propionate (SPDP) in DMF (1000 µM final concentration). This reaction mixture was vortexed briefly and kept at room temperature for 90 min, followed by removal of excess SPDP.

A second 3' guide molecule fragment (e.g. a 69-mer) was synthesized with a TEG-$NH_2$ linker at the 5' end. A solution of this oligonucleotide fragment (100 µM final concentration) in pH 8.0 buffer with 20 mM phosphate buffer with 40% DMF was added succinimidyl 3-(2-pyridyldithio) propionate (SPDP) in DMF (1000 µM final concentration). This reaction mixture was vortexed briefly and kept at room temperature for 90 min, followed by removal of excess SPDP.

The two guide molecules were then mixed at a molar ratio of 1:1 in pH 7.5 buffer with 20 mM phosphate, 150 mM NaCl, and 5 mM $MgCl_2$. The resulting guide molecule concentration is about 50 to 100 µM. A solution of pH adjusted tris(2-carboxyethyl)phosphine hydrochloride (TCEP) were then added to a final concentration of 1 mM. The solution was briefly vortexed and allowed to sit at room temperature for 20 min. The solution was then concentrated and exchanged into a pH 7.0 buffer with 20 mM phosphate, 150 mM NaCl, and 5 mM $MgCl_2$. The solution was then kept at room temperature for 2 h and then 4° C. overnight, followed by desalting and HPLC purification. Using upper stem variant B, a guide molecule with the following disulfide linkage was detected by LCMS (calculated: 34560.5 Da, observed: 34560.6 Da):

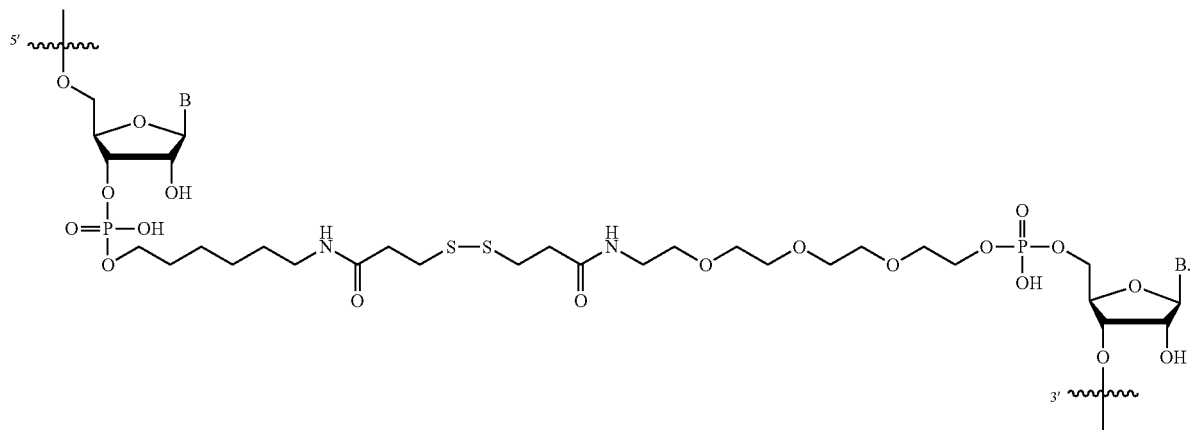

LC-MS analysis of RNAse T1 and RNAse A digestion products confirms the assignment of the above linkage.

Example 24: Exemplary Process for Conjugation Through Disulfide Linkage (III)

A first 5' guide molecule fragment (e.g. a 37-mer) was synthesized with a $C_6$—$NH_2$ linker at the 3' end. A solution of this oligonucleotide fragment (100 μM final concentration) in pH 8.0 buffer with 20 mM phosphate and 40% DMF was added succinimidyl 3-(2-pyridyldithio) propionate (SPDP) in DMF (1000 μM final concentration). This reaction mixture was vortexed briefly and kept at room temperature for 90 min, followed by removal of excess SPDP.

A second 3' guide molecule fragment (e.g. a 69-mer) was synthesized with a TEG-$NH_2$ linker at the 5' end. A solution of this oligonucleotide fragment (100 μM final concentration) in pH 8.0 buffer with 20 mM phosphate buffer was added to 2-iminothiolane in water (1000 μM final concentration). This reaction mixture was vortexed briefly and kept at room temperature for 90 min, followed by removal of excess 2-iminothiolane.

The two guide molecules were then mixed at a molar ratio of 1:1 in pH 7.5 buffer with 20 mM phosphate, 150 mM NaCl, and 5 mM $MgCl_2$. The resulting guide molecule concentration was about 50 to 100 μM. A solution of pH-adjusted tris(2-carboxyethyl)phosphine hydrochloride (TCEP) was then added to a final concentration of 1 mM. The solution was briefly vortexed and kept at room temperature for 20 min. The solution was then concentrated and exchanged into a pH 7.0 buffer with 20 mM phosphate, 150 mM NaCl, and 5 mM $MgCl_2$. The solution was then kept at room temperature for 2 h and then 4° C. overnight, followed by desalting and HPLC purification. Using upper stem variant B, a guide molecule with the following disulfide linkage was detected by LCMS (calculated: 34573.5 Da, observed: 34573.5 Da):

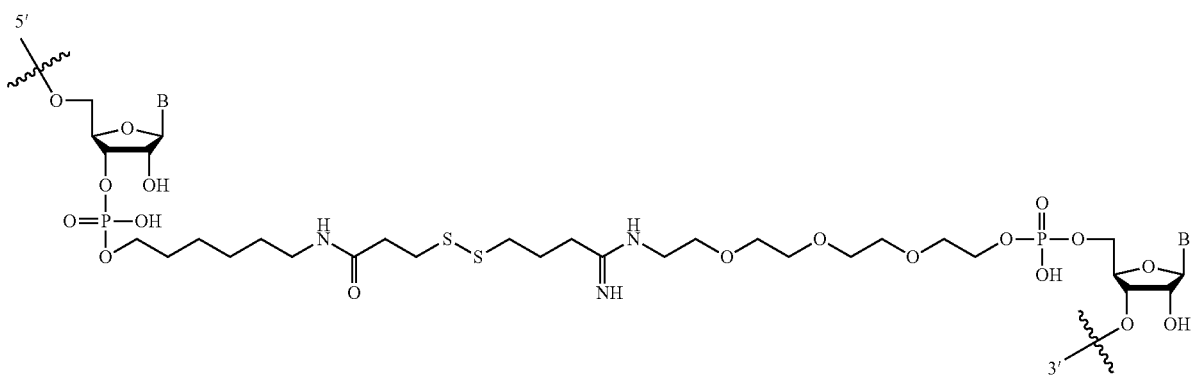

Example 25: Exemplary Process for Conjugation Through Disulfide Linkage (IV)

A first 5' guide molecule fragment (e.g. a 37-mer) was synthesized with a $C_6$—$NH_2$ linker at the 3' end, and a second 3' guide molecule fragment (e.g. a 69-mer) was synthesized with a TEG-$NH_2$ linker at the 5' end. The two guide molecule fragments were mixed at a molar ratio of 1:1 in pH 8.0 buffer with 20 mM phosphate and 150 mM NaCl. The resulting guide molecule concentration was about 50 to 100 μM. The two guide molecule fragments were annealed, followed by addition of 2-iminothiolate (2 mM final concentration). The reaction mixture was vortexed briefly and kept at room temperature for 1 h. The solution was exchanged into a pH 7.0 buffer with 20 mM phosphate and 150 mM NaCl. This solution was kept at room temperature for 3 h, followed by overnight incubation at 4° C. Excess traut's reagent was then removed and the solution desalted and stored at −20° C. until further analysis. Further analysis indicated the following disulfide linkage was provided:

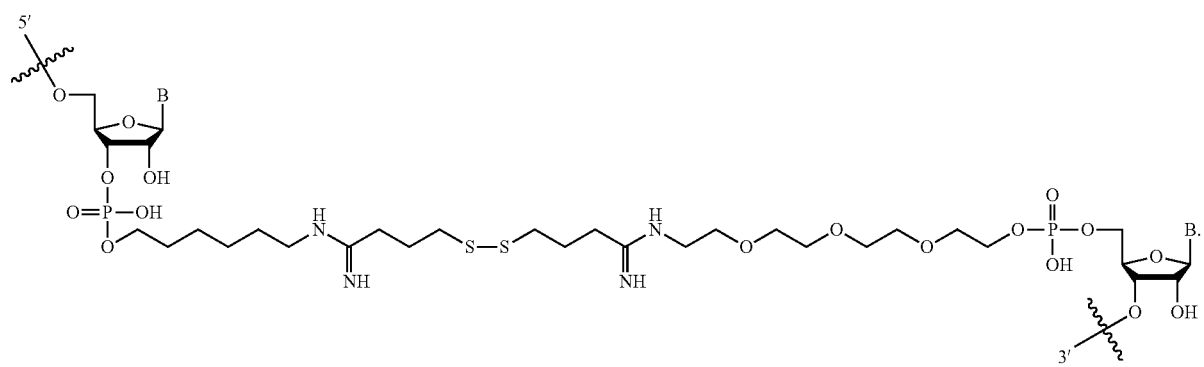

Table 23 summarizes results from conjugation with disulfide linkages.

TABLE 23

| Upper Stem Variant | LCMS (Calculated) | LCMS (Observed) |
|---|---|---|
| B | 34586.6 Da | 34586.6 Da |
| H | 33300.8 Da | 33301.1 Da |

Example 26: Exemplary Process for Conjugation Through Thioether Linkage (I)

A first 5' guide molecule fragment (e.g. a 37-mer) was synthesized with a $C_6$—$NH_2$ linker at the 3' end. A solution of this oligonucleotide fragment (100 μM final concentration) in pH 8.0 buffer with 20 mM phosphate buffer with 40% DMF was added succinimidyl 3-(2-pyridyldithio) propionate (SPDP) in DMF (1000 μM final concentration). This reaction mixture was vortexed briefly and kept at room temperature for 90 min, followed by removal of excess SPDP.

A second 3' guide molecule fragment (e.g. a 69-mer) was synthesized with a TEG-$NH_2$ linker at the 5' end. A solution of this oligonucleotide fragment (100 μM final concentration) in pH 8.0 buffer with 20 mM phosphate buffer with 40% DMF was added succinimidyl 3-(bromoacetamido) propionate (SBAP) in DMF (1000 μM final concentration). This reaction mixture was vortexed briefly and kept at room temperature for 90 min, followed by removal of excess SBAP.

The two guide molecules were then mixed at a molar ratio of 1:1 in pH 7.5 buffer with 20 mM phosphate, 150 mM NaCl, and 5 mM $MgCl_2$. The resulting guide molecule concentration was about 50 to 100 μM. A solution of pH adjusted tris(2-carboxyethyl)phosphine hydrochloride (TCEP) was then added to a final concentration of 1 mM. The solution was briefly vortexed and kept at room temperature for 2 h, followed by desalting and HPLC purification. Using upper stem variant B, a guide molecule with the following thioether linkage was detected by LCMS (calculated: 34585.5 Da, observed: 34585.5 Da):

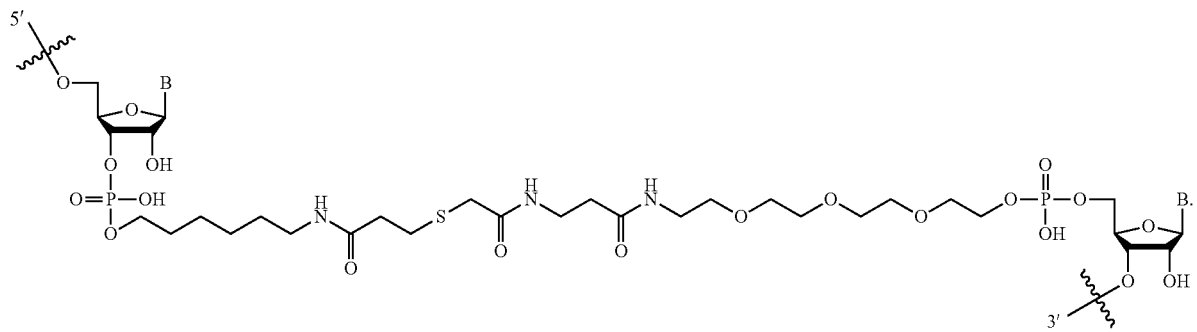

LC-MS analysis of RNAse T1 and RNAse A digestion products confirms the assignment of the above linkage.

Example 27: Exemplary Process for Conjugation Through Thioether Linkage (II)

A first 5' guide molecule fragment (e.g. a 37-mer) is synthesized with a $C_6$—$NH_2$ linker at the 3' end. A solution of this oligonucleotide fragment (100 µM final concentration) in pH 8.0 buffer with 20 mM phosphate and 40% DMF is added succinimidyl 3-(bromoacetamido) propionate (SBAP) in DMF (1000 µM final concentration). This reaction mixture is vortexed briefly and kept at room temperature for 90 min, followed by removal of excess SBAP.

A second 3' guide molecule fragment (e.g. a 69-mer) is synthesized with a TEG-$NH_2$ linker at the 5' end. A solution of this oligonucleotide fragment (100 µM final concentration) in pH 8.0 buffer with 20 mM phosphate and 40% DMF is added succinimidyl 3-(2-pyridyldithio) propionate (SPDP) in DMF (1000 µM final concentration). This reaction mixture is vortexed briefly and kept at room temperature for 90 min, followed by removal of excess SPDP.

The two guide molecules are then mixed at a molar ratio of 1:1 in pH 7.5 buffer with 20 mM phosphate, 150 mM NaCl, and 5 mM $MgCl_2$. The resulting guide molecule concentration is about 50 to 100 µM. A solution of pH adjusted tris(2-carboxyethyl)phosphine hydrochloride (TCEP) was then added to a final concentration of 1 mM. The solution was briefly vortexed and kept at room temperature for 2 h, followed by desalting and HPLC purification. Using upper stem variant B, a guide molecule with the following thioether linkage was detected by LCMS (calculated: 34744.3 Da, observed: 34745.8 Da):

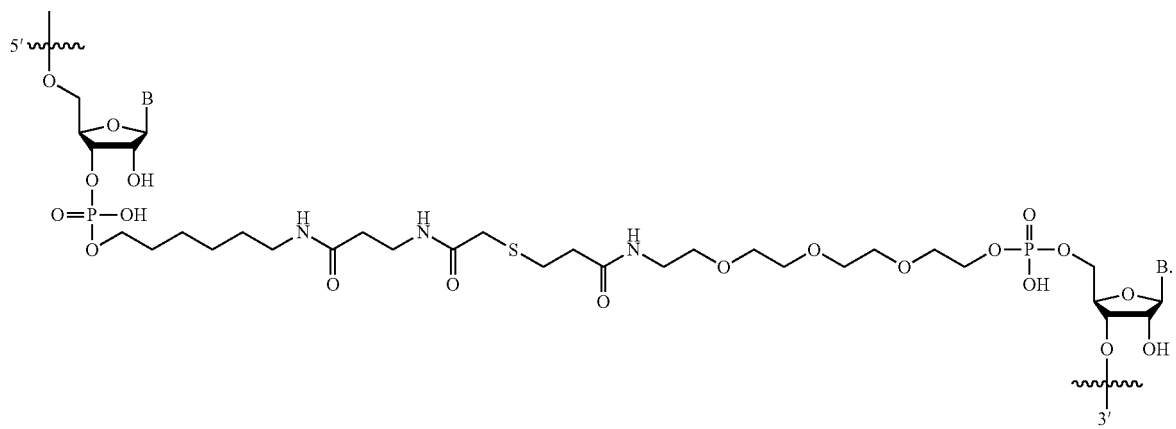

LC-MS/MS analysis (e.g., as described in Example 9) of RNAse T1 and RNAse A digestion products confirms the assignment of the above linkage.

Example 28: Exemplary Process for Conjugation Through Thioether Linkage (III)

A first 5' guide molecule fragment (e.g. a 37-mer) is synthesized with a $C_6$—$NH_2$ linker at the 3' end. A solution of this oligonucleotide fragment (100 μM final concentration) in pH 8.0 buffer with 20 mM phosphate buffer with 40% DMF is added succinimidyl iodoacetate (SIA) in DMF (1000 μM final concentration). This reaction mixture is vortexed briefly and kept at room temperature for 90 min, followed by removal of excess SIA.

A second 3' guide molecule fragment (e.g. a 69-mer) is synthesized with a TEG-$NH_2$ linker at the 5' end. A solution of this oligonucleotide fragment (100 μM final concentration) in pH 8.0 buffer with 20 mM phosphate buffer with 40% DMF is added succinimidyl 3-(2-pyridyldithio) propionate (SPDP) in DMF (1000 μM final concentration). This reaction mixture is vortexed briefly and kept at room temperature for 90 min, followed by removal of excess SPDP.

The two guide molecules are then mixed at a molar ratio of 1:1 in pH 7.5 buffer with 20 mM phosphate, 150 mM NaCl, and 5 mM $MgCl_2$. The resulting guide molecule concentration is about 50 to 100 μM. A solution of pH adjusted tris(2-carboxyethyl)phosphine hydrochloride (TCEP) was then added to a final concentration of 1 mM. The solution was briefly vortexed and kept at room temperature for 2 h, followed by desalting and HPLC purification. Using upper stem variant B, a guide molecule with the following thioether linkage was detected by LCMS (calculated: 34514.5 Da, observed: 34514.7 Da):

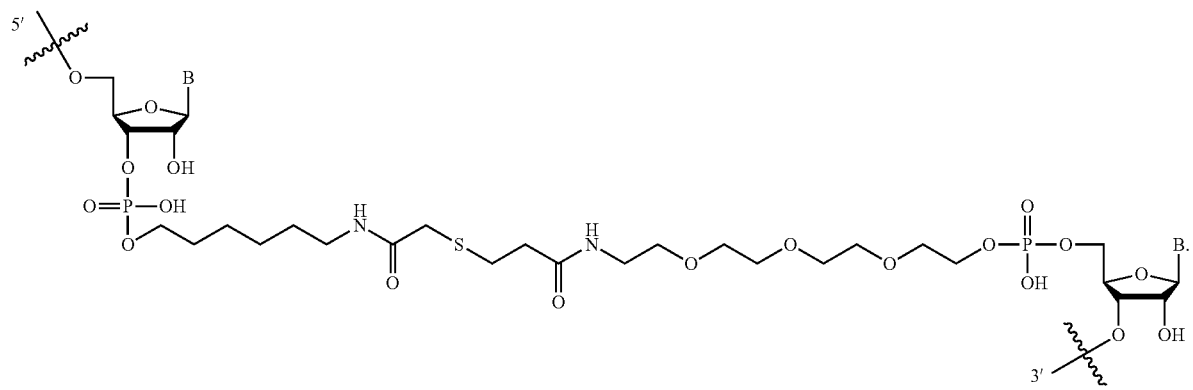

LC-MS analysis of RNAse T1 and RNAse A digestion products confirms the assignment of the above linkage.

Example 29: Exemplary Process for Conjugation Through Thioether Linkage (IV)

A first 5' guide molecule fragment (e.g. a 37-mer) was synthesized with a $C_6$—$NH_2$ linker at the 3' end. A solution of this oligonucleotide fragment (100 μM final concentration) in pH 8.0 buffer with 20 mM phosphate and 40% DMF was added succinimidyl 3-(2-pyridyldithio) propionate (SPDP) in DMF (1000 μM final concentration). This reaction mixture was vortexed briefly and kept at room temperature for 90 min, followed by removal of excess SPDP.

A second 3' guide molecule fragment (e.g. a 69-mer) was synthesized with a TEG-$NH_2$ linker at the 5' end. A solution of this oligonucleotide fragment (100 μM final concentration) in pH 8.0 buffer with 20 mM phosphate and 40% DMF was added succinimidyl iodoacetate (SIA) in DMF (1000 μM final concentration). This reaction mixture was vortexed briefly and kept at room temperature for 90 min, followed by removal of excess SIA.

The two guide molecules were then mixed at a molar ratio of 1:1 in pH 7.5 buffer with 20 mM phosphate, 150 mM NaCl, and 5 mM $MgCl_2$. The resulting guide molecule concentration was about 50 to 100 μM. A solution of pH adjusted tris(2-carboxyethyl)phosphine hydrochloride (TCEP) was then added to a final concentration of 1 mM. The solution was briefly vortexed and kept at room temperature for 2 h, followed by desalting and HPLC purification. Using upper stem variant B, a guide molecule with the following thioether linkage was detected by LCMS (calculated: 34514.5 Da, observed: 34514.7 Da):

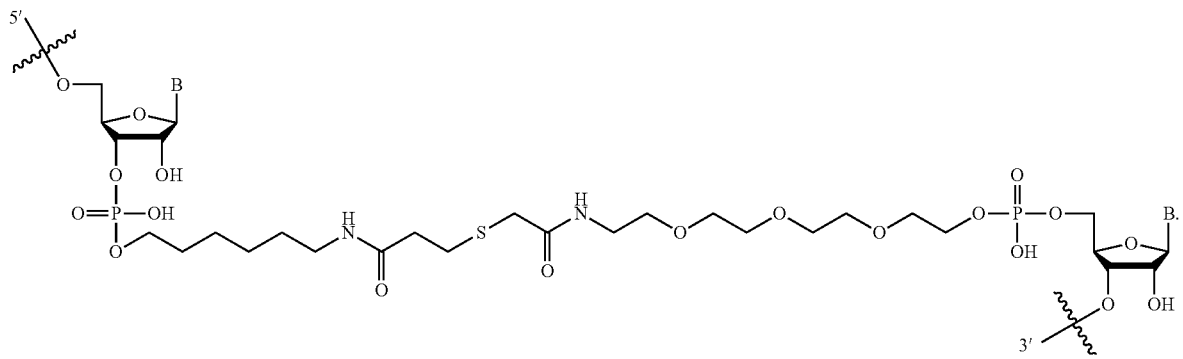

LC-MS analysis of RNAse T1 and RNAse A digestion products confirms the assignment of the above linkage.

Example 30: Exemplary Process for Conjugation Through Maleimide

A first 5' guide molecule fragment (e.g. a 37-mer) was synthesized with a $C_6$—$NH_2$ linker at the 3' end, and a second 3' guide molecule fragment (e.g. a 69-mer) was synthesized with a TEG-$NH_2$ linker at the 5' end. The two guide molecule fragments were mixed at a molar ratio of 1:1 in pH 8.5 buffer with 10 mM sodium borate, 150 mM NaCl, and 5 mM $MgCl_2$. The resulting guide molecule concentration was about 50 to 100 μM. The two guide molecule fragments were annealed, followed by addition of dithiobis (succinimidyl propionate) (DSP) in DMF (2.2 mM final concentration). The reaction mixture was vortexed briefly and kept at room temperature for 1 h, followed by removal of excess DSP. The reaction mixture was buffer exchanged into a pH 8.0 buffer with 10 mM sodium borate, 150 mM NaCl, and 5 mM $MgCl_2$. The resulting guide concentration was 20-100 μM. TCEP was then added to a final concentration of 1 mM and the solution was kept at room temperature of 30 min. A solution of dibromomaleimide in DMF was then added (2 mM final concentration). After 90 min, the solution was desalted and stored at −20° C. until further analysis. Using upper stem variant B, a guide molecule with the following maleimide linkage was detected by LCMS (calculated: 34655.5 Da, observed: 34655.7 Da):

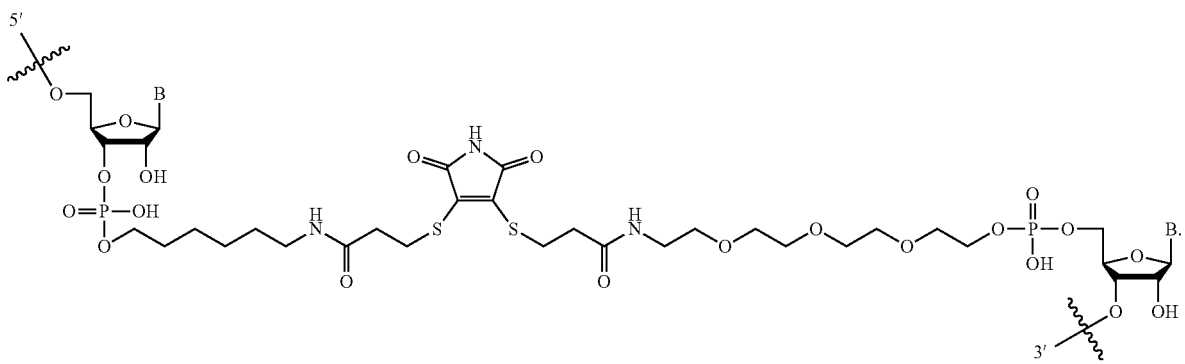

LC-MS analysis of RNAse A digestion products confirms the assignment of the above linkage.

Example 31: Exemplary Process for Conjugation Through Amine

A first 5' guide molecule fragment (e.g. a 37-mer) was synthesized with a $C_6$—$NH_2$ linker at the 3' end, and a second 3' guide molecule fragment (e.g. a 69-mer) was synthesized with a TEG-$NH_2$ linker at the 5' end. The two guide molecule fragments were mixed at a molar ratio of 1:1 in pH 7.0 buffer with 20 mM phosphate. The resulting guide molecule concentration was about 50 to 100 µM. The two guide molecule fragments were annealed, followed by addition of formaldehyde (0.36% final). The reaction mixture was vortexed briefly and kept at room temperature for 1 h, followed by removal of excess formaldehyde. Using upper stem variant H, a guide molecule with the following methylene linkage was detected by LCMS (calculated: 33112.7 Da, observed: 33112.4 Da):

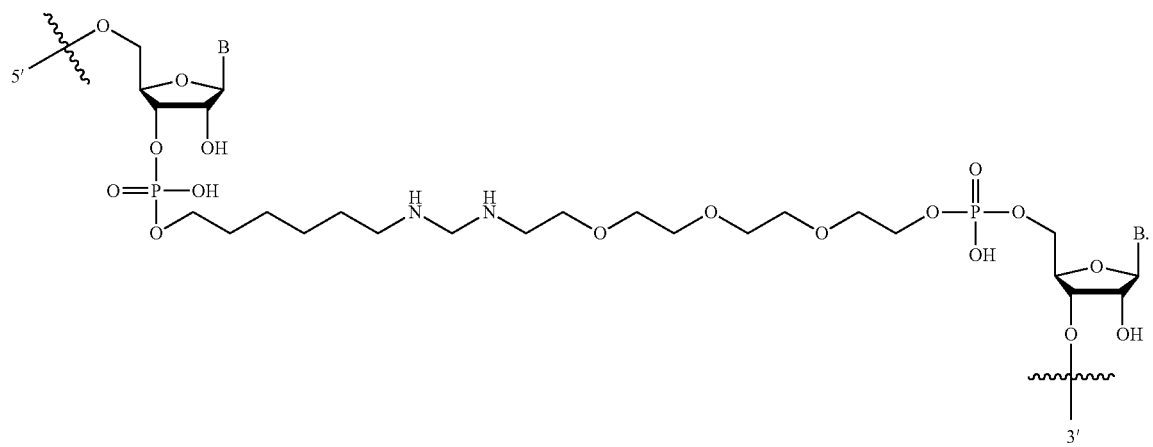

Example 32: Evaluating Activity of Conjugated Guide Molecules

Figure 19:
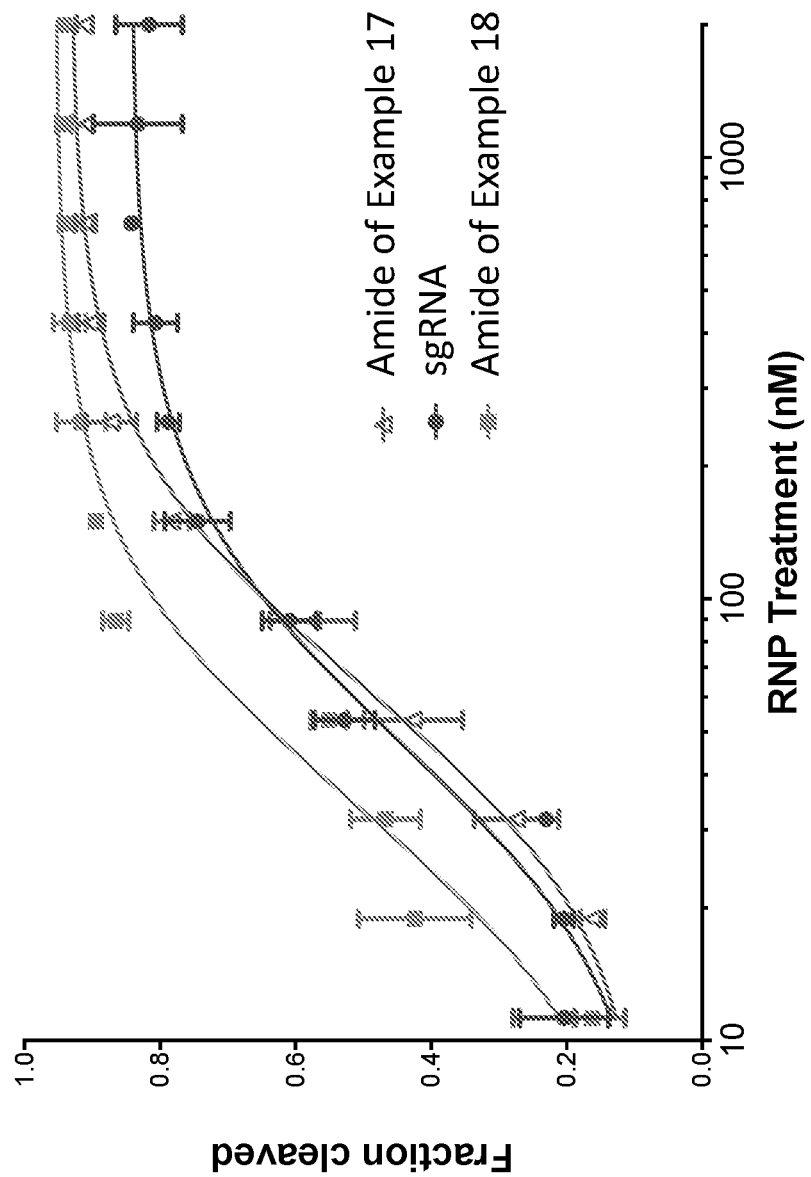
FIG. 19 is a graph of fraction of dsDNA cleaved as a function of RNP concentration as described in Example 32.

Synthetic guide molecules were incubated with Cas9 to form a ribonucleoprotein complex (RNP). The RNP was then incubated at varying concentrations with synthetic dsDNA. Following incubation, the fraction of cleaved dsDNA was determined using a fragment analyzer. The data was then plotted as fraction dsDNA cleaved as a function of RNP concentration to provide a dose-response curve for each RNP. FIG. 19 shows the results of Example 32 and demonstrates that conjugated guide molecules demonstrate similar or better activity than a sgRNA in the assay.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments described herein. Such equivalents are intended to be encompassed by the following claims.

The invention claimed is:

1. A synthetic unimolecular guide molecule for a CRISPR system, wherein the guide molecule is of formula A$_3$'-ii or A$_2$'-ii:

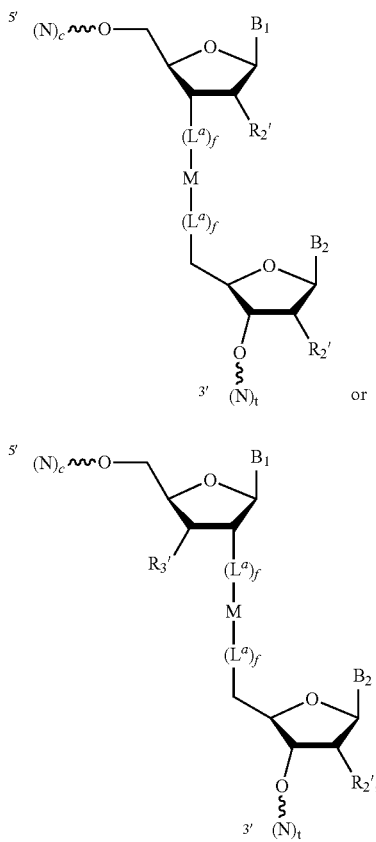

or a pharmaceutically acceptable salt thereof, wherein:

each N in (N)$_c$ and (N)$_t$ is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;

(N)$_c$ includes a 3' region that is complementary or partially complementary to, and forms a duplex with, a 5' region of (N)$_t$;

c is an integer 20 or greater;

t is an integer 20 or greater;

B$_1$ and B$_2$ are each independently a nucleobase;

each of R$_2$' and R$_3$' is independently H, OH, fluoro, chloro, bromo, NH$_2$, SH, S—R', or O—R' wherein each R' is independently a protection group or an alkyl group, wherein the alkyl group may be optionally substituted;

each ∿∿ represents independently a phosphodiester linkage, a phosphorothioate linkage, a phosphonoacetate linkage, a thiophosphonoacetate linkage, or a phosphoroamidate linkage;

-(L$^a$)$_f$-M-(L$^a$)$_f$- is

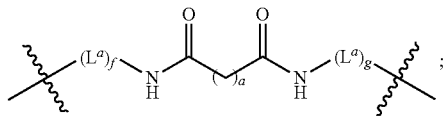

each L$^a$ is independently a covalent bond or an optionally substituted, bivalent, straight or branched, saturated or unsaturated C$_1$-C$_{50}$ hydrocarbon chain, wherein one or more methylene units are optionally replaced by —O—, —S—, —N(R)—, —C(O)—, —C(S)—, —C(NR)—, —C(NOR)—, —C(NNR$_2$)—, —OC(O)—, —C(O)O—, —C(O)N(R)—, —N(R)C(O)—, —C(NR)O—, —OC(NR)—, —C(NR)NR—, —N(R)C(NR)—, —N(R)C(O)N(R)—, —N(R)C(O)O—, —OC(O)N(R)—, —N(R)C(O)S—, —SC(O)N(R)—, —N(R)C(NR)N(R)—, —SO$_2$—, —SO$_2$N(R)—, —N(R)SO$_2$—, —OP(O)(OH)O—, —OP(S)(OH)O—, —OP(S)(SH)O—, —OP(S)(COOH)O—, —OP(O)(COOH)O—, —OP(O)(NR2)O—, —NP(O)(OH)O—, —OP(O)(OH)N—, or -Cy-;

each R is independently hydrogen or an optionally substituted group selected from C$_{1-6}$ aliphatic, phenyl, a 4- to 7-membered heterocyclic ring having 1-2 heteroatoms independently selected from nitrogen, oxygen, and sulfur, and a 5- to 6-membered monocyclic heteroaryl ring having 1-4 heteroatoms independently selected from nitrogen, oxygen, and sulfur;

Cy is an optionally substituted, mono- or multicyclic, 3- to 20-membered, bivalent ring system, wherein the ring system is fully saturated, fully or partially unsaturated, or aromatic, and wherein the ring system contains 0-6 heteroatoms selected from the group consisting of O, N, and S;

each a is independently an integer between 0 and 16, inclusive;

each g is independently 0, 1, 2, 3, 4, or 5; and each f is independently 0, 1, 2, 3, 4, 5, or 6.

2. The guide molecule of claim 1, wherein:

each L$^a$ is independently selected from:

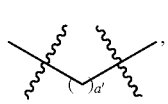 L$^a$-1'

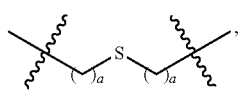 L$^a$-3

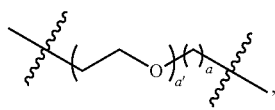 L$^a$-5'

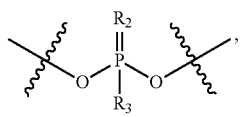 L$^a$-26

-continued

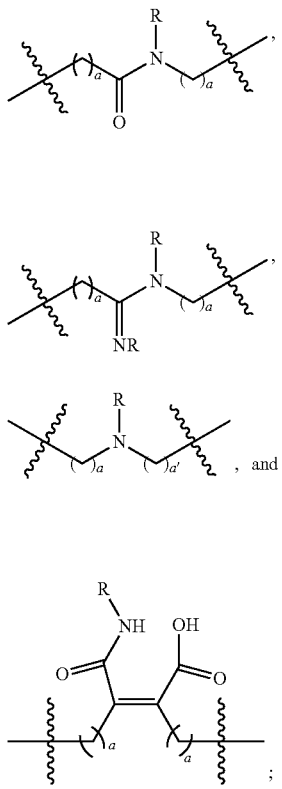

$L^a$-27

$L^a$-31

$L^a$-37'

$L^a$-41 each a' is independently an integer between 1 and 16, inclusive;

each $R_2$ is independently O or S; and each $R_3$ is independently OH or COOH.

3. The guide molecule of claim 1, wherein the guide molecule is of formula $B_{3'}$-ii or $B_{2'}$-ii:

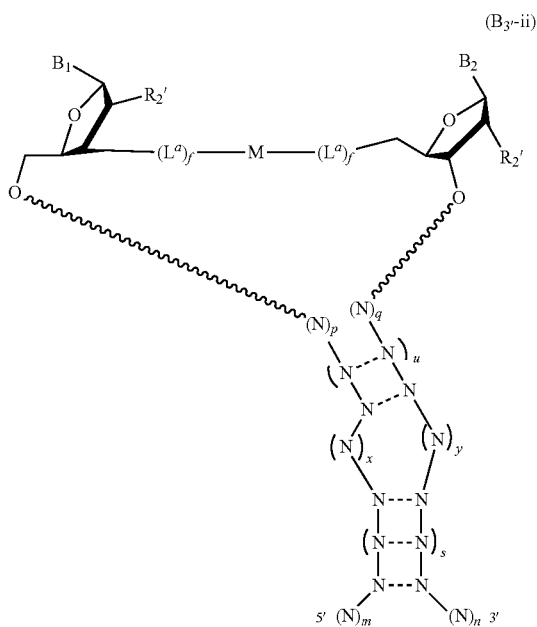

($B_{3'}$-ii)

-continued

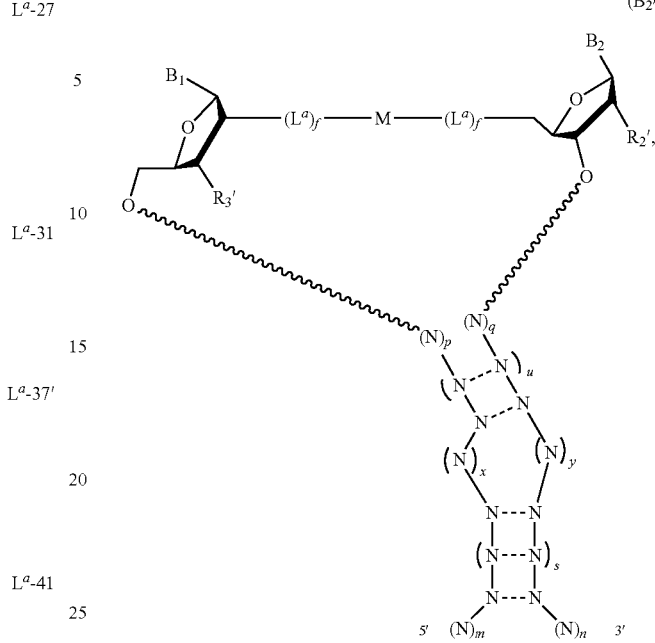

($B_{2'}$-ii)

wherein:
each N is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage;
each N—N independently represents two complementary nucleotides;
p and q are each independently an integer between 0 and 6, inclusive, and p+q is an integer between 0 and 6, inclusive;
u is an integer between 2 and 22, inclusive;
s is an integer between 1 and 10, inclusive;
x is an integer between 1 and 3, inclusive;
y is >x and an integer between 3 and 5, inclusive;
m is an integer 15 or greater; and
n is an integer 30 or greater.

4. A composition comprising or consisting essentially of the guide molecule of claim 1, or a pharmaceutically acceptable salt thereof.

5. A method of synthesizing the guide molecule of claim 1, comprising steps of:
providing a first oligonucleotide and a second oligonucleotide, capable of forming a duplex between a 3' region of the first oligonucleotide and a 5' region of the second oligonucleotide, wherein the first oligonucleotide comprises a first reactive group which is at least one of a 2' reactive group and a 3' reactive group, and wherein the second oligonucleotide comprises a second reactive group which is a 5' reactive group; and
conjugating the first and second oligonucleotides via the first and second reactive groups to form a unimolecular guide molecule that includes a covalent bond linking the first and second oligonucleotides;
wherein the first reactive group and the second reactive group are each independently an amine moiety.

6. The guide molecule of claim 3, wherein p is at least one greater than q, or q is at least one greater than p.

7. The guide molecule of claim 3, wherein the guide molecule is of formula C₃'-ii, C₂'-ii, D₃'-ii or D₂'-ii:

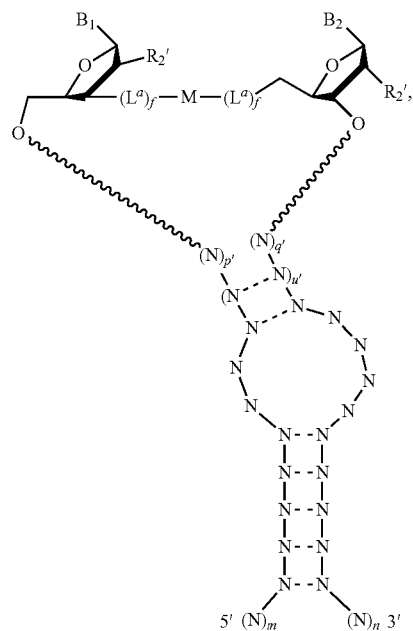

(C₃'-ii)

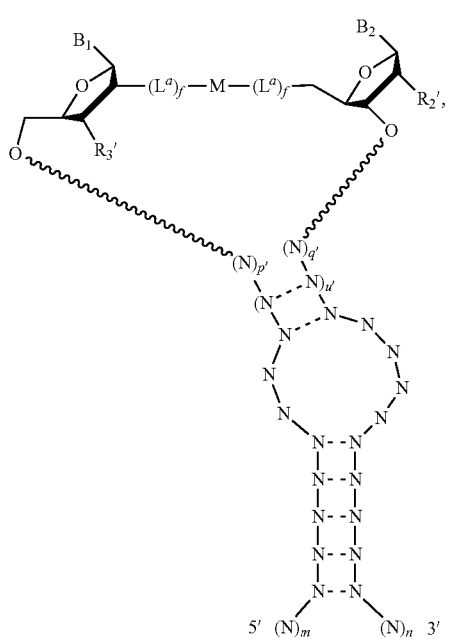

(C₂'-ii)

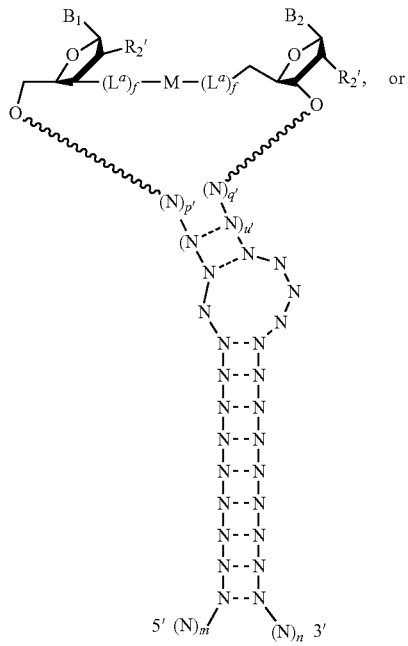

(D₃'-ii)

or

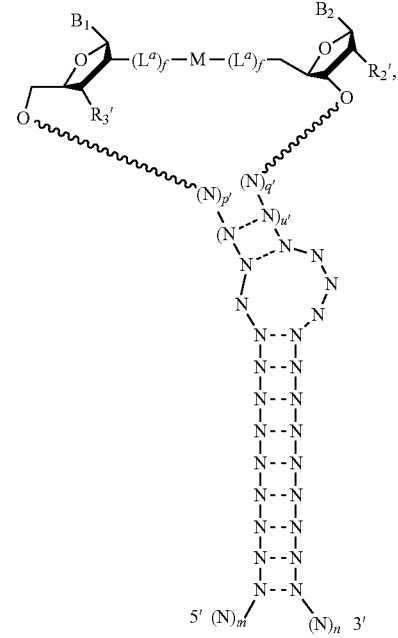

(D₂'-ii)

wherein:
u' is an integer between 2 and 22, inclusive; and
p' and q' are each independently an integer between 0 and 4, inclusive, and p'+q' is an integer between 0 and 4, inclusive.

8. The guide molecule of claim 7, wherein p' is at least one greater than q', or q' is at least one greater than p'.

9. The guide molecule of claim 1, wherein -(L$^a$)$_f$-M-(L$^a$)$_g$- is:

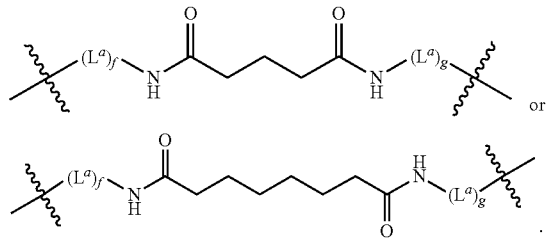

or

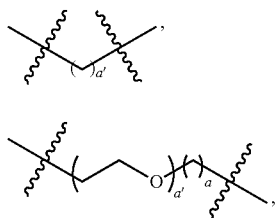

10. The guide molecule of claim 1, wherein each L$^a$ is independently selected from:

L$^a$-1′

L$^a$-5′

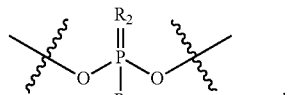

L$^a$-26

, and

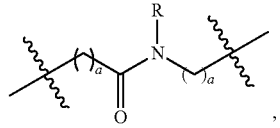

L$^a$-27 wherein:
each a' is independently an integer between 1 and 16, inclusive;
each R$_2$ is independently O or S; and
each R$_3$ is independently OH or COOH.

11. The guide molecule of claim 10, wherein -(L$^a$)$_f$-M-(L$^a$)$_g$- is:

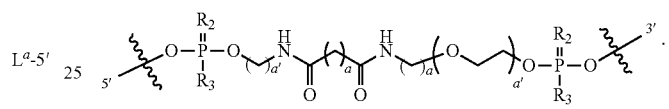

12. The guide molecule of claim 11, wherein -(L$^a$)$_f$-M-(L$^a$)$_g$- is:

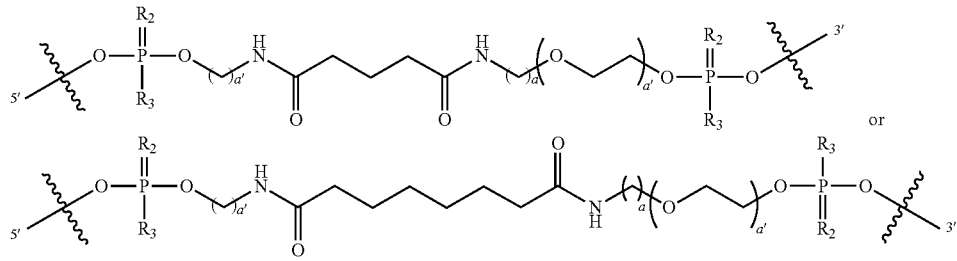

or

13. The guide molecule of claim 12, wherein -(L$^a$)$_f$-M-(L$^a$)$_g$- is:

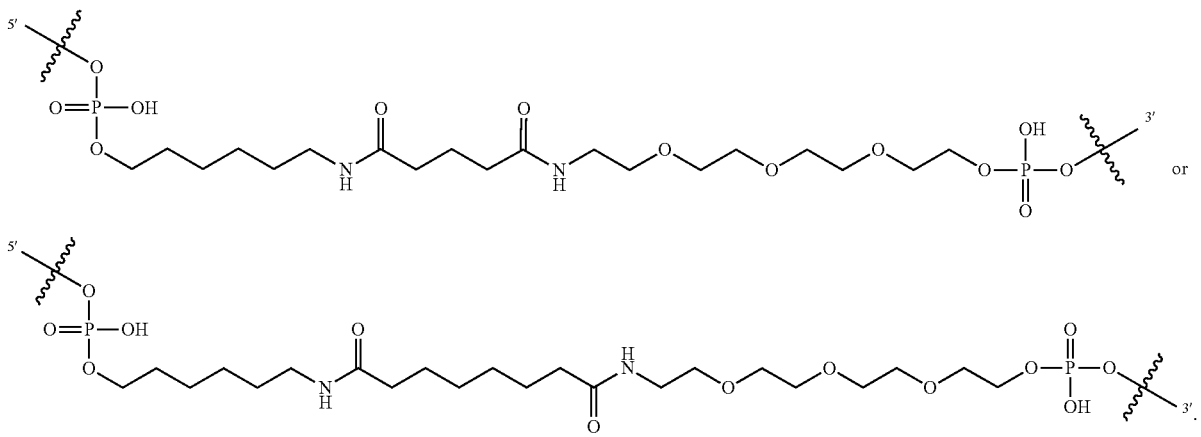

or

14. The method of claim 5, wherein the method comprises a step of annealing the first oligonucleotide and the second oligonucleotide to form a duplex between a 3' region of the first oligonucleotide and a 5' region of the second oligonucleotide.

15. The composition of claim 4, wherein the guide molecule is suspended in solution or in a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 12,338,436 B2 | Page 1 of 1 |
| APPLICATION NO. | : 17/255140 | |
| DATED | : June 24, 2025 | |
| INVENTOR(S) | : Sam Saccomano et al. | |

It is certified that error appears in the above-identified patent and that said Letters Patent is hereby corrected as shown below:

In the Claims

In Claim 3, Column 502, Lines 36-37, please delete:
"each N—N independently represents two complementary nucleotides;"
And insert:
-- each N- - -N independently represents two complementary nucleotides; --

Signed and Sealed this
Fourth Day of November, 2025

John A. Squires
*Director of the United States Patent and Trademark Office*